(12) United States Patent
Yoshihara et al.

(10) Patent No.: US 8,716,470 B2
(45) Date of Patent: May 6, 2014

(54) GUANIDINE COMPOUND

(71) Applicant: Astellas Pharma Inc., Chuo-ku (JP)

(72) Inventors: Kousei Yoshihara, Chuo-ku (JP); Daisuke Suzuki, Chuo-ku (JP); Susumu Yamaki, Chuo-ku (JP); Hiroyoshi Yamada, Chuo-ku (JP); Hisashi Mihara, Chuo-ku (JP); Norio Seki, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 9 days.

(21) Appl. No.: 13/755,822

(22) Filed: Jan. 31, 2013

(65) Prior Publication Data

US 2013/0143860 A1   Jun. 6, 2013

Related U.S. Application Data

(63) Continuation-in-part of application No. PCT/JP2012/056429, filed on Mar. 13, 2012.

(30) Foreign Application Priority Data

Mar. 15, 2011   (JP) ................. 2011-056031

(51) Int. Cl.
*C07D 417/04* (2006.01)
*A61K 31/5377* (2006.01)

(52) U.S. Cl.
USPC .................. 544/122; 514/235.8

(58) Field of Classification Search
USPC .................. 544/122; 514/235.8
See application file for complete search history.

(56) References Cited

U.S. PATENT DOCUMENTS

| 4,888,283 | A | 12/1989 | Bertini |
| 5,753,710 | A | 5/1998 | Kleemann et al. |
| 2002/0173521 | A1 | 11/2002 | Smith et al. |
| 2007/0254931 | A1 | 11/2007 | Inoue et al. |
| 2011/0059957 | A1 | 3/2011 | Matsukawa et al. |
| 2012/0184520 | A1 | 7/2012 | Yoshihara et al. |

FOREIGN PATENT DOCUMENTS

| DE | 195 18 073 | 11/1996 |
| DE | 199 45 302 | 3/2001 |
| JP | 61-239891 | 10/1986 |
| JP | 8-311012 | 11/1996 |
| JP | 2004-500338 | 1/2004 |
| JP | 2008-508188 | 3/2008 |
| WO | WO 93/23023 | 11/1993 |
| WO | WO 01/21582 | 3/2001 |
| WO | WO 02/02541 | 1/2002 |
| WO | WO 02/02990 | 1/2002 |
| WO | WO 02/38152 | 5/2002 |
| WO | WO 02/38153 | 5/2002 |
| WO | WO 2004/067521 | 8/2004 |
| WO | WO 2004/087138 | 10/2004 |
| WO | WO 2006/011631 | 2/2006 |
| WO | WO 2008/025800 | 3/2008 |
| WO | WO 2008/070692 | 6/2008 |
| WO | WO 2009/096609 | 8/2009 |
| WO | WO 2009/145360 | 12/2009 |
| WO | WO 2011/034078 | 3/2011 |

OTHER PUBLICATIONS

English translation of International Preliminary Report on Patentability issued Sep. 17, 2013 (Form PCT/IB/373) in PCT/JP2012/056429, 7 pp.
International Search Report issued Apr. 17, 2012, in international application No. PCT/JP2012/056429 (w/ English translation).
International Preliminary Report on Patentability issued Apr. 17, 2012, in international application No. PCT/JP2012/056429.
Oliverti et al, "L-lysine as a recognition molecule for the VAP-1 function of SSAO" *J. Neural. Transm*, (2007) 114: 747-749.
Boomsma et al, "Circulating semicarbazide-sensitive amine oxidase is raised both in Type I (insulin-dependent), in Type II (non-insulin-dependent) diabetes . . ." *Diabetologia* (1999) 42: 233-237.
Garpenstrand et al, "Elevated plasma semicarbazide-sensitive amine oxidase (SSAO) activity in Type 2 diabetes mellitus complicated by retinopathy", British Diabetic Association, *Diabetic Medicine* (1999) 16, 514-521.
Yu et al, "Aminoguanidine inhibits semicarbazide-sensitive amine oxidase activity: implications for advanced glycation and diabetic complications", *Diabetologia* (1997) 40: 1243-1250.
Nemcsik et al, "Alteration of serum semicarbazide-sensitive amine oxidase activity in chronic renal failure", *J. Neural Transm*. (2007) 114: 841-843.
Tuchman-Shukron et al, "Cyclic 2:1 and 1:2 Aldehyde-to-Acetone Byproduct Adducts in Aldol Reactions Promoted by Supported Proline-Incorporated Catalysts", *Eur. J. Org. Chem*., (2009), 7: 992-996.

*Primary Examiner* — Robert Havlin
(74) *Attorney, Agent, or Firm* — Oblon, Spivak, McClelland, Maier & Neustadt, L.L.P.

(57) ABSTRACT

[Problem]
The present invention provides a compound which is useful as an active ingredient of a pharmaceutical composition, in particular, a pharmaceutical composition for preventing and/or treating VAP-1-related diseases.
[Means for Solution]
The present inventors have conducted intensive studies on a compound having a VAP-1 inhibitory activity, and as a result, they have found that the compound or a salt thereof of the present invention exhibits an excellent VAP-1 inhibitory activity and is useful for preventing and/or treating VAP-1-related diseases, in particular, diabetic nephropathy or diabetic macular edema, thereby completing the present invention. In addition, the present invention relates to a pharmaceutical composition, in particular, a pharmaceutical composition for preventing and/or treating VAP-1-related diseases, which comprises the compound or a salt thereof of the present invention, and an excipient.

10 Claims, No Drawings

GUANIDINE COMPOUND

TECHNICAL FIELD

The present invention relates to a guanidine compound which is useful as an active ingredient of a pharmaceutical composition, in particular, a pharmaceutical composition for preventing and/or treating vascular adhesion protein-1 (hereinafter abbreviated as VAP-1)-related diseases.

BACKGROUND ART

VAP-1 is an amine oxidase (semicarbazide-sensitive amine oxidase, SSAO) which is abundant in human plasma (Non-Patent Document 1), and shows remarkably increased expression in vascular endothelium and vascular smooth muscle of inflammatory regions. While the physiological role of VAP-1 has not been clarified until recently, VAP-1 gene was cloned in 1998, and VAP-1 has been reported to be a membrane protein that regulates rolling and migration of lymphocytes and NK cells as an adhesion molecule under regulation of expression by inflammatory cytokines. Although the amine acting as a substrate is unknown, it is considered to be methylamine generated in any part of a living body. It is also known that hydrogen peroxide and aldehydes produced due to the amine oxidase activity in the molecule are important factors of adhesion activity.

A recent report has demonstrated that the VAP-1 enzyme activity in plasma increases in patients with diabetes mellitus, whether type I or type II, and the increase is particularly remarkable in patients with diabetes mellitus suffering from retinopathy complications (Non-Patent Documents 2 and 3).

In addition, it has been reported that VAP-1 is related to the following diseases:

(1) cirrhosis, essential stabilized hypertension, diabetes mellitus, and arthrosis (Patent Documents 1 and 2);

(2) endothelium damage (in diabetes mellitus, arteriosclerosis, and hypertension), cardiovascular diseases related to diabetes mellitus and uremia, pain related to gout and arthritis, and retinopathy (in diabetes mellitus patients) (Patent Document 3);

(3) inflammatory diseases or conditions (of connective tissue) (rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematosus, systemic sclerosis, eosinophilic fasciitis, polymyositis, dermatomyositis, polymyalgia rheumatica, vasculitis, temporal arteritis, polyarteritis nodosa, Wegener's granulomatosis, mixed connective tissue disease, and juvenile rheumatoid arthritis); gastrointestinal inflammatory diseases or conditions [Crohn's disease, ulcerative colitis, irritable bowel syndrome (spastic colon), fibrotic conditions of the liver, inflammation of the oral mucosa (stomatitis), and recurrent aphtous stomatitis]; central nervous system inflammatory diseases or conditions (multiple sclerosis, Alzheimer's disease, and ischemia-reperfusion injury related to ischemic stroke); pulmonary inflammatory diseases or conditions (asthma, adult respiratory distress syndrome, and chronic obstructive pulmonary disease); (chronic) skin inflammatory diseases or conditions (psoriasis, allergic lesions, lichen planus, pityriasis rosea, contact dermatitis, atopic dermatitis, and pityriasis rubra pilaris); diseases related to carbohydrate metabolism (diabetes mellitus and complications from diabetes mellitus) including microvascular and macrovascular diseases (arteriosclerosis, vascular retinopathies, retinopathy, nephropathy, nephrotic syndrome and neuropathy (polyneuropathy, mononeuropathies and autonomic neuropathy), foot ulcers, joint problems, and increased risk of infection); diseases related to aberrations in adipocyte differentiation or function or smooth muscle cell function (arterosclerosis and obesity); vascular diseases [atheromatous arteriosclerosis, nonatheromatous arterosclerosis, ischemic heart disease including myocardial infarction and peripheral arterial occlusion, Raynaud's disease and phenomenon, and thromboangiitis obliterans (Buerger's disease)]; chronic arthritis; inflammatory bowel diseases; and skin dermatoses (Patent Documents 4, 5, and 6, and Non-Patent Documents 4 and 5);

(4) diabetes mellitus (Patent Document 7);

(5) SSAO-mediated complications [diabetes mellitus (insulin dependent diabetes mellitus (IDDM) and non-insulin dependent diabetes mellitus (NIDDM)) and vascular complications (heart attack, angina, strokes, amputations, blindness, and renal insufficiency)], and macular edema (for example, diabetic and non-diabetic macular edema) (Patent Documents 8 and 9); and (6) hepatitis, transplantation, and the like.

Accordingly, the compounds acting on a VAP-1 enzyme may be used as an agent for preventing and/or treating the above-described diseases.

On the other hand, in Patent Document 9, it is disclosed that a compound represented by the formula (A) has a VAP-1 inhibitory activity.

[Chem. 19]

(A)

(wherein Z represents

[Chem. 20]

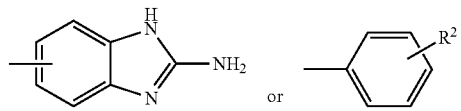

For the other symbols in the formula, refer to the corresponding patent publications)

Further, in Patent Document 10, it is disclosed that a compound represented by the formula (B) has a VAP-1 inhibitory activity.

[Chem. 21]

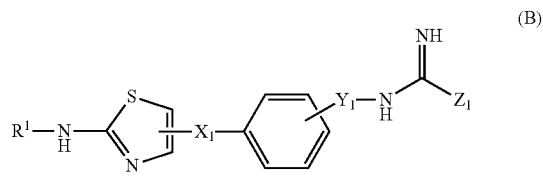
(B)

(For the symbols in the formula, refer to the corresponding patent publications)

In Patent Document 11, it is disclosed that a compound represented by the formula (C) has a VAP-1 inhibitory activity and is effective in applications for treatment of VAP-1-related diseases, in particular, macular edema.

[Chem. 22]

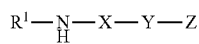
(C)

(wherein Z represents

[Chem. 23]

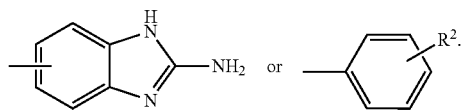

For the other symbols in the formula, refer to the corresponding patent publications)

In addition, in Patent Document 12, it is disclosed that a compound represented by the formula (D) has a VAP-1 inhibitory activity.

[Chem. 24]

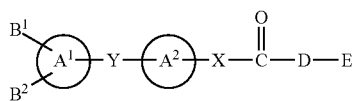
(D)

(wherein

D represents —NR$^3$ and E represents amino which may be substituted (optionally substituted amino), for the other symbols, refer to the corresponding patent publications)

In Patent Document 13, it is disclosed that a compound represented by the formula (E) has a VAP-1 inhibitory activity.

[Chem. 25]

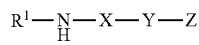
(E)

(wherein

X represents a divalent residue derived from thiazole which may be substituted (divalent residue derived from optionally substituted thiazole), Z represents A-B-D-E, A represents a divalent residue derived from benzene which may be substituted (divalent residue derived from optionally substituted benzene) or a divalent residue derived from thiophene which may be substituted (divalent residue derived from optionally substituted thiophene), B represents —(CH$_2$)$_1$—NR$^2$—CO—, D represents —NR$^3$, and E represents amino which may be substituted (optionally substituted amino), for the other symbols, refer to the corresponding patent publications)

In Patent Document 14, it is disclosed that a compound represented by the formula (F) has a GPR119 agonistic activity, and is thus useful for, for example, treatment of diabetes mellitus or the like.

[Chem. 26]

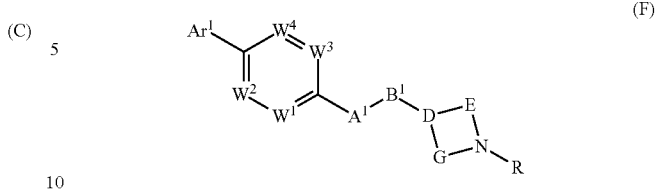
(F)

(For the symbols in the formula, refer to the corresponding patent publications)

In Patent Document 15, it is disclosed that a compound represented by the formula (G) has a GPR119 agonistic activity, and is thus useful for, for example, treatment of diabetes mellitus or the like.

[Chem. 27]

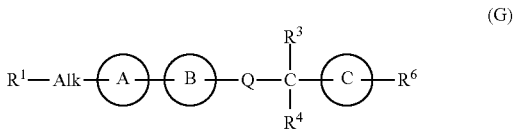
(G)

(For the symbols in the formula, refer to the corresponding patent publications)

In Patent Document 16, which is a patent application published after the filing date of the application which forms the basis of the priority of the present application, it is disclosed that a compound represented by the formula (H) has a VAP-1 activity.

[Chem. 28]

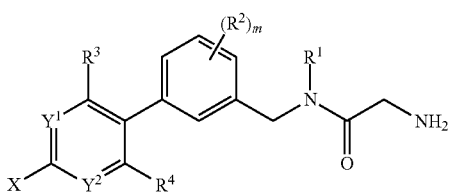
(H)

RELATED ART

Patent Document

Patent Document 1: JP-A-61-239891
Patent Document 2: U.S. Pat. No. 4,888,283
Patent Document 3: Pamphlet of International Publication WO 93/23023
Patent Document 4: Pamphlet of International Publication WO 02/02090
Patent Document 5: Pamphlet of International Publication WO 02/02541
Patent Document 6: US Patent Application Publication No. 2002/0173521
Patent Document 7: Pamphlet of International Publication WO 02/38152
Patent Document 8: Pamphlet of International Publication WO 02/38153
Patent Document 9: Pamphlet of International Publication WO 04/067521

Patent Document 10: Pamphlet of International Publication WO 06/011631
Patent Document 11: Pamphlet of International Publication WO 04/087138
Patent Document 12: Pamphlet of International Publication WO 09/145,360
Patent Document 13: Pamphlet of International Publication WO 09/096,609
Patent Document 14: Pamphlet of International Publication WO 08/025,800
Patent Document 15: Pamphlet of International Publication WO 08/070,692
Patent Document 16: Pamphlet of International Publication WO 11/034,078

Non-Patent Document

Non-Patent Document 1: J Neural Transm, Vol. 114, pp. 747-749, 2007
Non-Patent Document 2: Diabetologia, Vol. 42, pp. 233-237, 1999
Non-Patent Document 3: Diabetic Medicine, Vol. 16, pp. 514-521, 1999
Non-Patent Document 4: Diabetologia, Vol. 40, pp. 1243-1250, 1997
Non-Patent Document 5: J Neural Transm, Vol. 114, pp. 841-843, 2007

DISCLOSURE OF INVENTION

Problems to Be Solved by the Invention

The present invention provides a compound which is useful as an active ingredient of a pharmaceutical composition, in particular, a pharmaceutical composition for preventing and/or treating VAP-1-related diseases.

Means for Solving the Problems

The present inventors have conducted intensive studies on a compound having a VAP-1 inhibitory activity, and as a result, they have found that a compound of the formula (I) or a salt thereof exhibits an excellent VAP-1 inhibitory activity and is useful for preventing and/or treating VAP-1-related diseases, in particular, diabetic nephropathy or diabetic macular edema, thereby completing the present invention.

That is, the present invention relates to a compound of the formula (I) or a salt thereof and a pharmaceutical composition comprising the compound of the formula (I) or a salt thereof and an excipient.

[Chem. 29]

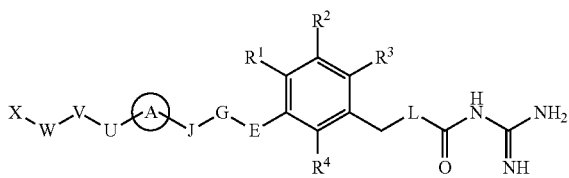

(I)

(wherein
A is aryl which may be substituted, or a hetero ring group which may be substituted, $R^1$, $R^2$, $R^3$ and $R^4$ are the same as or different from each other, and are H, halogen, or lower alkyl which may be substituted, E is a single bond, or lower alkylene which may be substituted, G is a single bond, O, NH, or N(lower alkyl which may be substituted), J is a single bond, or lower alkylene which may be substituted, L is O, NH, or N(lower alkyl which may be substituted), U is a single bond, O, NH, N(lower alkyl which may be substituted), $SO_2$, or lower alkylene which may be substituted, V is a single bond, O, NH, N(lower alkyl which may be substituted), or lower alkylene which may be substituted, W is a single bond, SO, $SO_2$, or lower alkylene which may be substituted, X is H, OH, $NH_2$, lower alkyl which may be substituted, O-(lower alkyl which may be substituted), NH(lower alkyl which may be substituted), N(lower alkyl which may be substituted)$_2$, NH—$SO_2$-(lower alkyl which may be substituted), N(lower alkyl which may be substituted)-$SO_2$-(lower alkyl which may be substituted), cycloalkyl which may be substituted, O-(cycloalkyl which may be substituted), cycloalkenyl which may be substituted, aryl which may be substituted, O-(aryl which may be substituted), a hetero ring group which may be substituted, or O-(hetero ring group which may be substituted).)

Furthermore, unless specified otherwise, in the case where the symbols of the chemical formulae in the present specification are also used in other chemical formulae, the same symbols denote the same meanings.

The present invention relates to a pharmaceutical composition comprising the compound of the formula (I) or a salt thereof, and an excipient.

Furthermore, the present invention relates to a pharmaceutical composition, in particular, a pharmaceutical composition for preventing and/or treating VAP-1-related diseases, which comprises the compound of the formula (I) or a salt thereof, and an excipient.

In addition, the present invention relates to use of the compound of the formula (I) or a salt thereof for the manufacture of a pharmaceutical composition for preventing and/or treating VAP-1-related diseases, use of the compound of the formula (I) or a salt thereof for preventing and/or treating VAP-1-related diseases, the compound of the formula (I) or a salt thereof for preventing and/or treating VAP-1-related diseases, and a method for preventing and/or treating VAP-1-related diseases, comprising administering to a patient an effective amount of the compound of the formula (I) or a salt thereof.

Effects of the Invention

The compound of the formula (I) or a salt thereof has a VAP-1 inhibitory action, and can be used as an agent for preventing and/or treating VAP-1-related diseases.

Further, the VAP-1-related diseases refer to diseases selected from the group consisting of:

(1) cirrhosis, essential stabilized hypertension, diabetes mellitus, and arthrosis;

(2) endothelium damage (in diabetes mellitus, arteroscle-rosis, and hypertension), cardiovascular diseases related to diabetes mellitus and uremia, pain related to gout and arthri-tis, and retinopathy (in diabetes mellitus patients);

(3) (connective tissue) inflammatory diseases or conditions (rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematosus, systemic sclerosis, eosinophilic fasciitis, polymyositis, dermatomyositis, polymyalgia rheumatica, vasculitis, temporal arteritis, polyarteritis nodosa, Wegener's granulomatosis, mixed connective tissue disease, and juvenile rheumatoid arthritis); gastrointestinal inflammatory diseases or conditions [Crohn's disease, ulcerative colitis, irritable bowel syndrome (spastic colon), fibrotic conditions of the liver, inflammation of the oral mucosa (stomatitis), and recurrent aphtous stomatitis]; central nervous system inflammatory diseases or conditions (multiple sclerosis, Alzheimer's disease, and ischemia-reperfusion injury related to ischemic stroke); pulmonary inflammatory diseases or conditions (asthma, adult respiratory distress syndrome, and chronic obstructive pulmonary disease); (chronic) skin inflammatory diseases or conditions (psoriasis, allergic lesions, lichen planus, pityriasis rosea, contact dermatitis, atopic dermatitis, and pityriasis rubra pilaris); diseases related to carbohydrate metabolism (diabetes mellitus and complications from diabetes mellitus) including microvascular and macrovascular diseases (arterosclerosis, vascular retinopathies, retinopathy, nephropathy, nephrotic syndrome and neuropathy (polyneuropathy, mononeuropathies and autonomic neuropathy), foot ulcers, joint problems, and increased risk of infection); diseases related to aberrations in adipocyte differentiation or function or smooth muscle cell function (arterosclerosis and obesity); vascular diseases [atheromatous arteriosclerosis, nonatheromatous arteriosclerosis, ischemic heart disease including myocardial infarction and peripheral arterial occlusion, Raynaud's disease and phenomenon, and thromboangiitis obliterans (Buerger's disease)]; chronic arthritis; inflammatory bowel diseases; and skin dermatoses;

(4) diabetes mellitus;

(5) SSAO-mediated complications [diabetes mellitus (insulin dependent diabetes mellitus (IDDM) and non-insulin dependent diabetes mellitus (NIDDM)) and vascular complications (heart attack, angina, strokes, amputations, blindness, and renal insufficiency)], macular edema (for example, diabetic and non-diabetic macular edema); and (6) hepatitis and transplantation.

EMBODIMENTS FOR CARRYING OUT THE INVENTION

Hereinafter, the present invention will be described in detail.

In the present specification, the "lower alkyl" refers to linear or branched alkyl having 1 to 6 carbon atoms (which is hereinafter simply referred to as $C_{1-6}$), for example, methyl, ethyl, n-propyl, isopropyl, n-butyl, isobutyl, sec-butyl, tert-butyl, n-pentyl, n-hexyl, or the like. In another embodiment, it is $C_{1-4}$ alkyl, and in still another embodiment, $C_{1-3}$ alkyl.

The "lower alkenyl" refers to linear or branched $C_{2-6}$ alkenyl, for example, vinyl, propenyl, butenyl, pentenyl, 1-methylvinyl, 1-methyl-2-propenyl, 1,3-butadienyl, 1,3-pentadienyl, or the like. In another embodiment, it is $C_{2-4}$ alkenyl, and in still another embodiment, $C_{2-3}$ alkenyl.

The "lower alkylene" refers to linear or branched $C_{1-6}$ alkylene, for example, methylene, dimethylene, trimethylene, or the like. In another embodiment, it is $C_{1-4}$ alkylene, and in still another embodiment, $C_{1-3}$ alkylene.

The "cycloalkyl" refers to a $C_{3-10}$ saturated hydrocarbon ring group, which may have a bridge. It is, for example, cyclopropyl, cyclobutyl, cyclopentyl, cyclohexyl, cycloheptyl, cyclooctyl, adamantyl, or the like. In another embodiment, it is $C_{3-8}$ cycloalkyl, and in still another embodiment, $C_{3-6}$ cycloalkyl.

The "cycloalkenyl" refers to a $C_{3-10}$ unsaturated hydrocarbon ring group, not including an aromatic hydrocarbon ring group. It is, for example, cyclopropenyl, cyclobutenyl, cyclopentenyl, cyclohexenyl, cycloheptenyl, cyclooctenyl, or the like. In another embodiment, it is $C_{3-8}$ cycloalkenyl, and in still another embodiment, $C_{3-6}$ cycloalkenyl.

The "aryl" refers to a $C_{6-14}$ monocyclic to tricyclic aromatic hydrocarbon ring group, and includes a ring group fused with $C_{5-8}$ cycloalkene at its double bond site. It is, for example, phenyl, naphthyl, 5-tetrahydronaphthyl, 4-indenyl, 1-fluorenyl, or the like. In another embodiment, it is phenyl.

The "hetero ring" means a ring group selected from i) a monocyclic 3- to 8-membered, and in another embodiment, a 5- to 7-membered hetero ring, containing 1 to 4 hetero atoms selected from oxygen, sulfur, and nitrogen, and ii) a bi- to tricyclic hetero ring containing 1 to 5 hetero atoms selected from oxygen, sulfur, and nitrogen, formed by ring-fusion of said monocyclic hetero ring with one or two rings which is selected from the group consisting of a monocyclic hetero ring, a benzene ring, $C_{5-8}$ cycloalkane, and $C_{5-8}$ cycloalkene. The ring atom, sulfur or nitrogen, may be oxidized to form an oxide or a dioxide.

Examples of the "hetero ring" group include the following embodiments:

(1) Monocyclic Saturated Hetero Ring Groups (a) those containing 1 to 4 nitrogen atoms, for example, azepanyl, diazepanyl, aziridinyl, azetidinyl, pyrrolidinyl, imidazolidinyl, piperidyl, pyrazolidinyl, piperazinyl, azocanyl, hexamethyleneimino, homopiperazinyl, and the like;

(b) those containing 1 to 3 nitrogen atoms and 1 to 2 sulfur atoms and/or 1 to 2 oxygen atoms, for example, thiomorpholinyl, thiazolidinyl, isothiazolidinyl, oxazolidinyl, morpholinyl, oxazepanyl, and the like;

(c) those containing 1 to 2 sulfur atoms, for example, tetrahydrothiopyranyl and the like;

(d) those containing 1 to 2 sulfur atoms and 1 to 2 oxygen atoms, for example, oxathiolanyl and the like;

(e) those containing 1 to 2 oxygen atoms, for example, oxiranyl, oxetanyl, dioxolanyl, tetrahydrofuranyl, tetrahydropyranyl, 1,4-dioxanyl, and the like;

(2) Monocyclic Unsaturated Hetero Ring Groups (a) those containing 1 to 4 nitrogen atoms, for example, pyrrolyl, 2-pyrrolinyl, imidazolyl, 2-imidazolinyl, pyrazolyl, 2-pyrazolinyl, pyridyl, dihydropyridyl, tetrahydropyridinyl, pyrimidinyl, pyrazinyl, pyridazinyl, triazolyl, tetrazolyl, triazinyl, dihydrotriazinyl, azepinyl, and the like;

(b) those containing 1 to 3 nitrogen atoms and 1 to 2 sulfur atoms and/or 1 to 2 oxygen atoms, for example, thiazolyl, isothiazolyl, thiadiazolyl, dihydrothiazinyl, oxazolyl, isoxazolyl, oxadiazolyl, oxazinyl, and the like;

(c) those containing 1 to 2 sulfur atoms, for example, thienyl, thiepinyl, dihydrodithiopyranyl, dihydrodithionyl, 2H-thiopyranyl, and the like;

(d) those containing 1 to 2 sulfur atoms and 1 to 2 oxygen atoms, for example, dihydroxathiopyranyl and the like;

(e) those containing 1 to 2 oxygen atoms, for example, furyl, dihydrofuryl, pyranyl, 2H-pyranyl, oxepinyl, dioxolyl, and the like;

(3) Fused Polycyclic Saturated Hetero Ring Groups (a) those containing 1 to 5 nitrogen atoms, for example, quinuclidinyl, 7-azabicyclo[2.2.1]heptyl, 3-azabicyclo[3.2.2]nonanyl, and the like;

(b) those containing 1 to 4 nitrogen atoms and 1 to 3 sulfur atoms and/or 1 to 3 oxygen atoms, for example, trithiadiazaindenyl, dioxoloimidazolidinyl, and the like;

(c) those containing 1 to 3 sulfur atoms and/or 1 to 3 oxygen atoms, for example, 2,6-dioxabicyclo[3.2.2]oct-7-yl and the like;

(4) Fused Polycyclic Unsaturated Hetero Ring Groups (a) those containing 1 to 5 nitrogen atoms, for example, indolyl, isoindolyl, indolinyl, indolidinyl, benzoimidazolyl, dihydrobenzoimidazolyl, tetrahydrobenzoimidazolyl, quinolyl, tetrahydroquinolyl, isoquinolyl, tetrahydroisoquinolyl, indazolyl, imidazopyridyl, dihydroimidazopyridyl, benzotriazolyl, tetrazolopyridazinyl, carbazolyl, acridinyl, quinoxalinyl, dihydroquinoxalinyl, tetrahydroquinoxalinyl, phthalazinyl, dihydroindazolyl, benzopyrimidinyl, naphthyridinyl, quinazolinyl, cinnolinyl, pyridopyrrolidinyl, triazolopiperidinyl, 9,10-dihydroacridine, and the like;

(b) those containing 1 to 4 nitrogen atoms and 1 to 3 sulfur atoms and/or 1 to 3 oxygen atoms, for example, benzothiazolyl, dihydrobenzothiazolyl, benzothiadiazolyl, imidazothiazolyl, imidazothiadiazolyl, benzoxazolyl, dihydrobenzoxazolyl, dihydrobenzoxadinyl, benzoxadiazolyl, benzoisothiazolyl, benzoisoxazolyl, thiazolopiperidinyl, 5,6-dihydro-4H-pyrrolo[3,4-d][1,3]thiazol-2-yl, 10H-phenothiazine, and the like;

(c) those containing 1 to 3 sulfur atoms, for example, benzothienyl, benzodithiopyranyl, chromanyl, dibenzo[b,d]thienyl, and the like;

(d) those containing 1 to 3 sulfur atoms and 1 to 3 oxygen atoms, for example, benzoxathiopyranyl, phenoxazinyl, and the like;

(e) those containing 1 to 3 oxygen atoms, for example, benzodioxolyl, benzofuranyl, dihydrobenzofuranyl, isobenzofuranyl, chromanyl, chromenyl, isochromenyl, dibenzo[b,d]furanyl, methylenedioxyphenyl, ethylenedioxyphenyl, xanthenyl, and the like;

etc.

Further, the "hetero ring" group in (1) to (4) above is described as a monovalent group, but this may represent a divalent or higher group in some cases.

The "hetero ring" group includes a bicyclic hetero ring group having a Spiro bond or a hetero ring group having a bridge structure, and it may be, for example, a ring group as shown below.

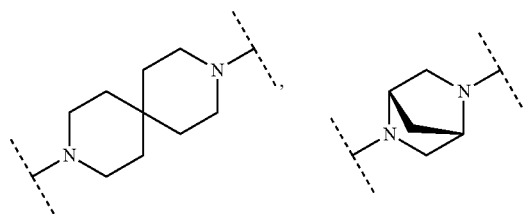

[Chem. 30]

The "monocyclic hetero ring" group refers to a hetero ring group having one ring structure which is not fused with other rings as in (1) and (2), among the "hetero ring" groups above.

The "monocyclic saturated hetero ring" group refers to a hetero ring group which is saturated as in (1), among the "monocyclic hetero ring" groups above.

The "nitrogen-containing hetero ring" group refers to one containing at least one nitrogen atom, as in (1)(a), (1)(b), (2)(a), (2)(b), (3)(a), (3)(b), (4)(a), (4)(b), and the like, among the "hetero rings" above.

The "nitrogen-containing monocyclic hetero ring" group refers to one containing at least one nitrogen atom, as in (1)(a), (1)(b), (2)(a), (2)(b), and the like, among the "monocyclic hetero ring" groups above.

The "nitrogen-containing monocyclic unsaturated hetero ring" group refers to an unsaturated hetero ring group, as in (2)(a), (2)(b), and the like, among the "nitrogen-containing monocyclic hetero ring" groups above.

The "nitrogen-containing monocyclic saturated hetero ring" group refers to a saturated hetero ring group, as in (1)(a), (1)(b), and the like, among the "nitrogen-containing monocyclic hetero ring" groups above.

The "halogen" means F, Cl, Br, or I.

In the present specification, the expression "which may be substituted" represents non-substitution or substitution with 1 to 5 substituents". Further, if it has a plurality of substituents, the substituents may be the same as or different from one other.

Examples of the acceptable substituent used in the present specification include the groups shown in (a) to (n) below, which may be chemically acceptable groups. Further, in another embodiment, the substituents may be the groups shown in (a) to (m) below.

(a) halogen.

(b) OH, O-(lower alkyl) (in which the lower alkyl may be substituted with OH, COOH, COO-(lower alkyl), O-(lower alkyl), aryl, hetero ring group(s) (in which the hetero ring group may be substituted with OH, cycloalkyl, or lower alkyl which may be substituted with oxo (=O)), or oxo (=O)), O-(hetero ring group), or O-(aryl) (in which the aryl may be substituted with O-(lower alkyl)); in another embodiment, OH, O-(lower alkyl) (in which the lower alkyl may be substituted with COOH, COO-(lower alkyl), O-(lower alkyl), or aryl), or O-(aryl) (in which the aryl may be substituted with O-(lower alkyl)); in still another embodiment, OH, O-(lower alkyl), or O-(aryl); and in further still another embodiment, OH, or O-(lower alkyl).

(c) amino which may be substituted with one or two lower alkyl group(s) (in which the lower alkyl may be substituted with one or more oxo (=O), OH, O-(lower alkyl), or aryl), $SO_2$-lower alkyl, cycloalkyl, aryl (in which the aryl may be substituted with COOH or COO-(lower alkyl)) or hetero ring group(s), or nitro; in another embodiment, amino which may be substituted with one or two lower alkyl group(s) (in which the lower alkyl may be substituted with one or more oxo (=O), OH, O-(lower alkyl), or aryl), $SO_2$-lower alkyl, aryl (in which the aryl may be substituted with COOH) or hetero ring group(s), or nitro; in another embodiment, amino which may be substituted with one or two lower alkyl group(s), $SO_2$-lower alkyl, aryl or hetero ring group(s), or nitro.

(d) CHO, CO-(lower alkyl) (in which the lower alkyl may be substituted with OH, O-(lower alkyl), or oxo (=O)), CO-(cycloalkyl) (in which the cycloalkyl may be substituted with OH), CO-(aryl), CO-(hetero ring group) (in which the hetero ring group may be substituted with O-(lower alkyl)), or cyano; and in another embodiment, CHO, CO-(lower alkyl), CO-(cycloalkyl), CO-(aryl), CO-(hetero ring group), or cyano.

(e) aryl or cycloalkyl; further, this group may be substituted with halogen, OH, COOH, COO-(lower alkyl which may be substituted with aryl), lower alkyl (in which the lower alkyl may be substituted with hetero ring group(s) which may be substituted with oxo (=O), OH, O-(lower alkyl), COOH, COO-(lower alkyl), or oxo (=O)), O-(lower alkyl) (in which the lower alkyl may be substituted with hetero ring group(s)), amino which may be substituted with one or two lower alkyl group(s) (in which the lower alkyl may be substituted with one or more oxo (═O) group(s)), NHSO$_2$-(lower alkyl), or SO$_2$-(lower alkyl); and in another embodiment, the group may be substituted with COOH, lower alkyl (in which the lower alkyl may be substituted with hetero ring group(s) which may be substituted with oxo (═O), OH or COOH), O-(lower alkyl) (in which the lower alkyl may be substituted with hetero ring group(s)), amino which may be substituted with one or two lower alkyl group(s) (in which the lower alkyl may be substituted with one or more oxo (═O) group(s)), NHSO$_2$-(lower alkyl), or SO$_2$-(lower alkyl).

(f) hetero ring group(s); and in another embodiment, monocyclic hetero ring group(s); further, these hetero ring group and monocyclic hetero ring group may be substituted with halogen, OH, oxo (═O), lower alkyl (in which the lower alkyl may be substituted with OH, O-(lower alkyl), or oxo (═O)), O-(lower alkyl which may be substituted with O-(lower alkyl) or oxo (═O)), aryl (in which the aryl may be substituted with halogen or COOH), NHCO-(lower alkyl) or hetero ring group(s) (in which the hetero ring group may be substituted with COOH or O-(lower alkyl)); and in another embodiment, the groups may be substituted with halogen, OH, oxo (═O), lower alkyl (in which the lower alkyl may be substituted with O-(lower alkyl) or oxo (═O)), O-(lower alkyl), aryl (in which the aryl may be substituted with halogen or COOH), NHCO-(lower alkyl) or hetero ring group(s) (in which the hetero ring group may be substituted with COOH, O-(lower alkyl)).

(g) COOH or COO-(lower alkyl); further, the lower alkyl in COO-(lower alkyl) may be substituted with aryl.

(h) CONH$_2$ or CONH(lower alkyl may be substituted with OH), CON(lower alkyl)$_2$; in another embodiment, CONH$_2$, CONH(lower alkyl), or CON(lower alkyl)$_2$.

(i) O—CO-(lower alkyl) or O—COO-(lower alkyl).

(j) oxo (═O).

(k) SO-(lower alkyl) (in which the lower alkyl may be substituted with O-(lower alkyl)), SO-(cycloalkyl), SO-(hetero ring group), SO-(aryl), SO$_2$-(lower alkyl) (in which the lower alkyl may be substituted with O-(lower alkyl)), SO$_2$-(cycloalkyl), SO$_2$-(hetero ring group), SO$_2$-(aryl), or sulfamoyl which may be substituted with one or two lower alkyl group(s); in another embodiment, SO-(lower alkyl), SO-(cycloalkyl), SO-(hetero ring), SO-(aryl), SO$_2$-(lower alkyl), SO$_2$-(cycloalkyl), SO$_2$-(hetero ring group), SO$_2$-(aryl), or sulfamoyl which may be substituted with one or two lower alkyl group(s).

(l) SO$_2$—NH$_2$, SO$_2$—NH(lower alkyl), or SO$_2$—N(lower alkyl)$_2$.

(m) lower alkyl group(s) which may each be substituted with one or more group(s) selected from the substituents shown in (a) to (k) above, or lower alkenyl group(s) which may each be substituted with one or more groups selected from the substituents shown in (a) to (k) above; in another embodiment, lower alkyl group(s) which may be substituted with one or more group(s) selected from the substituents shown in (a) to (k) above.

(n) lower alkyl group(s) which may each be substituted with one or more group(s) selected from the substituents shown in (a) to (l) above, or lower alkenyl group(s) which may each be substituted with one or more group(s) selected from the substituents shown in (a) to (l) above; in another embodiment, lower alkyl group(s) which may be substituted with one or more group(s) selected from the substituents shown in (a) to (l) above.

Examples of the acceptable substituent of the "aryl which may be substituted" and the "hetero ring group which may be substituted" in A include the groups exemplified in (a) to (n) above, in another embodiment, the groups exemplified in (a) to (m) above, in still another embodiment, the groups exemplified in (b), (c), and (m) above, and in further still another embodiment, the groups exemplified in (b) and (c) above.

Examples of the acceptable substituent of the "lower alkyl which may be substituted" in $R^1$, $R^2$, $R^3$, and $R^4$ include the groups exemplified in (a) to (n) above, in another embodiment, the groups exemplified in (a) to (m) above, and in still another embodiment, the groups exemplified in (a) and (m) above.

Examples of the acceptable substituent of the "lower alkylene which may be substituted" in E and J include the groups exemplified in (a) to (n) above, in another embodiment, the groups exemplified in (a) to (m) above, and in still another embodiment, the groups exemplified in (j) above.

Examples of the acceptable substituent of the "lower alkyl which may be substituted" in G include the groups exemplified in (a) to (n) above, and in another embodiment, the groups exemplified in (a) to (m) above.

Examples of the acceptable substituent of the "lower alkyl which may be substituted" in L include the groups exemplified in (a) to (n) above, and in another embodiment, the groups exemplified in (a) to (m) above.

Examples of the acceptable substituent of the "lower alkylene which may be substituted" in U, V, and W include the groups exemplified in (a) to (n) above, in another embodiment, the groups exemplified in (a) to (m) above, and in still another embodiment, the groups exemplified in (j) above.

Examples of the acceptable substituent of the "lower alkyl which may be substituted" in U and V include the groups exemplified in (a) to (n) above, in another embodiment, the groups exemplified in (a) to (m) above, and in still another embodiment, the groups exemplified in (b) and (c) above.

Examples of the acceptable substituent of the "lower alkyl which may be substituted" in X include the groups exemplified in (a) to (n) above, in another embodiment, the groups exemplified in (a) to (m) above, and in still another embodiment, the groups exemplified in (a) above.

Examples of the acceptable substituent of the "cycloalkyl which may be substituted" in X include the groups exemplified in (a) to (n) above, in another embodiment, the groups exemplified in (a) to (m) above, and in still another embodiment, the groups exemplified in (b) above.

Examples of the acceptable substituent of the "cycloalkenyl which may be substituted" in X include the groups exemplified in (a) to (n) above, in another embodiment, the groups exemplified in (a) to (m) above, and in still another embodiment, the groups exemplified in (b) above.

Examples of the acceptable substituent of the "aryl which may be substituted" in X include the groups exemplified in (a) to (n) above, in another embodiment, the groups exemplified in (a) to (m) above, and in still another embodiment, the groups exemplified in (b), (f), and (l) above.

Examples of the acceptable substituent of the "hetero ring group which may be substituted" in X include the groups exemplified in (a) to (n) above, and in another embodiment, the groups exemplified in (a) to (m) above.

Examples of the acceptable substituent of the "lower alkyl which may be substituted" in $R^{Q11}$, $R^{Q12}$, $R^{Q13}$, $R^{Q21}$, $R^{Q22}$, $R^{Q23}$, $R^{Q31}$, $R^{Q41}$, $R^{Q42}$, $R^{Q43}$, $R^{Q51}$, $R^{Q52}$, $R^{Q53}$, and $R^{Q61}$ include the groups exemplified in (a) to (n) above, and in another embodiment, the groups exemplified in (a) to (m) above.

Examples of the acceptable substituent of the "lower alkyl which may be substituted" in $R^{T11}$, $R^{T12}$, $R^{T13}$, $R^{T21}$, $R^{T22}$, $R^{T23}$, $R^{T31}$, $R^{T41}$, $R^{T42}$, $R^{T43}$, $R^{T51}$, $R^{T52}$, $R^{T53}$, $R^{T61}$, $R^{T62}$, and $R^{T63}$ include the groups exemplified in (a) to (n) above, another embodiment, the groups exemplified in (a) to (m)

above, and in still another embodiment, the groups exemplified in (b), (c), (e), (f), (g), and (j) above.

Examples of the acceptable substituent of the "cycloalkyl which may be substituted" in $R^{T11}$, $R^{T12}$, $R^{T13}$, $R^{T21}$, $R^{T22}$, $R^{T23}$, $R^{T31}$, $R^{T41}$, $R^{T42}$, $R^{T43}$, $R^{T51}$, $R^{T52}$, $R^{T53}$, $R^{T61}$, $R^{T62}$, and $R^{T63}$ include the groups exemplified in (a) to (n) above, in another embodiment, the groups exemplified in (a) to (m) above, and in still another embodiment, the groups exemplified in (m) above.

Examples of the acceptable substituent of the "aryl which may be substituted" in $R^{T11}$, $R^{T12}$, $R^{T13}$, $R^{T21}$, $R^{T22}$, $R^{T23}$, $R^{T31}$, $R^{T41}$, $R^{T42}$, $R^{T43}$, $R^{T51}$, $R^{T52}$, $R^{T53}$, $R^{T61}$, $R^{T62}$, and $R^{T63}$ include the groups exemplified in (a) to (n) above, in another embodiment, the groups exemplified in (a) to (m) above, and in still another embodiment, the groups exemplified in (a), (g), and (m) above.

Examples of the acceptable substituent of the "hetero ring group which may be substituted" in $R^{T11}$, $R^{T12}$, $R^{T13}$, $R^{T21}$, $R^{T22}$, $R^{T23}$, $R^{T31}$, $R^{T41}$, $R^{T42}$, $R^{T43}$, $R^{T51}$, $R^{T52}$, $R^{T53}$, $R^{T61}$, $R^{T62}$, and $R^{T63}$ include the groups exemplified in (a) to (n) above, in another embodiment, the groups exemplified in (a) to (m) above, and in still another embodiment, the groups exemplified in (a), (b), (d), (g), and (m) above.

In another embodiment of the present invention, a compound represented by the formula (I') or a salt thereof is provided.

[Chem. 31]

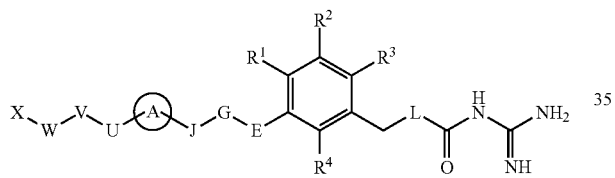
(I')

(wherein

A is aryl which may be substituted or a hetero ring group which may be substituted, $R^1$, $R^2$, $R^3$, and $R^4$ are the same as or different from each other, and are H, halogen, or lower alkyl which may be substituted, E is a single bond, or lower alkylene which may be substituted, G is a single bond, O, NH, or N(lower alkyl which may be substituted), J is a single bond, or lower alkylene which may be substituted, L is O, NH, or N(lower alkyl which may be substituted), U is a single bond, O, NH, N(lower alkyl which may be substituted), $SO_2$, or lower alkylene which may be substituted, V is a single bond, O, NH, N(lower alkyl which may be substituted), or lower alkylene which may be substituted, W is a single bond, $SO_2$, or lower alkylene which may be substituted, and X is H, OH, $NH_2$, lower alkyl which may be substituted, O-(lower alkyl which may be substituted), NH(lower alkyl which may be substituted), N(lower alkyl which may be substituted)$_2$, cycloalkyl which may be substituted, O-(cycloalkyl which may be substituted), aryl which may be substituted, O-(aryl which may be substituted), a hetero ring group which may be substituted, or O-(hetero ring group which may be substituted)).

Embodiments of the groups of the present invention are described below.

(1) A is

[Chem. 32]

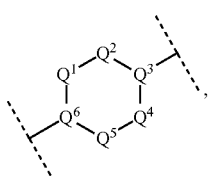

$Q^1$ is a single bond, $CR^{Q11}R^{Q12}$, or $NR^{Q13}$, $Q^2$ is $CR^{Q21}R^{Q22}$, or $NR^{Q23}$, $Q^3$ is $CR^{Q31}$ or N, $Q^4$ is $CR^{Q41}R^{Q42}$ or $NR^{Q43}$, $Q^5$ is a single bond, $CR^{Q51}R^{Q52}$, or $NR^{Q53}$, $Q^6$ is $CR^{Q61}$ or N, $R^{Q11}$, $R^{Q12}$, $R^{Q13}$, $R^{Q21}$, $R^{Q22}$, $R^{Q23}$, $R^{Q31}$, $R^{Q41}$, $R^{Q42}$, $R^{Q43}$, $R^{Q51}$, $R^{Q52}$, $R^{Q53}$ and $R^{Q61}$ are the same as or different from each other, and are H, lower alkyl which may be substituted, or O-(lower alkyl which may be substituted), or $R^{Q11}$ and $R^{Q21}$, $R^{Q11}$ and $R^{Q23}$, $R^{Q13}$ and $R^{Q21}$, $R^{Q13}$ and $R^{Q23}$, $R^{Q13}$ and $R^{Q23}$, $R^{Q31}$ and $R^{Q41}$, $R^{Q31}$ and $R^{Q43}$, $R^{Q51}$ and $R^{Q61}$, or $R^{Q53}$ and $R^{Q61}$ may be combined with each other to form a new bond, or $R^{Q11}$ and $R^{Q61}$, $R^{Q13}$ and $R^{Q61}$, $R^{Q21}$ and $R^{Q31}$, $R^{Q41}$ and $R^{Q51}$, $R^{Q43}$ and $R^{Q51}$, $R^{Q41}$ and $R^{Q53}$, or $R^{Q43}$ and $R^{Q53}$ may be combined with each other to form a new bond, or $R^{Q11}$ and $R^{Q12}$, $R^{Q21}$ and $R^{Q22}$, $R^{Q41}$ and $R^{Q42}$, $R^{Q51}$ and $R^{Q52}$ may be combined with each other to form oxo (=O).

(2) A is

[Chem. 33]

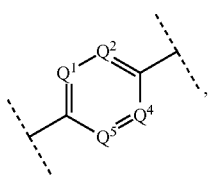

$Q^1$ is $CR^{Q12}$ or N, $Q^2$ is $CR^{Q22}$ or N, $Q^4$ is $CR^{Q42}$ or N, $Q^5$ is $CR^{Q52}$ or N, and $R^{Q12}$, $R^{Q22}$, $R^{Q42}$ and $R^{Q52}$ are the same as or different from each other, and are H, lower alkyl which may be substituted, or O-(lower alkyl which may be substituted).

(3) A is

[Chem. 34]

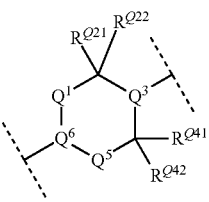

$Q^1$ is a single bond or $CR^{Q11}R^{Q12}$, $Q^3$ is $CR^{Q31}$ or N, $Q^5$ is a single bond or $CR^{Q51}R^{Q52}$, $Q^6$ is $CR^{Q61}$ or N, in which either one of $Q^3$ and $Q^6$ is N, $R^{Q11}$, $R^{Q12}$, $R^{Q21}$, $R^{Q22}$, $R^{Q31}$, $R^{Q41}$, $R^{Q42}$, $R^{Q51}$, $R^{Q52}$ and $R^{Q61}$ are the same as or different from each other, and are H, lower alkyl which may be substituted, or O-(lower alkyl which may be substituted), or $R^{Q51}$ and $R^{Q61}$ may be combined with each other to form a new bond, or $R^{Q11}$ and $R^{Q12}$, $R^{Q21}$ and $R^{Q22}$, $R^{Q41}$ and $R^{Q42}$, or $R^{Q51}$ and $R^{Q52}$ may be combined with each other to form oxo (=O).

(4) $R^{Q12}$, $R^{Q22}$, $R^{Q42}$ and $R^{Q52}$ are H.

(5) $R^{Q11}$, $R^{Q12}$, $R^{Q21}$, $R^{Q22}$, $R^{Q31}$, $R^{Q41}$, $R^{Q42}$, $R^{Q51}$, $R^{Q52}$ and $R^{Q61}$ are the same as or different from each other, and are H, or $R^{Q51}$ and $R^{Q61}$ may be combined with each other to form a new bond, or $R^{Q11}$ and $R^{Q12}$ may be combined with each other to form oxo (=O); and in another embodiment, $R^{Q11}$, $R^{Q12}$, $R^{Q21}$, $R^{Q22}$, $R^{Q31}$, $R^{Q41}$, $R^{Q42}$, $R^{Q51}$, $R^{Q52}$ and $R^{Q61}$ are H.

(6) $Q^1$ is N, $Q^2$ is $CR^{Q22}$, $Q^4$ is $CR^{Q42}$, and $Q^5$ is N.

(7) $Q^1$ is $CR^{Q12}$, $Q^2$ is $CR^{22}$, $Q^4$ is $CR^{Q42}$, and $Q^5$ is N.

(8) $Q^1$ is $CR^{Q11}R^{Q12}$, $Q^3$ is N, $Q^5$ is $CR^{Q51}R^{Q52}$, and $Q^6$ is $CR^{Q61}$ or N.

(9) $Q^1$ is $CR^{Q11}R^{Q12}$, $Q^3$ is N, $Q^5$ is $CR^{Q51}R^{Q52}$, and $Q^6$ is N.

(10) $Q^1$ is $CR^{Q11}R^{Q12}$, $Q^3$ is N, $Q^5$ is $CR^{Q51}R^{Q52}$, and $Q^6$ is $CR^{Q61}$.

(11) $Q^1$ is $CR^{Q11}R^{Q12}$, $Q^3$ is $CR^{Q31}$, $Q^5$ is $CR^{Q51}R^{Q52}$, and $Q^6$ is N.

(12) $Q^1$ is a single bond, $Q^3$ is N, $Q^5$ is a single bond, and $Q^6$ is $CR^{Q61}$.

(13) $R^1$, $R^2$, $R^3$ and $R^4$ are the same as or different from each other, and are H or halogen; in another embodiment, $R^1$, $R^2$ and $R^3$ are H, and $R^4$ is halogen; and in still another embodiment, $R^1$, $R^2$ and $R^3$ are H, and $R^4$ is F.

(14) E is a single bond.

(15) E is lower alkylene which may be substituted with oxo (=O).

(16) G is a single bond.

(17) G is O.

(18) G is NH.

(19) J is a single bond.

(20) J is lower alkylene which may be substituted.

(21) L is O.

(22) L is NH.

(23) U is a single bond.

(24) U is O.

(25) U is NH or N(lower alkyl which may be substituted).

(26) V is a single bond.

(27) V is lower alkylene which may be substituted with oxo (=O).

(28) W is a single bond.

(29) W is lower alkylene which may be substituted.

(30) X is H, OH, or $NH_2$.

(31) X is

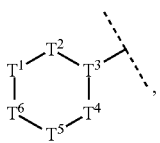

[Chem. 35]

$T^1$ is a single bond, $CR^{T11}R^{T12}$, or $NR^{T13}$, $T^2$ is $CR^{T21}R^{T22}$ or $NR^{T23}$, $T^3$ is $CR^{T31}$ or N, $T^4$ is $CR^{T41}R^{T42}$ or $NR^{T43}$, $T^5$ is a single bond, $(CR^{T51}R^{T52})_m$, or $NR^{T53}$, $T^6$ is $CR^{T61}R^{T62}$, O, or $NR^{T63}$, $R^{T11}$, $R^{T12}$, $R^{T13}$, $R^{T21}$, $R^{T22}$, $R^{T23}$, $R^{T31}$, $R^{T41}$, $R^{T42}$, $R^{T43}$, $R^{T51}$, $R^{T52}$, $R^{T53}$, $R^{T61}$, $R^{T62}$ and $R^{T63}$ are the same as or different from each other, and are H, OH, halogen, lower alkyl which may be substituted, aryl which may be substituted, cycloalkyl which may be substituted, a hetero ring group which may be substituted, O-(lower alkyl which may be substituted), NH(lower alkyl which may be substituted), N(lower alkyl which may be substituted)$_2$, NH(aryl which may be substituted), N(aryl which may be substituted)$_2$, $SO_2$-(lower alkyl which may be substituted), or $SO_2$-(cycloalkyl which may be substituted), or $R^{T11}$ and $R^{T61}$, $R^{T11}$ and $R^{T63}$, $R^{T13}$ and $R^{T61}$, $R^{T13}$ and $R^{T63}$, $R^{T21}$ and $R^{T31}$, $R^{T23}$ and $R^{T31}$, $R^{T41}$ and $R^{T51}$, $R^{T43}$ and $R^{T51}$, $R^{T41}$ and $R^{T53}$, or $R^{T43}$ and $R^{T53}$ may be combined with each other to form a new bond, or $R^{T11}$ and $R^{T12}$, $R^{T21}$ and $R^{T22}$, $R^{T41}$ and $R^{T42}$, $R^{T51}$ and $R^{T52}$, or $R^{T61}$ and $R^{T62}$ may be combined with each other to form oxo (=O), and m is 1 or 2.

(32) X is

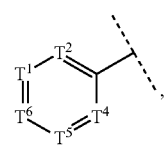

[Chem. 36]

$T^1$ is $CR^{T12}$ or N, $T^2$ is $CR^{T22}$ or N, $T^4$ is $CR^{T42}$ or N, $T^5$ is $CR^{T52}$ or N, $T^6$ is $CR^{T62}$ or N, $R^{T12}$, $R^{T22}$, $R^{T42}$, $R^{T52}$ and $R^{T62}$ are the same as or different from each other, and are H, OH, halogen, lower alkyl which may be substituted, aryl which may be substituted, cycloalkyl which may be substituted, a hetero ring group which may be substituted, O-(lower alkyl which may be substituted), NH-(lower alkyl which may be substituted), N(lower alkyl which may be substituted)$_2$, NH-(aryl which may be substituted), N(aryl which may be substituted)$_2$, $SO_2$-(lower alkyl which may be substituted), or $SO_2$-(cycloalkyl which may be substituted).

(33) $R^{T11}$, $R^{T12}$, $R^{T21}$, $R^{T22}$, $R^{T31}$, $R^{T41}$, $R^{T42}$, $R^{T51}$ and $R^{T52}$ are the same as or different from each other, and are H, halogen, or lower alkyl which may be substituted; and in another embodiment, $R^{T11}$, $R^{T12}$, $R^{T21}$, $R^{T22}$, $R^{T31}$, $R^{T41}$, $R^{T42}$, $R^{T51}$ and $R^{T52}$ are H; and in still another embodiment, $R^{T11}$, $R^{T12}$, $R^{T21}$, $R^{T22}$, $R^{T31}$, $R^{T41}$, $R^{T42}$, $R^{T51}$ and $R^{T52}$ are the same as or different from each other, and are H or OH.

(34) $R^{T13}$, $R^{T23}$, $R^{T43}$, $R^{T53}$ are H.

(35) $R^{T12}$, $R^{T22}$, $R^{T42}$ and $R^{T52}$ are the same as or different from each other, and are H, halogen, lower alkyl which may be substituted, or O-(lower alkyl which may be substituted); in another embodiment, $R^{T12}$, $R^{T22}$, $R^{T42}$ and $R^{T52}$ are the same as or different from each other, and are H, lower alkyl which may be substituted with O-(lower alkyl), or O-(lower alkyl which may be substituted with O-(lower alkyl)); in still another embodiment, $R^{T12}$, $R^{T22}$, $R^{T42}$ and $R^{T52}$ are the same as or different from each other, and are H, methyl, methoxymethyl, or 2-methoxyethoxy; and in further still another embodiment, $R^{T12}$, $R^{T22}$, $R^{T42}$ and $R^{T52}$ are H.

(36) $R^{T62}$ is H.

(37) $R^{T62}$ is halogen, OH, lower alkyl which may be substituted, or O-(lower alkyl which may be substituted).

(38) $R^{T62}$ is OH, lower alkyl (in which the lower alkyl may be substituted with O-(lower alkyl) or COOH), or O-(lower alkyl which may be substituted with O-(lower alkyl)).

(39) $R^{T63}$ is CO—($C_{1-5}$ alkyl which may be substituted), CO-(cycloalkyl which may be substituted), CO-(aryl which may be substituted), CO-(nitrogen-containing monocyclic unsaturated hetero ring group which may be substituted), CON(lower alkyl which may be substituted)$_2$, or $SO_2$-(lower alkyl which may be substituted); in another embodiment, $R^{T63}$ is CO—($C_{1-5}$ alkyl which may be substituted with O-(lower alkyl) or nitrogen-containing monocyclic unsaturated hetero ring(s)), CO-(cycloalkyl), CO-(aryl), CO-(nitrogen-containing monocyclic unsaturated hetero ring group), CON(lower alkyl)$_2$, or $SO_2$-(lower alkyl); in still another embodiment, $R^{T63}$ is CO—($C_{1-5}$ alkyl which may be substituted with O-(lower alkyl)), CO-(cycloalkyl), CO-(aryl), CO- (nitrogen-containing monocyclic unsaturated hetero ring group), CON(lower alkyl)$_2$, or SO$_2$-(lower alkyl); in further still another embodiment, R$^{T63}$ is CO—(C$_{1-5}$ lower alkyl which may be substituted with O-(lower alkyl), CO-(cycloalkyl), or SO$_2$-(lower alkyl); in further still another embodiment, R$^{T63}$ is acetyl, propionyl, isobutyryl, pivaloyl, 2-ethoxy-1-oxoethyl, 2-methoxy-1-oxoethyl, 3-methoxy-1-oxopropyl, 3-methoxy-2,2-dimethyl-1-oxopropyl, cyclopropylcarbonyl, benzoyl, pyridin-3-ylcarbonyl, dimethylaminocarbonyl, methylsulfonyl, or ethylsulfonyl; in further still another embodiment, R$^{T63}$ is acetyl, propionyl, isobutyryl, pivaloyl, 2-ethoxy-1-oxoethyl, 2-methoxy-1-oxoethyl, 3-methoxy-1-oxopropyl, cyclopropylcarbonyl, benzoyl, pyridin-3-ylcarbonyl, dimethylaminocarbonyl, methylsulfonyl, or ethylsulfonyl; and in further still another embodiment, R$^{T63}$ is acetyl, propionyl, isobutyryl, pivaloyl, 2-ethoxy-1-oxoethyl, cyclopropylcarbonyl, benzoyl, pyridin-3-ylcarbonyl, dimethylaminocarbonyl, or methylsulfonyl.

(40) T$^1$ is a single bond, CR$^{T11}$R$^{T12}$, or NR$^{T13}$, T$^2$ is CR$^{T21}$R$^{T22}$, T$^3$ is CR$^{T31}$ or N, T$^4$ is CR$^{T41}$R$^{T42}$, T$^5$ is a single bond, (CR$^{T51}$R$^{T52}$)$_m$, or NR$^{T53}$, T$^6$ is CR$^{T61}$R$^{T62}$, O, or NR$^{T63}$, R$^{T21}$ and R$^{T31}$ may be combined with each other to form a new bond, or R$^{T11}$ and R$^{T12}$ may be combined with each other to form oxo (=O).

(41) T$^1$ is a single bond or CR$^{T11}$R$^{T12}$, T$^2$ is CR$^{T21}$R$^{T22}$, T$^3$ is CR$^{T31}$ or N, T$^4$ is CR$^{T41}$R$^{T42}$, T$^5$ is a single bond or (CR$^{T51}$R$^{T52}$)$_m$, and T$^6$ is NR$^{T63}$.

(42) T$^1$ is CR$^{T11}$R$^{T12}$, T$^2$ is CR$^{T21}$R$^{T22}$, T$^3$ is CR$^{T31}$, T$^4$ is CR$^{T41}$R$^{T42}$, T$^5$ is (CR$^{T51}$R$^{T52}$)$_m$, and T$^6$ is NR$^{T63}$.

(43) T$^1$ is CR$^{T11}$R$^{T12}$, T$^2$ is CR$^{T21}$R$^{T22}$, T$^3$ is CR$^{T31}$, T$^4$ is CR$^{T41}$R$^{T42}$, T$^5$ is (CR$^{T51}$R$^{T52}$)$_m$, and T$^6$ is O.

(44) T$^1$ is a single bond, T$^2$ is CR$^{T21}$R$^{T22}$, T$^3$ is CR$^{T31}$, T$^4$ is CR$^{T41}$R$^{T42}$, T$^5$ is (CR$^{T51}$R$^{T52}$)$_m$, and T$^6$ is O.

(45) T$^1$ is CR$^{T11}$R$^{T12}$, T$^2$ is CR$^{T21}$R$^{T22}$, T$^3$ is N, T$^4$ is CR$^{T41}$R$^{T42}$, T$^5$ is (CR$^{T51}$R$^{T52}$)$_m$, and T$^6$ is O.

(46) T$^1$ is CR$^{T11}$R$^{T12}$, T$^2$ is CR$^{T21}$R$^{T22}$, T$^3$ is N, T$^4$ is CR$^{T41}$R$^{T42}$, T$^5$ is (CR$^{T51}$R$^{T52}$)$_m$, and T$^6$ is CR$^{T61}$R$^{T62}$.

(47) T$^1$ is a single bond, T$^2$ is CR$^{T21}$R$^{T22}$, T$^3$ is N, T$^4$ is CR$^{T41}$R$^{T42}$, T$^5$ is a single bond, and T$^6$ is CR$^{T61}$R$^{T62}$.

(48) T$^1$ is a single bond, T$^2$ is CR$^{T21}$R$^{T22}$, T$^3$ is N, T$^4$ is CR$^{T41}$R$^{T42}$, T$^5$ is (CR$^{T51}$R$^{T52}$)$_m$, and T$^6$ is CR$^{T61}$R$^{T62}$.

(49) T$^1$ is CR$^{T11}$R$^{T12}$, T$^2$ is CR$^{T21}$R$^{T22}$, T$^3$ is N, T$^4$ is CR$^{T41}$R$^{T42}$, T$^5$ is (CRT R$^{T52}$)$_m$, and T$^6$ is NR$^{T63}$.

(50) T$^1$ is CR$^{T11}$R$^{T12}$, T$^2$ is CR$^{T21}$R$^{T22}$, T$^3$ is CR$^{T31}$, T$^4$ is CR$^{T41}$R$^{T42}$, T$^5$ is (CR$^{T51}$R$^{T52}$)$_m$, and T$^6$ is CR$^{T61}$R$^{T62}$.

(51) T$^1$ is N, T$^2$ is CR$^{T22}$, T$^4$ is CR$^{T42}$, T$^5$ is N, and T$^6$ is CR$^{T62}$.

(52) T$^1$ is CR$^{T12}$, T$^2$ is CR$^{T22}$, T$^4$ is N, T$^5$ is CR$^{T52}$, and T$^6$ is CR$^{T62}$.

(53) T$^1$ is CR$^{T12}$, T$^2$ is CR$^{T22}$, T$^4$ is CR$^{T42}$, T$^5$ is N, and T$^6$ is CR$^{T62}$.

(54) T$^1$ is CR$^{T12}$, T$^2$ is CR$^{T22}$ T$^4$ is CR$^{T42}$, T$^5$ is CR$^{T52}$, and T$^6$ is N.

(55) m is 1.

(56) m is 2.

Other embodiments of the present invention are described below.

(57) A is

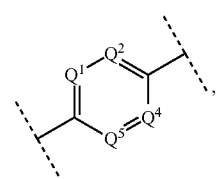

[Chem. 37]

Q$^1$ is CR$^{Q12}$ or N, Q$^2$ is CR$^{Q22}$ or N, Q$^4$ is CR$^{Q42}$ or N, Q$^5$ is CR$^{Q52}$ or N, R$^{Q12}$, R$^{Q22}$, R$^{Q42}$ and R$^{Q52}$ are the same as or different from each other, and are H, lower alkyl, O-(lower alkyl), or N(lower alkyl)$_2$, or A is

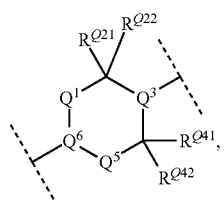

[Chem. 38]

Q is a single bond or CR$^{Q11}$R$^{Q12}$, Q$^3$ is CR$^{Q31}$ or N, Q$^5$ is a single bond or (CR$^{Q51}$R$^{Q52}$)$_a$, Q$^6$ is CR$^{Q61}$ or N, in which either one of Q$^3$ and Q$^6$ is N, R$^{Q11}$, R$^{Q12}$, R$^{Q21}$, R$^{Q22}$, R$^{Q31}$, R$^{Q41}$, R$^{Q42}$, R$^{Q51}$, R$^{Q52}$ and R$^{Q61}$ are the same as or different from each other, and are H, OH, lower alkyl, or R$^{Q51}$ and R$^{Q61}$ may be combined with each other to form a new bond, or R$^{Q11}$ and R$^{Q12}$ may be combined with each other to form oxo (=O), and a is 1 or 2.

(58)

(58-1) A is

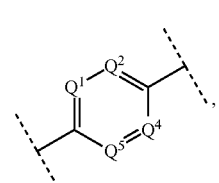

[Chem. 39]

Q$^1$ is CR$^{Q12}$ or N, Q$^2$ is CR$^{Q22}$ or N, Q$^4$ is CR$^{Q42}$ or N, Q$^5$ is CR$^{Q52}$ or N, and R$^{Q12}$, R$^{Q22}$, R$^{Q42}$ and R$^{Q52}$ are the same as or different from each other, and are H, lower alkyl, O-(lower alkyl), or N(lower alkyl)$_2$.

(58-2) In (57) and (58-1), R$^{Q12}$, R$^{Q22}$, R$^{Q42}$ and R$^{Q52}$ are H.

(58-3) In (57) and (58-1) to (58-2), Q$^1$ is N, Q$^2$ is CR$^{Q22}$, Q$^4$ is CR$^{Q42}$, and Q$^5$ is N.

(58-4) In (57) and (58-1) to (58-2), Q$^1$ is CR$^{Q12}$, Q$^2$ is CR$^{Q22}$, Q$^4$ is CR$^{Q42}$, and Q$^5$ is N.

(59)
(59-1) A is

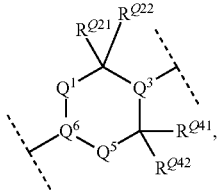

Q$^1$ is a single bond or CR$^{Q11}$R$^{Q12}$, Q$^3$ is CR$^{Q31}$ or N, Q$^5$ is a single bond or (CR$^{Q51}$R$^{Q52}$)$_a$, Q$^6$ is CR$^{Q61}$ or N, in which either one of Q$^3$ and Q$^6$ is N, R$^{Q11}$, R$^{Q12}$, R$^{Q21}$, R$^{Q22}$, R$^{Q31}$, R$^{Q41}$, R$^{Q42}$, R$^{Q51}$, R$^{Q52}$ and R$^{Q61}$ are the same as or different from each other, and are H, OH, or lower alkyl, or R$^{Q51}$ and R$^{Q61}$ may be combined with each other to form a new bond, or R$^{Q11}$ and R$^{Q12}$ may be combined with each other to form oxo (=O), and a is 1 or 2.

(59-2) In (57) and (59-1), a is 1.

(59-3) In (57) and (59-1) to (59-2), R$^{Q11}$, R$^{Q12}$, R$^{Q21}$, R$^{Q22}$, R$^{Q31}$, R$^{Q41}$, R$^{Q42}$, R$^{Q51}$, R$^{Q52}$ and R$^{Q61}$ are the same as or different from each other, and are H, or R$^{Q51}$ and R$^{Q61}$ may be combined with each other to form a new bond, or R$^{Q11}$ and R$^{Q12}$ may be combined with each other to form oxo (=O).

(59-4) In (57) and (59-1) to (59-3), Q$^1$ is CR$^{Q11}$R$^{Q12}$, Q$^3$ is N, Q$^5$ is CR$^{Q51}$R$^{Q52}$, and Q$^6$ is CR$^{Q61}$, or N.

(59-5) In (57) and (59-1) to (59-3), Q$^1$ is CR$^{Q11}$R$^{Q12}$, Q$^3$ is N, Q$^5$ is CR$^{Q51}$R$^{Q52}$, and Q$^6$ is N.

(59-6) In (57) and (59-1) to (59-3), Q$^1$ is CR$^{Q11}$R$^{Q12}$, Q$^3$ is N, Q$^5$ is CR$^{Q51}$R$^{Q52}$, and Q$^6$ is CR$^{Q61}$.

(59-7) In (57) and (59-1) to (59-3), Q$^1$ is CR$^{Q11}$R$^{Q12}$, Q$^3$ is CR$^{Q31}$, Q$^5$ is CR$^{Q51}$R$^{Q52}$, and Q$^6$ is N.

(59-8) In (57) and (59-1) to (59-3), Q' is a single bond, Q$^3$ is N, Q$^5$ is a single bond, and Q$^6$ is CR$^{Q61}$.

(60)
(60-1) X is
H,
OH,
NH$_2$,
lower alkyl which may be substituted with halogen,
O-(lower alkyl which may be substituted with OH),
NH(lower alkyl which may be substituted with oxo (=O)),
N(lower alkyl which may be substituted with O-(lower alkyl) or oxo (=O))$_2$,
NH—SO$_2$-(lower alkyl),
N(lower alkyl)-SO$_2$-(lower alkyl),
cycloalkyl which may be substituted with group(s) selected from Group G$^{XA1}$ below,
O-(cycloalkyl),
cycloalkenyl which may be substituted with group(s) selected from Group G$^{XA1}$ below,
aryl which may be substituted with group(s) selected from Group G$^{XA1}$ below,
O-(aryl which may be substituted with O-(lower alkyl)), or
a hetero ring group which may be substituted with group(s) selected from Group G$^{XA1}$ below, and
Group G$^{XA1}$ is
i) halogen,
ii) OH,
iii) lower alkyl which may be substituted with group(s) selected from the group consisting of halogen; OH; O-(lower alkyl which may be substituted with OH, aryl, O-(lower alkyl), or oxo (=O)); NH$_2$; NH(lower alkyl which may be substituted with OH); N(lower alkyl)$_2$; NH(cycloalkyl); NH(hetero ring group); cycloalkyl which may be substituted with OH; aryl which may be substituted with O-(lower alkyl), COOH, or COO-(lower alkyl which may be substituted with aryl); hetero ring group(s) which may be substituted with O-(lower alkyl), oxo (=O), NH(lower alkyl which may be substituted with oxo (=O)), or lower alkyl; and oxo (=O), iv) O-(lower alkyl which may be substituted with OH, O-(lower alkyl), aryl, hetero ring group(s) (in which the hetero ring group may be substituted with lower alkyl which may be substituted with cycloalkyl or oxo (=O)), or oxo (=O)), v) NH-(lower alkyl which may be substituted with O-(lower alkyl) or oxo (=O)), vi) N(lower alkyl which may be substituted with oxo (=O))$_2$, vii) NH-(aryl which may be substituted with COOH or COO-(lower alkyl)), viii) cycloalkyl which may be substituted with group(s) selected from the group consisting of lower alkyl which may be substituted with OH; COOH; and COO-(lower alkyl), ix) aryl which may be substituted with group(s) selected from the group consisting of halogen; lower alkyl (in which the lower alkyl may be substituted with COOH or COO-(lower alkyl)); O-(lower alkyl); COOH; and COO-(lower alkyl), x) hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), xi) O-(hetero ring group), xii) SO$_2$-(lower alkyl which may be substituted with O-(lower alkyl)), xiii) SO$_2$-(cycloalkyl), xiv) SO$_2$-(aryl), xv) NHSO$_2$-(lower alkyl), or xvi) oxo (=O).

(60-2) X is
H,
OH,
NH$_2$,
lower alkyl which may be substituted with halogen,
O-(lower alkyl which may be substituted with OH),
NH(lower alkyl which may be substituted with oxo (=O)),
N(lower alkyl which may be substituted with O-(lower alkyl) or oxo (=O))$_2$,
NH—SO$_2$-(lower alkyl),
N(lower alkyl)-SO$_2$-(lower alkyl),
cycloalkyl which may be substituted with group(s) selected from Group G$^{XA2}$ below,
O-(cycloalkyl),
cycloalkenyl which may be substituted with group(s) selected from Group G$^{XA2}$ below,
aryl which may be substituted with group(s) selected from Group G$^{XA2}$ below,
O-(aryl which may be substituted with O-(lower alkyl)), or
a hetero ring group which may be substituted with group(s) selected from Group G$^{XA2}$ below,
G$^{XA2}$ is
i) halogen,
ii) OH,
iii) lower alkyl which may be substituted with group(s) selected from the group consisting of halogen; OH; O-(lower alkyl which may be substituted with OH, phenyl, O-(lower alkyl), or oxo (=O)); NH$_2$; NH(lower alkyl which may be substituted with OH); N(lower alkyl)$_2$; NH(cycloalkyl); NH(nitrogen-containing monocyclic hetero ring group); cycloalkyl which may be substituted with OH; phenyl which may be substituted with O-(lower alkyl), COOH, or COO-(lower alkyl which may be substituted with phenyl); monocyclic hetero ring group(s) which may be substituted with O-(lower alkyl), oxo (=O), NH(lower alkyl which may be substituted with oxo (=O)) or lower alkyl; and oxo (=O), iv) O-(lower alkyl which may be substituted with OH, O-(lower alkyl), phenyl, nitrogen-containing monocyclic hetero ring group(s) (in which the nitrogen-containing monocyclic hetero ring group may be substituted with lower alkyl which may be substituted with cycloalkyl or oxo (=O)), or oxo (=O)), v) NH-(lower alkyl which may be substituted with O-(lower alkyl) or oxo (=O)), vi) N(lower alkyl which may be substituted with oxo (=O))$_2$, vii) NH-(aryl which may be substituted with COOH or COO-(lower alkyl)), viii) cycloalkyl which may be substituted with group(s) selected from the group consisting of lower alkyl which may be substituted with OH; COOH; and COO-(lower alkyl), ix) aryl which may be substituted with group(s) selected from the group consisting of halogen; lower alkyl (in which the lower alkyl may be substituted with COOH or COO-(lower alkyl)); O-(lower alkyl); COOH; and COO-(lower alkyl), x) hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), xi) O-(monocyclic saturated hetero ring group), xii) SO$_2$-(lower alkyl which may be substituted with O-(lower alkyl)), xiii) SO$_2$-(cycloalkyl), xiv) SO$_2$-(phenyl), xv) NHSO$_2$-(lower alkyl), or xvi) oxo (=O).

(60-3) X is

H,

OH,

NH$_2$, lower alkyl which may be substituted with halogen,

O-(lower alkyl which may be substituted with OH),

NH(lower alkyl which may be substituted with oxo (=O)),

N(lower alkyl which may be substituted with O-(lower alkyl) or oxo (=O))$_2$,

NH—SO$_2$-(lower alkyl),

N(lower alkyl)-SO$_2$-(lower alkyl), cycloalkyl which may be substituted with group(s) selected from Group $G^{XA3}$ below, O-(cycloalkyl), cycloalkenyl which may be substituted with group(s) selected from Group $G^{XA3}$ below, phenyl which may be substituted with group(s) selected from Group $G^{XA3}$ below, O-(phenyl which may be substituted with O-(lower alkyl)), or a hetero ring group which may be substituted with group(s) selected from Group $G^{XA3}$ below, and Group $G^{XA3}$ is i) halogen, ii) OH, iii) lower alkyl which may be substituted with group(s) selected from the group consisting of halogen; OH; O-(lower alkyl which may be substituted with OH, phenyl, O-(lower alkyl), or oxo (=O)); NH$_2$; NH(lower alkyl which may be substituted with OH); N(lower alkyl)$_2$; NH(cycloalkyl); NH(thiazolyl); cycloalkyl which may be substituted with OH; phenyl which may be substituted with O-(lower alkyl), COOH, or COO-(lower alkyl which may be substituted with phenyl); tetrahydropyranyl, furanyl, thiazolyl, morphonyl, azetidinyl, oxazolidinyl, or pyridyl, each of which may be substituted with O-(lower alkyl), oxo (=O), NH(lower alkyl which may be substituted with oxo (=O)) or lower alkyl; and oxo (=O), iv) O-(lower alkyl which may be substituted with OH, O-(lower alkyl), phenyl, piperidinyl or morphonyl (in which the piperidinyl or morphonyl group may be substituted with lower alkyl which may be substituted with cycloalkyl or oxo (=O)), or oxo (=O)), v) NH-(lower alkyl which may be substituted with O-(lower alkyl) or oxo (=O)), vi) N(lower alkyl which may be substituted with oxo (=O))$_2$, vii) NH-(phenyl which may be substituted with COOH or COO-(lower alkyl)), viii) cycloalkyl which may be substituted with group(s) selected from the group consisting of lower alkyl which may be substituted with OH; COOH; and COO-(lower alkyl), ix) phenyl which may be substituted with group(s) selected from the group consisting of halogen; lower alkyl (in which the lower alkyl may be substituted with COOH or COO-(lower alkyl)); O-(lower alkyl); COOH; and COO-(lower alkyl), x) hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), xi) O-(tetrahydropyranyl)

xii) SO$_2$-(lower alkyl which may be substituted with O-(lower alkyl)), xiii) SO$_2$-(cycloalkyl), xv) SO$_2$-(phenyl), xv) NHSO$_2$-(lower alkyl), or xvi) oxo (=O).

(60-4) X is

H,

OH,

NH$_2$, lower alkyl which may be substituted with halogen,

O-(lower alkyl which may be substituted with OH),

NH(lower alkyl which may be substituted with oxo (=O)),

N(lower alkyl which may be substituted with O-(lower alkyl) or oxo (=O))$_2$,

NH—SO$_2$-(lower alkyl),

N(lower alkyl)-SO$_2$-(lower alkyl), cycloalkyl which may be substituted with OH or O-(lower alkyl which may be substituted with aryl or oxo (=O)), O-(cycloalkyl), cycloalkenyl which may be substituted with OH or O-(lower alkyl which may be substituted with aryl or oxo (=O)), aryl which may be substituted with group(s) selected from the group consisting of lower alkyl which may be substituted with OH, O-(lower alkyl), hetero ring group(s) (in which the hetero ring group may be substituted with oxo (=O)) or oxo (=O); O-(lower alkyl which may be substituted with hetero ring group(s)); hetero ring group(s); NH(lower alkyl which may be substituted with oxo (=O)); N(lower alkyl which may be substituted with oxo (=O))$_2$; NHSO$_2$-(lower alkyl); and SO$_2$-(lower alkyl), O-(aryl which may be substituted with O-(lower alkyl)), or a hetero ring group which may be substituted with group(s) selected from Group $G^{XA4}$ below, and Group $G^{XA4}$ is i) halogen, ii) OH, iii) lower alkyl which may be substituted with group(s) selected from the group consisting of halogen; OH; O-(lower alkyl which may be substituted with OH, aryl, O-(lower alkyl), or oxo (=O)); NH$_2$; NH(lower alkyl which may be substituted with OH); N(lower alkyl)$_2$; NH(cycloalkyl); NH(hetero ring group); cycloalkyl which may be substituted with OH; aryl which may be substituted with O-(lower alkyl), COOH, or COO-(lower alkyl which may be substituted with aryl); hetero ring group(s) which may be substituted with O-(lower alkyl), NH(lower alkyl which may be substituted with oxo (=O)), or lower alkyl; and oxo (=O), iv) O-(lower alkyl which may be substituted with OH, O-(lower alkyl), aryl, hetero ring group(s) (in which the hetero ring group may be substituted with lower alkyl which may be substituted with cycloalkyl or oxo (=O)), or oxo (=O)), v) NH-(lower alkyl which may be substituted with O-(lower alkyl) or oxo (=O)), vi) NH-(aryl which may be substituted with COOH or COO-(lower alkyl)), vii) cycloalkyl which may be substituted with group(s) selected from the group consisting of lower alkyl which may be substituted with OH; COOH; and COO-(lower alkyl), viii) aryl which may be substituted with group(s) selected from the group consisting of halogen; lower alkyl (in which the lower alkyl may be substituted with COOH or COO-(lower alkyl)); O-(lower alkyl); COOH; and COO-(lower alkyl), ix) hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), x) O-(hetero ring group), xi) SO$_2$-(lower alkyl which may be substituted with O-(lower alkyl)), xii) SO$_2$-(cycloalkyl), xiii) SO$_2$-(aryl), or xiv) oxo (=O).

(60-5) X is

H,

OH,

NH$_2$, lower alkyl which may be substituted with halogen,

O-(lower alkyl which may be substituted with OH),

NH(lower alkyl which may be substituted with oxo (=O)),

N(lower alkyl which may be substituted with O-(lower alkyl) or oxo (=O))$_2$,

NH—SO$_2$-(lower alkyl),

N(lower alkyl)-SO$_2$-(lower alkyl), cycloalkyl which may be substituted with OH or O-(lower alkyl which may be substituted with phenyl or oxo (=O)), O-(cycloalkyl), cycloalkenyl which may be substituted with OH or O-(lower alkyl which may be substituted with phenyl or oxo (=O)), aryl which may be substituted with group(s) selected from the group consisting of lower alkyl which may be substituted with OH, O-(lower alkyl), nitrogen-containing monocyclic hetero ring group(s) (in which the nitrogen-containing monocyclic hetero ring group may be substituted with oxo (=O)) or oxo (=O); O-(lower alkyl which may be substituted with nitrogen-containing monocyclic hetero ring group(s)); nitrogen-containing monocyclic hetero ring group(s); NH(lower alkyl which may be substituted with oxo (=O)); N(lower alkyl which may be substituted with oxo (=O))$_2$; NHSO$_2$-(lower alkyl); and SO$_2$-(lower alkyl), O-(aryl which may be substituted with O-(lower alkyl)), or a hetero ring group which may be substituted with group(s) selected from Group G$^{X45}$ below, and Group G$^{X45}$ is i) halogen, ii) OH, iii) lower alkyl which may be substituted with group(s) selected from the group consisting of halogen; OH; O-(lower alkyl which may be substituted with OH, phenyl, O-(lower alkyl), or oxo (=O)); NH$_2$; NH(lower alkyl which may be substituted with OH); N(lower alkyl)$_2$; NH(cycloalkyl); NH(nitrogen-containing monocyclic hetero ring group); cycloalkyl which may be substituted with OH; phenyl which may be substituted with O-(lower alkyl), COOH, or COO-(lower alkyl which may be substituted with phenyl); monocyclic hetero ring group(s) which may be substituted with O-(lower alkyl), NH(lower alkyl which may be substituted with oxo (=O)) or lower alkyl; and oxo (=O), iv) O-(lower alkyl which may be substituted with OH, O-(lower alkyl), phenyl, nitrogen-containing monocyclic hetero ring group(s) (in which the nitrogen-containing monocyclic hetero ring group may be substituted with lower alkyl which may be substituted with cycloalkyl or oxo (=O)), or oxo (=O)), v) NH-(lower alkyl which may be substituted with O-(lower alkyl) or oxo (=O)), vi) NH-(aryl which may be substituted with COOH or COO-(lower alkyl)), vii) cycloalkyl which may be substituted with group(s) selected from the group consisting of lower alkyl which may be substituted with OH; COOH; and COO-(lower alkyl), viii) aryl which may be substituted with group(s) selected from the group consisting of halogen; lower alkyl (in which the lower alkyl may be substituted with COOH or COO-(lower alkyl)); O-(lower alkyl); COOH; and COO-(lower alkyl), ix) hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), x) O-(monocyclic saturated hetero ring group), xi) SO$_2$-(lower alkyl which may be substituted with O-(lower alkyl)), xii) SO$_2$-(cycloalkyl), xiii) SO$_2$-(phenyl), or xiv) oxo (=O).

(60-6) X is

H,

OH,

NH$_2$, lower alkyl which may be substituted with halogen,

O-(lower alkyl which may be substituted with OH),

NH(lower alkyl which may be substituted with oxo (=O)),

N(lower alkyl which may be substituted with O-(lower alkyl) or oxo (=O))$_2$,

NH—SO$_2$-(lower alkyl),

N(lower alkyl)-SO$_2$-(lower alkyl), cycloalkyl which may be substituted with OH or O-(lower alkyl which may be substituted with phenyl or oxo (=O)), O-(cycloalkyl), cycloalkenyl which may be substituted with OH or O-(lower alkyl which may be substituted with phenyl or oxo (=O)), phenyl which may be substituted with group(s) selected from the group consisting of lower alkyl which may be substituted with OH, O-(lower alkyl), oxazolidinyl (in which the oxazolidinyl group may be substituted with oxo (=O)) or oxo (=O); O-(lower alkyl which may be substituted with morphonyl); pyridyl; morphonyl; NH(lower alkyl which may be substituted with oxo (=O)); N(lower alkyl which may be substituted with oxo (=O))$_2$; NHSO$_2$-(lower alkyl); and SO$_2$-(lower alkyl), O-(phenyl which may be substituted with O-(lower alkyl)), or a hetero ring group which may be substituted with group(s) selected from Group G$^{XA6}$ below, and Group G$^{XA6}$ is i) halogen, ii) OH, iii) lower alkyl which may be substituted with group(s) selected from the group consisting of halogen; OH; O-(lower alkyl which may be substituted with OH, phenyl, O-(lower alkyl), or oxo (=O)); NH$_2$; NH(lower alkyl which may be substituted with OH); N(lower alkyl)$_2$; NH(cycloalkyl); NH(thiazolyl); cycloalkyl which may be substituted with OH; phenyl which may be substituted with O-(lower alkyl), COOH, or COO-(lower alkyl which may be substituted with phenyl); tetrahydropyranyl, furanyl, thiazolyl, morphonyl, azetidinyl, or pyridyl, each of which may be substituted with O-(lower alkyl), NH(lower alkyl which may be substituted with oxo (=O)) or lower alkyl; and oxo (=O), iv) O-(lower alkyl which may be substituted with OH, O-(lower alkyl), phenyl, piperidinyl or morphonyl (in which the piperidinyl or morphonyl group may be substituted with lower alkyl which may be substituted with cycloalkyl or oxo (=O)), or oxo (=O)), v) NH-(lower alkyl which may be substituted with O-(lower alkyl) or oxo (=O)), vi) NH-(phenyl which may be substituted with COOH or COO-(lower alkyl)), vii) cycloalkyl which may be substituted with group(s) selected from the group consisting of lower alkyl which may be substituted with OH; COOH; and COO-(lower alkyl), viii) phenyl which may be substituted with group(s) selected from the group consisting of halogen; lower alkyl (in which the lower alkyl may be substituted with COOH or COO-(lower alkyl)); O-(lower alkyl); COOH; and COO-(lower alkyl), ix) hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), x) O-(tetrahydropyranyl)

xi) SO$_2$-(lower alkyl which may be substituted with O-(lower alkyl)), xii) SO$_2$-(cycloalkyl), xiii) SO$_2$-(phenyl), or xiv) oxo (=O).

(61)

(61-1) X is H, lower alkyl, O-(lower alkyl), O-(cycloalkyl), cycloalkyl which may be substituted with group(s) selected from Group G$^{XB1}$ below, cycloalkenyl which may be substituted with group(s) selected from Group G$^{XB1}$ below, aryl which may be substituted with group(s) selected from Group G$^{XB1}$ below, or a hetero ring group which may be substituted with group(s) selected from Group G$^{XB1}$ below, and Group G$^{XB1}$ is i) OH, ii) lower alkyl which may be substituted with group(s) selected from the group consisting of OH; O-(lower alkyl which may be substituted with aryl); NH(lower alkyl); N(lower alkyl)$_2$; NH(cycloalkyl); cycloalkyl which may be substituted with OH; aryl; hetero ring group(s) which may be substituted with lower alkyl; and oxo (=O), iii) O-(lower alkyl which may be substituted with O-(lower alkyl), aryl, hetero ring group(s) (in which the hetero ring group may be substituted with lower alkyl which may be substituted with cycloalkyl or oxo (=O)) or oxo (=O)), iv) NH-(lower alkyl which may be substituted with O-(lower alkyl) or oxo (=O)), v) cycloalkyl which may be substituted with COOH or COO-(lower alkyl), vi) hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), vii) O-(hetero ring group), viii) SO$_2$-(lower alkyl), ix) SO$_2$-(cycloalkyl), or x) oxo (=O).

(61-2) X is H, lower alkyl, O-(lower alkyl), O-(cycloalkyl), cycloalkyl which may be substituted with group(s) selected from Group G$^{XB2}$ below, cycloalkenyl which may be substituted with group(s) selected from Group G$^{XB2}$ below, aryl which may be substituted with group(s) selected from Group G$^{XB2}$ below, or a hetero ring group which may be substituted with group(s) selected from Group G$^{XB2}$ below, and Group G$^{XB2}$ is i) OH, ii) lower alkyl which may be substituted with group(s) selected from the group consisting of OH; O-(lower alkyl which may be substituted with phenyl); NH(lower alkyl); N(lower alkyl)$_2$; NH(cycloalkyl); cycloalkyl which may be substituted with OH; phenyl; monocyclic hetero ring group(s) which may be substituted with lower alkyl; and oxo (=O), iii) O-(lower alkyl which may be substituted with O-(lower alkyl), phenyl, nitrogen-containing monocyclic saturated hetero ring group(s) (in which the nitrogen-containing monocyclic saturated hetero ring group may be substituted with lower alkyl which may be substituted with cycloalkyl or oxo (=O)) or oxo (=O)), iv) NH-(lower alkyl which may be substituted with O-(lower alkyl) or oxo (=O)), v) cycloalkyl which may be substituted with COOH or COO-(lower alkyl), vi) monocyclic hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), vii) O-(monocyclic saturated hetero ring group), viii) SO$_2$-(lower alkyl), ix) SO$_2$-(cycloalkyl), or x) oxo (=O).

(61-3) In (61-2), vi) is vi) nitrogen-containing monocyclic hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O).

(61-4) X is H,
lower alkyl, O-(lower alkyl), O-(cycloalkyl),
cycloalkyl which may be substituted with group(s) selected from Group $G^{XB3}$ below,
cycloalkenyl which may be substituted with group(s) selected from Group $G^{XB3}$ below,
phenyl which may be substituted with group(s) selected from Group $G^{XB3}$ below, or
tetrahydropyranyl, tetrahydrofuranyl, 1,2-dihydropyridyl, thiazolyl, azetidinyl, pyrrolidinyl, piperidinyl, morpholinyl, pyridyl, pyrimidinyl, pyrazinyl, pyridazinyl, imidazo[1,2-a]pyridyl, or benzothiazolyl, which may substituted with group(s) selected from Group $G^{XB3}$ below, and
Group $G^{XB3}$ is
i) OH,
ii) lower alkyl which may be substituted with group(s) selected from the group consisting of OH; O-(lower alkyl which may be substituted with phenyl); NH(lower alkyl); N(lower alkyl)$_2$; NH(cycloalkyl); cycloalkyl which may be substituted with OH; phenyl; pyridyl which may be substituted with lower alkyl; tetrahydropyranyl; and oxo (=O),
iii) O-(lower alkyl which may be substituted with O-(lower alkyl), phenyl, piperidinyl (in which piperidinyl group may be substituted with lower alkyl which may be substituted with cycloalkyl or oxo (=O)) or oxo (=O)),
iv) NH-(lower alkyl which may be substituted with O-(lower alkyl) or oxo (=O)),
v) cycloalkyl which may be substituted with COOH or COO-(lower alkyl),
vi) 1,2-dihydropyridyl, pyridyl, azetidinyl, pyrrolidinyl, piperidinyl, piperazinyl, morpholinyl, oxazepanyl, or tetrahydropyranyl, each of which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O),
vii) O-(tetrahydropyranyl),
viii) SO$_2$-(lower alkyl),
ix) SO$_2$-(cycloalkyl), or
x) oxo (=O).
(61-5) X is H,
lower alkyl, O-(lower alkyl), O-(cycloalkyl),
cycloalkyl which may be substituted with group(s) selected from Group $G^{XB4}$ below,
cycloalkenyl which may be substituted with group(s) selected from Group $G^{XB4}$ below,
phenyl which may be substituted with group(s) selected from Group $G^{XB4}$ below, or
azetidinyl, pyrrolidinyl, piperidinyl, pyridyl, tetrahydrofuranyl, tetrahydropyranyl, or morpholinyl, each of which may be substituted with group(s) selected from Group $G^{XB4}$ below, and
Group $G^{XB4}$ is
i) OH,
ii) lower alkyl which may be substituted with group(s) selected from the group consisting of OH; O-(lower alkyl which may be substituted with phenyl); NH(lower alkyl); N(lower alkyl)$_2$; NH(cycloalkyl); cycloalkyl which may be substituted with OH; phenyl; pyridyl which may be substituted with lower alkyl; tetrahydropyranyl; and oxo (=O),
iii) O-(lower alkyl which may be substituted with O-(lower alkyl), phenyl, piperidinyl (in which the piperidinyl group may be substituted with lower alkyl which may be substituted with cycloalkyl or oxo (=O)), or oxo (=O)),
iv) NH-(lower alkyl which may be substituted with O-(lower alkyl) or oxo (=O)),
v) cycloalkyl which may be substituted with COOH or COO-(lower alkyl),
vi) 1,2-dihydropyridyl, pyridyl, azetidinyl, pyrrolidinyl, piperidinyl, piperazinyl, morpholinyl, or oxazepanyl, each of which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O)
vii) O-(tetrahydropyranyl),
viii) SO$_2$-(lower alkyl),
ix) SO$_2$-(cycloalkyl), or
x) oxo (=O).
(61-6) X is H,
lower alkyl, O-(lower alkyl), O-(cycloalkyl),
cycloalkyl which may be substituted with group(s) selected from Group $G^{XB4}$ above,
cycloalkenyl which may be substituted with group(s) selected from Group $G^{XB4}$ above,
phenyl which may be substituted with group(s) selected from Group $G^{XB4}$ above, or
tetrahydropyranyl, tetrahydrofuranyl, 1,2-dihydropyridyl, thiazolyl, azetidinyl, piperidinyl, morpholinyl, pyridyl, pyrimidinyl, pyrazinyl, pyridazinyl, imidazo[1,2-a]pyridyl, or benzothiazolyl, each of which may be substituted with group(s) selected from Group $G^{XB4}$ above.
(61-7) X is H,
lower alkyl, O-(lower alkyl), O-(cycloalkyl),
cycloalkyl which may be substituted with OH or O-(lower alkyl which may be substituted with aryl or oxo (=O)),
cycloalkenyl which may be substituted with OH or O-(lower alkyl which may be substituted with aryl or oxo (=O)),
aryl which may be substituted with group(s) selected from the group consisting of lower alkyl which may be substituted with OH, O-(lower alkyl), or oxo (=O); O-(lower alkyl); and hetero ring group(s), or
a hetero ring group which may be substituted with group(s) selected from Group $G^{XB5}$ below, and
Group $G^{XB5}$ is
i) OH,
ii) lower alkyl which may be substituted with group(s) selected from the group consisting of OH; O-(lower alkyl which may be substituted with aryl); NH(lower alkyl); N(lower alkyl)$_2$; NH(cycloalkyl); cycloalkyl which may be substituted with OH; aryl; hetero ring group(s) which may be substituted with lower alkyl; and oxo (=O),
iii) O-(lower alkyl which may be substituted with O-(lower alkyl) or hetero ring group(s) (in which the hetero ring group may be substituted with lower alkyl which may be substituted with cycloalkyl or oxo (=O))),
iv) NH-(lower alkyl which may be substituted with O-(lower alkyl) or oxo (=O)),
v) cycloalkyl which may be substituted with COOH or COO-(lower alkyl),
vi) hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O),
vii) O-(hetero ring group),
viii) SO$_2$-(lower alkyl),
ix) SO$_2$-(cycloalkyl), or
x) oxo (=O).
(61-8) X is H,
lower alkyl, O-(lower alkyl), O-(cycloalkyl), cycloalkyl which may be substituted with OH or O-(lower alkyl which may be substituted with phenyl or oxo (=O)), cycloalkenyl which may be substituted with OH or O-(lower alkyl which may be substituted with phenyl or oxo (=O)), aryl which may be substituted with group(s) selected from the group consisting of lower alkyl which may be substituted with OH, O-(lower alkyl), or oxo (=O); O-(lower alkyl); and nitrogen-containing monocyclic unsaturated hetero ring group(s), or a hetero ring group which may be substituted with group(s) selected from Group $G^{XB6}$ below, Group $G^{XB6}$ is i) OH, ii) lower alkyl which may be substituted with group(s) selected from the group consisting of OH; O-(lower alkyl which may be substituted with phenyl); NH(lower alkyl); N(lower alkyl)$_2$; NH(cycloalkyl); cycloalkyl which may be substituted with OH; phenyl; monocyclic hetero ring group(s) which may be substituted with lower alkyl; and oxo (=O), iii) O-(lower alkyl which may be substituted with O-(lower alkyl) or nitrogen-containing monocyclic saturated hetero ring group(s) (in which the nitrogen-containing monocyclic saturated hetero ring group may be substituted with lower alkyl which may be substituted with cycloalkyl or oxo (=O))), iv) NH-(lower alkyl which may be substituted with O-(lower alkyl) or oxo (=O)), v) cycloalkyl which may be substituted with COOH or COO-(lower alkyl), vi) monocyclic hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), vii) O-(monocyclic saturated hetero ring group), viii) SO$_2$-(lower alkyl), ix) SO$_2$-(cycloalkyl), or x) oxo (=O).

(61-9) In (61-8), vi) is vi) nitrogen-containing monocyclic hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O).

(61-10) X is H, lower alkyl, O-(lower alkyl), O-(cycloalkyl), cycloalkyl which may be substituted with OH or O-(lower alkyl which may be substituted with phenyl or oxo (=O)), cycloalkenyl which may be substituted with OH or O-(lower alkyl which may be substituted with phenyl or oxo (=O)), phenyl which may be substituted with group(s) selected from the group consisting of lower alkyl which may be substituted with OH, O-(lower alkyl), or oxo (=O); O-(lower alkyl); and pyridyl, or tetrahydropyranyl, tetrahydrofuranyl, 1,2-dihydropyridyl, thiazolyl, azetidinyl, pyrrolidinyl, piperidinyl, morpholinyl, pyridyl, pyrimidinyl, pyrazinyl, pyridazinyl, imidazo[1,2-a]pyridyl, or benzothiazolyl, each of which may be substituted with group(s) selected from Group $G^{XB7}$ below, and Group $G^{XB7}$ is i) OH, ii) lower alkyl which may be substituted with group(s) selected from the group consisting of OH; O-(lower alkyl which may be substituted with phenyl); NH(lower alkyl); N(lower alkyl)$_2$; NH(cycloalkyl); cycloalkyl which may be substituted with OH; phenyl; pyridyl which may be substituted with lower alkyl; tetrahydropyranyl; and oxo (=O), iii) O-(lower alkyl which may be substituted with O-(lower alkyl) or piperidinyl (in which the piperidinyl group may be substituted with lower alkyl which may be substituted with cycloalkyl or oxo (=O))), iv) NH-(lower alkyl which may be substituted with O-(lower alkyl) or oxo (=O)), v) cycloalkyl which may be substituted with COOH or COO-(lower alkyl), vi) 1,2-dihydropyridyl, pyridyl, azetidinyl, pyrrolidinyl, piperidinyl, piperazinyl, morpholinyl, oxazepanyl, or tetrahydropyranyl, each of which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), vii) O-(tetrahydropyranyl), viii) SO$_2$-(lower alkyl), ix) SO$_2$-(cycloalkyl), or x) oxo (=O).

(61-11) X is H, lower alkyl, O-(lower alkyl), O-(cycloalkyl), cycloalkyl which may be substituted with OH or O-(lower alkyl which may be substituted with phenyl or oxo (=O)), cycloalkenyl which may be substituted with OH or O-(lower alkyl which may be substituted with phenyl or oxo (=O)), phenyl which may be substituted with group(s) selected from the group consisting of lower alkyl which may be substituted with OH, O-(lower alkyl), or oxo (=O); O-(lower alkyl); and pyridyl, or azetidinyl, pyrrolidinyl, piperidinyl, pyridyl, tetrahydrofuranyl, tetrahydropyranyl, or morpholinyl, each of which may be substituted with group(s) selected from Group $G^{XB8}$ below, and Group $G^{XB8}$ is i) OH, ii) lower alkyl which may be substituted with group(s) selected from the group consisting of OH; O-(lower alkyl which may be substituted with phenyl); NH(lower alkyl); N(lower alkyl)$_2$; NH(cycloalkyl); cycloalkyl which may be substituted with OH; phenyl; pyridyl which may be substituted with lower alkyl; tetrahydropyranyl; and oxo (=O), iii) O-(lower alkyl which may be substituted with O-(lower alkyl) or piperidinyl (in which the piperidinyl group may be substituted with lower alkyl which may be substituted with cycloalkyl or oxo (=O))), iv) NH-(lower alkyl which may be substituted with O-(lower alkyl) or oxo (=O)), v) cycloalkyl which may be substituted with COOH or COO-(lower alkyl), vi) 1,2-dihydropyridyl, pyridyl, azetidinyl, pyrrolidinyl, piperidinyl, piperazinyl, morpholinyl, or oxazepanyl, each of which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O)

vii) O-(tetrahydropyranyl), viii) SO$_2$-(lower alkyl), ix) SO$_2$-(cycloalkyl), or x) oxo (=O).

(61-12) X is H, lower alkyl, O-(lower alkyl), O-(cycloalkyl), cycloalkyl which may be substituted with OH or O-(lower alkyl which may be substituted with phenyl or oxo (=O)), cycloalkenyl which may be substituted with OH or O-(lower alkyl which may be substituted with phenyl or oxo (=O)), phenyl which may be substituted with group(s) selected from the group consisting of lower alkyl which may be substituted with OH, O-(lower alkyl), or oxo (=O); O-(lower alkyl); and pyridyl, or tetrahydropyranyl, tetrahydrofuranyl, 1,2-dihydropyridyl, thiazolyl, azetidinyl, piperidinyl, morpholinyl, pyridyl, pyrimidinyl, pyrazinyl, pyridazinyl, imidazo[1,2-a]pyridyl, or benzothiazolyl, each of which may be substituted with group(s) selected from Group $G^{XB8}$ above.

(62)

(62-1) X is OH, $NH_2$, lower alkyl which may be substituted with halogen,

O-(lower alkyl which may be substituted with OH), NH(lower alkyl which may be substituted with oxo (=O)), N(lower alkyl which may be substituted with O-(lower alkyl) or oxo (=O))$_2$, NH—$SO_2$-(lower alkyl), N(lower alkyl)-$SO_2$-(lower alkyl), O-(cycloalkyl), or O-(aryl which may be substituted with O-(lower alkyl)), or X is

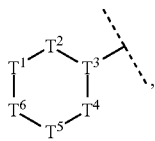

[Chem. 41]

$T^1$ is a single bond, $CR^{T11}R^{T12}$, O, or $NR^{T13}$, $T^2$ is $CR^{T21}R^{T22}$, O, or $NR^{T23}$, $T^3$ is $CR^{T31}$ or N, $T^4$ is $CR^{T41}R^{T42}$ or O, $T^5$ is a single bond, $(CR^{T51}R^{T52})_m$, or $NR^{Q53}$, $T^6$ is $CR^{T61}R^{T62}$, O, S, $SO_2$, or $NR^{T63}$, $R^{T11}$, $R^{T12}$, $R^{T21}$, $R^{T22}$, $R^{T31}$, $R^{T41}$, $R^{T42}$, $R^{T51}$ and $R^{T52}$ are the same as or different from each other, and are H, OH, lower alkyl (in which the lower alkyl may be substituted with OH, $NH_2$, NH(lower alkyl which may be substituted with OH), O-(lower alkyl), or oxo (=O)), O-(lower alkyl), or nitrogen-containing monocyclic saturated hetero ring group(s), $R^{T13}$, $R^{T23}$ and $R^{T53}$ are the same as or different from each other, and are H or lower alkyl (in which the lower alkyl may be substituted with O-(lower alkyl) or oxo (=O)), $R^{T61}$ is H, OH, or halogen, $R^{T62}$ is H, OH, halogen, lower alkyl (in which the lower alkyl may be substituted with OH, halogen, O-(lower alkyl which may be substituted with OH, O-(lower alkyl), or oxo (=O)), $NH_2$, NH(lower alkyl which may be substituted with OH), nitrogen-containing monocyclic saturated hetero ring group(s) which may be substituted with O-(lower alkyl), or oxo (=O)), O-(lower alkyl which may be substituted with OH, O-(lower alkyl), aryl, or oxo (=O)), NH(lower alkyl which may be substituted with oxo (=O)), NH(aryl which may be substituted with COOH or COO-(lower alkyl)), $SO_2$-(lower alkyl), $SO_2$-(aryl), or a hetero ring group (in which the hetero ring group may be substituted with lower alkyl which may be substituted with OH, O-(lower alkyl), or oxo (=O), or oxo (=O)), $R^{T63}$ is H, lower alkyl which may be substituted with group(s) selected from the group consisting of OH; O-(lower alkyl); aryl (in which the aryl may be substituted with O-(lower alkyl), COOH, or COO-(lower alkyl which may be substituted with aryl)); $NH_2$; NH(lower alkyl); N(lower alkyl)$_2$; NH(cycloalkyl); cycloalkyl which may be substituted with OH; monocyclic hetero ring group(s) which may be substituted with NH(lower alkyl which may be substituted with oxo (=O)); NH(nitrogen-containing monocyclic unsaturated hetero ring group); and oxo (=O), a nitrogen-containing monocyclic unsaturated hetero ring group which may be substituted with lower alkyl, cycloalkyl which may be substituted with group(s) selected from the group consisting of lower alkyl which may be substituted with OH; COOH; and COO-(lower alkyl), aryl which may be substituted with group(s) selected from the group consisting of halogen; lower alkyl (in which the lower alkyl may be substituted with COOH or COO-(lower alkyl)); O-(lower alkyl); COOH; and COO-(lower alkyl), $SO_2$-(lower alkyl which may be substituted with O-(lower alkyl)), or $SO_2$-(cycloalkyl), or $R^{T21}$ and $R^{T31}$ may be combined with each other to form a new bond, or $R^{T1}$ and $R^{T12}$, $R^{T21}$ and $R^{T22}$, $R^{T41}$ and $R^{T42}$, $R^{T51}$ and $R^{T52}$, or $R^{T61}$ and $R^{T62}$ may be combined with each other to form oxo (=O), and m is 1 or 2, or X is

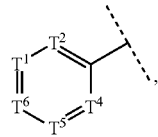

[Chem. 42]

$T^1$ is $CR^{T12}$ or N, $T^2$ is $CR^{T22}$ or N, $T^4$ is $CR^{T42}$ or N, $T^5$ is $CR^{T52}$ or N, $T^6$ is $CR^{T62}$ or N, and $R^{T12}$, $R^{T22}$, $R^{T42}$, $R^{T52}$ and $R^{T62}$ are the same as or different from each other, and are H, lower alkyl which may be substituted with OH or oxazolidinyl (in which the oxazolidinyl group may be substituted with oxo (=O)), O-(lower alkyl which may be substituted with nitrogen-containing monocyclic saturated hetero ring group(s)), NH(lower alkyl which may be substituted with oxo (=O)), N(lower alkyl which may be substituted with oxo (=O))$_2$, NH—$SO_2$-(lower alkyl), $SO_2$-(lower alkyl), or a nitrogen-containing monocyclic saturated hetero ring group.

(62-2) X is OH, $NH_2$, lower alkyl which may be substituted with halogen, O-(lower alkyl which may be substituted with OH), NH(lower alkyl which may be substituted with oxo (=O)), N(lower alkyl which may be substituted with O-(lower alkyl) or oxo (=O))$_2$, NH—$SO_2$-(lower alkyl), N(lower alkyl)-$SO_2$-(lower alkyl), O-(cycloalkyl), or O-(phenyl which may be substituted with O-(lower alkyl)), or X is

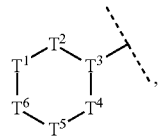

[Chem. 43]

$T^1$ is a single bond, $CR^{T11}R^{T12}$, O, or $NR^{T13}$, $T^2$ is $CR^{T21}R^{T22}$, O, or $NR^{T23}$, $T^3$ is $CR^{T31}$ or N, $T^4$ is $CR^{T41}R^{T42}$ or O, $T^5$ is a single bond, $(CR^{T51}R^{T52})_m$, or $NR^{T53}$, $T^6$ is $CR^{T61}R^{T62}$, O, S, $SO_2$, or $NR^{T63}$, $R^{T11}$, $R^{T12}$, $R^{T21}$, $R^{T22}$, $R^{T31}$, $R^{T41}$, $R^{T42}$, $R^{T51}$ and $R^{T52}$ are the same as or different from each other, and are H, OH, lower alkyl (in which the lower alkyl may be substituted with OH, $NH_2$, NH(lower alkyl which may be substituted with OH), O-(lower alkyl), or oxo (=O)), O-(lower alkyl), or morpholinyl, $R^{T13}$, $R^{T23}$ and $R^{T53}$ are the same as or different from each other, and are H or lower alkyl (in which the lower alkyl may be substituted with O-(lower alkyl) or oxo (=O)), $R^{T61}$ is H, OH, or halogen, $R^{T62}$ is H, OH, halogen, lower alkyl (in which the lower alkyl is OH, halogen, O-(lower alkyl which may be substituted with OH, O-(lower alkyl), or oxo (=O)), $NH_2$, NH(lower alkyl which may be substituted with OH), azetidinyl which may be substituted with O-(lower alkyl), morpholinyl, or oxo (=O)), O-(lower alkyl which may be substituted with OH, O-(lower alkyl), phenyl, or oxo (=O)), NH(lower alkyl which may be substituted with oxo (=O)), NH(phenyl which may be substituted with COOH or COO-(lower alkyl)), $SO_2$-(lower alkyl), $SO_2$-(phenyl), or tetrahydropyranyl, piperidinyl, morpholinyl, pyridyl, dihydrobenzoimidazolinyl, or dihydroimidazopyridyl, each of which may be substituted with lower alkyl (in which the lower alkyl may be substituted with OH, O-(lower alkyl), or oxo (=O)) or oxo (=O), $R^{T63}$ is H, lower alkyl which may be substituted with group(s) selected from the group consisting of OH; O-(lower alkyl); phenyl (in which the phenyl may be substituted with O-(lower alkyl), COOH, or COO-(lower alkyl which may be substituted with phenyl)); $NH_2$; NH(lower alkyl); N(lower alkyl)$_2$; NH(cycloalkyl); cycloalkyl which may be substituted with OH; tetrahydropyranyl, thiazolyl, pyridyl, or furanyl, each of which may be substituted with NH(lower alkyl which may be substituted with oxo (=O)); NH(thiazolyl); and oxo (=O), pyridyl which may be substituted with lower alkyl, cycloalkyl which may be substituted with group(s) selected from the group consisting of lower alkyl which may be substituted with OH; COOH; and COO-(lower alkyl), phenyl which may be substituted with group(s) selected from the group consisting of halogen; lower alkyl (in which the lower alkyl may be substituted with COOH or COO-(lower alkyl)); O-(lower alkyl); COOH; and COO-(lower alkyl), $SO_2$-(lower alkyl which may be substituted with O-(lower alkyl)), or $SO_2$-(cycloalkyl), or $R^{T21}$ and $R^{T31}$ may be combined with each other to form a new bond, or $R^{T11}$ and $R^{T12}$, $R^{T21}$ and $R^{T22}$, $R^{T41}$ and $R^{T42}$, $R^{T51}$ and $R^{T52}$, or $R^{T61}$ and $R^{T62}$ may be combined with each other to form oxo (=O), m is 1 or 2, or X is

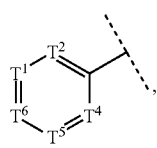

[Chem. 44]

$T^1$ is $CR^{T12}$ or N, $T^2$ is $CR^{T22}$ or N, $T^4$ is $CR^{T42}$ or N, $T^5$ is $CR^{T52}$ or N, $T^6$ is $CR^{T62}$ or N, and $R^{T12}$, $R^{T22}$, $R^{T42}$, $R^{T52}$ and $R^{T62}$ are the same as or different from each other, and are H, lower alkyl which may be substituted with OH, or oxazolidinyl (in which the oxazolidinyl group may be substituted with oxo (=O)), O-(lower alkyl which may be substituted with morpholinyl), NH(lower alkyl which may be substituted with oxo (=O)), N(lower alkyl which may be substituted with oxo (=O))$_2$, NH—$SO_2$-(lower alkyl), $SO_2$-(lower alkyl), or morpholinyl.

(63)

(63-1) X is lower alkyl, O-(lower alkyl), or O-(cycloalkyl), or

X is

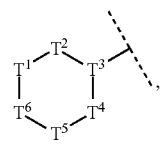

[Chem. 45]

$T^1$ is a single bond or $CR^{T11}R^{T12}$, $T^2$ is $CR^{T21}R^{T22}$, O, or $NR^{T23}$, $T^3$ is $CR^{T31}$ or N, $T^4$ is $CR^{T41}R^{T42}$, $T^5$ is a single bond or $(CR^{T51}R^{T52})_m$, $T^6$ is $CR^{T61}R^{T62}$, O, or $NR^{T63}$ $R^{T11}$, $R^{T12}$, $R^{T21}$, $R^{T22}$, $R^{T31}$, $R^{T41}$, $R^{T42}$, $R^{T51}$ and $R^{T52}$ are the same as or different from each other, and are H, or OH, $R^{T23}$ is H, or CO—($C_{1-5}$ alkyl), $R^{T61}$ is H, $R^{T62}$ is H, $R^{T63}$ is cycloalkyl which may be substituted with COOH or COO-(lower alkyl), CO—($C_{1-5}$ alkyl which may be substituted with OH, oxo (=O), O-(lower alkyl) or nitrogen-containing monocyclic unsaturated hetero ring(s)), CO-(cycloalkyl which may be substituted with OH), CO-(aryl), CO-(nitrogen-containing monocyclic unsaturated hetero ring group), CO—O—($C_{1-5}$ alkyl), CONH (lower alkyl), CON (lower alkyl)$_2$, CONH (cycloalkyl), $SO_2$-(lower alkyl), or $SO_2$-(cycloalkyl), and m is 1 or 2, or X is

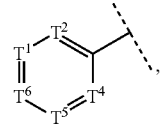

[Chem. 46]

$T^1$ is $CR^{T12}$ or N, $T^2$ is $CR^{T22}$ or N, $T^4$ is $CR^{T42}$ or N, $T^5$ is $CR^{T52}$ or N, $T^6$ is $CR^{T62}$ or N, and $R^{T12}$, $R^{T22}$, $R^{T42}$, $R^{T52}$ and $R^{T62}$ are the same as or different from each other, and are H, or O-(lower alkyl).

(63-2)

(63-2-1) In (63-1), $R^{T63}$ is CO—($C_{1-5}$ alkyl which may be substituted with O-(lower alkyl) or nitrogen-containing monocyclic unsaturated hetero ring(s)), CO-(cycloalkyl), CO-(aryl), CO-(nitrogen-containing monocyclic unsaturated hetero ring group), CON(lower alkyl)$_2$, or $SO_2$-(lower alkyl).

(63-2-2) In (63-1), $R^{T63}$ is CO—($C_{1-5}$ alkyl which may be substituted with O-(lower alkyl)), CO-(cycloalkyl), CO-(aryl), CO-(nitrogen-containing monocyclic unsaturated hetero ring group), CON(lower alkyl)$_2$, or $SO_2$-(lower alkyl).

(63-2-3) In (63-1), $R^{T63}$ is CO—($C_{1-5}$ lower alkyl which may be substituted with O-(lower alkyl)), CO-(cycloalkyl), or $SO_2$-(lower alkyl).

(63-2-4) In (63-1), $R^{T63}$ is acetyl, propionyl, isobutyryl, pivaloyl, 2-ethoxy-1-oxoethyl, 2-methoxy-1-oxoethyl, 3-methoxy-1-oxopropyl, 3-methoxy-2,2-dimethyl-1-oxopropyl, cyclopropylcarbonyl, benzoyl, pyridin-3-ylcarbonyl, dimethylaminocarbonyl, methylsulfonyl, or ethylsulfonyl.

(63-2-5) In (63-1), $R^{T63}$ is acetyl, propionyl, isobutyryl, pivaloyl, 2-ethoxy-1-oxoethyl, 2-methoxy-1-oxoethyl, 3-methoxy-1-oxopropyl, cyclopropylcarbonyl, benzoyl, pyridin-3-ylcarbonyl, dimethylaminocarbonyl, methylsulfonyl, or ethylsulfonyl.

(63-2-6) In (63-1), $R^{T63}$ is acetyl, propionyl, isobutyryl, pivaloyl, 2-ethoxy-1-oxoethyl, cyclopropylcarbonyl, benzoyl, pyridin-3-ylcarbonyl, dimethylaminocarbonyl, or methylsulfonyl.

(63-3)

(63-3-1) In (63-1) to (63-2), $R^{T11}$, $R^{T12}$, $R^{T21}$, $R^{T22}$, $R^{T31}$, $R^{T41}$, $R^{T42}$, $R^{T51}$ and $R^{T52}$ are the same as or different from each other, and are H or OH.

(63-3-2) In (63-1) to (63-2), $R^{T11}$, $R^{T12}$, $R^{T21}$, $R^{T22}$, $R^{T31}$, $R^{T41}$, $R^{T42}$, $R^{T51}$ and $R^{T52}$ are H.

(63-4) In (63-1) to (63-3), $R^{T23}$ is H.

(63-5) In (63-1) to (63-4), X is

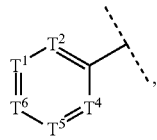

[Chem. 47]

$T^1$ is $CR^{T12}$, $T^2$ is CH, $T^4$ is CH, $T^5$ is $CR^{T52}$ or N, $T^6$ is CH, and $R^{T12}$ and $R^{T52}$ are the same as or different from each other, and are H or O-(lower alkyl).

(63-6)

(63-6-1) In (63-1) to (63-5), $T^1$ is a single bond or $CR^{T11}R^{T12}$, $T^2$ is $CR^{T21}R^{T22}$, $T^3$ is $CR^{T31}$ or N, $T^4$ is $CR^{T41}R^{T42}$, $T^5$ is a single bond or $(CR^{T51}R^{T52})_m$, and $T^6$ is $NR^{T63}$.

(63-6-2) In (63-1) to (63-5), $T^1$ is $CR^{T11}R^{T12}$, $T^2$ is $CR^{T21}R^{T22}$, $T^3$ is $CR^{T31}$, $T^4$ is $CR^{T41}R^{T42}$, $T^5$ is $(CR^{T51}R^{T52})_m$, and $T^6$ is $NR^{T63}$.

(63-7) In (63-1) to (63-6), m is 1.

(64)

(64-1) X is H, lower alkyl, O-(lower alkyl), cycloalkyl which may be substituted with group(s) selected from Group $G^{XC1}$ below, cycloalkenyl which may be substituted with group(s) selected from Group $G^{XC1}$ below, aryl which may be substituted with group(s) selected from Group $G^{XC1}$ below, or a hetero ring group which may be substituted with group(s) selected from Group $G^{XC1}$ below, and Group $G^{XC1}$ is i) OH, ii) lower alkyl which may be substituted with group(s) selected from the group consisting of OH; O-(lower alkyl which may be substituted with aryl); N(lower alkyl)$_2$; cycloalkyl; hetero ring group(s) which may be substituted with lower alkyl; and oxo (=O), iii) O-(lower alkyl which may be substituted with O-(lower alkyl), aryl, hetero ring group(s) (in which the hetero ring group may be substituted with lower alkyl which may be substituted with cycloalkyl or oxo (=O)), or oxo (=O)), iv) NH-(lower alkyl which may be substituted with O-(lower alkyl) or oxo (=O)), v) cycloalkyl, vi) hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), vii) O-(hetero ring group), viii) SO$_2$-(lower alkyl), ix) SO$_2$-(cycloalkyl), or x) oxo (=O).

(64-2) X is H, lower alkyl, O-(lower alkyl), cycloalkyl which may be substituted with group(s) selected from Group $G^{XC2}$ below, cycloalkenyl which may be substituted with group(s) selected from Group $G^{XC2}$ below, aryl which may be substituted with group(s) selected from Group $G^{XC2}$ below, or a hetero ring group which may be substituted with group(s) selected from Group $GXC^2$ below, and Group $G^{XC2}$ is i) OH, ii) lower alkyl which may be substituted with group(s) selected from the group consisting of OH; O-(lower alkyl which may be substituted with phenyl); N(lower alkyl)$_2$; cycloalkyl; monocyclic hetero ring group(s) which may be substituted with lower alkyl; and oxo (=O), iii) O-(lower alkyl which may be substituted with O-(lower alkyl), phenyl, nitrogen-containing monocyclic saturated hetero ring group(s) (in which the nitrogen-containing monocyclic saturated hetero ring group may be substituted with lower alkyl which may be substituted with cycloalkyl or oxo (=O)), iv) NH-(lower alkyl which may be substituted with O-(lower alkyl) or oxo (=O)), v) cycloalkyl, vi) monocyclic hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), vii) O-(tetrahydropyranyl), viii) SO$_2$-(lower alkyl), ix) SO$_2$-(cycloalkyl), or x) oxo (=O).

(64-3) In (64-2), vi) of Group $G^{XC2}$ is vi) nitrogen-containing monocyclic hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O).

(64-4) X is H, lower alkyl, O-(lower alkyl), cycloalkyl which may be substituted with group(s) selected from Group $G^{XC3}$ below, cycloalkenyl which may be substituted with group(s) selected from Group $G^{XC3}$ below phenyl which may be substituted with group(s) selected from Group $G^{XC3}$ below, or tetrahydropyranyl, tetrahydrofuranyl, 1,2-dihydropyridyl, thiazolyl, piperidinyl, morpholinyl, pyridyl, pyrimidinyl, pyrazinyl, pyridazinyl, imidazo[1,2-a]pyridyl, or benzothiazolyl, each of which may be substituted with group(s) selected from Group $G^{XC3}$ below, and $G^{XC3}$ is
i) OH,
ii) lower alkyl which may be substituted with group(s) selected from the group consisting of OH; O-(lower alkyl which may be substituted with phenyl); N(lower alkyl)$_2$; cycloalkyl; pyridyl which may be substituted with lower alkyl; tetrahydropyranyl; and oxo (=O),
iii) O-(lower alkyl which may be substituted with O-(lower alkyl), phenyl, piperidinyl (in which the piperidinyl group may be substituted with lower alkyl which may be substituted with cycloalkyl or oxo (=O)), or oxo (=O)),
iv) NH-(lower alkyl which may be substituted with O-(lower alkyl) or oxo (=O)),
v) cycloalkyl,
vi) 1,2-dihydropyridyl, pyridyl, azetidinyl, pyrrolidinyl, piperidinyl, piperazinyl, morpholinyl, oxazepanyl, or tetrahydropyranyl, each of which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O),
vii) O-(tetrahydropyranyl),
viii) SO$_2$-(lower alkyl),
ix) SO$_2$-(cycloalkyl), or
x) oxo (=O).
(64-5) X is H,
lower alkyl, O-(lower alkyl),
cycloalkyl which may be substituted with group(s) selected from Group $G^{XC4}$ below,
cycloalkenyl which may be substituted with group(s) selected from Group $G^{XC4}$
phenyl which may be substituted with group(s) selected from Group $G^{XC4}$, or
tetrahydropyranyl, tetrahydrofuranyl, 1,2-dihydropyridyl, piperidinyl, pyridyl, pyrimidinyl, or imidazo[1,2-a]pyridyl, each of which may be substituted with group(s) selected from Group $G^{XC4}$, and
$G^{XC4}$ is
i) OH,
ii) lower alkyl which may be substituted with group(s) selected from the group consisting of OH; O-(lower alkyl which may be substituted with phenyl); N(lower alkyl)$_2$; cycloalkyl; pyridyl which may be substituted with lower alkyl; tetrahydropyranyl; and oxo (=O),
iii) O-(lower alkyl which may be substituted with O-(lower alkyl), phenyl, piperidinyl (in which the piperidinyl group may be substituted with lower alkyl which may be substituted with cycloalkyl or oxo (=O)), or oxo (=O)),
iv) NH-(lower alkyl which may be substituted with O-(lower alkyl) or oxo (=O)),
v) cycloalkyl,
vi) 1,2-dihydropyridyl, pyridyl, azetidinyl, pyrrolidinyl, piperidinyl, piperazinyl, morpholinyl, or oxazepanyl, each of which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O),
vii) O-(tetrahydropyranyl),
viii) SO$_2$-(lower alkyl),
ix) SO$_2$-(cycloalkyl), or
x) oxo (=O).
(64-6) X is H,
lower alkyl, O-(lower alkyl),
cycloalkyl which may be substituted with OH or O-(lower alkyl which may be substituted with aryl or oxo (=O)),
cycloalkenyl which may be substituted with OH or O-(lower alkyl which may be substituted with aryl or oxo (=O)),
aryl which may be substituted with group(s) selected from the group consisting of lower alkyl which may be substituted with OH, O-(lower alkyl), or oxo (=O); O-(lower alkyl); and hetero ring group(s), or
a hetero ring group which may be substituted with group(s) selected from Group $G^{XC5}$ below, and
$G^{XC5}$ is
i) lower alkyl which may be substituted with group(s) selected from the group consisting of OH; O-(lower alkyl which may be substituted with aryl); N(lower alkyl)$_2$; cycloalkyl; hetero ring group(s) which may be substituted with lower alkyl; and oxo (=O),
ii) O-(lower alkyl which may be substituted with O-(lower alkyl) or hetero ring group(s) (in which the hetero ring group may be substituted with lower alkyl which may be substituted with cycloalkyl or oxo (=O))),
iii) NH-(lower alkyl which may be substituted with O-(lower alkyl) or oxo (=O)),
iv) cycloalkyl,
v) hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O),
vi) O-(hetero ring group),
vii) SO$_2$-(lower alkyl),
viii) SO$_2$-(cycloalkyl), or
ix) oxo (=O).
(64-7) X is H,
lower alkyl, O-(lower alkyl),
cycloalkyl which may be substituted with OH or O-(lower alkyl which may be substituted with phenyl or oxo (=O)),
cycloalkenyl which may be substituted with OH or O-(lower alkyl which may be substituted with phenyl or oxo (=O)),
aryl which may be substituted with group(s) selected from the group consisting of lower alkyl which may be substituted with OH, O-(lower alkyl), or oxo (=O); O-(lower alkyl); and nitrogen-containing monocyclic unsaturated hetero ring group(s), or
a hetero ring group which may be substituted with group(s) selected from Group $G^{XC6}$ below, and
GXC$^6$ is
i) lower alkyl which may be substituted with group(s) selected from the group consisting of OH; O-(lower alkyl which may be substituted with phenyl); N(lower alkyl)$_2$; cycloalkyl; monocyclic hetero ring group(s) which may be substituted with lower alkyl; and oxo (=O),
ii) O-(lower alkyl which may be substituted with O-(lower alkyl) or nitrogen-containing monocyclic saturated hetero ring group(s) (in which the nitrogen-containing monocyclic saturated hetero ring group may be substituted with lower alkyl which may be substituted with cycloalkyl or oxo (=O))),
iii) NH-(lower alkyl which may be substituted with O-(lower alkyl) or oxo (=O)),
iv) cycloalkyl,
v) monocyclic hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O),
vi) O-(tetrahydropyranyl),
vii) SO$_2$-(lower alkyl), viii) SO$_2$-(cycloalkyl), or ix) oxo (=O).

(64-8) In (64-7), v) of Group G$^{XC6}$ is v) nitrogen-containing monocyclic hetero ring group(s) which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O).

(64-9) X is H, lower alkyl, O-(lower alkyl), cycloalkyl which may be substituted with OH or O-(lower alkyl which may be substituted with phenyl or oxo (=O)), cycloalkenyl which may be substituted with OH or O-(lower alkyl which may be substituted with phenyl or oxo (=O)), phenyl which may be substituted with group(s) selected from the group consisting of lower alkyl which may be substituted with OH, O-(lower alkyl), or oxo (=O); O-(lower alkyl); and pyridyl, or tetrahydropyranyl, tetrahydrofuranyl, 1,2-dihydropyridyl, thiazolyl, azetidinyl, piperidinyl, morpholinyl, pyridyl, pyrimidinyl, pyrazinyl, pyridazinyl, imidazo[1,2-a]pyridyl, or benzothiazolyl, each of which may be substituted with group(s) selected from Group G$^{XC7}$ below, and G$^{XC7}$ is i) lower alkyl which may be substituted with group(s) selected from the group consisting of OH; O-(lower alkyl which may be substituted with phenyl); N(lower alkyl)$_2$; cycloalkyl; pyridyl which may be substituted with lower alkyl; tetrahydropyranyl; and oxo (=O), ii) O-(lower alkyl which may be substituted with O-(lower alkyl) or piperidinyl (in which the piperidinyl group may be substituted with lower alkyl which may be substituted with cycloalkyl or oxo (=O))), iii) NH-(lower alkyl which may be substituted with O-(lower alkyl) or oxo (=O)), iv) cycloalkyl, v) 1,2-dihydropyridyl, pyridyl, azetidinyl, pyrrolidinyl, piperidinyl, piperazinyl, morpholinyl, oxazepanyl, or tetrahydropyranyl, each of which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), vi) O-(tetrahydropyranyl), vii) SO$_2$-(lower alkyl), viii) SO$_2$-(cycloalkyl), or ix) oxo (=O).

(64-10) X is H, lower alkyl, O-(lower alkyl), cycloalkyl which may be substituted with OH or O-(lower alkyl which may be substituted with phenyl or oxo (=O)), cycloalkenyl which may be substituted with OH or O-(lower alkyl which may be substituted with phenyl or oxo (=O)), phenyl which may be substituted with group(s) selected from the group consisting of lower alkyl which may be substituted with OH, O-(lower alkyl), or oxo (=O); O-(lower alkyl); and pyridyl, or tetrahydropyranyl, tetrahydrofuranyl, 1,2-dihydropyridyl, azetidinyl, piperidinyl, pyridyl, pyrimidinyl, or imidazo[1,2-a]pyridyl, each of which may be substituted with group(s) selected from Group G$^{XC8}$ below, and G$^{XC8}$ is i) lower alkyl which may be substituted with group(s) selected from the group consisting of OH; O-(lower alkyl which may be substituted with phenyl); N(lower alkyl)$_2$; cycloalkyl; pyridyl which may be substituted with lower alkyl; tetrahydropyranyl; and oxo (=O), ii) O-(lower alkyl which may be substituted with O-(lower alkyl) or piperidinyl (in which the piperidinyl group may be substituted with lower alkyl which may be substituted with cycloalkyl or oxo (=O))), iii) NH-(lower alkyl which may be substituted with O-(lower alkyl) or oxo (=O)), iv) cycloalkyl, v) 1,2-dihydropyridyl, pyridyl, azetidinyl, pyrrolidinyl, piperidinyl, piperazinyl, morpholinyl, or oxazepanyl, each of which may be substituted with group(s) selected from the group consisting of OH; halogen; lower alkyl which may be substituted with OH, O-(lower alkyl), or oxo (=O); O-(lower alkyl which may be substituted with O-(lower alkyl)); and oxo (=O), vi) O-(tetrahydropyranyl), vii) SO$_2$-(lower alkyl), viii) SO$_2$-(cycloalkyl), or ix) oxo (=O).

(65)

(65-1) X is

H, lower alkyl, or O-(lower alkyl), or

X is

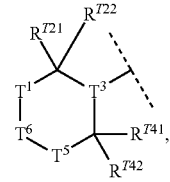

[Chem. 48]

T$^1$ is a single bond, CR$^{T11}$R$^{T12}$, or NR$^{T13}$, T$^3$ is CR$^{T31}$ or N, T$^5$ is a single bond or CR$^{T51}$R$^{T52}$, T$^6$ is a single bond, CR$^{T61}$R$^{T62}$, O, or NR$^{T63}$, R$^{T11}$, R$^{T12}$, R$^{T13}$, R$^{T21}$, R$^{T22}$, R$^{T31}$, R$^{T41}$, R$^{T42}$, R$^{T51}$, R$^{T52}$, R$^{T61}$, R$^{T62}$ and R$^{T63}$ are the same as or different from each other, and are

H,

OH, lower alkyl which may be substituted with group(s) selected from the group consisting of O-(lower alkyl which may be substituted with aryl); N(lower alkyl)$_2$; cycloalkyl; hetero ring group(s) which may be substituted with lower alkyl; and oxo (=O), O-(lower alkyl which may be substituted with aryl or oxo (=O)), a hetero ring group which may be substituted with group(s) selected from the group consisting of lower alkyl which may be substituted with OH or oxo (=O); and oxo (=O), SO$_2$-(lower alkyl), or SO$_2$-(cycloalkyl), or R$^{T21}$ and R$^{T31}$, or R$^{T41}$ and R$^{T51}$ may be combined with each other to form a new bond, or R$^{T61}$ and R$^{T62}$ may be combined with each other to form oxo (=O), or X is

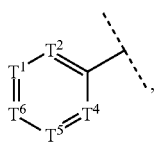

[Chem. 49]

$T^1$ is $CR^{T12}$ or N, $T^2$ is $CR^{T22}$ or N, $T^4$ is $CR^{T42}$ or N, $T^5$ is $CR^{T52}$ or N, $T^6$ is $CR^{T62}$ or N, $R^{T12}$, $R^{T22}$, $R^{T42}$, $R^{T52}$ and $R^{T62}$ are the same as or different from each other, and are

H, lower alkyl which may be substituted with OH, O-(lower alkyl), or oxo (=O),

O-(lower alkyl which may be substituted with O-(lower alkyl) or hetero ring group(s) (in which the hetero ring group may be substituted with lower alkyl which may be substituted with cycloalkyl or oxo (=O))), NH-(lower alkyl which may be substituted with O-(lower alkyl)), cycloalkyl, a hetero ring group which may be substituted with group(s) selected from the group consisting of OH; halogen; lower alkyl which may be substituted with O-(lower alkyl) or oxo (=O); and O-(lower alkyl which may be substituted with O-(lower alkyl)), or O-(hetero ring group), or X is thiazolyl which may be substituted with morpholinyl or NH(lower alkyl which may be substituted with oxo (=O)), benzothiazolyl, or imidazo[1,2-a]pyridyl which may be substituted with lower alkyl.

(65-2) X is

H, lower alkyl, or O-(lower alkyl), or

X is

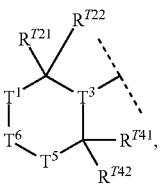

[Chem. 50]

$T^1$ is a single bond, $CR^{T11}R^{T12}$, or $NR^{T13}$, $T^3$ is $CR^{T31}$ or N, $T^5$ is a single bond or $CR^{T51}R^{T52}$, $T^6$ is a single bond, $CR^{T61}R^{T62}$, O, or $NR^{T63}$, $R^{T11}$, $R^{T12}$, $R^{T13}$, $R^{T21}$, $R^{T22}$, $R^{T31}$, $R^{T41}$, $R^{T42}$, $R^{T51}$, $R^{T52}$, $R^{T61}$, $R^{T62}$ and $R^{T63}$ are the same as or different from each other, and are

H,

OH, lower alkyl which may be substituted with group(s) selected from the group consisting of O-(lower alkyl which may be substituted with phenyl); N(lower alkyl)$_2$; cycloalkyl; monocyclic hetero ring group(s) which may be substituted with lower alkyl; and oxo (=O), O-(lower alkyl which may be substituted with phenyl or oxo (=O)), a monocyclic hetero ring group which may be substituted with group(s) selected from the group consisting of lower alkyl which may be substituted with OH or oxo (=O); and oxo (=O), $SO_2$-(lower alkyl), or $SO_2$-(cycloalkyl), or $R^{T21}$ and $R^{T31}$, or $R^{T41}$ and $R^{T51}$ may be combined with each other to form a new bond, or $R^{T61}$ and $R^{T62}$ may be combined with each other to form oxo (=O), or X is

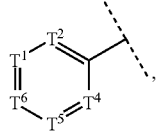

[Chem. 51]

$T^1$ is $CR^{T12}$ or N, $T^2$ is $CR^{T22}$ or N, $T^4$ is $CR^{T42}$ or N, $T^5$ is $CR^{T52}$ or N, $T^6$ is $CR^{T62}$ or N, $R^{T12}$, $R^{T22}$, $R^{T42}$, $R^{T52}$ and $R^{T62}$ are the same as or different from each other, and are

H, lower alkyl which may be substituted with OH, O-(lower alkyl), or oxo (=O),

O-(lower alkyl which may be substituted with O-(lower alkyl) or nitrogen-containing monocyclic saturated hetero ring group(s) (in which the nitrogen-containing monocyclic saturated hetero ring group may be substituted with lower alkyl which may be substituted with cycloalkyl or oxo (=O))), NH-(lower alkyl which may be substituted with O-(lower alkyl)), cycloalkyl, a monocyclic hetero ring group which may be substituted with group(s) selected from the group consisting of OH; halogen; lower alkyl which may be substituted with O-(lower alkyl) or oxo (=O); and O-(lower alkyl which may be substituted with O-(lower alkyl)), or O-(monocyclic hetero ring group), or X is thiazolyl which may be substituted with morpholinyl or NH(lower alkyl which may be substituted with oxo (=O)), benzothiazolyl, or imidazo[1,2-a]pyridyl which may be substituted with lower alkyl.

(65-3) X is

H, lower alkyl, or O-(lower alkyl), or

X is

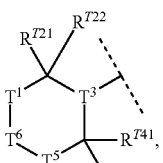

[Chem. 52]

$T^1$ is a single bond, $CR^{T11}R^{T12}$, or $NR^{T13}$, $T^3$ is $CR^{T31}$ or N, $T^5$ is a single bond or $CR^{T51}R^{T52}$, $T^6$ is a single bond, $CR^{T61}R^{T62}$, O, or $NR^{T63}$, $R^{T11}$, $R^{T12}$, $R^{T13}$, $R^{T21}$, $R^{T22}$, $R^{T31}$, $R^{T41}$, $R^{T42}$, $R^{T51}$, $R^{T52}$, $R^{T61}$, $R^{T62}$ and $R^{T63}$ are the same as or different from each other, and are

H,

OH, lower alkyl which may be substituted with group(s) selected from the group consisting of O-(lower alkyl which may be substituted with phenyl); N(lower alkyl)$_2$; cycloalkyl;

monocyclic hetero ring group(s) which may be substituted with lower alkyl; and oxo (=O), O-(lower alkyl which may be substituted with phenyl or oxo (=O)), a nitrogen-containing monocyclic hetero ring group which may be substituted with group(s) selected from the group consisting of lower alkyl which may be substituted with OH or oxo (=O); and oxo (=O), SO$_2$-(lower alkyl), or SO$_2$-(cycloalkyl), or $R^{T21}$ and $R^{T31}$, or $R^{T41}$ and $R^{T51}$ may be combined with each other to form a new bond, or $R^{T61}$ and $R^{T62}$ may be combined with each other to form oxo (=O), or X is

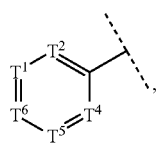
[Chem. 53]

$T^1$ is $CR^{T12}$ or N, $T^2$ is $CR^{T22}$ or N, $T^4$ is $CR^{T42}$ or N, $T^5$ is $CR^{T52}$ or N, $T^6$ is $CR^{T62}$ or N, $R^{T12}$, $R^{T22}$, $R^{T42}$, $R^{T52}$ and $R^{T62}$ are the same as or different from each other, and are

H, lower alkyl which may be substituted with OH, O-(lower alkyl), or oxo (=O),

O-(lower alkyl which may be substituted with O-(lower alkyl) or nitrogen-containing monocyclic saturated hetero ring group(s) (in which the nitrogen-containing monocyclic saturated hetero ring group may be substituted with lower alkyl which may be substituted with cycloalkyl or oxo (=O))), NH-(lower alkyl which may be substituted with O-(lower alkyl)), cycloalkyl, a nitrogen-containing monocyclic hetero ring group which may be substituted with group(s) selected from the group consisting of OH; halogen; lower alkyl which may be substituted with O-(lower alkyl) or oxo (=O); and O-(lower alkyl which may be substituted with O-(lower alkyl)), or O-(monocyclic saturated hetero ring group), or X is thiazolyl which may be substituted with morpholinyl or NH(lower alkyl which may be substituted with oxo (=O)), benzothiazolyl, or imidazo[1,2-a]pyridyl which may be substituted with lower alkyl.

(65-4) X is

H, lower alkyl, or

O-(lower alkyl), or

X is

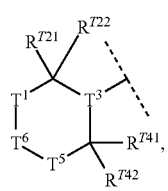
[Chem. 54]

$T^1$ is a single bond, $CR^{T11}R^{T12}$, or $NR^{T13}$, $T^3$ is $CR^{T31}$ or N, $T^5$ is a single bond or $CR^{T51}R^{T52}$, $T^6$ is a single bond, $CR^{T61}R^{T62}$, O, or $NR^{T63}$, $R^{T11}$, $R^{T12}$, $R^{T13}$, $R^{T21}$, $R^{T22}$, $R^{T31}$, $R^{T41}$, $R^{T42}$, $R^{T51}$, $R^{T52}$, $R^{T61}$, $R^{T62}$ and $R^{T63}$ are the same as or different from each other, and are

H,

OH, lower alkyl which may be substituted with group(s) selected from the group consisting of O-(lower alkyl which may be substituted with phenyl); N(lower alkyl)$_2$; cycloalkyl; pyridyl which may be substituted with lower alkyl; tetrahydropyranyl; and oxo (=O), O-(lower alkyl which may be substituted with phenyl or oxo (=O)), 1,2-dihydropyridyl, pyridyl, or tetrahydropyranyl, each of which may be substituted with group(s) selected from the group consisting of lower alkyl which may be substituted with OH or oxo (=O); and oxo (=O), SO$_2$-(lower alkyl), or SO$_2$-(cycloalkyl), or $R^{T21}$ and $R^{T31}$, or $R^{T41}$ and $R^{T51}$ may be combined with each other to form a new bond, or $R^{T61}$ and $R^{T62}$ may be combined with each other to form oxo (=O), or, X is

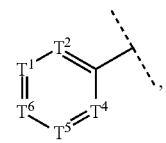
[Chem. 55]

$T^1$ is $CR^{T12}$ or N, $T^2$ is $CR^{T22}$ or N, $T^4$ is $CR^{T42}$ or N, $T^5$ is $CR^{T52}$ or N, $T^6$ is $CR^{T62}$ or N, $R^{T12}$, $R^{T22}$, $R^{T42}$, $R^{T52}$ and $R^{T62}$ are the same as or different from each other, and are

H, lower alkyl which may be substituted with OH, O-(lower alkyl), or oxo (=O),

O-(lower alkyl which may be substituted with O-(lower alkyl) or piperidinyl (in which the piperidinyl group may be substituted with lower alkyl which may be substituted with cycloalkyl or oxo (=O))), NH-(lower alkyl which may be substituted with O-(lower alkyl)), cycloalkyl, pyridyl, azetidinyl, pyrrolidinyl, piperidinyl, piperazinyl, morpholinyl, or oxazepanyl, each of which may be substituted with group(s) selected from the group consisting of OH; halogen; lower alkyl which may be substituted with O-(lower alkyl) or oxo (=O); and O-(lower alkyl which may be substituted with O-(lower alkyl)), or O-(tetrahydropyranyl), or X is thiazolyl which may be substituted with morpholinyl or NH(lower alkyl which may be substituted with oxo (=O)), benzothiazolyl, or imidazo[1,2-a]pyridyl which may be substituted with lower alkyl.

(65-5) X is

H, lower alkyl, or

O-(lower alkyl), or

X is

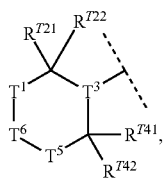

[Chem. 56]

$T^1$ is a single bond, $CR^{T11}R^{T12}$, or $NR^{T13}$, $T^3$ is $CR^{T31}$ or N, $T^5$ is a single bond or $CR^{T51}R^{T52}$, $T^6$ is a single bond, $CR^{T61}R^{T62}$, O, or $NR^{T63}$, $R^{T11}$, $R^{T12}$, $R^{T13}$, $R^{T21}$, $R^{T22}$, $R^{T31}$, $R^{T41}$, $R^{T42}$, $R^{T51}$, $R^{T52}$, $R^{T61}$, $R^{T62}$ and $R^{T63}$ are the same as or different from each other, and are

H,

OH, lower alkyl which may be substituted with group(s) selected from the group consisting of O-(lower alkyl which may be substituted with phenyl); N(lower alkyl)$_2$; cycloalkyl; pyridyl which may be substituted with lower alkyl; tetrahydropyranyl; and oxo (=O), O-(lower alkyl which may be substituted with phenyl or oxo (=O)), 1,2-dihydropyridyl or pyridyl, each of which may be substituted with group(s) selected from the group consisting of lower alkyl which may be substituted with OH or oxo (=O); and oxo (=O), SO$_2$-(lower alkyl), or SO$_2$-(cycloalkyl), or $R^{T21}$ and $R^{T31}$, or $R^{T41}$ and $R^{T51}$ may be combined with each other to form a new bond, or $R^{T61}$ and $R^{T62}$ may be combined with each other to form oxo (=O), or X is

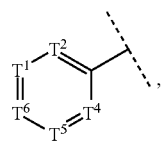

[Chem. 57]

$T^1$ is $CR^{T12}$ or N, $T^2$ is $CR^{T22}$ or N, $T^4$ is $CR^{T42}$ or N, $T^5$ is $CR^{T52}$ or N, $T^6$ is $CR^{T62}$ or N, $R^{T12}$, $R^{T22}$, $R^{T42}$, $R^{T52}$ and $R^{T62}$ are the same as or different from each other, and are

H, lower alkyl which may be substituted with OH, O-(lower alkyl), or oxo (=O), O-(lower alkyl which may be substituted with O-(lower alkyl) or piperidinyl (in which the piperidinyl group may be substituted with lower alkyl which may be substituted with cycloalkyl or oxo (=O))), NH-(lower alkyl which may be substituted with O-(lower alkyl)), cycloalkyl, pyridyl, azetidinyl, pyrrolidinyl, piperidinyl, piperazinyl, morpholinyl, or oxazepanyl, each of which may be substituted with group(s) selected from the group consisting of OH; halogen; lower alkyl which may be substituted with O-(lower alkyl) or oxo (=O); and O-(lower alkyl which may be substituted with O-(lower alkyl)), or O-(tetrahydropyranyl), or X is thiazolyl which may be substituted with morpholinyl or NH(lower alkyl which may be substituted with oxo (=O)), benzothiazolyl, or imidazo[1,2-a]pyridyl which may be substituted with lower alkyl.

(66)

(66-1) In (65-1) to (65-5), X is

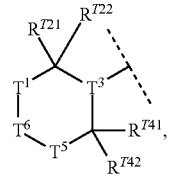

[Chem. 58]

or

X is

[Chem. 59]

(66-2) In (65-1) to (65-5), X is

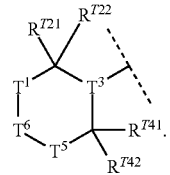

[Chem. 60]

(66-3) In (66-1) to (66-2), $R^{T11}$, $R^{T12}$, $R^{T13}$, $R^{T21}$, $R^{T22}$, $R^{T31}$, $R^{T41}$, $R^{T42}$, $R^{T51}$, $R^{T52}$, $R^{T61}$, $R^{T62}$ and $R^{T63}$ are the same as or different from each other, and are

H,

OH, lower alkyl which may be substituted with group(s) selected from the group consisting of O-(lower alkyl which may be substituted with phenyl); N(lower alkyl)$_2$; cycloalkyl; monocyclic hetero ring group(s) which may be substituted with lower alkyl; and oxo (=O), O-(lower alkyl which may be substituted with phenyl or oxo (=O)), a monocyclic hetero ring group which may be substituted with group(s) selected from the group consisting of lower alkyl which may be substituted with OH or oxo (=O); and oxo (=O), SO$_2$-(lower alkyl), or SO$_2$-(cycloalkyl), or $R^{T21}$ and $R^{T31}$, or $R^{T41}$ and $R^{T51}$ may be combined with each other to form a new bond, or $R^{T61}$ and $R^{T62}$ may be combined with each other to form oxo (=O).

(66-4) In (66-1) to (66-2), $R^{T11}$, $R^{T12}$, $R^{T13}$, $R^{T21}$, $R^{T22}$, $R^{T31}$, $R^{T41}$, $R^{T42}$, $R^{T51}$, $R^{T52}$, $R^{T61}$, $R^{T62}$ and $R^{T63}$ are the same as or different from each other, and are

H,

OH, lower alkyl which may be substituted with group(s) selected from the group consisting of O-(lower alkyl which may be substituted with phenyl); N(lower alkyl)$_2$; cycloalkyl; pyridyl which may be substituted with lower alkyl; tetrahydropyranyl; and oxo (=O), O-(lower alkyl which may be substituted with phenyl or oxo (=O)), 1,2-dihydropyridyl or pyridyl, each of which may be substituted with group(s) selected from the group consisting of lower alkyl which may be substituted with OH or oxo (=O); and oxo (=O), SO$_2$-(lower alkyl), or SO$_2$-(cycloalkyl), or $R^{T21}$ and $R^{T31}$, or $R^{T41}$ and $R^{T51}$ may be combined with each other to form a new bond, or $R^{T61}$ and $R^{T62}$ may be combined with each other to form oxo (=O).

(66-5) In (65-1) to (65-5), X is

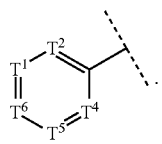

[Chem. 61]

(67)

(67-1) In (66-1) to (66-4), $T^1$ is $CR^{T11}R^{T12}$ or $NR^{T13}$, $T^3$ is $CR^{T31}$, $T^5$ is $CR^{T51}R^{T52}$, $T^6$ is $CR^{T61}R^{T62}$, or $NR^{T63}$, $R^{T11}$, $R^{T12}$, $R^{T13}$, $R^{T21}$, $R^{T22}$, $R^{T31}$, $R^{T41}$, $R^{T42}$, $R^{T51}$, $R^{T52}$, $R^{T61}$ and $R^{T62}$ are the same as or different from each other, and are H, or lower alkyl, or $R^{T61}$ and $R^{T62}$ may be combined with each other to form oxo (=O), $R^{T63}$ is lower alkyl which may be substituted with group(s) selected from the group consisting of O-(lower alkyl); N(lower alkyl)$_2$; cycloalkyl; hetero ring group(s) which may be substituted with lower alkyl; and oxo (=O), a monocyclic hetero ring group which may be substituted with group(s) selected from the group consisting of lower alkyl which may be substituted with OH or oxo (=O); and oxo (=O), SO$_2$-(lower alkyl), or SO$_2$-(cycloalkyl), or $R^{T21}$ and $R^{T31}$, or $R^{T41}$ and $R^{T51}$ may be combined with each other to form a new bond.

(67-2) In (67-1), $R^{T63}$ is lower alkyl which may be substituted with group(s) selected from the group consisting of O-(lower alkyl); N(lower alkyl)$_2$; cycloalkyl; nitrogen-containing monocyclic unsaturated hetero ring group(s) which may be substituted with lower alkyl; monocyclic saturated hetero ring group(s); and oxo (=O), a nitrogen-containing monocyclic hetero ring group which may be substituted with group(s) selected from the group consisting of lower alkyl which may be substituted with OH or oxo (=O); and oxo (=O), SO$_2$-(lower alkyl), or SO$_2$-(cycloalkyl).

(67-3) In (67-1) to (67-2), $R^{T63}$ is lower alkyl which may be substituted with group(s) selected from the group consisting of O-(lower alkyl); N(lower alkyl)$_2$; cyclopropyl; pyridyl which may be substituted with lower alkyl; tetrahydropyranyl; and oxo (=O), 1,2-dihydropyridyl or pyridyl, each of which may be substituted with group(s) selected from the group consisting of lower alkyl which may be substituted with OH or oxo (=O); and oxo (=O), SO$_2$-(lower alkyl), or SO$_2$-(cyclopropyl).

(67-4)

(67-4-1) In (66-1) to (66-4), and (67-1) to (67-3), $R^{T11}$, $R^{T12}$, $R^{T21}$, $R^{T22}$, $R^{T31}$, $R^{T41}$ and $R^{T42}$ are H, $R^{T51}$ and $R^{T52}$ are the same as or different from each other, and are H, lower alkyl, or O-(lower alkyl), $R^{T61}$ and $R^{T62}$ are the same as or different from each other, and are H, OH, O-(lower alkyl which may be substituted with aryl or oxo (=O)), or a monocyclic hetero ring group, $R^{T13}$ is H or lower alkyl, or $R^{T61}$ and $R^{T62}$ may be combined with each other to form oxo (=O), or $R^{T21}$ and $R^{T31}$, or $R^{T41}$ and $R^{T51}$ may be combined with each other to form a new bond.

(67-4-2) In (66-1) to (66-4), and (67-1) to (67-3), $R^{T11}$, $R^{T12}$, $R^{T21}$, $R^{T22}$, $R^{T31}$, $R^{T41}$ and $R^{T42}$ are H, $R^{T51}$ and $R^{T52}$ are the same as or different from each other, and are H, lower alkyl, or O-(lower alkyl), $R^{T61}$ and $R^{T62}$ are the same as or different from each other, and are H, OH, O-(lower alkyl which may be substituted with phenyl or oxo (=O)), or a monocyclic saturated hetero ring group, $R^{T13}$ is H or lower alkyl, or $R^{T61}$ and $R^{T62}$ may be combined with each other to form oxo (=O), or $R^{T21}$ and $R^{T31}$, or $R^{T41}$ and $R^{T51}$ may be combined with each other to form a new bond.

(67-4-3) In (66-1) to (66-4), and (67-1) to (67-3), $R^{T11}$, $R^{T12}$, $R^{T21}$, $R^{T22}$, $R^{T31}$, $R^{T41}$ and $R^{T42}$ are H, $R^{T511}$ and $R^{T52}$ are the same as or different from each other, and are H, lower alkyl, or O-(lower alkyl), $R^{T61}$ and $R^{T62}$ are the same as or different from each other, and are H, OH, O-(lower alkyl which may be substituted with phenyl or oxo (=O)), or tetrahydropyranyl, $R^{T13}$ is H or lower alkyl, or $R^{T61}$ and $R^{T62}$ may be combined with each other to form oxo (=O), or $R^{T21}$ and $R^{T31}$, or $R^{T41}$ and $R^{T51}$ may be combined with each other to form a new bond.

(67-5) In (67-1) to (67-3), $R^{T11}$, $R^{T12}$, $R^{T21}$, $R^{T22}$, $R^{T31}$, $R^{T41}$, $R^{T42}$, $R^{T51}$, $R^{T52}$, $R^{T61}$ and $R^{T62}$ are H, $R^{T13}$ is H or lower alkyl, or $R^{T61}$ and $R^{T62}$ may be combined with each other to form oxo (=O), or $R^{T21}$ and $R^{T31}$, or $R^{T41}$ and $R^{T51}$ may be combined with each other to form a new bond.

(67-6) In (67-1) to (67-5), $T^1$ is $CR^{T11}R^{T12}$, $T^3$ is $CR^{T31}$, $T^5$ is $CR^{T51}R^{T52}$, and $T^6$ is $NR^{T63}$.

(67-7) In (67-1) to (67-5), $T^1$ is $NR^{T13}$, $T^3$ is $CR^{T31}$, $T^5$ is $CR^{T51}R^{T52}$, and $T^6$ is $CR^{T61}R^{T62}$.

(68) E is a single bond, or lower alkylene which may be substituted with oxo (=O).

(69)

(69-1) G is a single bond, O, NH, or N(lower alkyl).

(69-2) G is a single bond, O, or NH.

(70) J is a single bond or lower alkylene.

(71)

(71-1) L is O, NH, or N(lower alkyl).

(71-2) L is O or NH.

(72)

(72-1) U is a single bond, O, NH, N(lower alkyl which may be substituted with O-(lower alkyl)), SO$_2$, or lower alkylene which may be substituted with oxo (=O).

(72-2) U is a single bond, O, NH, N(lower alkyl), SO$_2$, or lower alkylene which may be substituted with oxo (=O).

(72-3) U is a single bond, O, or lower alkylene.

(72-4) U is a single bond, O, NH, or N(lower alkyl which may be substituted with O-(lower alkyl)).

(72-5) U is a single bond or O.

(73)

(73-1) V is a single bond, O, NH, N(lower alkyl), or lower alkylene which may be substituted with OH, O-(lower alkyl), or oxo (=O).

(73-2) V is a single bond, O, N(lower alkyl), or lower alkylene which may be substituted with oxo (=O).

(73-3) V is a single bond, O, or lower alkylene.

(73-4) V is a single bond or lower alkylene which may be substituted with OH, O-(lower alkyl), or oxo (=O).

(73-5) V is a single bond, O, or lower alkylene which may be substituted with oxo (=O).

(73-6) V is a single bond, or lower alkylene which may be substituted with oxo (=O).

(74)

(74-1) W is a single bond, SO, SO$_2$, or lower alkylene.

(74-2) W is a single bond, SO, or SO$_2$.

(74-3) W is a single bond or lower alkylene.

(74-4) W is a single bond.

(75) $R^1$, $R^2$, $R^3$ and $R^4$ are the same as or different from each other, and are H, halogen, or lower alkyl.

(76) $R^{T61}$ is H.

Furthermore, other embodiments of the compound (I) of the present invention include compounds or salts thereof including a consistent combination of two or more groups among the groups described in (1) to (56) above, and specifically, the following compounds or salts thereof.

(77) The compound of the formula (I), wherein A is as described in (1).

(78) The compound of the formula (I), wherein A is as described in (2).

(79) The compound as described in (77) to (78), wherein $R^{Q12}$, $R^{Q22}$, $R^{Q42}$ and $R^{Q52}$ are as described in (4).

(80) The compound as described in (77) to (79), wherein $Q^1$, $Q^2$, $Q^4$ and $Q^5$ are as described in (6).

(81) The compound as described in (77) to (80), wherein $R^1$, $R^2$, $R^3$ and $R^4$ are as described in (13).

(82) The compound as described in (77) to (81), wherein E is as described in (14).

(83) The compound as described in (77) to (82), wherein G is as described in (16).

(84) The compound as described in (77) to (83), wherein J is as described in (19).

(85) The compound as described in (77) to (84), wherein L is as described in (21).

(86) The compound as described in (77) to (85), wherein U is as described in (24).

(87) The compound as described in (77) to (86), wherein V is as described in (27).

(88) The compound as described in (77) to (87), wherein W is as described in (28).

(89) The compound as described in (77) to (88), wherein X is as described in (31).

(90) The compound as described in (89), wherein $R^{T11}$, $R^{T12}$, $R^{T21}$, $R^{T22}$, $R^{T31}$, $R^{T41}$, $R^{T42}$, $R^{T51}$ and $R^{T52}$ are as described in (33).

(91) The compound as described in (89) to (90), wherein $R^{T63}$ is as described in (39).

(92) The compound as described in (89) to (91), wherein $T^1$, $T^2$, $T^3$, $T^4$, $T^5$ and $T^6$ are as described in (40).

(93) The compound as described in (89) to (91), wherein $T^1$, $T^2$, $T^3$, $T^4$, $T^5$ and $T^6$ are as described in (41).

(94) The compound as described in (89) to (91), wherein $T^1$, $T^2$, $T^3$, $T^4$, $T^5$ and $T^6$ are as described in (42).

(95) The compound as described in (89) to (91), wherein $T^1$, $T^2$, $T^3$, $T^4$, $T^5$ and $T^6$ are as described in (43).

(96) The compound as described in (89) to (95), wherein m is as described in (55).

(97) The compound as described in (89) to (95), wherein m is as described in (56).

(98) The compound of the formula (I), wherein A is as described in (3).

(99) The compound as described in (77) or (98), wherein $R^{Q11}$, $R^{Q12}$, $R^{Q13}$, $R^{Q31}$, $R^{Q51}$, $R^{Q52}$, $R^{Q53}$ and $R^{Q61}$ are as described in (5).

(100) The compound as described in (77), or (98) to (99), wherein $Q^1$, $Q^3$, $Q^5$ and $Q^6$ are as described in (9).

(101) The compound as described in (77), or (98) to (99), wherein $Q^1$, $Q^3$, $Q^5$ and $Q^6$ are as described in (12).

(102) The compound as described in (98) to (101), wherein $R^1$, $R^2$, $R^3$ and $R^4$ are as described in (13).

(103) The compound as described in (98) to (102), wherein E is as described in (14).

(104) The compound as described in (98) to (103), wherein G is as described in (16).

(105) The compound as described in (98) to (104), wherein J is as described in (19).

(106) The compound as described in (98) to (105), wherein L is as described in (21).

(107) The compound as described in (98) to (106), wherein U is as described in (23).

(108) The compound as described in (98) to (107), wherein V is as described in (26).

(109) The compound as described in (98) to (108), wherein W is as described in (28).

(110) The compound as described in (98) to (109), wherein X is as described in (31).

(111) The compound as described in (110), wherein $R^{T11}$, $R^{T12}$, $R^{T21}$, $R^{T22}$, $R^{T31}$ $R^{T41}$, $R^{T42}$, $R^{T51}$ and $R^{T52}$ are as described in (33).

(112) The compound as described in (110) to (111), wherein $R^{T63}$ is as described in (39).

(113) The compound as described in (110) to (112), wherein $T^1$, $T^2$, $T^3$, $T^4$, $T^5$ and $T^6$ are as described in (40).

(114) The compound as described in (110) to (112), wherein $T^1$, $T^2$, $T^3$, $T^4$, $T^5$ and $T^6$ are as described in (41).

(115) The compound as described in (110) to (112), wherein $T^1$, $T^2$, $T^3$, $T^4$, $T^5$ and $T^6$ are as described in (42).

(116) The compound as described in (110) to (115), wherein m is as described in (55).

(117) The compound as described in (110) to (115), wherein m is as described in (56).

In addition, still other embodiments of the compound (I) of the present invention include compounds or salts thereof including a consistent combination of two or more groups, among the groups described in (1) to (56) and (76) above, and specifically, the following compounds or salts thereof.

(118) The compound as described in (77) to (117), wherein $R^{T61}$ is as described in (76).

(119) The compound as described in (77) to (117), or (118), wherein $R^{T62}$ is as described in (36) to (38).

In addition, further still other embodiments of the compound (I) of the present invention include compounds or salts thereof including a consistent combination of two or more groups, among the groups described in (1) to (76) above, and specifically, the following compounds or salts thereof.

(120) The compound of the formula (I), wherein A is as described in (1) or (57).

(121) The compound of the formula (I), wherein A is as described in (2) or (58).

(122) The compound as described in (120) to (121), wherein $R^1$, $R^2$, $R^3$ and $R^4$ are as described in (13) or (75).

(123) The compound as described in (120) to (122), wherein E is as described in (14), (15), or (68).

(124) The compound as described in (120) to (123), wherein G is as described in (16), (17), (18), or (69).

(125) The compound as described in (120) to (124), wherein J is as described in (19), (20), or (70).

(126) The compound as described in (120) to (125), wherein L is as described in (21), (22), or (71).

(127) The compound as described in (120) to (126), wherein U is as described in (23), (24), (25), or (72).

(128) The compound as described in (120) to (127), wherein V is as described in (26), (27), or (73).

(129) The compound as described in (120) to (128), wherein W is as described in (28), (29), or (74).

(130) The compound as described in (120) to (129), wherein X is as described in (60) or (61).

(131) The compound as described in (120) to (129), wherein X is as described in (31), or (62) to (63).

(132) The compound as described in (131), wherein $R^{T11}$, $R^{T12}$, $R^{T21}$, $R^{T22}$, $R^{T31}$, $R^{T41}$, $R^{T42}$, $R^{T51}$ and $R^{T52}$ are as described in (33).

(133) The compound as described in (131) to (132), wherein $R^{T61}$ is as described in (76).

(134) The compound as described in (131) to (133), wherein $R^{T62}$ is as described in (36) to (38).

(135) The compound as described in (131) to (134), wherein $R^{T63}$ is as described in (39).

(136) The compound as described in (131) to (135), wherein $T^1$, $T^2$, $T^3$, $T^4$, $T^5$ and $T^6$ are as described in (40).

(137) The compound as described in (131) to (135), wherein $T^1$, $T^2$, $T^3$, $T^4$, $T^5$ and $T^6$ are as described in (41).

(138) The compound as described in (131) to (135), wherein $T^1$, $T^2$, $T^3$, $T^4$, $T^5$ and $T^6$ are as described in (42).

(139) The compound as described in (131) to (135), wherein $T^1$, $T^2$, $T^3$, $T^4$, $T^5$ and $T^6$ are as described in (43).

(140) The compound as described in (131) to (139), wherein m is as described in (55).

(141) The compound as described in (131) to (139), wherein m is as described in (56).

(142) The compound as described in (I), wherein A is as described in (3) or (59).

(143) The compound as described in (120), or (142) wherein $R^1$, $R^2$, $R^3$ and $R^4$ are as described in (13) or (75).

(144) The compound as described in (120), or (142) to (143), wherein E is as described in (14), (15), or (68).

(145) The compound as described in (120), or (142) to (144), wherein G is as described in (16), (17), (18), or (69).

(146) The compound as described in (120), or (142) to (145), wherein J is as described in (19), (20), or (70).

(147) The compound as described in (120), or (142) to (146), wherein L is as described in (21), (22), or (71).

(148) The compound as described in (120), or (142) to (147), wherein U is as described in (23), (24), (25), or (72).

(149) The compound as described in (120), or (142) to (148), wherein V is as described in (26), (27), or (73).

(150) The compound as described in (120), or (142) to (149), wherein W is as described in (28), (29), or (74).

(151) The compound as described in (120), or (142) to (150), wherein X is as described in (60), (61), or (64).

(152) The compound as described in (120), or (142) to (150), wherein X is as described in (31), (65) to (67).

(153) The compound as described in (152), wherein $R^{T11}$, $R^{T12}$, $R^{T21}$, $R^{T22}$, $R^{T31}$ $R^{T41}$, $R^{T42}$, $R^{T51}$ and $R^{T52}$ are as described in (33).

(154) The compound as described in (152) to (153), wherein $R^{T61}$ is as described in (76).

(155) The compound as described in (152) to (154), wherein $R^{T62}$ is as described in (36) to (38).

(156) The compound as described in (152) to (155), wherein $R^{T63}$ is as described in (39).

(157) The compound as described in (152) to (156), wherein $T^1$, $T^2$, $T^3$, $T^4$, $T^5$ and $T^6$ are as described in (40).

(158) The compound as described in (152) to (156), wherein $T^1$, $T^2$, $T^3$, $T^4$, $T^5$ and $T^6$ are as described in (41).

(159) The compound as described in (152) to (156), wherein $T^1$, $T^2$, $T^3$, $T^4$, $T^5$ and $T^6$ are as described in (42).

(160) The compound as described in (152) to (159), wherein m is as described in (55).

(161) The compound as described in (152) to (159), wherein m is as described in (56).

Specific examples of the compound encompassed by the present invention include the following compounds or salts thereof:

1-carbamimidoyl-3-{3-[2-(morpholin-4-yl)pyrimidin-5-yl]benzyl}urea, 2-fluoro-3-[2-(morpholin-4-yl)pyrimidin-5-yl]benzyl carbamimidoylcarbamate, 3-{2-[(3S)-3-fluoropyrrolidin-1-yl]pyrimidin-5-yl}benzyl carbamimidoylcarbamate, N-{4-[2-(3-{[(carbamimidoylcarbamoyl)amino]methyl}phenyl)ethyl]-1,3-thiazol-2-yl}acetamide, 2-fluoro-3-[2-(3-methoxyazetidin-1-yl)pyrimidin-5-yl]benzyl carbamimidoylcarbamate, 2-fluoro-3-[4-(pyridin-4-yl)piperidin-1-yl]benzyl carbamimidoylcarbamate, 3-(4-{4-[5-(3-{[(carbamimidoylcarbamoyl)oxy]methyl}-2-fluorophenyl)pyrimidin-2-yl]piperazin-1-yl}phenyl)propanoic acid, 2-fluoro-3-{4-[2-(3-methoxyazetidin-1-yl)pyrimidin-5-yl]piperazin-1-yl}benzyl carbamimidoylcarbamate, 2-fluoro-3-{4-[2-(4-hydroxy-4-methylpiperidin-1-yl)pyrimidin-5-yl]piperazin-1-yl}benzyl carbamimidoylcarbamate, 2-fluoro-3-(4-{2-[(3R)-3-fluoropyrrolidin-1-yl]pyrimidin-5-yl}piperazin-1-yl)benzyl carbamimidoylcarbamate, 2-fluoro-3-[4-(2-methoxypyrimidin-5-yl)piperazin-1-yl]benzyl carbamimidoylcarbamate, 3-{2-[(1-acetylpiperidin-4-yl)methoxy]pyrimidin-5-yl}-2-fluorobenzyl carbamimidoylcarbamate, 3-(2-{[1-(cyclopropylcarbonyl)piperidin-4-yl]methoxy}pyrimidin-5-yl)-2-fluorobenzyl carbamimidoylcarbamate, 2-fluoro-3-(2-{[1-(pyridin-3-ylcarbonyl)piperidin-4-yl]methoxy}pyrimidin-5-yl)benzyl carbamimidoylcarbamate, 2-fluoro-3-{4-[(trans-4-methoxycyclohexyl)carbonyl]piperazin-1-yl}benzyl carbamimidoylcarbamate, 2-fluoro-3-[4-(tetrahydro-2H-pyran-4-ylacetyl)piperazin-1-yl]benzyl carbamimidoylcarbamate, 3-[4-(ethylsulfonyl)piperazin-1-yl]-2-fluorobenzyl carbamimidoylcarbamate, 3-{4-[(1-acetylpiperidin-4-yl)oxy]piperidin-1-yl}-2-fluorobenzyl carbamimidoylcarbamate, 1-(3-{2-[(1-acetylpiperidin-4-yl)methoxy]pyrimidin-5-yl}-2-fluorobenzyl)-3-carbamimidoylurea, 2-fluoro-3-[4-(pyridin-3-yl)piperazin-1-yl]benzyl carbamimidoylcarbamate,
2-fluoro-3-[4-(6-methylpyridin-3-yl)piperazin-1-yl]benzyl carbamimidoylcarbamate,
2-fluoro-3-[3-oxo-4-(pyridin-3-yl)piperazin-1-yl]benzyl carbamimidoylcarbamate,
2-fluoro-3-{3-[(1-propionylpiperidin-4-yl)oxy]azetidin-1-yl}benzyl carbamimidoylcarbamate,
2-fluoro-3-{3-[(6-methylpyridin-3-yl)oxy]azetidin-1-yl}benzyl carbamimidoylcarbamate,
2-fluoro-3-(3-{[6-(methoxymethyl)pyridin-3-yl]oxy}azetidin-1-yl)benzyl carbamimidoylcarbamate,
3-{3-[(2,6-dimethylpyridin-4-yl)methoxy]azetidin-1-yl}-2-fluorobenzyl carbamimidoylcarbamate,
2-fluoro-3-{4-[6-(methoxymethyl)pyridin-3-yl]piperazin-1-yl}benzyl carbamimidoylcarbamate,
2-fluoro-3-[4-(imidazo[1,2-a]pyridin-7-yl)piperazin-1-yl]benzyl carbamimidoylcarbamate,
2-fluoro-3-{3-[(1-methyl-6-oxo-1,6-dihydropyridin-3-yl)oxy]azetidin-1-yl}benzyl carbamimidoylcarbamate,
2-fluoro-3-{4-[5-(methoxymethyl)pyridin-3-yl]piperazin-1-yl}benzyl carbamimidoylcarbamate,
2-fluoro-3-{4-[2-(2-methoxyethoxy)pyridin-4-yl]piperazin-1-yl}benzyl carbamimidoylcarbamate,
3-[3-(1-acetylpiperidin-4-yl)azetidin-1-yl]-2-fluorobenzyl carbamimidoylcarbamate,
2-fluoro-3-[3-(1-propionylpiperidin-4-yl)azetidin-1-yl]benzyl carbamimidoylcarbamate,
3-{3-[1-(cyclopropylcarbonyl)piperidin-4-yl]azetidin-1-yl}-2-fluorobenzyl carbamimidoylcarbamate,
2-fluoro-3-{3-[1-(methoxyacetyl)piperidin-4-yl]azetidin-1-yl}benzyl carbamimidoylcarbamate,
2-fluoro-3-{3-[1-(3-methoxypropanoyl)piperidin-4-yl]azetidin-1-yl}benzyl carbamimidoylcarbamate,
2-fluoro-3-{3-[1-(methylsulfonyl)piperidin-4-yl]azetidin-1-yl}benzyl carbamimidoylcarbamate, or
2-fluoro-3-{4-[2-(methoxymethyl)pyridin-4-yl]piperazin-1-yl}benzyl carbamimidoylcarbamate.

The compound of the formula (I) may exist in the form of tautomers or geometrical isomers depending on the kind of substituents. In the present specification, the compound of the formula (I) shall be described in only one form of isomer, yet the present invention includes other isomers, an isolated form of the isomers, or a mixture thereof.

In addition, the compound of the formula (I) may have asymmetric carbon atoms or axial asymmetry in some cases, and correspondingly, it may exist in the form of optical isomers based thereon. The present invention includes both an isolated form of the optical isomers of the compound of the formula (I) or a mixture thereof.

Moreover, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Drug Design, 163-198.

Furthermore, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

In addition, the present invention also includes various hydrates or solvates, and polymorphic crystalline substances of the compound of the formula (I) and salts thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituents thereof and by applying various known synthesis methods. During the preparation, replacing the relevant functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis ($4^{th}$ edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, the prodrug of the compound of the formula (I) can be prepared by introducing a specific group at the stage from a starting material to an intermediate, as in the case of the above-mentioned protective group, or by carrying out the reaction using the obtained compound of the formula (I). The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the present invention are not limited to the examples as shown below. Further, depending on the compounds, the preparation method can be carried out while changing the sequence of the production processes.

(Production Process 1)

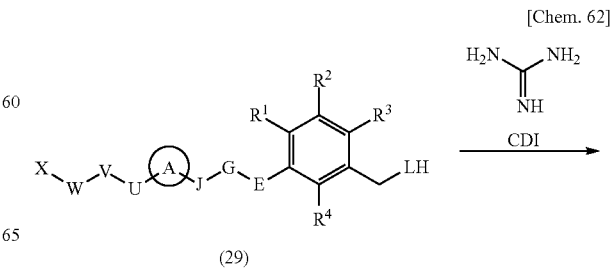

[Chem. 62]

(29)

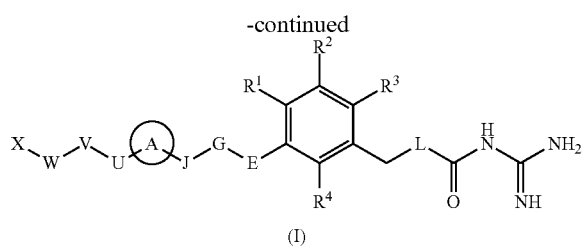

(I)

The compound (I) of the present invention can be obtained by the condensation of the compound (29) with guanidine in the presence of 1,1'-carbonyldiimidazole (CDI).

In this reaction, the compound (29) and guanidine in an equivalent amount or an excess amount are used, and a mixture thereof is stirred in a range of from cooling to heating, preferably at −20° C. to 60° C., usually for about 0.1 hours to 5 days, in a solvent which is inert to the reaction, in the presence of CDI. The solvent as used herein is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, dioxane, dimethoxyethane, and the like, DMF, DMSO, EtOAc, acetonitrile, or water, and a mixture thereof. It may be in some cases advantageous for smooth progress of the reaction to carry out the reaction in the presence of organic bases such as triethylamine, N,N-diisopropylethylamine, N-methylmorpholine, DBU, and the like, or inorganic bases such as sodium hydride, potassium carbonate, sodium carbonate, potassium hydroxide, and the like.

[Document]
Synthesis 2006, 4, 629-632

(Starting Material Synthesis 1)

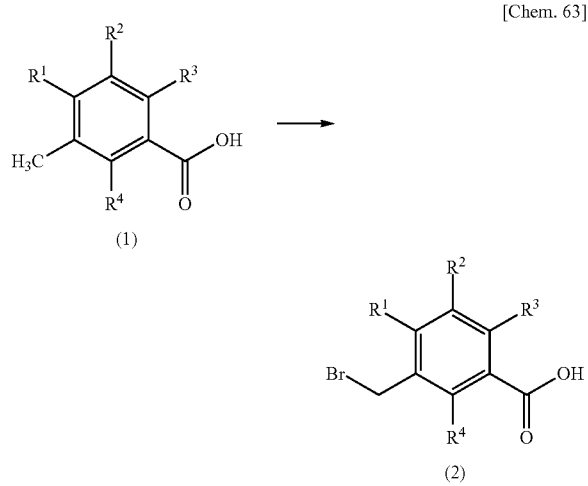

[Chem. 63]

The compound (2) can be obtained by the bromination reaction of the compound (1).

For the bromination reaction, the compound (1) and a brominating agent in an equivalent amount or an excess amount are used, and a mixture thereof is stirred in a range of from cooling to heating and refluxing, preferably at −20° C. to 200° C., and more preferably at a temperature from −10° C. to 150° C., usually for about 0.1 hours to 5 days, without a solvent or in a solvent which is inert to the reaction. The solvent as used herein is not particularly limited, but examples thereof include alcohols such as methanol, ethanol, tert-butanol, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, and a mixture thereof. It may be in some cases advantageous for smooth progress of the reaction to carry out the reaction in the presence of a Lewis acid such as aluminum chloride ($AlCl_3$), boron trifluoride ($BF_3$), and the like, or a radical initiator such as α,α'-azobisisobutyronitrile (AIBN) and the like. Examples of the brominating reagent include N-bromosuccinimide, in addition to bromine ($Br_2$).

(Starting Material Synthesis 2)

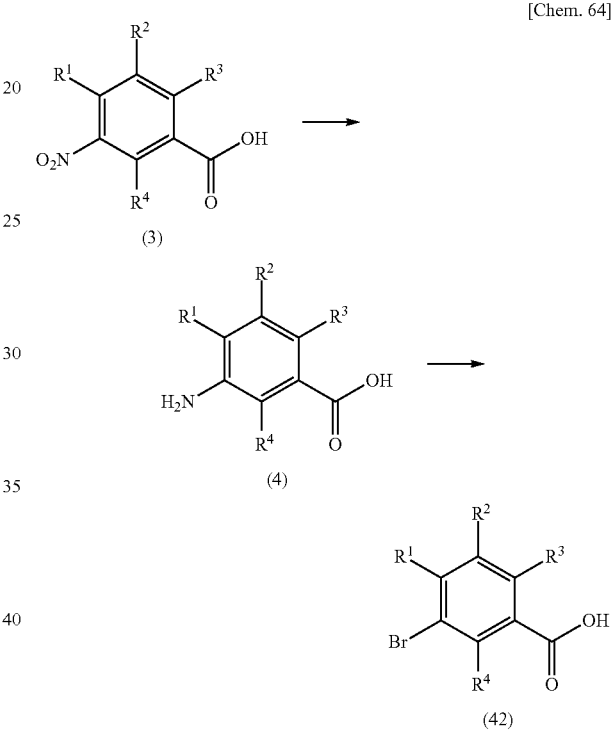

[Chem. 64]

The compound (4) can be obtained by the reduction reaction of a compound (3).

In this reaction, the compound (3) is treated by using a reducing agent in an equivalent amount or an excess amount, or a metallic catalyst in a catalytic amount or an excess amount in a range of from cooling to heating, preferably at −20° C. to 80° C., usually for about 0.1 hours to 3 days, in a solvent which is inert to the reaction. The solvent as used herein is not particularly limited, but examples thereof include ethers such as diethyl ether, tetrahydrofuran, dioxane, dimethoxyethane, and the like, alcohols such as methanol, ethanol, 2-propanol, and the like, aromatic hydrocarbons such as benzene, toluene, xylene, and the like, N,N-dimethylformamide, dimethylsulfoxide, ethyl acetate, and a mixture thereof. As the reducing agent, metal reducing agents such as zinc, iron, tin, and the like, and reducing agents described in the documents below are suitably used. Alternatively, in the reaction using a metal catalyst such as palladium, platinum, and the like, hydrogen gas atmosphere or ammonium formate is used as a hydrogen source.

[Documents]

M. Hudlicky, "Reductions in Organic Chemistry, 2nd Ed. (ACS Monograph: 188)", ACS, 1996

R. C. Larock, "Comprehensive Organic Transformations", 2nd Ed., VCH Publishers, Inc., 1999

T. J. Donohoe, "Oxidation and Reduction in Organic Synthesis (Oxford Chemistry Primers 6)", Oxford Science Publications, 2000

"Jikken Kagaku Koza" (Courses in Experimental Chemistry) (5th Edition), edited by The Chemical Society of Japan, Vol. 14 (2005) (Maruzen)

The compound (42) can be obtained by subjecting the compound (4) to a Sandmeyer's Reaction.

In this reaction, the compound (4) is converted into a diazonium salt by reaction of the compound (4) in the presence of hydrogen halide and sodium nitrite in an equivalent amount or an excess amount, in a range of from cooling to heating, preferably at −20° C. to 80° C., usually for about 0.1 hours to 3 days, in a solvent which is inert to the reaction. The solvent as used herein is not particularly limited, but examples thereof include ethers such as diethyl ether, tetrahydrofuran, dioxane, dimethoxyethane, and the like, alcohols such as methanol, ethanol, 2-propanol, and the like, aromatic hydrocarbons such as benzene, toluene, xylene, and the like, N,N-dimethylformamide, dimethylsulfoxide, ethyl acetate, and a mixture thereof. Next, the compound (42) can be obtained by reaction of the obtained diazonium salt of the compound (4) in the presence of copper (I) halide in an equivalent amount or an excess amount, in a range of from room temperature to heating, preferably at −20° C. to 80° C., usually for about 0.1 hours to 3 days, in a solvent which is inert to the reaction. The solvent as used herein is not particularly limited, but examples thereof include ethers such as diethyl ether, tetrahydrofuran, dioxane, dimethoxyethane, and the like, alcohols such as methanol, ethanol, 2-propanol, and the like, aromatic hydrocarbons such as benzene, toluene, xylene, and the like, N,N-dimethylformamide, dimethylsulfoxide, ethyl acetate, and a mixture thereof. Further, examples of the copper (I) halide as used herein include copper (I) chloride and copper (I) bromide.

(Starting Material Synthesis 3)

[Chem. 65]

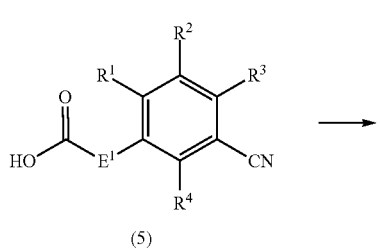

(5)

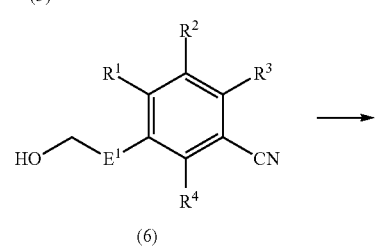

(6)

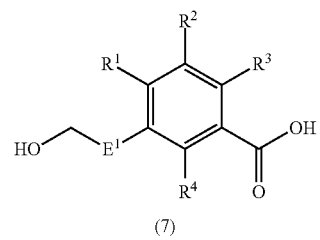

(7)

(wherein $E^1$ represents lower alkylene which may be substituted having a number of carbon atoms one less than that of carbon atoms in lower alkylene which may be substituted in E).

The compound (6) can be obtained by the reduction reaction of the compound (5).

In this reduction reaction, the compound (5) is converted into an ester or treated with CDI, and then treated with a reducing agent in an equivalent amount or an excess amount in a range of from cooling to heating, preferably at −78° C. to 120° C., usually for about 0.1 hours to 3 days, in a solvent which is inert to the reaction. The solvent as used herein is not particularly limited, but examples thereof include ethers such as diethyl ether, tetrahydrofuran, dioxane, dimethoxyethane, and the like, aromatic hydrocarbons such as benzene, toluene, xylene, and the like, and a mixture thereof. As the reducing agent, sodium borohydride, diisobutylaluminum hydride, or the like is suitably used.

A compound (7) can be obtained by the hydrolysis reaction of a compound (6).

In this hydrolysis reaction, the compound (6) is treated with an acid or base in an equivalent amount or an excess amount in a range of from cooling to heating, preferably at 25° C. to 120° C., usually for about 0.1 hours to 3 days, in a solvent which is inert to the reaction. The solvent as used herein is not particularly limited, but examples thereof include ethers such as diethyl ether, tetrahydrofuran, dioxane, dimethoxyethane, and the like, aromatic hydrocarbons such as benzene, toluene, xylene, and the like, N,N-dimethylformamide, dimethylsulfoxide, water, and a mixture thereof. As the acid, for example, hydrochloric acid, sulfuric acid, or the like is suitably used. As the base, sodium hydroxide, lithium hydroxide, or the like is suitably used, and the reaction is carried out in the presence of hydrogen peroxide, it maybe advantageous in the reaction to proceed smoothly.

[Documents]

B. M. Trost, "Comprehensive Organic Synthesis", Vol. 7, 1991

M. Hudlicky, "Oxidation in Organic Chemistry (ACS Monograph: 186)", ACS, 1990

"Jikken Kagaku Koza" (Courses in Experimental Chemistry) (5th Edition), edited by The Chemical Society of Japan, Vol. 17 (2005) (Maruzen)

(Starting Material Synthesis 4)

[Chem. 66]

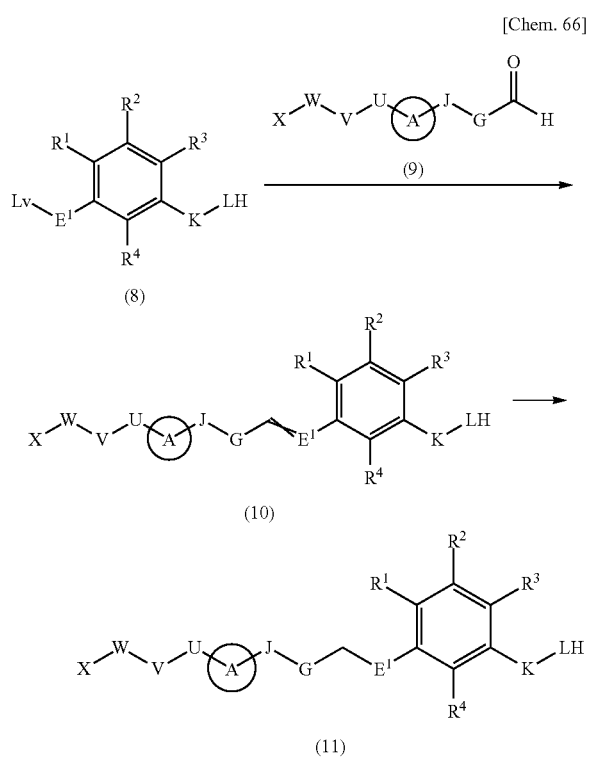

(wherein Lv represents a leaving group, K represents CH$_2$ or C(=O), and when K is C(=O), L represents O).

A compound (10) can be synthesized by subjecting the compound (8) to a Wittig reaction. Here, examples of the leaving group, Lv, include halogen, a methanesulfonyloxy group, a p-toluenesulfonyloxy group, and the like.

In this reaction, the compound (8) is converted into a phosphonium salt in the presence of a phosphorous compound in an equivalent amount or in an excess amount in a range of from cooling to heating, preferably at −20° C. to 150° C., usually for about 0.1 hours to 3 days, in a solvent which is inert to the reaction. The solvent as used herein is not particularly limited, but examples thereof include ethers such as diethyl ether, tetrahydrofuran, dioxane, dimethoxyethane, and the like, aromatic hydrocarbons such as benzene, toluene, xylene, and the like, N,N-dimethylformamide, dimethylsulfoxide, and a mixture thereof. As the phosphorous compound, for example, an alkyltriphenylphosphonium salt is suitably used, and specific examples thereof include (methoxymethyl)triphenylphosphonium chloride, (methylthiomethyl)triphenylphosphonium chloride, and the like. Thereafter, the phosphonium salt of the compound (8) and the compound (9) are converted into the compound (10) by treating them in a range of from cooling to heating, preferably at −20° C. to 80° C., usually for about 0.1 hours to 3 days, in a solvent which is inert to the reaction. The solvent as used herein is not particularly limited, but examples thereof include ethers such as diethyl ether, tetrahydrofuran, dioxane, dimethoxyethane, and the like, aromatic hydrocarbons such as benzene, toluene, xylene, and the like, N,N-dimethylformamide, dimethylsulfoxide, and a mixture thereof. It may be in some cases advantageous for smooth progress of the reaction to carry out the reaction in the presence of a base such as sodium bis(trimethylsilyl)amide, n-butyllithium, potassium tert-butoxide, sodium ethoxide, sodium methoxide, and the like.

The compound (11) can be obtained by the hydrogenation reaction of the compound (10).

In this reaction, the compound (10) is stirred under hydrogen atmosphere, preferably at normal pressure to 3 atm., in a range of from cooling to heating, preferably at room temperature to 50° C., usually for about 1 hour to 5 days, in the presence of a metallic catalyst, in a solvent which is inert to the reaction. The solvent as used herein is not particularly limited, but examples thereof include alcohols such as methanol, ethanol, 2-propanol, and the like, ethers such as diethyl ether, tetrahydrofuran, dioxane, dimethoxyethane, and the like, water, ethyl acetate, N,N-dimethylformamide, dimethylsulfoxide, and a mixture thereof. As the metal catalyst, palladium catalysts such as palladium carbon, palladium black, palladium hydroxide, and the like, platinum catalysts such as a platinum plate, platinum oxide, and the like, nickel catalysts such as reduced nickel, Raney nickel, and the like, rhodium catalysts such as tetrakistriphenylphosphine chlororhodium, and the like, or iron catalysts such as reduced iron and the like are suitably used. Instead of the hydrogen gas, formic acid or ammonium formate in an equivalent amount or an excess amount may also be used as a hydrogen source, relative to the compound (10).

[Documents]

M. Hudlicky, "Reductions in Organic Chemistry, 2$^{nd}$ ed (ACS Monograph: 188)", ACS, 1996

"Jikken Kagaku Koza" (Courses in Experimental Chemistry) (5$^{th}$ Edition), edited by The Chemical Society of Japan, Vol. 19 (2005) (Maruzen)

(Starting Material Synthesis 5)

[Chem. 67]

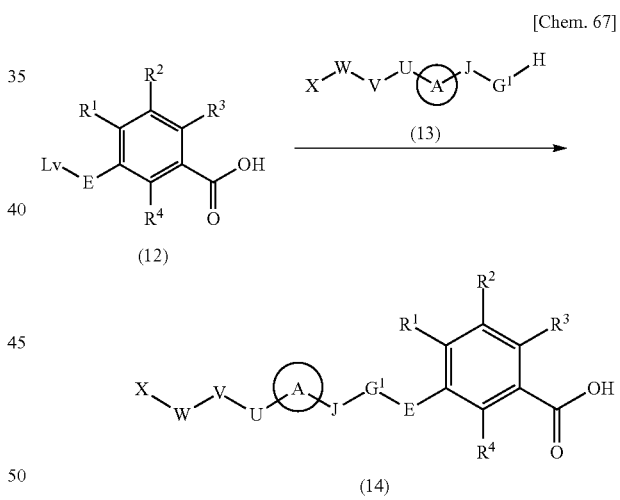

(wherein G$^1$ represents O, NH, N(lower alkyl which may be substituted)).

The compound (14) can be obtained by the substitution reaction of the compound (12) and the compound (13).

In this reaction, the compound (12) and the compound (13) in an equivalent amount or an excess amount are used, a mixture thereof is stirred in a range of from cooling to heating and refluxing, preferably at 0° C. to 200° C., and more preferably at 60° C. to 150° C., usually for 0.1 hours to 5 days in a solvent which is inert to the reaction or without a solvent. It is in some cases advantageous for smooth progress of the reaction to carry out the reaction under irradiation with microwaves. The solvent used herein is not particularly limited, but examples thereof include alcohols such as methanol, ethanol, tert-butanol, and the like, aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. It may be advantageous in some cases for the smooth progress of the reaction to carry out the reaction in the presence of an organic base such as triethylamine, N,N-diisopropylethylamine, N-methylmorpholine, and the like, or an inorganic base such as sodium tert-butoxide, potassium carbonate, sodium bis(methylsilyl)amide, sodium carbonate, potassium hydroxide, sodium hydride and the like.

Furthermore, the reaction may be carried out by using a catalyst which is not particularly limited, but includes catalysts used for Ullmann reaction, a Buchwald-Hartwig reaction, or the like. The catalyst as used herein is not particularly limited, but a suitable combination of tris(dibenzylideneacetone)dipalladium, tetrakis(triphenylphosphine)palladium, or the like with 1,1'-binaphthalene-2,2'-diylbis(diphenylphosphine), 4,5-bis(diphenylphosphino)-9,9'-dimethylxanthene (Xantphos), 2-dicyclohexylphosphino-2',6'-dimethoxybiphenyl (SPhos), 2-dicyclohexylphosphino-2',4',6'-triisopropylbiphenyl (XPhos), and the like can be used.

[Documents]

S. R. Sandler and W. Karo, "Organic Functional Group Preparations", 2$^{nd}$ Ed., Vol. 1, Academic Press Inc., 1991

"Jikken Kagaku Koza" (Courses in Experimental Chemistry) (5$^{th}$ Edition), edited by The Chemical Society of Japan, Vol. 14 (2005) (Maruzen)

Synthesis 2006, 4, 629 to 632

(Starting Material Synthesis 6)

[Chem. 68]

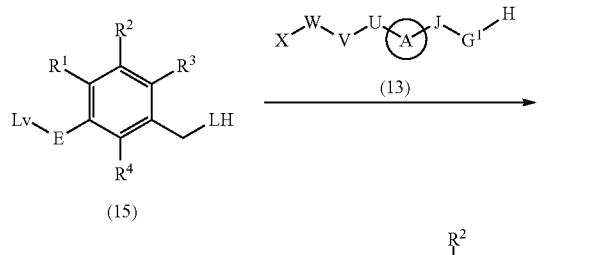

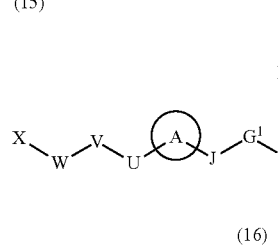

The compound (16) can be obtained by the substitution reaction of the compound (15) and the compound (13). This reaction can be carried out using the same conditions as for the substitution reaction in Starting Material Synthesis 5.

(Starting Material Synthesis 7)

[Chem. 69]

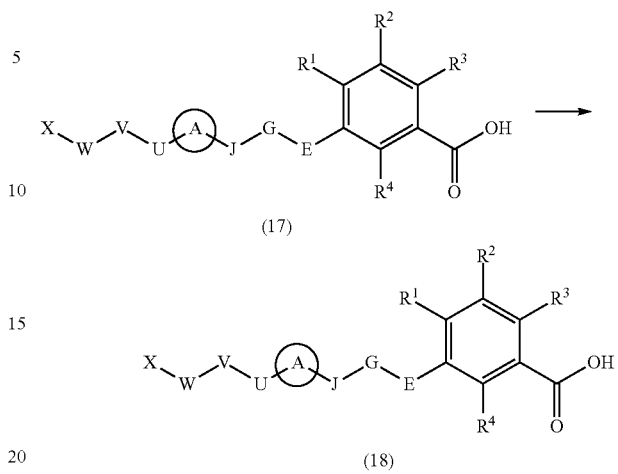

The compound (18) can be obtained by the reduction reaction of the compound (17). The present reaction can be carried out using the same reaction conditions in Starting Material Synthesis 3. As the reducing agent in the present reaction, lithium aluminum hydride, borane, sodium borohydride, diisobutylaluminum hydride, or the like can be used.

(Starting Material Synthesis 8)

[Chem. 70]

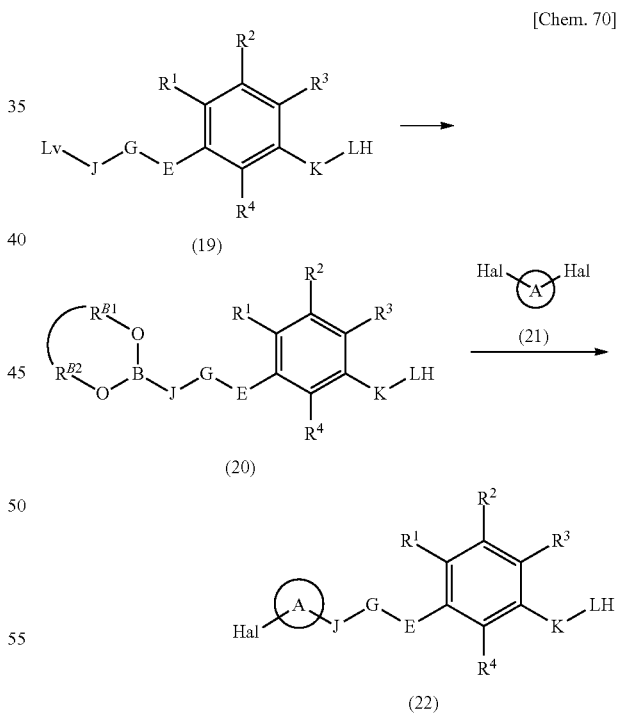

($R^{B1}$ and $R^{B2}$ are the same as or different from each other, and are H or lower alkyl, or $R^{B1}$ and $R^{B2}$ are combined with each other to represent lower alkylene).

The compound (20) can be obtained by formation reaction of boronate ester of the compound (19).

For the reaction, a mixture of the compound (19) and the reagent for the formation of boronate ester in an equivalent amount or an excess amount is stirred in a range of from cooling to heating, preferably at −20° C. to 60° C., usually for about 0.1 hours to 5 days, in a solvent which is inert to the reaction, in the presence of an organic metal compound. The solvent as used herein is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, dioxane, dimethoxyethane, and the like, DMF, DMSO, EtOAc, acetonitrile, water, and a mixture thereof. Examples of the reagent for the formation of boronate ester include triisopropyl borate, tributyl borate, and the like. Examples of the organic metal compound as used in the present reaction include organic lithium compounds such as n-butyl lithium and the like.

Furthermore, the compound (22) can be obtained by the coupling reaction of the compound (20) and the compound (21).

In this reaction, a mixture of the compound (20) and the compound (21) in an equivalent amount or an excess amount is stirred in a range of from cooling to heating and refluxing, and preferably 0° C. to 80° C., in a solvent which is inert to the reaction or without a solvent, usually for 0.1 hours to 5 days. The solvent as used herein is not particularly limited, but examples thereof include aromatic hydrocarbons such as benzene, toluene, xylene, and the like, ethers such as dimethyl ether, diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile and a mixture thereof. It may be in some cases advantageous for smooth progress of the reaction to carry out the reaction in the presence of organic bases such as triethylamine, N,N-diisopropylethylamine, N-methylmorpholine, and the like, or inorganic bases such as potassium carbonate, sodium carbonate, potassium phosphate, potassium hydroxide, and the like.

Furthermore, the reaction can also be carried out using, for example, a catalyst used for the Suzuki-Miyaura cross-coupling reaction, but is not limited thereto. The catalyst as used herein is not particularly limited, but tetrakis(triphenylphosphine)palladium (0), palladium acetate (II), dichloro[1,1'-bis(diphenylphosphenylphosphino)ferrocene]palladium (II), bistriphenylphosphine palladium chloride (II), or the like can be used. Further, the coupling reaction can also be carried out using metal palladium (0).

(Starting Material Synthesis 9)

[Chem. 71]

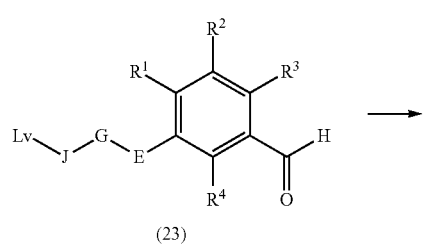

(23)

-continued

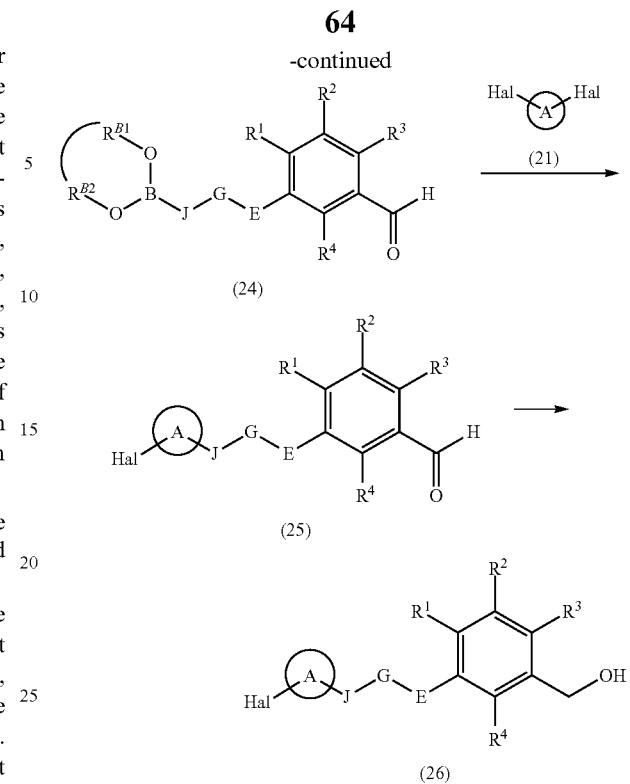

The compound (24) can be prepared by formation reaction of boronate ester of the compound (23). This reaction can be carried out using the same reaction conditions as in Starting Material Synthesis 8 as described above.

The compound (25) can be obtained by the coupling reaction of the compound (24) and the compound (21). This reaction can be carried out using the same reaction conditions as in Starting Material Synthesis 8 as described above.

Furthermore, a compound (26) can be obtained by the reduction reaction of the compound (25). In this reduction reaction, the compound (25) is treated with a reducing agent in an equivalent amount or an excess amount in a range of from cooling to heating, preferably at −78° C. to 120° C., usually for about 0.1 hours to 3 days, in a solvent which is inert to the reaction. The solvent as used herein is not particularly limited, but examples thereof include ethers such as diethyl ether, tetrahydrofuran, dioxane, dimethoxyethane, and the like, aromatic hydrocarbons such as benzene, toluene, xylene, and the like, and a mixture thereof. As the reducing agent, sodium borohydride, diisobutylaluminum hydride, or the like is suitably used.

(Starting Material Synthesis 10)

[Chem. 72]

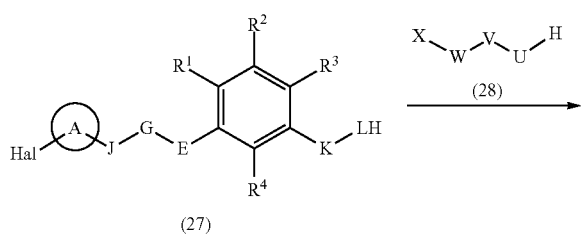

(27)

-continued

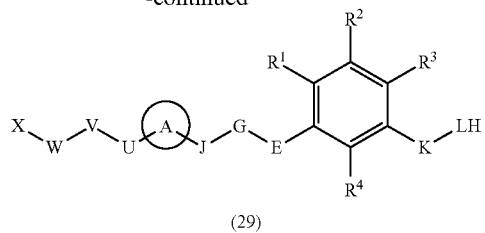

(29)

(Starting Material Synthesis 11)

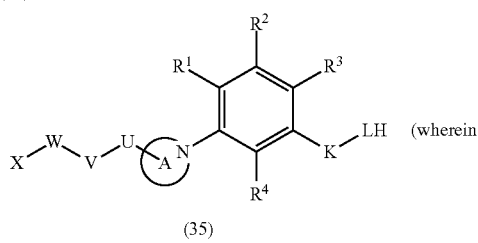

The compound (30) can be prepared by the boronic acid esterification reaction of the compound (29). This reaction can be carried out using the same reaction conditions as in Starting Material Synthesis 8 as described above.

The compound (31) can be obtained by the hydrolysis reaction of the compound (30).

In this reaction, a mixture of the compound (30) and water in an equivalent amount or an excess amount is stirred in a range of from cooling to heating and refluxing, preferably at 0° C. to 80° C., usually for about 0.1 hours to 5 hours, in a solvent which is inert to the reaction or without a solvent. The solvent as used herein is not particularly limited, but examples thereof include aromatic hydrocarbons such as benzene, toluene, xylene, and the like, ethers such as dimethyl ether, diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. Examples of the oxidant include sodium perborate.hexahydrate, aqueous hydrogen peroxide, and the like.

The compound (29) can be obtained by the substitution reaction of the compound (27) and the compound (28). This reaction can be carried out using the same reaction conditions in Starting Material Synthesis 5.

(Starting Material Synthesis 12)

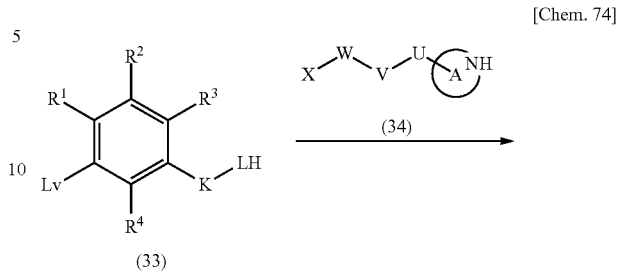

(wherein

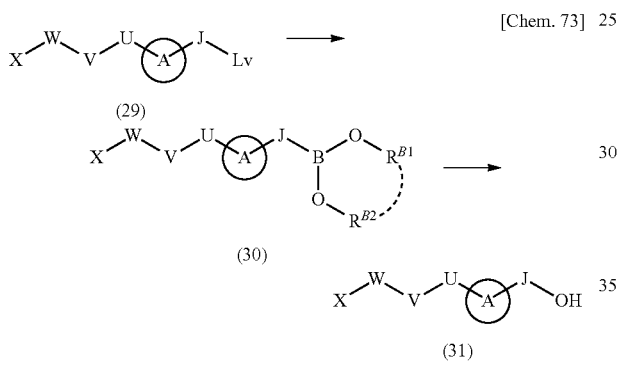

represents a nitrogen-containing hetero ring group which may be substituted, and the substituent represents an acceptable substituent in the hetero ring group which may be substituted in A).

The compound (35) can be obtained by the substitution reaction of the compound (33) and the compound (34). This reaction can be carried out using the same conditions as for the substitution reaction in Starting Material Synthesis 5.

(Starting Material Synthesis 13)

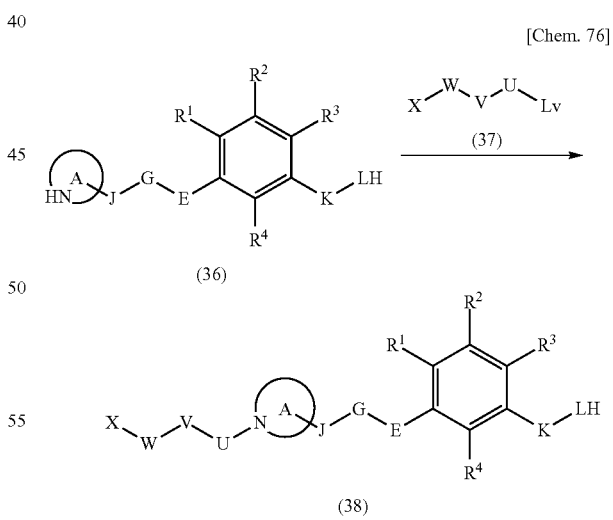

The compound (38) can be obtained by the substitution reaction of the compound (36) and the compound (37). This reaction can be carried out using the same conditions as for the substitution reaction in Starting Material Synthesis 5.

(Starting Material Synthesis 14)

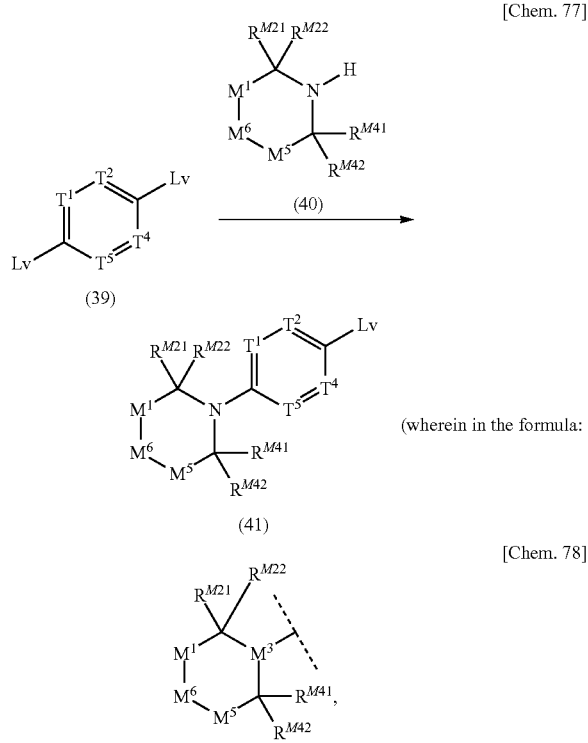

[Chem. 77]

(wherein in the formula:

[Chem. 78]

$M^1$ is a single bond or $CR^{M11}R^{M12}$, $M^3$ is $CR^{M31}$ or N, $M^5$ is a single bond or $(CR^{M51}R^{M52})_n$, $M^6$ is $CR^{M61}R^{M62}$, O, or $NR^{M63}$, wherein either one of $M^3$ and $M^6$ is N, $R^{M11}$, $R^{M12}$, $R^{M21}$, $R^{M22}$, $R^{M31}$, $R^{M41}$, $R^{M42}$, $R^{M51}$, $R^{M51}$, $R^{M61}$, $R^{M62}$ and $R^{M63}$ are the same as or different from each other, and are H, OH, halogen, lower alkyl which may be substituted, O-(lower alkyl which may be substituted), or $SO_2$-(lower alkyl which may be substituted), or $R^{M21}$ and $R^{M31}$ may be combined with each other to form a new bond, or $R^{M11}$ and $R^{M12}$, $R^{M21}$ and $R^{M22}$, $R^{M41}$ and $R^{M42}$, $R^{M51}$ and $R^{M52}$, or $R^{M61}$ and $R^{M62}$ may be combined with each other to form oxo (=O), and n is 1 or 2).

The compound (41) among the compounds (37) can be obtained by the substitution reaction of the compound (39) and the compound (40). This reaction can be carried out using the same conditions as for the substitution reaction in Starting Material Synthesis 5.

The compounds of the formula (I) can be isolated and purified as their free compounds, salts, hydrates, solvates, or polymorphic crystalline substances thereof. The salts of the compound of the formula (I) can be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting compound.

The pharmacological activity of the compound of the formula (I) was confirmed by the tests shown below.

Test Example 1

Inhibitory Effect on Human VAP-1 Enzyme (SSAO) Activity

A human VAP-1 enzyme (SSAO) (reference: J Exp Med. 1998 Jul. 6; 188(1): 17 to 27) activity was measured by a radiochemistry-enzymatic assay using $^{14}$C-benzylamine as an artificial substrate. After homogenizing CHO (Chinese Hamster Ovary) cells stably expressing a human VAP-1 enzyme (SSAO) in a 50 mM phosphate buffer containing 1% NP-40, an enzyme suspension was obtained by taking the supernatant obtained by centrifugation. The enzyme suspension was preincubated with the compound of the present invention in a 96-well microplate at room temperature for 30 minutes. Subsequently, the enzyme suspension was incubated with $^{14}$C-benzylamine (a final concentration of $1 \times 100^{-5}$ mol/L) to a final volume of 50 mL at 37° C. for 1 hour. The enzymatic reaction was stopped by the addition of 2 mol/L (50 μL) of citric acid. The oxidation products were extracted directly into a 200 μL toluene scintillator, and the radioactivity was measured with a scintillation spectrometer.

Test Example 2

Inhibitory Effect on Rat VAP-1 Enzyme (SSAO) Activity

A rat VAP-1 enzyme (SSAO) (reference: Biol Pharm Bull. 2005 March; 28(3): 413-8) activity was measured by a radiochemistry-enzymatic assay using $^{14}$C-benzylamine as an artificial substrate. After homogenizing CHO (Chinese Hamster Ovary) cells stably expressing a rat VAP-1 enzyme (SSAO) in a 50 mM phosphate buffer containing 1% NP-40, an enzyme suspension was obtained by taking the supernatant obtained by centrifugation. The enzyme suspension was preincubated with the compound of the present invention in a 96-well microplate at room temperature for 30 minutes. Subsequently, the enzyme suspension was incubated with $^{14}$C-benzylamine (a final concentration of $1 \times 10^{-5}$ mol/L) to a final volume of 50 mL at 37° C. for 1 hour. The enzymatic reaction was stopped by the addition of 2 mol/L (50 μL) of citric acid. The oxidation products were extracted directly in a 200 μL toluene scintillator, and the radioactivity was measured with a scintillation spectrometer.

The results are shown in Table 1. In addition, the inhibitory activity is expressed as an $IC_{50}$ (nmol/L) value. Further, Ex in the tables represents Example No.

TABLE 1

| Ex | human (nM) | rat (nM) |
|---|---|---|
| 11 | 5.2 | 2.2 |
| 29 | 7.2 | 1.9 |
| 52 | 23 | 1.7 |
| 63 | 3.4 | 1.1 |
| 74 | 5.3 | 1.8 |
| 81 | 9.7 | 3.9 |
| 83 | 25 | 1.9 |
| 105 | 14 | 2.6 |
| 110 | 32 | 1.4 |
| 118 | 29 | 1.7 |
| 126 | 15 | 0.53 |
| 157 | 49 | 2.1 |

TABLE 1-continued

| Ex | human (nM) | rat (nM) |
|---|---|---|
| 178 | 33 | 4.4 |
| 220 | 25 | 1 |
| 273 | 19 | 0.95 |
| 293 | 19 | 0.97 |
| 300 | 19 | 1.7 |
| 304 | 34 | 6.6 |
| 316 | 11 | 0.9 |
| 322 | 51 | 22 |
| 335 | 11 | 2 |
| 551 | 14 | 1.8 |
| 552 | 25 | 5.5 |
| 553 | 20 | 3 |
| 554 | 21 | 0.97 |
| 555 | 20 | 3.5 |
| 556 | 2.7 | 1.3 |
| 557 | 11 | 1.6 |
| 558 | 23 | 1.2 |
| 559 | 4.3 | 0.81 |
| 560 | 9 | 1.4 |
| 561 | 9.6 | 1.6 |
| 562 | 14 | 1.4 |
| 563 | 20 | 1.5 |
| 564 | 19 | 1.5 |
| 565 | 19 | 2.5 |
| 566 | 6.3 | 1.2 |
| 567 | 4.3 | 0.81 |

From these test, it was confirmed that the compound of the present invention has an extremely high inhibitory activity on human and rat VAP-1.

Test Example 3

Inhibitory Effect on Rat VAP-1 Enzyme (SSAO) Activity in Rat Plasma

Eight-week to twelve-week Wistar male rats were fasted for 20 hours, and orally administered with a test drug (0.3 mg/l kg). Heparin blood collection from the tail vein was performed immediately before the administration, and at 1 h, 3 h, 6 h, 12 h, or 24 h after the administration. The resulting blood was subjected to centrifugation at 14000 rpm for 5 minutes to separate plasma, and the VAP-1 enzyme activity in the resulting plasma was measured by a radio-enzyme assay method.

For the radio-enzyme assay method, $^{14}$C-benzylamine which is a synthetic substrate (10 μM) was reacted with the resulting plasma at 37° C., and the resulting metabolite was extracted with a mixture of toluene/ethyl acetate. The radioactivity was measured and taken as a VAP-1 enzyme activity in the plasma. The effect of the test drug was calculated from the inhibitory ratio (%) of the VAP-1 activity after the administration of the test drug relative to the VAP-1 activity in the plasma immediately before the administration. Further, Ex in the tables represents Example No.

Reference Document Diabetologia (1997) 40 1243-1250

TABLE 2

| Ex | Inhibition Ratio (%) | | | | |
|---|---|---|---|---|---|
| | 1 h | 3 h | 6 h | 12 h | 24 h |
| 11 | 64 | 70 | 63 | | 12 |
| 29 | 46 | 60 | 58 | | 22 |
| 52 | 90 | 68 | 52 | 37 | |
| 63 | 83 | 87 | 80 | 68 | |
| 74 | 79 | 74 | 81 | | 40 |
| 81 | 78 | 78 | 78 | 53 | |
| 83 | 34 | 66 | 86 | 53 | |
| 105 | 22 | 38 | 31 | | 6 |
| 110 | 96 | 96 | 95 | | 75 |
| 118 | 87 | 86 | 88 | | 59 |
| 126 | 98 | 97 | 97 | | 69 |
| 157 | 95 | 91 | 80 | | 39 |
| 178 | 63 | 73 | 67 | 80 | |
| 220 | 80 | 80 | 84 | | 27 |
| 273 | 55 | 74 | 54 | | 19 |
| 293 | 59 | 83 | 72 | | 60 |
| 300 | 92 | 93 | 88 | | 85 |
| 304 | 52 | 56 | 56 | | 18 |
| 316 | 91 | 99 | 98 | 91 | |
| 322 | 40 | 55 | 50 | 38 | |
| 335 | 82 | 84 | 86 | 83 | |
| 551 | 68 | 59 | 51 | | 5 |
| 552 | 93 | 81 | 75 | | 24 |
| 553 | 67 | 57 | 50 | | 40 |
| 554 | 99 | 100 | 87 | | 72 |
| 555 | 67 | 69 | 54 | | 27 |
| 556 | 55 | 70 | 46 | | 19 |
| 557 | 53 | 71 | 56 | | 22 |
| 558 | 84 | 87 | 81 | | 62 |
| 559 | 86 | 89 | 82 | | 59 |
| 560 | 89 | 91 | 84 | | 58 |
| 561 | 91 | 92 | 85 | | 64 |
| 562 | 79 | 81 | 78 | | 37 |
| 563 | 69 | 77 | 70 | | 43 |
| 564 | 89 | 90 | 85 | | 59 |
| 565 | 77 | 83 | 71 | | 47 |
| 566 | 75 | 74 | 70 | | 38 |
| 567 | 86 | 89 | 82 | | 59 |

Test Example 4

Effect on Albuminuria in Rats with Diabetes Mellitus

Seven- to eight-week SD rats (having weights up to 200 to 250 g during fasting) were used and fasted for 20 hours, and then intraperitoneally administered with 60 mg/ml/kg of streptozotocin (STZ) prepared with a 2 mmol/l citric acid buffer (pH 4.5). At the same time, the control rats were injected with the same amount of a 2 mmol/l citric acid buffer (pH 4.5). The blood glucose value was measured using a colorimetric method, and the rats that had showed a value of 350 mg/dl blood glucose levels on day 3 after the treatment with STZ were diagnosed with diabetes mellitus.

The test substance was given daily for 4 weeks after the treatment with STZ. After 4 weeks of the treatment with the test substance, 24-hour urine collection was performed using metabolic cages.

The amounts of urinary albunmin excretion after 4 weeks were 67 (mg/gCr) and 236 (mg/gCr) with the control group and the STZ-treated group, respectively, and the amount of urinary albunmin excretion of the STZ-treated group increased 3.5 times than that of the control group. On the other hand, as a result of the oral administration of the compound of Example 11 in the amount of 0.3 mg/kg once daily, an amount of urinary albunmin excretion was 103 (mg/gCr), which was decreased to 1.5 times than that of the control group.

Furthermore, in the test with the compound of Example 557, the amount of urinary albunmin excretion after 4 weeks were 45 (mg/gCr) and 234 (mg/gCr) with the control group and the STZ-treated group, respectively, and the amount of urinary albunmin excretion of the STZ-treated group was increased to 5.2 times than that of the control group. On the other hand, as a result of the oral administration of the compound of Example 557 in the amount of 0.3 mg/kg once daily, amount of urinary albunmin excretion was 105 (mg/gCr), which was decreased to 2.3 times than that of the control group.

Test Example 5

Effect on Eye Permeability in Rats with Diabetes Mellitus

Seven-week Long-Evans rats (having weights up to 200 to 250 g during fasting) were used and fasted for 20 hours, and then intraperitoneally administered with 60 mg/ml/kg of streptozotocin (STZ) prepared with a 2 mmol/l citric acid buffer (pH 4.5). At the same time, the control rats were injected with the same amount of a 2 mmol/l citric acid buffer (pH 4.5). The blood glucose value was measured using a colorimetric method, and the rats that had showed a value of 350 mg/dl blood glucose levels on day 3 after the treatment with STZ were diagnosed with diabetes mellitus.

The test substance was given daily for 2 weeks after the treatment with STZ. After 2 weeks of the treatment with the test substance, the retinal vascular permeability was examined after 24 hours from the date of the final administration. The retinal permeability was examined on the basis of the dye leakage into the retina after 2 h from the tail vein administration of 40 mg/ml/kg of Evans Blue Dye solution. The permeability as an index of the evaluation was expressed in the ratio of the retinal concentration/plasma concentration of the Evans Blue Dye. Measurement of the Evans Blue Dye concentration was carried out by measuring the absorbance using a plate reader.

After the result of the tests above, it was confirmed that some of the compounds of the formula (I) constantly exhibit a VAP-1 activity in blood in the oral administration test with rats. Therefore, the compounds can be used for treatment of VAP-1-related diseases or the like.

In the present specification, the thermal analysis measurement was carried out in the following order.

(Differential Scanning Calorimetry (DSC Analysis))

The DSC analysis was carried out using a Q1000 manufactured by TA Instruments. Approximately 2 mg of a sample was charged in an exclusively-used aluminum-made sample pan, and the change in heat amount generated between the sample and a reference (an empty aluminum sample pan), with a measurement range from room temperature to 300° C. under nitrogen atmosphere (50 mL/min) and a temperature elevating rate of 10° C./min were continuously measured and recorded. Furthermore, the devices including data processing was handled in accordance to the methods and procedures as instructed in each device.

Furthermore, the term "around" as used in the values of the endothermic onset temperature in DSC largely means the values of the temperature of the endothermic onset (extrapolation initiation), preferably, it means that the values be not more or less than the values by 2° C., and more preferably, it means that the values be not more or less than the values by 1° C.

A pharmaceutical composition containing one or two or more kinds of the compound of the formula (I) or a salt thereof as an active ingredient can be prepared using excipients that are usually used in the art, that is, excipients for pharmaceutical preparations, carriers for pharmaceutical preparations, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, ophthalmic solutions, eye ointments, transdermal liquid preparations, ointments, transdermal patches, transmucosal liquid preparations, transmucosal patches, inhalers, and the like.

The solid composition for use in the oral administration is used in the form of tablets, powders, granules, or the like. In such a solid composition, one or more active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics, or antiseptics.

The injections for parenteral administration include sterile aqueous or non-aqueous solutions, suspensions and emulsions. The aqueous solvent includes, for example, distilled water for injection and physiological saline. Examples of the non-aqueous solvent include alcohols such as ethanol. Such a composition may further contain a tonicity agent, an antiseptic, a moistening agent, an emulsifying agent, a dispersing agent, a stabilizer, or a solubilizing aid. These are sterilized, for example, by filtration through a bacteria retaining filter, by blending a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, poultices, sprays, lotions, eye drops, eye ointments, and the like. The agents contain generally used ointment bases, lotion bases, aqueous or non-aqueous liquid preparations, suspensions, emulsions, and the like.

As the transmucosal agents such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizer, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 separate portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided upon in response to the individual case by taking the symptoms, the age, and the gender, and the like into consideration.

The compound of the formula (I) can be used in combination with various therapeutic or prophylactic agents for the diseases for which the compound of the formula (I) is considered to be effective, as described above. The combined preparation may be administered simultaneously, or separately and continuously, or at a desired time interval. The preparations to be administered simultaneously may be a blend, or may be prepared individually.

EXAMPLES

Hereinbelow, the preparation methods for the compound of the formula (I) will be described in more detail with reference to Examples. Further, the present invention is not limited to only the preparation methods of the specific Examples and Preparation Examples are shown below, but the compound of the formula (I) can be prepared by any combination of the preparation methods or the methods that are apparent to a person skilled in the art.

Furthermore, the following abbreviations may be used in some cases in the Examples, Preparation Examples, and Tables below.
Rf: Preparation Example No.,
Ex: Example No.,
Data: Physicochemical data,
ESI+: representing m/z values in ESI-MS (positive ions), and representing [M+H]$^+$ peaks unless otherwise specified,
APCI/ESI+: representing m/z values in APCI-MS (positive ions) and ESI-MS (positive ions), and representing [M+H]$^+$ peaks unless otherwise specified,
FAB+: representing m/z values in FAB-MS (positive ions), and representing [M+H]$^+$ peaks unless otherwise specified,
EI: representing m/z values in EI-MS (positive ions), and representing [M] peaks unless otherwise specified,
NMR-DMSO-d$_6$: δ (ppm) in $^1$H-NMR in DMSO-d$_6$,
NMR-CDCl$_3$: δ (ppm) in $^1$H-NMR in CDCl$_3$,
in the present specification, in the formula:

[Chem. 79]

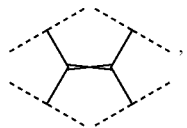

the double bond indicates that a mixture of isomers of E isomers and Z isomers exists,
Structure: Structural formula (A case where HCl, PA, or L-TA is described in the structural formula means that the compound forms a salt with the acid. Further, a case where a numeral is present before the acid means that the compound forms a salt having a valence with that number, for example, 2HCl means formation of dihydrochloride).
cis: indicating that a steric structure in the structural formula is in the cis configuration,
trans: indicating that a steric structure in the structural formula is in the trans configuration,
Syn: preparation method (in which the numeral alone shows that the compound is prepared by the same preparation method as the compound having the Example No. and R prefixed before the numeral shows that the compound is prepared by the same preparation method as the compound having the Preparation Example No.),
L-TA: L-tartaric acid,
HCl: hydrochloric acid,
PA: phosphoric acid,
Boc: tert-butoxycarbonyl group,
CDI: 1,1'-carbonyldiimidazole
DMSO: dimethylsulfoxide,
THF: tetrahydrofuran,
EtOAc: ethyl acetate,
MgSO$_4$: anhydrous magnesium sulfate,
DMF: N,N-dimethylformamide,
Na$_2$SO$_4$: anhydrous sodium sulfate,
MeOH: methanol,
EtOH: ethanol
CHCl$_3$: chloroform,
NMP: N-methyl-2-pyrrolidone,
WSC: 1-(3-dimethylaminopropyl)-3-ethylcarbodiimide,
HOBt: 1-hydroxybenzotriazole,
TEA: triethylamine,
DIPEA: diisopropylethylamine,
MeCN: acetonitrile,
TFA: trifluoroacetic acid,
DME: 1,2-dimethoxyethane,
DBU: diazabicycloundecene,
TBAF: tetrabutylammonium fluoride,
BINAP: 1,1'-binaphthalene-2,2'-diylbis(diphenylphosphine),
Pd$_2$(dba)$_3$: tris(dibenzylideneacetone)dipalladium,
NaBH$_4$: sodium borohydride,
DIAD: diisopropyl azodicarboxylate,
DCE: 1,2-dichloroethane,
MsCl: methanesulfonyl chloride,
TBSCl: tert-butyldimethylchlorosilane,
Boc$_2$O: di-tert-butyldicarbonate,
DMAP: 4-(dimethylamino)pyridine,
iPrNH$_2$: isopropylamine,
NaH: sodium hydride (55% suspended in oil),
NaOH: sodium hydroxide,
IPA: isopropyl alcohol,
NaHCO$_3$: sodium hydrogen carbonate,
CH$_2$Cl$_2$: dichloromethane,
NH$_3$: ammonia,
M: mol/L.

Preparation Example 12

Tetrakis(triphenylphosphine)palladium (36 mg) and sodium carbonate (330 mg) were added to a mixture of 4-[4-(4,4,5,5-tetramethyl-1,3,2-dioxaborolan-2-yl)phenyl]morpholine (300 mg), (3-bromophenyl)methanol (233 mg), DME (6 ml), and water (3 ml), followed by stirring at 80° C. overnight, and then the reaction mixture was concentrated under reduced pressure. Water and CHCl$_3$ were added to the obtained residue, and the organic layer was dried over MgSO$_4$, and then concentrated under reduced pressure. The obtained residue was purified by silica gel column chromatography (EtOAc/hexane/CHCl$_3$) to obtain [4'-(morpholin-4-yl)biphenyl-3-yl]methanol (242 mg).

Preparation Example 32

Under argon atmosphere, sodium carbonate (1000 mg) and tetrakis(triphenylphosphine)palladium (170 mg) were added to a mixture of (2-fluoro-3-formylphenyl)boronic acid (700 mg), tert-butyl 4-{[(trifluoromethyl)sulfonyl]oxy}-3,6-dihydropyridine-1(2H)-carboxylate (1000 mg), toluene (15 ml), EtOH (5 ml) and water (5 ml) followed by stirring at 80° C. overnight. The reaction mixture was concentrated under reduced pressure, and CHCl$_3$ and a saturated aqueous sodium hydrogen carbonate solution were then added thereto. The organic layer was dried over Na$_2$SO$_4$ and concentrated under reduced pressure. The obtained residue was purified by silica gel column chromatography (hexane/EtOAc). The purified product thus obtained was mixed with EtOH, and NaBH$_4$ (120 mg) was added thereto, followed by stirring at room temperature for 30 minutes. The reaction mixture was concentrated under reduced pressure, and then EtOAc and water were added thereto. The organic layer was dried over Na$_2$SO$_4$ and concentrated under reduced pressure. The obtained residue was purified by silica gel column chromatography (hexane/EtOAc) to obtain tert-butyl 4-[2-fluoro-3-(hydroxymethyl)phenyl]-3,6-dihydropyridine-1(2H)-carboxylate (637 mg).

Preparation Example 33

(3-Bromophenyl)methanol (10 g) was mixed with dioxane (100 ml), and 4,4,4',4',5,5,5',5'-octamethyl-2,2'-bi-1,3,2-dioxaborolane (15 g), bis(triphenylphosphine)palladium chloride (1.2 g), and potassium acetate (15.8 g) were added thereto, followed by stirring at 80° C. for 1 day. The reaction mixture was concentrated under reduced pressure, and CHCl$_3$ and a saturated aqueous sodium hydrogen carbonate solution were added thereto. The organic layer was dried over Na$_2$SO$_4$ and concentrated under reduced pressure. The obtained residue was purified by silica gel column chromatography (hexane/EtOAc) to obtain [3-(4,4,5,5-tetramethyl-1,3,2-dioxaborolan-2-yl)phenyl]methanol (12.5 g).

Preparation Example 38

A mixture of 4-(5-bromopyrimidin-2-yl)morpholine (2 g), 4,4,4',4',5,5,5',5'-octamethyl-2,2'-bi-1,3,2-dioxaborolane (2.5 g), bis(triphenylphosphine)palladium chloride (180 mg), potassium acetate (2.5 g), and dioxane (20 ml) was stirred at 80° C. overnight under argon atmosphere. Water and EtOAc were added to the reaction mixture, and the organic layer was dried over MgSO$_4$ and concentrated under reduced pressure. The obtained residue was mixed with THF (10 ml) and water (10 ml), and sodium perborate.tetrahydrate (3.5 g) was added thereto, followed by stirring at room temperature overnight. Then, a saturated aqueous ammonium chloride solution was added thereto. The aqueous layer was extracted with EtOAc, and the organic layer was dried over MgSO$_4$ and concentrated under reduced pressure. The obtained residue was purified by silica gel column chromatography (hexane/EtOAc) to obtain 2-(morpholin-4-yl)pyrimidin-5-ol (610 mg).

Preparation Example 39

Calcium carbonate (11 g) was added to a mixture of ethyl [3-(bromomethyl)phenyl]acetate (4.56 g), dioxane (70 ml) and water (70 ml), followed by stirring at 80° C. for 6 hours. EtOAc and water were added to the reaction mixture, and the organic layer was dried over Na$_2$SO$_4$ and concentrated under reduced pressure. The obtained residue was purified by silica gel column chromatography (hexane/EtOAc). The purified product thus obtained was mixed with EtOH (50 ml), and a 1 M aqueous NaOH solution (35 ml) was added thereto, followed by stirring at room temperature for 1 hour. 1 M hydrochloric acid (35 ml) was added to the reaction mixture, followed by concentration under reduced pressure. MeOH and Na$_2$SO$_4$ were added to the obtained residue, and the insoluble matter was removed by filtration. The filtrate was concentrated under reduced pressure to obtain [3-(hydroxymethyl)phenyl]acetic acid (1.9 g).

Preparation Example 41

Using [(3-bromo-2-fluorobenzyl)oxy](tert-butyl)dimethylsilane (6.5 g) as a starting material and cesium carbonate as a base under the same reaction conditions as in Preparation Example 228

1-[3-({[tert-butyl(dimethyl)silyl]oxy}methyl)-2-fluorophenyl]piperidin-4-yl benzoate (4.5 g) was prepared.

Preparation Example 42

Under argon atmosphere, [(3-bromo-2-fluorobenzyl)oxy](tert-butyl)dimethylsilane (2 g) and ethyl piperidine-4-carboxylate (1.6 g) were mixed with toluene (30 ml), and Pd$_2$(dba)$_3$ (150 mg), BINAP (300 mg), and cesium carbonate (3.2 g) were added thereto, followed by stirring at 100° C. for 1 hour. The reaction mixture was cooled to room temperature, and EtOAc was added thereto, followed by filtration using Celite as a filtration adjuvant. The filtrate was concentrated under reduced pressure, the residue was then mixed with THF (30 ml), and a 1 M TBAF/THF solution (12 ml) was added thereto, followed by stirring at room temperature for 1 hour. To the reaction mixture were added EtOAc and water, and the organic layer was dried over Na$_2$SO$_4$ and concentrated under reduced pressure. The obtained residue was purified by silica gel column chromatography (hexane/EtOAc) to obtain ethyl 1-[2-fluoro-3-(hydroxymethyl)phenyl]piperidine-4-carboxylate (1.02 g).

Preparation Example 44 tert-Butyl [(3-ethynyl-2-fluorobenzyl)oxy]dimethylsilane (1 g) was mixed with THF (20 ml), and a 1.65 M n-butyl lithium/hexane solution (2.5 ml) was added dropwise thereto at −78° C., followed by stirring at −78° C. for 30 minutes. Benzyl chloroformate (774 mg) was added dropwise thereto at the same temperature, followed by stirring overnight while raising the temperature to room temperature. A saturated aqueous ammonium chloride solution was added thereto at 0° C., followed by extraction with CHCl$_3$. The organic layer was washed with water and saturated brine, and dried over Na$_2$SO$_4$, and the solvent was concentrated under reduced pressure. The obtained residue was purified by silica gel column chromatography (EtOAc/hexane) to obtain benzyl 3-[3-({[tert-butyl(dimethyl)silyl]oxy}methyl)-2-fluorophenyl]prop-2-ynoate (1.41 g).

Preparation Example 45 tert-Butyl{2-[(chloroacetyl)(tetrahydro-2H-pyran-4-yl)amino]ethyl}carbamate (6.86 g) was mixed with THF (70 ml), and sodium hydride (55% suspended in oil) (1.4 g) was added thereto at 0° C., followed by stirring at room temperature overnight. To the reaction mixture was added a saturated aqueous ammonium chloride solution at 0° C., followed by extraction with CHCl$_3$. The organic layer was washed with water and saturated brine, and dried over Na$_2$SO$_4$, and the solvent was concentrated under reduced pressure. The obtained residue was purified by silica gel column chromatography (EtOAc/hexane/MeOH) to obtain tert-butyl 3-oxo-4-(tetrahydro-2H-pyran-4-yl)piperazine-1-carboxylate (5.25 g).

Preparation Example 48

Using ({1-[(benzyloxy)carbonyl]piperidin-4-yl}methyl)(triphenyl)phosphonium iodide (6.0 g) as a starting material and lithium bis(trimethylsilyl)amide as a base under the same conditions as in Preparation Example 581, benzyl tert-butyl 4,4'-(Z)-ethene-1,2-diyldipiperidine-1-carboxylate (2.5 g) was prepared.

Preparation Example 50

1-Benzyl-4-(tetrahydro-2H-pyran-4-ylmethoxy)pyridinium bromide (1.9 g) was mixed with MeOH (35 ml), and $NaBH_4$ (850 mg) was added thereto, followed by stirring at room temperature for 1 hour. Acetone (6 ml) was added to the reaction mixture, followed by stirring at room temperature for 30 minutes, and then activated carbon (1 g) was added thereto, followed by stirring at room temperature for 30 minutes and filtering using Celite as a filtration adjuvant. The filtrate was concentrated under reduced pressure. EtOAc and a saturated aqueous sodium hydrogen carbonate solution were added to the obtained residue, and the organic layer was dried over $Na_2SO_4$ and concentrated under reduced pressure. The obtained residue was mixed with MeOH (35 ml), and ammonium formate (3 g) and 10% palladium carbon (400 mg) were added thereto, followed by stirring at 50° C. for 4 hours and filtering using Celite, and the filtrate was concentrated under reduced pressure. EtOAc and a saturated aqueous sodium hydrogen carbonate solution were added to the residue, and the organic layer was dried over $Na_2SO_4$ and concentrated under reduced pressure. The obtained residue was purified by basic silica gel column chromatography ($CHCl_3$/MeOH) to obtain 4-(tetrahydro-2H-pyran-4-ylmethoxy)piperidine (1.01 g).

Preparation Example 54

4-(Tetrahydro-2H-pyran-4-ylmethoxy)pyridine (1.1 g) was mixed with THF (12 ml), and benzyl bromide (1.4 g) was added thereto, followed by stirring at room temperature overnight. The precipitated solid was collected by filtration to obtain 1-benzyl-4-(tetrahydro-2H-pyran-4-ylmethoxy)pyridinium bromide (1.9 g).

Preparation Example 57

2-Fluoro-3-methylbenzoic acid (4 g), THF (55 ml), and tert-butanol (55 ml) were mixed, and $Boc_2O$ (7.5 g) and DMAP (1.0 g) were added thereto at room temperature, followed by stirring at room temperature overnight. The solvent was concentrated under reduced pressure, and EtOAc and water were added thereto. The organic layer was dried over $Na_2SO_4$, and concentrated under reduced pressure. The obtained residue was purified by silica gel column chromatography (hexane/EtOAc) to obtain tert-butyl 2-fluoro-3-methylbenzoate (3.50 g).

Preparation Example 58 tert-Butyl 3-hydroxyazetidine-1-carboxylate (4.0 g) and pyridin-4-ol (1.8 g) were mixed with THF (50 ml), and triphenylphosphine (6.23 g) was added thereto. A 1.9 M DIAD/toluene solution (12.5 ml) was added dropwise, followed by stirring at 55° C. overnight. Triphenylphosphine (5 g) and a 1.9 M DIAD/toluene solution (10 ml) were added to the reaction mixture, followed by stirring at 55° C. overnight. The reaction mixture was concentrated under reduced pressure, and a liquid separation operation was carried out by the addition of EtOAc and 0.5 M hydrochloric acid. The aqueous layer was adjusted to a pH of around 10 by the addition of a 4 M aqueous NaOH solution, and extracted with $CHCl_3$. The organic layer was dried over $Na_2SO_4$ and concentrated under reduced pressure. The obtained residue was purified by silica gel column chromatography ($CHCl_3$/MeOH) to obtain tert-butyl 3-(pyridin-4-yloxy)azetidine-1-carboxylate (4.2 g).

Preparation Example 60

1-[3-({[tert-Butyl(dimethyl)silyl]oxy}methyl)-2-fluorophenyl]piperidin-4-ol (200 mg) and pyridin-4-ol (65 mg) were mixed with THF (3 ml), and triphenylphosphine (250 mg) was added thereto. A 1.9 M DIAD/toluene solution (0.5 ml) was added dropwise to the reaction mixture, followed by stirring at 55° C. overnight. Then, a 1 M TBAF/THF solution (1 ml) was added to the reaction mixture, followed by stirring at room temperature for 1 hour. The reaction mixture was concentrated under reduced pressure, and diethyl ether and 1 M hydrochloric acid were added thereto. The organic layer was separated by a liquid separation operation, and the aqueous layer was washed with diethyl ether twice again. The aqueous layer was adjusted to a pH of around 10 by the addition of a 4 M aqueous NaOH solution, and extracted with $CHCl_3$. The organic layer was dried over $Na_2SO_4$ and concentrated under reduced pressure. The obtained residue was purified by silica gel column chromatography ($CHCl_3$/MeOH) to obtain {2-fluoro-3-[4-(pyridin-4-yloxy)piperidin-1-yl]phenyl}methanol (84 mg).

Preparation Example 62 tert-Butyl 3-hydroxyazetidine-1-carboxylate (3.0 g) was mixed with THF (30 ml), and sodium hydride (55% suspended in oil) (600 mg) was added thereto, followed by stirring at room temperature for 10 minutes. Benzyl bromide (2.5 ml) was added thereto, followed by stirring at room temperature for 3 hours. Water and EtOAc were added to the reaction mixture, and the organic layer was dried over $Na_2SO_4$ and concentrated under reduced pressure. The obtained residue was mixed with DCE (30 ml), and TFA (15 g) was added thereto, followed by stirring at room temperature for 3 hours. The reaction mixture was concentrated under reduced pressure and purified by basic silica gel column chromatography ($CHCl_3$/MeOH) to obtain 3-(benzyloxy)azetidine (2.2 g).

Preparation Example 63 tert-Butyl 4-[(methylsulfonyl)oxy]piperidine-1-carboxylate (1.1 g), 2-methylpyridin-3-ol (500 mg), potassium carbonate (1.7 g), and DMF (10 ml) were mixed, followed by stirring at 100° C. for 6 hours. The reaction mixture was concentrated under reduced pressure, and $CHCl_3$ and a saturated aqueous sodium hydrogen carbonate solution were then added thereto. The organic layer was dried over $Na_2SO_4$ and concentrated under reduced pressure. The obtained residue was purified by silica gel column chromatography ($CHCl_3$/MeOH). The purified product thus obtained was mixed with DCE (10 ml), and TFA (4.5 g) was added thereto, followed by stirring at room temperature for 3 hours. The reaction mixture was concentrated under reduced pressure, and CHCl$_3$ and a 1 M aqueous NaOH solution were the added thereto, and the organic layer was dried over Na$_2$SO$_4$ and concentrated under reduced pressure to obtain 2-methyl-3-(piperidin-4-yloxy)pyridine (355 mg).

Preparation Example 67

1-[3-({[tert-Butyl(dimethyl)silyl]oxy}methyl)-2-fluorophenyl]piperazine (500 mg) was mixed with dioxane (15 ml), and methyl 5-bromopyridine-2-carboxylate (399 mg), palladium acetate (35 mg), 2-dicyclohexylphosphino-2',4',6'-tri-isopropyl-1,1'-biphenyl (147 mg), and potassium phosphate (981 mg) were added thereto, followed by stirring at 100° C. for 48 hours. The reaction mixture was cooled to room temperature, and filtered by the addition of CHCl$_3$ and Celite, and the filtrate was concentrated under reduced pressure. The obtained residue was purified by silica gel column chromatography (EtOAc/hexane) to obtain methyl 5-{4-[3-({[tert-butyl(dimethyl)silyl]oxy}methyl)-2-fluorophenyl]piperazin-1-yl}pyridine-2-carboxylate (310 mg).

Preparation Example 69

1-[3-({[tert-Butyl(dimethyl)silyl]oxy}methyl)-2-fluorophenyl]-4-(pyridin-3-yl)piperidin-4-ol (908 mg) was mixed with dichloromethane (15 ml), and TEA (1.1 g), DMAP (799 mg), and MsCl (749 mg) were added thereto at 0° C., followed by stirring at room temperature overnight. Water and EtAOc were added to the reaction mixture, and the organic layer was washed with water and saturated brine, and dried over anhydrous sodium carbonate. The solvent was concentrated under reduced pressure. The obtained residue was purified by silica gel column chromatography (EtOAc/hexane) to obtain 1'-[3-({[tert-butyl(dimethyl)silyl]oxy}methyl)-2-fluorophenyl]-1',2',3',6'-tetrahydro-3,4'-bipyridine (477 mg).

Preparation Example 70

Dioxane (12 ml) was added to a mixture of 5-iodo-2-(3-methoxyazetidin-1-yl)pyrimidine (1.14 g), tert-butyl 3-oxopiperazine-1-carboxylate (941 mg), rel-(1R,2R)-N,N'-dimethyl cyclohexane-1,2-diamine (223 mg), copper iodide (149 mg), and potassium phosphate (2.5 g), followed by stirring at 100° C. overnight. The reaction mixture was cooled to room temperature and then filtered by the addition of CHCl$_3$ and Celite, and the filtrate was concentrated. The obtained residue was purified by basic silica gel column chromatography (EtOAc/hexane) to obtain tert-butyl 4-[2-(3-methoxyazetidin-1-yl)pyrimidin-5-yl]-3-oxopiperazine-1-carboxylate (867 mg).

Preparation Example 81

2-Fluoro-4'-(morpholin-4-yl)biphenyl-3-carboaldehyde (288 mg) was mixed with THF (3 ml), and NaBH$_4$ (40 mg) was added thereto. MeOH (3 ml) was added to the reaction mixture dropwise, followed by stirring at room temperature for 30 minutes. EtOAc and 1 M hydrochloric acid were added to the reaction mixture, and the organic layer was dried over Na$_2$SO$_4$ and concentrated under reduced pressure. The obtained residue was purified by silica gel column chromatography (hexane/EtOAc) to obtain [2-fluoro-4'-(morpholin-4-yl)biphenyl-3-yl]methanol (259 mg).

Preparation Example 135

[3-(2-Chloropyrimidin-5-yl)phenyl]methanol (200 mg) was mixed with DMF (4 ml), and 4-methoxypiperidine hydrochloride (180 mg) and potassium carbonate (500 mg) were added thereto, followed by stirring at 70° C. for 5 hours. The reaction mixture was concentrated under reduced pressure, and CHCl$_3$ and a saturated aqueous sodium hydrogen carbonate solution were then added thereto. The organic layer was dried over Na$_2$SO$_4$ and concentrated under reduced pressure. The obtained residue was purified by silica gel column chromatography (hexane/EtOAc) to obtain {3-[2-(4-methoxypiperidin-1-yl)pyrimidin-5-yl]phenyl}methanol (249 mg).

Preparation Example 159

5-{4-[3-({[tert-Butyl(dimethyl)silyl]oxy}methyl)-2-fluorophenyl]piperazin-1-yl}pyrimidin-2-yltrifluoromethanesulfonate (200 mg) was mixed with DMF (4 ml), and 1-acetylpiperazine (72 mg) and potassium carbonate (300 mg) were added thereto, followed by stirring at 60° C. overnight. The reaction mixture was concentrated under reduced pressure, and water and EtOAc were added to the residue. The organic layer was washed with saturated brine, then dried over Na$_2$SO$_4$, and concentrated under reduced pressure. The obtained residue was mixed with THF, and a 1 M TBAF/THF solution was added thereto, followed by stirring at room temperature for 3 hours. Water and EtOAc were added to the reaction mixture, and the organic layer was concentrated under reduced pressure. The obtained residue was purified by silica gel column chromatography (EtOAc/hexane/MeOH/CHCl$_3$) to obtain 1-[4-(5-{4-[2-fluoro-3-(hydroxymethyl)phenyl]piperazin-1-yl}pyrimidin-2-yl)piperazin-1-yl]ethanone (133 mg).

Preparation Example 162

Ethyl 3-(2-ethoxy-2-oxoethyl)benzoate (1.41 g) was mixed with THF (20 ml), and lithium borohydride (260 mg) was added thereto at 0° C., followed by stirring at room temperature overnight. A saturated ammonium chloride solution and EtOAc were added to the reaction mixture at 0° C. The organic layer was washed with water and saturated brine, dried over Na$_2$SO$_4$, and concentrated under reduced pressure. The obtained residue was purified by silica gel column chromatography (EtOAc/hexane) to obtain ethyl 3-(2-hydroxyethyl)benzoate (824 mg).

Preparation Example 163

2,5-Dibromo-1,3-thiazole (500 mg) was mixed with morpholine (2 ml), followed by stirring at 60° C. for 5 hours. Water was added to the reaction mixture, followed by stirring for 1 hour, and the resulting insoluble matter was collected by filtration, followed by washing with water, to obtain 4-(5-bromo-1,3-thiazol-2-yl)morpholine (475 mg).

Preparation Example 174

CHCl$_3$ and a saturated aqueous sodium hydrogen carbonate solution were added to [3-(piperazin-1-yl)phenyl]methanol dihydrochloride (240 mg) to carry out liquid separation. The organic layer was dried over MgSO$_4$ and concentrated under reduced pressure. The obtained residue was mixed with dichloromethane (5 ml), and tetrahydro-4H-pyran-4-one (100 mg) and acetic acid (168 mg) were added thereto, followed by stirring at room temperature for 15 minutes. Sodium triacetoxyborohydride (576 mg) was added to the reaction mixture at 0° C., followed by stirring at room temperature for 5 hours. Water and CHCl$_3$ were added to the reaction mixture, and the aqueous layer was adjusted to a pH of 8 to 9 by the addition of a saturated aqueous sodium hydrogen carbonate solution. The organic layer was washed with water, dried over MgSO$_4$, and then concentrated under reduced pressure. The residue was purified by silica gel column chromatography (CHCl$_3$/MeOH) to obtain {3-[4-(tetrahydro-2H-pyran-4-yl)piperazin-1-yl]phenyl}methanol (45 mg).

Preparation Example 177

Ethyl 1-{5-[2-fluoro-3-(hydroxymethyl)phenyl]pyrimidin-2-yl}piperidine-4-carboxylate (1.4 g) was mixed with THF (10 ml) and EtOH (15 ml), and a 1 M aqueous NaOH solution (5.8 ml) was added thereto, followed by stirring at room temperature overnight. The insoluble matter was collected by filtration, and the filtrate was concentrated under reduced pressure. Water and 1 M hydrochloric acid (5.8 ml) were added to the obtained residue at 0° C., followed by stirring at 0° C. for 30 minutes. The solid was collected by filtration, washed with water, and then dried at 50° C. under reduced pressure to obtain 1-{5-[2-fluoro-3-(hydroxymethyl)phenyl]pyrimidin-2-yl}piperidine-4-carboxylic acid (1.29 g).

Preparation Example 182

(3-Bromophenyl)methanol (500 mg) was mixed with DMF (10 ml), and sodium hydride (55% suspended in oil) was added thereto at 0° C., followed by stirring for 10 minutes under ice-cooling. 1-(Chloromethyl)-4-methoxybenzene (520 mg) was added to the reaction mixture, followed by stirring at room temperature for 2 hours. Water and EtOAc were added to the reaction mixture, and the organic layer was dried over MgSO$_4$ and concentrated under reduced pressure. The obtained residue was purified by silica gel column chromatography (CHCl$_3$/hexane) to obtain 1-bromo-3-{[(4-methoxybenzyl)oxy]methyl}benzene (801 mg).

Preparation Example 228

[(3-Bromo-2-fluorobenzyl)oxy](tert-butyl)dimethylsilane (300 mg) was mixed with toluene (6 ml), and 1-(2-methylpyridin-4-yl)piperazine (200 mg), Pd$_2$(dba)$_3$ (43 mg), BINAP (88 mg), and sodium tert-butoxide (135 mg) were added thereto, followed by stirring at 80° C. for 5 hours. After cooling to room temperature, filtration was carried out by the addition of CHCl$_3$ and Celite, and the filtrate was concentrated under reduced pressure. The obtained residue was purified by silica gel column chromatography (EtOAc/hexane/28% aqueous ammonia/MeOH/) to obtain 1-[3-({[tert-butyl(dimethyl)silyl]oxy}methyl)-2-fluorophenyl]-4-(2-methylpyridin-4-yl)piperazine (259 mg).

Preparation Example 285

Under argon atmosphere, [(3-bromo-2-fluorobenzyl)oxy](tert-butyl)dimethylsilane (800 mg) and 4-(azetidin-3-yloxy)pyridine (268 mg) were mixed with toluene (6 ml), and Pd$_2$(dba)$_3$ (80 mg), BINAP (160 mg), and sodium tert-butoxide (300 mg) were added thereto, followed by stirring at 90° C. for 3 hours. The reaction mixture was cooled to room temperature, and EtOAc was added thereto, followed by carrying out filtration using Celite as a filtration adjuvant. The filtrate was concentrated under reduced pressure, and then the residue was purified by silica gel column chromatography (hexane/EtOAc). The purified product thus obtained was mixed with THF (6 ml), and a 1 M TBAF/THF solution (3 ml) was added thereto, followed by stirring at room temperature for 1 hour. To the reaction mixture were added a saturated aqueous ammonium chloride solution and CHCl$_3$, and the organic layer was dried over Na$_2$SO$_4$ and concentrated under reduced pressure. The obtained residue was purified by silica gel column chromatography (hexane/EtOAc) to obtain {2-fluoro-3-[3-(pyridin-4-yloxy)azetidin-1-yl]phenyl}methanol (335 mg).

Preparation Example 290

Under argon atmosphere, 4-(5-bromopyrimidin-2-yl)morpholine (700 mg) and tert-butyl piperazine-1-carboxylate (800 mg) were mixed with toluene (10 ml), and Pd$_2$(dba)$_3$ (130 mg), BINAP (260 mg), and potassium tert-butoxide (500 mg) were added thereto, followed by stirring at 90° C. overnight. The reaction mixture was cooled to room temperature, the reaction mixture was concentrated under reduced pressure, and the residue was purified by silica gel column chromatography (hexane/EtOAc). The purified product thus obtained was mixed with EtOH (10 ml), and 4 M hydrogen chloride/dioxane (7 ml) was added thereto, followed by stirring at room temperature overnight. The reaction mixture was concentrated under reduced pressure, and CHCl$_3$ and a saturated aqueous sodium hydrogen carbonate solution were then added thereto. The organic layer was dried over Na$_2$SO$_4$ and concentrated under reduced pressure. The obtained residue was purified by silica gel column chromatography (CHCl$_3$/MeOH) to obtain 4-[5-(piperazin-1-yl)pyrimidin-2-yl]morpholine (239 mg).

Preparation Example 294

1-(3-{[(4-Methoxybenzyl)oxy]methyl}phenyl)-4-(pyridin-4-yl)piperazine (308 mg) was mixed with dichloromethane (2 ml), and TFA (1 ml) was added thereto. The reaction mixture was stirred at room temperature for 1 hour, and then the reaction mixture was concentrated under reduced pressure. To the obtained residue were added a saturated aqueous sodium hydrogen carbonate solution and CHCl$_3$, and the organic layer was dried over MgSO$_4$ and concentrated under reduced pressure. The obtained residue was purified by basic silica gel column chromatography to obtain {3-[4-(pyridin-4-yl)piperazin-1-yl]phenyl}methanol (167 mg).

Preparation Example 297

(3-Bromophenyl)methanol (5.0 g) was mixed with THF (60 ml), and TBSCl (5.0 g) and imidazole (3 g) were added thereto, followed by stirring at room temperature overnight. The reaction mixture was concentrated under reduced pressure, and water and EtOAc were added thereto. The organic layer was dried over Na$_2$SO$_4$ and concentrated under reduced pressure. The obtained residue was purified by silica gel column chromatography to obtain [(3-bromobenzyl)oxy](tert-butyl)dimethylsilane (8.0 g).

Preparation Example 301

[(3-Bromobenzyl)oxy](tert-butyl)dimethylsilane (860 mg) was mixed with THF (10 ml), followed by cooling to −78° C. under argon atmosphere. A 1.60 M n-butyl lithium/hexane solution (1.8 ml) was added dropwise thereto, followed by stirring at −78° C. for 10 minutes, and then 2-morpholin-4-ylpyrimidine-5-carboaldehyde (500 mg) was added thereto. The mixture was warmed to 0° C. over 1 hour and then stirred again at 0° C. for 1 hour. Water and EtOAc were added to the reaction mixture, and the organic layer was dried over $Na_2SO_4$ and concentrated under reduced pressure. The obtained residue was purified by silica gel column chromatography (hexane/EtOAc) to obtain [3-({[tert-butyl(dimethyl)silyl]oxy}methyl)phenyl][2-(morpholin-4-yl)pyrimidin-5-yl]methanol (914 mg).

Preparation Example 302

[3-({[tert-Butyl(dimethyl)silyl]oxy}methyl)phenyl][2-(morpholin-4-yl)pyrimidin-5-yl]methanol (400 mg), triethylsilane (364 mg), and TFA (4 ml) were mixed, followed by stirring at room temperature overnight. The reaction mixture was concentrated under reduced pressure, and EtOAc and water were added to the obtained residue. The organic layer was dried over $MgSO_4$ and concentrated under reduced pressure. The obtained residue was purified by silica gel column chromatography to obtain (3-{[2-(morpholin-4-yl)pyrimidin-5-yl]methyl}phenyl)methanol (39 mg).

Preparation Example 304

1-[3-({[tert-Butyl(dimethyl)silyl]oxy}methyl)-2-fluorophenyl]piperazine (355 mg) was mixed with IPA (4.5 ml), and 4-chloro-pyrimidine hydrochloride (150 mg) and TEA (302 mg) were added thereto, followed by stirring at 60° C. overnight. The reaction mixture was cooled to room temperature and then concentrated under reduced pressure, and the residue was purified by silica gel column chromatography (MeOH/$CHCl_3$) to obtain 4-{4-[3-({[tert-butyl(dimethyl)silyl]oxy}methyl)-2-fluorophenyl]piperazin-1-yl}pyrimidine (391 mg).

Preparation Example 305

Ethyl 2-fluoro-3-({[2-(morpholin-4-yl)pyrimidin-5-yl]oxy}methyl)benzoate (375 mg) was mixed with toluene (5 ml), followed by cooling to 0° C. A 1.01 M diisobutylaluminum hydride/toluene solution (3 ml) was added dropwise thereto, followed by stirring at the same temperature for 1 hour. The reaction mixture was subjected to liquid separation by the addition of a 1 M aqueous NaOH solution and toluene. The organic layer was dried over $Na_2SO_4$ and concentrated under reduced pressure. The obtained residue was purified by silica gel column chromatography (hexane/EtOAc) to obtain [2-fluoro-3-({[2-(morpholin-4-yl)pyrimidin-5-yl]oxy}methyl)phenyl]methanol (282 mg).

Preparation Example 306

1-(6-Chloropyridazine-3-yl)azetidin-3-ol (599 mg) was mixed with DMF (6 ml), and sodium hydride (55% suspended in oil) (211 mg) was added thereto at 0° C., followed by stirring at 0° C. for 10 minutes. Then, methyl iodide (916 mg) was added thereto at 0° C., followed by stirring at room temperature overnight. To the reaction mixture were added water, EtOAc, and $CHCl_3$, and the organic layer was washed with water and saturated brine, then dried over anhydrous $Na_2CO_3$, and concentrated under reduced pressure. The obtained residue was purified by silica gel column chromatography (EtOAc/hexane) to obtain 3-chloro-6-(3-methoxyazetidin-1-yl)pyridazine (323 mg).

Preparation Example 307 tert-Butyl 4-hydroxypiperidine-1-carboxylate (1.0 g) was mixed with DMF (15 ml), and sodium hydride (55% suspended in oil) (300 mg) was added thereto, followed by stirring at room temperature for 10 minutes. To the reaction mixture was added 1-bromo-3-methoxypropane (1.0 g), followed by stirring at room temperature overnight. Water was added to the reaction mixture, and the reaction mixture was concentrated under reduced pressure. EtOAc and water were added to the obtained residue, and the organic layer was dried over $Na_2SO_4$ and concentrated under reduced pressure. The obtained residue was purified by silica gel column chromatography (hexane/EtOAc). The purified product thus obtained was mixed with EtOH (10 ml), and a 4 M hydrogen chloride/dioxane (10 ml) was added thereto, followed by stirring at room temperature overnight. The reaction mixture was concentrated under reduced pressure to obtain 4-(3-methoxypropoxy)piperidine hydrochloride (302 mg).

Preparation Example 309

2-Fluoro-3-methylbenzoic acid (8.0 g) was mixed with EtOH (100 ml), and concentrated sulfuric acid was added thereto, followed by stirring at 90° C. overnight. The reaction mixture was concentrated under reduced pressure, and EtOAc and water were then added thereto. The organic layer was washed with a saturated aqueous sodium hydrogen carbonate solution, then dried over $Na_2SO_4$, and concentrated under reduced pressure to obtain ethyl 2-fluoro-3-methylbenzoate (7.84 g).

Preparation Example 336

1-[2-Fluoro-3-(hydroxymethyl)phenyl]piperidine-4-carboxylic acid (100 mg) and morpholine (50 mg) were mixed with DCE (3 ml), and WSC hydrochloride (140 mg) and HOBt (95 mg) were added thereto, followed by stirring at room temperature for 3 hours. A saturated aqueous sodium hydrogen carbonate solution and $CHCl_3$ were added to the reaction mixture, and the organic layer was dried over $Na_2SO_4$ and concentrated under reduced pressure. The obtained residue was purified by silica gel column chromatography ($CHCl_3$/MeOH) to obtain {1-[2-fluoro-3-(hydroxymethyl)phenyl]piperidin-4-yl}(morpholin-4-yl)methanone (126 mg).

Preparation Example 341

(2-Fluoro-3-{4-[2-(piperidin-4-yl)ethyl]piperidin-1-yl}phenyl)methanol (200 mg) and acetic acid (63 mg) were mixed with DCE (3 ml), and WSC hydrochloride (220 mg) and HOBt (155 mg) were added thereto, followed by stirring at room temperature for 3 hours. A saturated aqueous sodium hydrogen carbonate solution and $CHCl_3$ were added to the reaction mixture, and the organic layer was liquid separation and concentrated under reduced pressure. The obtained residue was mixed with MeOH (3 ml), and a 1 M aqueous NaOH solution (1 ml) was added thereto, followed by stirring at room temperature for 30 minutes. The reaction mixture was concentrated under reduced pressure, and $CHCl_3$ and a saturated aqueous sodium hydrogen carbonate solution were then added thereto. The organic layer was dried over $Na_2SO_4$ and concentrated under reduced pressure. The obtained residue was purified by silica gel column chromatography ($CHCl_3$/MeOH) to obtain 1-[4-(2-{1-[2-fluoro-3-(hydroxymethyl)phenyl]piperidin-4-yl}ethyl)piperidin-1-yl]ethanone (211 mg).

Preparation Example 343

5-[3-({[tert-Butyl(dimethyl)silyl]oxy}methyl)-2-fluorophenyl]-2-(piperidin-4-yloxy)pyrimidine (150 mg) and cyclohexane carboxylic acid (82 mg) were mixed with DCE (3.6 ml), and WSC hydrochloride (125 mg) and HOBt (85 mg) were added thereto, followed by stirring at room temperature for 3 hours. A saturated aqueous sodium hydrogen carbonate solution and CHCl$_3$ were added to the reaction mixture, and the organic layer was dried over Na$_2$SO$_4$ and concentrated under reduced pressure. The obtained residue was mixed with THF (3.6 ml), and a 1 M TBAF/THF solution (0.85 ml) was added thereto, followed by stirring at room temperature for 1 hour. EtOAc and an aqueous ammonium chloride solution were added to the reaction mixture, and the organic layer was dried over Na$_2$SO$_4$ and concentrated under reduced pressure. The obtained residue was purified by silica gel column chromatography (CHCl$_3$/MeOH) to obtain cyclohexyl [4-({5-[2-fluoro-3-(hydroxymethyl)phenyl]pyrimidin-2-yl}oxy)piperidin-1-yl]methanone (148 mg).

Preparation Example 347

1-(3-Bromophenyl)methanamine (10 g) was mixed with THF (100 ml), and Boc$_2$O (12.9 g) was added thereto, followed by stirring at room temperature overnight. The reaction mixture was concentrated under reduced pressure and the residue was purified by silica gel column chromatography (EtOAc/hexane) to obtain tert-butyl (3-bromobenzyl)carbamate (15.0 g).

Preparation Example 376

1-[3-({[tert-Butyl(dimethyl)silyl]oxy}methyl)-2-fluorophenyl]-3-methoxyazetidine (121 mg) was mixed with THF (4 ml), and a 1 M TBAF/THF solution (0.8 ml) was added thereto, followed by stirring at room temperature for 1 hour. Water and EtOAc were added to the reaction mixture, and the organic layer was dried over Na$_2$SO$_4$ and concentrated under reduced pressure. The obtained residue was purified by silica gel column chromatography to obtain [2-fluoro-3-(3-methoxyazetidin-1-yl)phenyl]methanol (72 mg).

Preparation Example 478 tert-Butyl 4-[2-(morpholin-4-yl)pyrimidin-5-yl]piperazine-1-carboxylate (1.42 g) was mixed with MeOH (20 ml) and THF (20 ml), and a 4 M hydrogen chloride/EtOAc (10 ml) was added thereto, followed by stirring at room temperature overnight and then stirring for minutes under ice-cooling. The precipitated solid was collected by filtration and washed with EtOAc to obtain 4-[5-(piperazin-1-yl)pyrimidin-2-yl]morpholine dihydrochloride (1.15 g).

Preparation Example 508 tert-Butyl 4-[2-fluoro-3-(hydroxymethyl)phenyl]piperidine-1-carboxylate (352 mg) was mixed with EtOH (5 ml), and 4 M hydrogen chloride/dioxane (3 ml) was added thereto, followed by stirring at room temperature overnight. The reaction mixture was concentrated under reduced pressure, and then EtOH and potassium carbonate were added thereto, followed by stirring at 60° C. for 5 hours. The reaction mixture was filtered and the filtrate was concentrated under reduced pressure. The reaction mixture was mixed with THF (5 ml), and TBSCl (450 mg) and imidazole (210 mg) were added thereto, followed by stirring at room temperature for 1 hour. EtOAc and water were added to the reaction mixture, and the organic layer was dried over Na$_2$SO$_4$ and concentrated under reduced pressure. The obtained residue was purified by silica gel column chromatography (CHCl$_3$/MeOH) to obtain 4-[3-({[tert-butyl(dimethyl)silyl]oxy}methyl)-2-fluorophenyl]piperidine (271 mg).

Preparation Example 514 tert-Butyl 4-{5-[3-({[tert-butyl(dimethyl)silyl]oxy}methyl)-2-fluorophenyl]pyrimidin-2-yl}piperidin e-1-carboxylate (170 mg) was mixed with MeOH (1.7 ml), and a 4 M hydrogen chloride/EtOAc (0.17 ml) was added thereto, followed by stirring at room temperature overnight. The reaction mixture was concentrated under reduced pressure, and 10% MeOH/CHCl$_3$ and a saturated aqueous sodium hydrogen carbonate solution were added to the residue. Then, the reaction mixture was concentrated under reduced pressure. 10% MeOH/CHCl$_3$ was added to the obtained residue, followed by stirring for 30 minutes. The filtrate was concentrated under reduced pressure to obtain {2-fluoro-3-[2-(piperidin-4-yl)pyrimidin-5-yl]phenyl}methanol (96 mg).

Preparation Example 516

Methyl 3-(bromomethyl)benzoate (4.0 g) was mixed with toluene (40 ml), and triphenylphosphine (5.0 g) was added thereto, followed by stirring at 90° C. overnight. The precipitated solid was collected by filtration to obtain [3-(methoxycarbonyl)benzyl](triphenyl)phosphonium bromide (8.2 g).

Preparation Example 518

1-[3-({[tert-Butyl(dimethyl)silyl]oxy}methyl)phenyl]-4-(pyridin-2-yl)piperazine (240 mg) was mixed with THF (2 ml), and a 1 M hydrochloric acid (2 ml) was added thereto, followed by stirring at room temperature for 5 hours. A saturated aqueous sodium hydrogen carbonate solution and CHCl$_3$ were added to the reaction mixture, and the organic layer was dried over MgSO$_4$ and concentrated under reduced pressure. The obtained residue was purified by silica gel column chromatography (hexane/EtOAc) to obtain {3-[4-(pyridin-2-yl)piperazin-1-yl]phenyl}methanol (166 mg).

Preparation Example 548

Benzyl 3-oxo-4-(pyridin-3-ylmethyl)piperazine-1-carboxylate (345 mg) was mixed with EtOH (7 ml), and 10% palladium carbon (70 mg) was added thereto under argon atmosphere to change the atmosphere to hydrogen atmosphere, followed by stirring at room temperature overnight. The reaction mixture was filtered using Celite as a filtration adjuvant, and the filtrate was concentrated under reduced pressure to obtain 1-(pyridin-3-ylmethyl)piperazin-2-one (190 mg).

Preparation Example 563 tert-Butyl 4-hydroxypiperidine-1-carboxylate (2.0 g) was mixed with THF (20 ml), and TEA (3 ml) and benzoyl chloride (1.2 g) were added thereto, followed by stirring at room temperature for 1 hour. Water and EtOAc were added to the reaction mixture, and the organic layer was dried over Na$_2$SO$_4$ and concentrated under reduced pressure. The obtained residue was purified by silica gel column chromatography (hexane/EtOAc) to obtain tert-butyl 4-(benzoyloxy)piperidine-1-carboxylate (2.45 g).

Preparation Example 564 tert-Butyl 4-hydroxypiperidine-1-carboxylate (3.0 g) was mixed with DCE (30 ml), and TEA (3.0 ml) and benzoyl chloride (2.4 g) was added thereto, followed by stirring at room temperature for 1 hour. A saturated aqueous sodium hydrogen carbonate solution and EtOAc were added to the reaction mixture, and the organic layer was dried over $Na_2SO_4$ and concentrated under reduced pressure. The obtained residue was mixed with DCE (30 ml), and TFA (10 ml) was added thereto, followed by stirring at room temperature for 5 hours. The reaction mixture was concentrated under reduced pressure, and then the residue was purified by basic silica gel column chromatography ($CHCl_3$/MeOH) to obtain piperidin-4-yl benzoate (3.1 g).

Preparation Example 568

Under argon atmosphere, ethynyl(trimethyl)silane (9.0 ml) was mixed with triethylamine (50 ml), and (3-bromo-2-fluorophenyl)methanol, bis(triphenylphosphine)palladium chloride (II) (1.54 g), and copper iodide (420 mg) were added thereto, followed by stirring at 90° C. overnight. The reaction mixture was cooled to room temperature, and EtOAc was added thereto, followed by filtering using Celite as a filtration adjuvant. The filtrate was concentrated under reduced pressure, and the residue was purified by silica gel column chromatography (hexane/EtOAc) to obtain {2-fluoro-3-[(trimethylsilyl)ethynyl]phenyl}methanol (4.88 g).

Preparation Example 572 tert-Butyl({2-fluoro-3-[(trimethylsilyl)ethynyl]benzyl}oxy)dimethylsilane (4.13 g) was mixed with EtOH (61 ml), and potassium carbonate (847 mg) was added thereto, followed by stirring at room temperature for 1 hour. Water and $CHCl_3$ were added to the reaction mixture at 0° C., and the organic layer was washed with water and saturated brine, dried over $Na_2SO_4$, and concentrated under reduced pressure. The obtained residue was purified by silica gel column chromatography (EtOAc/hexane) to obtain tert-butyl [(3-ethynyl-2-fluorobenzyl)oxy]dimethylsilane (3.19 g).

Preparation Example 573

$H_2SO_4$ (44 g) was added to water (18 ml) at 0° C., and (3-cyanophenyl)acetic acid (1.5 g) was added thereto at 0° C., followed by stirring at 100° C. overnight, then warming to 130° C., and stirring for 5 hours. The reaction mixture was cooled to room temperature, and EtOH (190 ml) was then added thereto, followed by stirring at 90° C. for 2 days. The reaction mixture was concentrated under reduced pressure, and EtOAc and water were added to the residue. Then, the organic layer was washed with water, a saturated aqueous sodium hydrogen carbonate solution, and saturated brine, dried over $Na_2SO_4$, and then concentrated under reduced pressure to obtain ethyl 3-(2-ethoxy-2-oxoethyl)benzoate (1.41 g).

Preparation Example 574

Ethyl 3-(2-hydroxyethyl)benzoate (824 mg) was mixed with dichloromethane (10 ml), DIPEA (1.5 ml) was added thereto, and methanesulfonyl chloride (972 mg) was added dropwise thereto at 0° C., followed by stirring for 1.5 hours while slowly warming to room temperature. Water was added to the reaction mixture, followed by stirring for 10 minutes, and then the organic layer was washed with water and saturated brine, dried over $Na_2SO_4$, and then concentrated under reduced pressure. The residue was purified by silica gel column chromatography (EtOAc/hexane) to obtain ethyl 3-{2-[(methylsulfonyl)oxy]ethyl}benzoate (1.12 g).

Preparation Example 581

[3-(Methoxycarbonyl)benzyl](triphenyl)phosphonium bromide (930 mg) was mixed with DMF (6 ml), and potassium tert-butoxide (300 mg) was added thereto at 0° C., followed by stirring for 30 minutes. 2-(Morpholin-4-yl)pyrimidine-5-carboaldehyde (300 mg) was added to the reaction mixture, followed by stirring at 0° C. for 1 hour, and stirring again at room temperature for 1 hour. The reaction mixture was concentrated under reduced pressure, and EtOAc and a saturated aqueous sodium hydrogen carbonate solution were then added thereto. The organic layer was dried over $Na_2SO_4$ and concentrated under reduced pressure. The obtained residue was purified by silica gel column chromatography (hexane/EtOAc) to obtain methyl 3-{2-[2-(morpholin-4-yl)pyrimidin-5-yl]vinyl}benzoate (377 mg).

Preparation Example 582

Ethyl 3-{2-[(methylsulfonyl)oxy]ethyl}benzoate (170 mg) was mixed with MeCN (3.4 ml), and 1,2,3,4,5,6-hexahydro-[4,4']bipyridinyl (122 mg) and potassium carbonate (173 mg) were added thereto, followed by stirring at 60° C. overnight. After cooling to room temperature, the insoluble matter was removed by filtration and the filtrate was concentrated under reduced pressure. The residue was purified by silica gel column chromatography (MeOH/$CHCl_3$) to obtain ethyl 3-{2-[4-(pyridin-4-yl)piperidin-1-yl]ethyl}benzoate (121 mg).

Preparation Example 584

Ethyl 3-{2-[4-morpholin-4-yl)piperidin-1-yl]ethyl}benzoate (337 mg) was mixed with THF (7 ml), and aluminum lithium hydride (74 mg) was added thereto at 0° C., followed by stirring at 0° C. for 1 hour. Sodium sulfate decahydrate was added to the reaction mixture at 0° C., followed by stirring at room temperature overnight, the insoluble matter was removed by filtration, and the filtrate was concentrated under reduced pressure to obtain (3-{2-[4-(morpholin-4-yl)piperidin-1-yl]ethyl}phenyl)methanol (281 mg).

Preparation Example 589

Ethyl (3-methylphenyl)acetate (5.36 g) was mixed with carbon tetrachloride (80 ml), followed by heating at 90° C. N-Bromosuccinimide (5.62 g) and α,α'-azobisisobutyronitrile (250 mg) were added thereto, followed by stirring at 90° C. for 5 hours. The reaction mixture was cooled to room temperature, and then the solid was removed by filtration. The filtrate was concentrated under reduced pressure, and the residue was purified by silica gel column chromatography (hexane/EtOAc) to obtain ethyl [3-(bromomethyl)phenyl]acetate (4.56 g).

Preparation Example 592

2-Fluoro-3-formylphenyl)boronic acid (5.14 g) was mixed with THF (51 ml) and water (51 ml), and sodium perborate.trihydrate (17 g) was added thereto, followed by stirring at room temperature overnight. EtOAc and 1 M hydrochloric acid were added to the reaction mixture, and the organic layer was dried over $Na_2SO_4$ and concentrated under reduced pressure. The obtained residue was mixed with EtOH (50 ml), and NaBH$_4$ (1.4 g) was added thereto, followed by stirring at room temperature for 1 hour. The reaction mixture was concentrated under reduced pressure, and EtOAc and 1 M hydrochloric acid were then added thereto. The organic layer was dried over Na$_2$SO$_4$ and concentrated under reduced pressure. The obtained residue was purified by silica gel column chromatography (hexane/EtOAc) to obtain 2-fluoro-3-(hydroxymethyl)phenol (2.2 g).

Preparation Example 593

2-(Morpholin-4-yl)pyrimidin-5-ol (300 mg) and ethyl 3-(bromomethyl)-2-fluorobenzoate (850 mg) were mixed with MeCN (5 ml), THF (2 ml) and DMF (1 ml), and potassium carbonate was added thereto, followed by stirring at room temperature for 1 hour. The reaction mixture was concentrated under reduced pressure, and EtOAc and water were then added thereto. The organic layer was dried over Na$_2$SO$_4$ and concentrated under reduced pressure. The obtained residue was purified by silica gel column chromatography (hexane/EtOAc) to obtain ethyl 2-fluoro-3-({[2-(morpholin-4-yl)pyrimidin-5-yl]oxy}methyl)benzoate (378 mg).

Preparation Example 594

5-Bromo-2-chloropyridine (5.0 g) was mixed with N,N-dimethylacetamide (25 ml), and morpholine (23 ml) was added thereto, followed by stirring at 130° C. for 2 days. The reaction mixture was concentrated under reduced pressure, and water was added to the residue, followed by extraction with EtOAc, and the organic layer was washed with saturated brine and dried over Na$_2$SO$_4$. The organic layer was concentrated under reduced pressure. The obtained residue was purified by silica gel column chromatography (hexane/EtOAc) to obtain 4-(5-bromopyridin-2-yl)morpholine (6.07 g).

Preparation Example 596

5-Bromo-2-fluoropyridine (1.7 g) was mixed with N,N-dimethylacetamide (5 ml), and 3-methoxyazetidine hydrochloride (335 mg) and potassium carbonate (1.5 g) were added thereto, followed by stirring at 100° C. overnight. The reaction mixture was concentrated under reduced pressure, and CHCl$_3$ and water were then added thereto. The organic layer was dried over Na$_2$SO$_4$ and concentrated under reduced pressure. The obtained residue was purified by silica gel column chromatography (hexane/EtOAc) to obtain 5-bromo-2-(3-methoxyazetidin-1-yl)pyridine (581 mg).

Preparation Example 603

1'-[3-({[tert-Butyl(dimethyl)silyl]oxy}methyl)-2-fluorophenyl]-1',2',3',6'-tetrahydro-3,4'-bipyridine (257 mg) was mixed with EtOH (5 ml), and 10% palladium carbon (55 mg) was added thereto under argon atmosphere, followed by stirring at room temperature overnight under hydrogen atmosphere. The reaction mixture was filtered using Celite as a filtration adjuvant, and the filtrate was concentrated under reduced pressure to obtain 3-{1-[3-({[tert-butyl(dimethyl)silyl]oxy}methyl)-2-fluorophenyl]piperidin-4-yl}pyridine (239 mg).

Preparation Example 613 tert-Butyl 4-[2-(3-methoxyazetidin-1-yl)pyrimidin-5-yl]-3,6-dihydropyridine-1(2H)-carboxylate (483 mg) was mixed with EtOH (5 ml), and 10% palladium carbon (100 mg) was added thereto, followed by stirring at room temperature for 5 hours under hydrogen atmosphere. The reaction mixture was filtered using Celite as a filtration adjuvant, and the filtrate was concentrated under reduced pressure. The residue was purified by silica gel column chromatography (hexane/EtOAc). The purified product thus obtained was mixed with EtOH (5 ml), and 4 M hydrogen chloride/dioxane (3.5 ml) was added thereto, followed by stirring at room temperature overnight. The reaction mixture was concentrated under reduced pressure, and then mixed with EtOH (5 ml), and potassium carbonate (2.0 g) was added thereto, followed by stirring at 80° C. for 2 hours. The reaction mixture was filtered and the filtrate was concentrated under reduced pressure to obtain 2-(3-methoxyazetidin-1-yl)-5-(piperidin-4-yl)pyrimidine (143 mg).

Preparation Example 614

4-(4-Methylpyrimidin-2-yl)morpholine (300 mg) was mixed with dichloromethane (4 ml), and N-bromosuccinimide (357 mg) was added thereto at 0° C., followed by stirring at room temperature for 1 hour. Hexane was added to the reaction mixture, followed by purification by silica gel column chromatography (EtOAc/hexane), to obtain 4-(5-bromo-4-methylpyrimidin-2-yl)morpholine (372 mg).

Preparation Example 617

{2-Fluoro-3-[2-(morpholin-4-yl)pyrimidin-5-yl]phenyl}methanol (337 mg), 1H-isoindole-1,3(2H)-dione (257 mg) and triphenylphosphine (458 mg) were mixed with THF, and diethyl azodicarboxylate (40% toluene solution) (0.68 ml) was added thereto at 0° C., followed by stirring at room temperature overnight. The reaction mixture was stirred at 0° C. for 30 minutes, then filtered, washed with ice-cooled THF, and dried at 50° C. under reduced pressure to obtain 2-{2-fluoro-3-[2-(morpholin-4-yl)pyrimidin-5-yl]benzyl}-1H-isoindole-1,3(2H)-dione (452 mg).

Preparation Example 631

4-(5-Bromo-4-methylpyrimidin-2-yl)morpholine (372 mg), (2-fluoro-3-formylphenyl)boronic acid (315 mg), and potassium phosphate (918 mg) were mixed with toluene (10 ml) and water (10 ml), and palladium acetate (16 mg) and dicyclohexyl(2',6'-dimethoxybiphenyl-2-yl)phosphine (59 mg) were added thereto, followed by stirring at 100° C. for 4 hours. (2-Fluoro-3-formylphenyl)boronic acid (315 mg), potassium phosphate (918 mg), palladium acetate (16 mg), dicyclohexyl(2',6'-dimethoxybiphenyl-2-yl)phosphine (59 mg), and water (1 ml) were added to the reaction mixture, followed by stirring at 100° C. overnight. The reaction mixture was cooled to room temperature, CHCl$_3$ and water were then added thereto, and the insoluble matter was removed by filtration. The organic layer of the filtrate was washed with water and saturated brine, dried over Na$_2$SO$_4$, and then concentrated under reduced pressure. The obtained residue was purified by silica gel column chromatography (EtOAc/hexane/CHCl$_3$) to obtain 2-fluoro-3-[4-methyl-2-(morpholin-4-yl)pyrimidin-5-yl]benzaldehyde (282 mg).

Preparation Example 638

Tetrahydro-2H-pyran-4-ol (200 mg) was mixed with THF (5 ml), and sodium hydride (55% suspended in oil) (120 mg) was added thereto, followed by stirring at room temperature for 5 minutes. 5-Bromo-2-chloropyrimidine (460 mg) was added to the reaction mixture, followed by stirring at room temperature. Water and EtOAc were added to the reaction mixture, and the organic layer was concentrated under reduced pressure. The obtained residue was purified by silica gel column chromatography (hexane/EtOAc) to obtain 5-bromo-2-(tetrahydro-2H-pyran-4-yloxy)pyrimidine (361 mg).

Preparation Example 651

1-[4-(Hydroxymethyl)piperidin-1-yl]ethan-1-one (200 mg) and THF (4 ml) were mixed, and NaH (70 mg) was added thereto, followed by stirring at room temperature for minutes. 5-[3-({[tert-Butyl(dimethyl)silyl]oxy}methyl)-2-fluorophenyl]-2-chloropyrimidine (200 mg) was added to the reaction mixture, followed by stirring at room temperature for 1 hour, and then 1 M TBAF/THF (1.2 ml) was added thereto, followed by stirring at room temperature. Water and EtOAc were added to the reaction mixture, and the organic layer was concentrated under reduced pressure. The obtained residue was purified by silica gel column chromatography (hexane/EtOAc/CHCl$_3$/MeOH) to obtain 1-{4-[({5-[2-fluoro-3-(hydroxymethyl)phenyl]pyrimidin-2-yl}oxy)methyl]piperidin-1-yl}ethan-1-one (167 mg).

Preparation Example 653

5-[3-({[tert-Butyl(dimethyl)silyl]oxy}methyl)-2-fluorophenyl]-2-chloropyrimidine (200 mg) was mixed with THF (4 ml), and sodium ethoxide (132 mg) was added thereto, followed by stirring at room temperature for 3 hours, and then a 1 M TBAF/THF solution (1.2 ml) was added thereto, followed by stirring at room temperature for 1 hour. Water and EtOAc were added to the reaction mixture, and the organic layer was concentrated under reduced pressure. The obtained residue was purified by silica gel column chromatography (hexane/EtOAc) to obtain [3-(2-ethoxypyrimidin-5-yl)-2-fluorophenyl]methanol (129 mg).

Preparation Example 663

Methyl 3-{[(tert-butoxycarbonyl)amino]methyl}benzoate (4.6 g) was mixed with toluene (50 ml), followed by cooling to 0° C. Sodium bis(2-methoxyethoxy)aluminum hydride (65% toluene solution) (20 g) was added dropwise over 30 minutes, followed by stirring at 0° C. for 1 hour. A 1 M aqueous NaOH solution (30 ml) was added dropwise to the reaction mixture, and CHCl$_3$ was then added thereto. The organic layer was dried over Na$_2$SO$_4$ and concentrated under reduced pressure. The obtained residue was purified by silica gel column chromatography (hexane/EtOAc) to obtain tert-butyl [3-(hydroxymethyl)benzyl]carbamate (4.1 g).

Preparation Example 671

4,4'-Bipiperidine dihydrochloride (2.95 g) was mixed with MeOH (25 ml), and a mixture of benzyl chloroformate (2.2 g) and toluene (5 ml) was added dropwise thereto over 1 hour while keeping the solution neutral by adding a 6 M aqueous NaOH solution at the same time. The reaction mixture was stirred at room temperature for 30 minutes and then concentrated under reduced pressure. CHCl$_3$, and a saturated aqueous sodium hydrogen carbonate solution were added to the reaction mixture. The organic layer was dried over Na$_2$SO$_4$ and concentrated under reduced pressure. The obtained residue was purified by silica gel column chromatography (CHCl$_3$/MeOH) to obtain benzyl 4,4'-bipiperidine-1-carboxylate (1.5 g).

Preparation Example 674 tert-Butyl 3-(piperidin-4-yloxy)azetidine-1-carboxylate (2.78 g) was mixed with THF (40 ml), and TEA (3.5 ml) and benzyl chloroformate (2.7 g) were added thereto, followed by stirring at room temperature for 3 hours. EtOAc and water were added to the reaction mixture, and the organic layer was dried over Na$_2$SO$_4$ and concentrated under reduced pressure. The obtained residue was purified by silica gel column chromatography (hexane/EtOAc).

The purified product thus obtained was mixed with EtOH (40 ml), and a 4 M hydrogen chloride/dioxane solution (30 ml) was added thereto, followed by stirring at room temperature overnight. The reaction mixture was concentrated under reduced pressure, and CHCl$_3$ and a 1 M aqueous NaOH solution were then added thereto. The organic layer was dried over Na$_2$SO$_4$ and then concentrated under reduced pressure to obtain benzyl 4-(azetidin-3-yloxy)piperidine-1-carboxylate (1.97 g).

Preparation Example 677

2-(Hydroxymethyl)pyrrolidine (500 mg) was mixed with dichloromethane (5 ml), and TEA (0.9 ml) and acetyl chloride (407 mg) were added thereto at 0° C., followed by stirring at room temperature overnight. 8 M Potassium hydroxide was added to the reaction mixture, followed by stirring at room temperature for 1 hour. The reaction mixture was extracted by the addition of water and CHCl$_3$/MeOH (4:1), the organic layer was washed with water and saturated brine, and dried over anhydrous Na$_2$SO$_4$, and the solvent was concentrated under reduced pressure. The obtained residue was purified by silica gel column chromatography (MeOH/CHCl$_3$) to obtain 1-[2-(hydroxymethyl)pyrrolidin-1-yl]ethanone (442 mg).

Preparation Example 680

{2-Fluoro-3-[2-(piperidin-4-yl)pyrimidin-5-yl]phenyl}methanol (80 mg) was mixed with dichloromethane (1.6 ml), and TEA (85 mg) and acetyl chloride (48 mg) were added thereto at 0° C. The reaction mixture was concentrated under reduced pressure, the residue was mixed with MeOH, and a 1 M aqueous NaOH solution (0.8 ml) was added thereto, followed by stirring for 3 hours. 1 M hydrochloric acid was added to the reaction mixture, and CHCl$_3$/water was added to the reaction liquid. The aqueous layer was extracted with CHCl$_3$, and the prepared organic layer was dried over Na$_2$SO$_4$ and then concentrated under reduced pressure. The obtained residue was purified by silica gel column chromatography (CHCl$_3$/MeOH) to obtain 1-(4-{5-[2-fluoro-3-(hydroxymethyl)phenyl]pyrimidin-2-yl}piperidin-1-yl)ethanone (90 mg).

Preparation Example 686

1-[3-({[tert-Butyl(dimethyl)silyl]oxy}methyl)-2-fluorophenyl]-4,4'-bipiperidine (125 mg) and TEA (0.15 ml) were mixed with DCE (3 ml), and acetyl chloride (39 mg) was added thereto, followed by stirring at room temperature for 1 hour. A saturated aqueous sodium hydrogen carbonate solution and CHCl$_3$ were added to the reaction mixture, and the organic layer was dried over Na$_2$SO$_4$ and concentrated under reduced pressure. The obtained residue was mixed with THF (3 ml), and a 1 M TBAF/THF solution (0.6 ml) was added thereto, followed by stirring at room temperature for 1 hour. To the reaction mixture were added an aqueous ammonium chloride solution and EtOAc, the organic layer was dried over Na$_2$SO$_4$, and the solvent was concentrated under reduced pressure. The obtained residue was purified by silica gel column chromatography (hexane/EtOAc) to obtain 1-{1'-[2-fluoro-3-(hydroxymethyl)phenyl]-4,4'-bipiperidin-1-yl}ethanone (84 mg).

Preparation Example 707

[3-(2-Chloropyrimidin-5-yl)-2-fluorophenyl]methanol (600 mg) was mixed with DMF (12 ml), and piperazine (2.2 g) was added thereto, followed by stirring at room temperature overnight. The reaction mixture was concentrated under reduced pressure, and water was added to the residue, followed by stirring at 0° C. for 1 hour. The produced solid was collected by filtration, washed with water, and then dried at 50° C. under reduced pressure to obtain {2-fluoro-3-[2-(piperazin-1-yl)pyrimidin-5-yl]phenyl}methanol (697 mg).

Preparation Example 709

5-{4-[3-({[tert-Butyl(dimethyl)silyl]oxy}methyl)-2-fluorophenyl]piperazin-1-yl}pyrimidin-2-yl trifluoromethanesulfonate (200 mg) was mixed with THF (4 ml), and 2-methoxyethanamine (864 mg) was added thereto, followed by stirring at 60° C. overnight. Water and EtOAc were added to the reaction mixture, and the organic layer was concentrated under reduced pressure. The obtained residue was mixed with THF (5 ml), and a 1 M TBAF/THF solution (1.6 ml) was added thereto, followed by stirring at room temperature overnight. Water and EtOAc were added to the reaction mixture, and the organic layer was concentrated under reduced pressure. The obtained residue was purified by silica gel column chromatography (EtOAc/hexane) to obtain [2-fluoro-3-(4-{2-[(2-methoxyethyl)amino]pyrimidin-5-yl}piperazin-1-yl) phenyl]methanol (105 mg).

Preparation Example 712 tert-Butyl 3-(pyridin-4-yloxy)azetidine-1-carboxylate (494 mg) was mixed with DCE (5 ml), and TFA (2 ml) was added thereto, followed by stirring at room temperature for 5 hours. The reaction mixture was concentrated under reduced pressure, and the obtained residue was purified by basic silica gel column chromatography (CHCl$_3$/MeOH) to obtain 4-(azetidin-3-yloxy)pyridine (268 mg).

Preparation Example 749

Using 2-(3-methoxyazetidin-1-yl)pyrazine (451 mg) as a starting material and N-chlorosuccinimide as a halogenating agent under the same reaction conditions as in Preparation Example 614, 2-chloro-5-(3-methoxyazetidin-1-yl)pyrazine (303 mg) was prepared.

Preparation Example 752

1-[3-({[tert-Butyl(dimethyl)silyl]oxy}methyl)-2-fluorophenyl]piperazine (400 mg) was suspended in toluene (8 ml), and 3-chloropyridazine hydrochloride (242 mg), Pd$_2$(dba)$_3$ (56 mg), dicyclohexyl(2',6'-dimethoxybiphenyl-2-yl)phosphine (51 mg), and sodium tert-butoxide (308 mg) were added thereto, followed by stirring at 100° C. overnight. The reaction mixture was cooled to room temperature, and filtered by the addition of CHCl$_3$ and Celite, and the filtrate was concentrated. The obtained residue was purified by silica gel column chromatography (EtOAc:hexane=70:30 to 100:0), and then purified by basic silica gel column chromatography (EtOAc/hexane) to obtain 3-{4-[3-({[tert-butyl(dimethyl)silyl]oxy}methyl)-2-fluorophenyl]piperazin-1-yl}pyridazine (325 mg).

Preparation Example 754

3-Methoxyazetidine hydrochloride (100 mg) was mixed with THF (3 ml), and chloroacetic acid anhydride (166 mg) and sodium hydrogen carbonate (272 mg) were added thereto, followed by stirring at room temperature overnight. Water and sodium chloride were added to the reaction mixture, followed by stirring for 30 minutes. Then, after extraction with EtOAc twice, the organic layer was washed with saturated brine and dried over Na$_2$SO$_4$, and the organic layer was concentrated under reduced pressure to obtain 2-chloro-1-(3-methoxyazetidin-1-yl)ethanone (130 mg).

Preparation Example 758

A mixture of 1-[3-({[tert-butyl(dimethyl)silyl]oxy}methyl)-2-fluorophenyl]piperazine and MeCN was added to 2-chloro-1-(3-methoxyazetidin-1-yl)ethanone (130 mg) and potassium carbonate (219 mg), followed by stirring at 80° C. for 3 hours. CHCl$_3$ was added to the reaction mixture, and the insoluble matter was removed by filtration. The filtrate was concentrated under reduced pressure, and the residue was purified by silica gel column chromatography (MeOH/CHCl$_3$) to obtain 2-{4-[3-({[tert-butyl(dimethyl)silyl]oxy}methyl)-2-fluorophenyl]piperazin-1-yl}-1-(3-methoxyazetidin-1-yl)ethanone (354 mg).

Preparation Example 760

5-[3-({[tert-Butyl(dimethyl)silyl]oxy}methyl)-2-fluorophenyl]-2-[4-(vinylsulfonyl)piperazin-1-yl]pyrimidine (360 mg) was mixed with THF (3 ml) and MeOH (4 ml), and a 1 M aqueous NaOH solution (1.46 ml) was added thereto, followed by stirring at room temperature for 3 hours. CHCl$_3$ was added to the reaction mixture, which was washed with water and saturated brine, and dried over Na$_2$SO$_4$. Then, the organic layer was concentrated under reduced pressure to obtain 5-[3-({[tert-butyl(dimethyl)silyl]oxy}methyl)-2-fluorophenyl]-2-{4-[(2-methoxyethyl)sulfonyl]piperazin-1-yl}pyrimidine (353 mg).

Preparation Example 761

1-Acetylpiperidine-4-carboxylic acid (161 mg) was mixed with dichloromethane (5 ml), and oxalyl chloride (124 mg) and DMF (3 mg) were added thereto, followed by stirring at room temperature for 1 hour. TEA and 3-(2-aminopyrimidin-5-yl)-2-fluorobenzaldehyde (170 mg) were added thereto at 0° C., followed by stirring at room temperature overnight. A mixture of 1-acetylpiperidine-4-carboxylic acid (161 mg), oxalyl chloride (0.084 ml), and DMF in dichloromethane (3 ml), which is mixed in advance and was stirred for 1 hour, was added thereto at 0° C., followed by stirring at room temperature for 3 hours. Furthermore, a mixture of 1-acetylpiperidine-4-carboxylic acid (161 mg), oxalyl chloride (0.084 ml), and DMF in dichloromethane (3 ml), after mixing with the reaction mixture in advance, and then stirring for 1 hour, was added thereto at 0° C., followed by stirring at room temperature overnight. Furthermore, a mixture of 1-acetylpiperidine- 4-carboxylic acid (322 mg), oxalyl chloride (0.168 ml), and DMF in dichloromethane (6 ml) which is mixed in advance and was stirred for 1 hour, was added thereto at 0° C., followed by stirring at room temperature for 3 hours. Furthermore, a mixture of 1-acetylpiperidine-4-carboxylic acid (322 mg), oxalyl chloride (0.168 ml), and DMF in dichloromethane (6 ml) which is mixed in advance and was stirred for 1 hour, was added thereto at 0° C., followed by stirring at room temperature overnight. $CHCl_3$ and water were added to the reaction mixture, and the insoluble matter was removed by filtration. The organic layer was washed with water and saturated brine, dried over $Na_2SO_4$, and then concentrated under reduced pressure. The obtained residue was mixed with MeOH, and $NaHCO_3$ was added thereto, followed by stirring at room temperature overnight. The reaction mixture was concentrated under reduced pressure, and the residue was purified by silica gel column chromatography (MeOH/$CHCl_3$) to obtain 1-acetyl-N-[5-(2-fluoro-3-formylphenyl)pyrimidin-2-yl]piperidine-4-carboxyamide (363 mg).

Preparation Example 766 tert-Butyl 4-(2-iodoethyl)piperidine-1-carboxylate (6.75 g) was mixed with dichloromethane (90 ml), and benzyl 4-hydroxypiperidine-1-carboxylate (4.0 g), silver trifluoromethane sulfonate (10.3 g), and 2,6-di-tert-butylpyridine (12 ml) was added thereto, followed by stirring at room temperature overnight. The reaction mixture was filtered using Celite as a filtration adjuvant, and the filtrate was concentrated under reduced pressure. The obtained residue was purified by silica gel column chromatography (hexane/EtOAc) to obtain tert-butyl 4-[2-({1-[(benzyloxy)carbonyl]piperidin-4-yl}oxy)ethyl]piperidine-1-carboxylate (3.4 g).

Preparation Example 767

5-[3-({[tert-Butyl(dimethyl)silyl]oxy}methyl)-2-fluorophenyl]-2-(piperidin-4-ylmethoxy)pyrimidine (200 mg) was mixed with THF (4 ml), and ethylisocyanate (91 mg) was added thereto, followed by stirring at room temperature overnight. A 1 M TBAF/THF solution (1 ml) was added to the reaction mixture, followed by further stirring at room temperature for 3 hours. Water and EtOAc were added to the reaction mixture, and the organic layer was dried over $Na_2SO_4$ and concentrated under reduced pressure. The obtained residue was purified by silica gel column chromatography (MeOH/$CHCl_3$) to obtain N-ethyl-4-[({5-[2-fluoro-3-(hydroxymethyl)phenyl]pyrimidin-2-yl}oxy)methyl]piperidine-1-carboxyamide (159.3 mg).

Preparation Example 772

5-[3-({[tert-Butyl(dimethyl)silyl]oxy}methyl)-2-fluorophenyl]-2-(piperazin-1-yl)pyrimidine (500 mg) was mixed with dichloromethane (10 ml), and DIPEA (482 mg) and 2-chloroethanesulfonyl chloride (304 mg) were added thereto at 0° C., followed by stirring at 0° C. for 1.5 hours. $CHCl_3$ and water were added to the reaction mixture, and the organic layer was washed with water and saturated brine, dried over $Na_2SO_4$, and then concentrated under reduced pressure. The obtained residue was purified by silica gel column chromatography (EtOAc/hexane) to obtain 5-[3-({[tert-butyl(dimethyl)silyl]oxy}methyl)-2-fluorophenyl]-2-[4-(vinylsulfonyl)piperazin-1-yl]pyrimidine (360 mg).

Preparation Example 776

1-[3-({[tert-Butyl(dimethyl)silyl]oxy}methyl)-2-fluorophenyl]piperazine (140 mg) was mixed with DCE (4 ml), and ethanesulfonyl chloride (122 mg) and TEA (145 mg) were added thereto, followed by stirring at room temperature for 2 hours. $CHCl_3$ and water were added to the reaction mixture, and the organic layer was dried over $Na_2SO_4$ and concentrated under reduced pressure. The obtained residue was mixed with THF (4 ml), and a 1 M TBAF/THF solution (0.9 ml) was added thereto, followed by stirring at room temperature for 2 hours. EtOAc and water were added to the reaction mixture, and the organic layer was dried over $Na_2SO_4$ and concentrated under reduced pressure. The obtained residue was purified by silica gel column chromatography (EtOAc/hexane) to obtain {3-[4-(ethylsulfonyl)piperazin-1-yl]-2-fluorophenyl}methanol (123.9 mg).

Preparation Example 791

4-Nitrophenyl 4-[({5-[3-({[tert-butyl(dimethyl)silyl]oxy}methyl)-2-fluorophenyl]pyrimidin-2-yl}oxy)methyl]piperidine-1-carboxylate (200 mg) was mixed with NMP (5 ml), and isopropyl amine (0.3 ml) was added thereto, followed by stirring at 70° C. for 6 hours. $iPrNH_2$ (0.3 ml) was added to the reaction mixture, followed by stirring at 70° C. overnight. $iPrNH_2$ (0.4 ml) was added to the reaction mixture, followed by stirring at 70° C. for 3 hours. The reaction mixture was cooled to room temperature and concentrated under reduced pressure, and then a 1 M aqueous NaOH solution and EtOAc were added thereto. The organic layer was concentrated under reduced pressure. The obtained residue was mixed with THF (4 ml), and a 1 M TBAF/THF solution (0.7 ml) was added thereto, followed by stirring at room temperature for 2 hours. EtOAc and water were added to the reaction mixture, and the organic layer was dried over $Na_2SO_4$ and concentrated under reduced pressure. The obtained residue was purified by silica gel column chromatography (EtOAc/hexane/MeOH/$CHCl_3$) to obtain 4-[({5-[2-fluoro-3-(hydroxymethyl)phenyl]pyrimidin-2-yl}oxy)methyl]-N-isopropylpiperidine-1-carboxyamide (107.4 mg).

Preparation Example 793 tert-Butyl 3-(pyridin-4-ylmethoxy)azetidine-1-carboxylate (4.8 g) was mixed with acetic acid (25 ml) and EtOAc (25 ml), and 10% platinum/carbon was added thereto under argon atmosphere, followed by stirring at room temperature overnight under hydrogen atmosphere of 1 atm. The reaction mixture was filtered using Celite as a filtration adjuvant, and the filtrate was concentrated under reduced pressure. The residue was purified by silica gel column chromatography ($CHCl_3$/MeOH) to obtain tert-butyl 3-(piperidin-4-ylmethoxy)azetidine-1-carboxylate (4.8 g).

Preparation Example 796

Benzyl 3-oxopiperazine-1-carboxylate (400 mg) and 3-(bromomethyl)pyridine hydrobromide (647 mg) were mixed with DMF (8 ml), and sodium hydride (55% suspended in oil) (194 mg) was added thereto at 0° C., followed by stirring at room temperature for 3 hours. Water and $CHCl_3$ were added to the reaction mixture at 0° C., and the organic layer was washed with water and saturated brine, dried over anhydrous sodium carbonate, and concentrated under reduced pressure. The obtained residue was purified by basic silica gel column chromatography (EtOAc/hexane) to obtain benzyl 3-oxo-4-(pyridin-3-ylmethyl)piperazine-1-carboxylate (345 mg).

Preparation Example 801

2-(2-Fluoro-3-{4-[2-(3-methoxyazetidin-1-yl)pyrimidin-5-yl]piperazin-1-yl}benzyl)-1H-isoindole-1,3(2H)-dione (135 mg) was suspended in EtOH (3 ml), and hydrazine hydrate (67 mg) was added thereto, followed by stirring at 80° C. overnight. The reaction mixture was concentrated under reduced pressure, and the obtained residue was purified by silica gel column chromatography (28% aqueous ammonia/MeOH/CHCl$_3$) to obtain 1-(2-fluoro-3-{4-[2-(3-methoxyazetidin-1-yl)pyrimidin-5-yl]piperazin-1-yl}phenyl)methan amine (100 mg).

Preparation Example 803 tert-Butyl 3-hydroxyazetidine-1-carboxylate (1.0 g) and 6-methylpyridin-3-ol (570 mg) were mixed with THF (10 ml), and triphenylphosphine (2.3 g) was added thereto. A 1.9 M DIAD/toluene solution (4.5 ml) was added dropwise thereto, followed by stirring at 55° C. overnight. The reaction mixture was concentrated under reduced pressure, and EtOAc and 1 M hydrochloric acid were added thereto. The aqueous layer was adjusted to pH of around 10 by the addition of a 4 M aqueous NaOH solution, followed by extraction with CHCl$_3$. The organic layer was dried over Na$_2$SO$_4$ and concentrated under reduced pressure. The obtained residue was purified by silica gel column chromatography (CHCl$_3$/MeOH). The purified product thus obtained was mixed with DCE (6 ml), and TFA (3 ml) was added thereto, followed by stirring at room temperature for 5 hours. The reaction mixture was concentrated under reduced pressure, and then CHCl$_3$ and a 1 M aqueous NaOH solution were added thereto. The organic layer was dried over Na$_2$SO$_4$ and then concentrated under reduced pressure to obtain 5-(azetidin-3-yloxy)-2-methylpyridine (269 mg).

Preparation Example 805

4-Bromo-2,6-dimethylpyridine (2 g) was mixed with THF (30 ml) and cooled to −78° C. under argon atmosphere. A 1.65 M n-butyl lithium/hexane solution (8.5 ml) was added dropwise thereto, followed by stirring at −78° C. for 10 minutes, and DMF (1.3 ml) was added thereto. The reaction mixture was warmed to 0° C. over 1 hour, followed by stirring at 0° C. for 1 hour. Water and EtOAc were added to the reaction mixture, and the organic layer was dried over Na$_2$SO$_4$, and the reaction mixture was concentrated under reduced pressure. The obtained residue was mixed with MeOH (30 ml), and NaBH$_4$ (610 mg) was added thereto, followed by stirring at room temperature for 1 hour. The reaction mixture was concentrated under reduced pressure, and CHCl$_3$ and water were added to the obtained residue. The organic layer was dried over Na$_2$SO$_4$ and concentrated under reduced pressure. The obtained residue was purified by silica gel column chromatography (CHCl$_3$/MeOH) to obtain (2,6-dimethylpyridin-4-yl)methanol (457 mg).

Preparation Example 806

(2,6-Dimethylpyridin-4-yl)methanol (457 mg) was mixed with DCE (8 ml), and thionyl chloride (0.6 ml) and DMF (19 mg) were added thereto, followed by stirring at room temperature for 1 hour. The reaction mixture was concentrated under reduced pressure to obtain 4-(chloromethyl)-2,6-dimethylpyridine hydrochloride (567 mg).

Preparation Example 807

1-(2-tert-Butoxypyridin-4-yl)-4-[3-({[tert-butyl(dimethyl)silyl]oxy}methyl)-2-fluorophenyl]piperazine (3.14 g) was mixed with CH$_2$Cl$_2$ (50 ml), and TFA (5.1 ml) was added thereto, followed by stirring at room temperature overnight. The reaction mixture was concentrated under reduced pressure, and the residue was mixed with MeOH (2 ml). A 8 M NH$_3$/MeOH solution (10 ml) was added thereto at 0° C., followed by stirring at room temperature for 2 hours. The solid in the reaction mixture was collected by filtration, washed with MeOH, and dried at 50° C. under reduced pressure to obtain 4-{4-[2-fluoro-3-(hydroxymethyl)phenyl]piperazin-1-yl}pyridin-2(1H)-one (1.76 g).

Preparation Example 809 tert-Butyl 4-[1-(diphenylmethyl)azetidin-3-yl]piperidine-1-carboxylate (1.9 g) was mixed with MeOH (50 ml), and 1 M hydrochloric acid (5.1 ml) and 20% palladium carbon hydroxide (600 mg) were added thereto, followed by stirring at room temperature for 4 hours under hydrogen atmosphere of 3 atm. After returning to normal pressure under argon atmosphere, a 1 M aqueous NaOH solution (1 ml) was added thereto. The reaction mixture was filtered using Celite as a filtration adjuvant, and the filtrate was concentrated under reduced pressure. CHCl$_3$ and a 1 M aqueous NaOH solution were added to the obtained residue, and the organic layer was dried over Na$_2$SO$_4$ and then concentrated under reduced pressure. The obtained residue was purified by basic silica gel column chromatography (CHCl$_3$/MeOH) to obtain tert-butyl 4-(azetidin-3-yl)piperidine-1-carboxylate (1.1 g).

Preparation Example 810 tert-Butyl 4-{1-[3-({[tert-butyl(dimethyl)silyl]oxy}methyl)-2-fluorophenyl]azetidin-3-yl}piperidine-1-carboxylate (2 g) was mixed with CH$_2$Cl$_2$ (20 ml), and TFA (5 ml) was added thereto, followed by stirring at room temperature for 3 hours. The reaction mixture was concentrated under reduced pressure. The obtained residue was mixed with CH$_2$Cl$_2$ (30 ml), and TEA (6 ml) and TBSCl (2.5 g) were added thereto at 60° C. overnight. Water was added to the reaction mixture, and the organic layer was dried over Na$_2$SO$_4$ and then concentrated under reduced pressure. The obtained residue was mixed with MeOH (20 ml), and a 1 M aqueous NaOH solution (5 ml), followed by stirring at room temperature for 1 hour. The reaction mixture was concentrated under reduced pressure, CHCl$_3$ and water were added to the obtained residue, and the organic layer was dried over Na$_2$SO$_4$ and then concentrated under reduced pressure. The obtained residue was purified by basic silica gel column chromatography (hexane/EtOAc) to obtain 4-{1-[3-({[tert-butyl(dimethyl)silyl]oxy}methyl)-2-fluorophenyl]azetidin-3-yl}piperidine (673 mg).

Preparation Example 821 tert-Butyl 3-{[6-(hydroxymethyl)pyridin-3-yl]oxy}azetidine-1-carboxylate (198 mg) was mixed with THF (3 ml), and sodium hydride (55% suspended in oil) (50 mg) was added thereto at 0° C., followed by stirring at 0° C. for 30 minutes. Methyl iodide (0.4 ml) was added to the reaction mixture, followed by stirring at room temperature for 3 hours. EtOAc and water were added to the reaction mixture, and the organic layer was dried over Na$_2$SO$_4$, and concentrated under reduced pressure. The obtained residue was purified by silica gel column chromatography (CHCl$_3$/MeOH). The purified product thus obtained was mixed with DCE (2.8 ml), and TFA (902 mg) was added thereto, followed by stirring at room temperature for 5 hours. CHCl$_3$ and a 1 M aqueous NaOH solution were added to the reaction mixture, and the organic layer was dried over Na₂SO₄ and concentrated under reduced pressure. The obtained residue was purified by basic silica gel column chromatography (CHCl₃/MeOH) to obtain 5-(azetidin-3-yloxy)-2-(methoxymethyl)pyridine.

Preparation Example 830

(3-{3-[(6-tert-Butoxypyridin-3-yl)oxy]azetidin-1-yl}-2-fluorophenyl)methanol (760 mg) was mixed with dichloromethane (5 ml), and TFA (2 ml) was added thereto, followed by stirring at room temperature for 3 hours. The reaction mixture was concentrated under reduced pressure, and a 1 M aqueous NaOH solution and CHCl₃ were added thereto. The organic layer was dried over Na₂SO₄ and then concentrated under reduced pressure. The obtained residue was purified by silica gel column chromatography (CHCl₃/MeOH) to obtain 5-({1-[2-fluoro-3-(hydroxymethyl)phenyl]azetidin-3-yl}oxy)pyridin-2(1H)-one (428 mg).

Preparation Example 834

4-{1-[3-({[tert-Butyl(dimethyl)silyl]oxy}methyl)-2-fluorophenyl]azetidin-3-yl}piperidine (120 mg) and triethylamine (145 mg) were mixed with dichloromethane (3 ml), and propanoyl chloride (48 mg) was added thereto, followed by stirring at room temperature for 1 hour. A 1 M aqueous NaOH solution and CHCl₃ were added to the reaction mixture, and the organic layer was dried over Na₂SO₄ and concentrated under reduced pressure. The obtained residue was mixed with THF (3 ml), and a 1 M TBAF/THF (0.5 ml) solution was added thereto, followed by stirring at room temperature for 1 hour. A saturated aqueous ammonium chloride solution and EtOAc were added to the reaction mixture, and the organic layer was dried over Na₂SO₄ and concentrated under reduced pressure. The obtained residue was purified by silica gel column chromatography (CHCl₃/MeOH) to obtain 1-(4-{1-[2-fluoro-3-(hydroxymethyl)phenyl]azetidin-3-yl}piperidin-1-yl)propan-1-one (98 mg).

Preparation Example 836

4-{1-[3-({[tert-butyl(dimethyl)silyl]oxy}methyl)-2-fluorophenyl]azetidin-3-yl}piperidine (120 mg) and methoxy acetic acid (47 mg) was mixed with dichloromethane (3 ml), and WSC hydrochloride (100 mg) and HOBt (70 mg) was added thereto, followed by stirring at room temperature for 3 hours. A 1 M aqueous NaOH solution and CHCl₃ were added to the reaction mixture, and the organic layer was dried over Na₂SO₄ and concentrated under reduced pressure. The obtained residue was mixed with THF (3 ml), and a 1 M TBAF/THF solution (0.66 ml) was added thereto, followed by stirring at room temperature for 1 hour. EtOAc and a saturated aqueous ammonium chloride solution were added to the reaction mixture, and the organic layer was dried over Na₂SO₄ and concentrated under reduced pressure. The obtained residue was purified by silica gel column chromatography (hexane/EtOAc) to obtain 1-(4-{1-[2-fluoro-3-(hydroxymethyl)phenyl]azetidin-3-yl}piperidin-1-yl)-2-methoxyethan one (106 mg).

Preparation Example 840

4-{4-[2-Fluoro-3-(hydroxymethyl)phenyl]piperazin-1-yl}pyridin-2(1H)-one (300 mg) was suspended in DMF (7.5 ml), and potassium carbonate (273 mg), 2-bromoethylmethyl ether (275 mg), and tetrabutylammonium iodide (37 mg) were added thereto, followed by stirring at 60° C. overnight. Water and CHCl₃ were added to the reaction mixture, and the organic layer was washed with saturated brine and then dried over Na₂SO₄. The solvent was evaporated under reduced pressure. The obtained residue was purified by silica gel column chromatography (MeOH/CHCl₃) to obtain (2-fluoro-3-{4-[2-(2-methoxyethoxy)pyridin-4-yl]piperazin-1-yl}phenyl)methanol (104 mg).

Preparation Example 841

Benzyl 3-hydroxyazetidine-1-carboxylate (2.3 g) and 6-tert-butoxypyridin-3-ol (1.5 g) were mixed with THF (25 ml), and triphenylphosphine (4 g) was added thereto. A 1.9 M DIAD/toluene solution (8 ml) was added dropwise thereto, followed by stirring at 55° C. overnight. The reaction mixture was concentrated under reduced pressure. The obtained residue was mixed with ethanol (25 ml), and 10% palladium carbon (800 mg) were added thereto, followed by stirring at room temperature for 5 hours under hydrogen atmosphere. The reaction mixture was filtered using Celite as a filtration adjuvant, and the filtrate was concentrated under reduced pressure. The obtained residue was purified by silica gel column chromatography (CHCl₃/MeOH) to obtain 5-(azetidin-3-yloxy)-2-tert-butoxypyridine (595 mg).

Preparation Example 842

5-({1-[2-Fluoro-3-(hydroxymethyl)phenyl]azetidin-3-yl}oxy)pyridin-2(1H)-one (160 mg) was mixed with DMF (3 ml), and methyl iodide (114 mg) and potassium carbonate (200 mg) were added thereto, followed by stirring at 60° C. for 2 hours. The reaction mixture was concentrated under reduced pressure, and to the residue were added CHCl₃ and water. The organic layer was dried over Na₂SO₄ and then concentrated under reduced pressure. The obtained residue was purified by silica gel column chromatography (CHCl₃/MeOH) to obtain 5-({1-[2-fluoro-3-(hydroxymethyl)phenyl]azetidin-3-yl}oxy)-1-methylpyridin-2(1H)-one (106 mg).

Preparation Example 845

4-({1-[3-({[tert-Butyl(dimethyl)silyl]oxy}methyl)-2-fluorophenyl]azetidin-3-yl}oxy)piperidine (250 mg) and dioxane (7 ml) were mixed, and methyl 5-bromopyridine-2-carboxylate (170 mg), palladium acetate (II)(15 mg), dicyclohexyl(2',4',6'-triisopropylbiphenyl-2-yl)phosphine (60 mg), and tripotassium phosphate (400 mg) were added thereto, followed by stirring 100° C. for 48 hours. The reaction mixture was cooled to room temperature, and filtered by the addition of CHCl₃ and Celite, and the filtrate was concentrated under reduced pressure. The residue was purified by silica gel column chromatography (hexane/EtOAc). The purified product thus obtained was mixed with THF (5 ml), and a 1.0 M TBAF/THF solution (0.63 ml) was added thereto, followed by stirring at room temperature for 1 hour. A saturated aqueous ammonium chloride solution and CHCl₃ were added to the reaction mixture, and the organic layer was dried over Na₂SO₄ and then concentrated under reduced pressure. The obtained residue was purified by silica gel column chromatography (CHCl₃/MeOH) to obtain methyl 5-[4-({1-[2-fluoro-3-(hydroxymethyl)phenyl]azetidin-3-yl}oxy)piperidin-1-yl]pyridine-2-carboxylate (92 mg).

Preparation Example 847 tert-Butyl 4-{1-[3-({[tert-butyl(dimethyl)silyl]oxy}methyl)-2-fluorophenyl]azetidin-3-yl}piperidine-1-carboxylate (2.9 g) and dichloromethane (29 ml) were mixed, and TFA (7.3 ml) was added thereto, followed by stirring at room temperature for 3 hours. The reaction mixture was concentrated under reduced pressure, and CHCl$_3$ and a saturated aqueous sodium hydrogen carbonate solution were added thereto. The aqueous layer was concentrated under reduced pressure, and CHCl$_3$ was added to the residue, followed by stirring and filtrating. The filtrate was dried over Na$_2$SO$_4$ and then concentrated under reduced pressure. The obtained residue was purified by basic silica gel column chromatography (CHCl$_3$/MeOH) to obtain {2-fluoro-3-[3-(piperidin-4-yl)azetidin-1-yl]phenyl}methanol (1.25 g).

Preparation Example 853

5-{4-[2-Fluoro-3-(hydroxymethyl)phenyl]piperazin-1-yl}pyridin-2(1H)-one (352 mg) and DMF (10 ml) were mixed, and potassium carbonate (240 mg) and methyl iodide (200 mg) were added thereto, followed by stirring at 60° C. overnight. Methyl iodide (49 mg) and potassium carbonate (48.1 mg) were added thereto, followed by stirring at 60° C. for 4 hours. The reaction mixture was cooled to room temperature, and water and CHCl$_3$ were added thereto at 0° C. The organic layer was washed with water and saturated brine, and then dried over Na$_2$SO$_4$, and the solvent was evaporated under reduced pressure. The obtained residue was purified by silica gel column chromatography (CHCl$_3$/MeOH) to obtain 5-{4-[2-fluoro-3-(hydroxymethyl)phenyl]piperazin-1-yl}-1-methylpyridin-2(1H)-one (256 mg).

Preparation Example 855

6-Iodoimidazo[1,2-a]pyridine (400 mg), tert-butyl 3-hydroxyazetidine-1-carboxylate (500 mg), and toluene (2 ml) were mixed, and copper iodide (I) (40 mg), 1,10-phenanthroline (60 mg), and cesium carbonate (1 g) were added thereto, followed by stirring at 100° C. overnight. CHCl$_3$ and water were added to the reaction mixture, and the organic layer was dried over Na$_2$SO$_4$ and then concentrated under reduced pressure. The obtained residue was purified by silica gel column chromatography (CHCl$_3$/MeOH). The purified product thus obtained was mixed with dichloromethane (5 ml), and TFA (1.5 ml) was added thereto, followed by stirring at room temperature for 3 hours. The reaction mixture was concentrated under reduced pressure, and the residue was purified by basic silica gel column chromatography (CHCl$_3$/MeOH) to obtain 6-(azetidin-3-yloxy)imidazo[1,2-a]pyridine (189 mg).

Preparation Example 857 tert-Butyl 3-oxoazetidine-1-carboxylate (1 g) and THF (20 ml), which had been cooled to 0° C., were mixed, and a 1.12 M methylmagnesium bromide/THF solution (10 ml) was added thereto, followed by stirring at the same temperature for 1 hour. Water and EtOAc were added to the reaction mixture, the organic layer was dried over Na$_2$SO$_4$, and the solvent was concentrated under reduced pressure. The obtained residue was purified by silica gel column chromatography (hexane/EtOAc) to obtain tert-butyl 3-hydroxy-3-methylazetidine-1-carboxylate (1.0 g).

Preparation Example 859

5-(Chloromethyl)-2-methylpyridine hydrochloride (1.13 g) and DMF (9 ml) were mixed, and triphenylphosphine (1.67 g) and sodium iodide (5 mg) were added thereto, followed by stirring at 90° C. for 6 hours. The reaction mixture was cooled to room temperature, and the precipitated solid was collected by filtration and washed with toluene to obtain [(6-methylpyridin-3-yl)methyl](triphenyl)phosphonium chloride hydrochloride (2.18 g).

Preparation Example 860

Under argon atmosphere, (2-bromopyridin-4-yl)methanol (2.53 g), cyclopropylboronic acid (3.6 g), tripotassium phosphate (10 g), tricyclohexylphosphine (750 mg), toluene (60 ml), and water (3 ml) were mixed, and palladium acetate (II) (300 mg) were added thereto, followed by stirring at 100° C. for 5 hours. Cyclopropylboronic acid (1.8 g) was added thereto, followed by stirring at 100° C. for 2 hours. The reaction mixture was concentrated under reduced pressure, and CHCl$_3$ and water were added thereto. The organic layer was dried over Na$_2$SO$_4$ and concentrated under reduced pressure.

The obtained residue was purified by silica gel column chromatography (hexane/EtOAc) to obtain (2-cyclopropylpyridin-4-yl)methanol (602 mg).

Preparation Example 893

Under argon atmosphere, [(3-bromo-2-fluorobenzyl)oxy](tert-butyl)dimethylsilane (5.5 g), 3-[(benzyloxy)methyl]azetidine (2.5 g), and toluene (50 ml) were mixed, and (1E,4E)-1,5-diphenylpenta-1,4-dien-3-one palladium (3:2) (900 mg), BINAP (1.8 g), and sodium tert-butoxide (2.5 g) were added thereto, followed by stirring at 90° C. for 3 hours. The reaction mixture was cooled to room temperature, and EtOAc were added thereto, followed by filtering using Celite as a filtration adjuvant. The filtrate was concentrated under reduced pressure, and the residue was purified by silica gel column chromatography (hexane/EtOAc). The purified product thus obtained was mixed with EtOH (40 ml), and 10% palladium carbon (1 g) was added thereto, followed by stirring at room temperature overnight under hydrogen atmosphere of 1 atm and filtering using Celite as a filtration adjuvant. The filtrate was concentrated under reduced pressure. The residue was purified by silica gel column chromatography (CHCl$_3$/MeOH) to obtain {1-[3-({[tert-butyl(dimethyl)silyl]oxy}methyl)-2-fluorophenyl]azetidin-3-yl}methanol (885 mg).

Preparation Example 894

Under argon atmosphere, 4-({1-[3-({[tert-butyl(dimethyl)silyl]oxy}methyl)-2-fluorophenyl]azetidin-3-yl}oxy)piperidine (500 mg), 5-bromo-2-tert-butoxypyridine (500 mg), and toluene (10 ml) were mixed, and (1E,4E)-1,5-diphenylpenta-1,4-dien-3-one palladium (3:2) (80 mg), BINAP (160 mg), sodium tert-butoxide (200 mg) were added thereto, followed by stirring at 90° C. for 3 hours.

The reaction mixture was cooled to room temperature, and EtOAc was added thereto, followed by filtering using Celite as a filtration adjuvant. The filtrate was concentrated under reduced pressure. The residue was purified by silica gel column chromatography (hexane/EtOAc). The purified product thus obtained was mixed with dichloromethane (5 ml), and TFA (2 ml) was added thereto, followed by stirring at room temperature overnight. The reaction mixture was concentrated under reduced pressure, and to the residue were added MeOH (3 ml) and a 1 M aqueous NaOH solution (2.5 ml), followed by stirring at room temperature for 1 hour. 1 M hydrochloric acid (2.5 ml) was added thereto, and the reaction mixture was concentrated under reduced pressure. To the residue were added CHCl₃ and water, and the organic layer was dried over Na₂SO₄ and concentrated under reduced pressure. The obtained residue was purified by silica gel column chromatography (CHCl₃/MeOH) to obtain 5-[4-({1-[2-fluoro-3-(hydroxymethyl)phenyl]azetidin-3-yl}oxy)piperidin-1-yl]pyridin-2(1H)-one (306 mg).

Preparation Example 922 tert-Butyl 3-{[6-(hydroxymethyl)pyridin-3-yl]oxy}azetidine-1-carboxylate (242 mg) and THF (3 ml) were mixed, and triethylamine (182 mg) and methanesulfonyl chloride (147 mg) were added thereto, followed by stirring at room temperature for 1 hour. In another flask, THF (3 ml) and EtOH (237 mg) were mixed, and NaH was added thereto, followed by stirring at room temperature for 10 minutes. The reaction mixture prepared immediately before was added thereto, followed by stirring at room temperature for 1 hour. Water and EtOAc were added to the reaction mixture, and the organic layer was concentrated under reduced pressure. DCE (4 ml) and TFA (1 ml) were added to the obtained residue, followed by stirring at room temperature for 5 hours, and then concentrating under reduced pressure. CHCl₃ and a 1 M aqueous NaOH solution were added to the residue, and the organic layer was dried over Na₂SO₄ and then concentrated under reduced pressure. The obtained residue was purified by silica gel column chromatography (CHCl₃/MeOH) to obtain 5-(azetidin-3-yloxy)-2-(ethoxymethyl)pyridine (131 mg).

Preparation Example 926

{1-[3-({[tert-Butyl(dimethyl)silyl]oxy}methyl)-2-fluorophenyl]azetidin-3-yl}methylmethanesulfonate (150 mg), 6-methylpyridin-3-ol (70 mg), and DMF (2 ml) were mixed, and potassium carbonate (120 mg) were added thereto, followed by stirring at 80° C. for 6 hours. The reaction mixture was concentrated under reduced pressure, and CHCl₃ and a saturated aqueous sodium hydrogen carbonate solution were then added thereto. The organic layer was dried over Na₂SO₄ and concentrated under reduced pressure. THF (2 ml) and a 1 M TBAF/THF solution (0.6 ml) were added to the obtained residue, followed by stirring at room temperature for 1 hour. CHCl₃ and a saturated aqueous ammonium chloride solution were added to the reaction mixture, and the organic layer was dried over Na₂SO₄ and then concentrated under reduced pressure. The obtained residue was purified by silica gel column chromatography (hexane/EtOAc) to obtain [2-fluoro-3-(3-{[(6-methylpyridin-3-yl)oxy]methyl}azetidin-1-yl)phenyl]methanol (74 mg).

Preparation Example 938

TFA (0.5 ml) was added to a mixture of [3-(3-{[(6-tert-butoxypyridin-3-yl)oxy]methyl}azetidin-1-yl)-2-fluorophenyl]methanol (146 mg) and dichloromethane (1 ml), followed by stirring at room temperature for 3 hours. The reaction mixture was concentrated under reduced pressure and the residue was purified by basic silica gel column chromatography (CHCl₃/methanol). The purified product thus obtained was mixed with DMF (2 ml), and potassium carbonate (100 mg) and methyl iodide (68 mg) was added thereto, followed by stirring at room temperature for 5 hours. The reaction mixture was concentrated under reduced pressure, and CHCl₃ and water were added to the residue. The organic layer was dried over Na₂SO₄ and then concentrated under reduced pressure. The obtained residue was purified by silica gel column chromatography (CHCl₃/methanol) to obtain 5-({1-[2-fluoro-3-(hydroxymethyl)phenyl]azetidin-3-yl}methoxy)-1-methylpyridin-2(1H)-one (82 mg).

The compounds of Preparation Examples shown in the tables below were prepared using the respective corresponding starting materials in the same manner as the methods of Preparation Examples above. The structures, the preparation methods, and the physicochemical data for the compounds of Preparation Examples are shown in the tables below.

TABLE 3

| Rf | Syn | Structure |
|---|---|---|
| 1 | R12 | 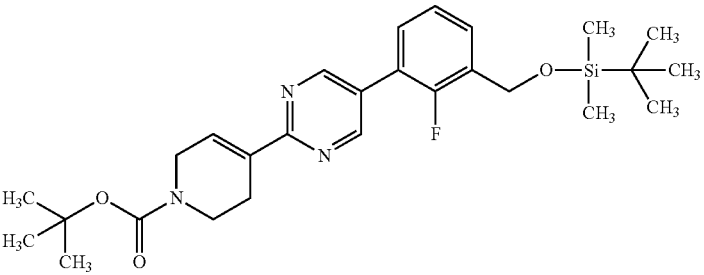 [SMILES: CC(C)(C)OC(=O)N1CC=C(c2ncc(-c3cccc(CO[Si](C)(C)C(C)(C)C)c3F)cn2)CC1] |
| 2 | R12 | 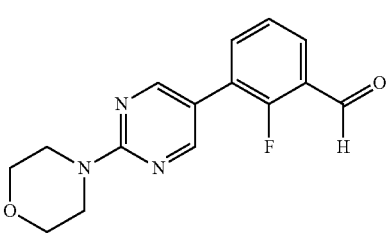 [SMILES: O=Cc1cccc(-c2cnc(N3CCOCC3)nc2)c1F] |

TABLE 3-continued
| Rf | Syn | Structure |
|---|---|---|
| 3 | R12 | 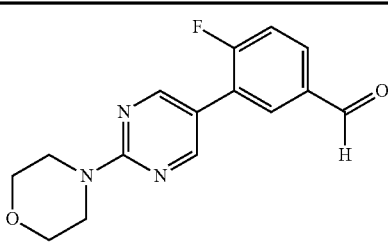 |
| 4 | R12 | 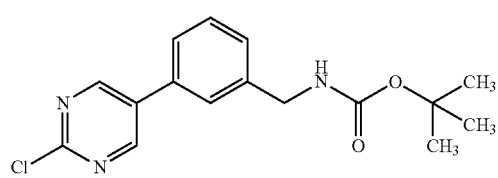 [SMILES: CC(C)(C)OC(=O)NCc1cccc(-c2cnc(Cl)nc2)c1] |
| 5 | R12 | 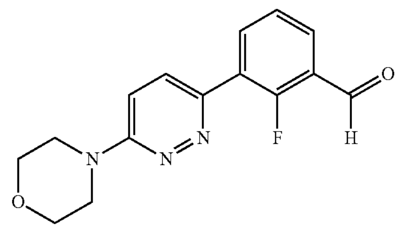 [SMILES: O=Cc1cccc(-c2ccc(N3CCOCC3)nn2)c1F] |
| 6 | R12 | 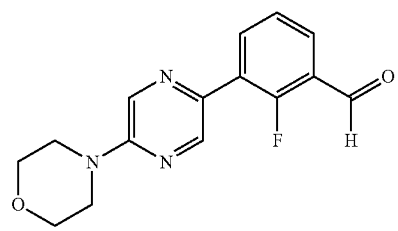 [SMILES: O=Cc1cccc(-c2cnc(N3CCOCC3)cn2)c1F] |
| 7 | R12 | 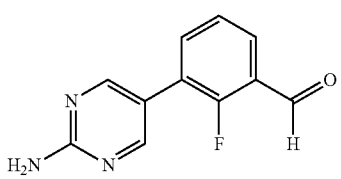 [SMILES: Nc1ncc(-c2cccc(C=O)c2F)cn1] |
| 8 | R12 | 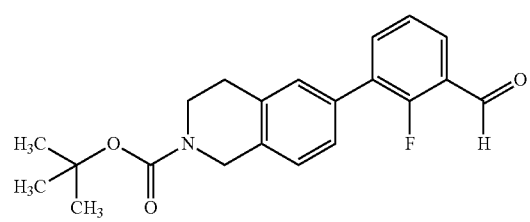 [SMILES: CC(C)(C)OC(=O)N1CCc2cc(-c3cccc(C=O)c3F)ccc2C1] |
| 9 | R12 | 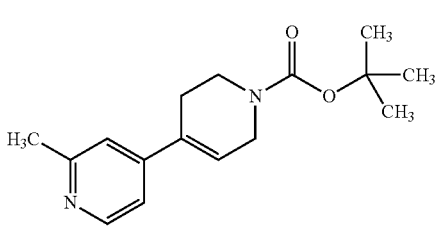 [SMILES: Cc1cc(C2=CCN(C(=O)OC(C)(C)C)CC2)ccn1] |

TABLE 3-continued

| Rf | Syn | Structure |
|---|---|---|
| 10 | R12 | tert-butyl 4-(2,6-dimethylpyridin-4-yl)-5,6-dihydropyridine-1(2H)-carboxylate |
| 11 | R12 | (3-(2-morpholinopyrimidin-5-yl)phenyl)methanol |
| 12 | R12 | (4'-morpholino-[1,1'-biphenyl]-3-yl)methanol |
| 13 | R12 | (3-(2-morpholinothiazol-5-yl)phenyl)methanol |
| 14 | R12 | tert-butyl 4-(4-(pyridin-3-yl)phenyl)piperazine-1-carboxylate |

TABLE 4

| Rf | Syn | Structure |
|---|---|---|
| 15 | R12 | tert-butyl methyl(3-(2-morpholinopyrimidin-5-yl)benzyl)carbamate |

TABLE 4-continued

| Rf | Syn | Structure |
|----|-----|-----------|
| 16 | R12 | 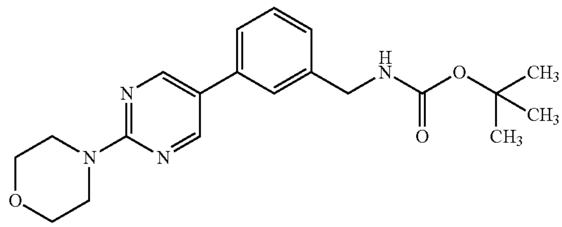 [SMILES: CC(C)(C)OC(=O)NCc1cccc(-c2cnc(N3CCOCC3)nc2)c1] |
| 17 | R12 | 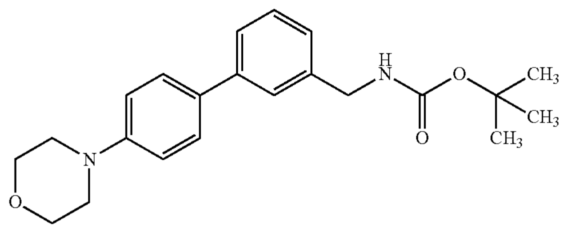 [SMILES: CC(C)(C)OC(=O)NCc1cccc(-c2ccc(N3CCOCC3)cc2)c1] |
| 18 | R12 | 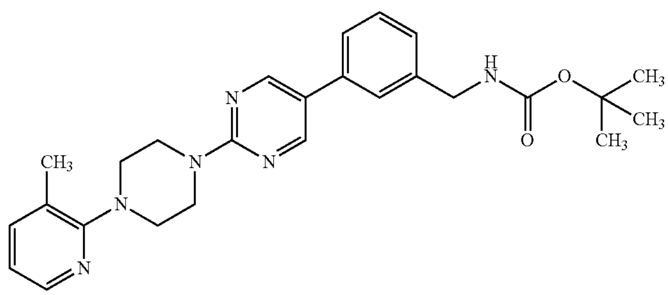 [SMILES: Cc1cccnc1N1CCN(c2ncc(-c3cccc(CNC(=O)OC(C)(C)C)c3)cn2)CC1] |
| 19 | R12 | 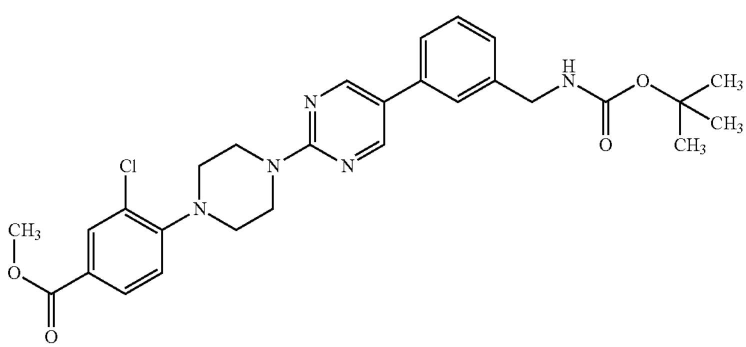 [SMILES: COC(=O)c1ccc(N2CCN(c3ncc(-c4cccc(CNC(=O)OC(C)(C)C)c4)cn3)CC2)c(Cl)c1] |
| 20 | R12 | 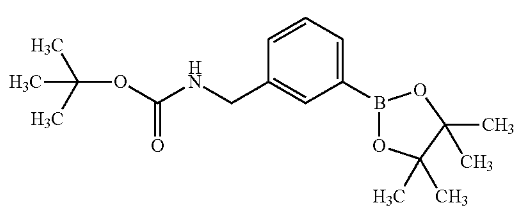 [SMILES: CC(C)(C)OC(=O)NCc1cccc(B2OC(C)(C)C(C)(C)O2)c1] |
| 21 | R12 | 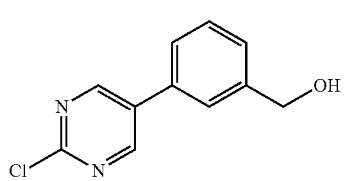 [SMILES: OCc1cccc(-c2cnc(Cl)nc2)c1] |

TABLE 4-continued
| Rf | Syn | Structure |
|---|---|---|
| 22 | R12 | 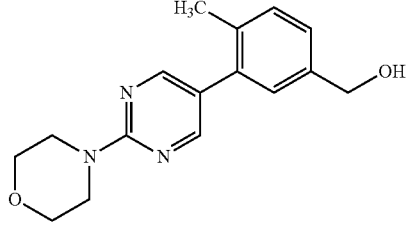 [SMILES: Cc1ccc(CO)cc1-c1cnc(N2CCOCC2)nc1] |
| 23 | R12 | 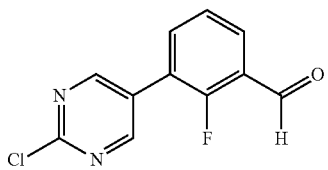 [SMILES: O=Cc1cccc(-c2cnc(Cl)nc2)c1F] |
| 24 | R12 | 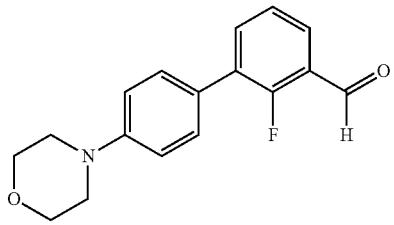 [SMILES: O=Cc1cccc(-c2ccc(N3CCOCC3)cc2)c1F] |
| 25 | R12 | 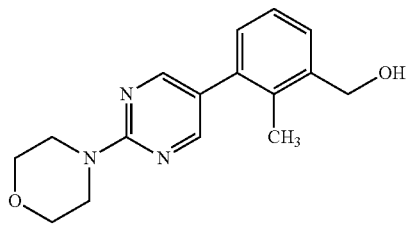 [SMILES: Cc1c(CO)cccc1-c1cnc(N2CCOCC2)nc1] |
| 26 | R12 | 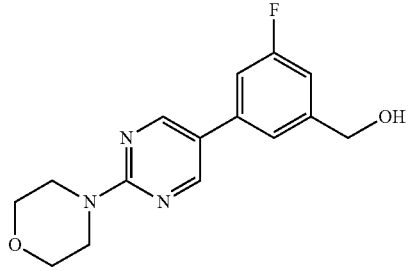 [SMILES: OCc1cc(F)cc(-c2cnc(N3CCOCC3)nc2)c1] |
| 27 | R12 | 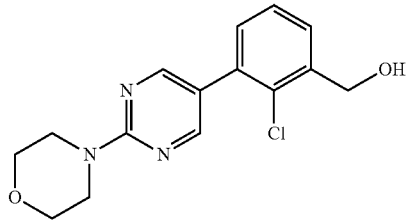 [SMILES: OCc1cccc(-c2cnc(N3CCOCC3)nc2)c1Cl] |

TABLE 4-continued

| Rf | Syn | Structure |
|---|---|---|
| 28 | R12 | (structure) |

TABLE 5

| Rf | Syn | Structure |
|---|---|---|
| 29 | R12 | (structure) |
| 30 | R12 | (structure) |
| 31 | R12 | (structure) |
| 32 | R32 | (structure) |
| 33 | R33 | (structure) |

TABLE 5-continued
| Rf | Syn | Structure |
|---|---|---|
| 34 | R33 | 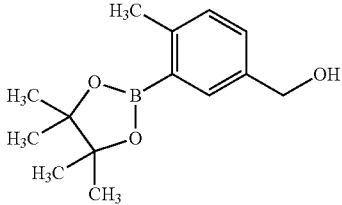 [SMILES: Cc1ccc(CO)cc1B1OC(C)(C)C(C)(C)O1] |
| 35 | R33 | 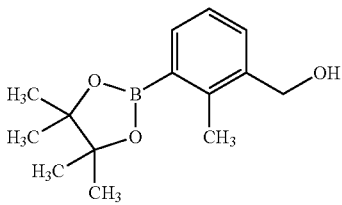 |
| 36 | R33 | 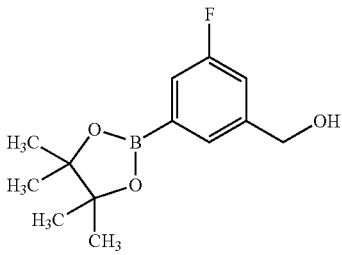 [SMILES: CC1(C)OB(c2cc(F)cc(CO)c2)OC1(C)C] |
| 37 | R33 | 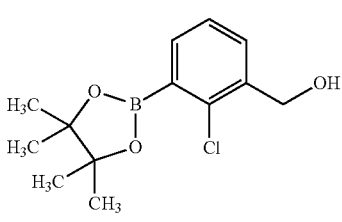 [SMILES: CC1(C)OB(c2cccc(CO)c2Cl)OC1(C)C] |
| 38 | R38 | 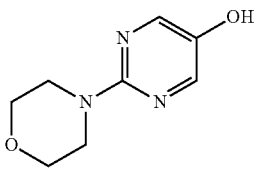 [SMILES: Oc1cnc(N2CCOCC2)nc1] |
| 39 | R39 | 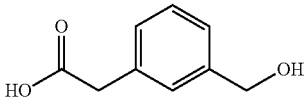 |
| 40 | R41 | 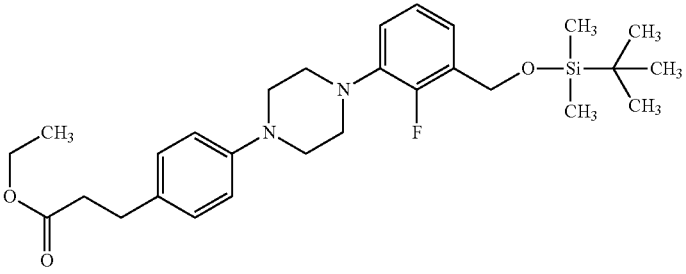 [SMILES: CCOC(=O)CCc1ccc(N2CCN(c3cccc(CO[Si](C)(C)C(C)(C)C)c3F)CC2)cc1] |

TABLE 5-continued

| Rf | Syn | Structure |
|---|---|---|
| 41 | R41 | 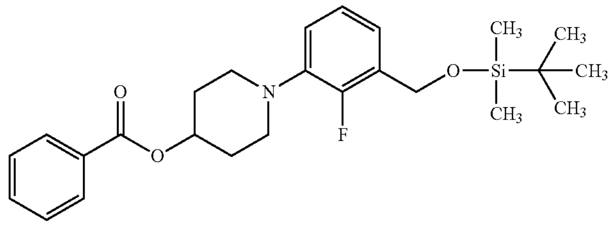 [SMILES: CC(C)(C)[Si](C)(C)OCc1cccc(N2CCC(OC(=O)c3ccccc3)CC2)c1F] |
| 42 | R42 | 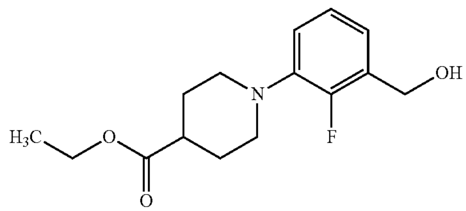 [SMILES: CCOC(=O)C1CCN(c2cccc(CO)c2F)CC1] |
| 43 | R42 | 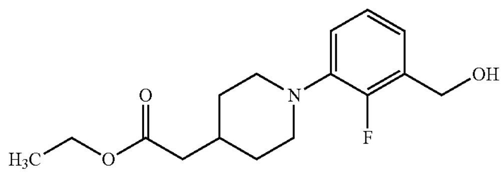 [SMILES: CCOC(=O)CC1CCN(c2cccc(CO)c2F)CC1] |
| 44 | R44 | 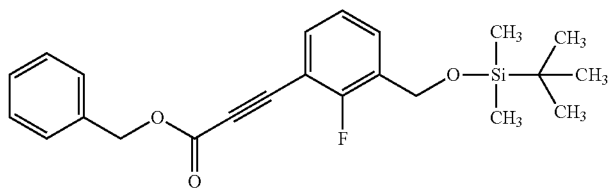 [SMILES: CC(C)(C)[Si](C)(C)OCc1cccc(C#CC(=O)OCc2ccccc2)c1F] |

TABLE 6

| Rf | Syn | Structure |
|---|---|---|
| 45 | R45 | 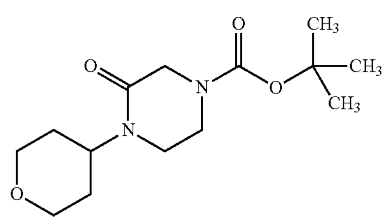 [SMILES: CC(C)(C)OC(=O)N1CCN(C2CCOCC2)C(=O)C1] |
| 46 | R45 | 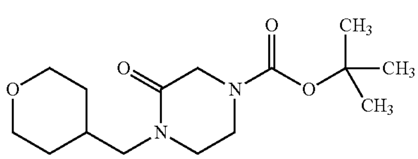 [SMILES: CC(C)(C)OC(=O)N1CCN(CC2CCOCC2)C(=O)C1] |
| 47 | R45 | 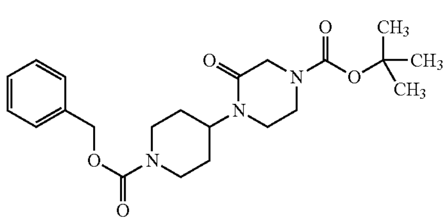 [SMILES: CC(C)(C)OC(=O)N1CCN(C2CCN(C(=O)OCc3ccccc3)CC2)C(=O)C1] |
| 48 | R48 | |
| 49 | R50 | |

TABLE 6-continued
| Rf | Syn | Structure |
|---|---|---|
| 50 | R50 | 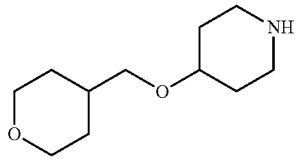 [SMILES: C1CC(OCC2CCOCC2)CCN1] |
| 51 | R50 | 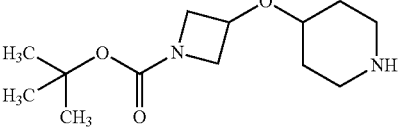 |
| 52 | R50 | 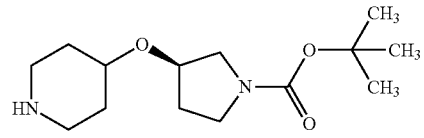 [SMILES: CC(C)(C)OC(=O)N1CC[C@@H](OC2CCNCC2)C1] |
| 53 | R54 | 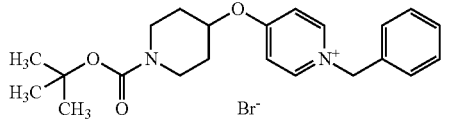 [SMILES: CC(C)(C)OC(=O)N1CCC(Oc2cc[n+](Cc3ccccc3)cc2)CC1 ; [Br-]] |
| 54 | R54 | 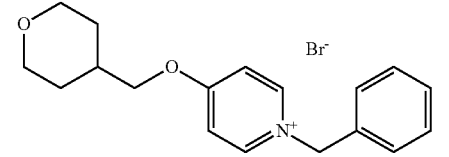 [SMILES: c1ccc(C[n+]2ccc(OCC3CCOCC3)cc2)cc1 ; [Br-]] |
| 55 | R54 | 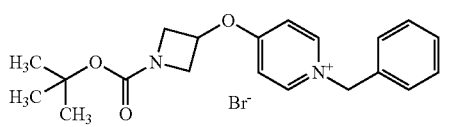 [SMILES: CC(C)(C)OC(=O)N1CC(Oc2cc[n+](Cc3ccccc3)cc2)C1 ; [Br-]] |
| 56 | R54 | 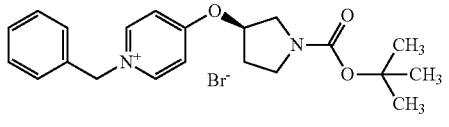 |
TABLE 6-continued
| Rf | Syn | Structure |
|---|---|---|
| 57 | R57 | 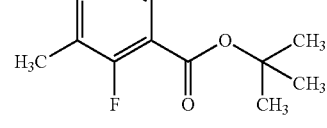 |
| 58 | R58 | 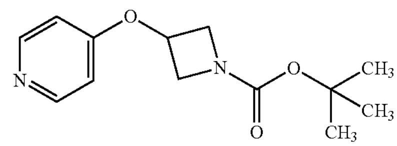 [SMILES: CC(C)(C)OC(=O)N1CC(Oc2ccncc2)C1] |
| 59 | R58 | 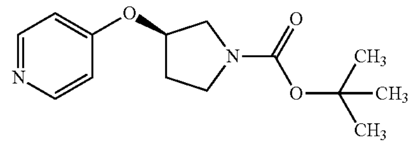 [SMILES: CC(C)(C)OC(=O)N1CC[C@@H](Oc2ccncc2)C1] |
| 60 | R60 | 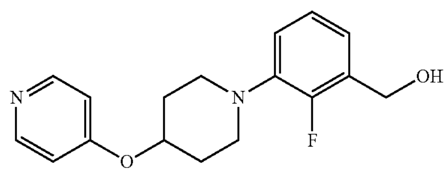 [SMILES: OCc1cccc(N2CCC(Oc3ccncc3)CC2)c1F] |
| 61 | R60 | 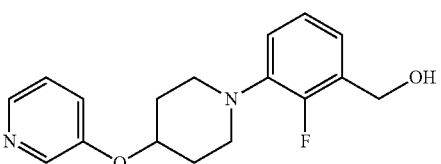 |
| 62 | R62 | 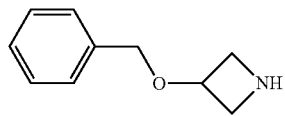 |
TABLE 7
| Rf | Syn | Structure |
|---|---|---|
| 63 | R63 | 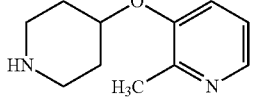 |
| 64 | R63 | 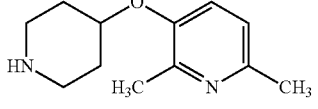 |
| 65 | R63 | 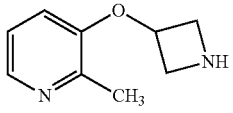 |

TABLE 7-continued

| Rf | Syn | Structure |
|---|---|---|
| 66 | R63 | 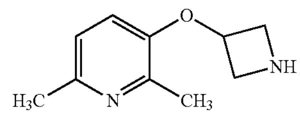 |
| 67 | R67 | 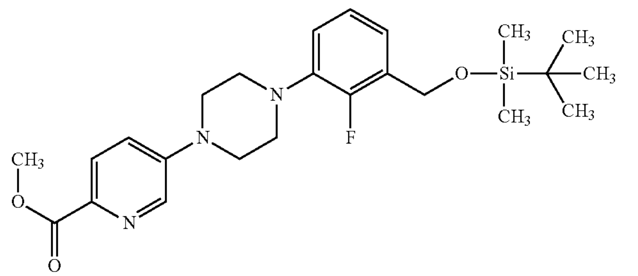 [SMILES: COC(=O)c1ccc(N2CCN(c3cccc(CO[Si](C)(C)C(C)(C)C)c3F)CC2)cn1] |
| 68 | R67 | 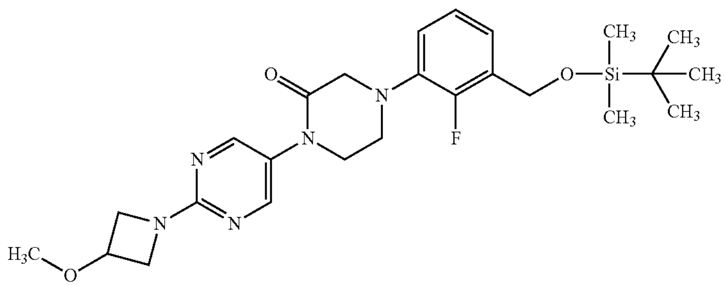 [SMILES: COC1CN(c2ncc(N3CCN(c4cccc(CO[Si](C)(C)C(C)(C)C)c4F)CC3=O)cn2)C1] |
| 69 | R69 | 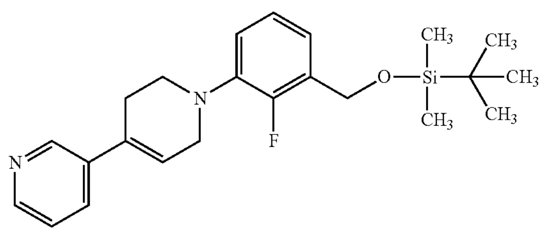 [SMILES: CC(C)(C)[Si](C)(C)OCc1cccc(N2CC=C(c3cccnc3)CC2)c1F] |
| 70 | R70 | 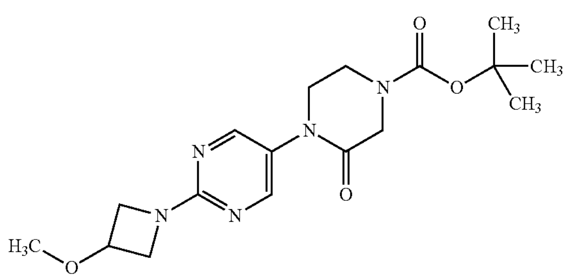 [SMILES: COC1CN(c2ncc(N3CCN(C(=O)OC(C)(C)C)CC3=O)cn2)C1] |
| 71 | R81 | 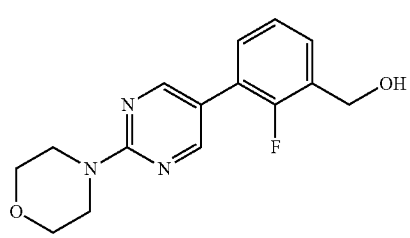 [SMILES: OCc1cccc(-c2cnc(N3CCOCC3)nc2)c1F] |

TABLE 7-continued
| Rf | Syn | Structure |
|---|---|---|
| 72 | R81 | 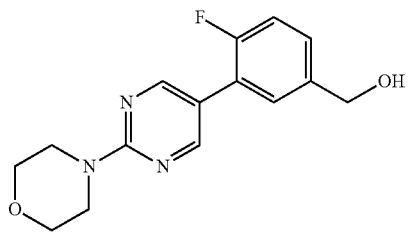 [SMILES: OCc1ccc(F)c(-c2cnc(N3CCOCC3)nc2)c1] |
| 73 | R81 | 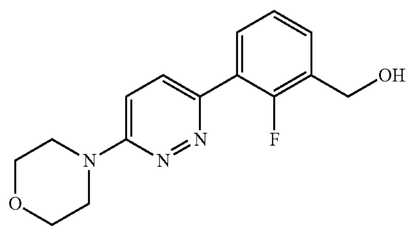 [SMILES: OCc1cccc(-c2ccc(N3CCOCC3)nn2)c1F] |
| 74 | R81 | 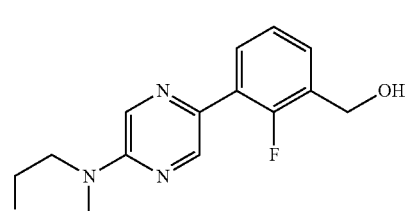 |
| 75 | R81 | 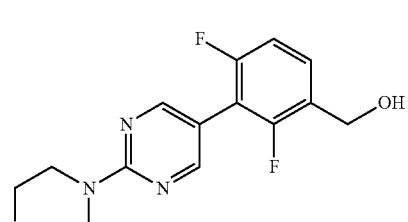 |
| 76 | R81 | 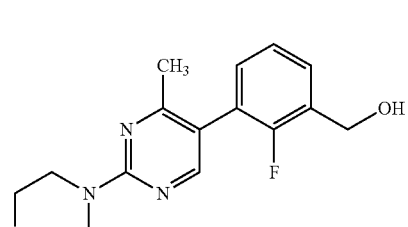 |
| 77 | R81 | 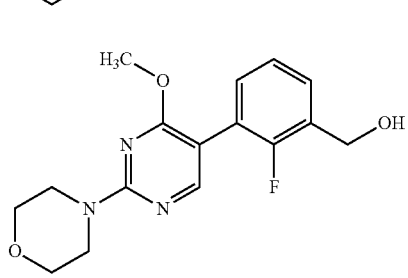 |

TABLE 7-continued
| Rf | Syn | Structure |
|---|---|---|
| 78 | R81 | 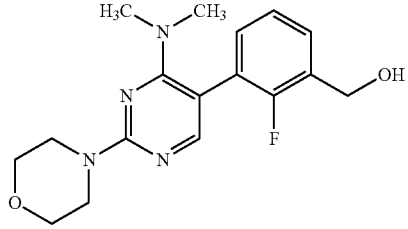 [SMILES: CN(C)c1nc(N2CCOCC2)ncc1-c1cccc(CO)c1F] |
TABLE 8
| Rf | Syn | Structure |
|---|---|---|
| 79 | R81 | 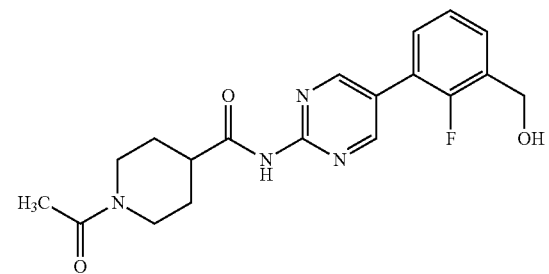 [SMILES: CC(=O)N1CCC(C(=O)Nc2ncc(-c3cccc(CO)c3F)cn2)CC1] |
| 80 | R81 | 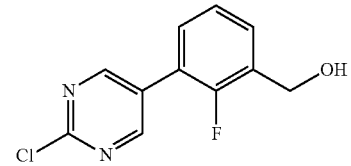 [SMILES: OCc1cccc(-c2cnc(Cl)nc2)c1F] |
| 81 | R81 | 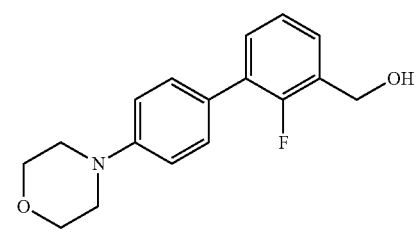 [SMILES: OCc1cccc(-c2ccc(N3CCOCC3)cc2)c1F] |
| 82 | R81 | 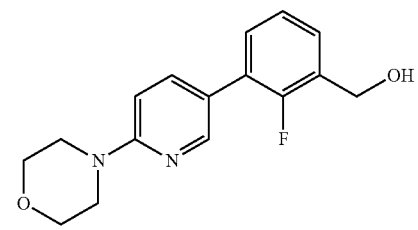 [SMILES: OCc1cccc(-c2ccc(N3CCOCC3)nc2)c1F] |
| 83 | R81 | 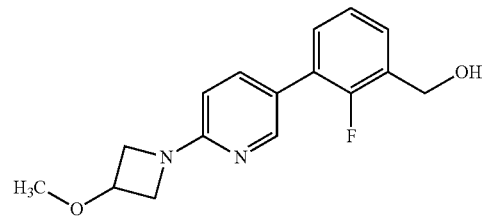 [SMILES: COC1CN(c2ccc(-c3cccc(CO)c3F)cn2)C1] |

TABLE 8-continued
| Rf | Syn | Structure |
|---|---|---|
| 84 | R135 | 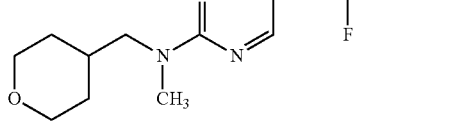 |
| 85 | R135 | 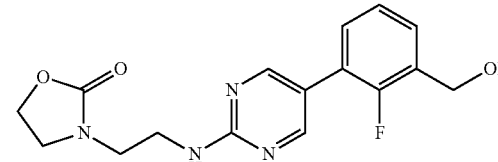 |
| 86 | R135 | 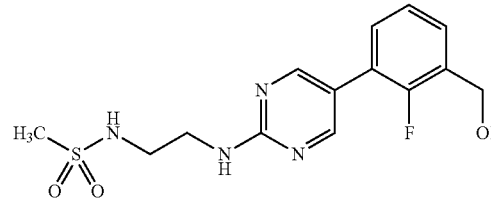 |
| 87 | R135 | 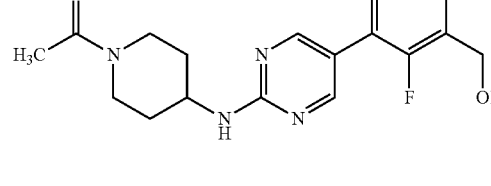 |
| 88 | R135 | 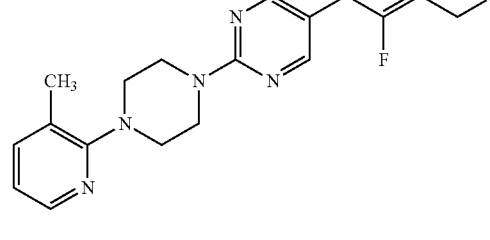 |
| 89 | R135 | 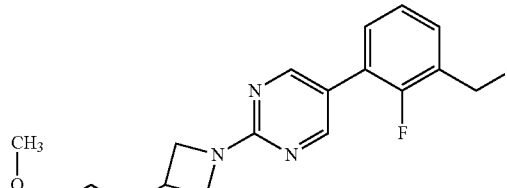 |

TABLE 8-continued
| Rf | Syn | Structure |
|---|---|---|
| 90 | R135 | 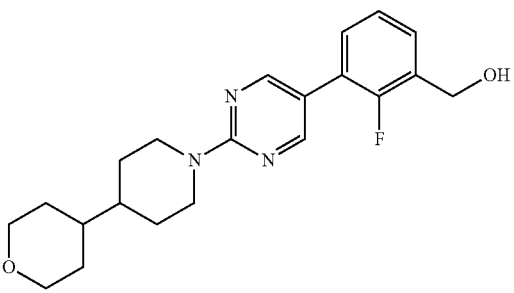 [SMILES: OCc1cccc(-c2cnc(N3CCC(C4CCOCC4)CC3)nc2)c1F] |
| 91 | R135 | 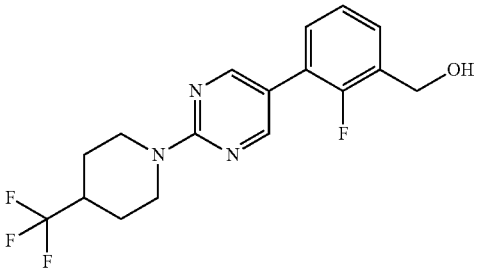 [SMILES: OCc1cccc(-c2cnc(N3CCC(C(F)(F)F)CC3)nc2)c1F] |
| 92 | R135 | 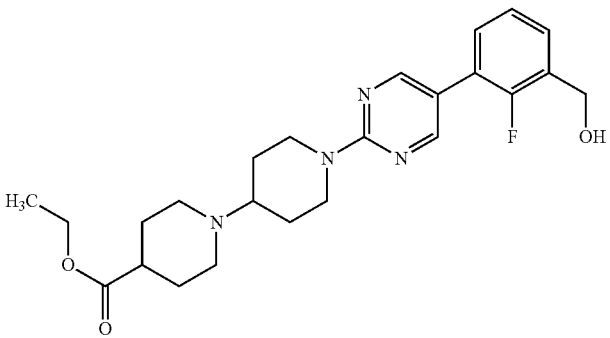 [SMILES: CCOC(=O)C1CCN(C2CCN(c3ncc(-c4cccc(CO)c4F)cn3)CC2)CC1] |
TABLE 9
| Rf | Syn | Structure |
|---|---|---|
| 93 | R135 | 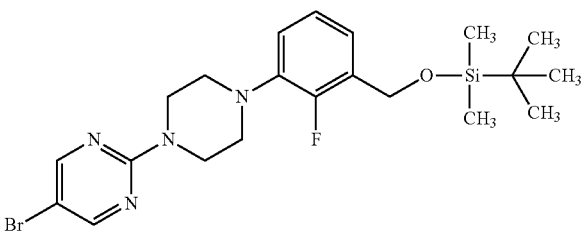 [SMILES: CC(C)(C)[Si](C)(C)OCc1cccc(N2CCN(c3ncc(Br)cn3)CC2)c1F] |
| 94 | R135 | 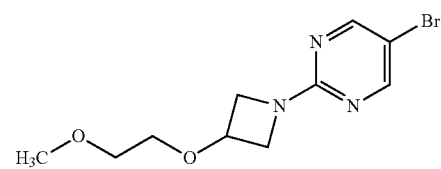 [SMILES: COCCOC1CN(c2ncc(Br)cn2)C1] |

TABLE 9-continued

| Rf | Syn | Structure |
|---|---|---|
| 95 | R135 | 5-bromo-2-(3,3-difluoropyrrolidin-1-yl)pyrimidine |
| 96 | R135 | tert-butyl (3-(2-(piperazin-1-yl)pyrimidin-5-yl)benzyl)carbamate |
| 97 | R135 | ethyl 4-((1-(5-(3-(((tert-butoxycarbonyl)amino)methyl)phenyl)pyrimidin-2-yl)piperidin-4-yl)amino)benzoate |
| 98 | R135 | ethyl 4-(4-((5-(3-(((tert-butoxycarbonyl)amino)methyl)phenyl)pyrimidin-2-yl)amino)piperidin-1-yl)benzoate |
| 99 | R135 | (3-(2-(piperazin-1-yl)pyrimidin-5-yl)phenyl)methanol |
| 100 | R135 | ethyl 2-(1-(5-(2-fluoro-3-(hydroxymethyl)phenyl)pyrimidin-2-yl)piperidin-4-yl)acetate |

TABLE 9-continued

| Rf | Syn | Structure |
|---|---|---|
| 101 | R135 | 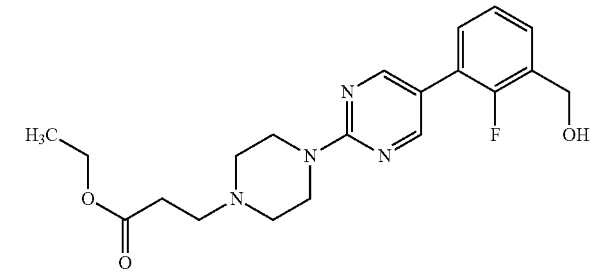 [SMILES: CCOC(=O)CCN1CCN(c2ncc(-c3cccc(CO)c3F)cn2)CC1] |
| 102 | R135 | 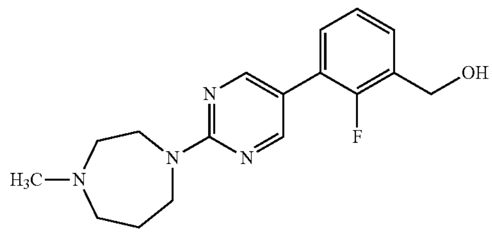 [SMILES: CN1CCCN(c2ncc(-c3cccc(CO)c3F)cn2)CC1] |
| 103 | R135 | 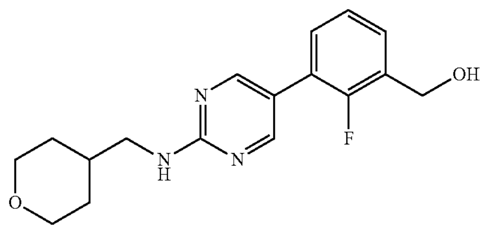 [SMILES: OCc1cccc(-c2cnc(NCC3CCOCC3)nc2)c1F] |
| 104 | R135 | 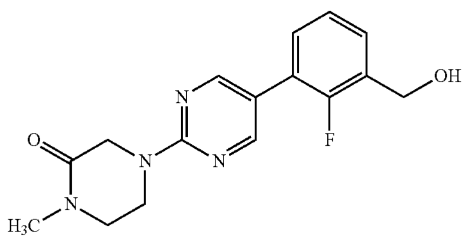 [SMILES: CN1CCN(c2ncc(-c3cccc(CO)c3F)cn2)CC1=O] |
| 105 | R135 | 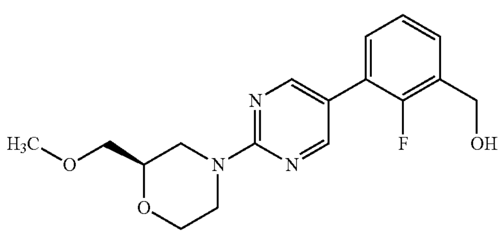 [SMILES: COC[C@H]1CN(c2ncc(-c3cccc(CO)c3F)cn2)CCO1] |
| 106 | R135 | 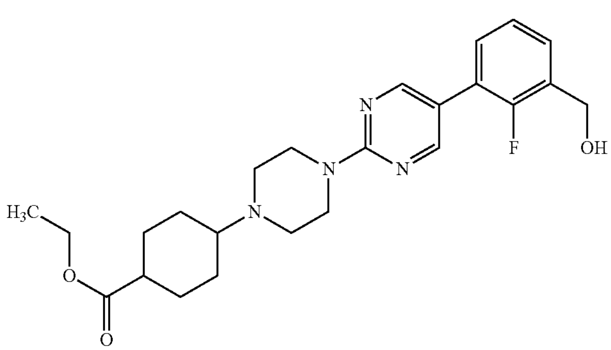 [SMILES: CCOC(=O)C1CCC(N2CCN(c3ncc(-c4cccc(CO)c4F)cn3)CC2)CC1] |

TABLE 9-continued
| Rf | Syn | Structure |
|---|---|---|
| 107 | R135 | 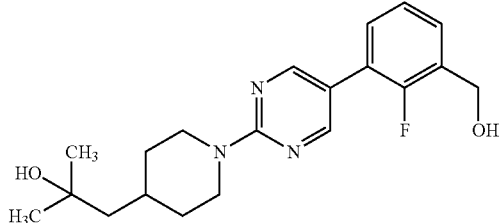 |
| 108 | R135 | 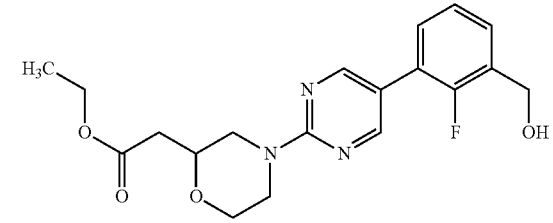 [SMILES: CCOC(=O)CC1CN(c2ncc(-c3cccc(CO)c3F)cn2)CCO1] |
TABLE 10
| Rf | Syn | Structure |
|---|---|---|
| 109 | R135 | 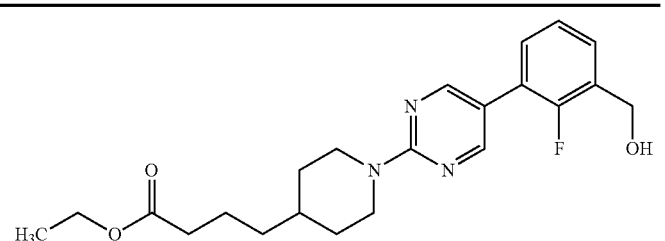 |
| 110 | R135 | 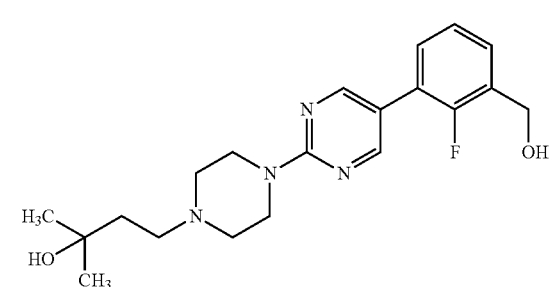 |
| 111 | R135 | 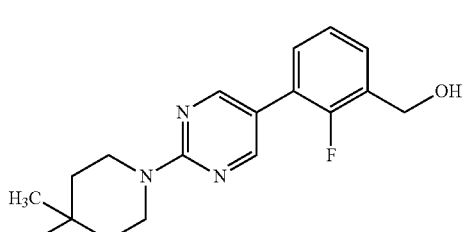 |
| 112 | R135 | 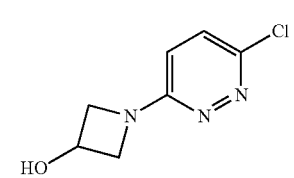 [SMILES: OC1CN(c2ccc(Cl)nn2)C1] |

TABLE 10-continued

| Rf | Syn | Structure |
|---|---|---|
| 113 | R135 | 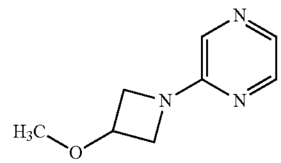 |
| 114 | R135 | 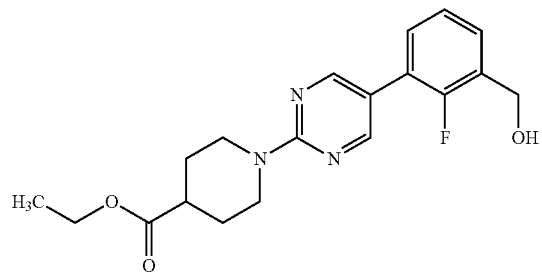 [SMILES: CCOC(=O)C1CCN(c2ncc(-c3cccc(CO)c3F)cn2)CC1] |
| 115 | R135 | 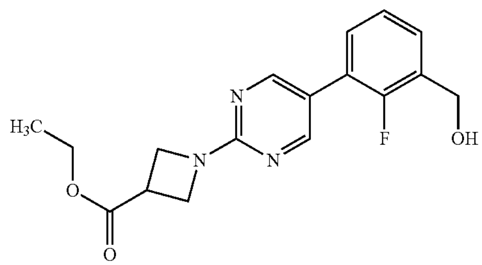 [SMILES: CCOC(=O)C1CN(c2ncc(-c3cccc(CO)c3F)cn2)C1] |
| 116 | R135 | 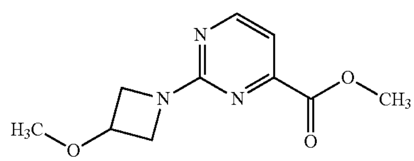 |
| 117 | R135 | 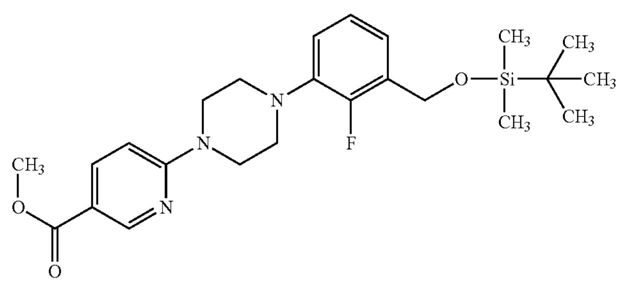 [SMILES: COC(=O)c1ccc(N2CCN(c3cccc(CO[Si](C)(C)C(C)(C)C)c3F)CC2)nc1] |
| 118 | R135 | 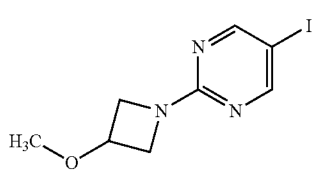 |
| 119 | R135 | 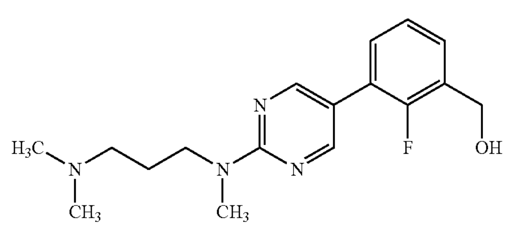 [SMILES: CN(C)CCCN(C)c1ncc(-c2cccc(CO)c2F)cn1] |

TABLE 10-continued

| Rf | Syn | Structure |
|---|---|---|
| 120 | R135 | 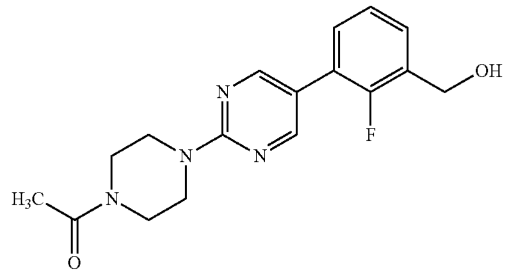 [SMILES: CC(=O)N1CCN(c2ncc(-c3cccc(CO)c3F)cn2)CC1] |
| 121 | R135 | 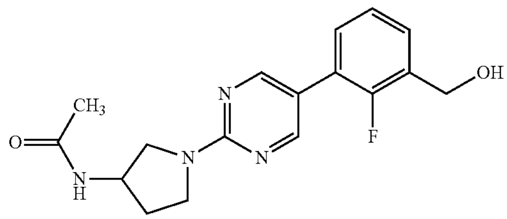 [SMILES: CC(=O)NC1CCN(c2ncc(-c3cccc(CO)c3F)cn2)C1] |
| 122 | R135 | 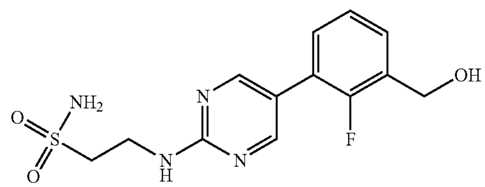 [SMILES: NS(=O)(=O)CCNc1ncc(-c2cccc(CO)c2F)cn1] |

TABLE 11

| Rf | Syn | Structure |
|---|---|---|
| 123 | R135 | 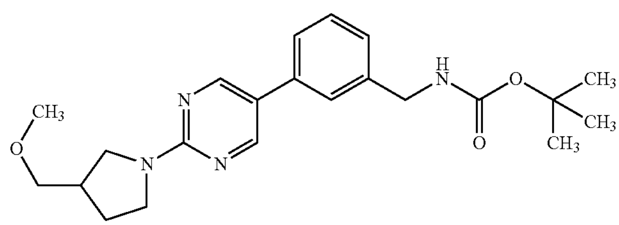 [SMILES: COCC1CCN(c2ncc(-c3cccc(CNC(=O)OC(C)(C)C)c3)cn2)C1] |
| 124 | R135 | 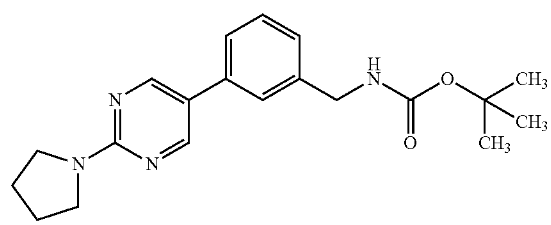 [SMILES: CC(C)(C)OC(=O)NCc1cccc(-c2cnc(N3CCCC3)nc2)c1] |
| 125 | R135 | 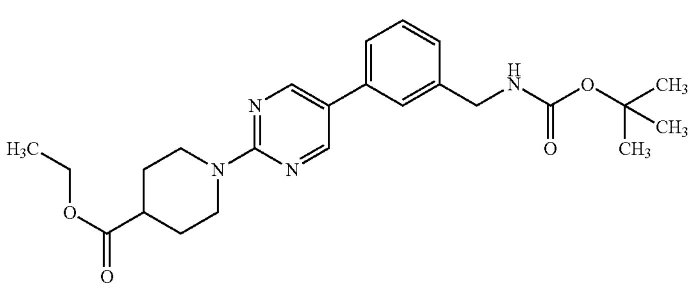 [SMILES: CCOC(=O)C1CCN(c2ncc(-c3cccc(CNC(=O)OC(C)(C)C)c3)cn2)CC1] |

TABLE 11-continued
| Rf | Syn | Structure |
|---|---|---|
| 126 | R135 | 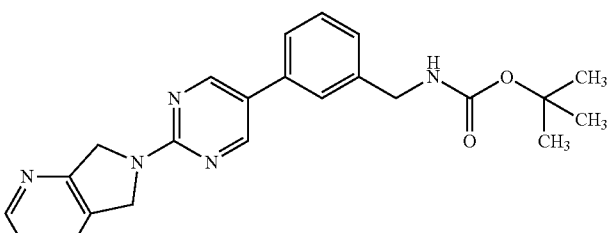 |
| 127 | R135 | 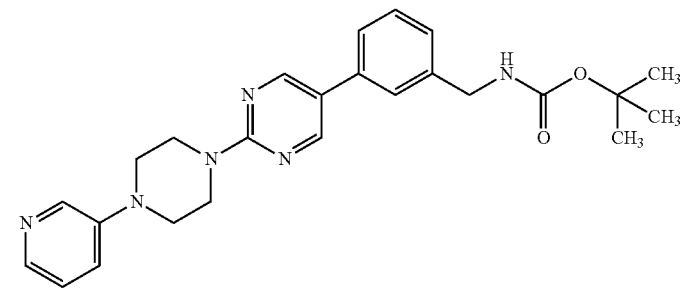 [SMILES: CC(C)(C)OC(=O)NCc1cccc(-c2cnc(N3CCN(c4cccnc4)CC3)nc2)c1] |
| 128 | R135 | 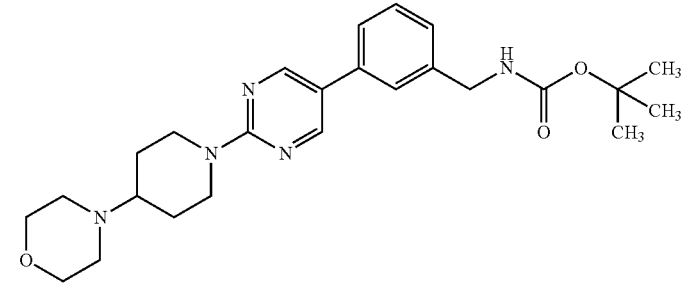 [SMILES: CC(C)(C)OC(=O)NCc1cccc(-c2cnc(N3CCC(N4CCOCC4)CC3)nc2)c1] |
| 129 | R135 | 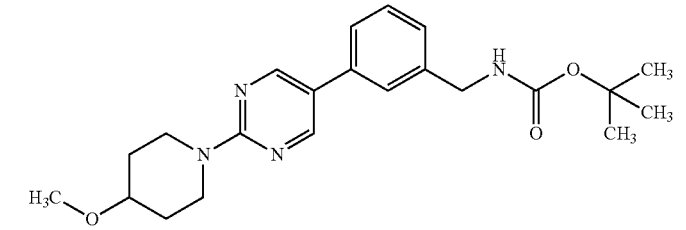 [SMILES: COC1CCN(c2ncc(-c3cccc(CNC(=O)OC(C)(C)C)c3)cn2)CC1] |
| 130 | R135 | 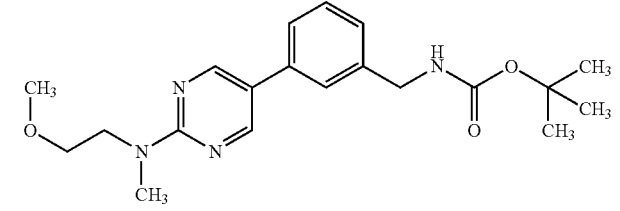 [SMILES: COCCN(C)c1ncc(-c2cccc(CNC(=O)OC(C)(C)C)c2)cn1] |
| 131 | R135 | 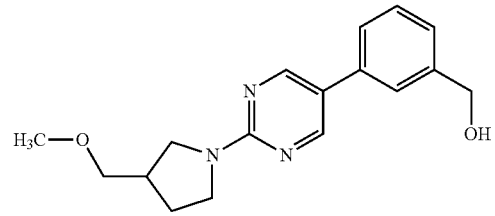 [SMILES: COCC1CCN(c2ncc(-c3cccc(CO)c3)cn2)C1] |

TABLE 11-continued

| Rf | Syn | Structure |
|---|---|---|
| 132 | R135 | (3-fluoropyrrolidin-1-yl)pyrimidine-phenyl-CH2OH |
| 133 | R135 | pyrrolidin-1-yl-pyrimidine-phenyl-CH2OH |
| 134 | R135 | N-(2-methoxyethyl)-N-methyl-pyrimidine-phenyl-CH2OH |
| 135 | R135 | (4-methoxypiperidin-1-yl)-pyrimidine-phenyl-CH2OH |
| 136 | R135 | |
| 137 | R135 | 4-(2-methoxyethyl)piperidin-1-yl-pyrimidine-phenyl-CH2OH |
| 138 | R135 | 4-(pyridin-3-yl)piperazin-1-yl-pyrimidine-phenyl-CH2OH |

TABLE 12

| Rf | Syn | Structure |
|---|---|---|
| 139 | R135 | (3S)-3-fluoropyrrolidin-1-yl pyrimidine with 2-fluoro-3-(hydroxymethyl)phenyl |
| 140 | R135 | N-(2-methoxyethyl)-N-methylamino pyrimidine with 2-fluoro-3-(hydroxymethyl)phenyl |
| 141 | R135 | pyrrolidin-1-yl pyrimidine with 2-fluoro-3-(hydroxymethyl)phenyl |
| 142 | R135 | N,N-dimethylamino pyrimidine with 2-fluoro-3-(hydroxymethyl)phenyl |
| 143 | R135 | 4-methoxypiperidin-1-yl pyrimidine with 2-fluoro-3-(hydroxymethyl)phenyl |
| 144 | R135 | piperidin-1-yl pyrimidine with 2-fluoro-3-(hydroxymethyl)phenyl |
| 145 | R135 | N-ethyl-N-(2-methoxyethyl)amino pyrimidine with 2-fluoro-3-(hydroxymethyl)phenyl |

TABLE 12-continued
| Rf | Syn | Structure |
|---|---|---|
| 146 | R135 | 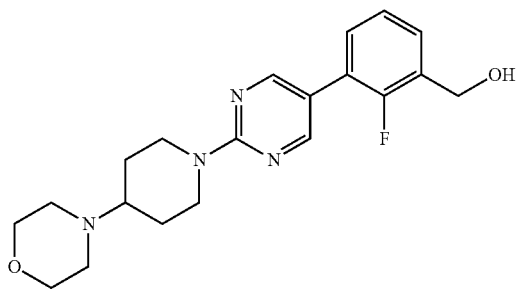 [SMILES: OCc1cccc(-c2cnc(N3CCC(N4CCOCC4)CC3)nc2)c1F] |
| 147 | R135 | 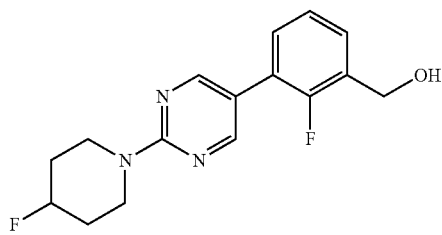 [SMILES: OCc1cccc(-c2cnc(N3CCC(F)CC3)nc2)c1F] |
| 148 | R135 | 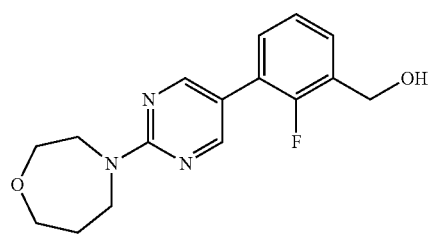 [SMILES: OCc1cccc(-c2cnc(N3CCCOCC3)nc2)c1F] |
| 149 | R135 | 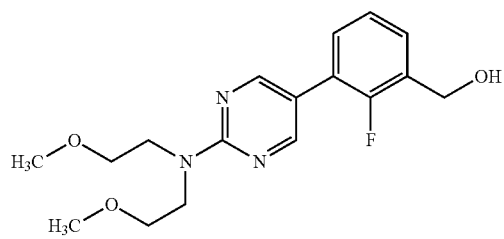 [SMILES: COCCN(CCOC)c1ncc(-c2cccc(CO)c2F)cn1] |
| 150 | R135 | 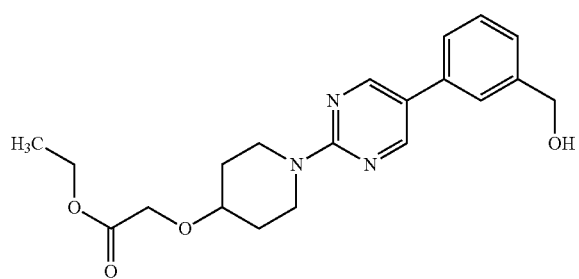 [SMILES: CCOC(=O)COC1CCN(c2ncc(-c3cccc(CO)c3)cn2)CC1] |
| 151 | R135 | 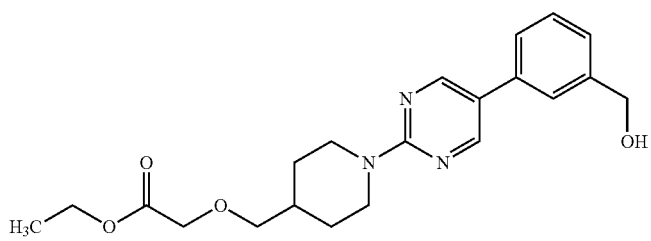 [SMILES: CCOC(=O)COCC1CCN(c2ncc(-c3cccc(CO)c3)cn2)CC1] |

TABLE 12-continued
| Rf | Syn | Structure |
|----|-----|-----------|
| 152 | R135 | 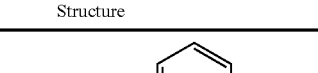 |
TABLE 13
| Rf | Syn | Structure |
|----|-----|-----------|
| 153 | R135 | 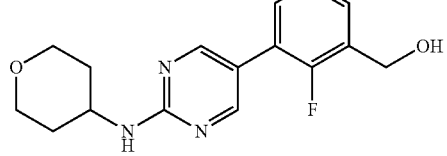 |
| 154 | R135 | 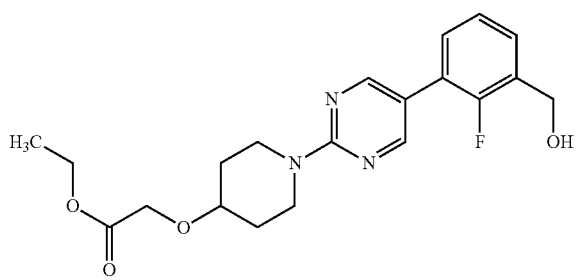 [SMILES: CCOC(=O)COC1CCN(c2ncc(-c3cccc(CO)c3F)cn2)CC1] |
| 155 | R135 | 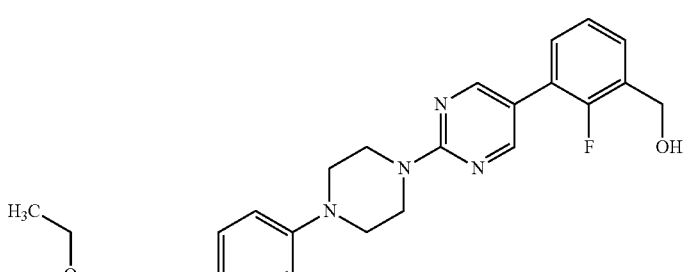 |
| 156 | R135 | 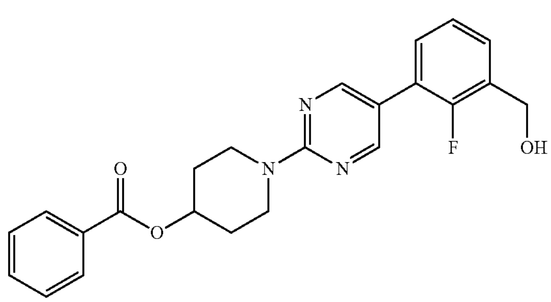 [SMILES: O=C(OC1CCN(c2ncc(-c3cccc(CO)c3F)cn2)CC1)c1ccccc1] |

TABLE 13-continued

| Rf | Syn | Structure |
|----|-----|-----------|
| 157 | R135 | 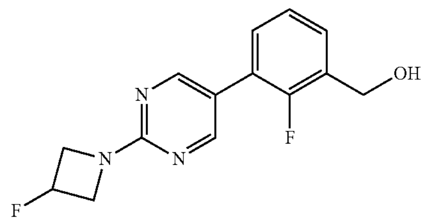 [SMILES: OCc1cccc(-c2cnc(N3CC(F)C3)nc2)c1F] |
| 158 | R159 | 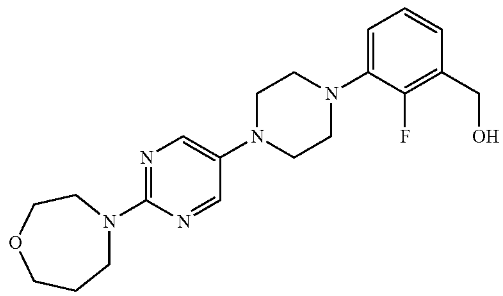 [SMILES: OCc1cccc(N2CCN(c3cnc(N4CCCOCC4)nc3)CC2)c1F] |
| 159 | R159 | 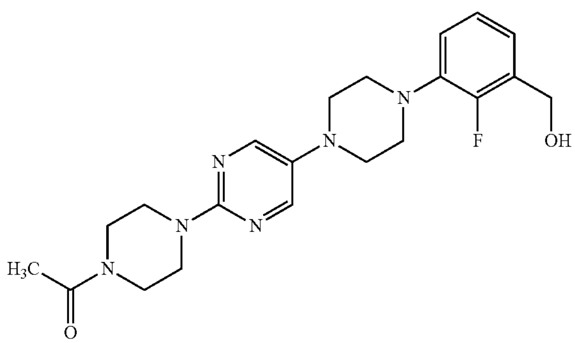 [SMILES: CC(=O)N1CCN(c2ncc(N3CCN(c4cccc(CO)c4F)CC3)cn2)CC1] |
| 160 | R159 | 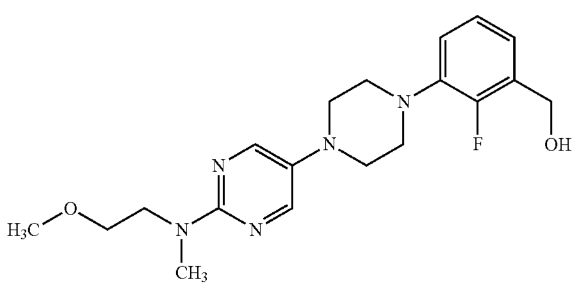 [SMILES: COCCN(C)c1ncc(N2CCN(c3cccc(CO)c3F)CC2)cn1] |
| 161 | R162 | 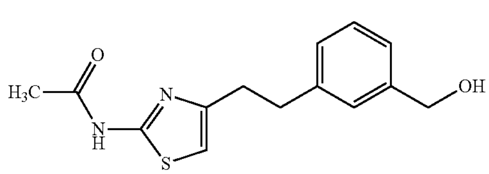 [SMILES: CC(=O)Nc1nc(CCc2cccc(CO)c2)cs1] |
| 162 | R162 | 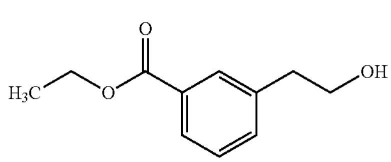 |
| 163 | R163 | 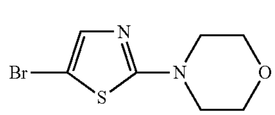 [SMILES: Brc1cnc(N2CCOCC2)s1] |

TABLE 13-continued

| Rf | Syn | Structure |
|---|---|---|
| 164 | R174 | 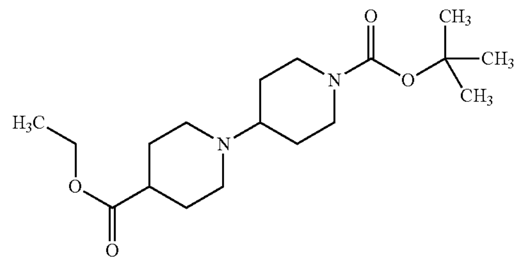 [SMILES: CCOC(=O)C1CCN(C2CCN(C(=O)OC(C)(C)C)CC2)CC1] |
| 165 | R174 | 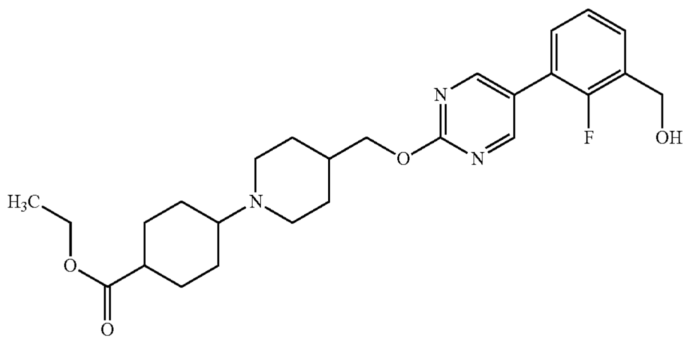 [SMILES: CCOC(=O)C1CCC(N2CCC(COc3ncc(-c4cccc(CO)c4F)cn3)CC2)CC1] |
| 166 | R174 | 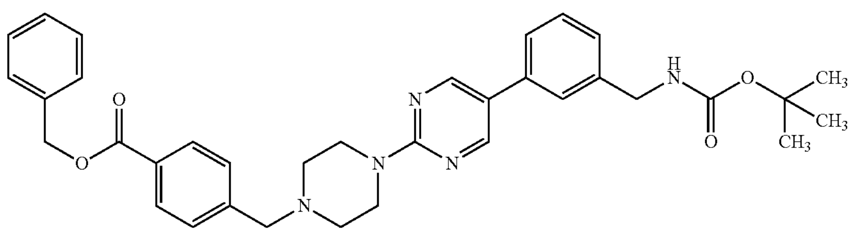 [SMILES: CC(C)(C)OC(=O)NCc1cccc(-c2cnc(N3CCN(Cc4ccc(C(=O)OCc5ccccc5)cc4)CC3)nc2)c1] |

TABLE 14

| Rf | Syn | Structure |
|---|---|---|
| 167 | R174 | 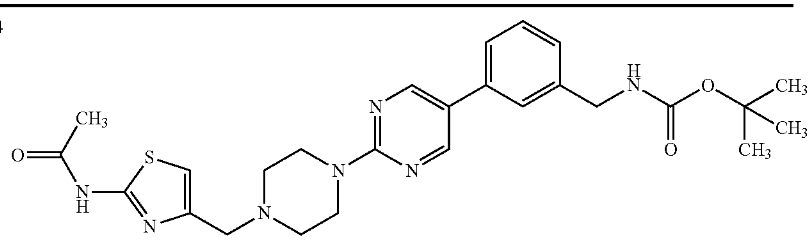 |
| 168 | R174 | 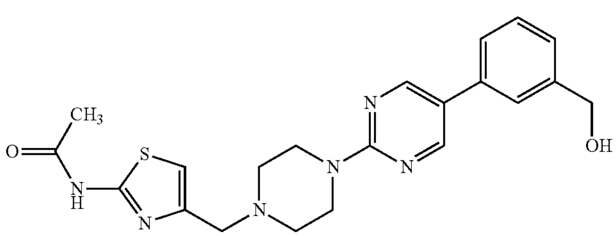 [SMILES: CC(=O)Nc1nc(CN2CCN(c3ncc(-c4cccc(CO)c4)cn3)CC2)cs1] |

TABLE 14-continued
| Rf | Syn | Structure |
|---|---|---|
| 169 | R174 | 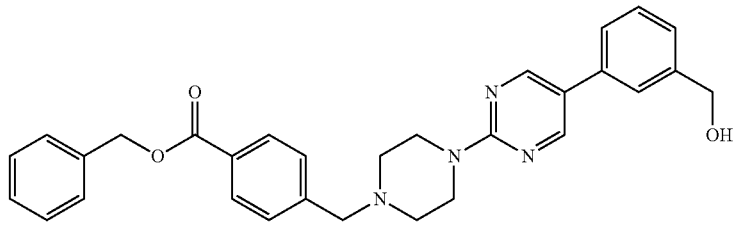 [SMILES: O=C(OCc1ccccc1)c1ccc(CN2CCN(c3ncc(-c4cccc(CO)c4)cn3)CC2)cc1] |
| 170 | R174 | 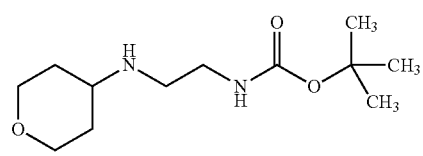 [SMILES: CC(C)(C)OC(=O)NCCNC1CCOCC1] |
| 171 | R174 | 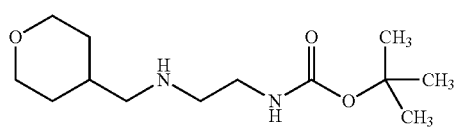 [SMILES: CC(C)(C)OC(=O)NCCNCC1CCOCC1] |
| 172 | R174 | 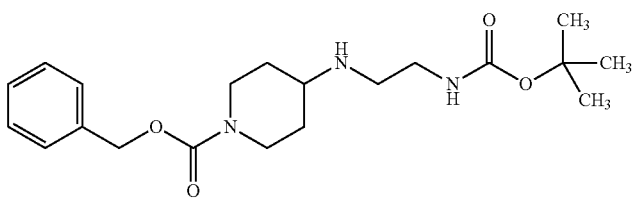 [SMILES: CC(C)(C)OC(=O)NCCNC1CCN(C(=O)OCc2ccccc2)CC1] |
| 173 | R174 | 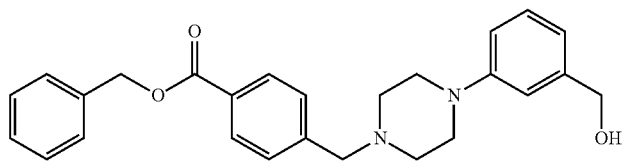 [SMILES: O=C(OCc1ccccc1)c1ccc(CN2CCN(c3cccc(CO)c3)CC2)cc1] |
| 174 | R174 | 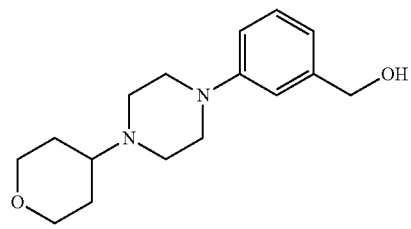 [SMILES: OCc1cccc(N2CCN(C3CCOCC3)CC2)c1] |
| 175 | R174 | 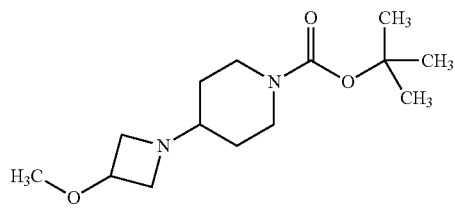 [SMILES: COC1CN(C2CCN(C(=O)OC(C)(C)C)CC2)C1] |
| 176 | R177 | 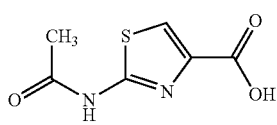 |

TABLE 14-continued
| Rf | Syn | Structure |
|---|---|---|
| 177 | R177 | 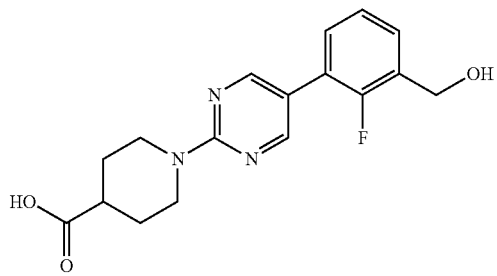 [SMILES: O=C(O)C1CCN(c2ncc(-c3cccc(CO)c3F)cn2)CC1] |
| 178 | R177 | 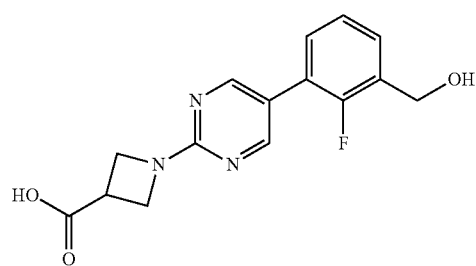 [SMILES: O=C(O)C1CN(c2ncc(-c3cccc(CO)c3F)cn2)C1] |
| 179 | R177 | 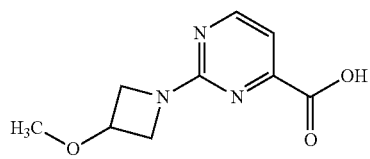 |
| 180 | R177 | 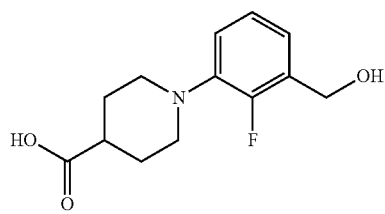 [SMILES: O=C(O)C1CCN(c2cccc(CO)c2F)CC1] |
| 181 | R177 | 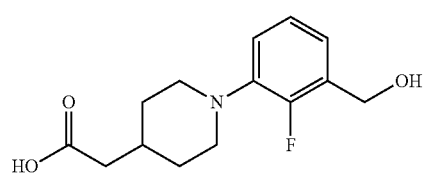 [SMILES: O=C(O)CC1CCN(c2cccc(CO)c2F)CC1] |
| 182 | R182 | 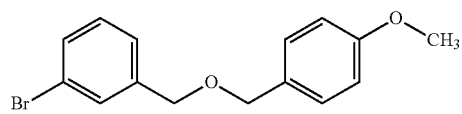 [SMILES: COc1ccc(COCc2cccc(Br)c2)cc1] |

TABLE 15

| Rf | Syn | Structure |
|---|---|---|
| 183 | R228 | 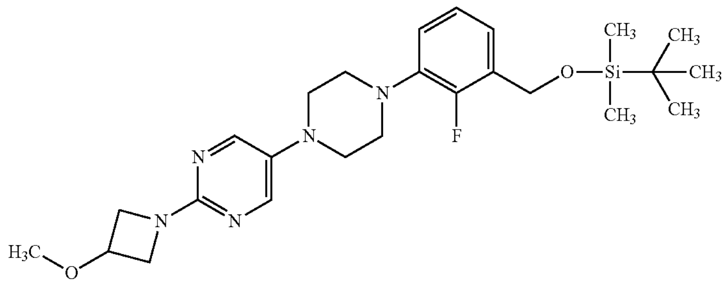 [SMILES: COC1CN(c2ncc(N3CCN(c4cccc(CO[Si](C)(C)C(C)(C)C)c4F)CC3)cn2)C1] |
| 184 | R228 | 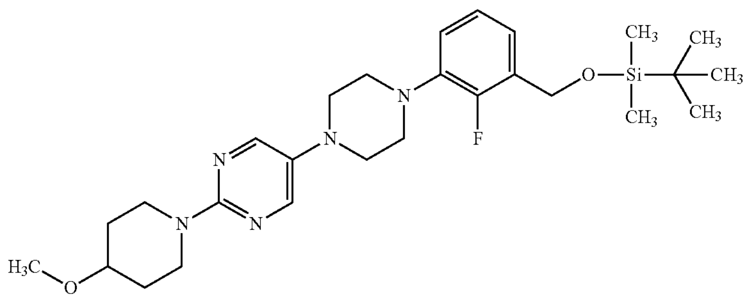 [SMILES: COC1CCN(c2ncc(N3CCN(c4cccc(CO[Si](C)(C)C(C)(C)C)c4F)CC3)cn2)CC1] |
| 185 | R228 | 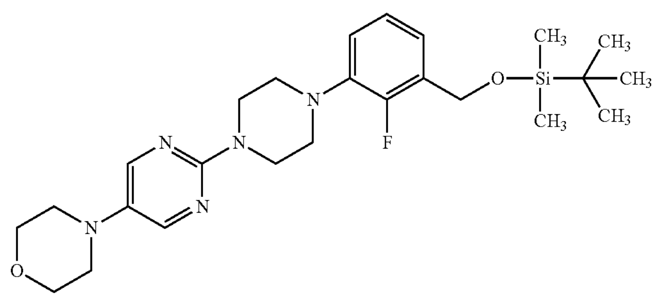 [SMILES: CC(C)(C)[Si](C)(C)OCc1cccc(N2CCN(c3ncc(N4CCOCC4)cn3)CC2)c1F] |
| 186 | R228 | 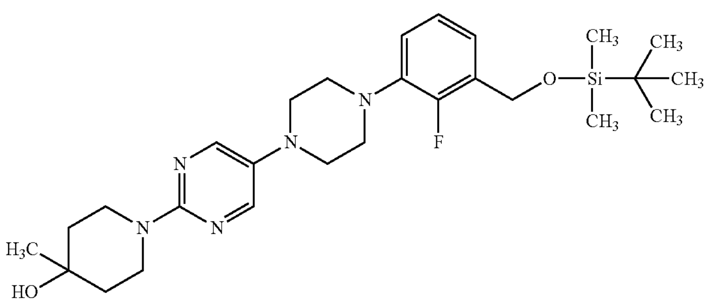 [SMILES: CC1(O)CCN(c2ncc(N3CCN(c4cccc(CO[Si](C)(C)C(C)(C)C)c4F)CC3)cn2)CC1] |
| 187 | R228 | 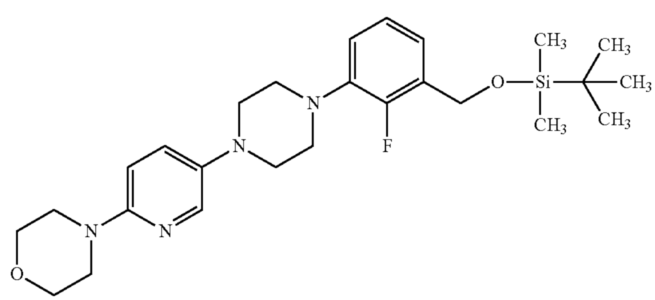 [SMILES: CC(C)(C)[Si](C)(C)OCc1cccc(N2CCN(c3ccc(N4CCOCC4)nc3)CC2)c1F] |

TABLE 15-continued

| Rf | Syn | Structure |
|---|---|---|
| 188 | R228 | 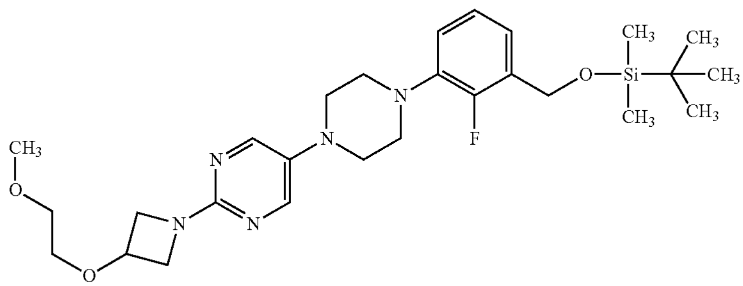 [SMILES: COCCOC1CN(c2ncc(N3CCN(c4cccc(CO[Si](C)(C)C(C)(C)C)c4F)CC3)cn2)C1] |
| 189 | R228 | 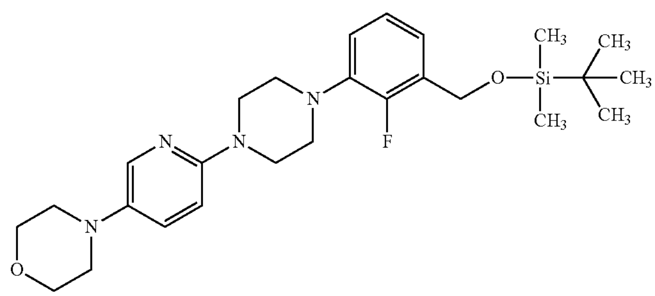 [SMILES: CC(C)(C)[Si](C)(C)OCc1cccc(N2CCN(c3ccc(N4CCOCC4)cn3)CC2)c1F] |
| 190 | R228 | 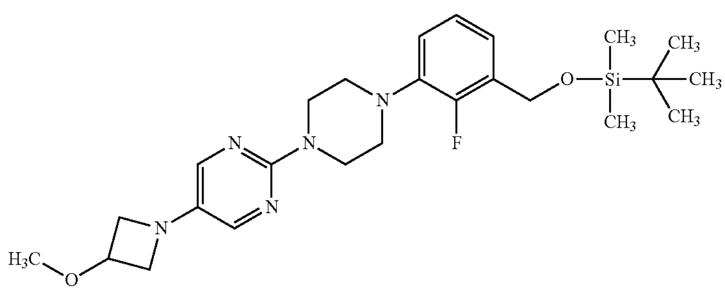 [SMILES: COC1CN(c2cnc(N3CCN(c4cccc(CO[Si](C)(C)C(C)(C)C)c4F)CC3)nc2)C1] |
| 191 | R228 | 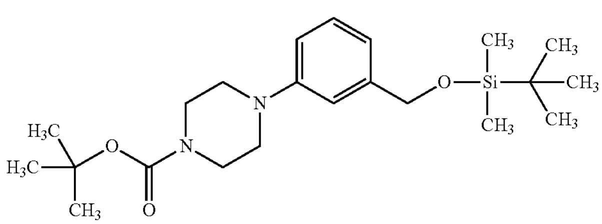 [SMILES: CC(C)(C)OC(=O)N1CCN(c2cccc(CO[Si](C)(C)C(C)(C)C)c2)CC1] |
| 192 | R228 | 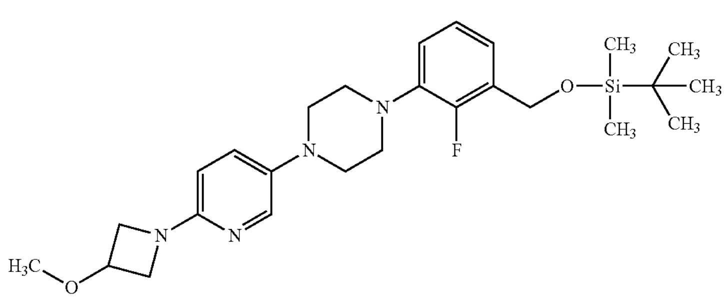 [SMILES: COC1CN(c2ccc(N3CCN(c4cccc(CO[Si](C)(C)C(C)(C)C)c4F)CC3)cn2)C1] |

TABLE 15-continued

| Rf | Syn | Structure |
|---|---|---|
| 193 | R228 | (structure) |
| 194 | R228 | (structure) |
| 195 | R228 | (structure) |
| 196 | R228 | (structure) |
| 197 | R228 | (structure) |
| 198 | R228 | (structure) |

TABLE 16
| Rf | Syn | Structure |
|---|---|---|
| 199 | R228 | trans- 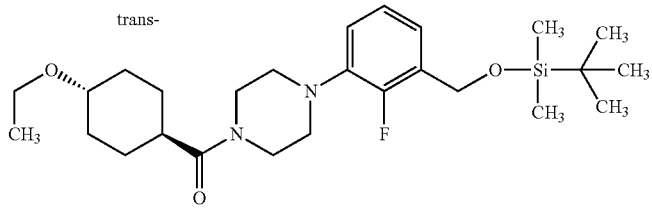 [SMILES: CCO[C@H]1CC[C@H](C(=O)N2CCN(c3cccc(CO[Si](C)(C)C(C)(C)C)c3F)CC2)CC1] |
| 200 | R228 | trans- 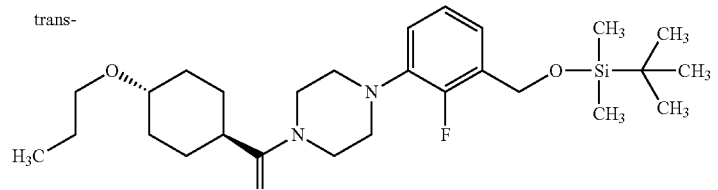 |
| 201 | R228 | cis- 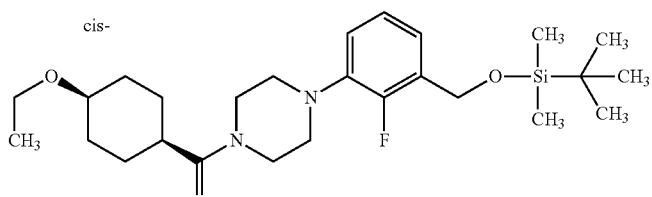 |
| 202 | R228 | cis- 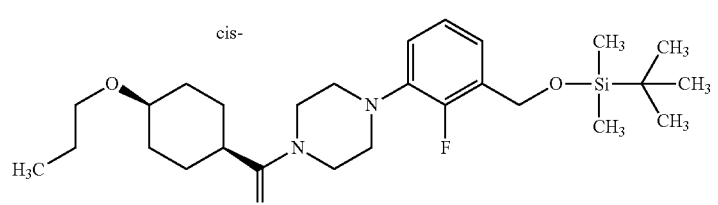 |
| 203 | R228 | trans- 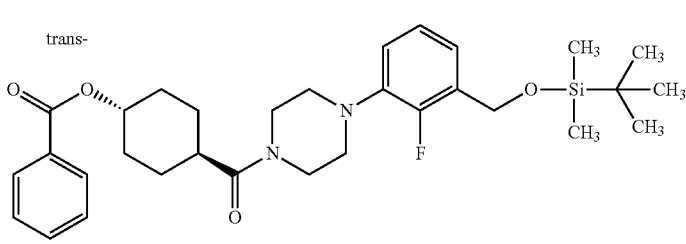 [SMILES: CC(C)(C)[Si](C)(C)OCc1cccc(N2CCN(C(=O)[C@H]3CC[C@H](OC(=O)c4ccccc4)CC3)CC2)c1F] |
| 204 | R228 | cis- 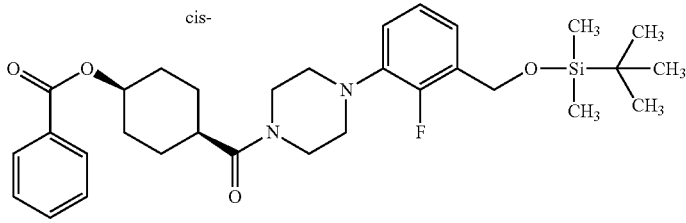 [SMILES: CC(C)(C)[Si](C)(C)OCc1cccc(N2CCN(C(=O)[C@H]3CC[C@@H](OC(=O)c4ccccc4)CC3)CC2)c1F] |
| 205 | R228 | 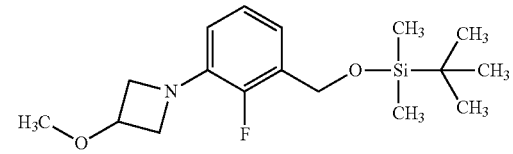 [SMILES: COC1CN(c2cccc(CO[Si](C)(C)C(C)(C)C)c2F)C1] |

TABLE 16-continued
| Rf | Syn | Structure |
|---|---|---|
| 206 | R228 | 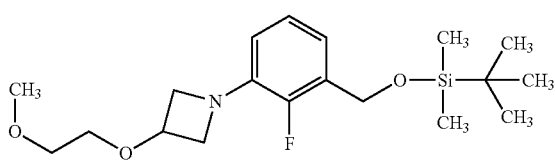 [SMILES: COCCOC1CN(c2cccc(CO[Si](C)(C)C(C)(C)C)c2F)C1] |
| 207 | R228 | 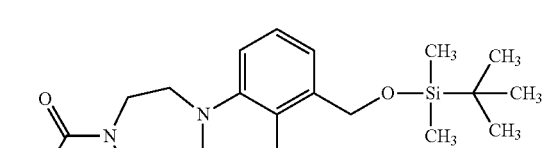 |
| 208 | R228 | 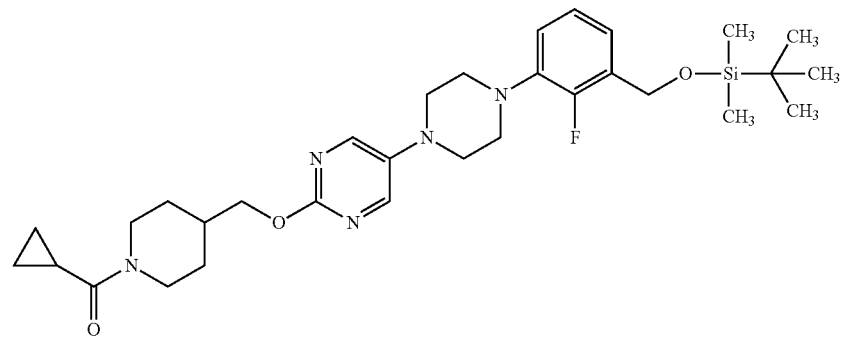 [SMILES: CC(C)(C)[Si](C)(C)OCc1cccc(N2CCN(c3cnc(OCC4CCN(C(=O)C5CC5)CC4)nc3)CC2)c1F] |
| 209 | R228 | 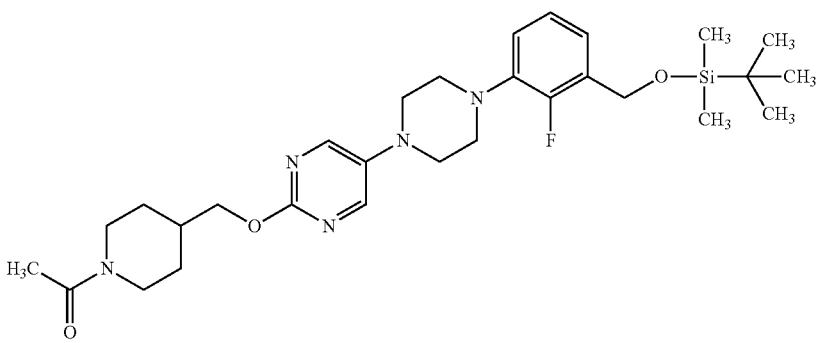 [SMILES: CC(=O)N1CCC(COc2ncc(N3CCN(c4cccc(CO[Si](C)(C)C(C)(C)C)c4F)CC3)cn2)CC1] |
| 210 | R228 | 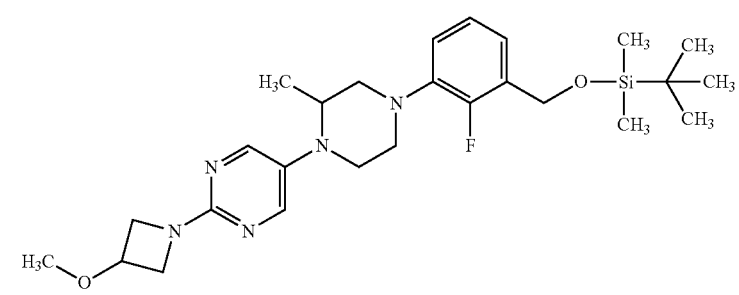 [SMILES: COC1CN(c2ncc(N3CCN(c4cccc(CO[Si](C)(C)C(C)(C)C)c4F)CC3C)cn2)C1] |
| 211 | R228 | 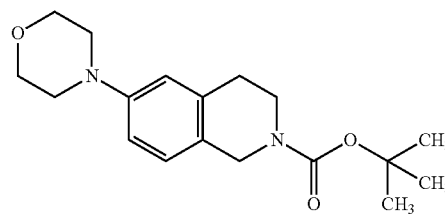 |

TABLE 16-continued

| Rf | Syn | Structure |
|---|---|---|
| 212 | R228 | 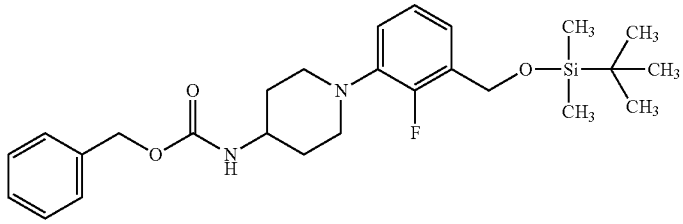 [SMILES: CC(C)(C)[Si](C)(C)OCc1cccc(N2CCC(NC(=O)OCc3ccccc3)CC2)c1F] |
| 213 | R228 | 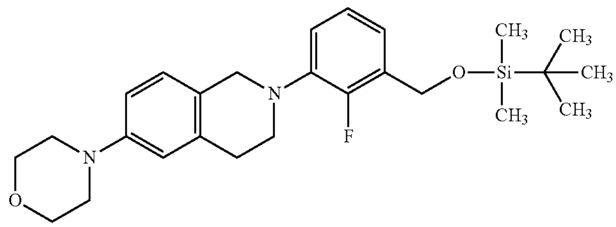 [SMILES: CC(C)(C)[Si](C)(C)OCc1cccc(N2CCc3cc(N4CCOCC4)ccc3C2)c1F] |
| 214 | R228 | 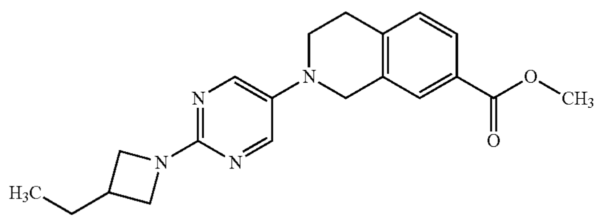 [SMILES: CCC1CN(c2ncc(N3CCc4ccc(C(=O)OC)cc4C3)cn2)C1] |
| 215 | R228 | 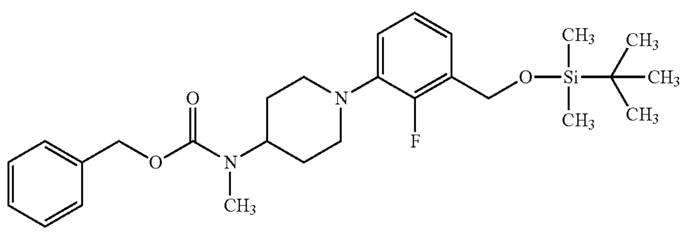 [SMILES: CN(C(=O)OCc1ccccc1)C1CCN(c2cccc(CO[Si](C)(C)C(C)(C)C)c2F)CC1] |
| 216 | R228 | 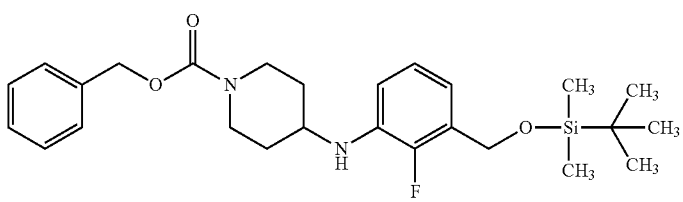 [SMILES: CC(C)(C)[Si](C)(C)OCc1cccc(NC2CCN(C(=O)OCc3ccccc3)CC2)c1F] |

TABLE 17

| Rf | Syn | Structure |
|---|---|---|
| 217 | R228 | 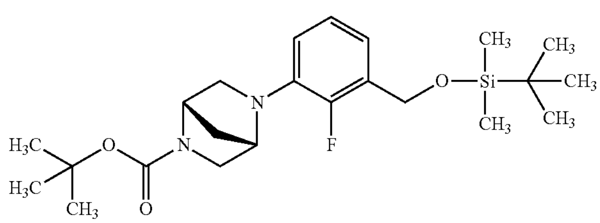 [SMILES: CC(C)(C)OC(=O)N1C[C@@H]2C[C@H]1CN2c1cccc(CO[Si](C)(C)C(C)(C)C)c1F] |

TABLE 17-continued
| Rf | Syn | Structure |
|---|---|---|
| 218 | R228 | 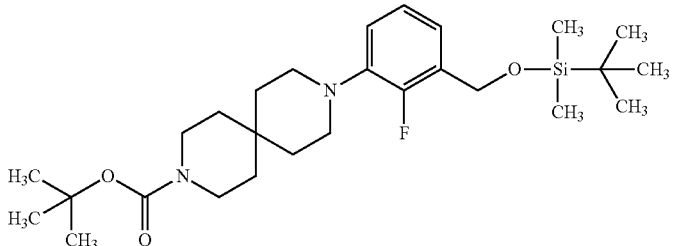 |
| 219 | R228 | 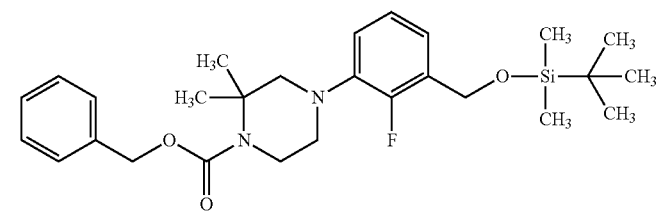 [SMILES: CC1(C)CN(c2cccc(CO[Si](C)(C)C(C)(C)C)c2F)CCN1C(=O)OCc1ccccc1] |
| 220 | R228 | 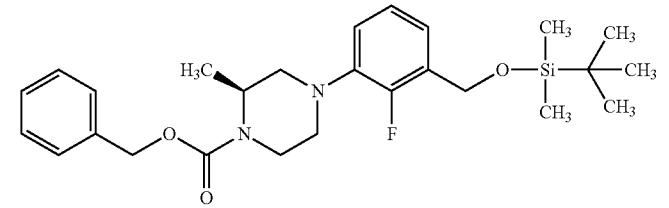 [SMILES: C[C@H]1CN(c2cccc(CO[Si](C)(C)C(C)(C)C)c2F)CCN1C(=O)OCc1ccccc1] |
| 221 | R228 | 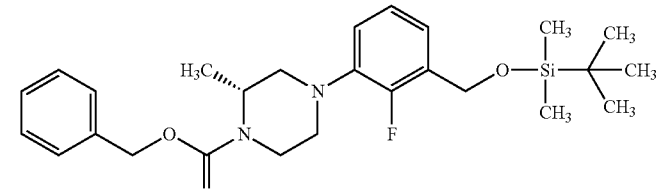 |
| 222 | R228 | 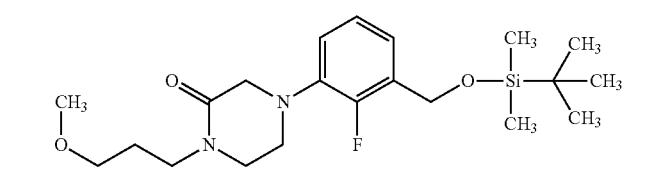 [SMILES: COCCCN1CCN(c2cccc(CO[Si](C)(C)C(C)(C)C)c2F)CC1=O] |
| 223 | R228 | 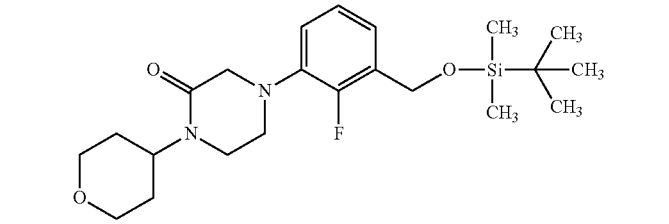 [SMILES: CC(C)(C)[Si](C)(C)OCc1cccc(N2CCN(C3CCOCC3)C(=O)C2)c1F] |
| 224 | R228 | 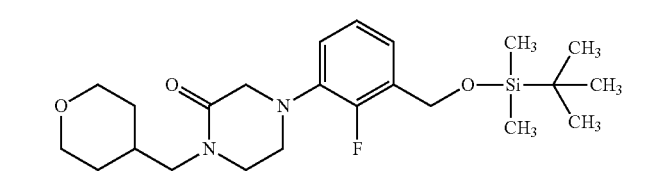 [SMILES: CC(C)(C)[Si](C)(C)OCc1cccc(N2CCN(CC3CCOCC3)C(=O)C2)c1F] |

TABLE 17-continued
| Rf | Syn | Structure |
|---|---|---|
| 225 | R228 | 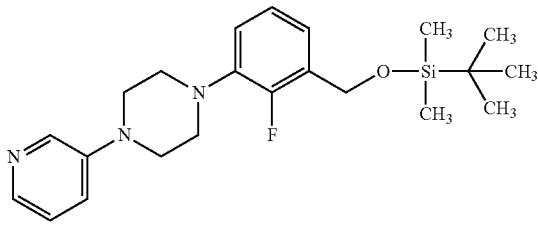 [SMILES: CC(C)(C)[Si](C)(C)OCc1cccc(N2CCN(c3cccnc3)CC2)c1F] |
| 226 | R228 | 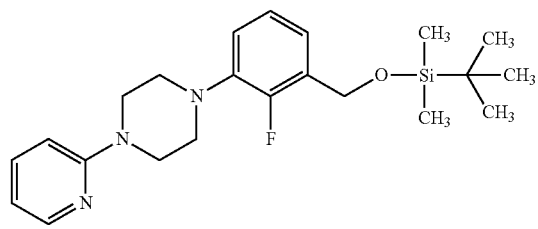 [SMILES: CC(C)(C)[Si](C)(C)OCc1cccc(N2CCN(c3ccccn3)CC2)c1F] |
| 227 | R228 | 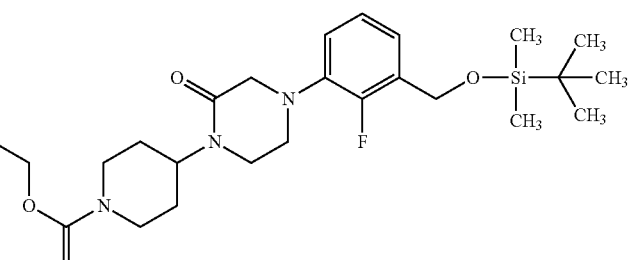 |
| 228 | R228 | 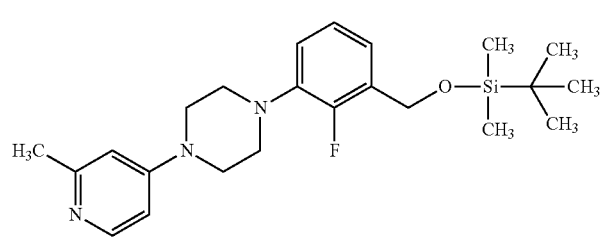 [SMILES: Cc1cc(N2CCN(c3cccc(CO[Si](C)(C)C(C)(C)C)c3F)CC2)ccn1] |
| 229 | R228 | 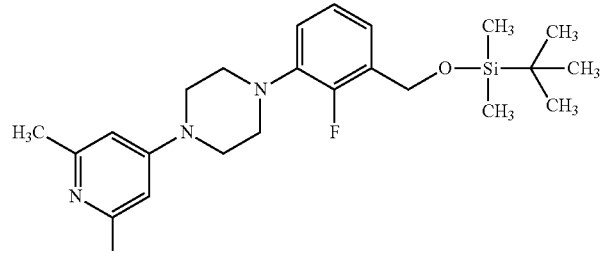 |
| 230 | R228 | 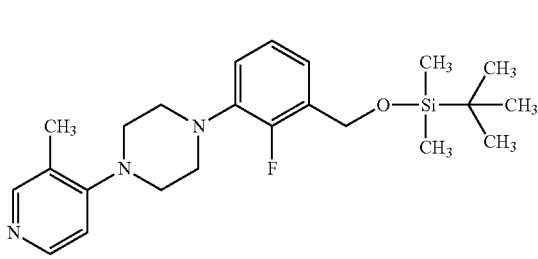 [SMILES: Cc1cnccc1N1CCN(c2cccc(CO[Si](C)(C)C(C)(C)C)c2F)CC1] |

TABLE 17-continued
| Rf | Syn | Structure |
|---|---|---|
| 231 | R228 | 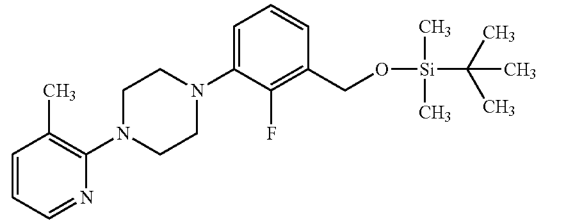 [SMILES: Cc1cccnc1N1CCN(c2cccc(CO[Si](C)(C)C(C)(C)C)c2F)CC1] |
| 232 | R228 | 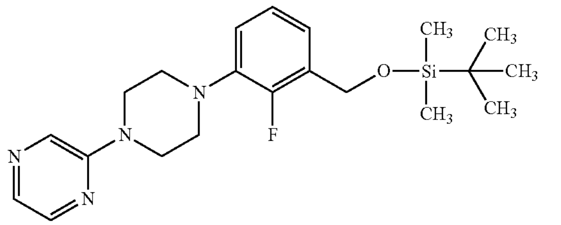 [SMILES: CC(C)(C)[Si](C)(C)OCc1cccc(N2CCN(c3cnccn3)CC2)c1F] |
| 233 | R228 | 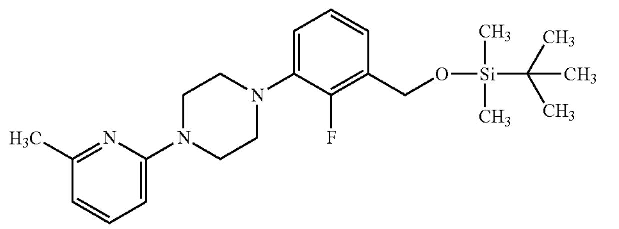 [SMILES: Cc1cccc(N2CCN(c3cccc(CO[Si](C)(C)C(C)(C)C)c3F)CC2)n1] |
| 234 | R228 | 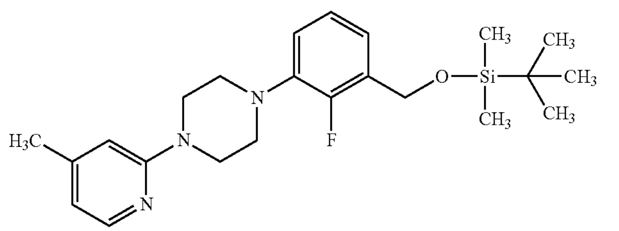 [SMILES: Cc1ccnc(N2CCN(c3cccc(CO[Si](C)(C)C(C)(C)C)c3F)CC2)c1] |
TABLE 18
| Rf | Syn | Structure |
|---|---|---|
| 235 | R228 | 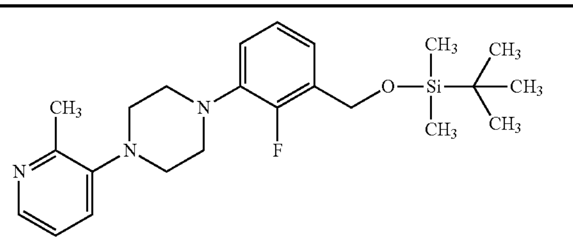 |
| 236 | R228 | 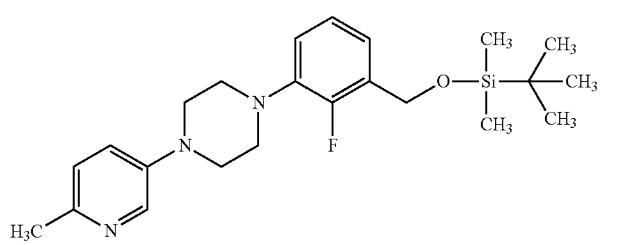 [SMILES: Cc1ccc(N2CCN(c3cccc(CO[Si](C)(C)C(C)(C)C)c3F)CC2)cn1] |

TABLE 18-continued
| Rf | Syn | Structure |
|---|---|---|
| 237 | R228 | 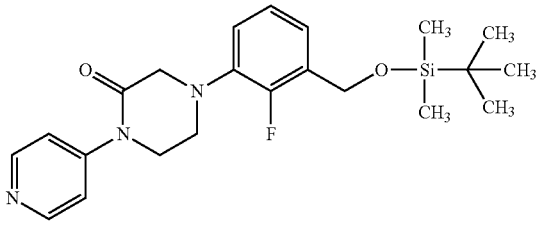 [SMILES: CC(C)(C)[Si](C)(C)OCc1cccc(N2CCN(c3ccncc3)C(=O)C2)c1F] |
| 238 | R228 | 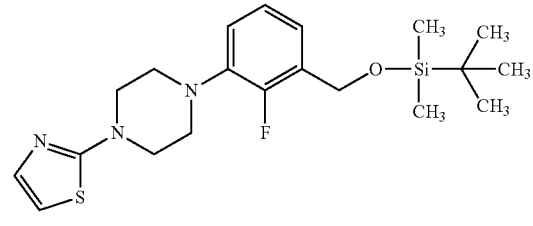 [SMILES: CC(C)(C)[Si](C)(C)OCc1cccc(N2CCN(c3nccs3)CC2)c1F] |
| 239 | R228 | 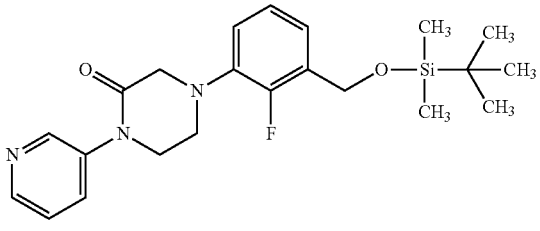 [SMILES: CC(C)(C)[Si](C)(C)OCc1cccc(N2CCN(c3cccnc3)C(=O)C2)c1F] |
| 240 | R228 | 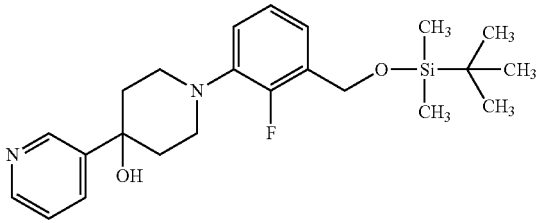 [SMILES: CC(C)(C)[Si](C)(C)OCc1cccc(N2CCC(O)(c3cccnc3)CC2)c1F] |
| 241 | R228 | 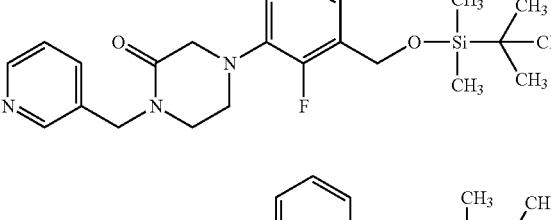 |
| 242 | R228 | 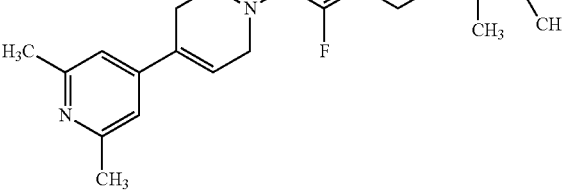 |

TABLE 18-continued

| Rf | Syn | Structure |
|---|---|---|
| 243 | R228 | 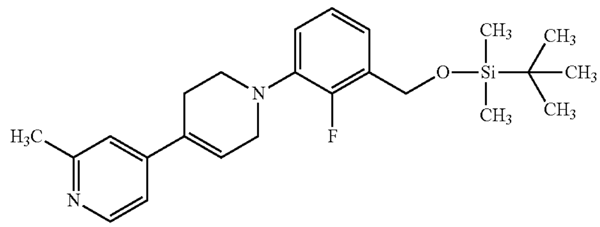 [SMILES: Cc1cc(C2=CCN(c3cccc(CO[Si](C)(C)C(C)(C)C)c3F)CC2)ccn1] |
| 244 | R228 | 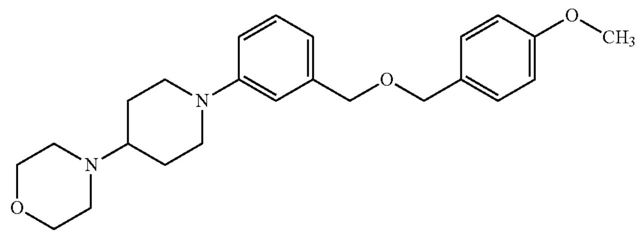 [SMILES: COc1ccc(COCc2cccc(N3CCC(N4CCOCC4)CC3)c2)cc1] |
| 245 | R228 | 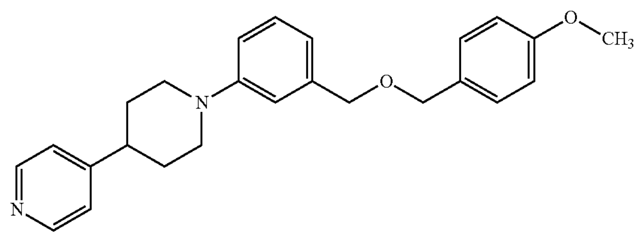 [SMILES: COc1ccc(COCc2cccc(N3CCC(c4ccncc4)CC3)c2)cc1] |
| 246 | R228 | 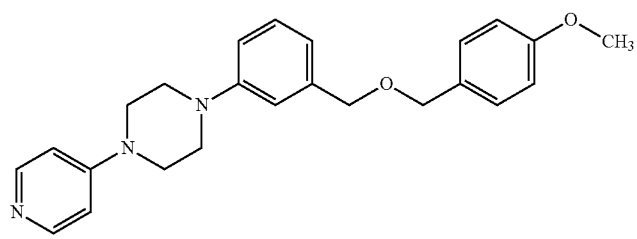 [SMILES: COc1ccc(COCc2cccc(N3CCN(c4ccncc4)CC3)c2)cc1] |
| 247 | R228 | 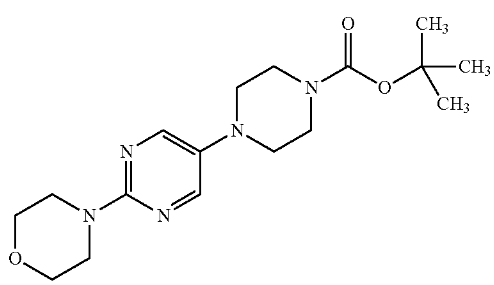 [SMILES: CC(C)(C)OC(=O)N1CCN(c2cnc(N3CCOCC3)nc2)CC1] |
| 248 | R228 | 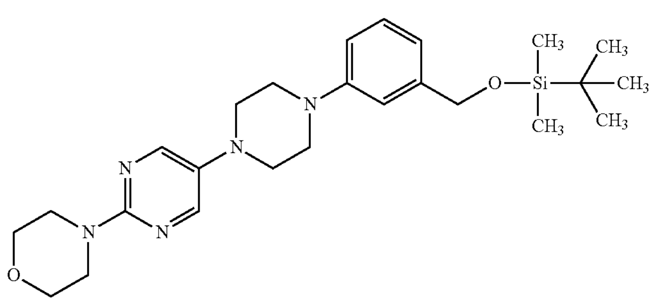 |

TABLE 18-continued
| Rf | Syn | Structure |
|---|---|---|
| 249 | R228 | 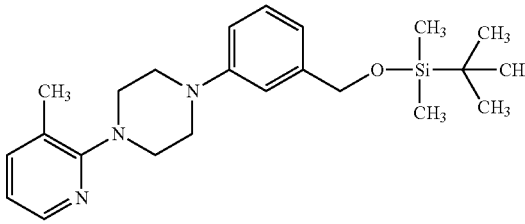 |
| 250 | R228 | 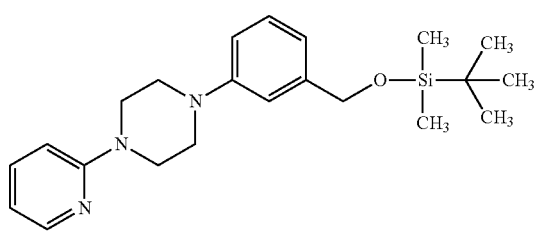 [SMILES: CC(C)(C)[Si](C)(C)OCc1cccc(N2CCN(c3ccccn3)CC2)c1] |
TABLE 19
| Rf | Syn | Structure |
|---|---|---|
| 251 | R228 | 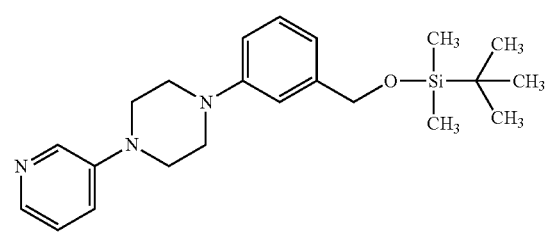 [SMILES: CC(C)(C)[Si](C)(C)OCc1cccc(N2CCN(c3cccnc3)CC2)c1] |
| 252 | R228 | 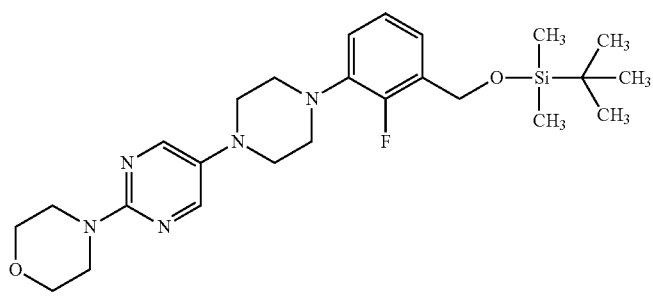 |
| 253 | R228 | 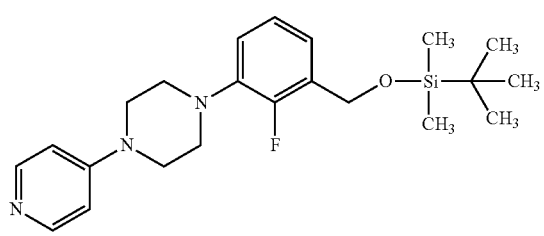 [SMILES: CC(C)(C)[Si](C)(C)OCc1cccc(N2CCN(c3ccncc3)CC2)c1F] |

TABLE 19-continued
| Rf | Syn | Structure |
|---|---|---|
| 254 | R228 | 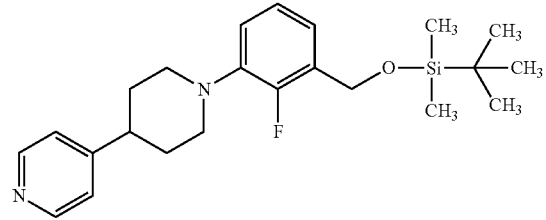 [SMILES: CC(C)(C)[Si](C)(C)OCc1cccc(N2CCC(c3ccncc3)CC2)c1F] |
| 255 | R228 | 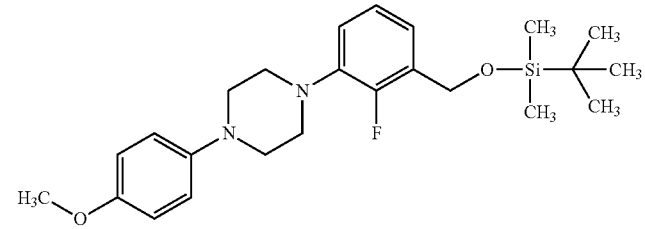 [SMILES: COc1ccc(N2CCN(c3cccc(CO[Si](C)(C)C(C)(C)C)c3F)CC2)cc1] |
| 256 | R228 | 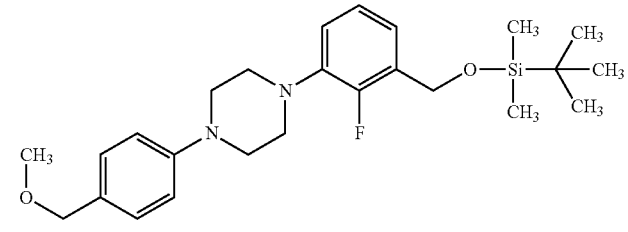 [SMILES: COCc1ccc(N2CCN(c3cccc(CO[Si](C)(C)C(C)(C)C)c3F)CC2)cc1] |
| 257 | R228 | 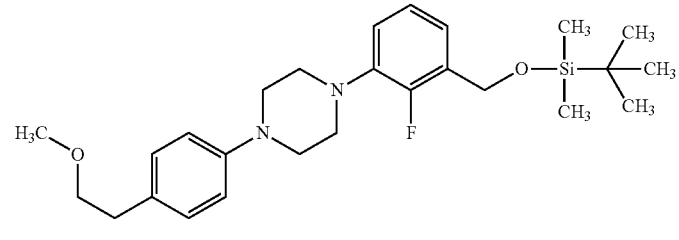 [SMILES: COCCc1ccc(N2CCN(c3cccc(CO[Si](C)(C)C(C)(C)C)c3F)CC2)cc1] |
| 258 | R228 | 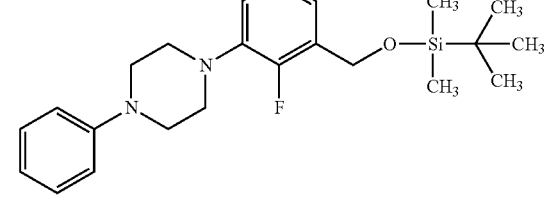 |
| 259 | R228 | 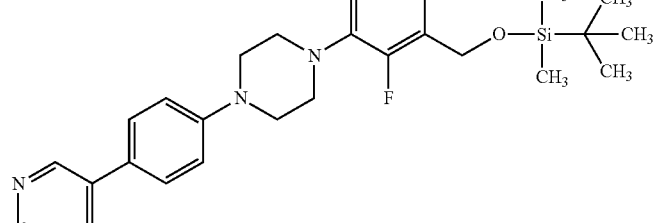 |

TABLE 19-continued

| Rf | Syn | Structure |
|---|---|---|
| 260 | R228 | 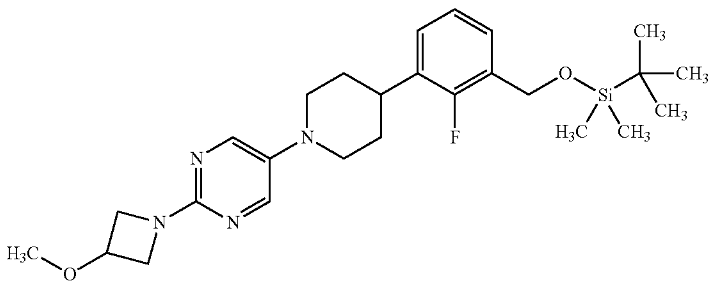 [SMILES: COC1CN(c2ncc(N3CCC(c4cccc(CO[Si](C)(C)C(C)(C)C)c4F)CC3)cn2)C1] |
| 261 | R228 | 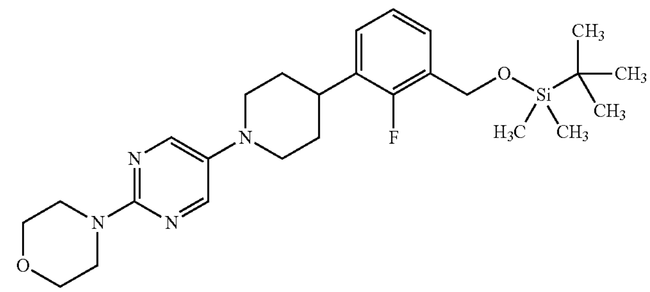 [SMILES: CC(C)(C)[Si](C)(C)OCc1cccc(C2CCN(c3cnc(N4CCOCC4)nc3)CC2)c1F] |
| 262 | R228 | 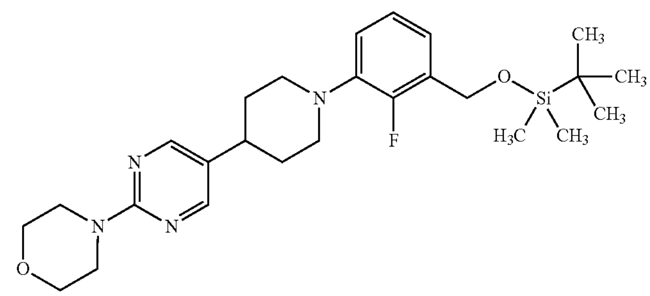 [SMILES: CC(C)(C)[Si](C)(C)OCc1cccc(N2CCC(c3cnc(N4CCOCC4)nc3)CC2)c1F] |
| 263 | R228 | 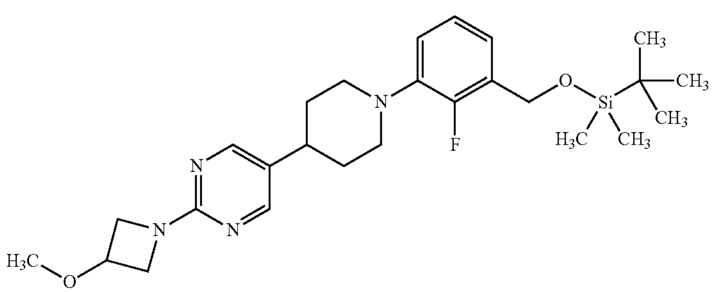 [SMILES: COC1CN(c2ncc(C3CCN(c4cccc(CO[Si](C)(C)C(C)(C)C)c4F)CC3)cn2)C1] |
| 264 | R228 | 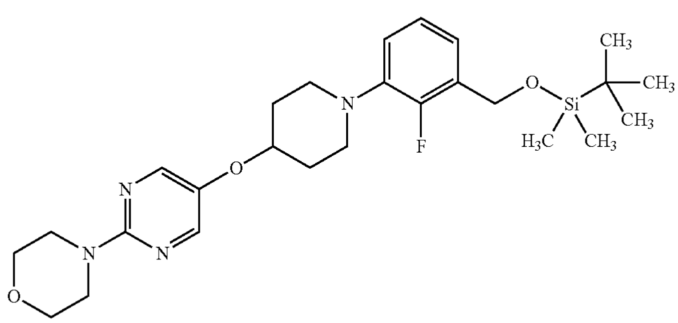 [SMILES: CC(C)(C)[Si](C)(C)OCc1cccc(N2CCC(Oc3cnc(N4CCOCC4)nc3)CC2)c1F] |

TABLE 19-continued

| Rf | Syn | Structure |
|---|---|---|
| 265 | R228 | 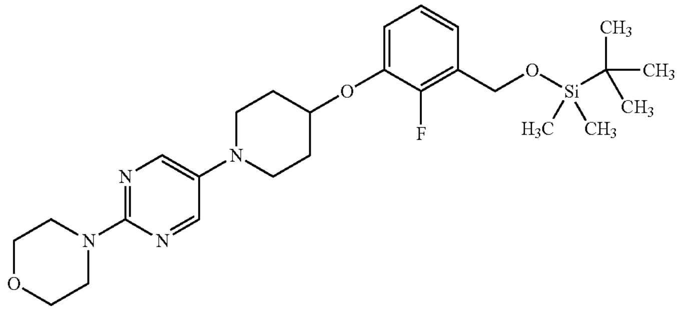 [SMILES: CC(C)(C)[Si](C)(C)OCc1cccc(OC2CCN(c3cnc(N4CCOCC4)nc3)CC2)c1F] |
| 266 | R228 | 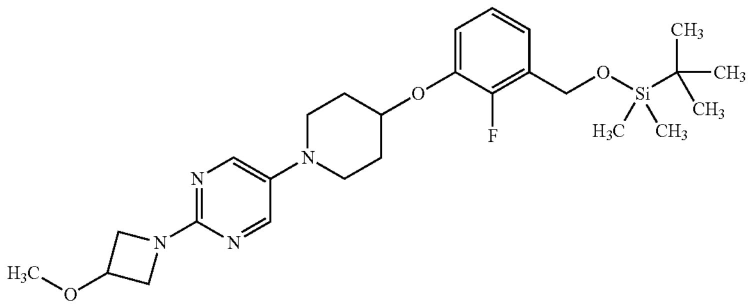 [SMILES: COC1CN(c2ncc(N3CCC(Oc4cccc(CO[Si](C)(C)C(C)(C)C)c4F)CC3)cn2)C1] |

TABLE 20

| Rf | Syn | Structure |
|---|---|---|
| 267 | R228 | 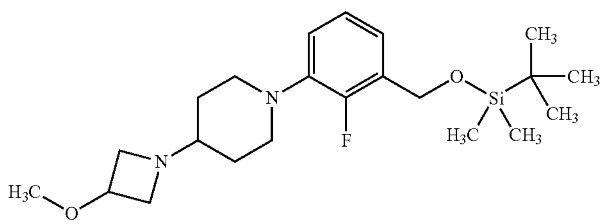 [SMILES: COC1CN(C2CCN(c3cccc(CO[Si](C)(C)C(C)(C)C)c3F)CC2)C1] |
| 268 | R228 | 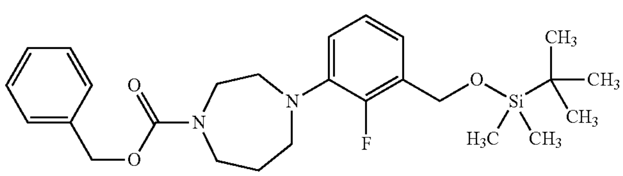 [SMILES: CC(C)(C)[Si](C)(C)OCc1cccc(N2CCCN(C(=O)OCc3ccccc3)CC2)c1F] |
| 269 | R228 | 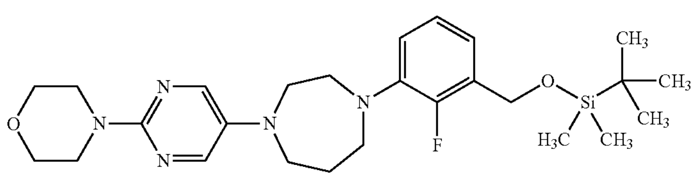 [SMILES: CC(C)(C)[Si](C)(C)OCc1cccc(N2CCCN(c3cnc(N4CCOCC4)nc3)CC2)c1F] |
| 270 | R228 | 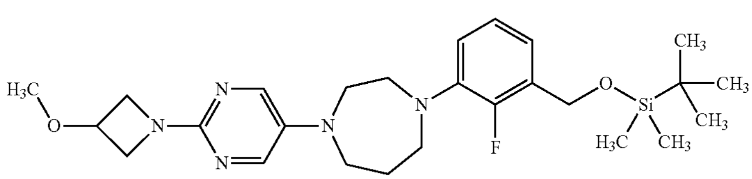 [SMILES: COC1CN(c2ncc(N3CCCN(c4cccc(CO[Si](C)(C)C(C)(C)C)c4F)CC3)cn2)C1] |

TABLE 20-continued
| Rf | Syn | Structure |
|---|---|---|
| 271 | R228 | 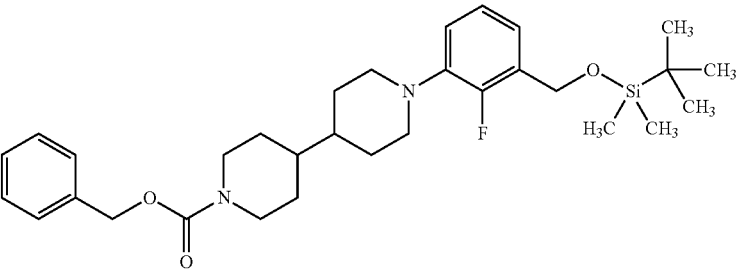 [SMILES: CC(C)(C)[Si](C)(C)OCc1cccc(N2CCC(C3CCN(C(=O)OCc4ccccc4)CC3)CC2)c1F] |
| 272 | R228 | 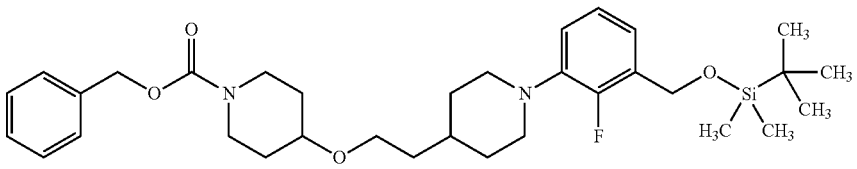 [SMILES: CC(C)(C)[Si](C)(C)OCc1cccc(N2CCC(CCOC3CCN(C(=O)OCc4ccccc4)CC3)CC2)c1F] |
| 273 | R228 | 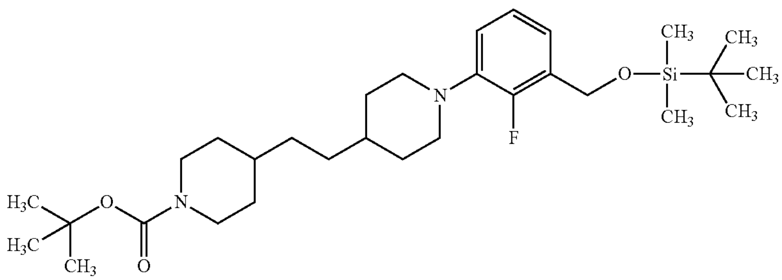 [SMILES: CC(C)(C)OC(=O)N1CCC(OCC2CCN(c3cccc(CO[Si](C)(C)C(C)(C)C)c3F)CC2)CC1] |
| 274 | R228 | 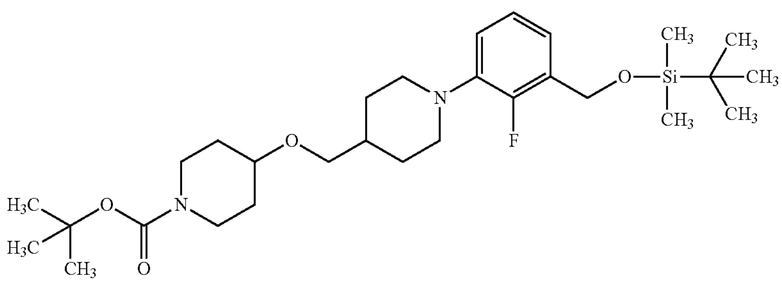 |
| 275 | R228 | 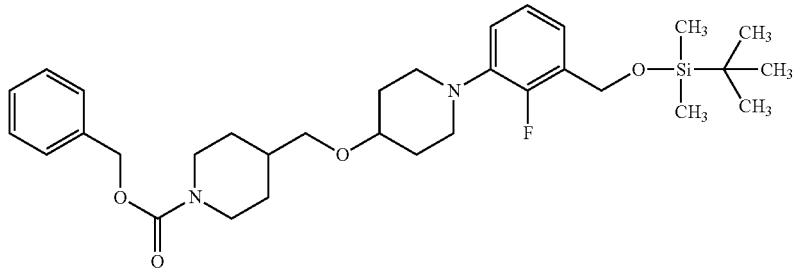 [SMILES: CC(C)(C)[Si](C)(C)OCc1cccc(N2CCC(OCC3CCN(C(=O)OCc4ccccc4)CC3)CC2)c1F] |
| 276 | R228 | 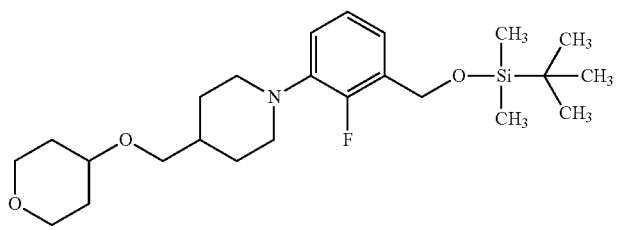 [SMILES: CC(C)(C)[Si](C)(C)OCc1cccc(N2CCC(COC3CCOCC3)CC2)c1F] |

TABLE 20-continued
| Rf | Syn | Structure |
|---|---|---|
| 277 | R228 | 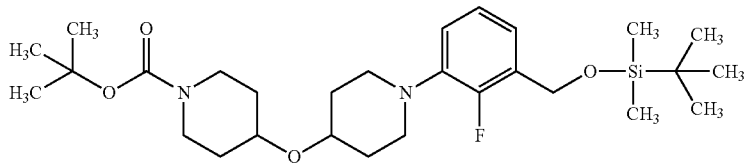 [SMILES: CC(C)(C)OC(=O)N1CCC(OC2CCN(c3cccc(CO[Si](C)(C)C(C)(C)C)c3F)CC2)CC1] |
| 278 | R228 | 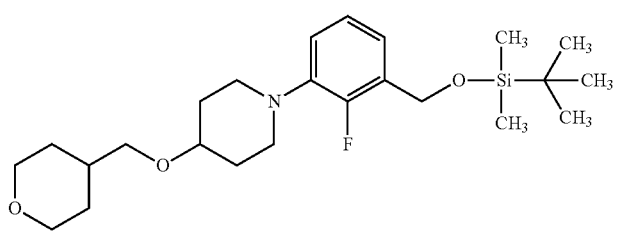 [SMILES: CC(C)(C)[Si](C)(C)OCc1cccc(N2CCC(OCC3CCOCC3)CC2)c1F] |
| 279 | R228 | 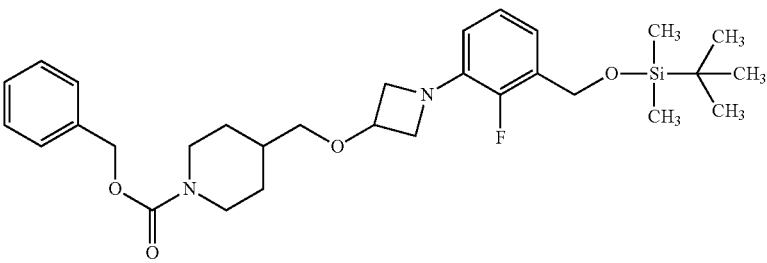 [SMILES: CC(C)(C)[Si](C)(C)OCc1cccc(N2CC(OCC3CCN(C(=O)OCc4ccccc4)CC3)C2)c1F] |
| 280 | R228 | 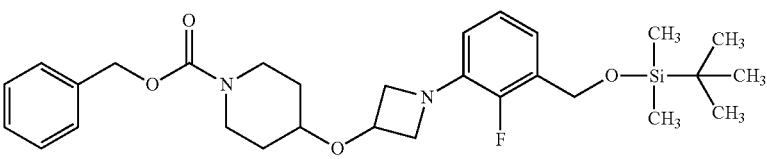 [SMILES: CC(C)(C)[Si](C)(C)OCc1cccc(N2CC(OC3CCN(C(=O)OCc4ccccc4)CC3)C2)c1F] |
| 281 | R228 | 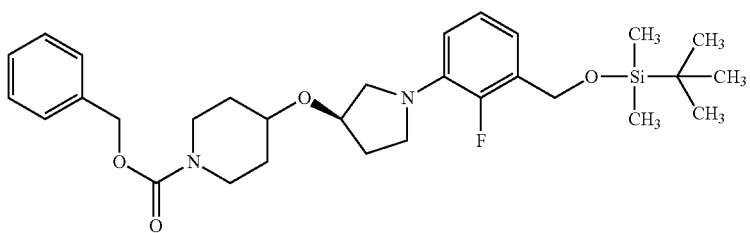 [SMILES: CC(C)(C)[Si](C)(C)OCc1cccc(N2CC[C@@H](OC3CCN(C(=O)OCc4ccccc4)CC3)C2)c1F] |
| 282 | R228 | 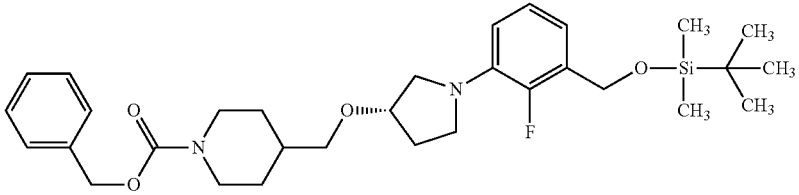 [SMILES: CC(C)(C)[Si](C)(C)OCc1cccc(N2CC[C@H](OCC3CCN(C(=O)OCc4ccccc4)CC3)C2)c1F] |
| 283 | R228 | 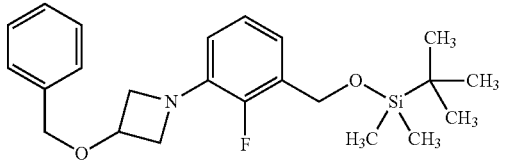 [SMILES: CC(C)(C)[Si](C)(C)OCc1cccc(N2CC(OCc3ccccc3)C2)c1F] |

TABLE 20-continued
| Rf | Syn | Structure |
|---|---|---|
| 284 | R285 | 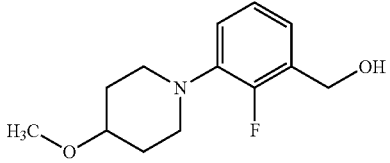 [SMILES: COC1CCN(c2cccc(CO)c2F)CC1] |
TABLE 21
| Rf | Syn | Structure |
|---|---|---|
| 285 | R285 | 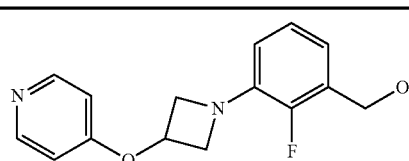 |
| 286 | R285 | 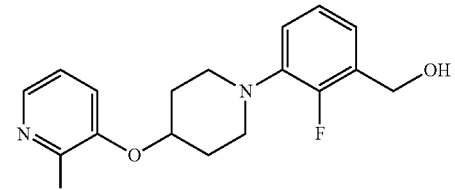 |
| 287 | R285 | 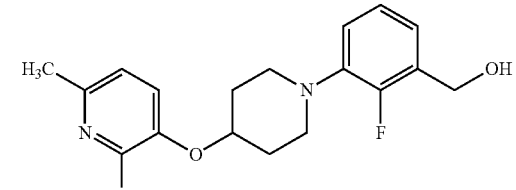 |
| 288 | R285 | 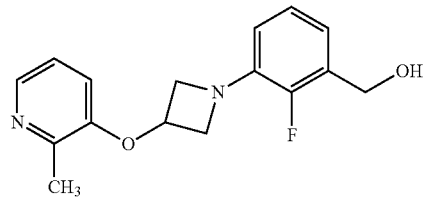 |
| 289 | R285 | 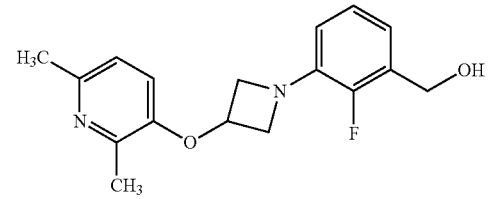 [SMILES: Cc1ccc(OC2CN(c3cccc(CO)c3F)C2)c(C)n1] |
| 290 | R290 | 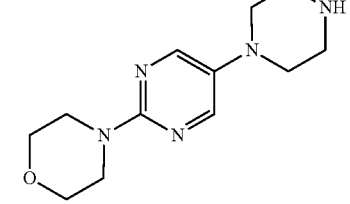 |

TABLE 21-continued

| Rf | Syn | Structure |
|---|---|---|
| 291 | R290 | 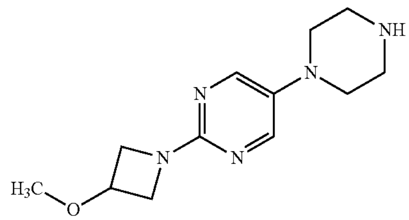 [SMILES: COC1CN(c2ncc(N3CCNCC3)cn2)C1] |
| 292 | R285 | 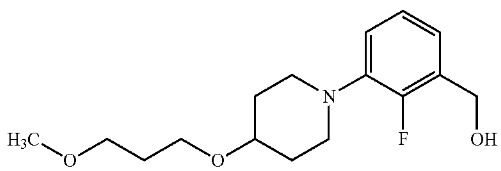 [SMILES: COCCCOC1CCN(c2cccc(CO)c2F)CC1] |
| 293 | R294 | 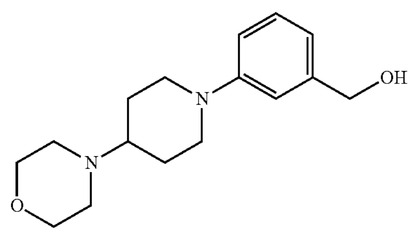 [SMILES: OCc1cccc(N2CCC(N3CCOCC3)CC2)c1] |
| 294 | R294 | 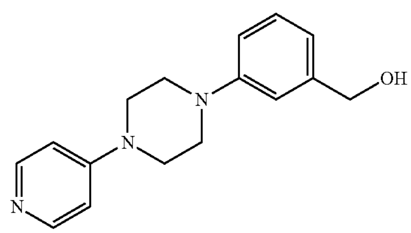 |
| 295 | R294 | 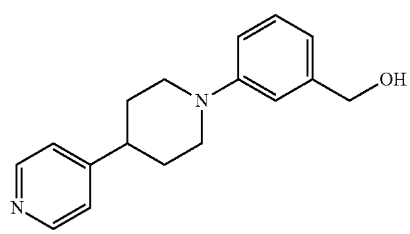 [SMILES: OCc1cccc(N2CCC(c3ccncc3)CC2)c1] |
| 296 | R297 | 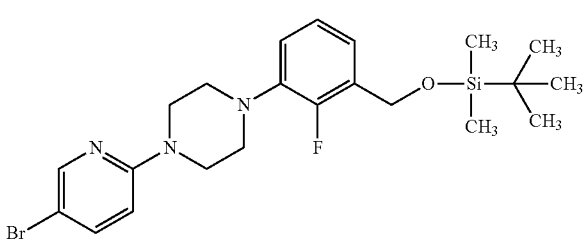 [SMILES: CC(C)(C)[Si](C)(C)OCc1cccc(N2CCN(c3ccc(Br)cn3)CC2)c1F] |
| 297 | R297 | 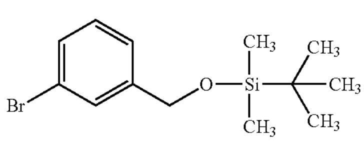 [SMILES: CC(C)(C)[Si](C)(C)OCc1cccc(Br)c1] |

TABLE 21-continued

| Rf | Syn | Structure |
|---|---|---|
| 298 | R297 | 3-bromo-2-fluorobenzyl tert-butyldimethylsilyl ether |
| 299 | R297 | 3-hydroxy-2-fluorobenzyl tert-butyldimethylsilyl ether |
| 300 | R297 | 2-chloro-5-[2-fluoro-3-((tert-butyldimethylsilyloxy)methyl)phenyl]pyrimidine |

TABLE 22

| Rf | Syn | Structure |
|---|---|---|
| 301 | R301 | (2-morpholinopyrimidin-5-yl){3-[((tert-butyldimethylsilyloxy)methyl)]phenyl}methanol |
| 302 | R302 | {3-[(2-morpholinopyrimidin-5-yl)methyl]phenyl}methanol |
| 303 | R304 | 1-(2-methylpyrimidin-4-yl)-4-[2-fluoro-3-((tert-butyldimethylsilyloxy)methyl)phenyl]piperazine |
| 304 | R304 | 1-(pyrimidin-4-yl)-4-[2-fluoro-3-((tert-butyldimethylsilyloxy)methyl)phenyl]piperazine |

TABLE 22-continued

| Rf | Syn | Structure |
|---|---|---|
| 305 | R305 | 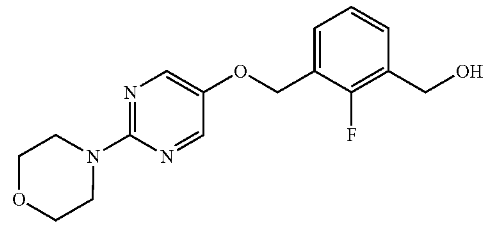 [SMILES: OCc1cccc(COc2cnc(N3CCOCC3)nc2)c1F] |
| 306 | R306 | 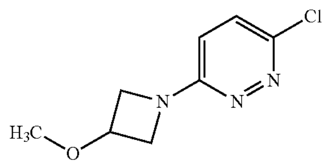 |
| 307 | R307 | 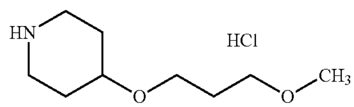 |
| 308 | R309 | 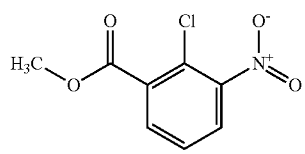 |
| 309 | R309 | 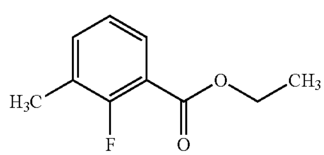 |
| 310 | R336 | 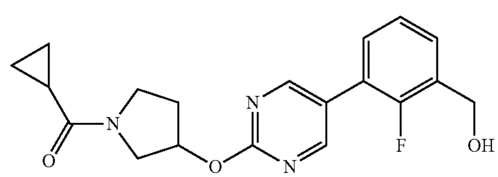 [SMILES: O=C(C1CC1)N1CCC(Oc2ncc(-c3cccc(CO)c3F)cn2)C1] |
| 311 | R336 | 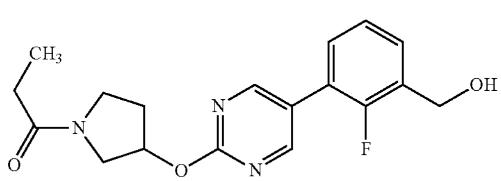 [SMILES: CCC(=O)N1CCC(Oc2ncc(-c3cccc(CO)c3F)cn2)C1] |
| 312 | R336 | 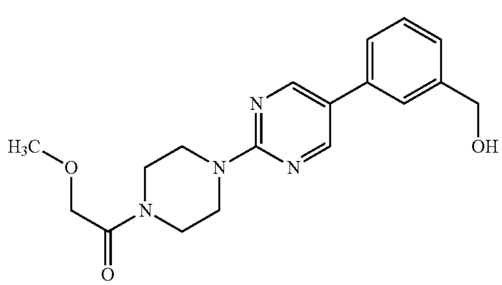 [SMILES: COCC(=O)N1CCN(c2ncc(-c3cccc(CO)c3)cn2)CC1] |

TABLE 22-continued
| Rf | Syn | Structure |
|---|---|---|
| 313 | R336 | 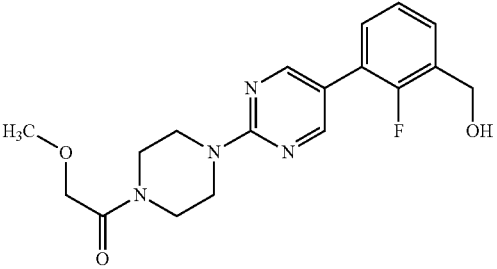 [SMILES: COCC(=O)N1CCN(c2ncc(-c3cccc(CO)c3F)cn2)CC1] |
| 314 | R336 | 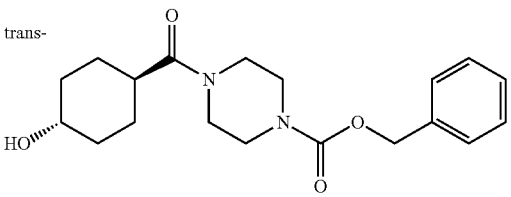 |
| 315 | R336 | 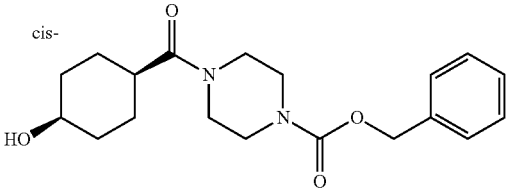 |
| 316 | R336 | 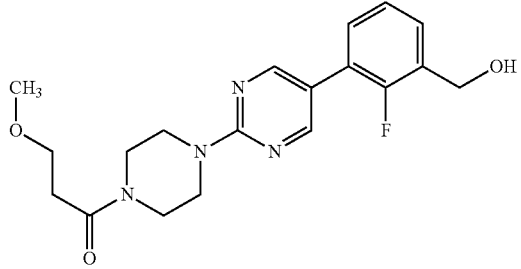 [SMILES: COCCC(=O)N1CCN(c2ncc(-c3cccc(CO)c3F)cn2)CC1] |
TABLE 23
| Rf | Syn | Structure |
|---|---|---|
| 317 | R336 | 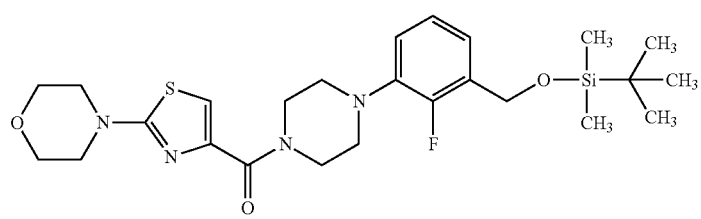 [SMILES: CC(C)(C)[Si](C)(C)OCc1cccc(N2CCN(C(=O)c3csc(N4CCOCC4)n3)CC2)c1F] |
| 318 | R336 | 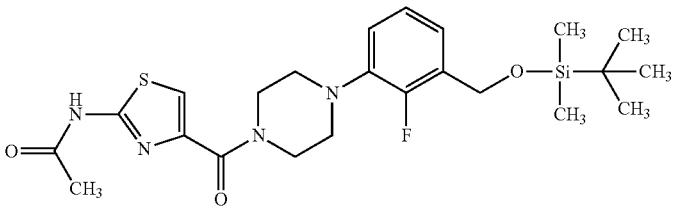 [SMILES: CC(=O)Nc1nc(C(=O)N2CCN(c3cccc(CO[Si](C)(C)C(C)(C)C)c3F)CC2)cs1] |

TABLE 23-continued
| Rf | Syn | Structure |
|---|---|---|
| 319 | R336 | 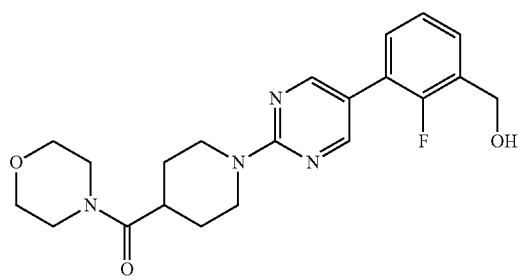 [SMILES: O=C(C1CCN(c2ncc(-c3cccc(CO)c3F)cn2)CC1)N1CCOCC1] |
| 320 | R336 | 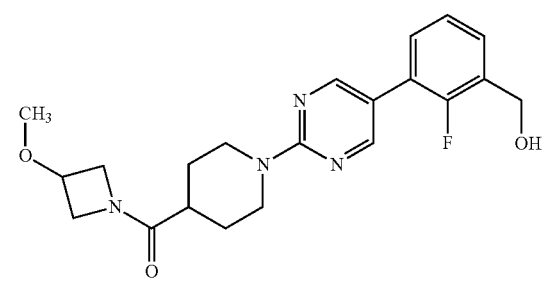 [SMILES: COC1CN(C(=O)C2CCN(c3ncc(-c4cccc(CO)c4F)cn3)CC2)C1] |
| 321 | R336 | 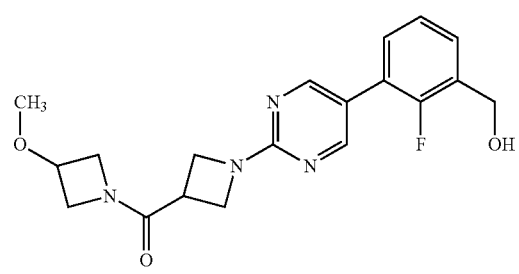 [SMILES: COC1CN(C(=O)C2CN(c3ncc(-c4cccc(CO)c4F)cn3)C2)C1] |
| 322 | R336 | 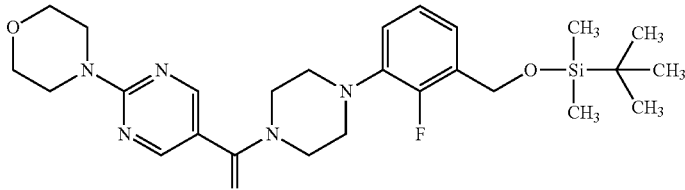 |
| 323 | R336 | 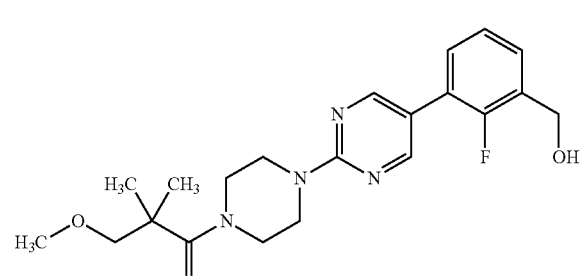 |
| 324 | R336 | 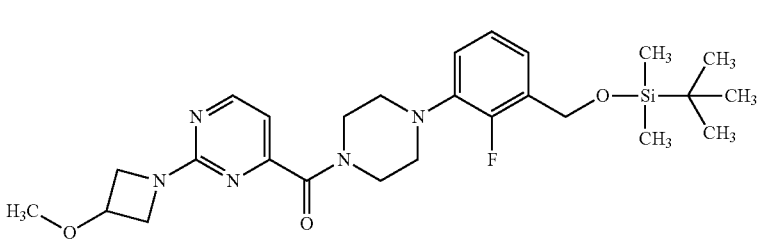 [SMILES: COC1CN(c2nccc(C(=O)N3CCN(c4cccc(CO[Si](C)(C)C(C)(C)C)c4F)CC3)n2)C1] |

TABLE 23-continued
| Rf | Syn | Structure |
|---|---|---|
| 325 | R336 | 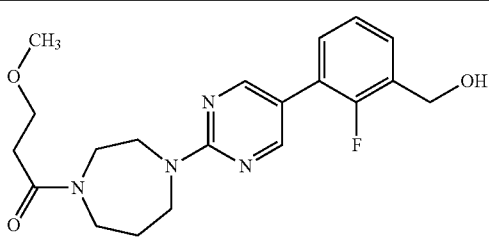 |
| 326 | R336 | 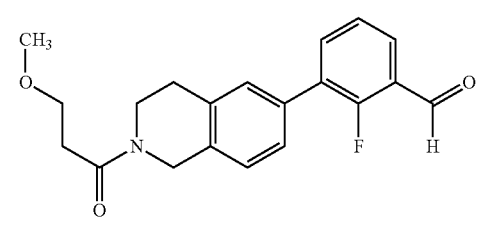 [SMILES: COCCC(=O)N1CCc2cc(-c3cccc(C=O)c3F)ccc2C1] |
| 327 | R336 | 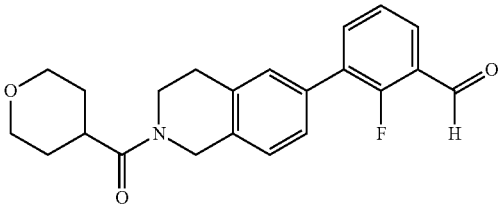 [SMILES: O=Cc1cccc(-c2ccc3c(c2)CCN(C(=O)C2CCOCC2)C3)c1F] |
| 328 | R336 | 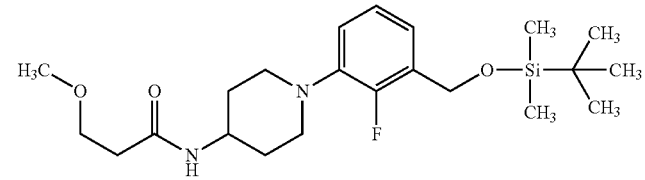 [SMILES: COCCC(=O)NC1CCN(c2cccc(CO[Si](C)(C)C(C)(C)C)c2F)CC1] |
| 329 | R336 | 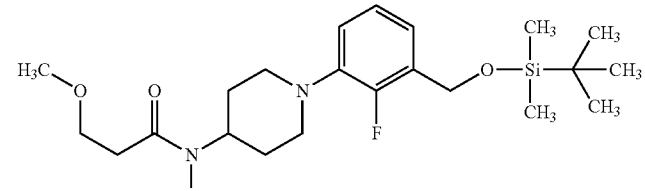 |
| 330 | R336 | 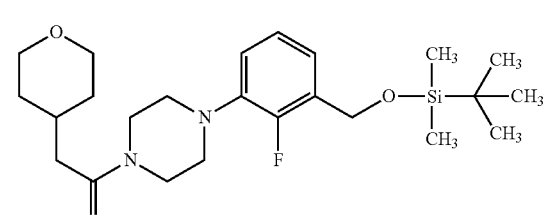 |
| 331 | R336 | 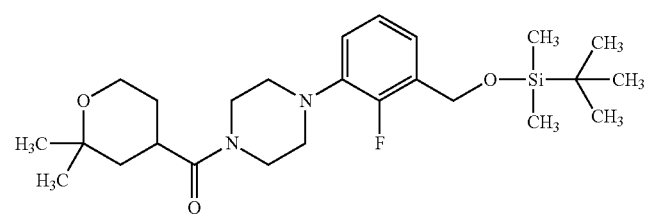 [SMILES: CC1(C)CC(C(=O)N2CCN(c3cccc(CO[Si](C)(C)C(C)(C)C)c3F)CC2)CCO1] |

TABLE 23-continued
| Rf | Syn | Structure |
|---|---|---|
| 332 | R336 | 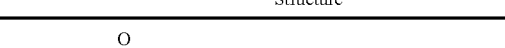 |
TABLE 24
| Rf | Syn | Structure |
|---|---|---|
| 333 | R336 | 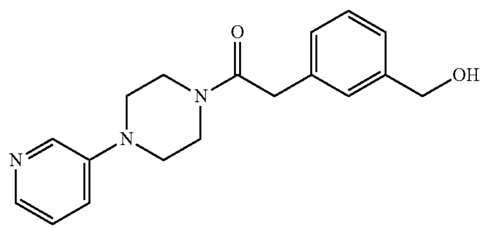 [SMILES: O=C(Cc1cccc(CO)c1)N1CCN(c2cccnc2)CC1] |
| 334 | R336 | 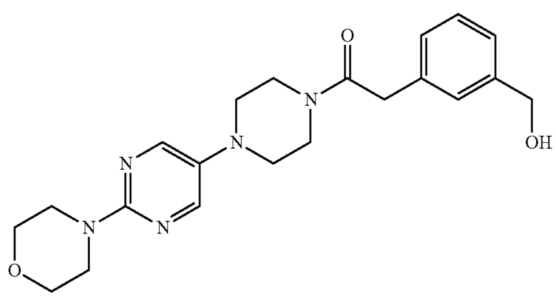 [SMILES: O=C(Cc1cccc(CO)c1)N1CCN(c2cnc(N3CCOCC3)nc2)CC1] |
| 335 | R336 | 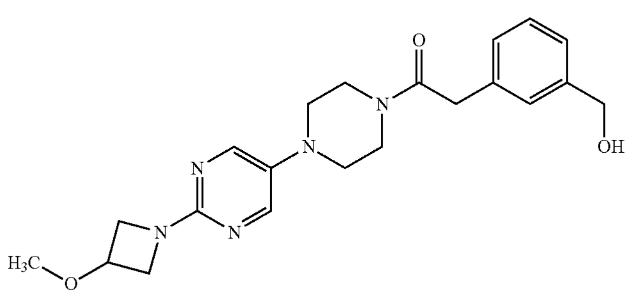 [SMILES: COC1CN(c2ncc(N3CCN(C(=O)Cc4cccc(CO)c4)CC3)cn2)C1] |
| 336 | R336 | 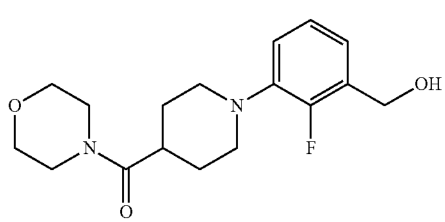 [SMILES: O=C(C1CCN(c2cccc(CO)c2F)CC1)N1CCOCC1] |

TABLE 24-continued
| Rf | Syn | Structure |
|---|---|---|
| 337 | R336 | 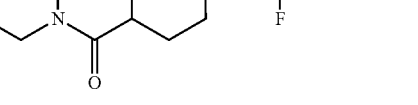 |
| 338 | R336 | 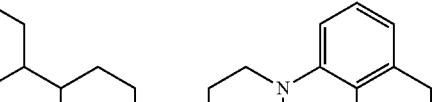 |
| 339 | R336 | 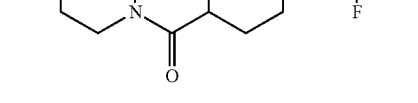 |
| 340 | R336 | 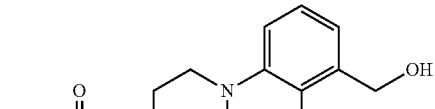 |
| 341 | R341 | 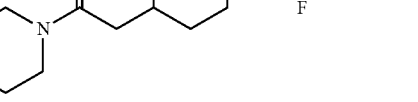 |
| 342 | R343 | 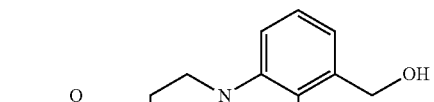 |
| 343 | R343 | 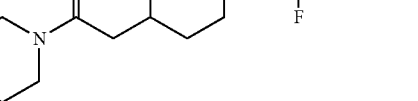 |

TABLE 24-continued

| Rf | Syn | Structure |
|---|---|---|
| 344 | R343 | 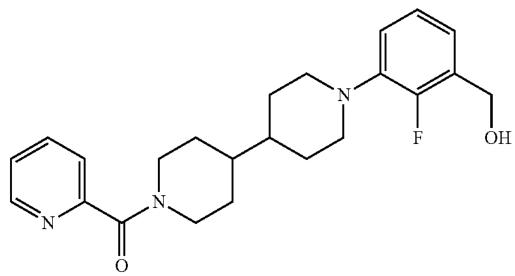 [SMILES: O=C(c1ccccn1)N1CCC(C2CCN(c3cccc(CO)c3F)CC2)CC1] |
| 345 | R343 | 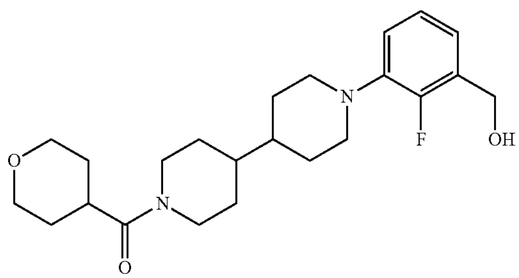 [SMILES: O=C(C1CCOCC1)N1CCC(C2CCN(c3cccc(CO)c3F)CC2)CC1] |
| 346 | R343 | 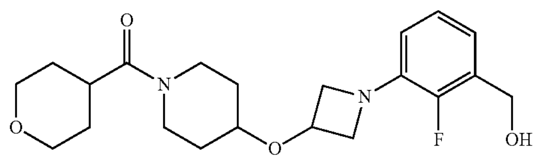 [SMILES: O=C(C1CCOCC1)N1CCC(OC2CN(c3cccc(CO)c3F)C2)CC1] |

TABLE 25

| Rf | Syn | Structure |
|---|---|---|
| 347 | R347 | 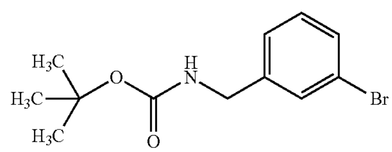 [SMILES: CC(C)(C)OC(=O)NCc1cccc(Br)c1] |
| 348 | R347 | 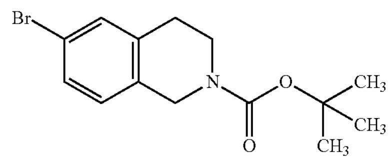 [SMILES: CC(C)(C)OC(=O)N1CCc2cc(Br)ccc2C1] |
| 349 | R347 | 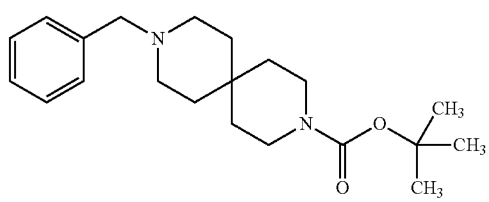 [SMILES: CC(C)(C)OC(=O)N1CCC2(CCN(Cc3ccccc3)CC2)CC1] |
| 350 | R347 | 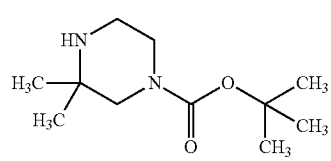 |

TABLE 25-continued
| Rf | Syn | Structure |
|---|---|---|
| 351 | R347 | 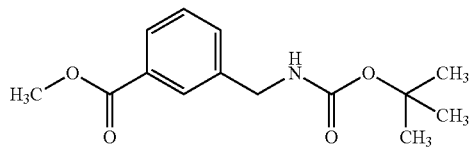 [SMILES: COC(=O)c1cccc(CNC(=O)OC(C)(C)C)c1] |
| 352 | R376 | 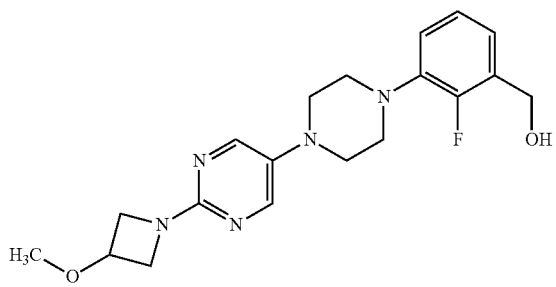 [SMILES: COC1CN(c2ncc(N3CCN(c4cccc(CO)c4F)CC3)cn2)C1] |
| 353 | R376 | 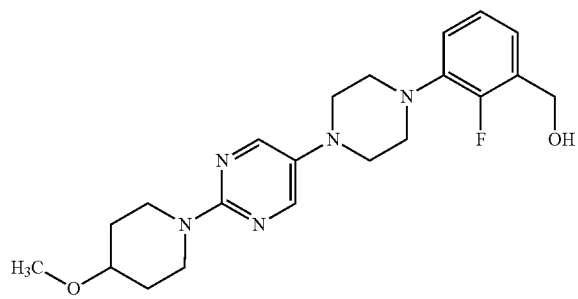 [SMILES: COC1CCN(c2ncc(N3CCN(c4cccc(CO)c4F)CC3)cn2)CC1] |
| 354 | R376 | 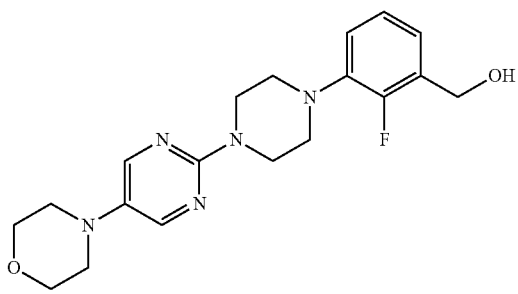 [SMILES: OCc1cccc(N2CCN(c3ncc(N4CCOCC4)cn3)CC2)c1F] |
| 355 | R376 | 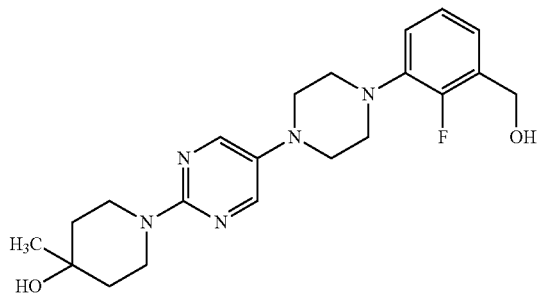 [SMILES: CC1(O)CCN(c2ncc(N3CCN(c4cccc(CO)c4F)CC3)cn2)CC1] |

TABLE 25-continued

| Rf | Syn | Structure |
|---|---|---|
| 356 | R376 | 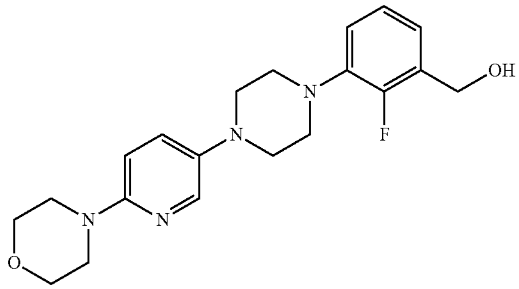 [SMILES: OCc1cccc(N2CCN(c3ccc(N4CCOCC4)nc3)CC2)c1F] |
| 357 | R376 | 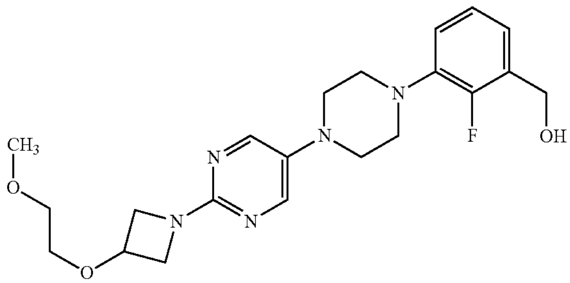 [SMILES: COCCOC1CN(c2ncc(N3CCN(c4cccc(CO)c4F)CC3)cn2)C1] |
| 358 | R376 | 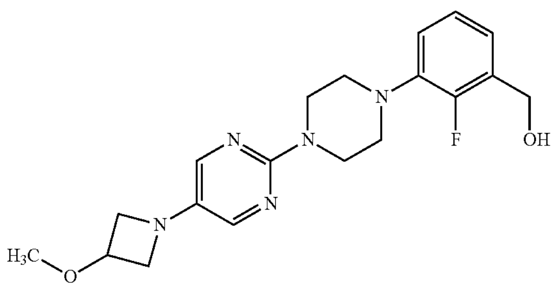 [SMILES: COC1CN(c2cnc(N3CCN(c4cccc(CO)c4F)CC3)nc2)C1] |
| 359 | R376 | 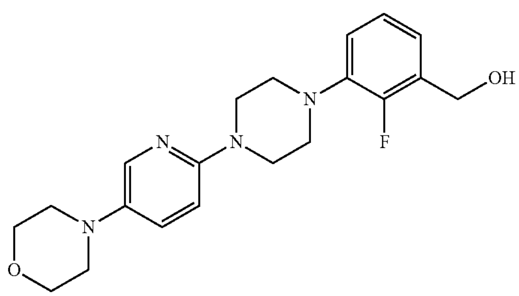 [SMILES: OCc1cccc(N2CCN(c3ccc(N4CCOCC4)cn3)CC2)c1F] |
| 360 | R376 | 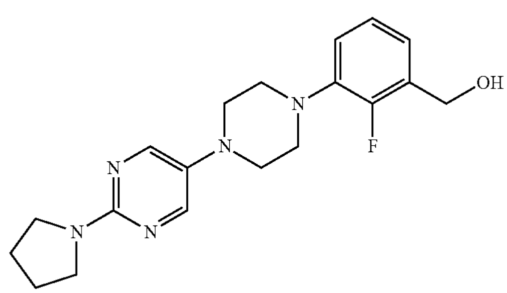 [SMILES: OCc1cccc(N2CCN(c3cnc(N4CCCC4)nc3)CC2)c1F] |

TABLE 26
| Rf | Syn | Structure |
|---|---|---|
| 361 | R376 | 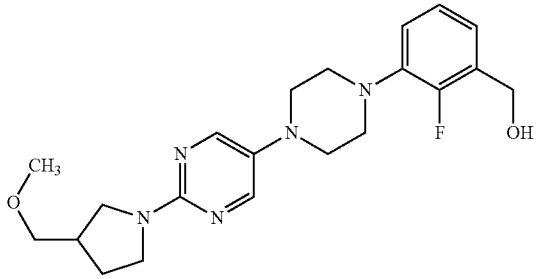 [SMILES: COCC1CCN(c2ncc(N3CCN(c4cccc(CO)c4F)CC3)cn2)C1] |
| 362 | R159 | 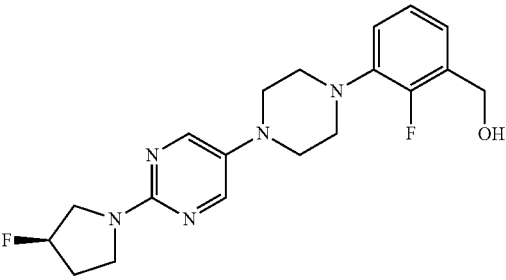 [SMILES: OCc1cccc(N2CCN(c3cnc(N4CC[C@@H](F)C4)nc3)CC2)c1F] |
| 363 | R376 | 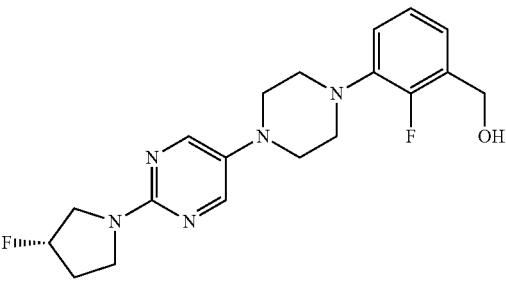 [SMILES: OCc1cccc(N2CCN(c3cnc(N4CC[C@H](F)C4)nc3)CC2)c1F] |
| 364 | R376 | 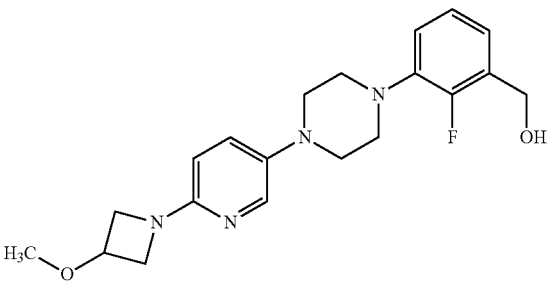 [SMILES: COC1CN(c2ccc(N3CCN(c4cccc(CO)c4F)CC3)cn2)C1] |
| 365 | R376 | 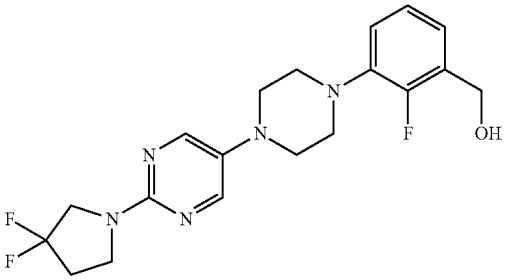 [SMILES: OCc1cccc(N2CCN(c3cnc(N4CCC(F)(F)C4)nc3)CC2)c1F] |

TABLE 26-continued
| Rf | Syn | Structure |
|---|---|---|
| 366 | R376 | 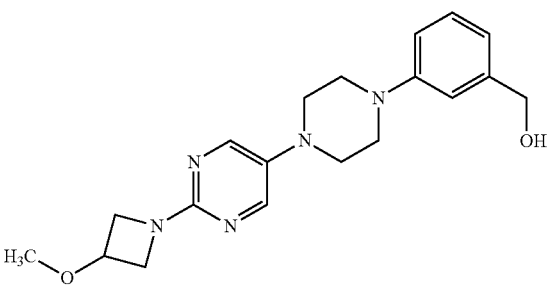 [SMILES: COC1CN(c2ncc(N3CCN(c4cccc(CO)c4)CC3)cn2)C1] |
| 367 | R376 | 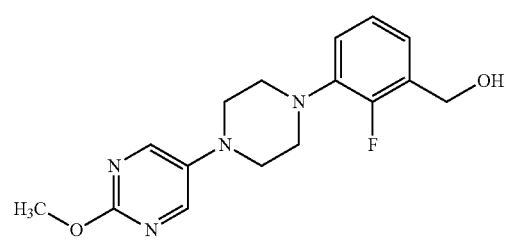 [SMILES: COc1ncc(N2CCN(c3cccc(CO)c3F)CC2)cn1] |
| 368 | R376 | 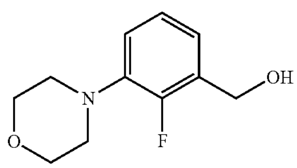 [SMILES: OCc1cccc(N2CCOCC2)c1F] |
| 369 | R376 | 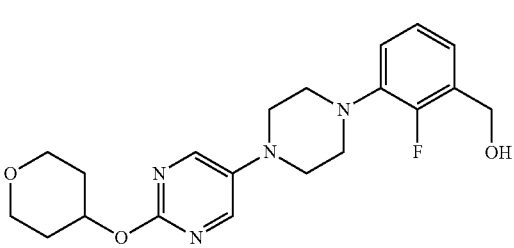 [SMILES: OCc1cccc(N2CCN(c3cnc(OC4CCOCC4)nc3)CC2)c1F] |
| 370 | R376 | trans- 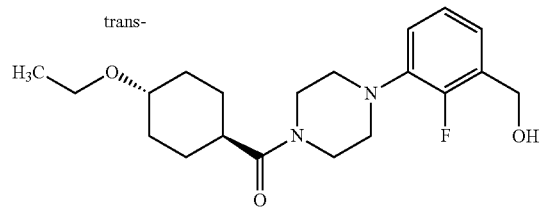 |
| 371 | R376 | trans- 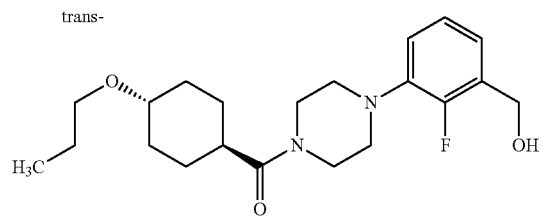 [SMILES: "trans-" ; CCCO[C@H]1CC[C@H](C(=O)N2CCN(c3cccc(CO)c3F)CC2)CC1] |
| 372 | R376 | cis- 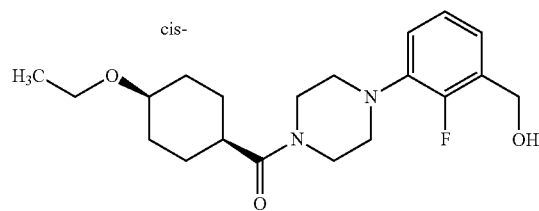 |

TABLE 26-continued

| Rf | Syn | Structure |
|---|---|---|
| 373 | R376 | cis- (propoxy cyclohexyl carbonyl piperazinyl fluoro benzyl alcohol) |
| 374 | R376 | trans- (benzoyloxy cyclohexyl carbonyl piperazinyl fluoro benzyl alcohol) |

TABLE 27

| Rf | Syn | Structure |
|---|---|---|
| 375 | R376 | cis- (benzoyloxy cyclohexyl carbonyl piperazinyl fluoro benzyl alcohol) |
| 376 | R376 | (methoxy azetidinyl fluoro benzyl alcohol) |
| 377 | R376 | (methoxyethoxy azetidinyl fluoro benzyl alcohol) |
| 378 | R376 | (acetyl diazepanyl fluoro benzyl alcohol) |

TABLE 27-continued

| Rf | Syn | Structure |
|---|---|---|
| 379 | R376 | 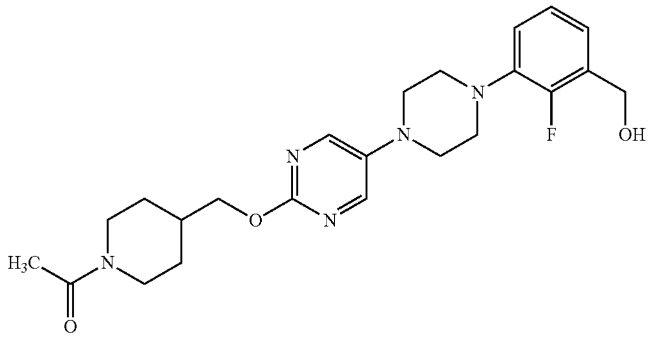 [SMILES: CC(=O)N1CCC(COc2ncc(N3CCN(c4cccc(CO)c4F)CC3)cn2)CC1] |
| 380 | R376 | 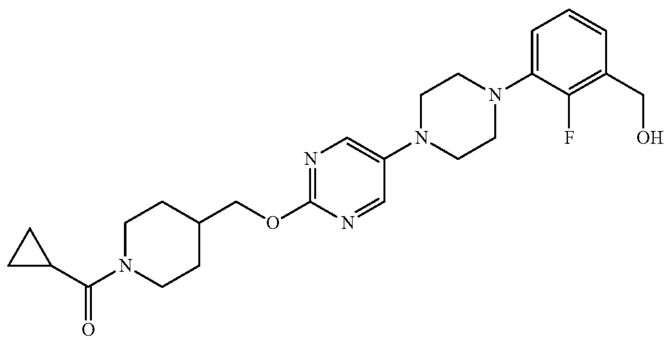 [SMILES: O=C(C1CC1)N1CCC(COc2ncc(N3CCN(c4cccc(CO)c4F)CC3)cn2)CC1] |
| 381 | R376 | 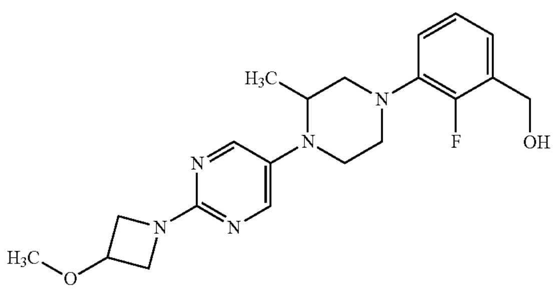 [SMILES: COC1CN(c2ncc(N3CCN(c4cccc(CO)c4F)CC3C)cn2)C1] |
| 382 | R376 | 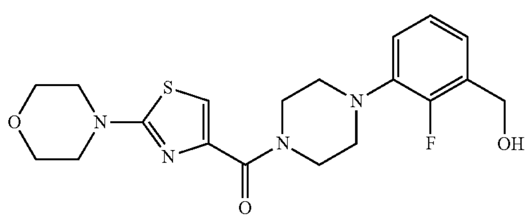 [SMILES: O=C(c1csc(N2CCOCC2)n1)N1CCN(c2cccc(CO)c2F)CC1] |
| 383 | R376 | 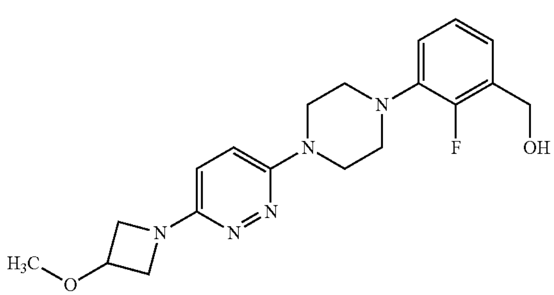 [SMILES: COC1CN(c2ccc(N3CCN(c4cccc(CO)c4F)CC3)nn2)C1] |

TABLE 27-continued
| Rf | Syn | Structure |
|---|---|---|
| 384 | R376 | 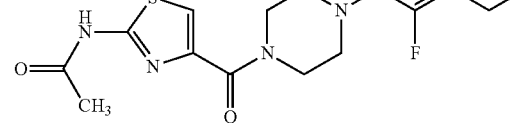 |
| 385 | R376 | 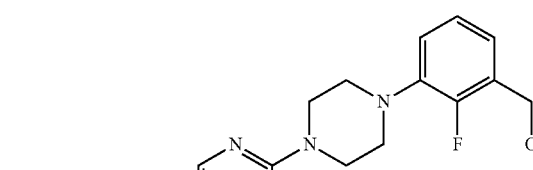 |
| 386 | R376 | 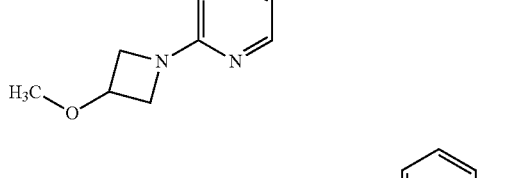 |
| 387 | R376 | 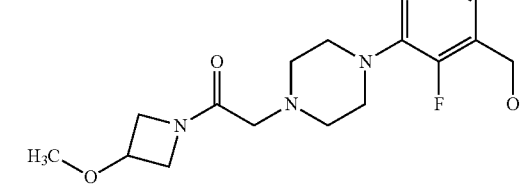 |
| 388 | R376 | 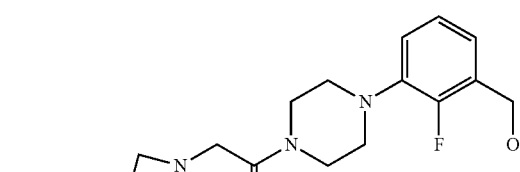 |
TABLE 28
| Rf | Syn | Structure |
|---|---|---|
| 389 | R376 | 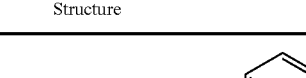 |

TABLE 28-continued
| Rf | Syn | Structure |
|---|---|---|
| 390 | R376 | 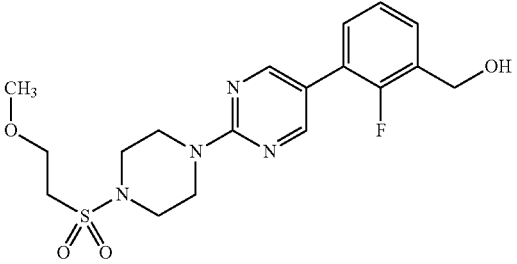 [SMILES: COCCS(=O)(=O)N1CCN(c2ncc(-c3cccc(CO)c3F)cn2)CC1] |
| 391 | R376 | 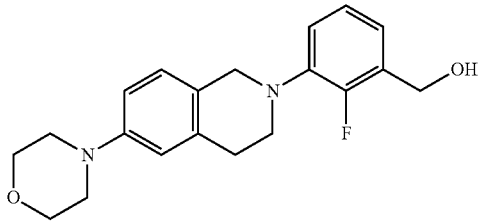 [SMILES: OCc1cccc(N2CCc3cc(N4CCOCC4)ccc3C2)c1F] |
| 392 | R376 | 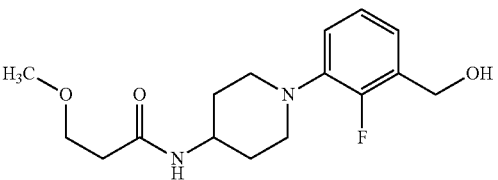 [SMILES: COCCC(=O)NC1CCN(c2cccc(CO)c2F)CC1] |
| 393 | R376 | 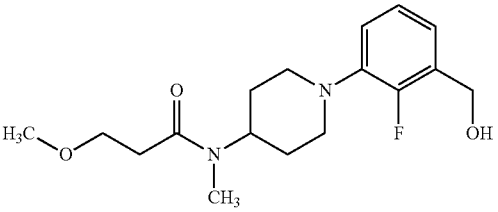 [SMILES: COCCC(=O)N(C)C1CCN(c2cccc(CO)c2F)CC1] |
| 394 | R376 | 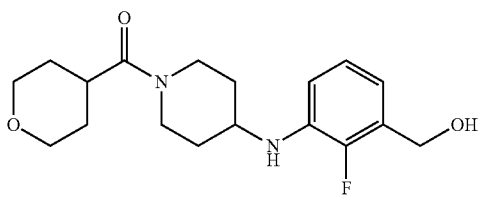 [SMILES: O=C(C1CCOCC1)N1CCC(Nc2cccc(CO)c2F)CC1] |
| 395 | R376 | 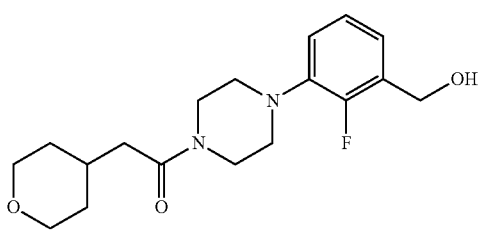 [SMILES: O=C(CC1CCOCC1)N1CCN(c2cccc(CO)c2F)CC1] |
| 396 | R376 | 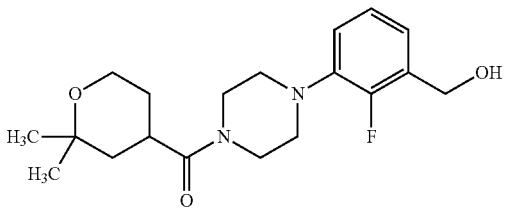 [SMILES: CC1(C)CC(C(=O)N2CCN(c3cccc(CO)c3F)CC2)CCO1] |

TABLE 28-continued

| Rf | Syn | Structure |
|---|---|---|
| 397 | R376 | 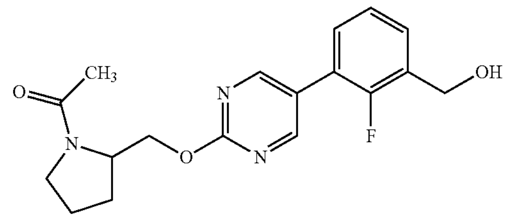 [SMILES: CC(=O)N1CCCC1COc1ncc(-c2cccc(CO)c2F)cn1] |
| 398 | R376 | 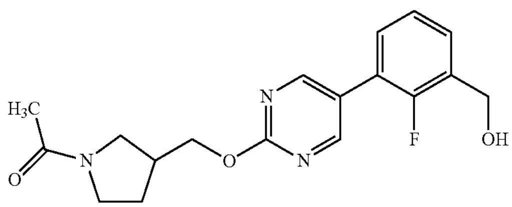 [SMILES: CC(=O)N1CCC(COc2ncc(-c3cccc(CO)c3F)cn2)C1] |
| 399 | R376 | 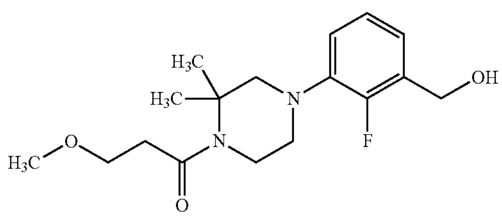 [SMILES: COCCC(=O)N1CCN(c2cccc(CO)c2F)CC1(C)C] |
| 400 | R376 | 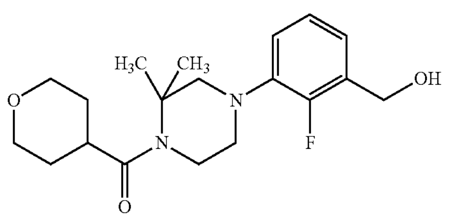 [SMILES: CC1(C)CN(c2cccc(CO)c2F)CCN1C(=O)C1CCOCC1] |
| 401 | R376 | 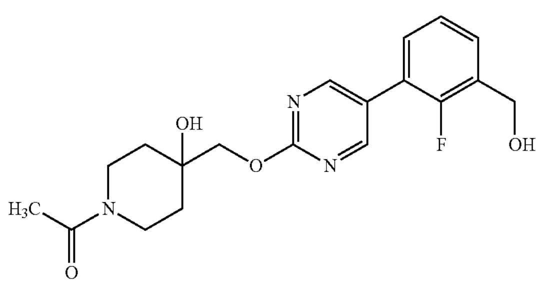 [SMILES: CC(=O)N1CCC(O)(COc2ncc(-c3cccc(CO)c3F)cn2)CC1] |
| 402 | R376 | 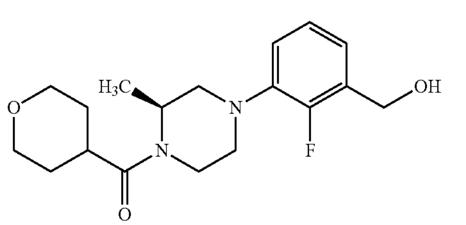 [SMILES: C[C@H]1CN(c2cccc(CO)c2F)CCN1C(=O)C1CCOCC1] |

TABLE 29

| Rf | Syn | Structure |
|---|---|---|
| 403 | R376 | 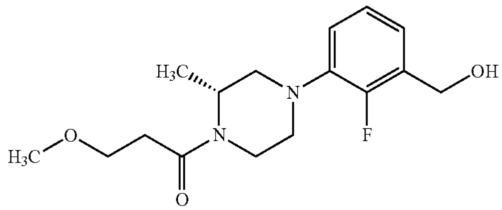 [SMILES: COCCC(=O)N1CCN(c2cccc(CO)c2F)C[C@H]1C] |
| 404 | R376 | 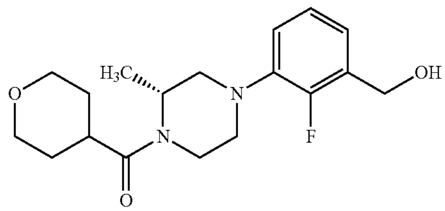 [SMILES: C[C@@H]1CN(c2cccc(CO)c2F)CCN1C(=O)C1CCOCC1] |
| 405 | R376 | 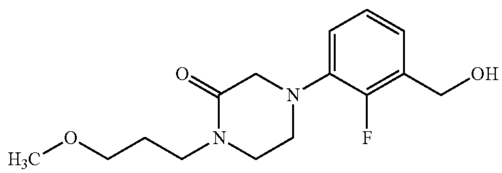 [SMILES: COCCCN1CCN(c2cccc(CO)c2F)CC1=O] |
| 406 | R376 | 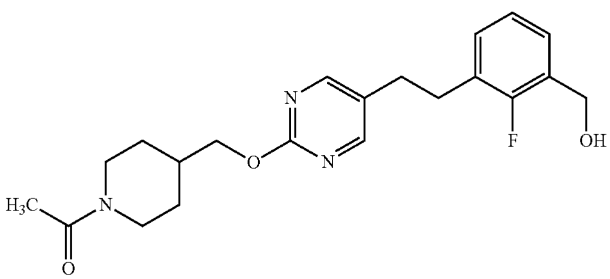 [SMILES: CC(=O)N1CCC(COc2ncc(CCc3cccc(CO)c3F)cn2)CC1] |
| 407 | R376 | 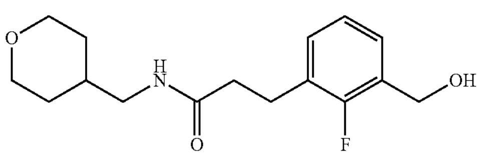 [SMILES: O=C(CCc1cccc(CO)c1F)NCC1CCOCC1] |
| 408 | R376 | 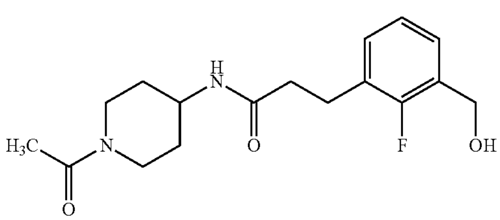 [SMILES: CC(=O)N1CCC(NC(=O)CCc2cccc(CO)c2F)CC1] |
| 409 | R376 | 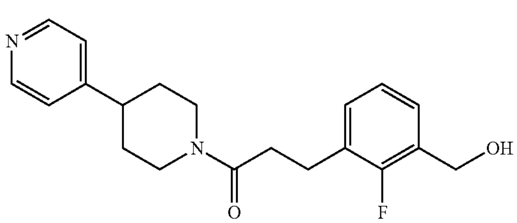 [SMILES: O=C(CCc1cccc(CO)c1F)N1CCC(c2ccncc2)CC1] |

TABLE 29-continued
| Rf | Syn | Structure |
|---|---|---|
| 410 | R376 | 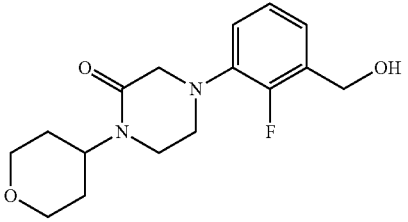 [SMILES: O=C1CN(c2cccc(CO)c2F)CCN1C1CCOCC1] |
| 411 | R376 | 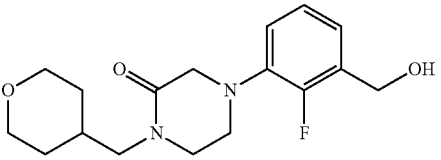 [SMILES: O=C1CN(c2cccc(CO)c2F)CCN1CC1CCOCC1] |
| 412 | R376 | 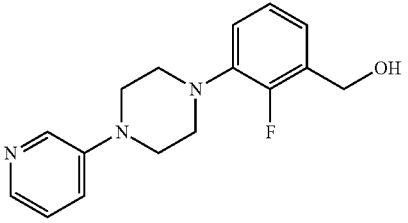 |
| 413 | R376 | 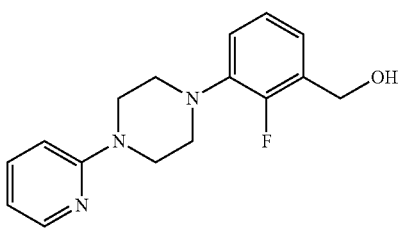 |
| 414 | R376 | 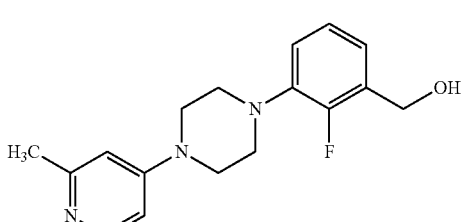 |
| 415 | R376 | 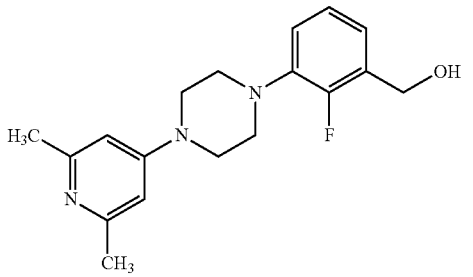 |

TABLE 29-continued

| Rf | Syn | Structure |
|----|-----|-----------|
| 416 | R376 | 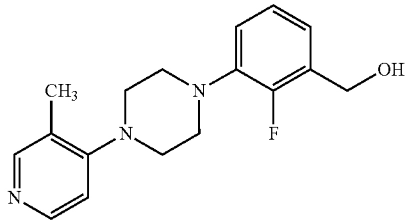 [SMILES: Cc1cnccc1N1CCN(c2cccc(CO)c2F)CC1] |

TABLE 30

| Rf | Syn | Structure |
|----|-----|-----------|
| 417 | R376 | 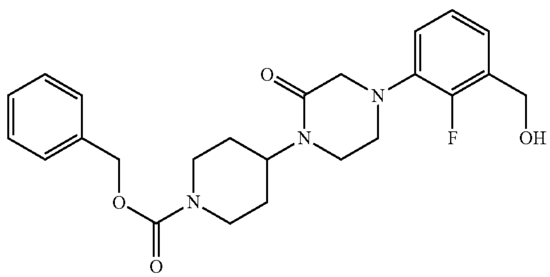 [SMILES: O=C(OCc1ccccc1)N1CCC(N2CCN(c3cccc(CO)c3F)CC2=O)CC1] |
| 418 | R376 | 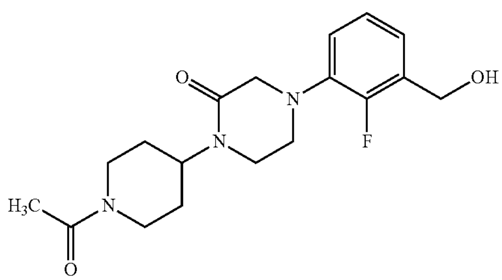 [SMILES: CC(=O)N1CCC(N2CCN(c3cccc(CO)c3F)CC2=O)CC1] |
| 419 | R376 | 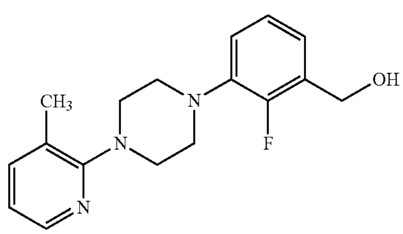 [SMILES: Cc1cccnc1N1CCN(c2cccc(CO)c2F)CC1] |
| 420 | R376 | 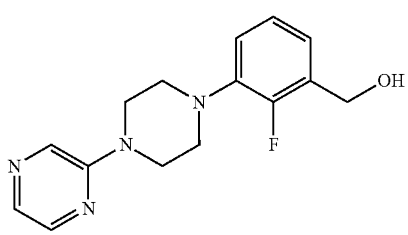 [SMILES: OCc1cccc(N2CCN(c3cnccn3)CC2)c1F] |

TABLE 30-continued

| Rf | Syn | Structure |
|---|---|---|
| 421 | R376 | 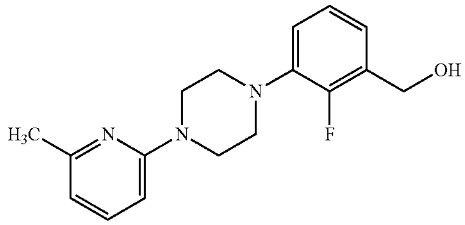 [SMILES: Cc1cccc(N2CCN(c3cccc(CO)c3F)CC2)n1] |
| 422 | R376 | 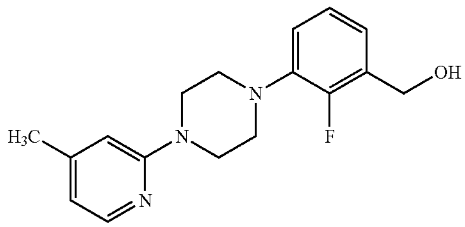 [SMILES: Cc1ccnc(N2CCN(c3cccc(CO)c3F)CC2)c1] |
| 423 | R376 | 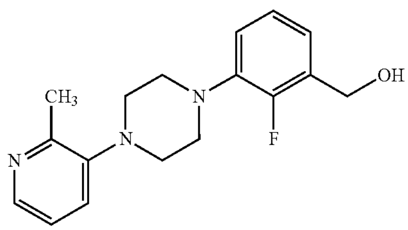 [SMILES: Cc1ncccc1N1CCN(c2cccc(CO)c2F)CC1] |
| 424 | R376 | 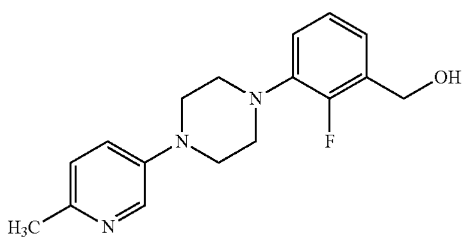 [SMILES: Cc1ccc(N2CCN(c3cccc(CO)c3F)CC2)cn1] |
| 425 | R376 | 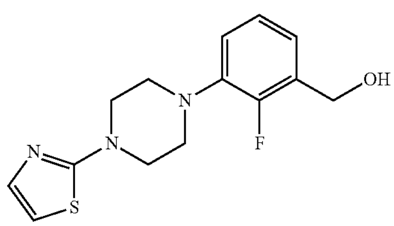 [SMILES: OCc1cccc(N2CCN(c3nccs3)CC2)c1F] |
| 426 | R376 | 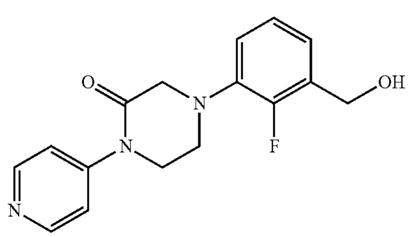 [SMILES: O=C1CN(c2cccc(CO)c2F)CCN1c1ccncc1] |

TABLE 30-continued

| Rf | Syn | Structure |
|---|---|---|
| 427 | R376 | 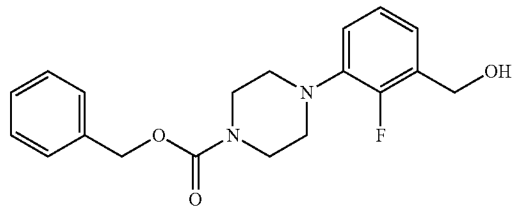 [SMILES: O=C(OCc1ccccc1)N1CCN(c2cccc(CO)c2F)CC1] |
| 428 | R376 | 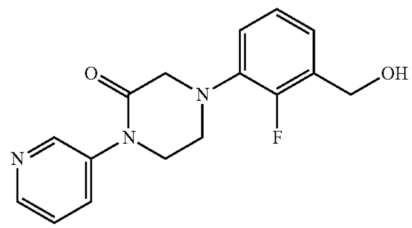 [SMILES: O=C1CN(c2cccc(CO)c2F)CCN1c1cccnc1] |
| 429 | R376 | 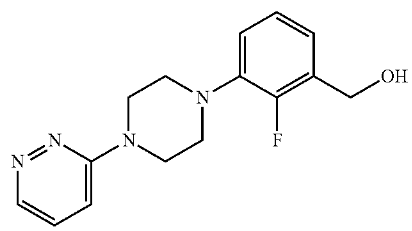 [SMILES: OCc1cccc(N2CCN(c3cccnn3)CC2)c1F] |
| 430 | R376 | 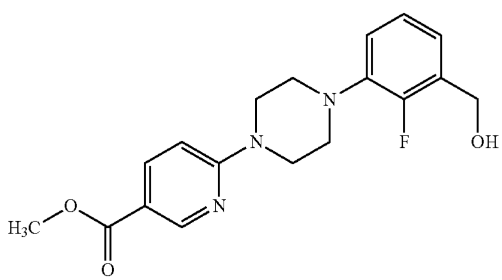 [SMILES: COC(=O)c1ccc(N2CCN(c3cccc(CO)c3F)CC2)nc1] |

TABLE 31

| Rf | Syn | Structure |
|---|---|---|
| 431 | R376 | 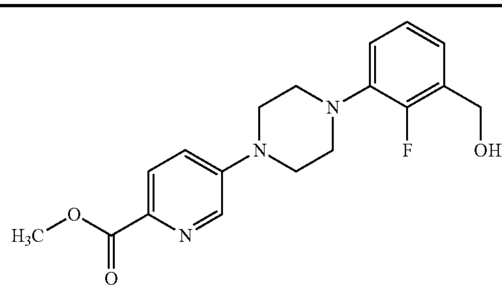 |

TABLE 31-continued

| Rf | Syn | Structure |
|---|---|---|
| 432 | R376 | 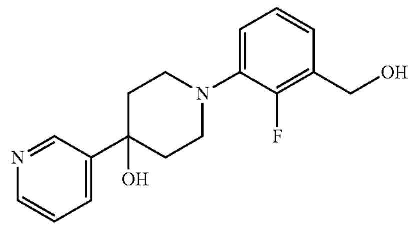 [SMILES: OCc1cccc(N2CCC(O)(c3cccnc3)CC2)c1F] |
| 433 | R376 | 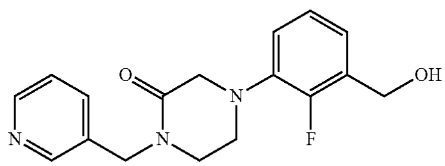 [SMILES: O=C1CN(c2cccc(CO)c2F)CCN1Cc1cccnc1] |
| 434 | R376 | 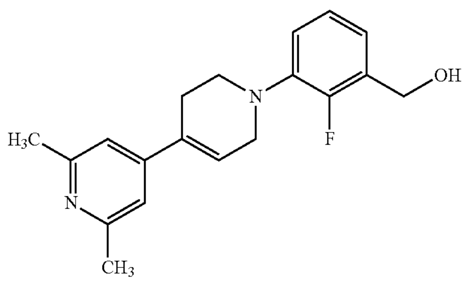 [SMILES: Cc1cc(C2=CCN(c3cccc(CO)c3F)CC2)cc(C)n1] |
| 435 | R376 | 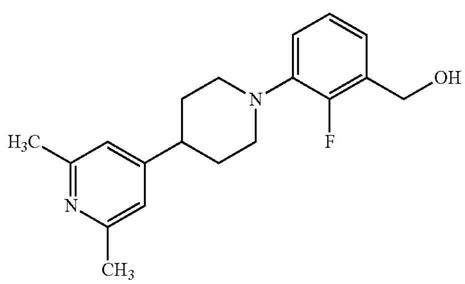 [SMILES: Cc1cc(C2CCN(c3cccc(CO)c3F)CC2)cc(C)n1] |
| 436 | R376 | 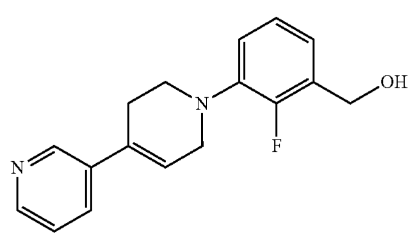 [SMILES: OCc1cccc(N2CC=C(c3cccnc3)CC2)c1F] |
| 437 | R376 | 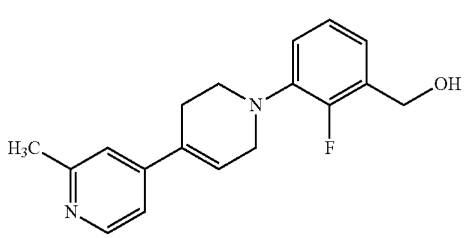 [SMILES: Cc1cc(C2=CCN(c3cccc(CO)c3F)CC2)ccn1] |

TABLE 31-continued
| Rf | Syn | Structure |
|---|---|---|
| 438 | R376 | 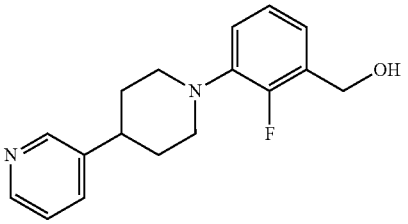 [SMILES: OCc1cccc(N2CCC(c3cccnc3)CC2)c1F] |
| 439 | R376 | 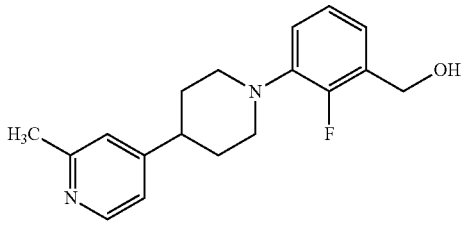 |
| 440 | R376 | 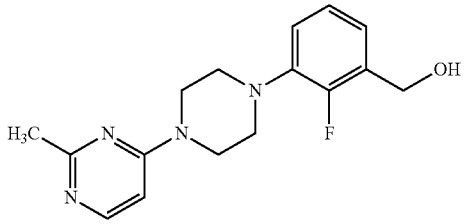 [SMILES: Cc1nccc(N2CCN(c3cccc(CO)c3F)CC2)n1] |
| 441 | R376 | 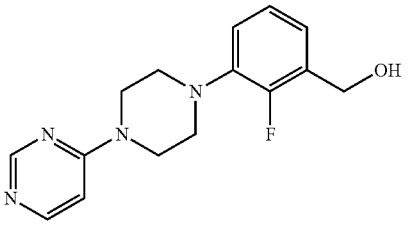 |
| 442 | R376 | 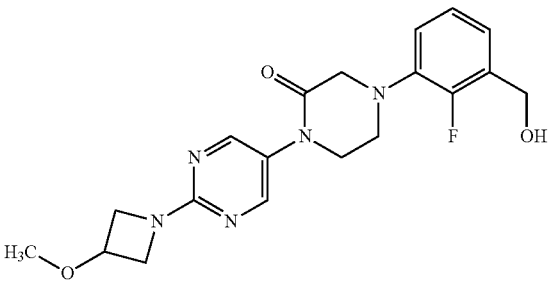 [SMILES: COC1CN(c2ncc(N3CCN(c4cccc(CO)c4F)CC3=O)cn2)C1] |
| 443 | R376 | 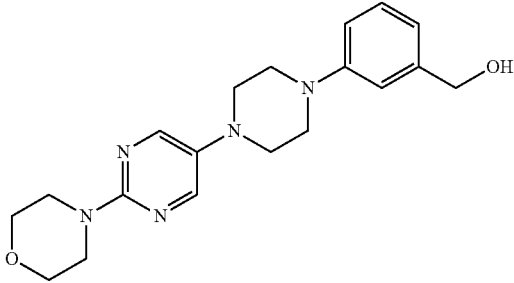 [SMILES: OCc1cccc(N2CCN(c3cnc(N4CCOCC4)nc3)CC2)c1] |

TABLE 31-continued
| Rf | Syn | Structure |
|---|---|---|
| 444 | R376 | 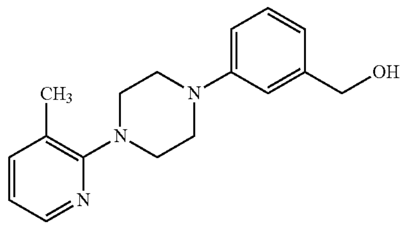 [SMILES: Cc1cccnc1N1CCN(c2cccc(CO)c2)CC1] |
TABLE 32
| Rf | Syn | Structure |
|---|---|---|
| 445 | R376 | 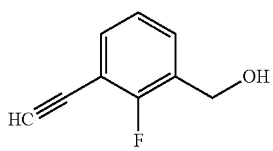 |
| 446 | R376 | 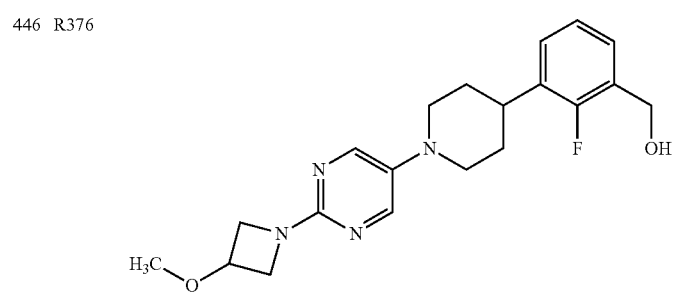 |
| 447 | R376 | 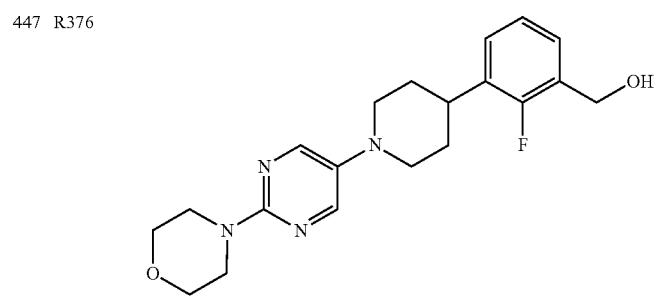 |
| 448 | R376 | 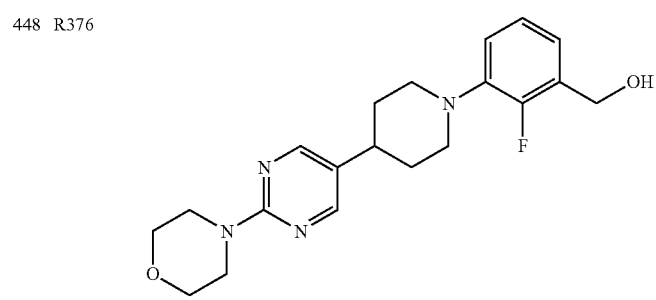 |

TABLE 32-continued
| Rf | Syn | Structure |
|---|---|---|
| 449 | R376 | 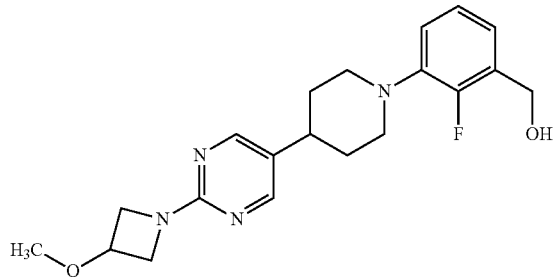 [SMILES: COC1CN(c2ncc(C3CCN(c4cccc(CO)c4F)CC3)cn2)C1] |
| 450 | R376 | 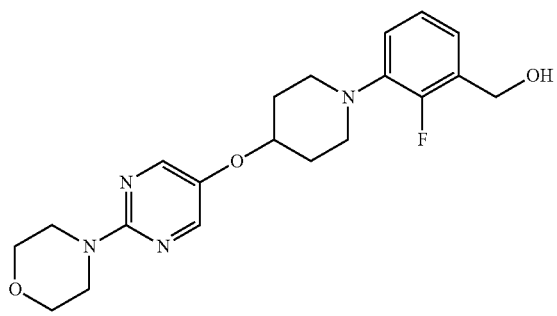 [SMILES: OCc1cccc(N2CCC(Oc3cnc(N4CCOCC4)nc3)CC2)c1F] |
| 451 | R376 | 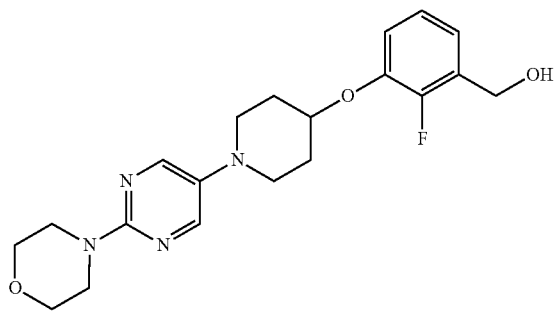 [SMILES: OCc1cccc(OC2CCN(c3cnc(N4CCOCC4)nc3)CC2)c1F] |
| 452 | R376 | 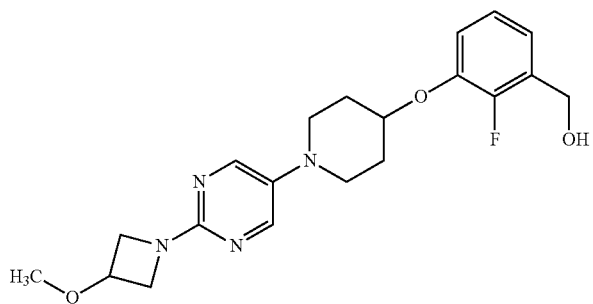 [SMILES: COC1CN(c2ncc(N3CCC(Oc4cccc(CO)c4F)CC3)cn2)C1] |
| 453 | R376 | 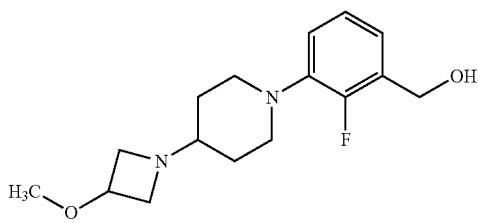 [SMILES: COC1CN(C2CCN(c3cccc(CO)c3F)CC2)C1] |

TABLE 32-continued
| Rf | Syn | Structure |
|---|---|---|
| 454 | R376 | 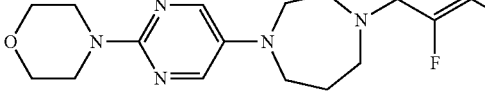 |
| 455 | R376 | 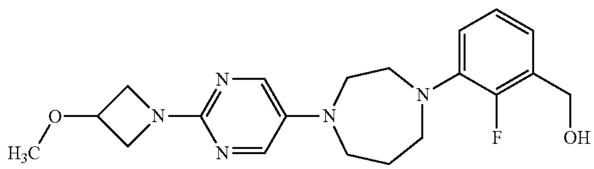 [SMILES: COC1CN(c2ncc(N3CCCN(c4cccc(CO)c4F)CC3)cn2)C1] |
| 456 | R376 | 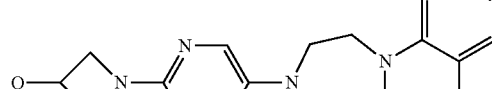 |
| 457 | R376 | 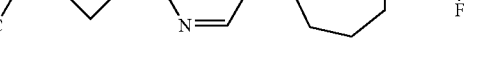 |
| 458 | R478 |   2HCl |
TABLE 33
| Rf | Syn | Structure |
|---|---|---|
| 459 | R478 | 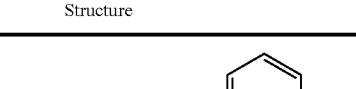 |

TABLE 33-continued

| Rf | Syn | Structure |
|---|---|---|
| 460 | R478 | 3-(2-methoxyethoxy)azetidine · HCl |
| 461 | R478 | N-(4-(2-(3-(aminomethyl)phenyl)ethyl)thiazol-2-yl)acetamide |
| 462 | R478 | benzyl 4-((4-(5-(3-(aminomethyl)phenyl)pyrimidin-2-yl)piperazin-1-yl)methyl)benzoate |
| 463 | R478 | N-(4-((4-(5-(3-(aminomethyl)phenyl)pyrimidin-2-yl)piperazin-1-yl)methyl)thiazol-2-yl)acetamide |
| 464 | R478 | ethyl 4-((1-(5-(3-(aminomethyl)phenyl)pyrimidin-2-yl)piperidin-4-yl)amino)benzoate |
| 465 | R478 | ethyl 4-(4-((5-(3-(aminomethyl)phenyl)pyrimidin-2-yl)amino)piperidin-1-yl)benzoate |
| 466 | R478 | benzyl piperidin-4-ylcarbamate · HCl |

TABLE 33-continued
| Rf | Syn | Structure |
|---|---|---|
| 467 | R478 | 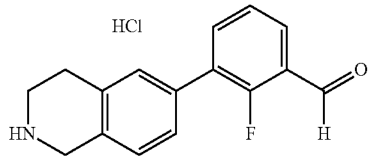 [SMILES: O=Cc1cccc(-c2ccc3c(c2)CCNC3)c1F ; Cl] |
| 468 | R478 | 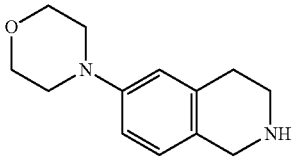 [SMILES: c1cc2c(cc1N1CCOCC1)CCNC2] |
| 469 | R478 | 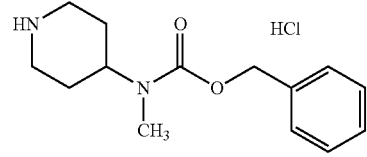 [SMILES: CN(C(=O)OCc1ccccc1)C1CCNCC1 ; Cl] |
| 470 | R478 | 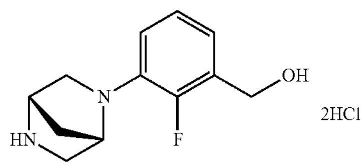 [SMILES: OCc1cccc(N2C[C@@H]3C[C@H]2CN3)c1F ; "2HCl"] |
| 471 | R478 | 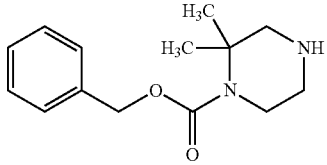 [SMILES: CC1(C)CNCCN1C(=O)OCc1ccccc1] |
| 472 | R478 | 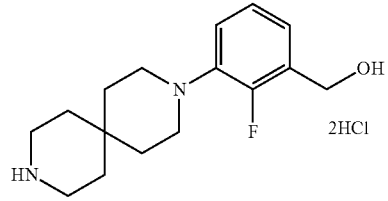 [SMILES: OCc1cccc(N2CCC3(CCNCC3)CC2)c1F] |
| 473 | R478 | 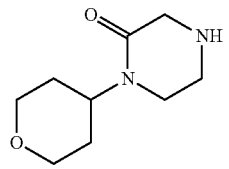 [SMILES: O=C1CNCCN1C1CCOCC1] |
| 474 | R478 | 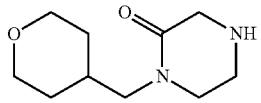 [SMILES: O=C1CNCCN1CC1CCOCC1] |
| 475 | R478 | 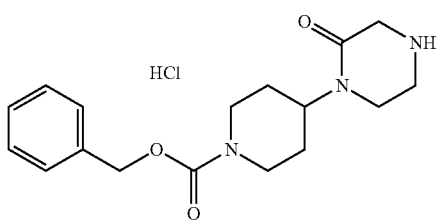 [SMILES: O=C(OCc1ccccc1)N1CCC(N2CCNCC2=O)CC1 ; Cl] |

TABLE 33-continued
| Rf | Syn | Structure |
|---|---|---|
| 476 | R478 | 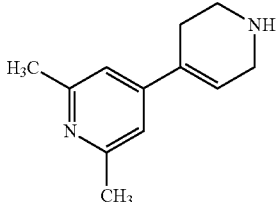 |
TABLE 34
| Rf | Syn | Structure |
|---|---|---|
| 477 | R478 | 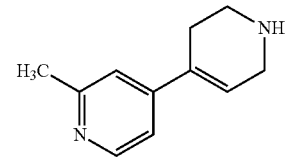 |
| 478 | R478 | 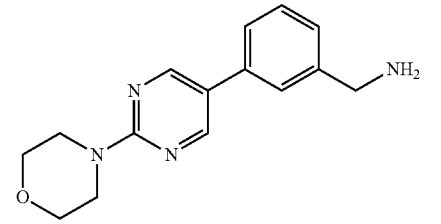 2HCl |
| 479 | R478 | 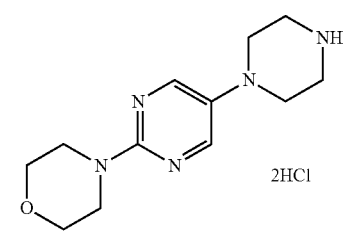 [SMILES: c1nc(N2CCOCC2)ncc1N1CCNCC1] 2HCl |
| 480 | R478 | 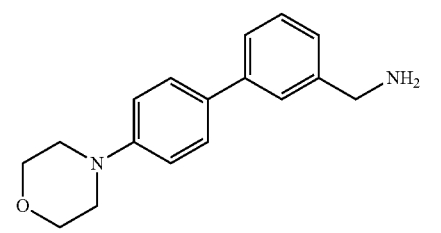 3HCl |
| 481 | R478 | 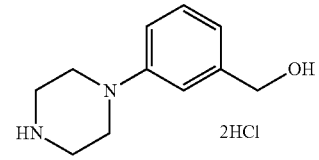 [SMILES: OCc1cccc(N2CCNCC2)c1] |
| 482 | R478 | 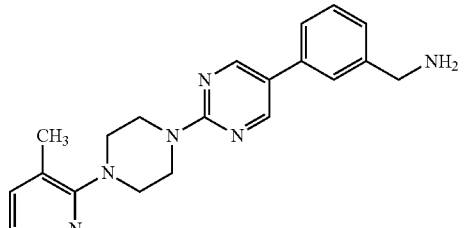 |
| 483 | R478 | 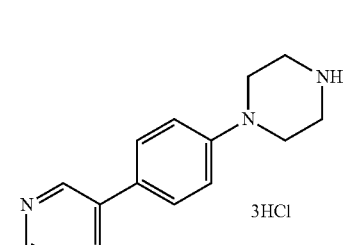 |
| 484 | R478 | 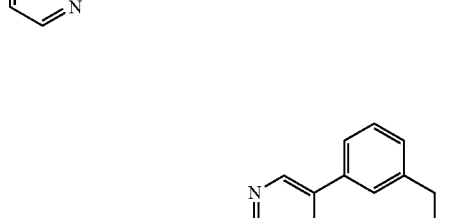 |
| 485 | R478 |  |

TABLE 34-continued
| Rf | Syn | Structure |
|----|-----|-----------|
| 486 | R478 | 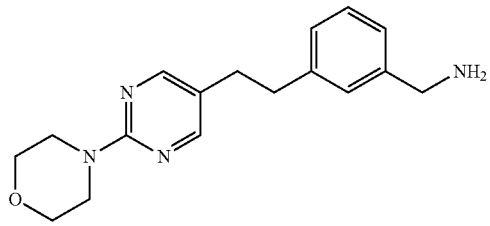 [SMILES: NCc1cccc(CCc2cnc(N3CCOCC3)nc2)c1] |
| 487 | R478 | 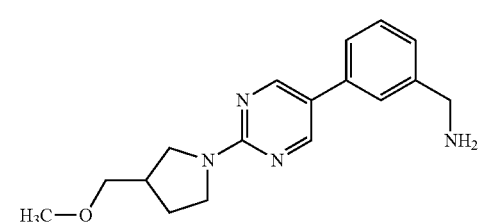 |
| 488 | R478 | 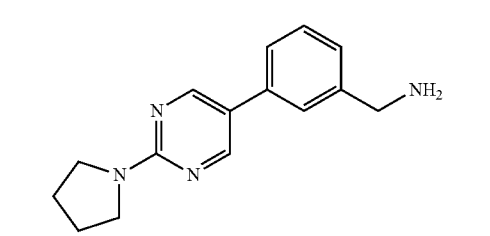 [SMILES: NCc1cccc(-c2cnc(N3CCCC3)nc2)c1] |
| 489 | R478 | 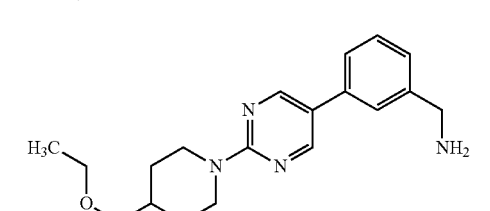 |
| 490 | R478 | 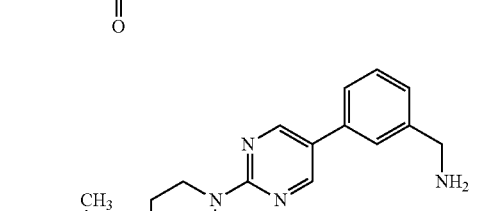 |
TABLE 35
| Rf | Syn | Structure |
|----|-----|-----------|
| 491 | R478 | 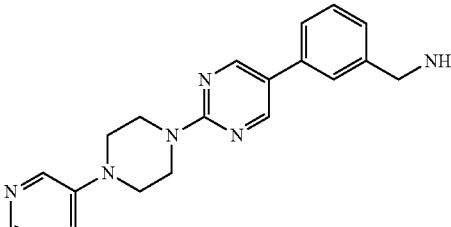 |
TABLE 35-continued
| Rf | Syn | Structure |
|----|-----|-----------|
| 492 | R478 | 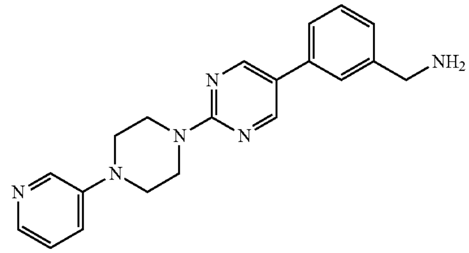 [SMILES: NCc1cccc(-c2cnc(N3CCN(c4cccnc4)CC3)nc2)c1] |
| 493 | R478 | 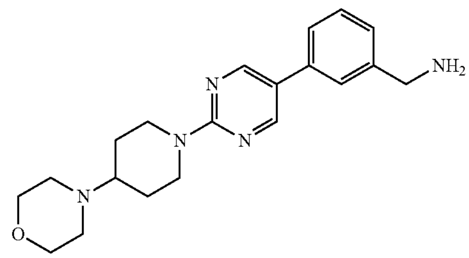 [SMILES: NCc1cccc(-c2cnc(N3CCC(N4CCOCC4)CC3)nc2)c1] |
| 494 | R478 | 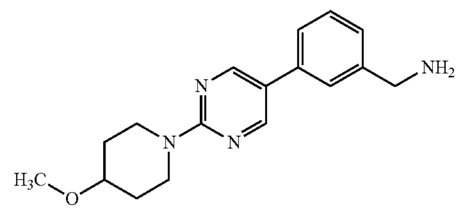 [SMILES: COC1CCN(c2ncc(-c3cccc(CN)c3)cn2)CC1] |
| 495 | R478 | 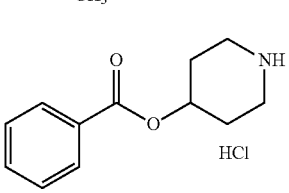 |
| 496 | R478 | 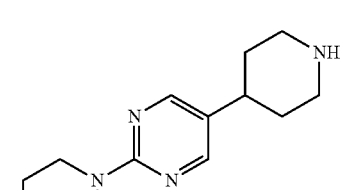 |
| 497 | R478 | 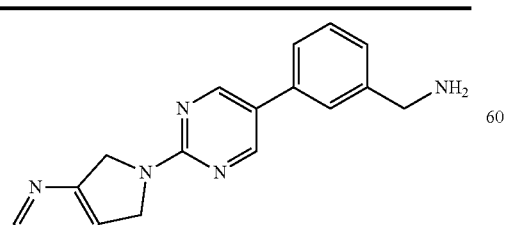 |
| 498 | R478 | 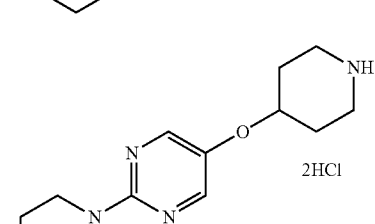 |

TABLE 35-continued
| Rf | Syn | Structure |
|---|---|---|
| 499 | R478 | 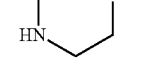 |
| 500 | R478 | 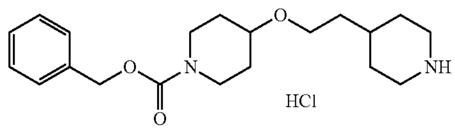 [SMILES: O=C(OCc1ccccc1)N1CCC(OCCC2CCNCC2)CC1 ; Cl] |
| 501 | R478 | 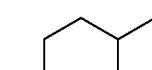 |
| 502 | R478 | 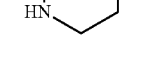 |
| 503 | R478 | 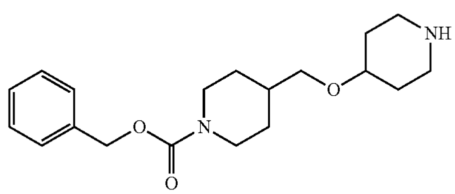 [SMILES: O=C(OCc1ccccc1)N1CCC(COC2CCNCC2)CC1] |
| 504 | R478 | 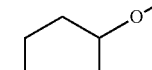 |
TABLE 36
| Rf | Syn | Structure |
|---|---|---|
| 505 | R478 | 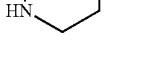 |
| 506 | R478 | 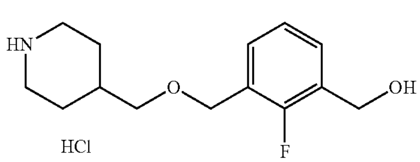 [SMILES: OCc1cccc(COCC2CCNCC2)c1F ; Cl] |
TABLE 36-continued
| Rf | Syn | Structure |
|---|---|---|
| 507 | R508 | 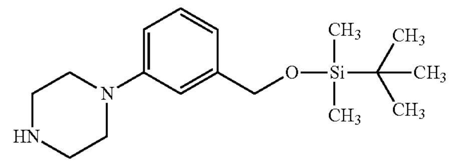 [SMILES: CC(C)(C)[Si](C)(C)OCc1cccc(N2CCNCC2)c1] |
| 508 | R508 | 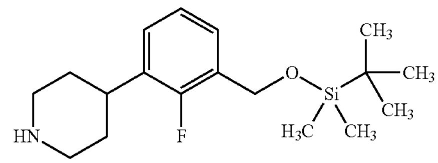 [SMILES: CC(C)(C)[Si](C)(C)OCc1cccc(C2CCNCC2)c1F] |
| 509 | R508 | 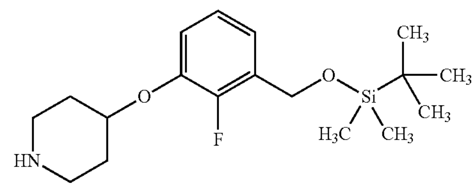 [SMILES: CC(C)(C)[Si](C)(C)OCc1cccc(OC2CCNCC2)c1F] |
| 510 | R508 | 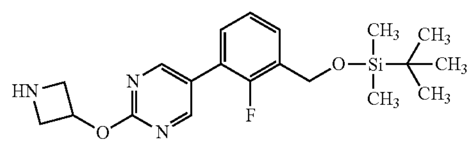 [SMILES: CC(C)(C)[Si](C)(C)OCc1cccc(-c2cnc(OC3CNC3)nc2)c1F] |
| 511 | R514 | 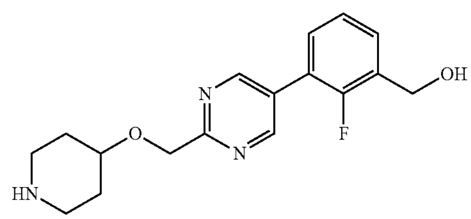 [SMILES: OCc1cccc(-c2cnc(COC3CCNCC3)nc2)c1F] |
| 512 | R514 | 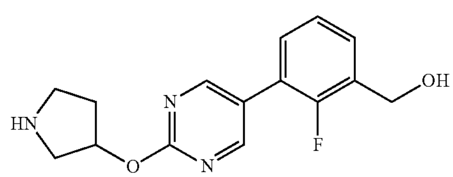 [SMILES: OCc1cccc(-c2cnc(OC3CCNC3)nc2)c1F] |
| 513 | R514 | 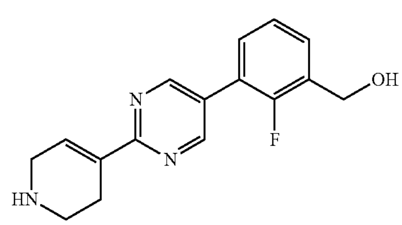 [SMILES: OCc1cccc(-c2cnc(C3=CCNCC3)nc2)c1F] |
| 514 | R514 | 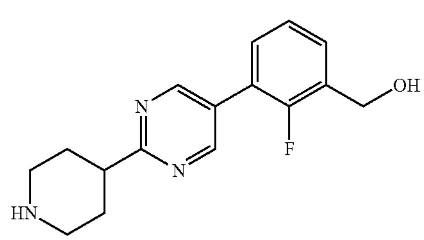 [SMILES: OCc1cccc(-c2cnc(C3CCNCC3)nc2)c1F] |

TABLE 36-continued

| Rf | Syn | Structure |
|---|---|---|
| 515 | R516 | 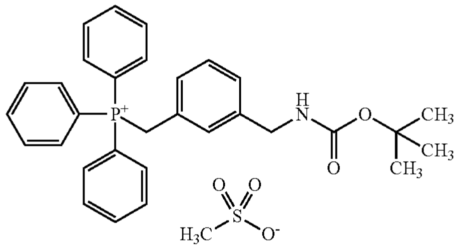 |
| 516 | R516 | 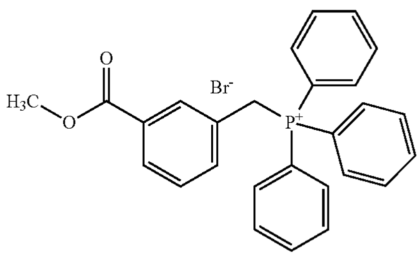 [SMILES: COC(=O)c1cccc(C[P+](c2ccccc2)(c2ccccc2)c2ccccc2)c1 ; [Br-]] |
| 517 | R516 | 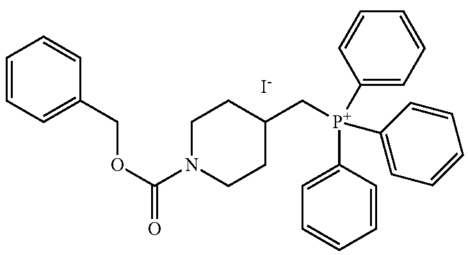 [SMILES: O=C(OCc1ccccc1)N1CCC(C[P+](c2ccccc2)(c2ccccc2)c2ccccc2)CC1 ; [I-]] |
| 518 | R518 | 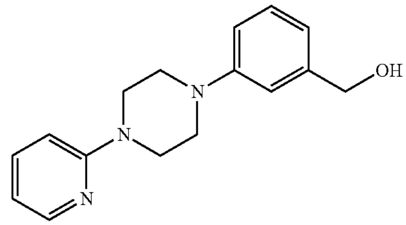 [SMILES: OCc1cccc(N2CCN(c3ccccn3)CC2)c1] |
| 519 | R518 | 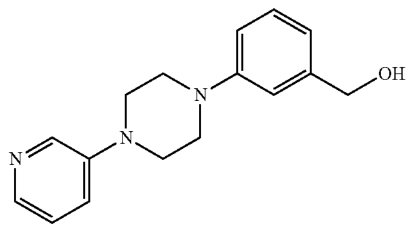 [SMILES: OCc1cccc(N2CCN(c3cccnc3)CC2)c1] |
| 520 | R518 | 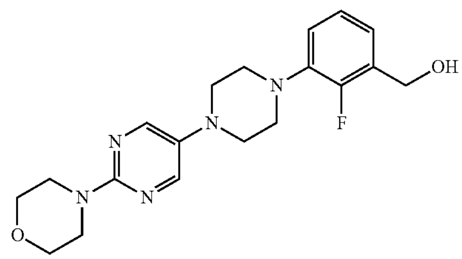 [SMILES: OCc1cccc(N2CCN(c3cnc(N4CCOCC4)nc3)CC2)c1F] |

TABLE 37

| Rf | Syn | Structure |
|---|---|---|
| 521 | R518 | 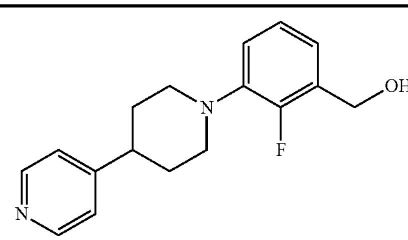 |
| 522 | R518 | 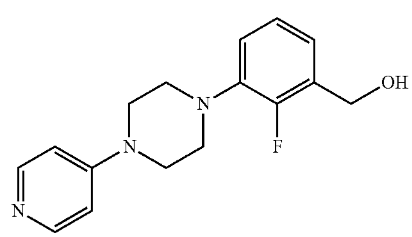 [SMILES: OCc1cccc(N2CCN(c3ccncc3)CC2)c1F] |
| 523 | R518 | 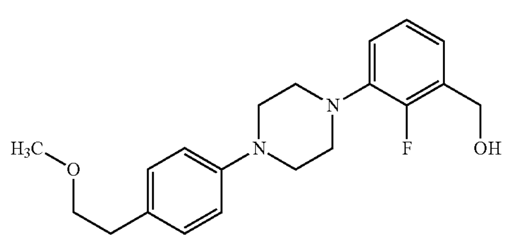 [SMILES: COCCc1ccc(N2CCN(c3cccc(CO)c3F)CC2)cc1] |

TABLE 37-continued

| Rf | Syn | Structure |
|---|---|---|
| 524 | R518 | 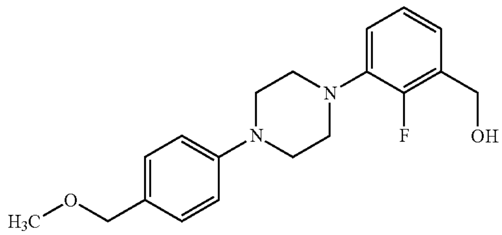 [SMILES: COCc1ccc(N2CCN(c3cccc(CO)c3F)CC2)cc1] |
| 525 | R518 | 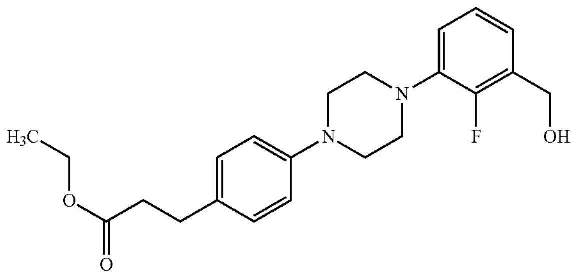 [SMILES: CCOC(=O)CCc1ccc(N2CCN(c3cccc(CO)c3F)CC2)cc1] |
| 526 | R518 | 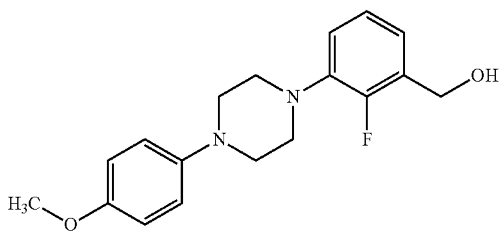 [SMILES: COc1ccc(N2CCN(c3cccc(CO)c3F)CC2)cc1] |
| 527 | R518 | 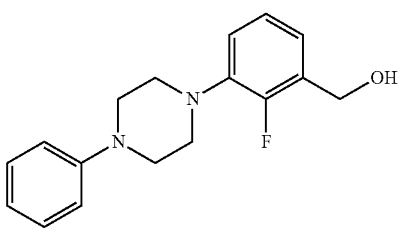 [SMILES: OCc1cccc(N2CCN(c3ccccc3)CC2)c1F] |
| 528 | R518 | 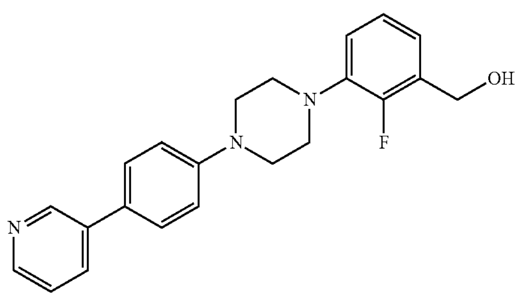 [SMILES: OCc1cccc(N2CCN(c3ccc(-c4cccnc4)cc3)CC2)c1F] |
| 529 | R548 | 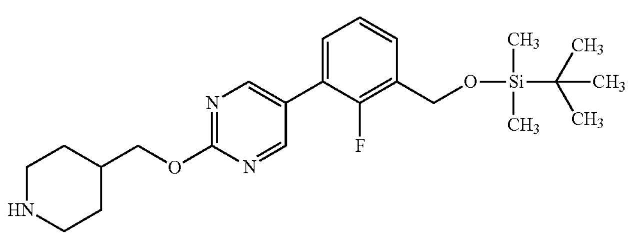 [SMILES: CC(C)(C)[Si](C)(C)OCc1cccc(-c2cnc(OCC3CCNCC3)nc2)c1F] |

TABLE 37-continued

| Rf | Syn | Structure |
|---|---|---|
| 530 | R548 | 3-(piperazin-1-yl)-2-fluoro-benzyl tert-butyldimethylsilyl ether |
| 531 | R548 | trans-4-ethoxycyclohexyl piperazin-1-yl ketone |
| 532 | R548 | trans-4-propoxycyclohexyl piperazin-1-yl ketone |
| 533 | R548 | cis-4-ethoxycyclohexyl piperazin-1-yl ketone |
| 534 | R548 | cis-4-propoxycyclohexyl piperazin-1-yl ketone |
| 535 | R548 | trans-4-(piperazin-1-ylcarbonyl)cyclohexyl benzoate |
| 536 | R548 | cis-4-(piperazin-1-ylcarbonyl)cyclohexyl benzoate |

TABLE 38
| Rf | Syn | Structure |
|---|---|---|
| 537 | R548 | 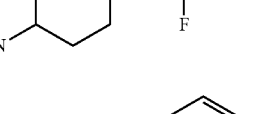 |
| 538 | R548 | 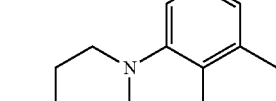 |
| 539 | R548 | 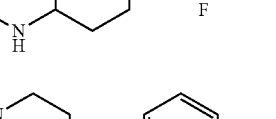 |
| 540 | R548 | 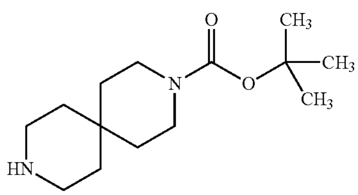 [SMILES: CC(C)(C)OC(=O)N1CCC2(CCNCC2)CC1] |
| 541 | R548 | 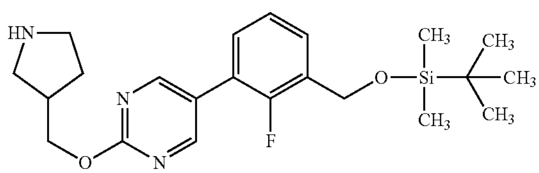 [SMILES: CC(C)(C)[Si](C)(C)OCc1cccc(-c2cnc(OCC3CCNC3)nc2)c1F] |
| 542 | R548 | 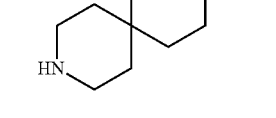 |
| 543 | R548 | 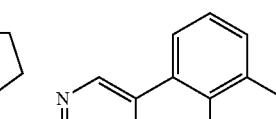 |
| 544 | R548 | 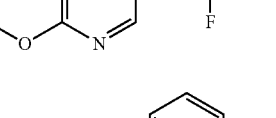 |

TABLE 38-continued

| Rf | Syn | Structure |
|---|---|---|
| 545 | R548 | 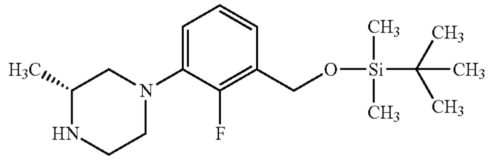 [SMILES: C[C@@H]1CN(c2cccc(CO[Si](C)(C)C(C)(C)C)c2F)CCN1] |
| 546 | R548 | 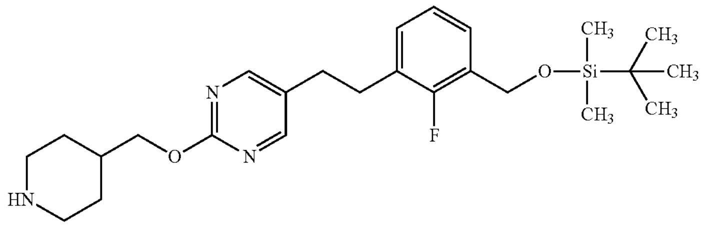 [SMILES: CC(C)(C)[Si](C)(C)OCc1cccc(CCc2cnc(OCC3CCNCC3)nc2)c1F] |
| 547 | R548 | 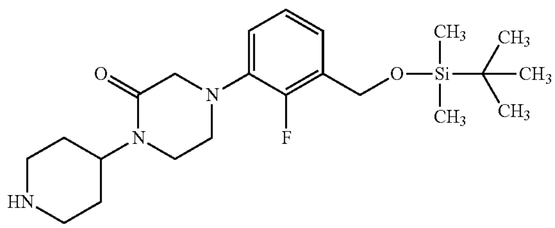 [SMILES: CC(C)(C)[Si](C)(C)OCc1cccc(N2CCN(C3CCNCC3)C(=O)C2)c1F] |
| 548 | R548 | 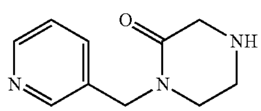 [SMILES: O=C1CNCCN1Cc1cccnc1] |
| 549 | R548 | 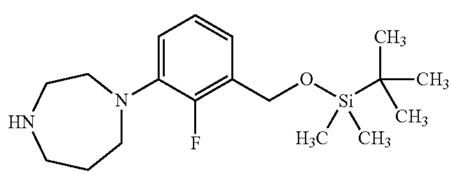 [SMILES: CC(C)(C)[Si](C)(C)OCc1cccc(N2CCCNCC2)c1F] |
| 550 | R548 | 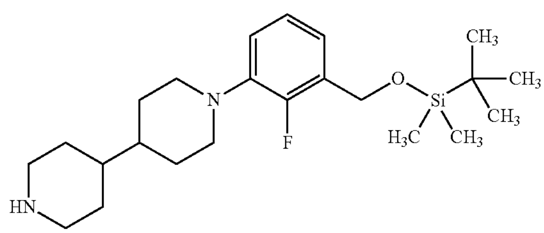 [SMILES: CC(C)(C)[Si](C)(C)OCc1cccc(N2CCC(C3CCNCC3)CC2)c1F] |
| 551 | R548 | 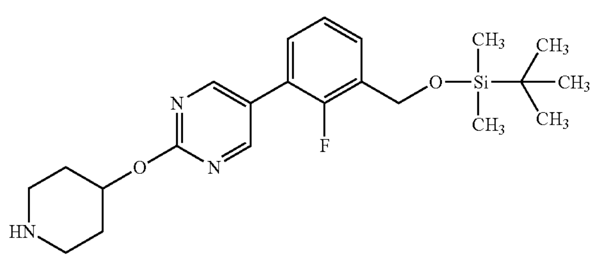 [SMILES: CC(C)(C)[Si](C)(C)OCc1cccc(-c2cnc(OC3CCNCC3)nc2)c1F] |
| 552 | R548 | 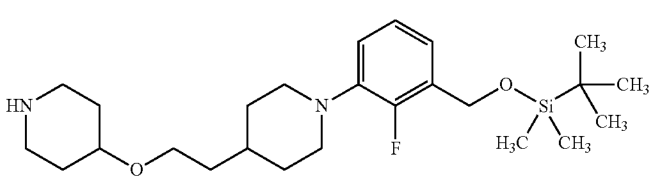 [SMILES: CC(C)(C)[Si](C)(C)OCc1cccc(N2CCC(CCOC3CCNCC3)CC2)c1F] |

TABLE 38-continued

| Rf | Syn | Structure |
|---|---|---|
| 553 | R548 | 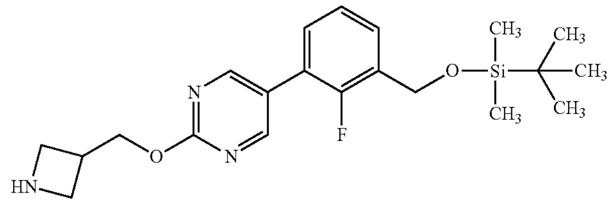 [SMILES: CC(C)(C)[Si](C)(C)OCc1cccc(-c2cnc(OCC3CNC3)nc2)c1F] |
| 554 | R548 | 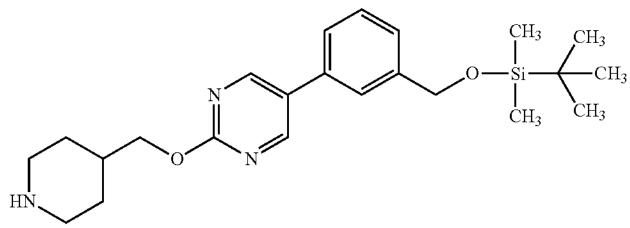 [SMILES: CC(C)(C)[Si](C)(C)OCc1cccc(-c2cnc(OCC3CCNCC3)nc2)c1] |

TABLE 39

| Rf | Syn | Structure |
|---|---|---|
| 555 | R548 | 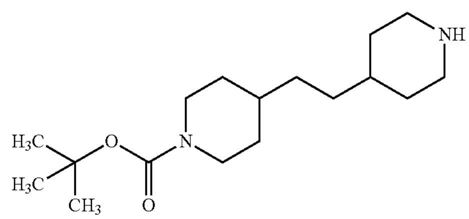 |
| 556 | R548 | 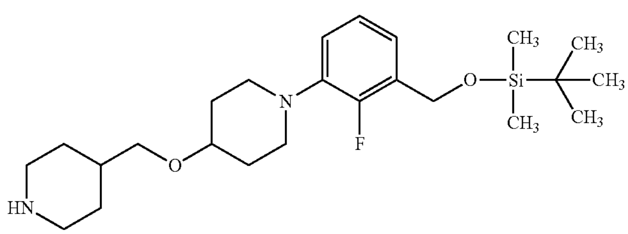 [SMILES: CC(C)(C)[Si](C)(C)OCc1cccc(N2CCC(OCC3CCNCC3)CC2)c1F] |
| 557 | R548 | 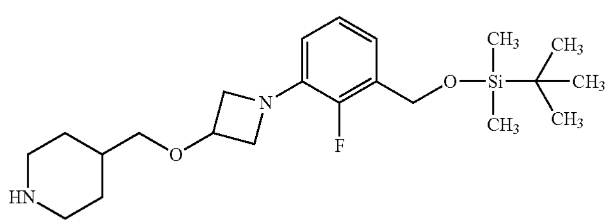 [SMILES: CC(C)(C)[Si](C)(C)OCc1cccc(N2CC(OCC3CCNCC3)C2)c1F] |
| 558 | R548 | 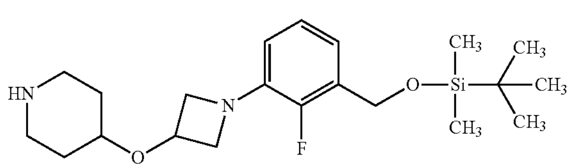 [SMILES: CC(C)(C)[Si](C)(C)OCc1cccc(N2CC(OC3CCNCC3)C2)c1F] |

TABLE 39-continued

| Rf | Syn | Structure |
|---|---|---|
| 559 | R548 | 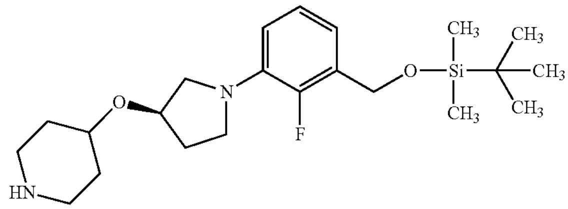 [SMILES: CC(C)(C)[Si](C)(C)OCc1cccc(N2CC[C@@H](OC3CCNCC3)C2)c1F] |
| 560 | R548 | 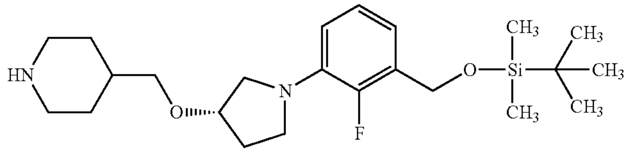 [SMILES: CC(C)(C)[Si](C)(C)OCc1cccc(N2CC[C@H](OCC3CCNCC3)C2)c1F] |
| 561 | R563 | trans- |
| 562 | R563 | cis- |
| 563 | R563 | 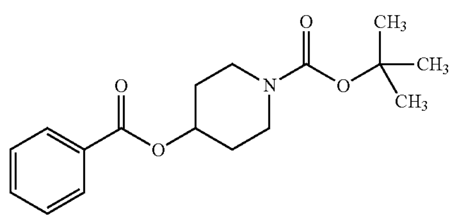 [SMILES: CC(C)(C)OC(=O)N1CCC(OC(=O)c2ccccc2)CC1] |
| 564 | R564 | 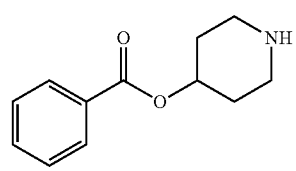 [SMILES: O=C(OC1CCNCC1)c1ccccc1] |
| 565 | R177 | 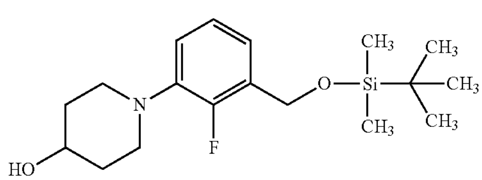 [SMILES: CC(C)(C)[Si](C)(C)OCc1cccc(N2CCC(O)CC2)c1F] |
| 566 | R568 | 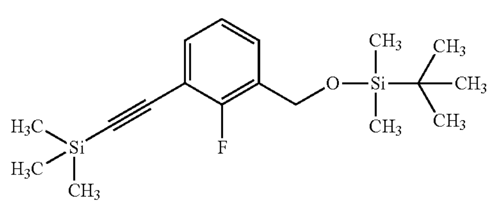 [SMILES: CC(C)(C)[Si](C)(C)OCc1cccc(C#C[Si](C)(C)C)c1F] |

TABLE 39-continued
| Rf | Syn | Structure |
|---|---|---|
| 567 | R568 | 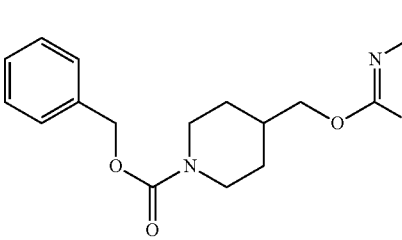 |
| 568 | R568 | 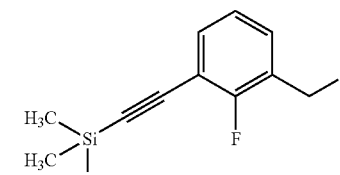 |
| 569 | R568 | 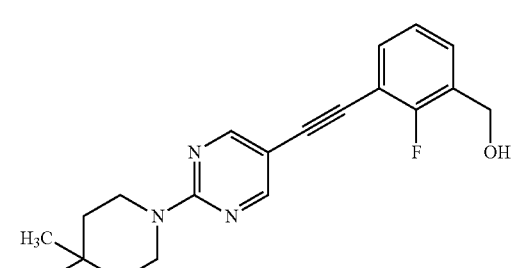 |
| 570 | R568 | 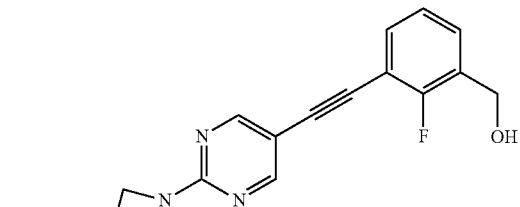 |
TABLE 40
| Rf | Syn | Structure |
|---|---|---|
| 571 | R568 | 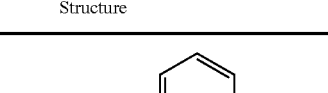 |

TABLE 40-continued

| Rf | Syn | Structure |
|---|---|---|
| 572 | R572 | 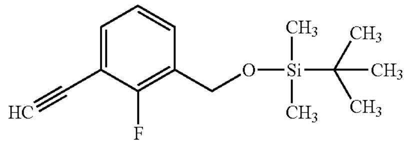 [SMILES: C#Cc1cccc(CO[Si](C)(C)C(C)(C)C)c1F] |
| 573 | R573 | 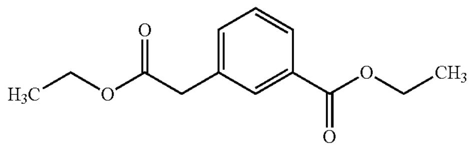 [SMILES: CCOC(=O)Cc1cccc(C(=O)OCC)c1] |
| 574 | R574 | 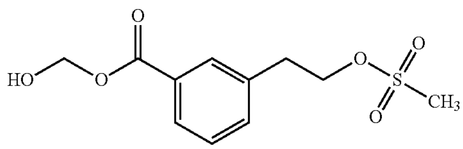 [SMILES: CS(=O)(=O)OCCc1cccc(C(=O)OCO)c1] |
| 575 | R574 | 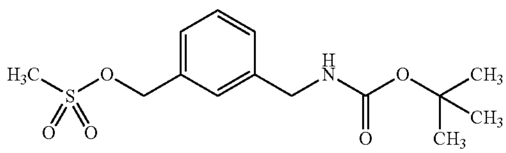 [SMILES: CC(C)(C)OC(=O)NCc1cccc(COS(C)(=O)=O)c1] |
| 576 | R574 | 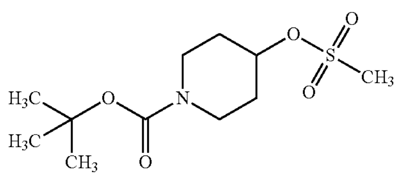 [SMILES: CC(C)(C)OC(=O)N1CCC(OS(C)(=O)=O)CC1] |
| 577 | R581 | 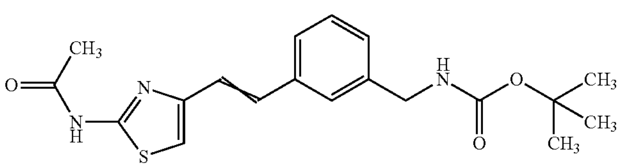 [SMILES: CC(=O)Nc1nc(C=Cc2cccc(CNC(=O)OC(C)(C)C)c2)cs1] |
| 578 | R581 | 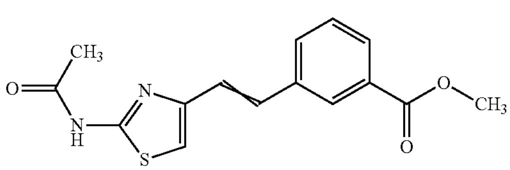 [SMILES: COC(=O)c1cccc(C=Cc2csc(NC(C)=O)n2)c1] |
| 579 | R581 | 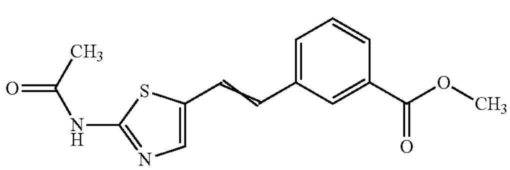 |
| 580 | R581 | 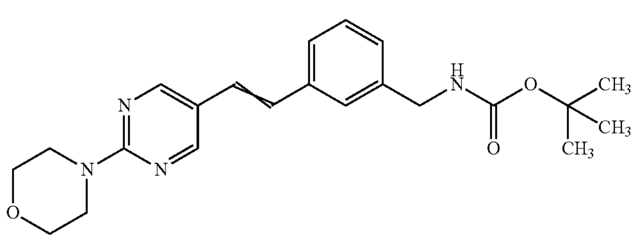 [SMILES: CC(C)(C)OC(=O)NCc1cccc(C=Cc2cnc(N3CCOCC3)nc2)c1] |

TABLE 40-continued
| Rf | Syn | Structure |
|---|---|---|
| 581 | R581 | 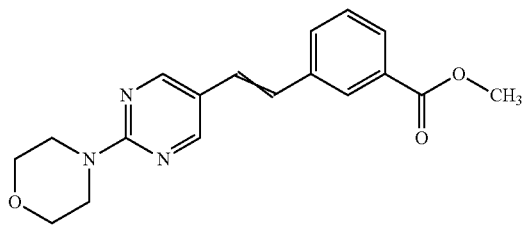 [SMILES: COC(=O)c1cccc(C=Cc2cnc(N3CCOCC3)nc2)c1] |
| 582 | R582 | 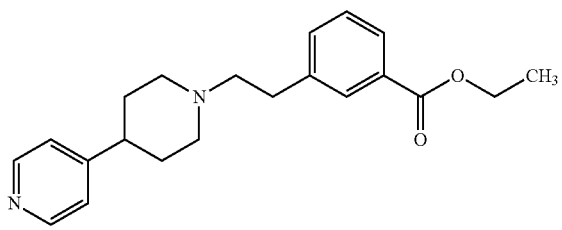 [SMILES: CCOC(=O)c1cccc(CCN2CCC(c3ccncc3)CC2)c1] |
| 583 | R582 | 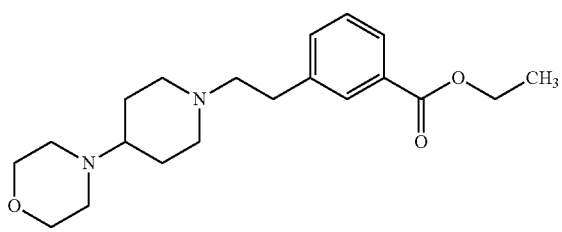 [SMILES: CCOC(=O)c1cccc(CCN2CCC(N3CCOCC3)CC2)c1] |
| 584 | R584 | 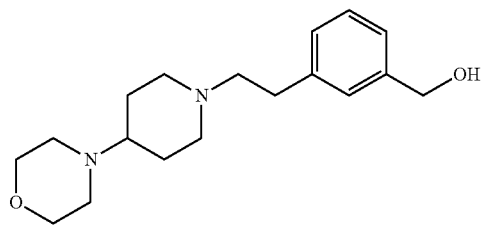 [SMILES: OCc1cccc(CCN2CCC(N3CCOCC3)CC2)c1] |
| 585 | R584 | 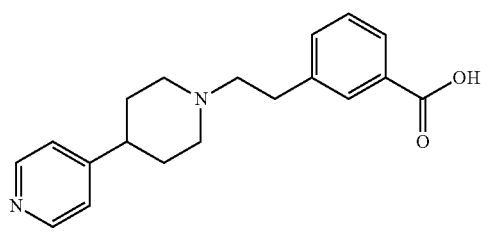 [SMILES: O=C(O)c1cccc(CCN2CCC(c3ccncc3)CC2)c1] |
| 586 | R584 | 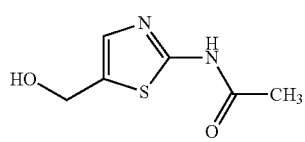 |

TABLE 41

| Rf | Syn | Structure |
|---|---|---|
| 587 | R584 | 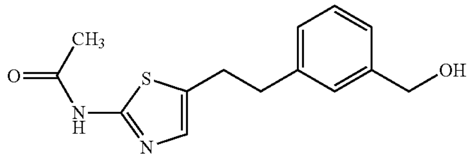 [SMILES: CC(=O)Nc1ncc(CCc2cccc(CO)c2)s1] |
| 588 | R584 | 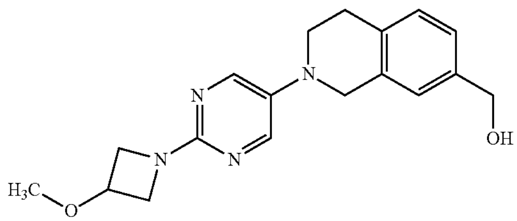 [SMILES: COC1CN(c2ncc(N3CCc4ccc(CO)cc4C3)cn2)C1] |
| 589 | R589 | 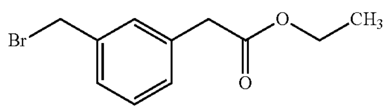 |
| 590 | R589 | 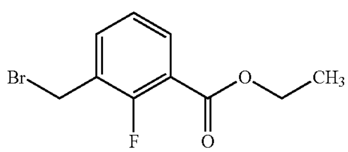 |
| 591 | R589 | 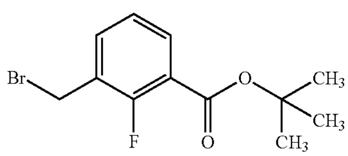 [SMILES: CC(C)(C)OC(=O)c1cccc(CBr)c1F] |
| 592 | R592 | 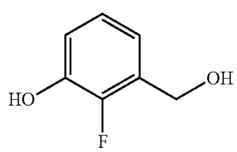 |
| 593 | R593 | 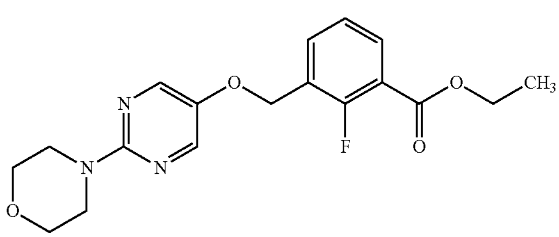 [SMILES: CCOC(=O)c1cccc(COc2cnc(N3CCOCC3)nc2)c1F] |
| 594 | R594 | 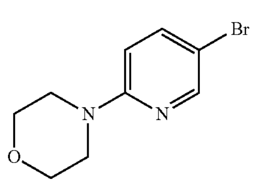 [SMILES: Brc1ccc(N2CCOCC2)nc1] |

TABLE 41-continued

| Rf | Syn | Structure |
|---|---|---|
| 595 | R596 | 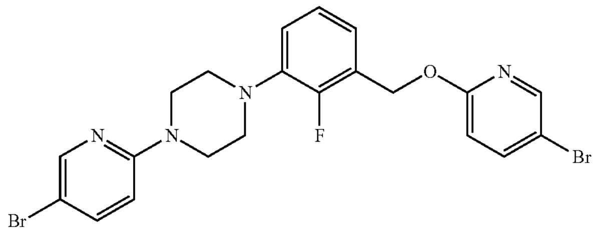 [SMILES: Fc1c(COc2ccc(Br)cn2)cccc1N1CCN(c2ccc(Br)cn2)CC1] |
| 596 | R596 | 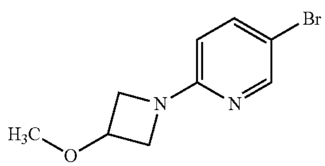 |
| 597 | R603 | 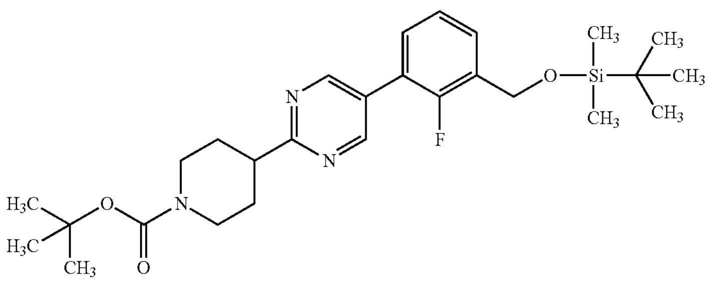 [SMILES: CC(C)(C)OC(=O)N1CCC(c2ncc(-c3cccc(CO[Si](C)(C)C(C)(C)C)c3F)cn2)CC1] |
| 598 | R603 | 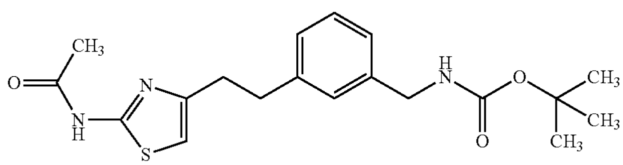 [SMILES: CC(=O)Nc1nc(CCc2cccc(CNC(=O)OC(C)(C)C)c2)cs1] |
| 599 | R603 | 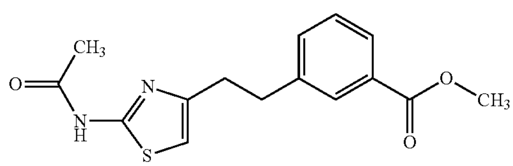 [SMILES: COC(=O)c1cccc(CCc2csc(NC(C)=O)n2)c1] |
| 600 | R603 | 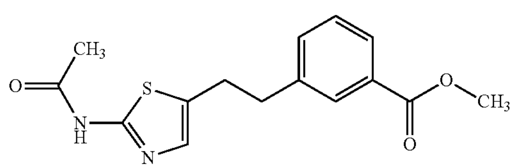 [SMILES: COC(=O)c1cccc(CCc2cnc(NC(C)=O)s2)c1] |
| 601 | R603 | 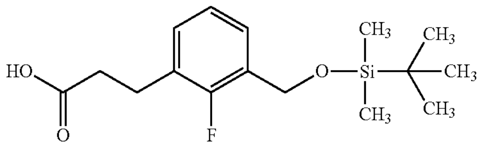 [SMILES: CC(C)(C)[Si](C)(C)OCc1cccc(CCC(=O)O)c1F] |

TABLE 41-continued
| Rf | Syn | Structure |
|---|---|---|
| 602 | R603 | 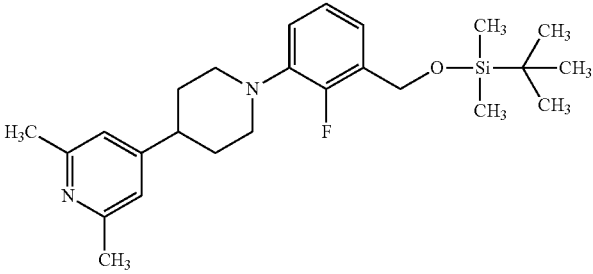 [SMILES: Cc1cc(C2CCN(c3cccc(CO[Si](C)(C)C(C)(C)C)c3F)CC2)cc(C)n1] |
| 603 | R603 | 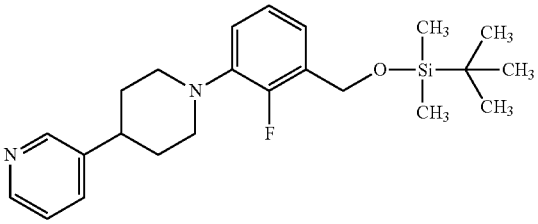 [SMILES: CC(C)(C)[Si](C)(C)OCc1cccc(N2CCC(c3cccnc3)CC2)c1F] |
| 604 | R603 | 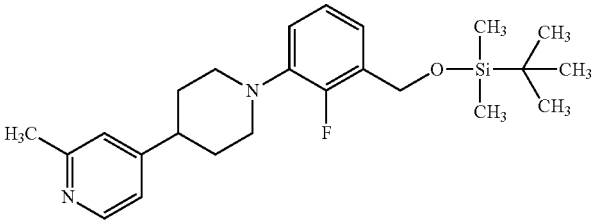 |
TABLE 42
| Rf | Syn | Structure |
|---|---|---|
| 605 | R603 | 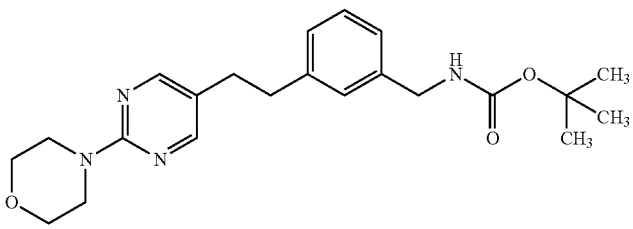 [SMILES: CC(C)(C)OC(=O)NCc1cccc(CCc2cnc(N3CCOCC3)nc2)c1] |
| 606 | R603 | 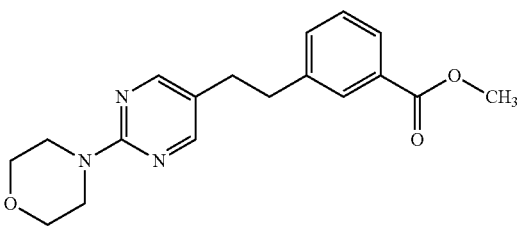 [SMILES: COC(=O)c1cccc(CCc2cnc(N3CCOCC3)nc2)c1] |

TABLE 42-continued

| Rf | Syn | Structure |
|---|---|---|
| 607 | R603 | 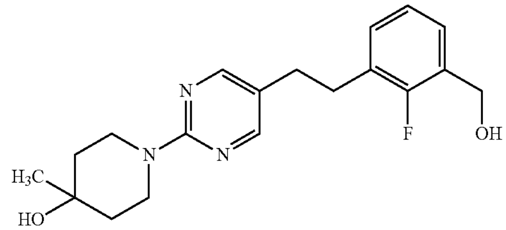 [SMILES: CC1(O)CCN(c2ncc(CCc3cccc(CO)c3F)cn2)CC1] |
| 608 | R603 | 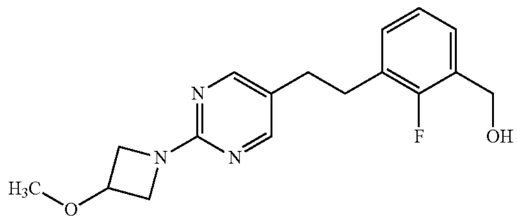 [SMILES: COC1CN(c2ncc(CCc3cccc(CO)c3F)cn2)C1] |
| 609 | R603 | 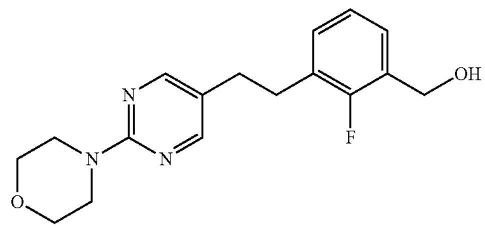 [SMILES: OCc1cccc(CCc2cnc(N3CCOCC3)nc2)c1F] |
| 610 | R603 | 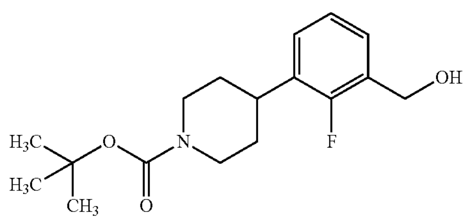 [SMILES: CC(C)(C)OC(=O)N1CCC(c2cccc(CO)c2F)CC1] |
| 611 | R603 | 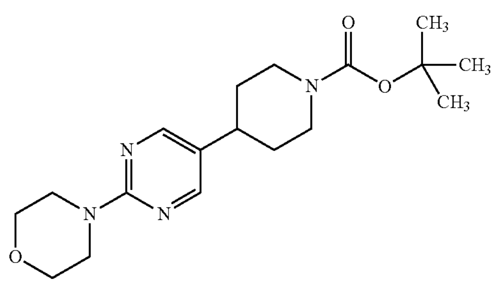 [SMILES: CC(C)(C)OC(=O)N1CCC(c2cnc(N3CCOCC3)nc2)CC1] |
| 612 | R603 | 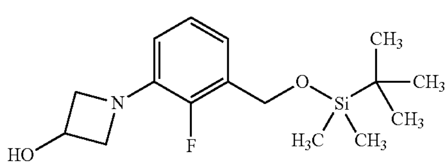 [SMILES: CC(C)(C)[Si](C)(C)OCc1cccc(N2CC(O)C2)c1F] |
| 613 | R613 | 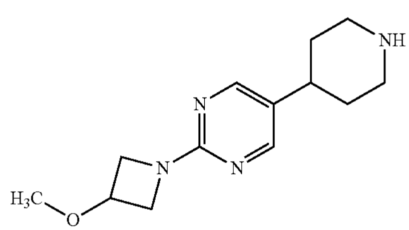 [SMILES: COC1CN(c2ncc(C3CCNCC3)cn2)C1] |

TABLE 42-continued

| Rf | Syn | Structure |
|---|---|---|
| 614 | R614 | 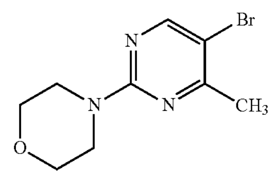 |
| 615 | R617 | 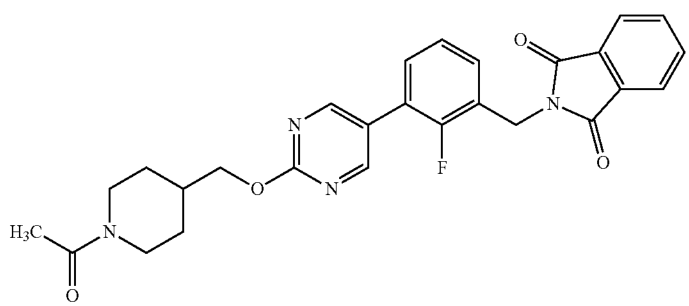 [SMILES: CC(=O)N1CCC(COc2ncc(-c3cccc(CN4C(=O)c5ccccc5C4=O)c3F)cn2)CC1] |
| 616 | R617 | 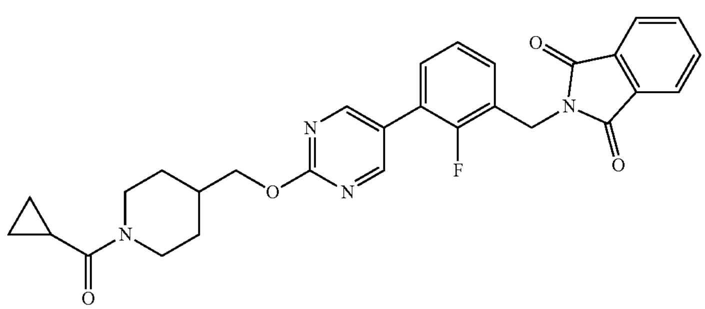 [SMILES: O=C(C1CC1)N1CCC(COc2ncc(-c3cccc(CN4C(=O)c5ccccc5C4=O)c3F)cn2)CC1] |
| 617 | R617 | 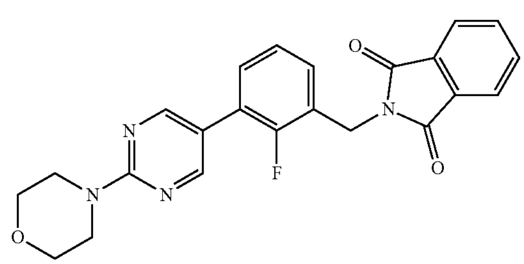 [SMILES: O=C1c2ccccc2C(=O)N1Cc1cccc(-c2cnc(N3CCOCC3)nc2)c1F] |
| 618 | R617 | 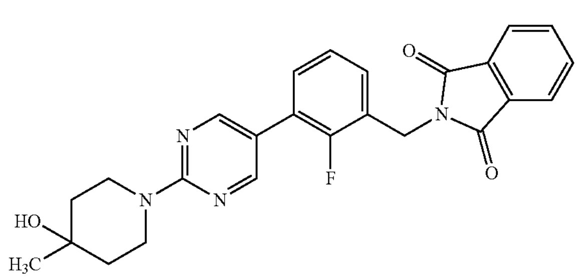 [SMILES: CC1(O)CCN(c2ncc(-c3cccc(CN4C(=O)c5ccccc5C4=O)c3F)cn2)CC1] |

TABLE 43
| Rf | Syn | Structure |
|---|---|---|
| 619 | R617 | 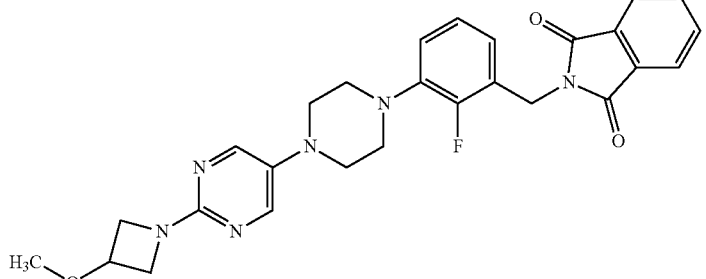 |
| 620 | R617 | 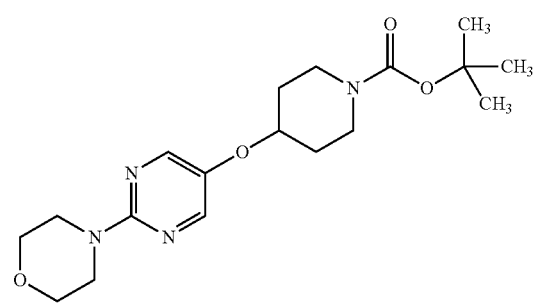 [SMILES: CC(C)(C)OC(=O)N1CCC(Oc2cnc(N3CCOCC3)nc2)CC1] |
| 621 | R306 | 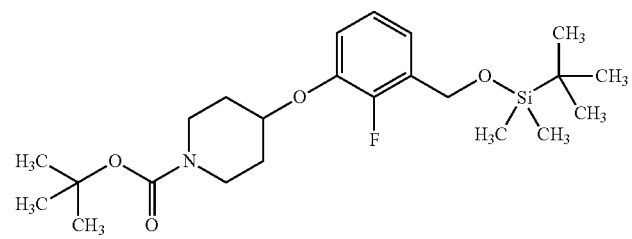 [SMILES: CC(C)(C)OC(=O)N1CCC(Oc2cccc(CO[Si](C)(C)C(C)(C)C)c2F)CC1] |
| 622 | R306 | 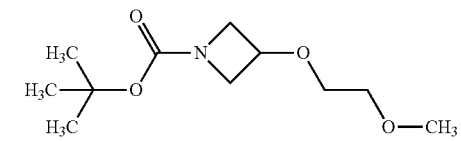 |
| 623 | R306 | 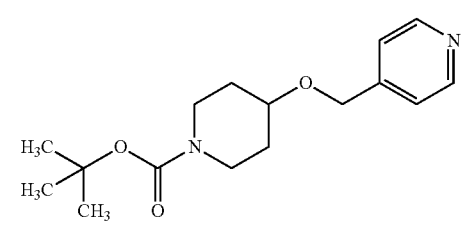 [SMILES: CC(C)(C)OC(=O)N1CCC(OCc2ccncc2)CC1] |
| 624 | R306 | 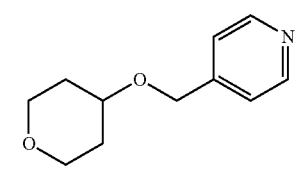 [SMILES: c1cc(COC2CCOCC2)ccn1] |

TABLE 43-continued
| Rf | Syn | Structure |
|---|---|---|
| 625 | R306 | 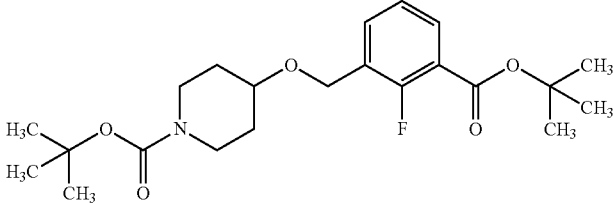 [SMILES: CC(C)(C)OC(=O)c1cccc(COC2CCN(C(=O)OC(C)(C)C)CC2)c1F] |
| 626 | R306 | 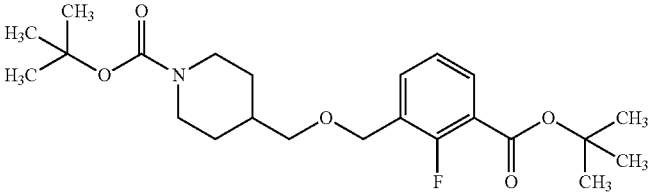 [SMILES: CC(C)(C)OC(=O)c1cccc(COCC2CCN(C(=O)OC(C)(C)C)CC2)c1F] |
| 627 | R306 | 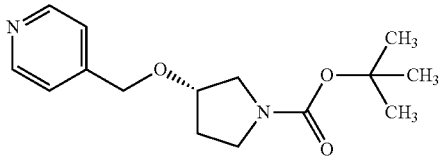 [SMILES: CC(C)(C)OC(=O)N1CC[C@H](OCc2ccncc2)C1] |
| 628 | R306 | 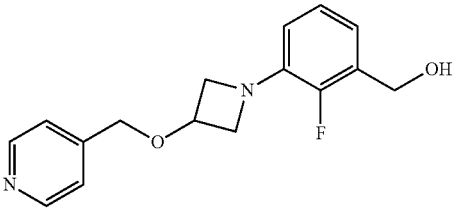 [SMILES: OCc1cccc(N2CC(OCc3ccncc3)C2)c1F] |
| 629 | R306 | 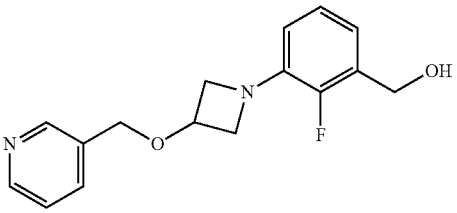 [SMILES: OCc1cccc(N2CC(OCc3cccnc3)C2)c1F] |
| 630 | R631 | 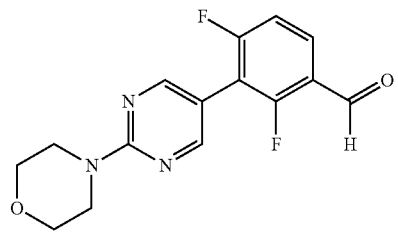 [SMILES: O=Cc1ccc(F)c(-c2cnc(N3CCOCC3)nc2)c1F] |
| 631 | R631 | 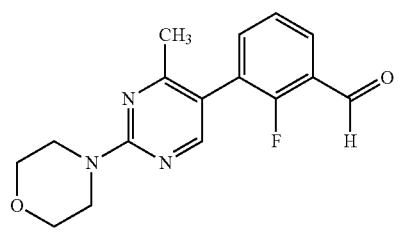 [SMILES: Cc1nc(N2CCOCC2)ncc1-c1cccc(C=O)c1F] |

TABLE 43-continued

| Rf | Syn | Structure |
|---|---|---|
| 632 | R631 | 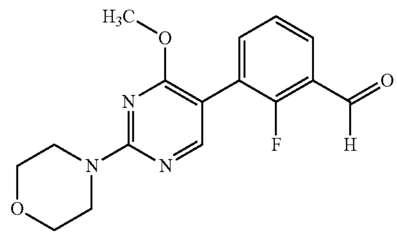 [SMILES: COc1nc(N2CCOCC2)ncc1-c1cccc(C=O)c1F] |
| 633 | R631 | 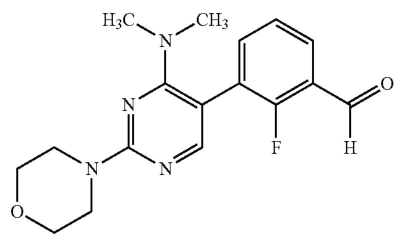 [SMILES: CN(C)c1nc(N2CCOCC2)ncc1-c1cccc(C=O)c1F] |
| 634 | R638 | 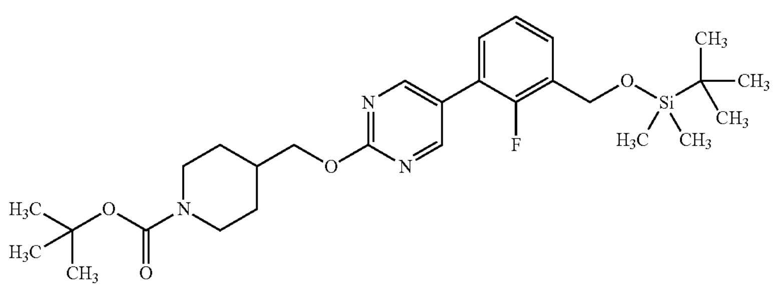 [SMILES: CC(C)(C)OC(=O)N1CCC(COc2ncc(-c3cccc(CO[Si](C)(C)C(C)(C)C)c3F)cn2)CC1] |

TABLE 44

| Rf | Syn | Structure |
|---|---|---|
| 635 | R638 | 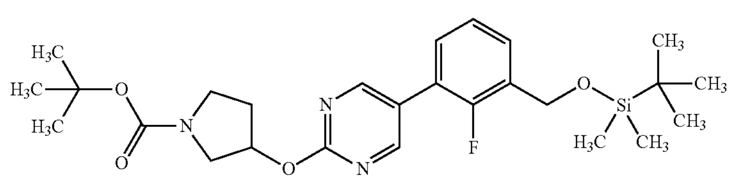 [SMILES: CC(C)(C)OC(=O)N1CCC(Oc2ncc(-c3cccc(CO[Si](C)(C)C(C)(C)C)c3F)cn2)C1] |
| 636 | R638 | 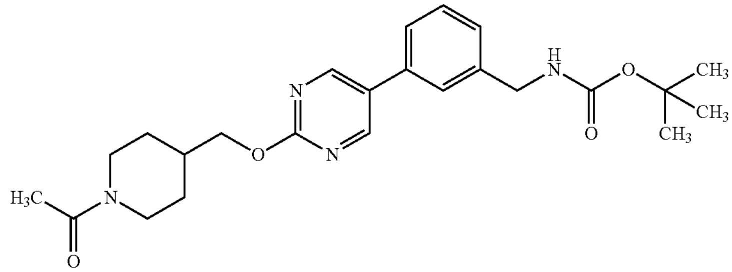 [SMILES: CC(=O)N1CCC(COc2ncc(-c3cccc(CNC(=O)OC(C)(C)C)c3)cn2)CC1] |

TABLE 44-continued
| Rf | Syn | Structure |
|---|---|---|
| 637 | R638 | 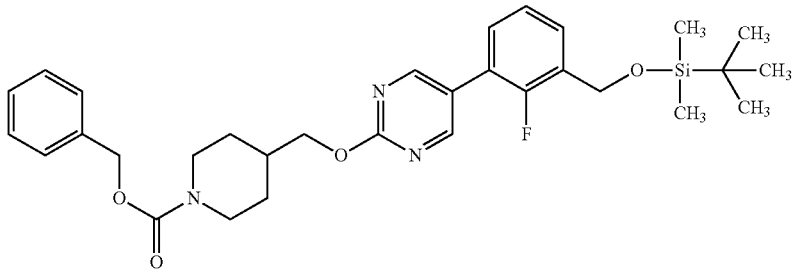 [SMILES: CC(C)(C)[Si](C)(C)OCc1cccc(-c2cnc(OCC3CCN(C(=O)OCc4ccccc4)CC3)nc2)c1F] |
| 638 | R638 | 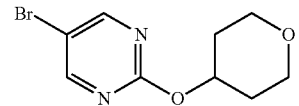 |
| 639 | R638 | 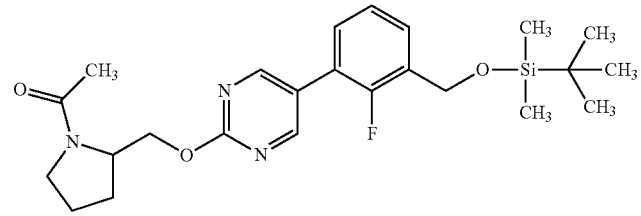 [SMILES: CC(=O)N1CCCC1COc1ncc(-c2cccc(CO[Si](C)(C)C(C)(C)C)c2F)cn1] |
| 640 | R638 | 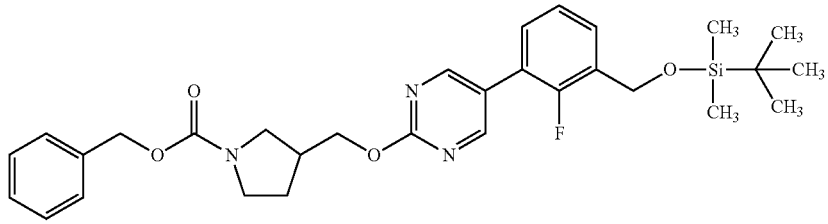 [SMILES: CC(C)(C)[Si](C)(C)OCc1cccc(-c2cnc(OCC3CCN(C(=O)OCc4ccccc4)C3)nc2)c1F] |
| 641 | R638 | 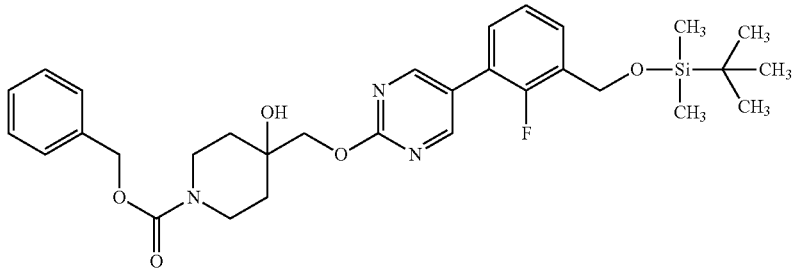 [SMILES: CC(C)(C)[Si](C)(C)OCc1cccc(-c2cnc(OCC3(O)CCN(C(=O)OCc4ccccc4)CC3)nc2)c1F] |
| 642 | R638 | 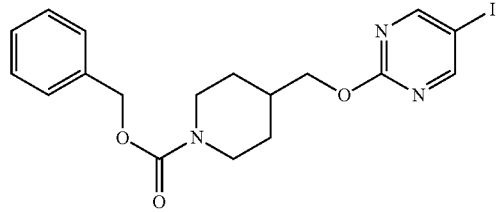 [SMILES: O=C(OCc1ccccc1)N1CCC(COc2ncc(I)cn2)CC1] |

US 8,716,470 B2
TABLE 44-continued
| Rf | Syn | Structure |
|---|---|---|
| 643 | R638 | 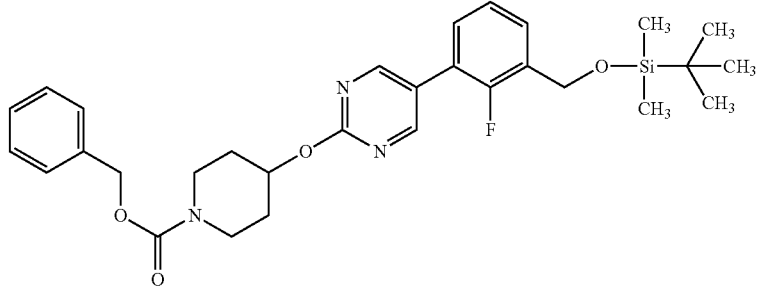 [SMILES: CC(C)(C)[Si](C)(C)OCc1cccc(-c2cnc(OC3CCN(C(=O)OCc4ccccc4)CC3)nc2)c1F] |
| 644 | R638 | 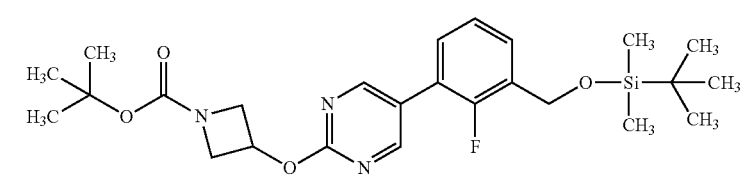 [SMILES: CC(C)(C)OC(=O)N1CC(Oc2ncc(-c3cccc(CO[Si](C)(C)C(C)(C)C)c3F)cn2)C1] |
| 645 | R638 | 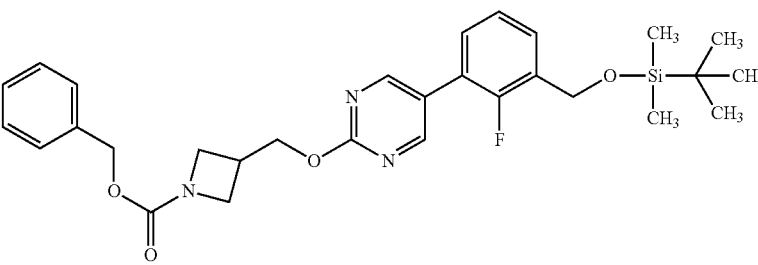 [SMILES: CC(C)(C)[Si](C)(C)OCc1cccc(-c2cnc(OCC3CN(C(=O)OCc4ccccc4)C3)nc2)c1F] |
| 646 | R638 | 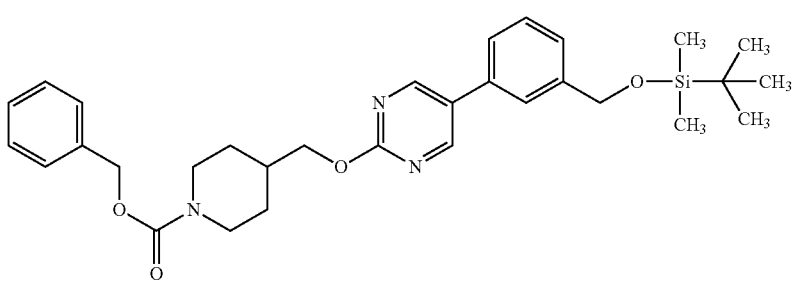 [SMILES: CC(C)(C)[Si](C)(C)OCc1cccc(-c2cnc(OCC3CCN(C(=O)OCc4ccccc4)CC3)nc2)c1] |
| 647 | R638 | 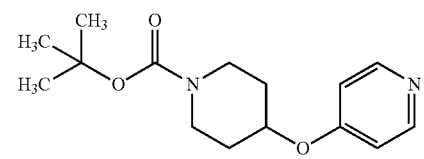 [SMILES: CC(C)(C)OC(=O)N1CCC(Oc2ccncc2)CC1] |
| 648 | R638 | 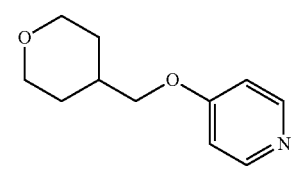 [SMILES: c1cc(OCC2CCOCC2)ccn1] |
| 649 | R651 | 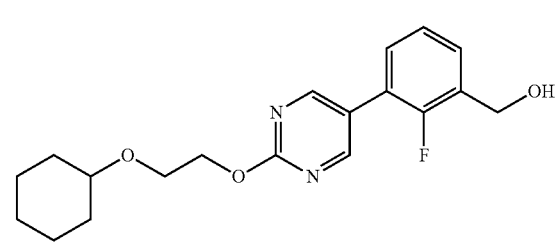 [SMILES: OCc1cccc(-c2cnc(OCCOC3CCCCC3)nc2)c1F] |

TABLE 44-continued
| Rf | Syn | Structure |
|---|---|---|
| 650 | R651 | 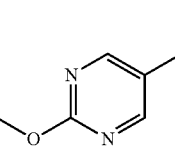 |
| 651 | R651 | 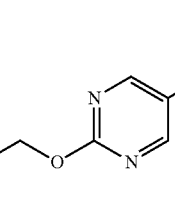 |
| 652 | R651 | 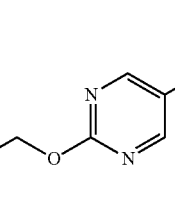 |
TABLE 45
| Rf | Syn | Structure |
|---|---|---|
| 653 | R653 | 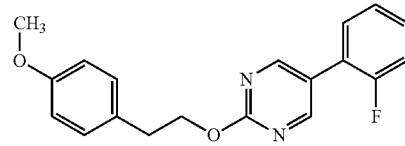 |
| 654 | R651 | 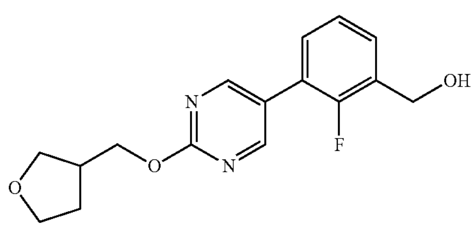 [SMILES: OCc1cccc(-c2cnc(OCC3CCOC3)nc2)c1F] |
| 655 | R651 | 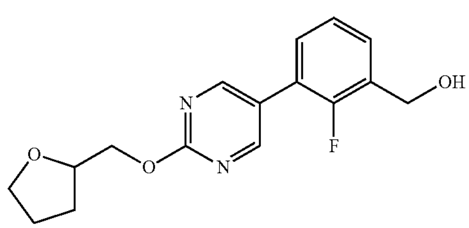 [SMILES: OCc1cccc(-c2cnc(OCC3CCCO3)nc2)c1F] |
| 656 | R651 | 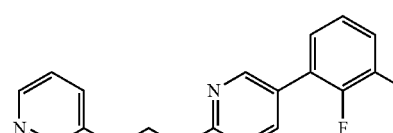 |
| 657 | R651 | |
| 658 | R651 | 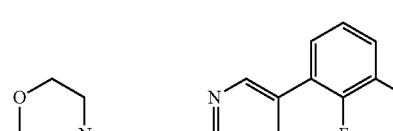 |

TABLE 45-continued

| Rf | Syn | Structure |
|---|---|---|
| 659 | R651 | 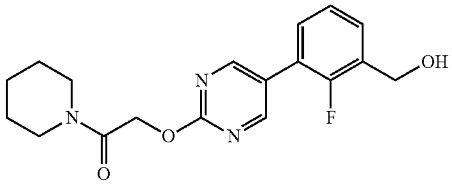 [SMILES: O=C(COc1ncc(-c2cccc(CO)c2F)cn1)N1CCCCC1] |
| 660 | R651 | 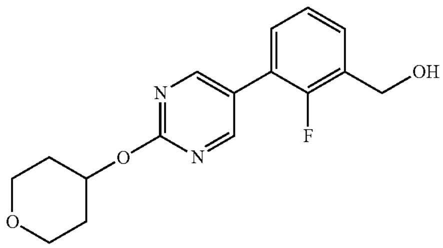 [SMILES: OCc1cccc(-c2cnc(OC3CCOCC3)nc2)c1F] |
| 661 | R651 | 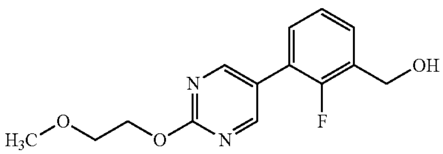 [SMILES: COCCOc1ncc(-c2cccc(CO)c2F)cn1] |
| 662 | R653 | 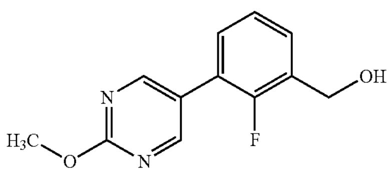 [SMILES: COc1ncc(-c2cccc(CO)c2F)cn1] |
| 663 | R663 | 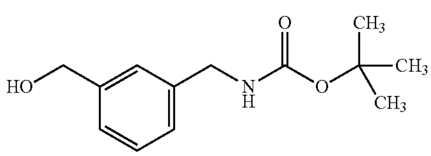 [SMILES: CC(C)(C)OC(=O)NCc1cccc(CO)c1] |
| 664 | R663 | |
| 665 | R663 | |
| 666 | R663 | |
| 669 | R671 | |
| 670 | R671 | |

TABLE 46

| Rf | Syn | Structure |
|---|---|---|
| 671 | R671 | 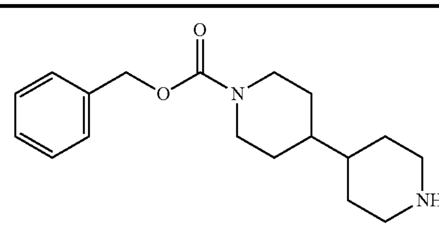 |
| 672 | R671 | 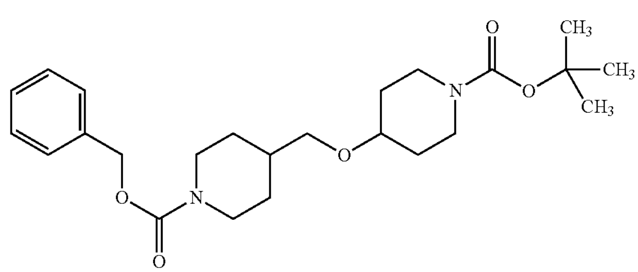 [SMILES: CC(C)(C)OC(=O)N1CCC(OCC2CCN(C(=O)OCc3ccccc3)CC2)CC1] |

TABLE 46-continued

| Rf | Syn | Structure |
|---|---|---|
| 673 | R674 | 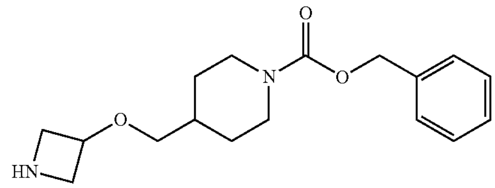 [SMILES: O=C(OCc1ccccc1)N1CCC(COC2CNC2)CC1] |
| 674 | R674 | 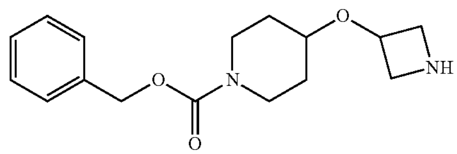 [SMILES: O=C(OCc1ccccc1)N1CCC(OC2CNC2)CC1] |
| 675 | R674 | 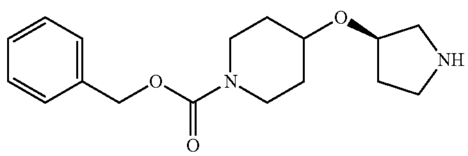 [SMILES: O=C(OCc1ccccc1)N1CCC(O[C@@H]2CCNC2)CC1] |
| 676 | R674 | 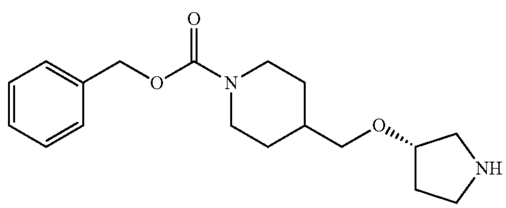 [SMILES: O=C(OCc1ccccc1)N1CCC(CO[C@H]2CCNC2)CC1] |
| 677 | R677 | 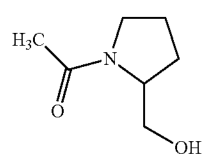 |
| 678 | R677 | 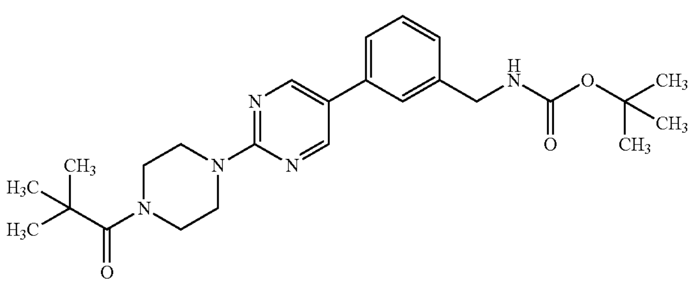 [SMILES: CC(C)(C)OC(=O)NCc1cccc(-c2cnc(N3CCN(C(=O)C(C)(C)C)CC3)nc2)c1] |
| 679 | R680 | 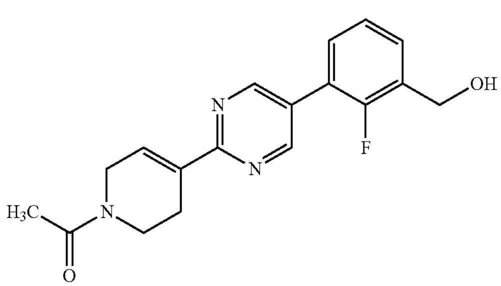 [SMILES: CC(=O)N1CC=C(c2ncc(-c3cccc(CO)c3F)cn2)CC1] |

TABLE 46-continued

| Rf | Syn | Structure |
|---|---|---|
| 680 | R680 | 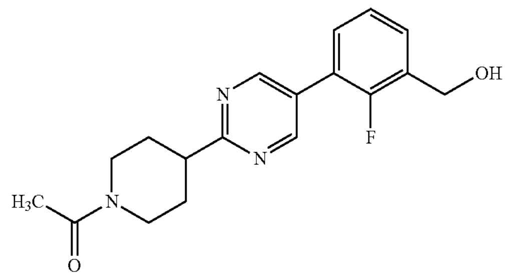 |
| 681 | R680 | 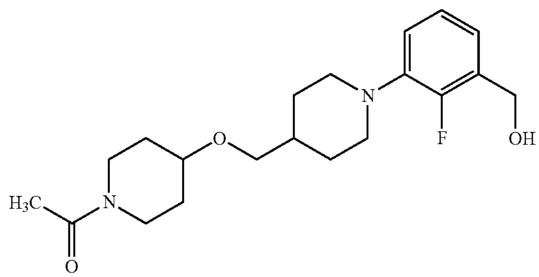 |
| 682 | R680 | 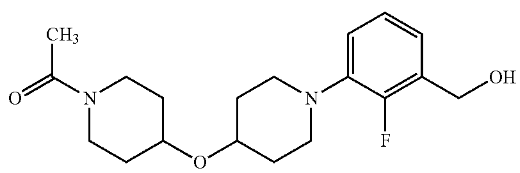 [SMILES: CC(=O)N1CCC(OC2CCN(c3cccc(CO)c3F)CC2)CC1] |
| 683 | R680 | 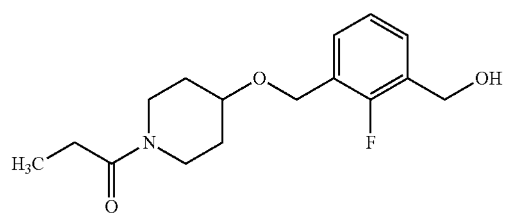 [SMILES: CCC(=O)N1CCC(OCc2cccc(CO)c2F)CC1] |
| 684 | R680 | 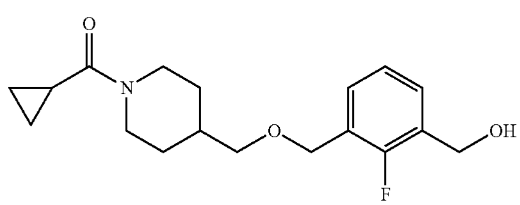 [SMILES: O=C(C1CC1)N1CCC(COCc2cccc(CO)c2F)CC1] |
| 685 | R686 | 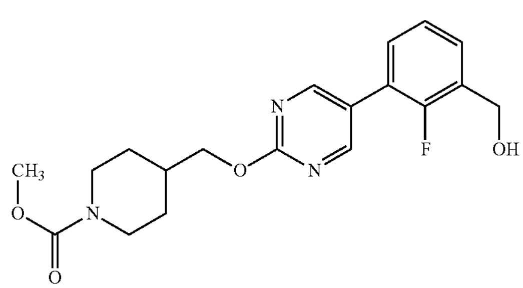 [SMILES: COC(=O)N1CCC(COc2ncc(-c3cccc(CO)c3F)cn2)CC1] |

TABLE 46-continued

| Rf | Syn | Structure |
|---|---|---|
| 686 | R686 | 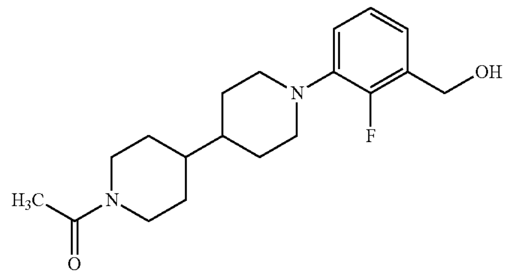 [SMILES: CC(=O)N1CCC(C2CCN(c3cccc(CO)c3F)CC2)CC1] |

TABLE 47

| Rf | Syn | Structure |
|---|---|---|
| 687 | R686 | 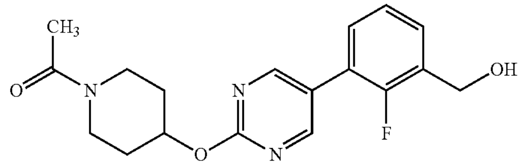 [SMILES: CC(=O)N1CCC(Oc2ncc(-c3cccc(CO)c3F)cn2)CC1] |
| 688 | R686 | 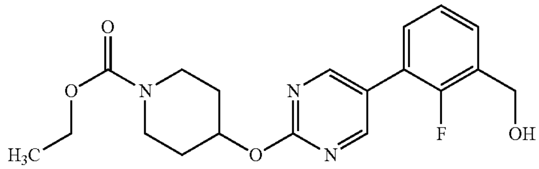 [SMILES: CCOC(=O)N1CCC(Oc2ncc(-c3cccc(CO)c3F)cn2)CC1] |
| 689 | R686 | 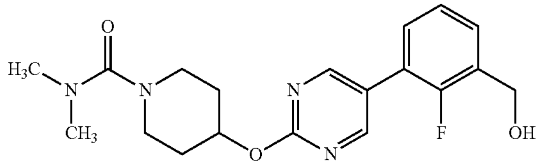 [SMILES: CN(C)C(=O)N1CCC(Oc2ncc(-c3cccc(CO)c3F)cn2)CC1] |
| 690 | R686 | 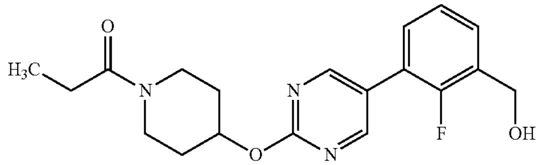 [SMILES: CCC(=O)N1CCC(Oc2ncc(-c3cccc(CO)c3F)cn2)CC1] |
| 691 | R686 | 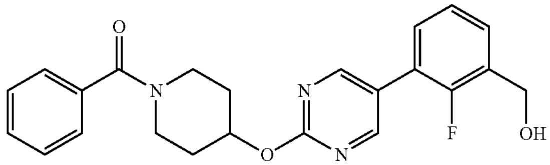 |
| 692 | R686 | 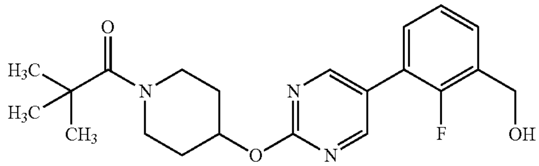 [SMILES: CC(C)(C)C(=O)N1CCC(Oc2ncc(-c3cccc(CO)c3F)cn2)CC1] |

TABLE 47-continued
| Rf | Syn | Structure |
|---|---|---|
| 693 | R686 | 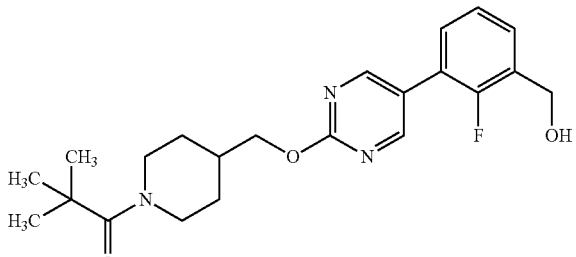 |
| 694 | R686 | 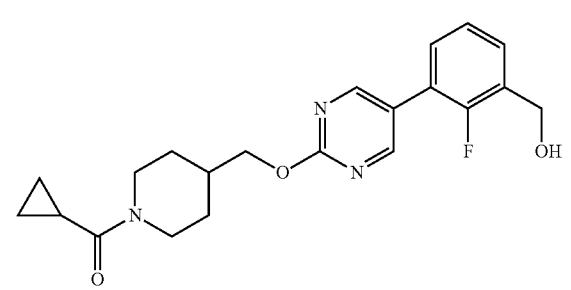 [SMILES: O=C(C1CC1)N1CCC(COc2ncc(-c3cccc(CO)c3F)cn2)CC1] |
| 695 | R686 | 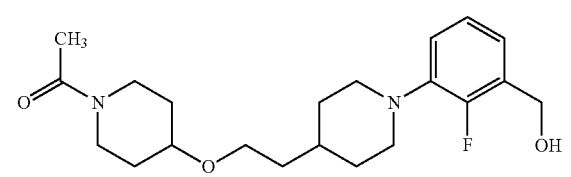 [SMILES: CC(=O)N1CCC(OCCC2CCN(c3cccc(CO)c3F)CC2)CC1] |
| 696 | R686 | 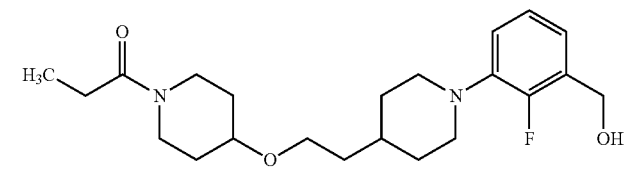 [SMILES: CCC(=O)N1CCC(OCCC2CCN(c3cccc(CO)c3F)CC2)CC1] |
| 697 | R686 | 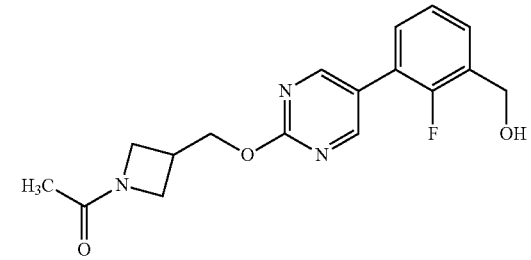 [SMILES: CC(=O)N1CC(COc2ncc(-c3cccc(CO)c3F)cn2)C1] |
| 698 | R686 | 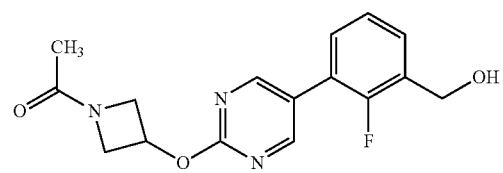 [SMILES: CC(=O)N1CC(Oc2ncc(-c3cccc(CO)c3F)cn2)C1] |

TABLE 47-continued

| Rf | Syn | Structure |
|---|---|---|
| 699 | R686 | ethyl 3-(((5-(2-fluoro-3-(hydroxymethyl)phenyl)pyrimidin-2-yl)oxy)methyl)azetidine-1-carboxylate |
| 700 | R686 | methyl 3-(((5-(2-fluoro-3-(hydroxymethyl)phenyl)pyrimidin-2-yl)oxy)methyl)azetidine-1-carboxylate |
| 701 | R686 | 1-(4-(((5-(3-(hydroxymethyl)phenyl)pyrimidin-2-yl)oxy)methyl)piperidin-1-yl)ethan-1-one |
| 702 | R686 | 1-(4-((1-(2-fluoro-3-(hydroxymethyl)phenyl)piperidin-4-yl)oxy)methyl)piperidin-1-yl)ethan-1-one |

TABLE 48

| Rf | Syn | Structure |
|---|---|---|
| 703 | R686 | 1-(4-(((1-(2-fluoro-3-(hydroxymethyl)phenyl)azetidin-3-yl)oxy)methyl)piperidin-1-yl)ethan-1-one |

TABLE 48-continued

| Rf | Syn | Structure |
|---|---|---|
| 704 | R686 | 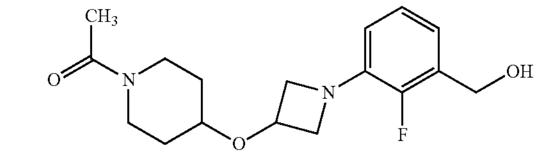 [SMILES: CC(=O)N1CCC(OC2CN(c3cccc(CO)c3F)C2)CC1] |
| 705 | R686 | 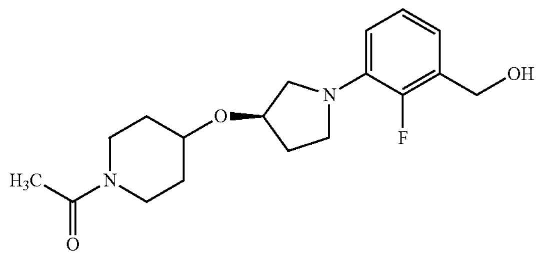 [SMILES: CC(=O)N1CCC(O[C@@H]2CCN(c3cccc(CO)c3F)C2)CC1] |
| 706 | R686 | 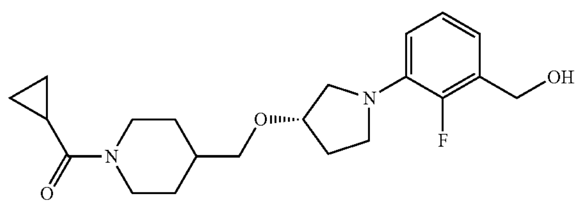 [SMILES: O=C(C1CC1)N1CCC(CO[C@H]2CCN(c3cccc(CO)c3F)C2)CC1] |
| 707 | R707 | 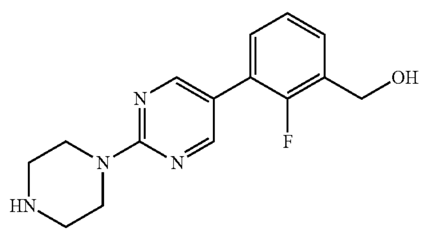 [SMILES: OCc1cccc(-c2cnc(N3CCNCC3)nc2)c1F] |
| 708 | R707 | 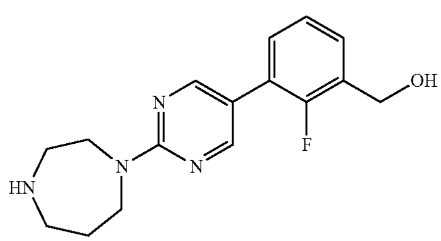 [SMILES: OCc1cccc(-c2cnc(N3CCCNCC3)nc2)c1F] |
| 709 | R709 | 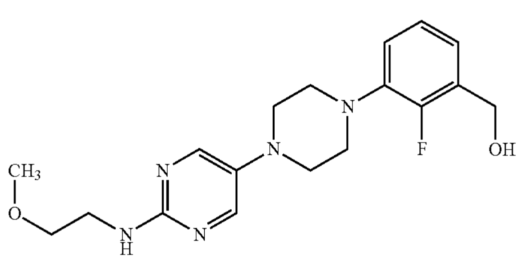 [SMILES: COCCNc1ncc(N2CCN(c3cccc(CO)c3F)CC2)cn1] |
| 710 | R712 | 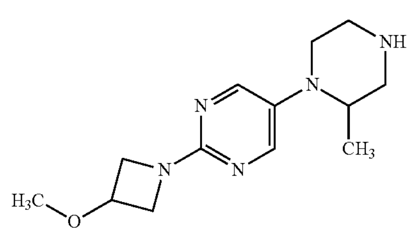 [SMILES: COC1CN(c2ncc(N3CCNCC3C)cn2)C1] |

TABLE 48-continued

| Rf | Syn | Structure |
|---|---|---|
| 711 | R712 | (structure) |
| 712 | R712 | (structure) |
| 713 | R686 | (structure) |
| 714 | R686 | (structure) |
| 715 | R686 | (structure) |
| 716 | R686 | (structure) |
| 717 | R686 | (structure) |

TABLE 48-continued
| Rf | Syn | Structure |
|---|---|---|
| 718 | R686 | 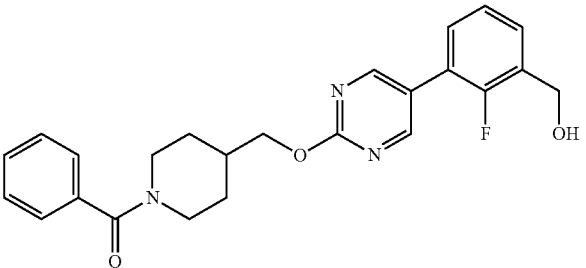 [SMILES: O=C(c1ccccc1)N1CCC(COc2ncc(-c3cccc(CO)c3F)cn2)CC1] |
TABLE 49
| Rf | Syn | Structure |
|---|---|---|
| 719 | R686 | 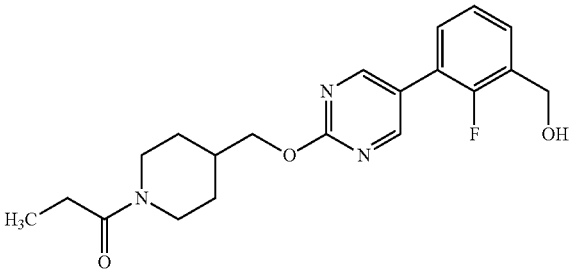 [SMILES: CCC(=O)N1CCC(COc2ncc(-c3cccc(CO)c3F)cn2)CC1] |
| 720 | R686 | 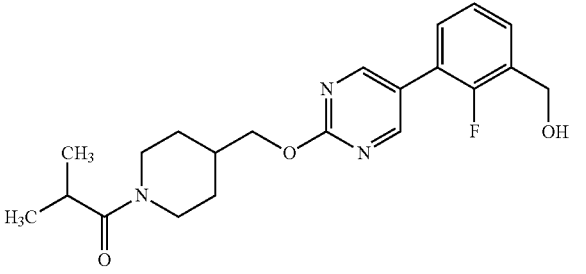 [SMILES: CC(C)C(=O)N1CCC(COc2ncc(-c3cccc(CO)c3F)cn2)CC1] |
| 721 | R686 | 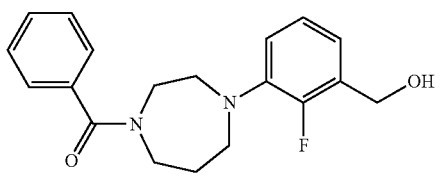 [SMILES: O=C(c1ccccc1)N1CCCN(c2cccc(CO)c2F)CC1] |
| 722 | R686 | 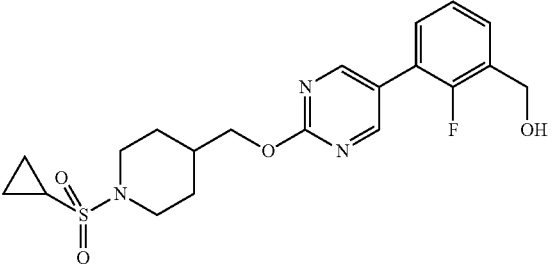 [SMILES: O=S(=O)(C1CC1)N1CCC(COc2ncc(-c3cccc(CO)c3F)cn2)CC1] |

TABLE 49-continued

| Rf | Syn | Structure |
|---|---|---|
| 723 | R686 | 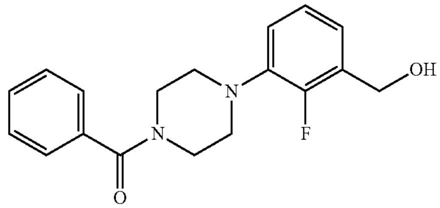 [SMILES: O=C(c1ccccc1)N1CCN(c2cccc(CO)c2F)CC1] |
| 724 | R686 | 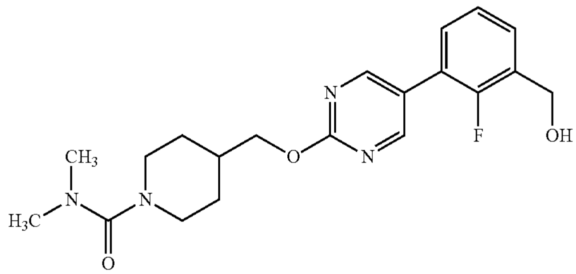 [SMILES: CN(C)C(=O)N1CCC(COc2ncc(-c3cccc(CO)c3F)cn2)CC1] |
| 725 | R686 | 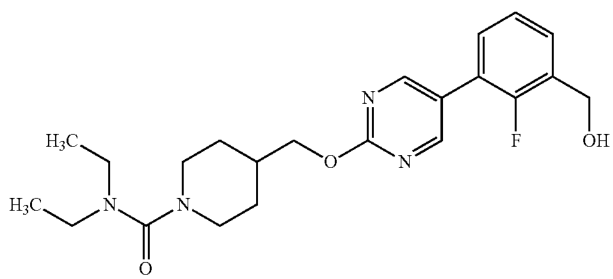 [SMILES: CCN(CC)C(=O)N1CCC(COc2ncc(-c3cccc(CO)c3F)cn2)CC1] |
| 726 | R343 | 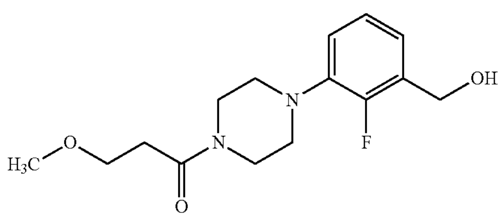 [SMILES: COCCC(=O)N1CCN(c2cccc(CO)c2F)CC1] |
| 727 | R343 | 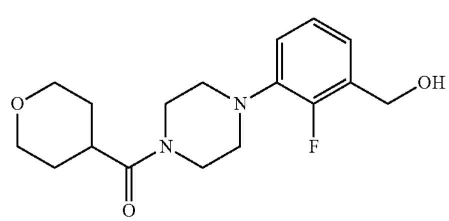 [SMILES: O=C(C1CCOCC1)N1CCN(c2cccc(CO)c2F)CC1] |
| 728 | R343 | 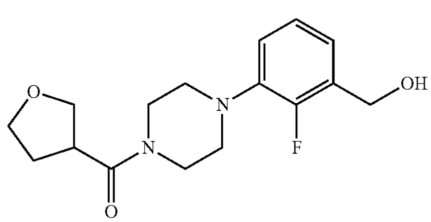 [SMILES: O=C(C1CCOC1)N1CCN(c2cccc(CO)c2F)CC1] |

TABLE 49-continued

| Rf | Syn | Structure |
|---|---|---|
| 729 | R343 | 1-acetylpiperidine-4-carbonyl linked to piperazine N-(2-fluoro-3-(hydroxymethyl)phenyl) |
| 730 | R343 | 4-methoxycyclohexanecarbonyl linked to piperazine N-(2-fluoro-3-(hydroxymethyl)phenyl) |
| 731 | R343 | 4-methoxybenzoyl linked to piperazine N-(2-fluoro-3-(hydroxymethyl)phenyl) |
| 732 | R343 | 2-methoxybenzoyl linked to piperazine N-(2-fluoro-3-(hydroxymethyl)phenyl) |
| 733 | R343 | pyridine-2-carbonyl linked to piperazine N-(2-fluoro-3-(hydroxymethyl)phenyl) |
| 734 | R343 | pyridine-3-carbonyl linked to piperazine N-(2-fluoro-3-(hydroxymethyl)phenyl) |

TABLE 50

| Rf | Syn | Structure |
|---|---|---|
| 735 | R343 | 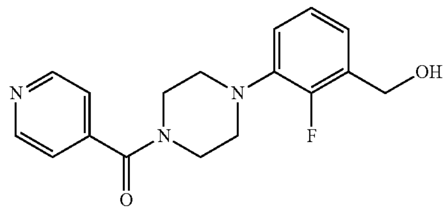 [SMILES: O=C(c1ccncc1)N1CCN(c2cccc(CO)c2F)CC1] |
| 736 | R343 | 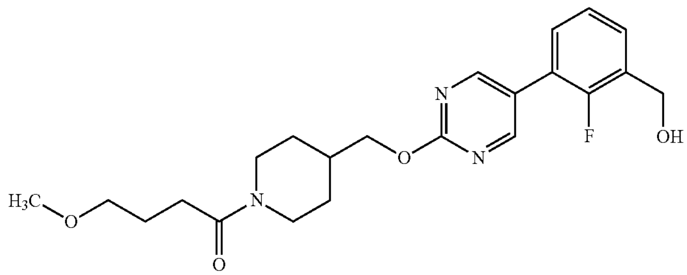 [SMILES: COCCCC(=O)N1CCC(COc2ncc(-c3cccc(CO)c3F)cn2)CC1] |
| 737 | R343 | 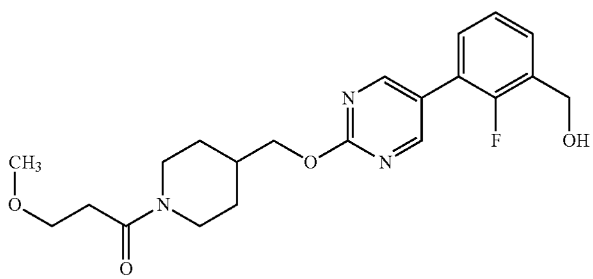 [SMILES: COCCC(=O)N1CCC(COc2ncc(-c3cccc(CO)c3F)cn2)CC1] |
| 738 | R343 | 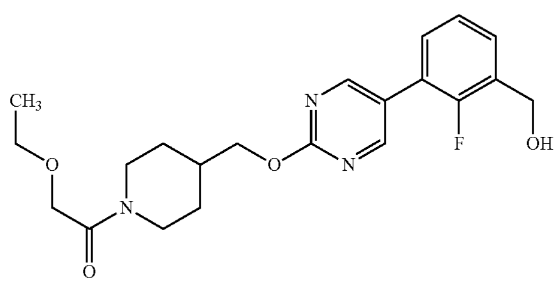 [SMILES: CCOCC(=O)N1CCC(COc2ncc(-c3cccc(CO)c3F)cn2)CC1] |
| 739 | R343 | 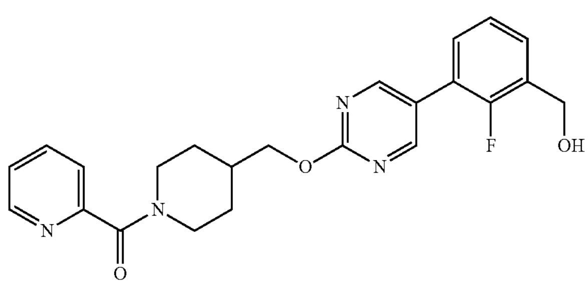 [SMILES: O=C(c1ccccn1)N1CCC(COc2ncc(-c3cccc(CO)c3F)cn2)CC1] |

TABLE 50-continued

| Rf | Syn | Structure |
|---|---|---|
| 740 | R343 | 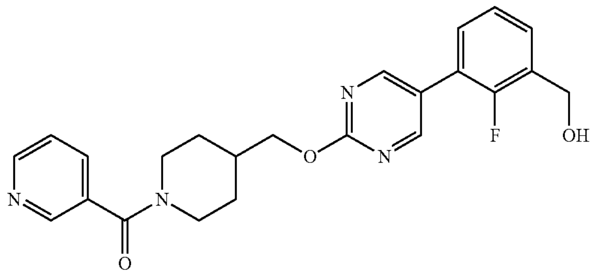 [SMILES: O=C(c1cccnc1)N1CCC(COc2ncc(-c3cccc(CO)c3F)cn2)CC1] |
| 741 | R343 | 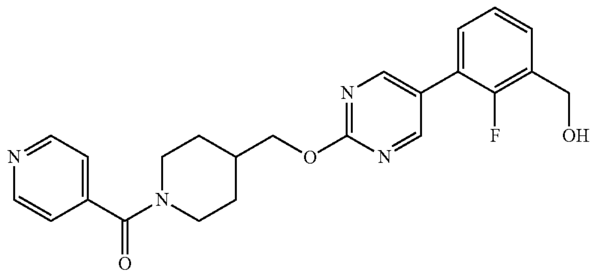 [SMILES: O=C(c1ccncc1)N1CCC(COc2ncc(-c3cccc(CO)c3F)cn2)CC1] |
| 742 | R343 | 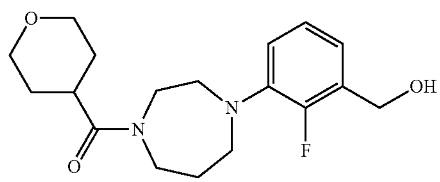 [SMILES: O=C(C1CCOCC1)N1CCCN(c2cccc(CO)c2F)CC1] |
| 743 | R343 | cis- |
| 744 | R343 | 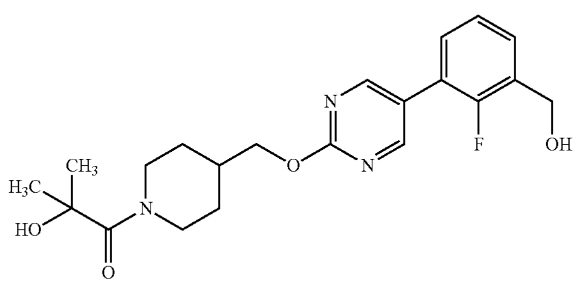 [SMILES: CC(C)(O)C(=O)N1CCC(COc2ncc(-c3cccc(CO)c3F)cn2)CC1] |
| 745 | R343 | 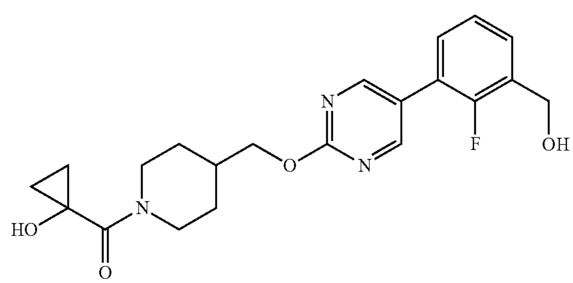 [SMILES: O=C(N1CCC(COc2ncc(-c3cccc(CO)c3F)cn2)CC1)C1(O)CC1] |

TABLE 50-continued

| Rf | Syn | Structure |
|---|---|---|
| 746 | R343 | 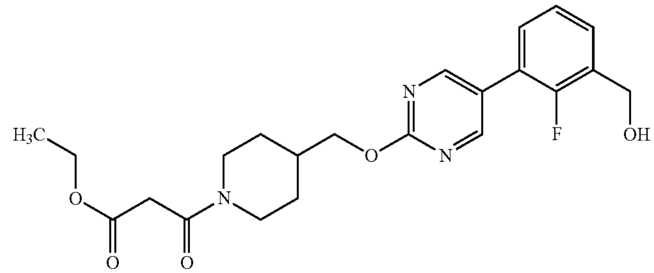 [SMILES: CCOC(=O)CC(=O)N1CCC(COc2ncc(-c3cccc(CO)c3F)cn2)CC1] |
| 747 | R343 | 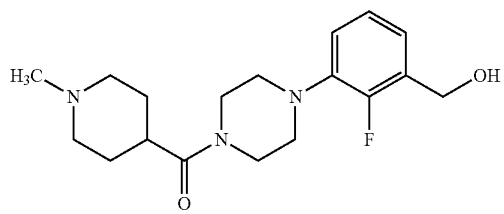 [SMILES: CN1CCC(C(=O)N2CCN(c3cccc(CO)c3F)CC2)CC1] |
| 748 | R343 | 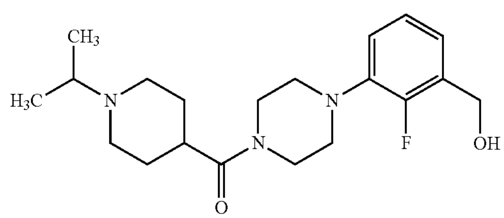 [SMILES: CC(C)N1CCC(C(=O)N2CCN(c3cccc(CO)c3F)CC2)CC1] |
| 749 | R749 | 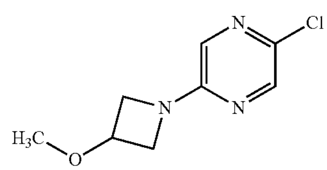 |
| 750 | R752 | 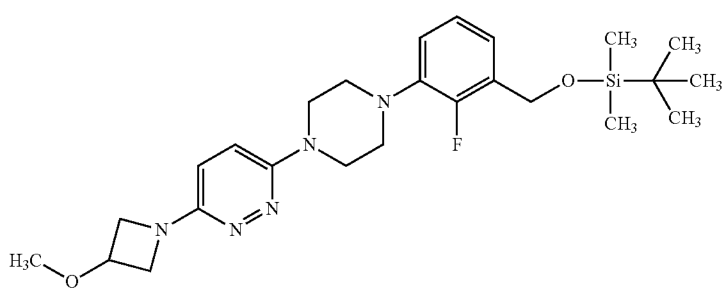 |

TABLE 51

| Rf | Syn | Structure |
|---|---|---|
| 751 | R752 | 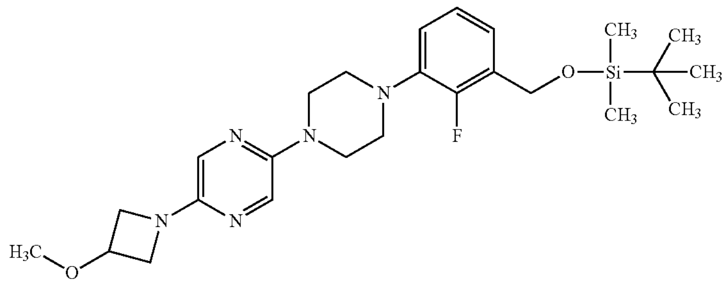 [SMILES: COC1CN(c2cnc(N3CCN(c4cccc(CO[Si](C)(C)C(C)(C)C)c4F)CC3)cn2)C1] |
| 752 | R752 | 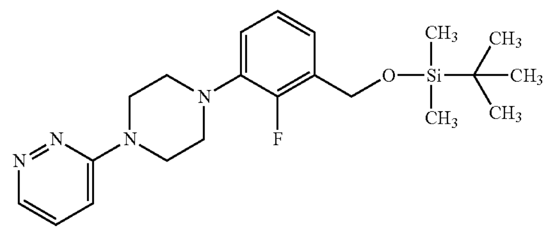 [SMILES: CC(C)(C)[Si](C)(C)OCc1cccc(N2CCN(c3cccnn3)CC2)c1F] |
| 753 | R754 | 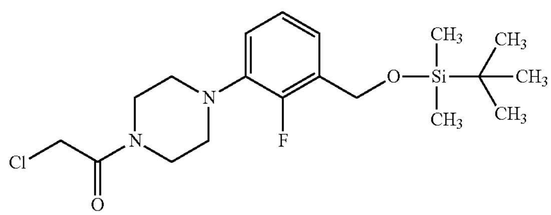 [SMILES: CC(C)(C)[Si](C)(C)OCc1cccc(N2CCN(C(=O)CCl)CC2)c1F] |
| 754 | R754 | 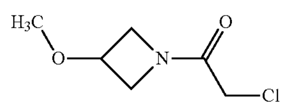 |
| 755 | R754 | 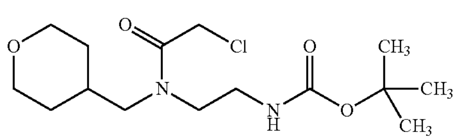 [SMILES: CC(C)(C)OC(=O)NCCN(CC1CCOCC1)C(=O)CCl] |
| 756 | R754 | 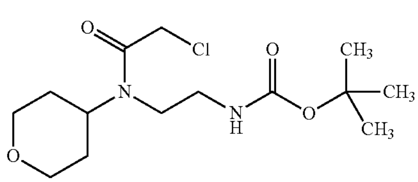 [SMILES: CC(C)(C)OC(=O)NCCN(C(=O)CCl)C1CCOCC1] |
| 757 | R754 | 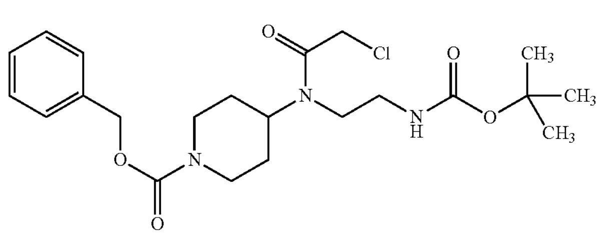 [SMILES: CC(C)(C)OC(=O)NCCN(C(=O)CCl)C1CCN(C(=O)OCc2ccccc2)CC1] |

TABLE 51-continued

| Rf | Syn | Structure |
|---|---|---|
| 758 | R758 | 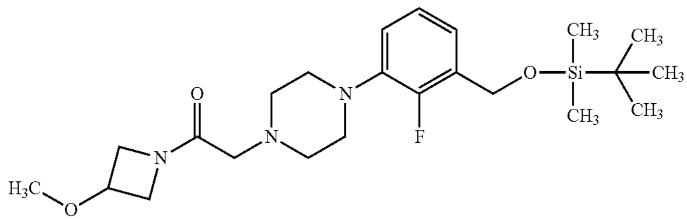 [SMILES: COC1CN(C(=O)CN2CCN(c3cccc(CO[Si](C)(C)C(C)(C)C)c3F)CC2)C1] |
| 759 | R758 | 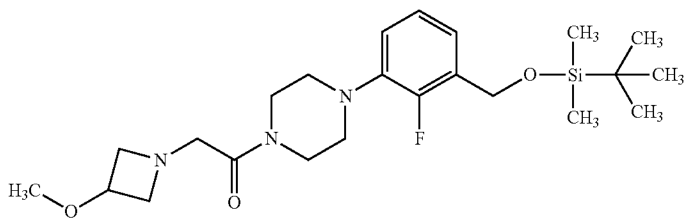 [SMILES: COC1CN(CC(=O)N2CCN(c3cccc(CO[Si](C)(C)C(C)(C)C)c3F)CC2)C1] |
| 760 | R760 | 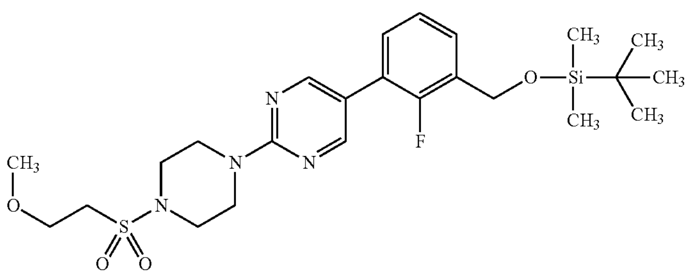 [SMILES: COCCS(=O)(=O)N1CCN(c2ncc(-c3cccc(CO[Si](C)(C)C(C)(C)C)c3F)cn2)CC1] |
| 761 | R761 | 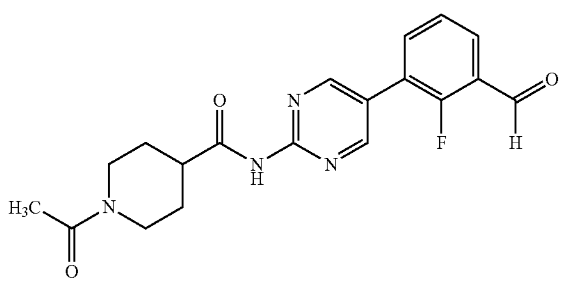 [SMILES: CC(=O)N1CCC(C(=O)Nc2ncc(-c3cccc(C=O)c3F)cn2)CC1] |
| 762 | R766 | 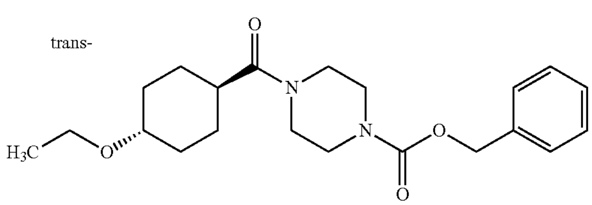 [SMILES: CCO[C@H]1CC[C@H](C(=O)N2CCN(C(=O)OCc3ccccc3)CC2)CC1] |
| 763 | R766 | 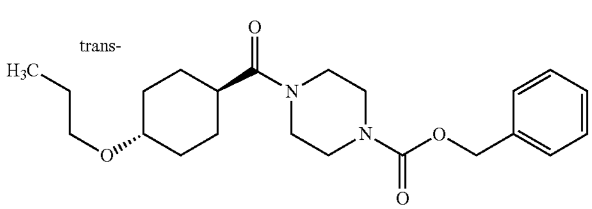 [SMILES: CCCO[C@H]1CC[C@H](C(=O)N2CCN(C(=O)OCc3ccccc3)CC2)CC1] |

TABLE 51-continued
| Rf | Syn | Structure |
|---|---|---|
| 764 | R766 | 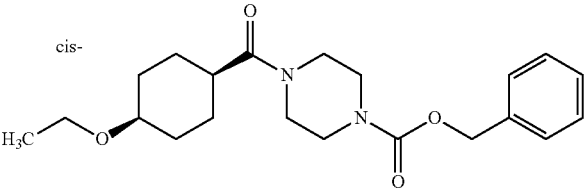 [SMILES: CCO[C@H]1CC[C@@H](C(=O)N2CCN(C(=O)OCc3ccccc3)CC2)CC1] |
| 765 | R766 | 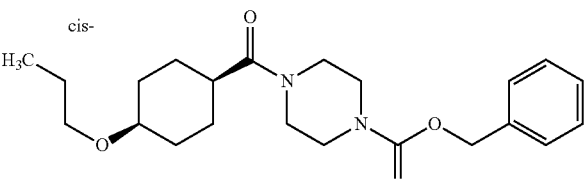 |
| 766 | R766 | 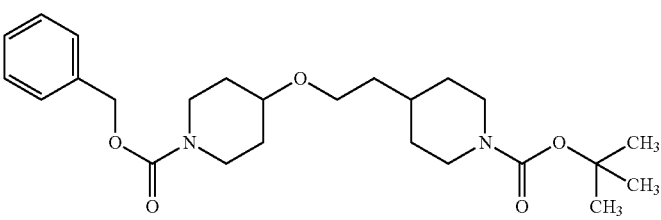 [SMILES: CC(C)(C)OC(=O)N1CCC(CCOC2CCN(C(=O)OCc3ccccc3)CC2)CC1] |
TABLE 52
| Rf | Syn | Structure |
|---|---|---|
| 767 | R767 | 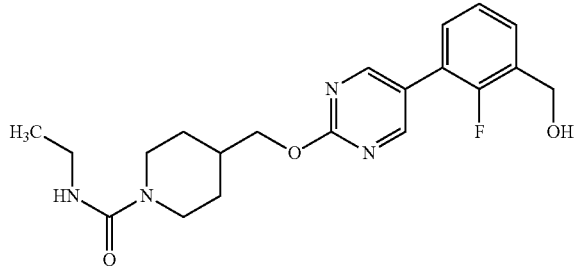 [SMILES: CCNC(=O)N1CCC(COc2ncc(-c3cccc(CO)c3F)cn2)CC1] |
| 768 | R767 | 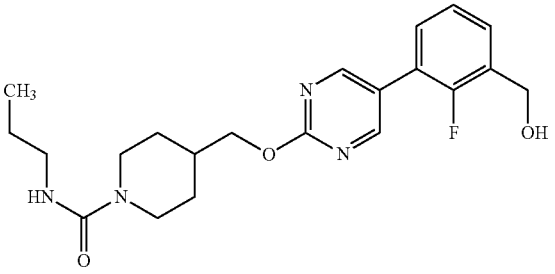 [SMILES: CCCNC(=O)N1CCC(COc2ncc(-c3cccc(CO)c3F)cn2)CC1] |
| 769 | R341 | 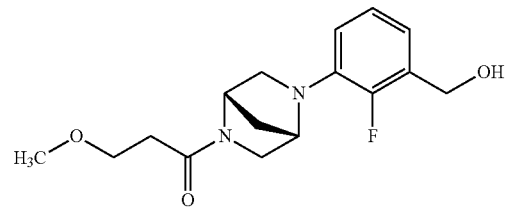 [SMILES: COCCC(=O)N1C[C@@H]2C[C@H]1CN2c1cccc(CO)c1F] |

TABLE 52-continued

| Rf | Syn | Structure |
|---|---|---|
| 770 | R341 | 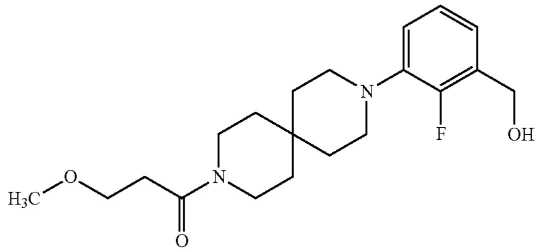 [SMILES: COCCC(=O)N1CCC2(CC1)CCN(c1cccc(CO)c1F)CC2] |
| 771 | R341 | 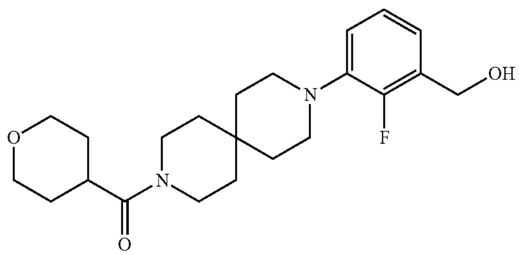 [SMILES: O=C(C1CCOCC1)N1CCC2(CC1)CCN(c1cccc(CO)c1F)CC2] |
| 772 | R772 | 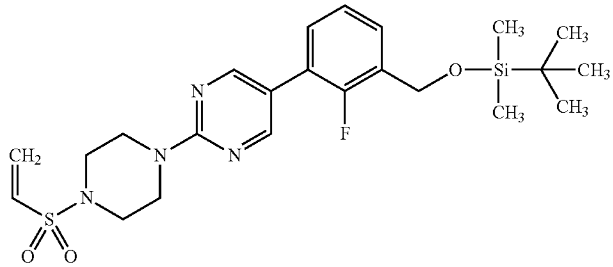 [SMILES: C=CS(=O)(=O)N1CCN(c2ncc(-c3cccc(CO[Si](C)(C)C(C)(C)C)c3F)cn2)CC1] |
| 773 | R776 | 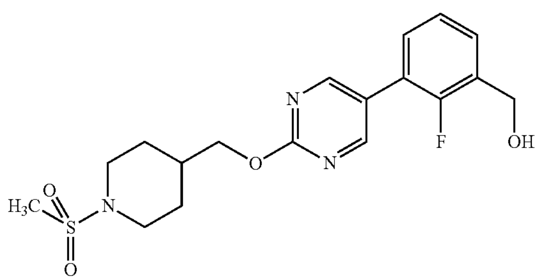 [SMILES: CS(=O)(=O)N1CCC(COc2ncc(-c3cccc(CO)c3F)cn2)CC1] |
| 774 | R776 | 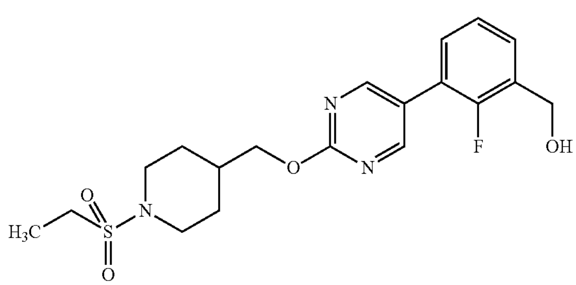 [SMILES: CCS(=O)(=O)N1CCC(COc2ncc(-c3cccc(CO)c3F)cn2)CC1] |
| 775 | R776 | 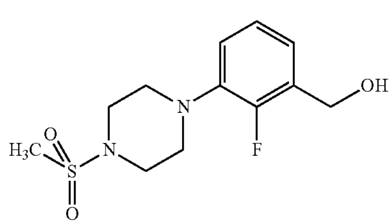 [SMILES: CS(=O)(=O)N1CCN(c2cccc(CO)c2F)CC1] |

TABLE 52-continued

| Rf | Syn | Structure |
|---|---|---|
| 776 | R776 | 3-(4-ethanesulfonylpiperazin-1-yl)-2-fluorobenzyl alcohol |
| 777 | R776 | 3-(4-cyclopropanesulfonylpiperazin-1-yl)-2-fluorobenzyl alcohol |
| 778 | R776 | 2-fluoro-3-(4-propane-1-sulfonylpiperazin-1-yl)benzyl alcohol |
| 779 | R776 | 2-fluoro-3-(4-propane-2-sulfonylpiperazin-1-yl)benzyl alcohol |
| 780 | R776 | 3-(4-cyclohexanesulfonylpiperazin-1-yl)-2-fluorobenzyl alcohol |
| 781 | R776 | 3-[4-(N,N-dimethylsulfamoyl)piperazin-1-yl]-2-fluorobenzyl alcohol |
| 782 | R776 | 3-[4-(N,N-diethylsulfamoyl)piperazin-1-yl]-2-fluorobenzyl alcohol |

TABLE 53
| Rf | Syn | Structure |
|---|---|---|
| 783 | R776 | 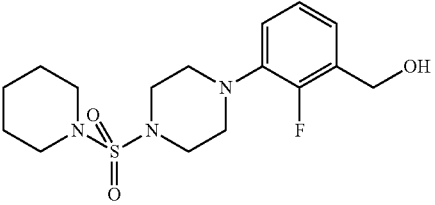 [SMILES: O=S(=O)(N1CCCCC1)N1CCN(c2cccc(CO)c2F)CC1] |
| 784 | R776 | 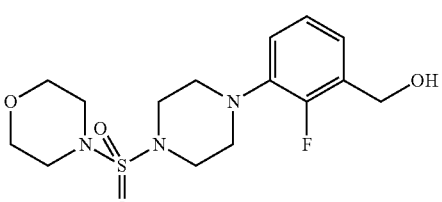 |
| 785 | R776 | 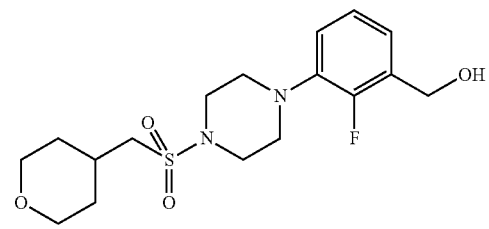 [SMILES: O=S(=O)(CC1CCOCC1)N1CCN(c2cccc(CO)c2F)CC1] |
| 786 | R776 | 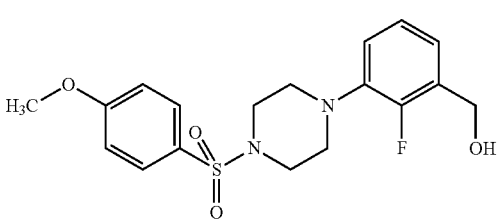 [SMILES: COc1ccc(S(=O)(=O)N2CCN(c3cccc(CO)c3F)CC2)cc1] |
| 787 | R776 | 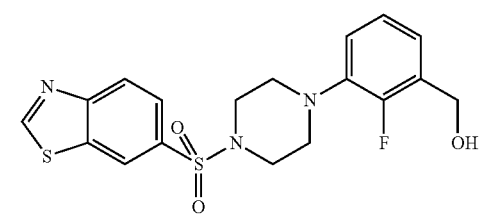 [SMILES: O=S(=O)(c1ccc2ncsc2c1)N1CCN(c2cccc(CO)c2F)CC1] |
| 788 | R776 | 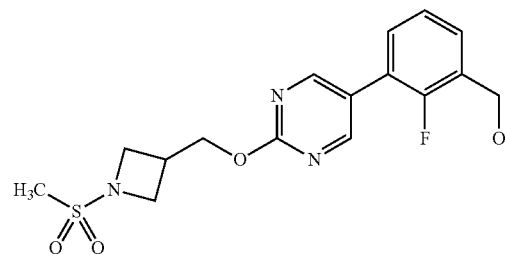 |

TABLE 53-continued

| Rf | Syn | Structure |
|---|---|---|
| 789 | R776 | 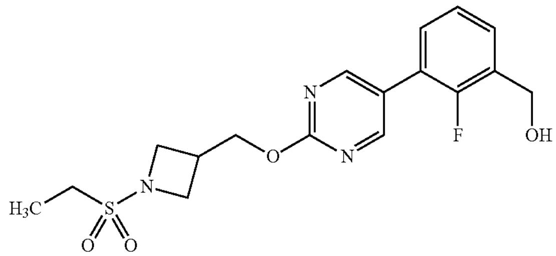 [SMILES: CCS(=O)(=O)N1CC(COc2ncc(-c3cccc(CO)c3F)cn2)C1] |
| 790 | R776 | 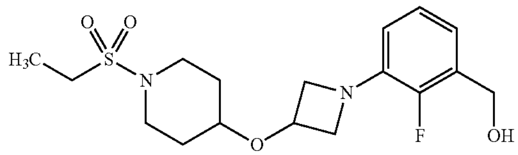 [SMILES: CCS(=O)(=O)N1CCC(OC2CN(c3cccc(CO)c3F)C2)CC1] |
| 791 | R791 | 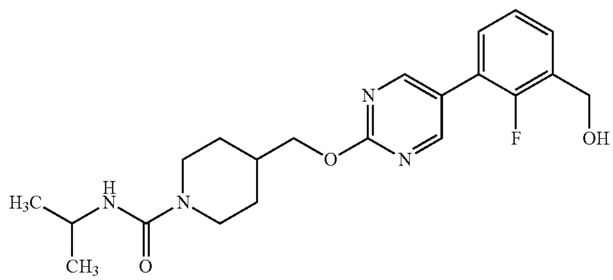 [SMILES: CC(C)NC(=O)N1CCC(COc2ncc(-c3cccc(CO)c3F)cn2)CC1] |
| 792 | R791 | 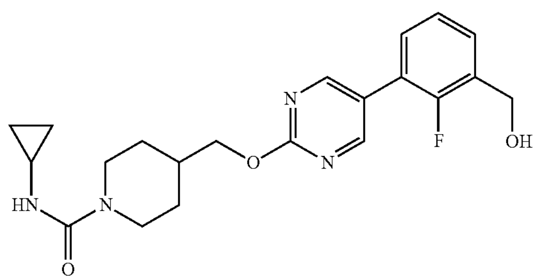 [SMILES: O=C(NC1CC1)N1CCC(COc2ncc(-c3cccc(CO)c3F)cn2)CC1] |
| 793 | R793 | 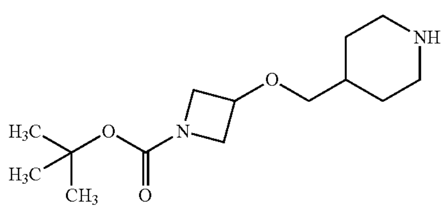 [SMILES: CC(C)(C)OC(=O)N1CC(OCC2CCNCC2)C1] |
| 794 | R793 | 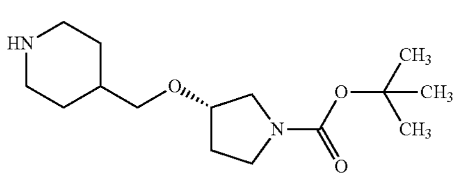 [SMILES: CC(C)(C)OC(=O)N1CC[C@H](OCC2CCNCC2)C1] |
| 795 | R796 | 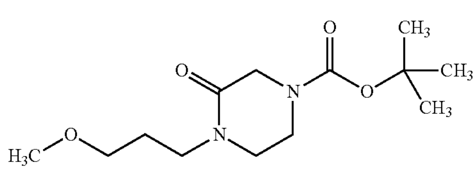 [SMILES: COCCCN1CCN(C(=O)OC(C)(C)C)CC1=O] |

TABLE 53-continued

| Rf | Syn | Structure |
| --- | --- | --- |
| 796 | R796 | 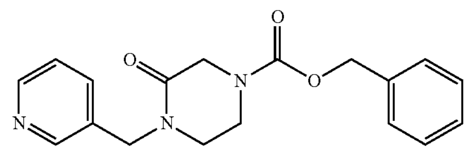 [SMILES: O=C1CN(C(=O)OCc2ccccc2)CCN1Cc1cccnc1] |
| 797 | R801 | 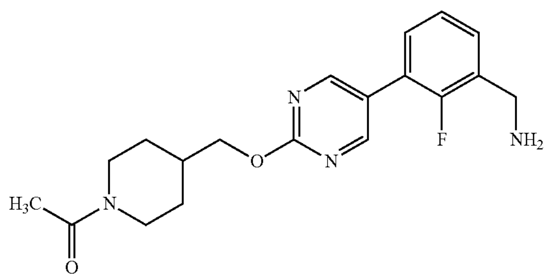 [SMILES: CC(=O)N1CCC(COc2ncc(-c3cccc(CN)c3F)cn2)CC1] |
| 798 | R801 | 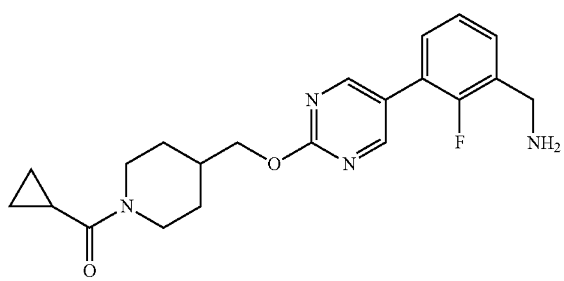 [SMILES: NCc1cccc(-c2cnc(OCC3CCN(C(=O)C4CC4)CC3)nc2)c1F] |

TABLE 54

| Rf | Syn | Structure |
| --- | --- | --- |
| 799 | R801 | 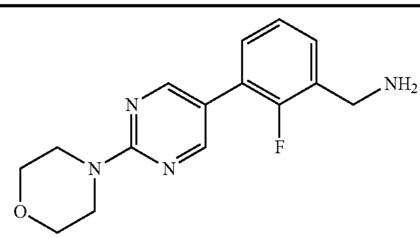 |
| 800 | R801 | 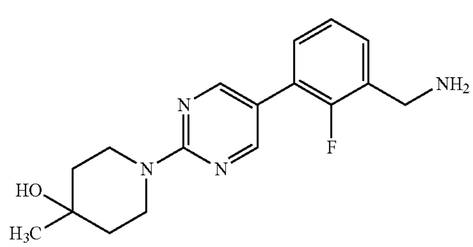 [SMILES: CC1(O)CCN(c2ncc(-c3cccc(CN)c3F)cn2)CC1] |

TABLE 54-continued

| Rf | Syn | Structure |
|---|---|---|
| 801 | R801 | 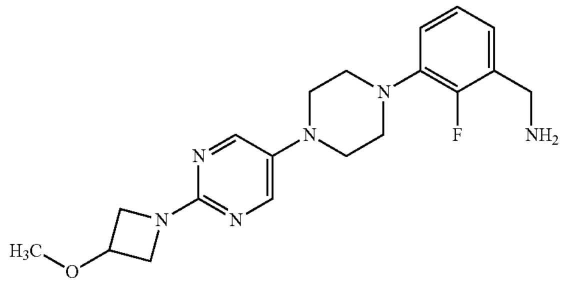 [SMILES: COC1CN(c2ncc(N3CCN(c4cccc(CN)c4F)CC3)cn2)C1] |
| 802 | R343 | trans- |
| 803 | R803 | 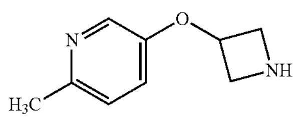 |
| 804 | R803 | 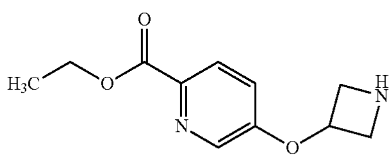 [SMILES: CCOC(=O)c1ccc(OC2CNC2)cn1] |
| 805 | R805 | 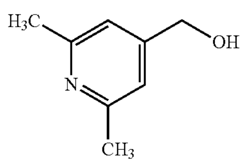 |
| 806 | R806 | HCl |
| 807 | R807 | 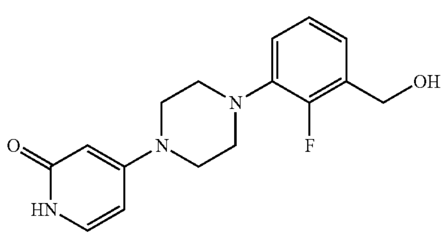 [SMILES: O=c1cc(N2CCN(c3cccc(CO)c3F)CC2)cc[nH]1] |
| 808 | R809 | 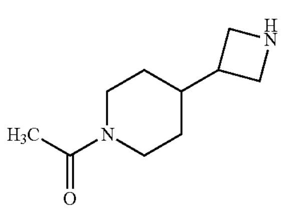 |

TABLE 54-continued
| Rf | Syn | Structure |
|---|---|---|
| 809 | R809 | 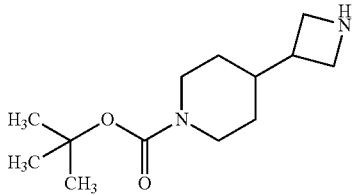 [SMILES: CC(C)(C)OC(=O)N1CCC(C2CNC2)CC1] |
| 810 | R810 | 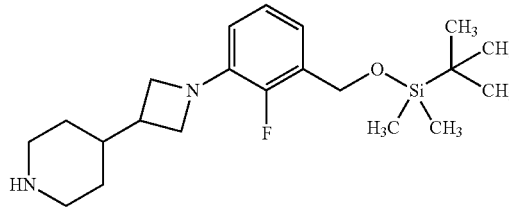 |
| 811 | R228 | 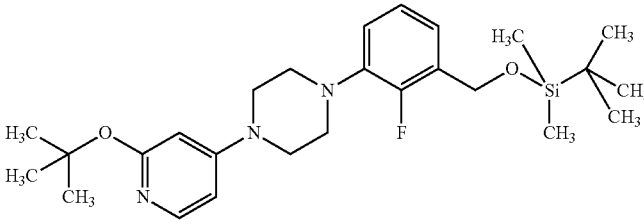 [SMILES: CC(C)(C)Oc1cc(N2CCN(c3cccc(CO[Si](C)(C)C(C)(C)C)c3F)CC2)ccn1] |
| 812 | R228 | 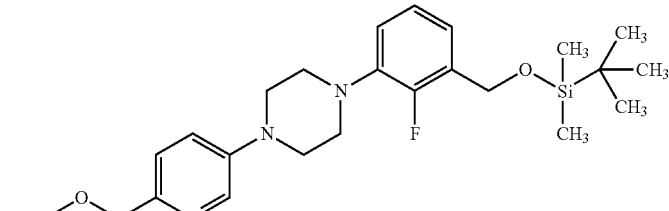 |
TABLE 55
| Rf | Syn | Structure |
|---|---|---|
| 813 | R228 | 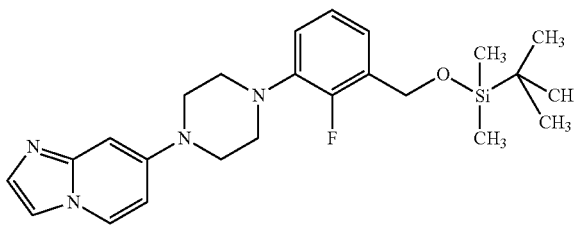 |
| 814 | R228 | 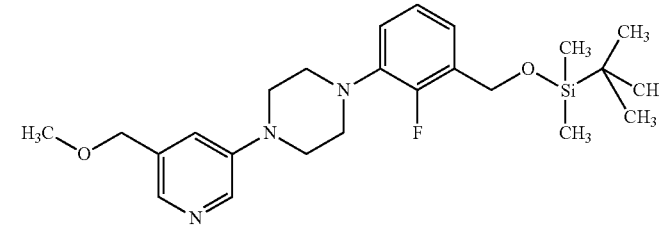 [SMILES: COCc1cncc(N2CCN(c3cccc(CO[Si](C)(C)C(C)(C)C)c3F)CC2)c1] |

TABLE 55-continued

| Rf | Syn | Structure |
|---|---|---|
| 815 | R228 | 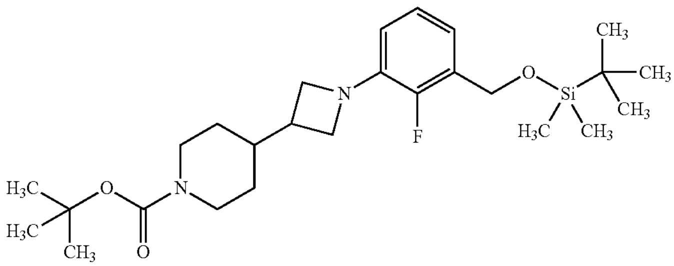 [SMILES: CC(C)(C)OC(=O)N1CCC(C2CN(c3cccc(CO[Si](C)(C)C(C)(C)C)c3F)C2)CC1] |
| 816 | R228 | 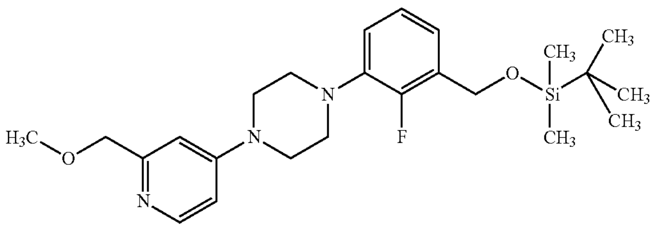 [SMILES: COCc1cc(N2CCN(c3cccc(CO[Si](C)(C)C(C)(C)C)c3F)CC2)ccn1] |
| 817 | R285 | 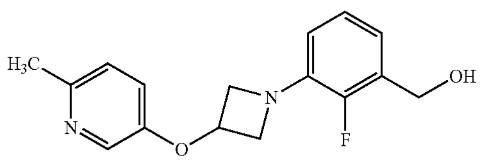 [SMILES: Cc1ccc(OC2CN(c3cccc(CO)c3F)C2)cn1] |
| 818 | R285 | 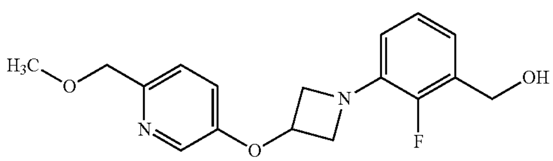 [SMILES: COCc1ccc(OC2CN(c3cccc(CO)c3F)C2)cn1] |
| 819 | R285 | 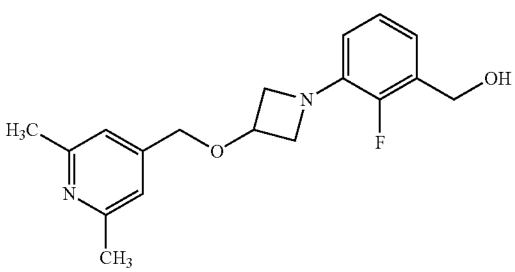 [SMILES: Cc1cc(COC2CN(c3cccc(CO)c3F)C2)cc(C)n1] |
| 820 | R285 | 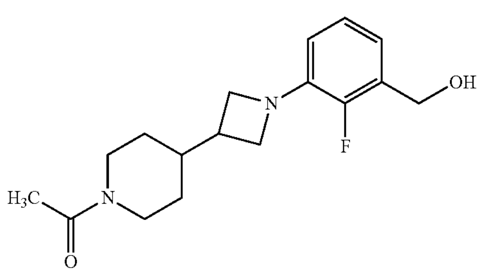 [SMILES: CC(=O)N1CCC(C2CN(c3cccc(CO)c3F)C2)CC1] |
| 821 | R821 | 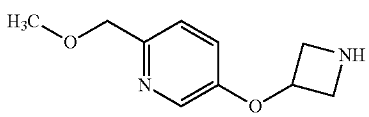 |

TABLE 55-continued

| Rf | Syn | Structure |
|---|---|---|
| 822 | R821 | 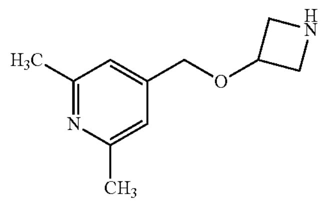 |
| 823 | R309 | 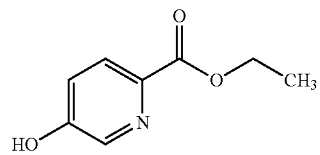 |
| 824 | R347 | 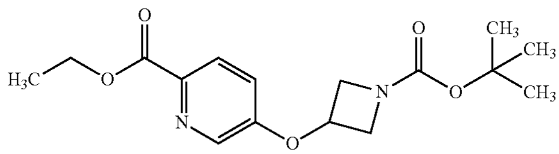 [SMILES: CCOC(=O)c1ccc(OC2CN(C(=O)OC(C)(C)C)C2)cn1] |
| 825 | R347 | 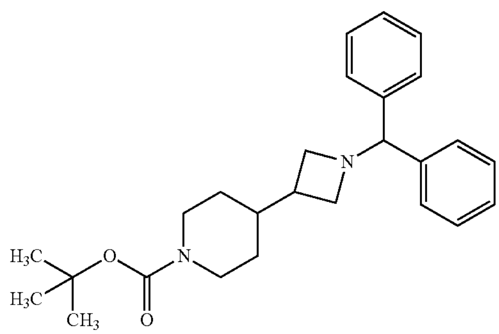 [SMILES: CC(C)(C)OC(=O)N1CCC(C2CN(C(c3ccccc3)c3ccccc3)C2)CC1] |
| 826 | R376 | 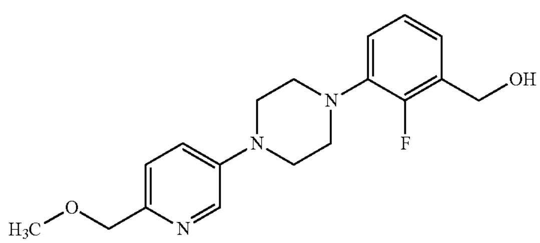 [SMILES: COCc1ccc(N2CCN(c3cccc(CO)c3F)CC2)cn1] |
| 827 | R376 | 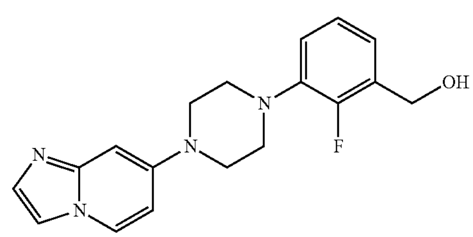 [SMILES: OCc1cccc(N2CCN(c3ccn4ccnc4c3)CC2)c1F] |
| 828 | R376 | 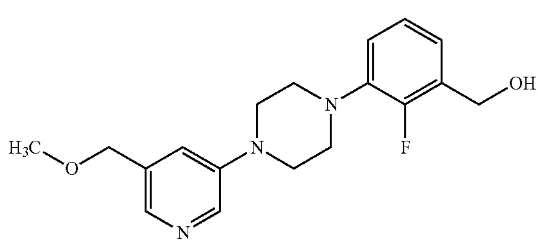 [SMILES: COCc1cncc(N2CCN(c3cccc(CO)c3F)CC2)c1] |

TABLE 56

| Rf | Syn | Structure |
|---|---|---|
| 829 | R376 | 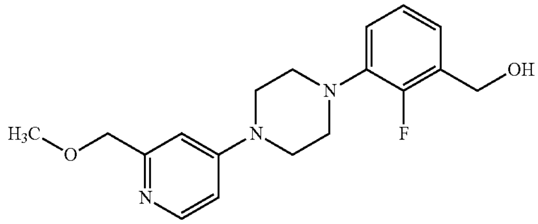 [SMILES: COCc1cc(N2CCN(c3cccc(CO)c3F)CC2)ccn1] |
| 830 | R830 | 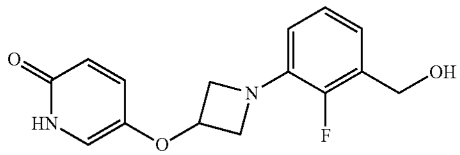 [SMILES: O=c1ccc(OC2CN(c3cccc(CO)c3F)C2)c[nH]1] |
| 831 | R663 | 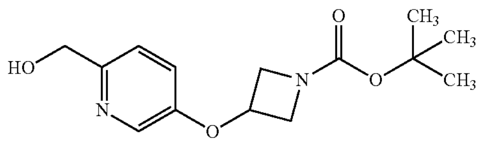 [SMILES: CC(C)(C)OC(=O)N1CC(Oc2ccc(CO)nc2)C1] |
| 832 | R677 | 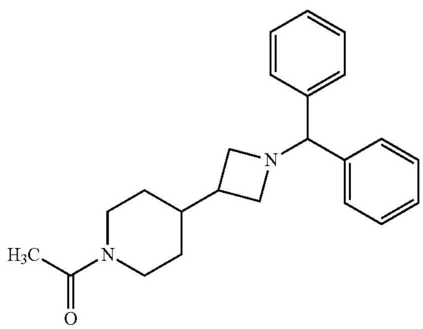 [SMILES: CC(=O)N1CCC(C2CN(C(c3ccccc3)c3ccccc3)C2)CC1] |
| 833 | R686 | 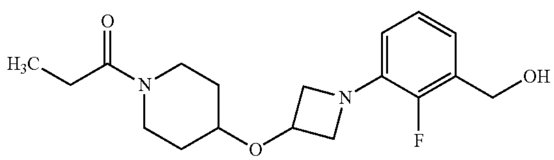 [SMILES: CCC(=O)N1CCC(OC2CN(c3cccc(CO)c3F)C2)CC1] |
| 834 | R834 | 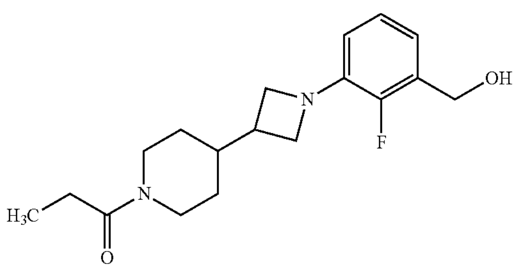 [SMILES: CCC(=O)N1CCC(C2CN(c3cccc(CO)c3F)C2)CC1] |
| 835 | R834 | 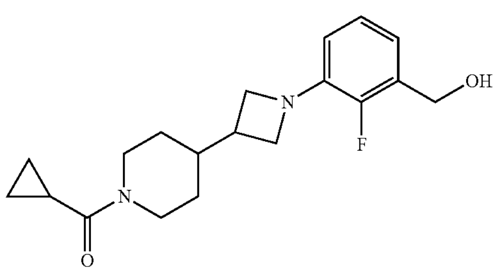 [SMILES: O=C(C1CC1)N1CCC(C2CN(c3cccc(CO)c3F)C2)CC1] |

TABLE 56-continued

| Rf | Syn | Structure |
|---|---|---|
| 836 | R836 | 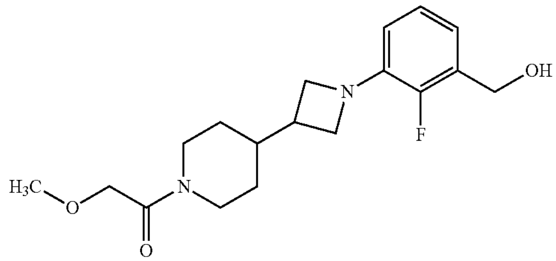 [SMILES: COCC(=O)N1CCC(C2CN(c3cccc(CO)c3F)C2)CC1] |
| 837 | R836 | 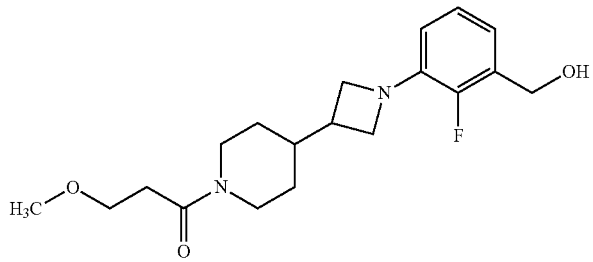 [SMILES: COCCC(=O)N1CCC(C2CN(c3cccc(CO)c3F)C2)CC1] |
| 838 | R776 | 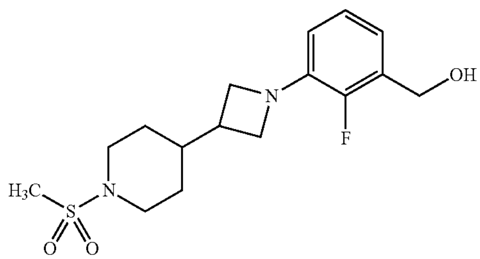 [SMILES: CS(=O)(=O)N1CCC(C2CN(c3cccc(CO)c3F)C2)CC1] |
| 839 | R285 | 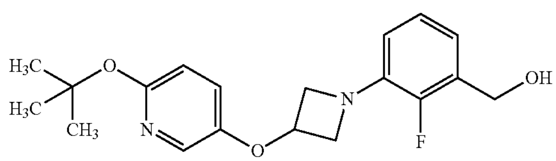 [SMILES: CC(C)(C)Oc1ccc(OC2CN(c3cccc(CO)c3F)C2)cn1] |
| 840 | R840 | 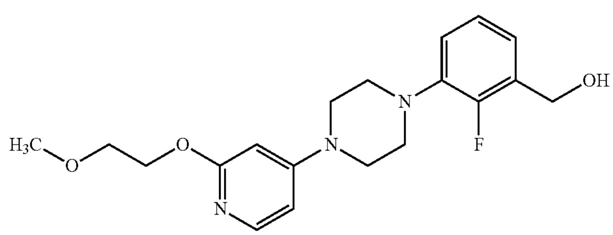 [SMILES: COCCOc1cc(N2CCN(c3cccc(CO)c3F)CC2)ccn1] |
| 841 | R841 | 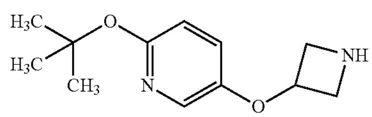 [SMILES: CC(C)(C)Oc1ccc(OC2CNC2)cn1] |
| 842 | R842 | 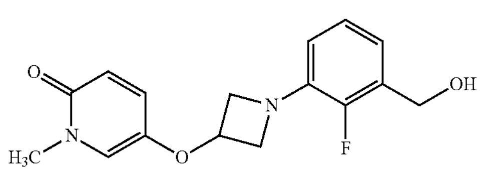 [SMILES: Cn1cc(OC2CN(c3cccc(CO)c3F)C2)ccc1=O] |

TABLE 57

| Rf | Data |
| --- | --- |
| 1 | ESI+: 500 |
| 2 | ESI+: 288 |
| 3 | ESI+: 288 |
| 4 | ESI+: 320 |
| 5 | ESI+: 288 |
| 6 | ESI+: 288 |
| 7 | ESI+: 218 |
| 8 | ESI+: 356 |
| 9 | ESI+: 275 |
| 10 | ESI+: 289 |
| 11 | ESI+: 272 |
| 12 | ESI+: 270 |
| 13 | ESI+: 277 |
| 14 | ESI+: 340 |
| 15 | ESI+: 385 |
| 16 | ESI+: 371 |
| 17 | ESI+: 369 |
| 18 | ESI+: 461 |
| 19 | ESI+: 538, 540 |
| 20 | ESI+: 334 |
| 21 | ESI+: 221 |
| 22 | ESI+: 286 |
| 23 | ESI+: 237 |
| 24 | ESI+: 286 |
| 25 | ESI+: 286 |
| 26 | APCI/ESI+: 290 |
| 27 | APCI/ESI+: 306 |
| 28 | APCI/ESI+: 347 |
| 29 | APCI/ESI+: 347 |
| 30 | APCI/ESI+: 287 |
| 31 | APCI/ESI+: 287 |
| 32 | ESI+: 308 |
| 33 | EI: 234 |

TABLE 58

| Rf | Data |
| --- | --- |
| 34 | EI: 248 |
| 35 | EI: 248 |
| 36 | EI: 252 |
| 37 | EI: 268 |
| 38 | APCI/ESI+: 182 |
| 39 | EI: 166 |
| 40 | ESI+: 501 |
| 41 | ESI+: 444 |
| 42 | APCI/ESI+: 282 |
| 43 | APCI/ESI+: 296 |
| 44 | ESI+: 399 |
| 45 | ESI+: 285 |
| 46 | ESI+: 299 |
| 47 | ESI+: 418 |
| 48 | ESI+: 429 |
| 49 | ESI+: 285 |
| 50 | ESI+: 200 |
| 51 | ESI+: 257 |
| 52 | ESI+: 271 |
| 53 | ESI+: 369 [M]+ |
| 54 | ESI+: 284 [M]+ |
| 55 | ESI+: 341 [M]+ |
| 56 | ESI+: 355 [M]+ |
| 57 | ESI+: 211 |
| 58 | ESI+: 251 |
| 59 | ESI+: 265 |
| 60 | ESI+: 303 |
| 61 | ESI+: 303 |
| 62 | ESI+: 164 |
| 63 | ESI+: 193 |
| 64 | ESI+: 207 |
| 65 | ESI+: 165 |
| 66 | ESI+: 179 |

TABLE 59

| Rf | Data |
| --- | --- |
| 67 | ESI+: 460 |
| 68 | ESI+: 502 |
| 69 | ESI+: 399 |
| 70 | ESI+: 364 |
| 71 | ESI+: 290 |
| 72 | ESI+: 290 |
| 73 | ESI+: 290 |
| 74 | ESI+: 290 |
| 75 | ESI+: 308 |
| 76 | ESI+: 304 |
| 77 | ESI+: 320 |
| 78 | ESI+: 333 |
| 79 | ESI+: 373 |
| 80 | ESI+: 239 |
| 81 | ESI+: 288 |
| 82 | APCI/ESI+: 289 |
| 83 | APCI/ESI+: 289 |
| 84 | ESI+: 332.15 |
| 85 | ESI+: 333.09 |
| 86 | ESI+: 341 |
| 87 | ESI+: 345 |
| 88 | ESI+: 380 |
| 89 | ESI+: 334 |
| 90 | ESI+: 372 |
| 91 | ESI+: 356 |
| 92 | ESI+: 443 |
| 93 | APCI/ESI+: 481, 483 |
| 94 | APCI/ESI+: 288, 290 |
| 95 | APCI/ESI+: 264, 266 |
| 96 | ESI+: 370 |
| 97 | ESI+: 532 |
| 98 | ESI+: 532 |
| 99 | ESI+: 271 |

TABLE 60

| Rf | Data |
| --- | --- |
| 100 | ESI+: 374 |
| 101 | ESI+: 389 |
| 102 | ESI+: 317 |
| 103 | ESI+: 318 |
| 104 | ESI+: 317 |
| 105 | ESI+: 334 |
| 106 | ESI+: 443 |
| 107 | ESI+: 360 |
| 108 | ESI+: 376 |
| 109 | ESI+: 402 |
| 110 | ESI+: 375 |
| 111 | ESI+: 318 |
| 112 | ESI+: 186 |
| 113 | ESI+: 166 |
| 114 | ESI+: 360 |
| 115 | ESI+: 332 |
| 116 | ESI+: 224 |
| 117 | ESI+: 460 |
| 118 | ESI+: 292 |
| 119 | ESI+: 319 |
| 120 | ESI+: 331 |
| 121 | ESI+: 331 |
| 122 | ESI+: 327 |
| 123 | ESI+: 399 |
| 124 | ESI+: 355 |
| 125 | ESI+: 441 |
| 126 | ESI+: 404 |
| 127 | ESI+: 447 |
| 128 | ESI+: 454 |
| 129 | ESI+: 399 |
| 130 | ESI+: 373 |
| 131 | ESI+: 300 |
| 132 | ESI+: 274 |

TABLE 61

| Rf | Data |
|---|---|
| 133 | ESI+: 256 |
| 134 | ESI+: 274 |
| 135 | ESI+: 300 |
| 136 | ESI+: 314 |
| 137 | ESI+: 328 |
| 138 | ESI+: 348 |
| 139 | ESI+: 292 |
| 140 | ESI+: 292 |
| 141 | ESI+: 274 |
| 142 | APCI/ESI+: 248 |
| 143 | APCI/ESI+: 318 |
| 144 | APCI/ESI+: 288 |
| 145 | ESI+: 306 |
| 146 | APCI/ESI+: 373 |
| 147 | APCI/ESI+: 306 |
| 148 | APCI/ESI+: 304 |
| 149 | APCI/ESI+: 336 |
| 150 | ESI+: 372 |
| 151 | ESI+: 386 |
| 152 | ESI+: 290 |
| 153 | APCI/ESI+: 304 |
| 154 | APCI/ESI+: 390 |
| 155 | APCI/ESI+: 465 |
| 156 | APCI/ESI+: 408 |
| 157 | APCI/ESI+: 278 |
| 158 | ESI+: 388 |
| 159 | ESI+: 415 |
| 160 | ESI+: 376 |
| 161 | ESI+: 277 |
| 162 | EI: 194 |
| 163 | ESI+: 249 |
| 164 | ESI+: 341 |
| 165 | ESI+: 472 |

TABLE 62

| Rf | Data |
|---|---|
| 166 | ESI+: 594 |
| 167 | ESI+: 524 |
| 168 | ESI+: 425 |
| 169 | ESI+: 495 |
| 170 | ESI+: 245 |
| 171 | ESI+: 259 |
| 172 | ESI+: 378 |
| 173 | ESI+: 417 |
| 174 | ESI+: 277 |
| 175 | ESI+: 271 |
| 176 | ESI+: 187 |
| 177 | ESI+: 332 |
| 178 | ESI+: 304 |
| 179 | ESI+: 210 |
| 180 | APCI/ESI+: 254 |
| 181 | APCI/ESI+: 268 |
| 182 | EI: 306 |
| 183 | APCI/ESI+: 488 |
| 184 | APCI/ESI+: 516 |
| 185 | APCI/ESI+: 488 |
| 186 | APCI/ESI+: 516 |
| 187 | APCI/ESI+: 487 |
| 188 | APCI/ESI+: 532 |
| 189 | APCI/ESI+: 487 |
| 190 | APCI/ESI+: 488 |
| 191 | APCI/ESI+: 407 |
| 192 | ESI+: 487 |
| 193 | APCI/ESI+: 508 |
| 194 | ESI+: 470 |
| 195 | APCI/ESI+: 433 |
| 196 | APCI/ESI+: 459 |
| 197 | APCI/ESI+: 503 |
| 198 | APCI/ESI+: 326 |

TABLE 63

| Rf | Data |
|---|---|
| 199 | APCI/ESI+: 479 |
| 200 | APCI/ESI+: 493 |
| 201 | APCI/ESI+: 479 |
| 202 | APCI/ESI+: 493 |
| 203 | APCI/ESI+: 555 |
| 204 | APCI/ESI+: 555 |
| 205 | APCI/ESI+: 326 |
| 206 | APCI/ESI+: 370 |
| 207 | APCI/ESI+: 381 |
| 208 | APCI/ESI+: 584 |
| 209 | APCI/ESI+: 558 |
| 210 | ESI+: 502 |
| 211 | ESI+: 319 |
| 212 | ESI+: 473 |
| 213 | ESI+: 457 |
| 214 | ESI+: 355 |
| 215 | ESI+: 487 |
| 216 | ESI+: 473 |
| 217 | ESI+: 437 |
| 218 | ESI+: 493 |
| 219 | ESI+: 487 |
| 220 | ESI+: 473 |
| 221 | ESI+: 473 |
| 222 | ESI+: 411 |
| 223 | ESI+: 423 |
| 224 | ESI+: 437 |
| 225 | ESI+: 402 |
| 226 | ESI+: 402 |
| 227 | ESI+: 556 |
| 228 | ESI+: 416 |
| 229 | ESI+: 430 |
| 230 | ESI+: 416 |
| 231 | ESI+: 416 |

TABLE 64

| Rf | Data |
|---|---|
| 232 | ESI+: 403 |
| 233 | ESI+: 416 |
| 234 | ESI+: 416 |
| 235 | ESI+: 416 |
| 236 | ESI+: 416 |
| 237 | ESI+: 416 |
| 238 | ESI+: 408 |
| 239 | ESI+: 416 |
| 240 | ESI+: 417 |
| 241 | ESI+: 430 |
| 242 | ESI+: 427 |
| 243 | ESI+: 413 |
| 244 | ESI+: 397 |
| 245 | ESI+: 389 |
| 246 | ESI+: 390 |
| 247 | ESI+: 350 |
| 248 | ESI+: 470 |
| 249 | ESI+: 398 |
| 250 | ESI+: 384 |
| 251 | ESI+: 384 |
| 252 | ESI+: 488 |
| 253 | ESI+: 402 |
| 254 | ESI+: 401 |
| 255 | ESI+: 431 |
| 256 | ESI+: 445 |
| 257 | ESI+: 459 |
| 258 | ESI+: 401 |
| 259 | ESI+: 478 |
| 260 | APCI/ESI+: 487 |
| 261 | APCI/ESI+: 487 |
| 262 | APCI/ESI+: 487 |
| 263 | APCI/ESI+: 487 |
| 264 | APCI/ESI+: 503 |

TABLE 65

| Rf | Data |
|---|---|
| 265 | ESI+: 503 |
| 266 | APCI/ESI+: 503 |
| 267 | APCI/ESI+: 409 |
| 268 | APCI/ESI+: 473 |
| 269 | APCI/ESI+: 502 |
| 270 | APCI/ESI+: 502 |
| 271 | APCI/ESI+: 541 |
| 272 | ESI+: 585 |
| 273 | ESI+: 535 |
| 274 | ESI+: 537 |
| 275 | ESI+: 571 |
| 276 | ESI+: 438 |
| 277 | ESI+: 523 |
| 278 | ESI+: 438 |
| 279 | ESI+: 543 |
| 280 | ESI+: 529 |
| 281 | ESI+: 543 |
| 282 | ESI+: 557 |
| 283 | ESI+: 402 |
| 284 | APCI/ESI+: 240 |
| 285 | ESI+: 275 |
| 286 | ESI+: 317 |
| 287 | ESI+: 331 |
| 288 | ESI+: 289 |
| 289 | ESI+: 303 |
| 290 | ESI+: 250 |
| 291 | ESI+: 250 |
| 292 | ESI+: 298 |
| 293 | ESI+: 277 |
| 294 | ESI+: 270 |
| 295 | ESI+: 269 |
| 296 | APCI/ESI+: 480, 482 |
| 297 | EI: 300, 302 |

TABLE 66

| Rf | Data |
|---|---|
| 298 | ESI+: 319 321 |
| 299 | ESI+: 257 |
| 300 | APCI/ESI+: 353 |
| 301 | ESI+: 416 |
| 302 | ESI+: 286 |
| 303 | ESI+: 417 |
| 304 | ESI+: 403 |
| 305 | APCI/ESI+: 320 |
| 306 | ESI+: 200 |
| 307 | APCI/ESI+: 174 |
| 308 | EI: 215 |
| 309 | EI: 182 |
| 310 | ESI+: 358 |
| 311 | ESI+: 346 |
| 312 | ESI+: 343 |
| 313 | APCI/ESI+: 361 |
| 314 | APCI/ESI+: 347 |
| 315 | APCI/ESI+: 347 |
| 316 | ESI+: 375 |
| 317 | |
| 318 | ESI+: 493 |
| 319 | ESI+: 401 |
| 320 | ESI+: 401 |
| 321 | ESI+: 373 |
| 322 | ESI+: 516 |
| 323 | ESI+: 403 |
| 324 | ESI+: 516 |
| 325 | ESI+: 389 |
| 326 | ESI+: 342 |
| 327 | ESI+: 368 |
| 328 | ESI+: 425 |
| 329 | ESI+: 439 |
| 330 | ESI+: 451 |

TABLE 67

| Rf | Data |
|---|---|
| 331 | ESI+: 465 |
| 332 | ESI+: 451 |
| 333 | APCI/ESI+: 312 |
| 334 | ESI+: 398 |
| 335 | ESI+: 398 |
| 336 | APCI/ESI+: 323 |
| 337 | APCI/ESI+: 321 |
| 338 | APCI/ESI+: 405 |
| 339 | APCI/ESI+: 337 |
| 340 | APCI/ESI+: 335 |
| 341 | ESI+: 363 |
| 342 | APCI/ESI+: 409 |
| 343 | APCI/ESI+: 414 |
| 344 | APCI/ESI+: 398 |
| 345 | APCI/ESI+: 405 |
| 346 | ESI+: 393 |
| 347 | FAB+: 286, 288 |
| 348 | ESI+: 312, 314 |
| 349 | ESI+: 345 |
| 350 | ESI+: 215 |
| 351 | FAB+: 266 |
| 352 | APCI/ESI+: 374 |
| 353 | APCI/ESI+: 402 |
| 354 | APCI/ESI+: 374 |
| 355 | APCI/ESI+: 402 |
| 356 | APCI/ESI+: 373 |
| 357 | APCI/ESI+: 418 |
| 358 | APCI/ESI+: 374 |
| 359 | APCI/ESI+: 373 |
| 360 | ESI+: 358 |
| 361 | ESI+: 402 |
| 362 | APCI/ESI+: 376 |
| 363 | APCI/ESI+: 376 |

TABLE 68

| Rf | Data |
|---|---|
| 364 | APCI/ESI+: 373 |
| 365 | APCI/ESI+: 394 |
| 366 | APCI/ESI+: 356 |
| 367 | APCI/ESI+: 319 |
| 368 | APCI/ESI+: 212 |
| 369 | APCI/ESI+: 389 |
| 370 | APCI/ESI+: 365 |
| 371 | APCI/ESI+: 379 |
| 372 | APCI/ESI+: 365 |
| 373 | APCI/ESI+: 379 |
| 374 | APCI/ESI+: 441 |
| 375 | APCI/ESI+: 441 |
| 376 | APCI/ESI+: 212 |
| 377 | APCI/ESI+: 256 |
| 378 | APCI/ESI+: 267 |
| 379 | APCI/ESI+: 444 |
| 380 | APCI/ESI+: 470 |
| 381 | ESI+: 388 |
| 382 | ESI+: 407 |
| 383 | ESI+: 374 |
| 384 | ESI+: 379 |
| 385 | ESI+: 374 |
| 386 | ESI+: 338 |
| 387 | ESI+: 338 |
| 388 | ESI+: 402 |
| 389 | ESI+: 402 |
| 390 | ESI+: 411 |
| 391 | ESI+: 343 |
| 392 | ESI+: 311 |
| 393 | ESI+: 325 |
| 394 | ESI+: 337 |
| 395 | ESI+: 337 |
| 396 | ESI+: 351 |

TABLE 69

| Rf | Data |
| --- | --- |
| 397 | ESI+: 346 |
| 398 | ESI+: 346 |
| 399 | ESI+: 325 |
| 400 | ESI+: 351 |
| 401 | ESI+: 376 |
| 402 | ESI+: 337 |
| 403 | ESI+: 311 |
| 404 | ESI+: 337 |
| 405 | ESI+: 297 |
| 406 | ESI+: 388 |
| 407 | ESI+: 296 |
| 408 | ESI+: 323 |
| 409 | ESI+: 343 |
| 410 | ESI+: 309 |
| 411 | ESI+: 323 |
| 412 | ESI+: 288 |
| 413 | ESI+: 288 |
| 414 | ESI+: 302 |
| 415 | ESI+: 316 |
| 416 | ESI+: 302 |
| 417 | ESI+: 442 |
| 418 | ESI+: 350 |
| 419 | ESI+: 302 |
| 420 | ESI+: 289 |
| 421 | ESI+: 302 |
| 422 | ESI+: 302 |
| 423 | ESI+: 302 |
| 424 | ESI+: 302 |
| 425 | ESI+: 294 |
| 426 | ESI+: 302 |
| 427 | ESI+: 345 |
| 428 | ESI+: 302 |
| 429 | ESI+: 289 |

TABLE 70

| Rf | Data |
| --- | --- |
| 430 | ESI+: 346 |
| 431 | ESI+: 346 |
| 432 | ESI+: 303 |
| 433 | ESI+: 316 |
| 434 | ESI+: 313 |
| 435 | ESI+: 315 |
| 436 | ESI+: 285 |
| 437 | ESI+: 299 |
| 438 | ESI+: 287 |
| 439 | ESI+: 301 |
| 440 | ESI+: 303 |
| 441 | ESI+: 289 |
| 442 | ESI+: 388 |
| 443 | ESI+: 356 |
| 444 | ESI+: 284 |
| 445 | EI: 150 |
| 446 | APCI/ESI+: 373 |
| 447 | APCI/ESI+: 373 |
| 448 | APCI/ESI+: 373 |
| 449 | APCI/ESI+: 373 |
| 450 | APCI/ESI+: 389 |
| 451 | APCI/ESI+: 389 |
| 452 | APCI/ESI+: 389 |
| 453 | APCI/ESI+: 295 |
| 454 | APCI/ESI+: 388 |
| 455 | APCI/ESI+: 388 |
| 456 | ESI+: 324 |
| 457 | ESI+: 324 |
| 458 | ESI+: 242 |
| 459 | ESI+: 341 |
| 460 | ESI+: 132 |
| 461 | ESI+: 276 |
| 462 | ESI+: 494 |

TABLE 71

| Rf | Data |
| --- | --- |
| 463 | ESI+: 424 |
| 464 | ESI+: 432 |
| 465 | ESI+: 432 |
| 466 | ESI+: 235 |
| 467 | ESI+: 256 |
| 468 | ESI+: 219 |
| 469 | ESI+: 249 |
| 470 | ESI+: 223 |
| 471 | ESI+: 249 |
| 472 | ESI+: 279 |
| 473 | ESI+: 185 |
| 474 | ESI+: 199 |
| 475 | ESI+: 318 |
| 476 | ESI+: 189 |
| 477 | ESI+: 175 |
| 478 | ESI+: 250 |
| 479 | ESI+: 193 |
| 480 | ESI+: 240 |
| 481 | ESI+: 285 |
| 482 | ESI+: 271 |
| 483 | ESI+: 269 |
| 484 | ESI+: 361 |
| 485 | ESI+: 438, 440 |
| 486 | ESI+: 299 |
| 487 | ESI+: 299 |
| 488 | ESI+: 255 |
| 489 | ESI+: 341 |
| 490 | ESI+: 354 |
| 491 | ESI+: 304 |
| 492 | ESI+: 347 |
| 493 | ESI+: 354 |
| 494 | ESI+: 299 |
| 495 | ESI+: 273 |

TABLE 72

| Rf | Data |
| --- | --- |
| 496 | ESI+: 206 |
| 497 | APCI/ESI+: 249 |
| 498 | APCI/ESI+: 265 |
| 499 | ESI+: 171 |
| 500 | ESI+: 347 |
| 501 | ESI+: 321 |
| 502 | ESI+: 323 |
| 503 | ESI+: 333 |
| 504 | ESI+: 309 |
| 505 | ESI+: 240 |
| 506 | ESI+: 254 |
| 507 | APCI/ESI+: 307 |
| 508 | APCI/ESI+: 324 |
| 509 | ESI+: 340 |
| 510 | APCI/ESI+: 390 |
| 511 | ESI+: 318 |
| 512 | ESI+: 290 |
| 513 | ESI+: 286 |
| 514 | ESI+: 288 |
| 515 | ESI+: 482 [M]+ |
| 516 | ESI+: 411 [M]+ |
| 517 | ESI+: 494 [M]+ |
| 518 | ESI+: 270 |
| 519 | ESI+: 270 |
| 520 | ESI+: 374 |
| 521 | ESI+: 287 |
| 522 | ESI+: 288 |
| 523 | ESI+: 345 |
| 524 | ESI+: 331 |
| 525 | ESI+: 387 |
| 526 | ESI+: 317 |
| 527 | ESI+: 287 |
| 528 | ESI+: 364 |

TABLE 73

| Rf | Data |
| --- | --- |
| 529 | ESI+: 432 |
| 530 | APCI/ESI+: 325 |
| 531 | APCI/ESI+: 241 |
| 532 | APCI/ESI+: 255 |
| 533 | APCI/ESI+: 241 |
| 534 | APCI/ESI+: 255 |
| 535 | APCI/ESI+: 317 |
| 536 | APCI/ESI+: 317 |
| 537 | ESI+: 339 |
| 538 | ESI+: 353 |
| 539 | ESI+: 339 |
| 540 | ESI+: 255 |
| 541 | ESI+: 418 |
| 542 | ESI+: 353 |
| 543 | ESI+: 448 |
| 544 | ESI+: 339 |
| 545 | ESI+: 339 |
| 546 | ESI+: 460 |
| 547 | ESI+: 422 |
| 548 | ESI+: 192 |
| 549 | APCI/ESI+: 339 |
| 550 | APCI/ESI+: 407 |
| 551 | APCI/ESI+: 418 |
| 552 | APCI/ESI+: 451 |
| 553 | APCI/ESI+: 404 |
| 554 | ESI+: 414 |
| 555 | ESI+: 297 |
| 556 | ESI+: 437 |
| 557 | ESI+: 409 |
| 558 | ESI+: 395 |
| 559 | ESI+: 409 |
| 560 | ESI+: 423 |
| 561 | APCI/ESI+: 451 |

TABLE 74

| Rf | Data |
| --- | --- |
| 562 | APCI/ESI+: 451 |
| 563 | ESI+: 306 |
| 564 | ESI+: 206 |
| 565 | ESI+: 340 |
| 566 | ESI+: 337 |
| 567 | ESI+: 590 |
| 568 | EI: 222 |
| 569 | ESI+: 342 |
| 570 | APCI/ESI+: 314 |
| 571 | APCI/ESI+: 314 |
| 572 | ESI+: 265 |
| 573 | EI: 236+ |
| 574 | FAB+: 273 |
| 575 | ESI+: 316 |
| 576 | FAB+: 280 |
| 577 | ESI+: 374 |
| 578 | ESI+: 303 |
| 579 | ESI+: 303 |
| 580 | ESI+: 397 |
| 581 | ESI+: 326 |
| 582 | ESI+: 339 |
| 583 | ESI+: 347 |
| 584 | ESI+: 305 |
| 585 | ESI+: 297 |
| 586 | ESI+: 173 |
| 587 | ESI+: 277 |
| 588 | ESI+: 327 |
| 589 | EI: 256, 258 |
| 590 | ESI+: 261, 263 |
| 591 | ESI+: 289, 291 |
| 592 | EI: 142 |
| 593 | APCI/ESI+: 362 |
| 594 | APCI/ESI+: 243, 245 |

TABLE 75

| Rf | Data |
| --- | --- |
| 595 | APCI/ESI+: 521, 523, 524 |
| 596 | APCI/ESI+: 243, 245 |
| 597 | ESI+: 502 |
| 598 | ESI+: 376 |
| 599 | ESI+: 305 |
| 600 | ESI+: 305 |
| 601 | ESI+: 313 |
| 602 | ESI+: 429 |
| 603 | ESI+: 401 |
| 604 | ESI+: 415 |
| 605 | ESI+: 399 |
| 606 | ESI+: 328 |
| 607 | APCI/ESI+: 346 |
| 608 | APCI/ESI+: 318 |
| 609 | APCI/ESI+: 318 |
| 610 | APCI/ESI+: 310 |
| 611 | APCI/ESI+: 349 |
| 612 | ESI+: 312 |
| 613 | APCI/ESI+: 249 |
| 614 | ESI+: 258, 260 |
| 615 | ESI+: 489 |
| 616 | ESI+: 515 |
| 617 | ESI+: 419 |
| 618 | ESI+: 447 |
| 619 | ESI+: 503 |
| 620 | APCI/ESI+: 365 |
| 621 | ESI+: 440 |
| 622 | FAB+: 232 |
| 623 | ESI+: 293 |
| 624 | ESI+: 194 |
| 625 | ESI+: 410 |
| 626 | ESI+: 424 |
| 627 | ESI+: 279 |

TABLE 76

| Rf | Data |
| --- | --- |
| 628 | ESI+: 289 |
| 629 | ESI+: 289 |
| 630 | ESI+: 306 |
| 631 | ESI+: 302 |
| 632 | ESI+: 318 |
| 633 | ESI+: 331 |
| 634 | ESI+: 532 |
| 635 | ESI+: 504 |
| 636 | ESI+: 441 |
| 637 | ESI+: 566 |
| 638 | APCI/ESI+: 259 |
| 639 | ESI+: 460 |
| 640 | ESI+: 552 |
| 641 | ESI+: 582 |
| 642 | ESI+: 454 |
| 643 | APCI/ESI+: 552 |
| 644 | ESI+: 490 |
| 645 | APCI/ESI+: 538 |
| 646 | ESI+: 548 |
| 647 | ESI+: 279 |
| 648 | ESI+: 194 |
| 649 | ESI+: 347 |
| 650 | APCI/ESI+: 319 |
| 651 | APCI/ESI+: 360 |
| 652 | APCI/ESI+: 390 |
| 653 | APCI/ESI+: 249 |
| 654 | APCI/ESI+: 305 |
| 655 | APCI/ESI+: 305 |
| 656 | APCI/ESI+: 355 |
| 657 | APCI/ESI+: 326 |
| 658 | APCI/ESI+: 348 |
| 659 | APCI/ESI+: 346 |
| 660 | APCI/ESI+: 305 |

TABLE 77

| Rf | Data |
|---|---|
| 661 | APCI/ESI+: 279 |
| 662 | APCI/ESI+: 235 |
| 663 | ESI+: 238 |
| 664 | ESI+: 300 |
| 665 | ESI+: 340 |
| 666 | ESI+: 354 |
| 669 | ESI+: 349 |
| 670 | ESI+: 236 |
| 671 | APCI/ESI+: 303 |
| 672 | ESI+: 433 |
| 673 | ESI+: 305 |
| 674 | ESI+: 291 |
| 675 | ESI+: 305 |
| 676 | ESI+: 319 |
| 677 | ESI+: 144 |
| 678 | ESI+: 454 |
| 679 | ESI+: 328 |
| 680 | ESI+: 330 |
| 681 | ESI+: 365 |
| 682 | ESI+: 351 |
| 683 | ESI+: 296 |
| 684 | ESI+: 322 |
| 685 | APCI/ESI+: 376 |
| 686 | APCI/ESI+: 335 |
| 687 | ESI+: 346 |
| 688 | APCI/ESI+: 376 |
| 689 | APCI/ESI+: 375 |
| 690 | APCI/ESI+: 360 |
| 691 | APCI/ESI+: 408 |
| 692 | APCI/ESI+: 388 |
| 693 | APCI/ESI+: 402 |
| 694 | APCI/ESI+: 386 |
| 695 | APCI/ESI+: 379 |

TABLE 78

| Rf | Data |
|---|---|
| 696 | APCI/ESI+: 393 |
| 697 | ESI+: 332 |
| 698 | ESI+: 318 |
| 699 | ESI+: 362 |
| 700 | ESI+: 348 |
| 701 | ESI+: 342 |
| 702 | ESI+: 365 |
| 703 | ESI+: 337 |
| 704 | ESI+: 323 |
| 705 | ESI+: 337 |
| 706 | ESI+: 377 |
| 707 | ESI+: 289 |
| 708 | ESI+: 303 |
| 709 | APCI/ESI+: 362 |
| 710 | ESI+: 264 |
| 711 | ESI+: 264 |
| 712 | ESI+: 151 |
| 713 | ESI+: 386 |
| 714 | APCI/ESI+: 283 |
| 715 | APCI/ESI+: 253 |
| 716 | APCI/ESI+: 281 |
| 717 | APCI/ESI+: 345 |
| 718 | APCI/ESI+: 422 |
| 719 | APCI/ESI+: 374 |
| 720 | APCI/ESI+: 388 |
| 721 | APCI/ESI+: 329 |
| 722 | APCI/ESI+: 422 |
| 723 | APCI/ESI+: 315 |
| 724 | ESI+: 389 |
| 725 | ESI+: 417 |
| 726 | APCI/ESI+: 297 |
| 727 | APCI/ESI+: 323 |
| 728 | APCI/ESI+: 309 |

TABLE 79

| Rf | Data |
|---|---|
| 729 | APCI/ESI+: 364 |
| 730 | APCI/ESI+: 351 |
| 731 | APCI/ESI+: 345 |
| 732 | APCI/ESI+: 345 |
| 733 | APCI/ESI+: 316 |
| 734 | APCI/ESI+: 316 |
| 735 | APCI/ESI+: 316 |
| 736 | APCI/ESI+: 418 |
| 737 | APCI/ESI+: 404 |
| 738 | APCI/ESI+: 404 |
| 739 | APCI/ESI+: 423 |
| 740 | APCI/ESI+: 423 |
| 741 | APCI/ESI+: 423 |
| 742 | APCI/ESI+: 337 |
| 743 | APCI/ESI+: 351 |
| 744 | APCI/ESI+: 404 |
| 745 | APCI/ESI+: 402 |
| 746 | APCI/ESI+: 432 |
| 747 | APCI/ESI+: 336 |
| 748 | APCI/ESI+: 364 |
| 749 | ESI+: 200 |
| 750 | ESI+: 488 |
| 751 | ESI+: 488 |
| 752 | ESI+: 403 |
| 753 | ESI+: 401 |
| 754 | ESI+: 164 |
| 755 | ESI+: 335 |
| 756 | ESI+: 321 |
| 757 | ESI+: 454 |
| 758 | ESI+: 452 |
| 759 | ESI+: 452 |
| 760 | |
| 761 | ESI+: 371 |

TABLE 80

| Rf | Data |
|---|---|
| 762 | APCI/ESI+: 375 |
| 763 | APCI/ESI+: 389 |
| 764 | APCI/ESI+: 375 |
| 765 | APCI/ESI+: 389 |
| 766 | ESI+: 447 |
| 767 | APCI/ESI+: 389 |
| 768 | APCI/ESI+: 403 |
| 769 | ESI+: 309 |
| 770 | ESI+: 365 |
| 771 | ESI+: 391 |
| 772 | ESI+: 493 |
| 773 | APCI/ESI+: 396 |
| 774 | APCI/ESI+: 410 |
| 775 | APCI/ESI+: 289 |
| 776 | APCI/ESI+: 303 |
| 777 | APCI/ESI+: 315 |
| 778 | APCI/ESI+: 317 |
| 779 | APCI/ESI+: 317 |
| 780 | APCI/ESI+: 357 |
| 781 | APCI/ESI+: 318 |
| 782 | APCI/ESI+: 346 |
| 783 | APCI/ESI+: 358 |
| 784 | APCI/ESI+: 360 |
| 785 | ESI+: 373 |
| 786 | ESI+: 381 |
| 787 | ESI+: 408 |
| 788 | ESI+: 368 |
| 789 | ESI+: 382 |
| 790 | ESI+: 373 |
| 791 | APCI/ESI+: 403 |
| 792 | APCI/ESI+: 401 |
| 793 | ESI+: 271 |
| 794 | ESI+: 285 |

TABLE 81

| Rf | Data |
|---|---|
| 795 | ESI+: 273 |
| 796 | ESI+: 326 |
| 797 | ESI+: 359 |
| 798 | ESI+: 385 |
| 799 | ESI+: 289 |
| 800 | ESI+: 317 |
| 801 | ESI+: 373 |
| 802 | APCI/ESI+: 351 |
| 803 | ESI+: 165 |
| 804 | ESI+: 223 |
| 805 | ESI+: 138 |
| 806 | ESI+: 156 |
| 807 | ESI+: 304 |
| 808 | ESI+: 183 |
| 809 | ESI+: 241 |
| 810 | ESI+: 379 |
| 811 | ESI+: 474 |
| 812 | ESI+: 446 |
| 813 | ESI+: 441 |
| 814 | ESI+: 446 |
| 815 | NMR-CDCl$_3$: 0.10(6H, s), 0.93(9H, s), 1.04-1.12 (2H, m), 1.60-1.70 (3H, m), 2.38-2.49(1H, m), 2.63-2.73 (2H, m), 3.60-3.66(2H, m), 4.00-4.19(4H, m), 4.75(2H, s), 6.37(1H, t, J = 7 Hz), 6.82-6.87 (1H, t, J = 7 Hz), 6.96(1H, t, J = 7 Hz). |
| 816 | ESI+: 446 |
| 817 | ESI+: 289 |
| 818 | ESI+: 319 |
| 819 | ESI+: 317 |
| 820 | ESI+: 307 |
| 821 | ESI+: 195 |
| 822 | ESI+: 193 |
| 823 | ESI+: 168 |
| 824 | ESI+: 323 |
| 825 | ESI+: 407 |
| 826 | ESI+: 332 |

TABLE 82

| Rf | Data |
|---|---|
| 827 | ESI+: 327 |
| 828 | ESI+: 332 |
| 829 | ESI+: 332 |
| 830 | ESI+: 291 |
| 831 | ESI+: 281 |
| 832 | ESI+: 349 |
| 833 | ESI+: 337 |
| 834 | ESI+: 321 |
| 835 | ESI+: 333 |
| 836 | ESI+: 337 |
| 837 | ESI+: 351 |
| 838 | ESI+: 343 |
| 839 | ESI+: 347 |
| 840 | ESI+: 362 |
| 841 | ESI+: 223 |
| 842 | ESI+: 305 |

Example 1

CDI (106 mg) was added to a mixture of 1-(3-{2-[2-(morpholin-4-yl)pyrimidin-5-yl]ethyl}phenyl)methaneamine (97 mg) and DMF (2 ml) at 0° C., followed by stirring at room temperature for 1 hour. The reaction mixture was concentrated under reduced pressure, and EtOAc and a saturated aqueous sodium hydrogen carbonate solution were then added thereto. The organic layer was dried over Na$_2$SO$_4$ and concentrated under reduced pressure to obtain a reaction mixture. Guanidine hydrochloride (40 mg) and potassium tert-butoxide (45 mg) were suspended in DMF (2 ml), and a solution of the reaction mixture obtained immediately before in DMF (1 ml) was added thereto, followed by stirring at room temperature for 2 hours. The reaction mixture was concentrated under reduced pressure, water was then added thereto, and the insoluble matter was collected by filtration. The solid thus obtained was purified by silica gel column chromatography (CHCl$_3$/MeOH), and L-tartaric acid (34 mg) was added to a mixture of the purified product (87 mg) in a mixed solvent (3 ml) of MeCN and water at 9:1, followed by stirring at room temperature for 1 hour. The insoluble matter was collected by filtration to obtain 1-carbamimidoyl-3-(3-{2-[2-(morpholin-4-yl)pyrimidin-5-yl]ethyl}benzyl)urea L-tartrate (78 mg).

Example 2

CDI (248 mg) was added to a mixture of {3-[4-(2,6-dimethylpyridin-4-yl)piperazin-1-yl]-2-fluorophenyl}methanol (241 mg) and DMF (7 ml), followed by stirring at room temperature for 2 hours. Guanidine carbonate (344 mg) was added to this mixture at room temperature, followed by stirring at room temperature overnight. The organic layer was evaporated under reduced pressure, water was added to the residue, and the generated solid was collected by filtration.

The obtained solid was purified by basic silica gel column chromatography (CHCl$_3$/MeOH). L-tartaric acid (99.3 mg) was added to a mixture of the purified product thus obtained (265 mg) and EtOH (10 ml), followed by stirring at room temperature for 3 hours. The solid was collected by filtration, washed with EtOH, and then dried under reduced pressure at 50° C. to obtain 3-[4-(2,6-dimethylpyridin-4-yl)piperazin-1-yl]-2-fluorobenzyl carbamimidoylcarbamate (268 mg).

Example 3

1-[2-Fluoro-3-(hydroxymethyl)phenyl]-4-(pyridin-3-yl)piperidin-4-ol (187 mg), DMF (5.5 ml), and CDI (201 mg) were mixed, followed by stirring at room temperature for 2 hours. Guanidine carbonate (279 mg) was added to the reaction mixture, followed by stirring at room temperature overnight. Water was added to the reaction mixture, followed by ice-cooling and stirring for 30 minutes, and the generated solid was collected by filtration, washed with water, and then dried at 50° C. under reduced pressure. The obtained solid was purified by silica gel column chromatography (CHCl$_3$/MeOH) to obtain 2-fluoro-3-[4-hydroxy-4-(pyridin-3-yl)piperidin-1-yl]benzyl carbamimidoylcarbamate (160 mg).

Example 23

CDI (110 mg) was added to a mixture of 1-{4-[({5-[2-fluoro-3-(hydroxymethyl)phenyl]pyrimidin-2-yl}oxy)methyl]piperidin-1-yl}propan-1-one (124 mg) and DMF (3 ml), followed by stirring at room temperature for 3 hours. Guanidine carbonate (220 mg) was added to the reaction mixture, followed by stirring at room temperature overnight. The organic layer was evaporated under reduced pressure, water was added to the residue, and the generated solid was collected by filtration.

The obtained solid was purified by silica gel column chromatography (CHCl$_3$/MeOH). A 4 M hydrogen chloride/dioxane solution (0.1 ml) was added to a mixture of the purified product thus obtained (135.1 mg) and EtOH (2 ml), followed by stirring at room temperature for 1 hour and concentrating under reduced pressure. The obtained solid was washed with ether and then collected by filtration to obtain 2-fluoro-3-{2-[(1-propionylpiperidin-4-yl)methoxy]pyrimidin-5-yl}benzyl carbamimidoylcarbamate dihydrochloride (140 mg) as a colorless solid.

Example 112

CDI (225 mg) was added to a mixture of 1-(4-{5-[3-(hydroxymethyl)phenyl]pyrimidin-2-yl}piperazin-1-yl)-2-methoxyethanone (216 mg) and DMF (6 ml), followed by stirring at room temperature for 2 hours. Then, guanidine carbonate (220 mg) was added to the mixture, followed by stirring at room temperature for 2 hours. Water was added to the reaction mixture, followed by extraction with CHCl₃. The organic layer was dried over Na₂SO₄ and evaporated under reduced pressure. A mixture obtained by dissolving L-tartaric acid (59 mg) in a mixed solvent (1 ml) of MeCN and water at 9:1 was added to a mixture of the obtained residue (166.9 mg) in a mixed solvent (4 ml) of MeCN and water at 9:1, followed by stirring at room temperature. The precipitated solid was collected by filtration to obtain 3-{2-[4-(methoxy acetyl)piperazin-1-yl]pyrimidin-5-yl}benzyl carbamimidoylcarbamate L-tartrate (177 mg) as a colorless solid.

Example 316

A 4 M hydrogen chloride/EtOH solution (1.5 ml) was added to a mixture of 2-fluoro-3-{4-[2-(3-methoxyazetidin-1-yl)pyrimidin-5-yl]piperazin-1-yl}benzyl carbamimidoylcarbamate (285 mg) and EtOH (5 ml), followed by stirring at room temperature. The precipitated yellow solid was collected by filtration and washed with EtOH. The obtained solid was dried at 40° C. under reduced pressure to obtain 2-fluoro-3-{4-[2-(3-methoxyazetidin-1-yl)pyrimidin-5-yl]piperazin-1-yl}benzyl carbamimidoylcarbamate trihydrochloride (330 mg).

Example 317

Ethyl({1-[5-(3-{[(carbamimidoylcarbamoyl)oxy]methyl}phenyl)pyrimidin-2-yl]piperidin-4-yl}oxy)acetate (45 mg) was mixed with ethanol, and L-tartaric acid (15 mg) was added thereto, followed by stirring at room temperature for 1 hour. The reaction mixture was concentrated under reduced pressure, and then diethyl ether was added thereto. The precipitated solid was collected by filtration to obtain ethyl ({1-[5-(3-{[(carbamimidoylcarbamoyl)oxy]methyl}phenyl)pyrimidin-2-yl]piperidin-4-yl}oxy)acetate L-tartrate (28 mg).

Example 318

A 1 M aqueous NaOH solution was added to a mixture of methyl 4-{4-[5-(3-{[(carbamimidoylcarbamoyl)amino]methyl}phenyl)pyrimidin-2-yl]piperazin-1-yl}-3-chlorobenzoate (208 mg), THF (2 ml), and EtOH (2 ml), followed by stirring at room temperature for 2 hours. The reaction mixture was neutralized with 1 M hydrochloric acid, and the precipitated solid was collected by filtration. A 4 M hydrogen chloride/dioxane solution (1 ml) was added to a mixture of the obtained solid and dioxane (3 ml), followed by stirring at room temperature overnight. The insoluble matter was collected by filtration to obtain 4-{4-[5-(3-{[(carbamimidoylcarbamoyl)amino]methyl}phenyl)pyrimidin-2-yl]piperazin-1-yl}-3-chlorobenzoic acid dihydrochloride (112 mg).

Example 319

Sodium hydride (50% suspended in mineral oil, 45 mg) was added to a mixture of {3-[2-(morpholin-4-yl)pyrimidin-5-yl]phenyl}methanol (230 mg) and DMF (6 ml) under ice-cooling. After stirring at the same temperature for 30 minutes, CDI (275 mg) was added thereto. The reaction mixture was stirred at room temperature for 2 hours, and guanidine carbonate (460 mg) and DBU (388 mg) were then added thereto, followed by stirring at room temperature overnight. The solvent was evaporated under reduced pressure, water was added to the obtained residue, and the generated insoluble matter was collected by filtration. The obtained solid was purified by basic silica gel column chromatography (CHCl₃/MeOH). L-tartaric acid (23 mg) was added to a mixture of the purified product thus obtained (54 mg), MeCN, and water, followed by stirring at room temperature for 30 minutes. The generated insoluble matter was collected by filtration, and washed with MeCN to obtain 3-[2-(morpholin-4-yl)pyrimidin-5-yl]benzyl carbamimidoylcarbamate L-tartrate (66 mg).

Example 328

A 1 M aqueous NaOH solution (1.14 ml) was added to a mixture of 5-[4-(3-{[(carbamimidoylcarbamoyl)oxy]methyl}-2-fluorophenyl)piperazin-1-yl]pyridine-2-carboxylate methyl ester (326 mg), THF (9 ml), and MeOH (3 ml), followed by stirring at room temperature overnight. 1 M hydrochloric acid (1.14 ml) was added to the reaction mixture, followed by stirring at room temperature for 1 hour. The generated solid was collected by filtration, washed with water, and then dried at 50° C. under reduced pressure to obtain 5-[4-(3-{[(carbamimidoylcarbamoyl)oxy]methyl}-2-fluorophenyl)piperazin-1-yl]pyridine-2-carboxylic acid (293 mg).

Example 344

A 1 M aqueous NaOH solution was added to a mixture of ethyl 4-{1-[5-(3-{[(carbamimidoylcarbamoyl)oxy]methyl}-2-fluorophenyl)pyrimidin-2-yl]piperidin-4-yl}butanoate (256 mg), THF (3.3 ml), and EtOH (3.3 ml), followed by stirring at room temperature overnight. The insoluble matter was removed by filtration, the solvent was evaporated under reduced pressure, and to the residue were then added water and 1 M hydrochloric acid (1.052 ml) at 0° C., followed by stirring at 0° C. for 30 minutes. The solid was collected by filtration, washed with water, and then dried at 50° C. under reduced pressure. To the reaction mixture was added MeCN (8 ml), and a mixture of L-tartaric acid (76.6 mg), MeCN (4 ml), and water (0.2 ml) was added thereto, followed by stirring at room temperature overnight. The solid was collected by filtration, washed with MeCN, and then dried at 50° C. under reduced pressure to obtain 4-{1-[5-(3-{[(carbamimidoylcarbamoyl)oxy]methyl}-2-fluorophenyl)pyrimidin-2-yl]piperidin-4-yl}butanoic acid L-tartrate (276 mg).

Example 345

To a mixture of 1-[5-(3-{[(carbamimidoylcarbamoyl)oxy]methyl}-2-fluorophenyl)pyrimidin-2-yl]piperidin-4-yl benzoic acid (252 mg) and MeOH was added a 1 M aqueous NaOH solution (1 ml), followed by stirring at room temperature for 3 hours. To the reaction mixture was added a 1 M aqueous HCl solution (1 ml), and then the reaction mixture was concentrated under reduced pressure. The residue was purified by silica gel column chromatography (CHCl₃/MeOH) as it was.

To the purified product thus obtained was added EtOH, and 4 M hydrogen chloride/dioxane (1 ml) was added thereto, followed by stirring at room temperature for 1 hour. The reaction mixture was concentrated under reduced pressure, and then diethyl ether were added thereto. The precipitated solid was collected by filtration to obtain 2-fluoro-3-[2-(4-hydroxypiperidin-1-yl)pyrimidin-5-yl]benzyl carbamimidoylcarbamate dihydrochloride (110 mg).

Example 347

To a mixture of 1-(3-{2-[3-(methoxymethyl)pyrrolidin-1-yl]pyrimidin-5-yl}phenyl)methanamine (158 mg) and DMF (3 ml) was added CDI (110 mg), followed by stirring at room temperature for 1 hour.

The reaction mixture was concentrated under reduced pressure, EtOAc and a saturated aqueous sodium hydrogen carbonate solution were then added thereto, and the organic layer was dried over $Na_2SO_4$ and concentrated under reduced pressure to obtain a reaction mixture. Guanidine hydrochloride and sodium hydride were suspended in DMF (2 ml), and a solution of the reaction mixture obtained immediately before in DMF (1 ml) was added thereto, followed by stirring at room temperature for 1 hour. The reaction mixture was concentrated under reduced pressure, water was added thereto, and the insoluble matter was collected by filtration. The obtained solid was purified by silica gel column chromatography ($CHCl_3$/MeOH). To the purified product thus obtained (73 mg) was added a mixed solvent (3.3 ml) of MeCN and water at 9:1, and further, L-tartaric acid (29 mg) was added thereto, followed by stirring at room temperature for 1 hour. The insoluble matter was collected by filtration to obtain 1-carbamimidoyl-3-(3-{2-[3-(methoxymethyl)pyrrolidin-1-yl]pyrimidin-5-yl}benzyl)urea L-tartrate (65 mg).

Example 397

Methyl 4-(4-{5-[3-(aminomethyl)phenyl]pyrimidin-2-yl}piperazin-1-yl)-3-chlorobenzoate (207 mg) was mixed with DMF (5 ml), and CDI (154 mg) was added thereto at 0° C., followed by stirring at room temperature for 2 hours. The reaction mixture was concentrated under reduced pressure, and EtOAc and a saturated aqueous sodium hydrogen carbonate solution were then added thereto. The organic layer was dried over $Na_2SO_4$ and concentrated under reduced pressure. The obtained residue was mixed with DMF (5 ml), and guanidine hydrochloride (50 mg) and DBU (204 mg) were added thereto, followed by stirring at 70° C. for 5 hours. The reaction mixture was concentrated under reduced pressure, water was then added thereto, and the insoluble matter was collected by filtration. The obtained solid was purified by basic silica gel column chromatography ($CHCl_3$/MeOH) to obtain methyl 4-{4-[5-(3-{[(carbamimidoylcarbamoyl)amino]methyl}phenyl)pyrimidin-2-yl]piperazin-1-yl}-3-chlorobenzoate (208 mg).

Example 398

Ethyl 1-{5-[3-(aminomethyl)phenyl]pyrimidin-2-yl}piperidine-4-carboxylate (303 mg) was mixed with DMF (5 ml), and CDI (188 mg) was added thereto, followed by stirring at room temperature for 1 hour. The reaction mixture was concentrated under reduced pressure, and EtOAc and a saturated aqueous sodium hydrogen carbonate solution were then added thereto. The organic layer was dried over $Na_2SO_4$ and concentrated under reduced pressure. Guanidine hydrochloride (170 mg) and sodium hydride (55% suspended in oil) (77 mg) were suspended in DMF (2 ml), and a solution of the reaction mixture obtained immediately before in DMF (1 ml) was added thereto, followed by stirring at room temperature for 1 hour. The reaction mixture was concentrated under reduced pressure, water was then added thereto, and the insoluble matter was collected by filtration. The obtained solid was purified by silica gel column chromatography ($CHCl_3$/MeOH) to obtain ethyl 1-[5-(3-{[(carbamimidoylcarbamoyl)amino]methyl}phenyl)pyrimidin-2-yl]piperidine-4-carboxylate (74 mg).

Example 546 tert-Butyl [3-(2-chloropyrimidin-5-yl)benzyl]carbamate (16 mg) and 1-methyl-2-pyrrolidinone (0.2 ml) were mixed, and ethyl 4-aminopiperidine-1-carboxylate (8 mg) and sodium carbonate (20 mg) were added thereto, followed by stirring at 90° C. overnight. The reaction mixture was cooled to room temperature and then filtered, and the filtrate was purified by preparative liquid chromatography (MeOH/0.1% aqueous formic acid solution). To the purified product thus obtained were added MeOH (0.5 ml) and a 4 M hydrogen chloride/EtOAc solution (0.5 ml), followed by shaking for 2 hours. The reaction mixture was concentrated, and to the obtained residue were added DMF (0.2 ml) and CDI (4 mg), followed by stirring at room temperature for 2 hours. To the reaction mixture was added guanidine carbonate (9 mg), followed by stirring at 90° C. overnight. The reaction mixture was cooled to room temperature, and the insoluble matter was then filtered. The filtrate was purified by preparative liquid chromatography (MeOH/0.1% aqueous formic acid solution) to obtain ethyl 4-{[5-(3-{[(carbamimidoylcarbamoyl)amino]methyl}phenyl)pyrimidin-2-yl]amino}piperidine-1-carboxylate (1.9 mg).

Example 567

4-{1-[3-({[tert-Butyl(dimethyl)silyl]oxy}methyl)-2-fluorophenyl]azetidin-3-yl}piperidine (70 mg) and TEA (73 mg) were mixed with dichloromethane (2 ml), and acetyl chloride (22 mg) was added thereto, followed by stirring at room temperature for 1 hour. To the reaction mixture were added $CHCl_3$ and a 1 M aqueous NaOH solution, the organic layer was dried over $Na_2SO_4$, and the organic layer was concentrated under reduced pressure. The obtained residue was mixed with THF (2 ml), and a 1 M TBAF/THF solution (0.3 ml) was added thereto, followed by stirring at room temperature for 1 hour. To the reaction mixture were added $CHCl_3$ and a saturated aqueous ammonium chloride solution, and the organic layer was dried over $Na_2SO_4$. The reaction mixture was concentrated under reduced pressure. The obtained residue was purified by silica gel column chromatography ($CHCl_3$/MeOH). The purified product thus obtained was mixed with DMF, and CDI (65 mg) was added thereto, followed by stirring at room temperature for 3 hours. To the reaction mixture was added guanidine carbonate (140 mg), followed by stirring at room temperature for 1 hour. The reaction mixture was concentrated under reduced pressure, water was added thereto, and the insoluble matter was collected by filtration. The obtained solid was purified by basic silica gel column chromatography ($CHCl_3$/MeOH). The purified product thus obtained was mixed with EtOH (1 ml), and L-tartaric acid (16 mg) was added thereto, followed by stirring at room temperature for 1 hour. The precipitated solid was collected by filtration to obtain 3-[3-(1-acetylpiperidin-4-yl)azetidin-1-yl]-2-fluorobenzyl carbamimidoylcarbamate L-tartrate (49 mg).

Example 568

3-[4-(6 tert-Butoxypyridin-3-yl)piperazin-1-yl]-2-fluorobenzyl carbamimidoylcarbamate (132 mg) was dissolved in dichloromethane (3.4 ml), and TFA (508 mg) was added thereto, followed by stirring at room temperature for 4 hours. The reaction mixture was concentrated under reduced pressure, the residue was mixed with CHCl$_3$/MeOH, and basic silica gel was added thereto, followed by concentrating under reduced pressure. The residue was purified by basic silica gel column chromatography (CHCl$_3$/MeOH). The purified product thus obtained was mixed with EtOH (5 ml), and L-tartaric acid (41.0 mg) were added thereto, followed by stirring at 80° C. for 1 hour, and then stirring at room temperature for 1 hour. The solid was collected by filtration, washed with EtOH, and then dried at 50° C. under reduced pressure to obtain 2-fluoro-3-[4-(6-oxo-1,6-dihydropyridin-3-yl)piperazin-1-yl]benzyl carbamimidoylcarbamate L-tartrate (125 mg).

Example 588

Methyl 5-{4-[({1-[2-fluoro-3-(hydroxymethyl)phenyl]azetidin-3-yl}oxy)methyl]piperidin-1-yl}pyridine-2-carboxylate (69 mg), DMF (2 ml), and CDI (60 mg) were mixed, followed by stirring at room temperature for 3 hours. To the reaction mixture was added guanidine carbonate (120 mg), followed by stirring at room temperature for 1 hour. The reaction mixture was concentrated under reduced pressure, and water and CHCl$_3$ were added thereto. The organic layer was dried over Na$_2$SO$_4$ and concentrated under reduced pressure. The obtained residue was purified by silica gel column chromatography (CHCl$_3$/MeOH).

The purified product thus obtained was mixed with methanol (1 ml) and THF (2 ml), and a 1 M aqueous NaOH solution (0.2 ml) was added thereto, followed by stirring at room temperature overnight. To the reaction mixture was added 1 M hydrochloric acid (0.2 ml), followed by concentrating under reduced pressure. To the residue was added methanol, the insoluble matter was separated by filtration, and the filtrate was concentrated under reduced pressure. To the residue was added methanol, the insoluble matter was separated by filtration, and the filtrate was concentrated under reduced pressure. To the residue were added a small amount of methanol and then diethyl ether. The precipitated solid was collected by filtration to obtain 5-[4-({[1-(3-{[(carbamimidoylcarbamoyl)oxy]methyl}-2-fluorophenyl)azetidin-3-yl]oxy}methyl)piperidin-1-yl]pyridine-2-carboxylic acid (23 mg).

Example 615

To a mixture of (3-{3-[(6-tert-butoxypyridin-3-yl)oxy]azetidin-1-yl}-2-fluorophenyl)methanol (120 mg) and DMF (2 ml) was added CDI (130 mg), followed by stirring at room temperature for 3 hours. To the reaction mixture was added guanidine carbonate (260 mg), followed by stirring at room temperature for 1 hour. The reaction mixture was concentrated under reduced pressure, water and CHCl$_3$ were added thereto, and the organic layer was dried over anhydrous sodium sulfate. After concentrating under reduced pressure, the obtained residue was purified by silica gel column chromatography (CHCl$_3$/MeOH). The purified product thus obtained was mixed with dichloromethane (2 ml), and TFA (0.5 ml) was added thereto, followed by stirring at room temperature overnight. The reaction solution was concentrated under reduced pressure, and a saturated aqueous sodium hydrogen carbonate solution and CHCl$_3$ were then added thereto. The organic layer was dried over Na$_2$SO$_4$ and then concentrated under reduced pressure. The obtained residue was mixed with a mixed solution of MeCN and H$_2$O at 95:5, and L-tartaric acid (41 mg) was added thereto, followed by stirring at room temperature for 1 hour. The solid was collected by filtration to obtain 2-fluoro-3-({3-[(6-oxo-1,6-dihydropyridin-3-yl)oxy]azetidin-1-yl}benzyl carbamimidoylcarbamate L-tartrate (118 mg).

Example 619

2-Fluoro-3-[2-(morpholin-4-yl)pyrimidin-5-yl]benzyl carbamimidoylcarbamate hydrochloride (54 mg), CHCl$_3$ (8 ml), and MeOH (3 ml) were mixed, and a saturated aqueous sodium hydrogen carbonate solution was added thereto, followed by stirring for minutes. The organic layer was dried over Na$_2$SO$_4$, and the solvent was evaporated under reduced pressure. The solid residue was washed with EtOAc and filtered to obtain a colorless solid.

The obtained solid was mixed with a mixed solvent of EtOH (0.54 ml) and water (0.54 ml), and a 1 M aqueous phosphoric acid solution, followed by stirring for 1 hour. The solid was collected by filtration, and washed with a mixture (1:1) of EtOH and water. The obtained solid was dried at 50° C. under reduced pressure to obtain 2-fluoro-3-[2-(morpholin-4-yl)pyrimidin-5-yl]benzyl carbamimidoylcarbamate phosphate (45 mg) as a colorless solid.

The compounds of Examples shown in the tables below were prepared using the respective corresponding starting materials in the same manner as the methods of Examples above. The structures, the preparation methods, and the physicochemical data for the compounds of Examples are shown in the tables below.

TABLE 83

| Ex | Syn | Structure |
|----|-----|-----------|
| 1  | 1   | 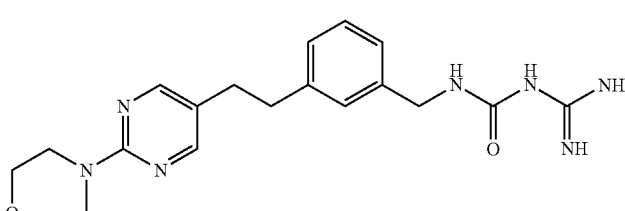 |

TABLE 83-continued

| Ex | Syn | Structure |
|----|-----|-----------|
| 2 | 2 | 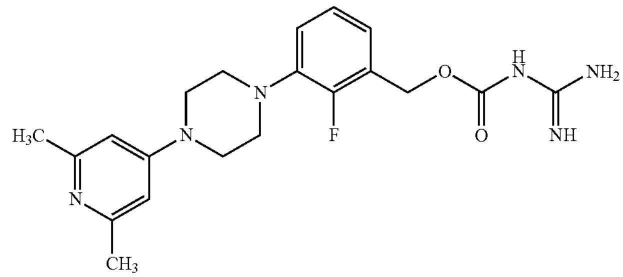 [SMILES: Cc1cc(N2CCN(c3cccc(COC(=O)NC(=N)N)c3F)CC2)cc(C)n1] |
| 3 | 3 | 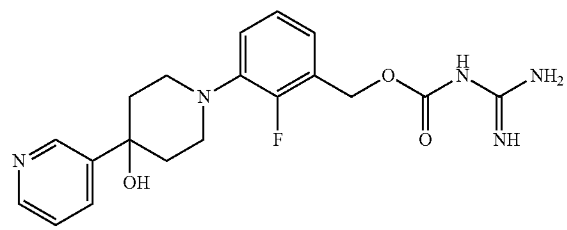 [SMILES: N=C(N)NC(=O)OCc1cccc(N2CCC(O)(c3cccnc3)CC2)c1F] |
| 4 | 23 | 2HCl |
| 5 | 23 | 2HCl |
| 6 | 23 | 2HCl |
| 7 | 23 | 2HCl |
| 8 | 23 | HCl |

TABLE 83-continued

| Ex | Syn | Structure |
|---|---|---|
| 9 | 23 | 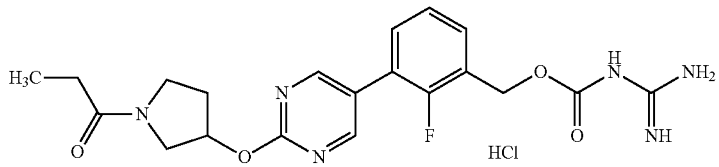 [SMILES: CCC(=O)N1CCC(Oc2ncc(-c3cccc(COC(=O)NC(=N)N)c3F)cn2)C1 ; Cl] |
| 10 | 23 | 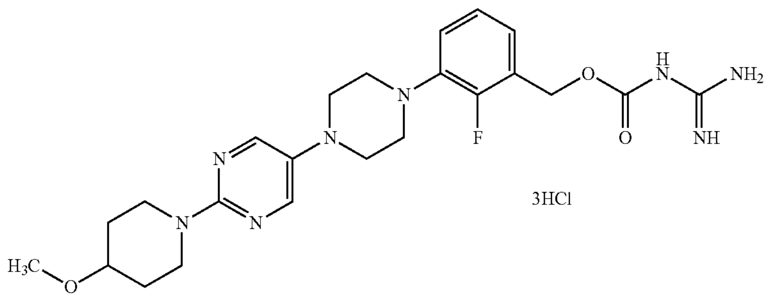 [SMILES: COC1CCN(c2ncc(N3CCN(c4cccc(COC(=O)NC(=N)N)c4F)CC3)cn2)CC1] |
| 11 | 23 | 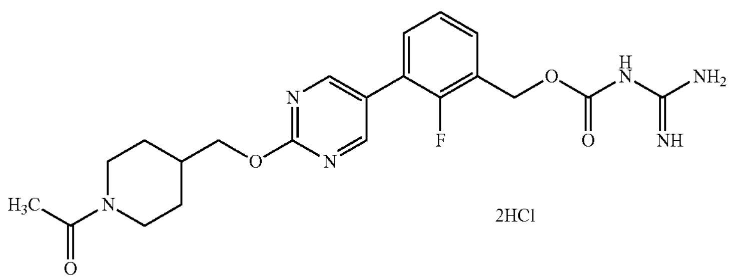 [SMILES: CC(=O)N1CCC(COc2ncc(-c3cccc(COC(=O)NC(=N)N)c3F)cn2)CC1] |
| 12 | 23 | 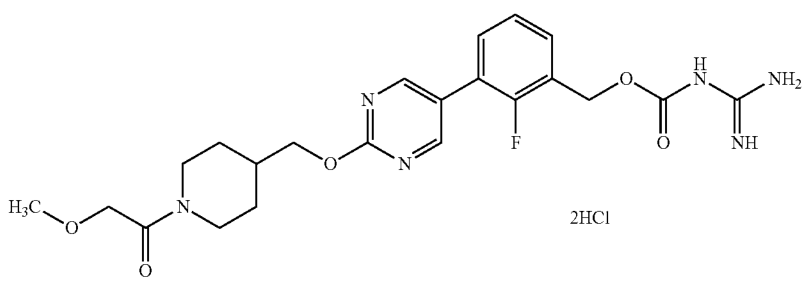 [SMILES: COCC(=O)N1CCC(COc2ncc(-c3cccc(COC(=O)NC(=N)N)c3F)cn2)CC1] |
| 13 | 23 | 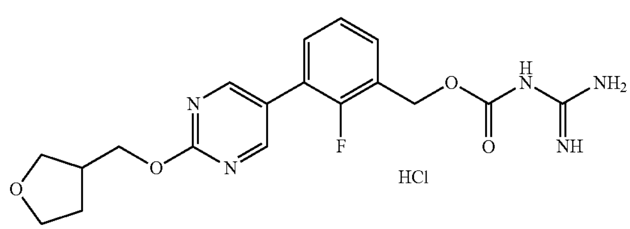 [SMILES: N=C(N)NC(=O)OCc1cccc(-c2cnc(OCC3CCOC3)nc2)c1F ; Cl] |
| 14 | 23 | 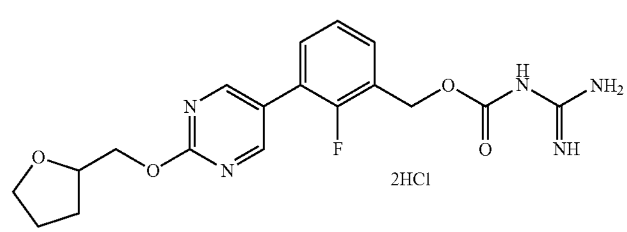 [SMILES: N=C(N)NC(=O)OCc1cccc(-c2cnc(OCC3CCCO3)nc2)c1F] |

TABLE 83-continued
| Ex | Syn | Structure |
|---|---|---|
| 15 | 23 | 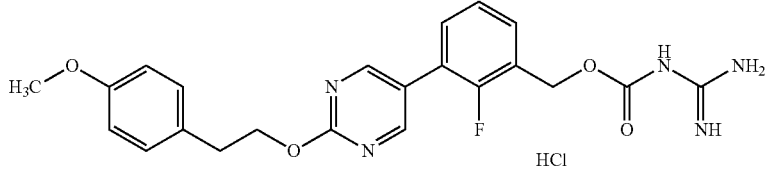 [SMILES: COc1ccc(CCOc2ncc(-c3cccc(COC(=O)NC(=N)N)c3F)cn2)cc1 ; Cl] HCl |
| 16 | 23 | 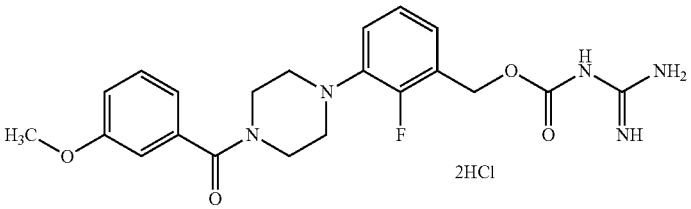 [SMILES: COc1cccc(C(=O)N2CCN(c3cccc(COC(=O)NC(=N)N)c3F)CC2)c1] 2HCl |
| 17 | 23 | 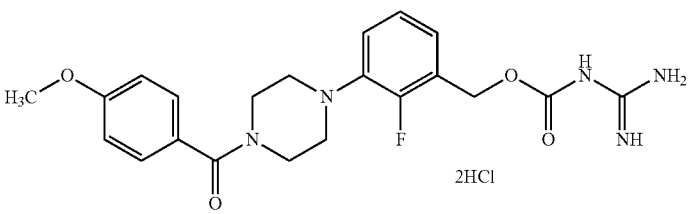 [SMILES: COc1ccc(C(=O)N2CCN(c3cccc(COC(=O)NC(=N)N)c3F)CC2)cc1] 2HCl |
| 18 | 23 | 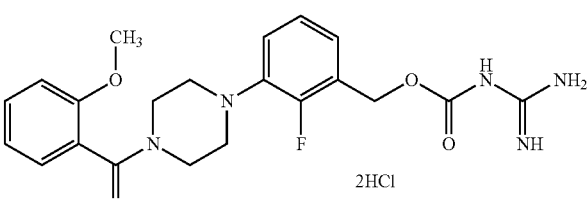 2HCl |
TABLE 84
| Ex | Syn | Structure |
|---|---|---|
| 19 | 23 | 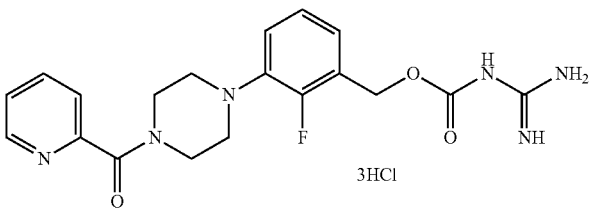 [SMILES: N=C(N)NC(=O)OCc1cccc(N2CCN(C(=O)c3ccccn3)CC2)c1F] 3HCl |
| 20 | 23 | 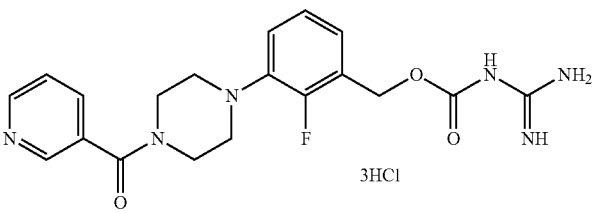 [SMILES: N=C(N)NC(=O)OCc1cccc(N2CCN(C(=O)c3cccnc3)CC2)c1F] 3HCl |

TABLE 84-continued

| Ex | Syn | Structure |
|----|-----|-----------|
| 21 | 23 | 3HCl |
| 22 | 23 | 2HCl |
| 23 | 23 | 2HCl |
| 24 | 23 | 2HCl |
| 25 | 23 | 2HCl |
| 26 | 23 | 2HCl |

TABLE 84-continued

| Ex | Syn | Structure |
|----|-----|-----------|
| 27 | 23 | 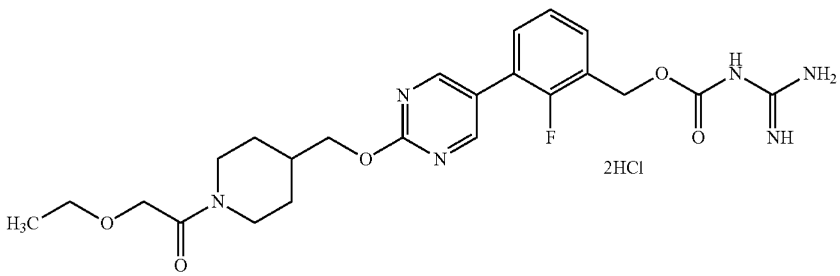 [SMILES: CCOCC(=O)N1CCC(COc2ncc(-c3cccc(COC(=O)NC(=N)N)c3F)cn2)CC1] |
| 28 | 23 | 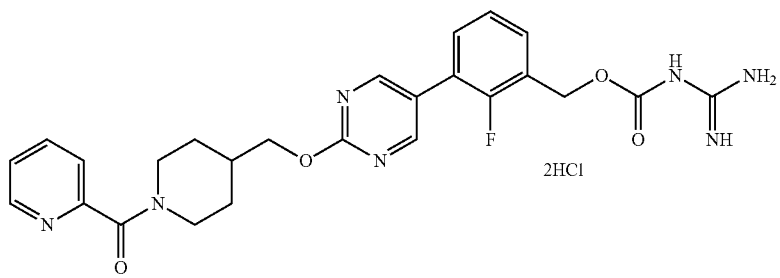 [SMILES: N=C(N)NC(=O)OCc1cccc(-c2cnc(OCC3CCN(C(=O)c4ccccn4)CC3)nc2)c1F] |
| 29 | 23 | 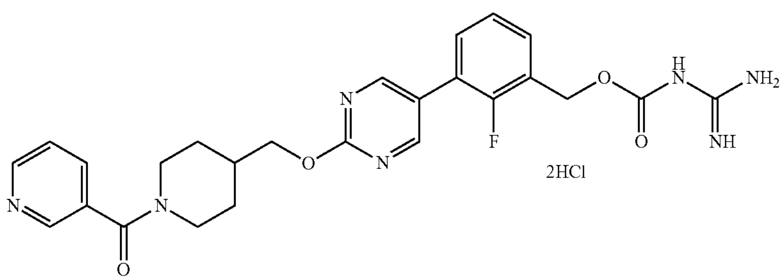 [SMILES: N=C(N)NC(=O)OCc1cccc(-c2cnc(OCC3CCN(C(=O)c4cccnc4)CC3)nc2)c1F] |
| 30 | 23 | 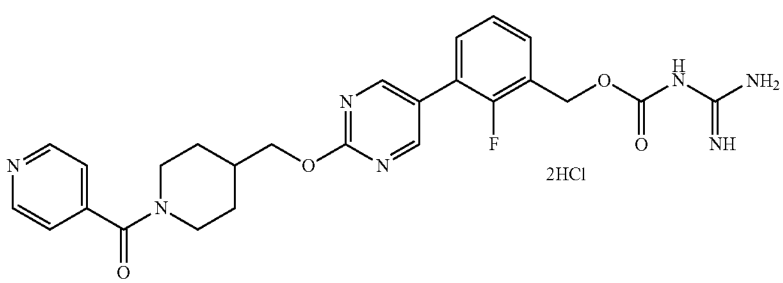 [SMILES: N=C(N)NC(=O)OCc1cccc(-c2cnc(OCC3CCN(C(=O)c4ccncc4)CC3)nc2)c1F] |
| 31 | 23 | 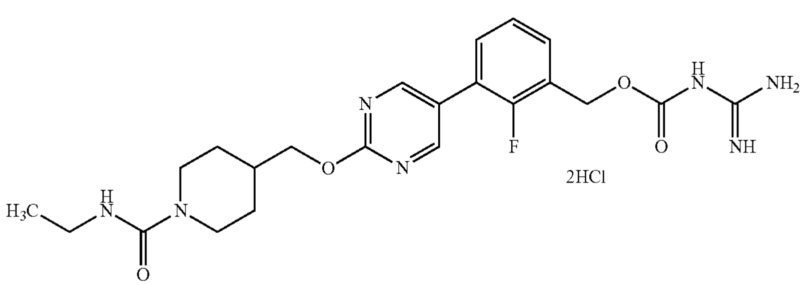 [SMILES: CCNC(=O)N1CCC(COc2ncc(-c3cccc(COC(=O)NC(=N)N)c3F)cn2)CC1] |

TABLE 84-continued

| Ex | Syn | Structure |
|---|---|---|
| 32 | 23 | (structure) HCl |
| 33 | 23 | (structure) HCl |
| 34 | 23 | (structure) HCl |
| 35 | 23 | (structure) HCl |
| 36 | 23 | (structure) 2HCl |

TABLE 85

| Ex | Syn | Structure |
|---|---|---|
| 37 | 23 | (structure with diethylcarbamoyl piperidine-methyl-oxy-pyrimidine-fluorophenyl-methyl carbamoyl guanidine, 2HCl) |
| 38 | 23 | (structure with cyclopropylaminocarbonyl piperidine-methyl-oxy-pyrimidine-fluorophenyl-methyl carbamoyl guanidine, 2HCl) |
| 39 | 23 | (structure with isopropylaminocarbonyl piperidine-methyl-oxy-pyrimidine-fluorophenyl-methyl carbamoyl guanidine, 2HCl) |
| 40 | 23 | (structure with propylaminocarbonyl piperidine-methyl-oxy-pyrimidine-fluorophenyl-methyl carbamoyl guanidine, 2HCl) |
| 41 | 23 | (structure with morpholino-thiazole-pyridine-methyl carbamoyl guanidine, 2HCl) |
| 42 | 23 | (structure with morpholino-piperidine-phenyl-methyl carbamoyl guanidine, 3HCl) |

TABLE 85-continued

| Ex | Syn | Structure |
|---|---|---|
| 43 | 23 | 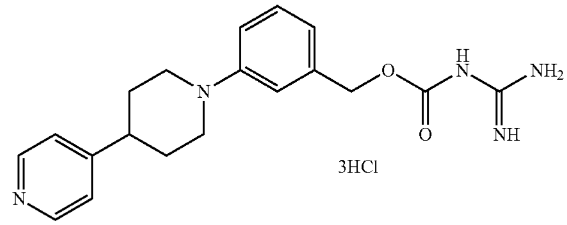 [SMILES: N=C(N)NC(=O)OCc1cccc(N2CCC(c3ccncc3)CC2)c1] |
| 44 | 23 | 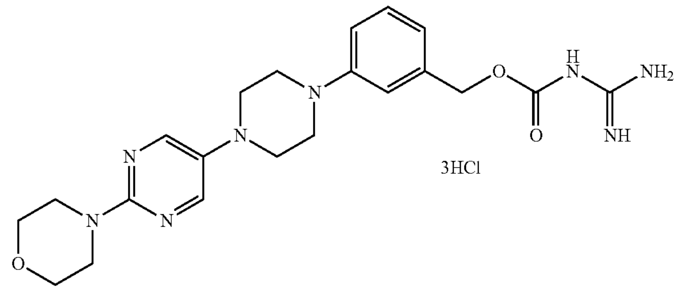 [SMILES: N=C(N)NC(=O)OCc1cccc(N2CCN(c3cnc(N4CCOCC4)nc3)CC2)c1] |
| 45 | 23 | 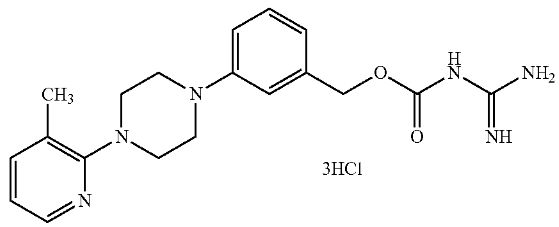 [SMILES: Cc1cccnc1N1CCN(c2cccc(COC(=O)NC(=N)N)c2)CC1] |
| 46 | 23 | 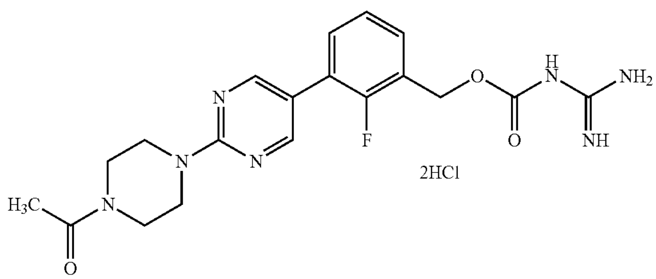 [SMILES: CC(=O)N1CCN(c2ncc(-c3cccc(COC(=O)NC(=N)N)c3F)cn2)CC1] |
| 47 | 23 | 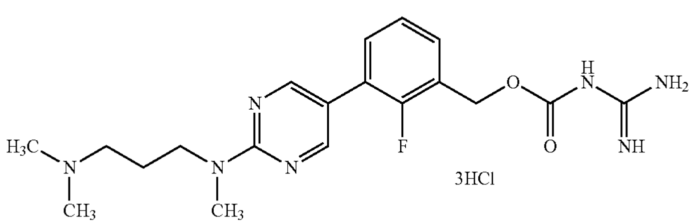 [SMILES: CN(C)CCCN(C)c1ncc(-c2cccc(COC(=O)NC(=N)N)c2F)cn1] |
| 48 | 23 | 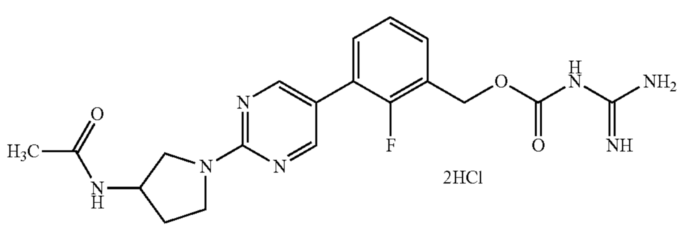 [SMILES: CC(=O)NC1CCN(c2ncc(-c3cccc(COC(=O)NC(=N)N)c3F)cn2)C1] |

TABLE 85-continued

| Ex | Syn | Structure |
|----|-----|-----------|
| 49 | 23 | (structure) 2HCl |
| 50 | 23 | (structure) 3HCl |
| 51 | 23 | (structure) 3HCl |
| 52 | 23 | (structure) 3HCl |
| 53 | 23 | (structure) 3HCl |
| 54 | 23 | (structure) 3HCl |

TABLE 86
| Ex | Syn | Structure |
|---|---|---|
| 55 | 23 | 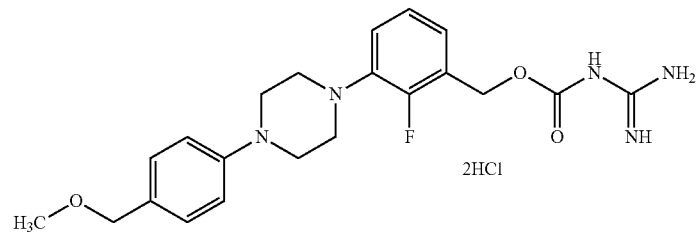 [SMILES: COCc1ccc(N2CCN(c3cccc(COC(=O)NC(=N)N)c3F)CC2)cc1] 2HCl |
| 56 | 23 | 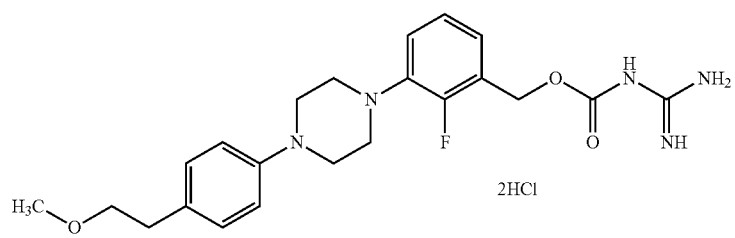 [SMILES: COCCc1ccc(N2CCN(c3cccc(COC(=O)NC(=N)N)c3F)CC2)cc1] 2HCl |
| 57 | 23 | 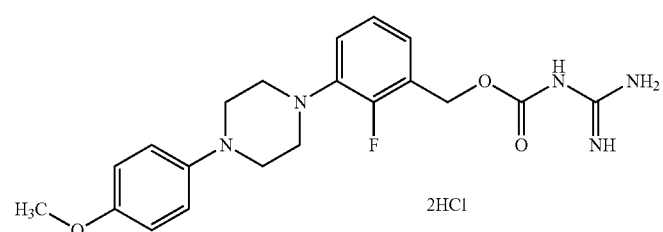 2HCl |
| 58 | 23 | 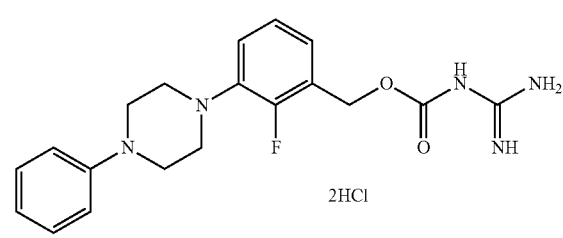 [SMILES: N=C(N)NC(=O)OCc1cccc(N2CCN(c3ccccc3)CC2)c1F] 2HCl |
| 59 | 23 | 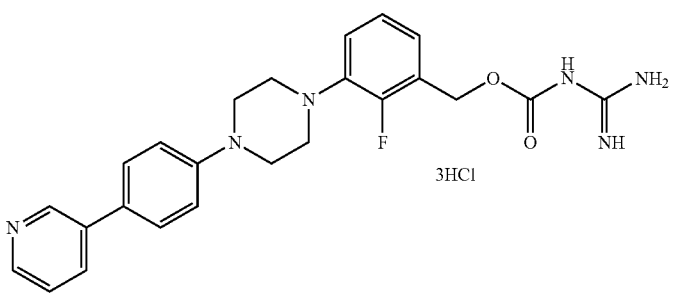 [SMILES: N=C(N)NC(=O)OCc1cccc(N2CCN(c3ccc(-c4cccnc4)cc3)CC2)c1F] 3HCl |
| 60 | 23 | 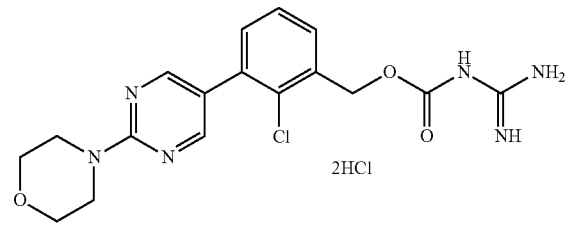 [SMILES: N=C(N)NC(=O)OCc1cccc(-c2cnc(N3CCOCC3)nc2)c1Cl] 2HCl |

TABLE 86-continued

| Ex | Syn | Structure |
|---|---|---|
| 61 | 23 | (structure: 4-(pyridin-3-yl)piperazin-1-yl ketone linked via CH2 to phenyl-CH2-O-C(O)-NH-C(=NH)NH2, 2HCl) |
| 62 | 23 | (structure: bis(2-methoxyethyl)amino-pyrimidin-5-yl attached to fluorophenyl-CH2-O-C(O)-NH-C(=NH)NH2, 2HCl) |
| 63 | 23 | (structure: 3-methoxyazetidin-1-yl-pyrimidin-5-yl attached to fluorophenyl-CH2-O-C(O)-NH-C(=NH)NH2, 2HCl) |
| 64 | 23 | (structure: 4-hydroxy-4-methylpiperidin-1-yl-pyrimidin-5-yl attached to fluorophenyl-CH2-O-C(O)-NH-C(=NH)NH2, 2HCl) |
| 65 | 23 | (structure: tetrahydropyran-4-ylamino-pyrimidin-5-yl attached to fluorophenyl-CH2-O-C(O)-NH-C(=NH)NH2, 2HCl) |
| 66 | 23 | (structure: 3-methoxyazetidin-1-yl-pyrimidin-5-yl-CH2CH2- attached to fluorophenyl-CH2-O-C(O)-NH-C(=NH)NH2, 2HCl) |
| 67 | 23 | (structure: morpholin-4-yl-pyrimidin-5-yl-CH2CH2- attached to fluorophenyl-CH2-O-C(O)-NH-C(=NH)NH2, 2HCl) |

TABLE 86-continued
| Ex | Syn | Structure |
|---|---|---|
| 68 | 23 | 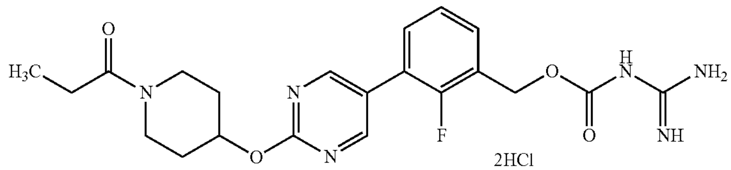 [SMILES: CCC(=O)N1CCC(Oc2ncc(-c3cccc(COC(=O)NC(=N)N)c3F)cn2)CC1] |
| 69 | 23 | 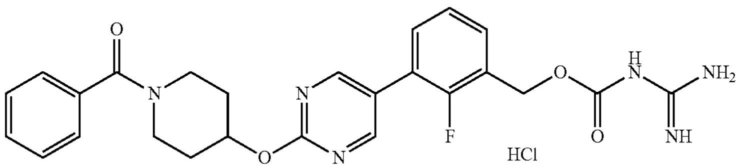 [SMILES: N=C(N)NC(=O)OCc1cccc(-c2cnc(OC3CCN(C(=O)c4ccccc4)CC3)nc2)c1F ; Cl] |
| 70 | 23 | 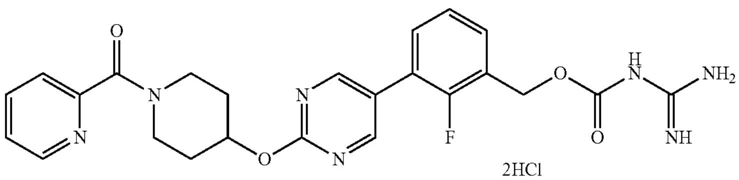 [SMILES: N=C(N)NC(=O)OCc1cccc(-c2cnc(OC3CCN(C(=O)c4ccccn4)CC3)nc2)c1F] |
| 71 | 23 | 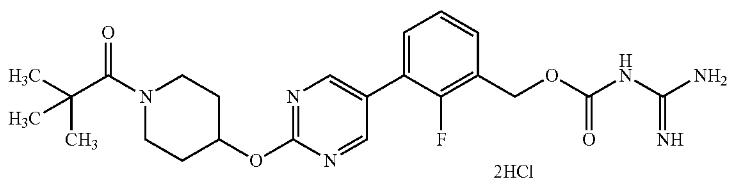 [SMILES: CC(C)(C)C(=O)N1CCC(Oc2ncc(-c3cccc(COC(=O)NC(=N)N)c3F)cn2)CC1] |
| 72 | 23 | 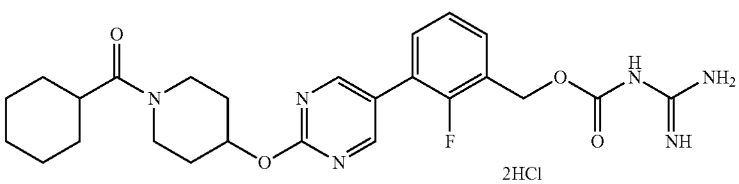 [SMILES: N=C(N)NC(=O)OCc1cccc(-c2cnc(OC3CCN(C(=O)C4CCCCC4)CC3)nc2)c1F] |
TABLE 87
| Ex | Syn | Structure |
|---|---|---|
| 73 | 23 | 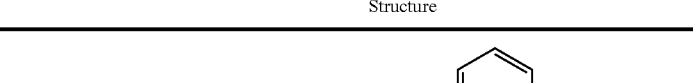 |

TABLE 87-continued

| Ex | Syn | Structure |
|---|---|---|
| 74 | 23 | 2HCl |
| 75 | 23 | 3HCl |
| 76 | 23 | 2HCl |
| 77 | 23 | 2HCl |
| 78 | 23 | 2HCl |
| 79 | 23 | HCl |

TABLE 87-continued

| Ex | Syn | Structure |
|---|---|---|
| 80 | 23 | 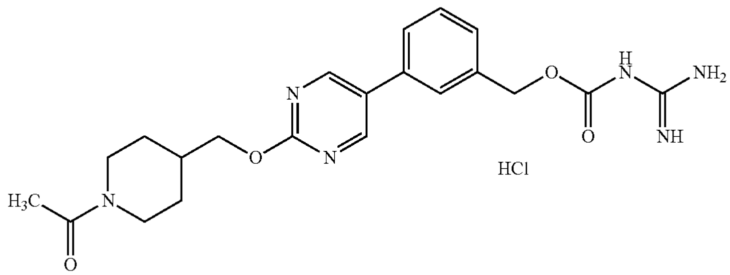 [SMILES: CC(=O)N1CCC(COc2ncc(-c3cccc(COC(=O)NC(=N)N)c3)cn2)CC1 ; Cl] |
| 81 | 23 | 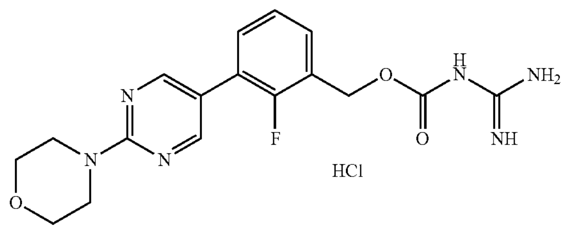 [SMILES: N=C(N)NC(=O)OCc1cccc(-c2cnc(N3CCOCC3)nc2)c1F ; Cl] |
| 82 | 23 | 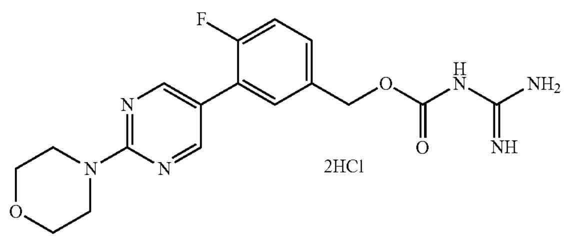 [SMILES: N=C(N)NC(=O)OCc1ccc(F)c(-c2cnc(N3CCOCC3)nc2)c1] |
| 83 | 23 | 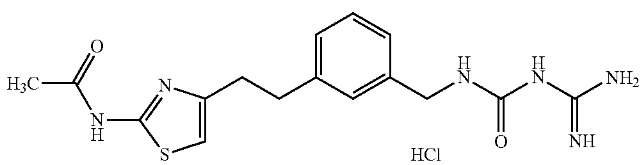 [SMILES: CC(=O)Nc1nc(CCc2cccc(CNC(=O)NC(=N)N)c2)cs1 ; Cl] |
| 84 | 23 | 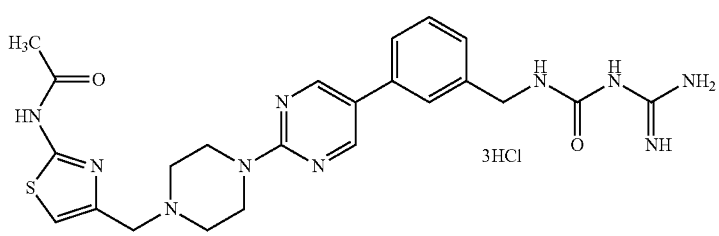 [SMILES: CC(=O)Nc1nc(CN2CCN(c3ncc(-c4cccc(CNC(=O)NC(=N)N)c4)cn3)CC2)cs1] |
| 85 | 23 | 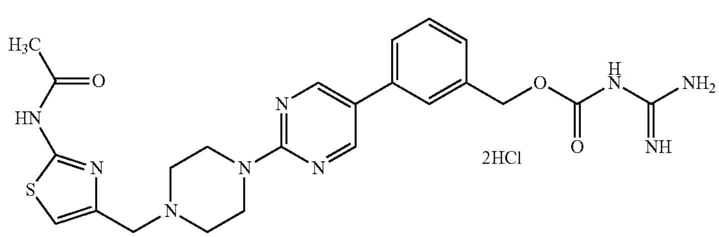 [SMILES: CC(=O)Nc1nc(CN2CCN(c3ncc(-c4cccc(COC(=O)NC(=N)N)c4)cn3)CC2)cs1] |
| 86 | 23 | 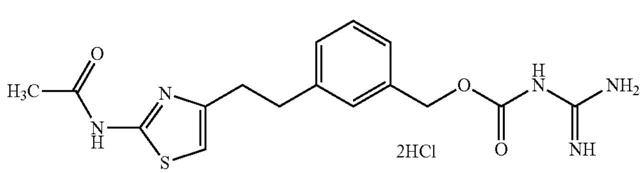 [SMILES: CC(=O)Nc1nc(CCc2cccc(COC(=O)NC(=N)N)c2)cs1] |

TABLE 87-continued
| Ex | Syn | Structure |
|---|---|---|
| 87 | 23 | 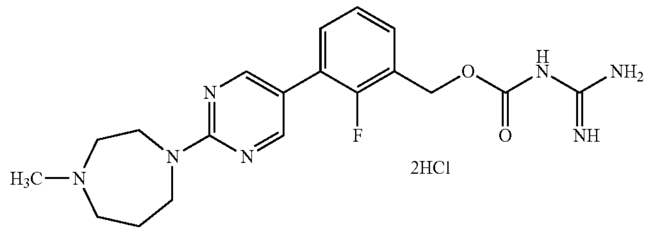 [SMILES: CN1CCCN(c2ncc(-c3cccc(COC(=O)NC(=N)N)c3F)cn2)CC1] |
| 88 | 23 | 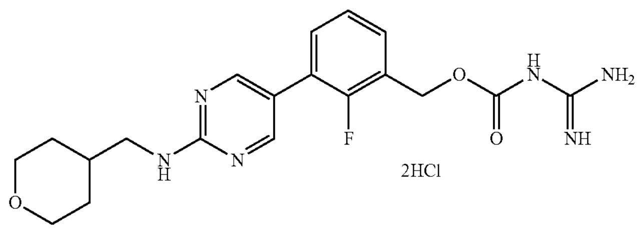 [SMILES: N=C(N)NC(=O)OCc1cccc(-c2cnc(NCC3CCOCC3)nc2)c1F] |
| 89 | 23 | 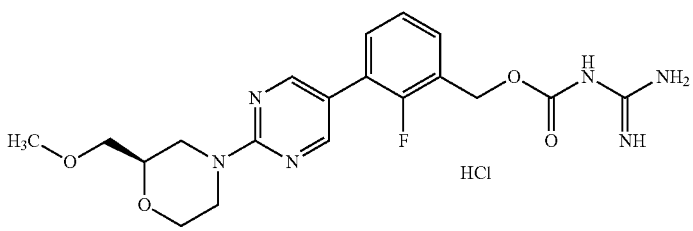 [SMILES: COC[C@H]1CN(c2ncc(-c3cccc(COC(=O)NC(=N)N)c3F)cn2)CCO1 ; Cl] |
| 90 | 23 | 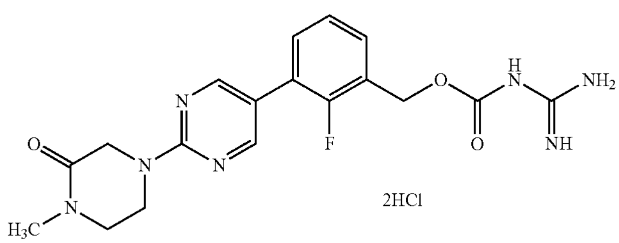 [SMILES: CN1CCN(c2ncc(-c3cccc(COC(=O)NC(=N)N)c3F)cn2)CC1=O] |
TABLE 88
| Ex | Syn | Structure |
|---|---|---|
| 91 | 23 | 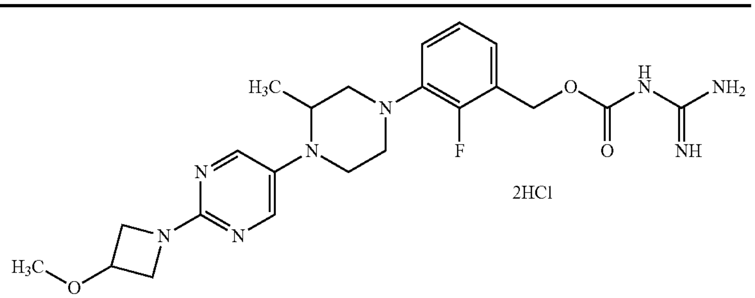 |
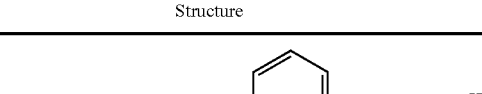

TABLE 88-continued

| Ex | Syn | Structure |
|----|-----|-----------|
| 92 | 23 | 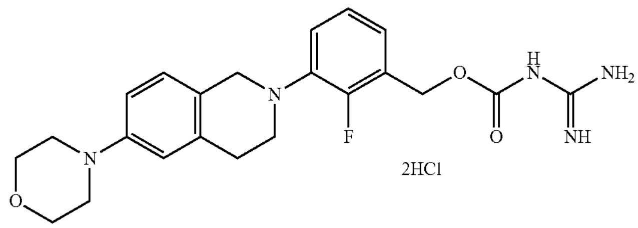 [SMILES: N=C(N)NC(=O)OCc1cccc(N2CCc3cc(N4CCOCC4)ccc3C2)c1F] |
| 93 | 23 | 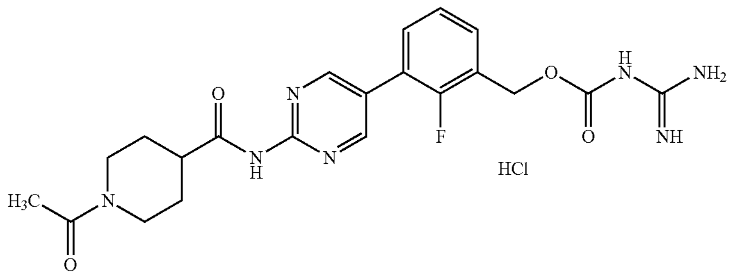 [SMILES: CC(=O)N1CCC(C(=O)Nc2ncc(-c3cccc(COC(=O)NC(=N)N)c3F)cn2)CC1 ; Cl] |
| 94 | 23 | 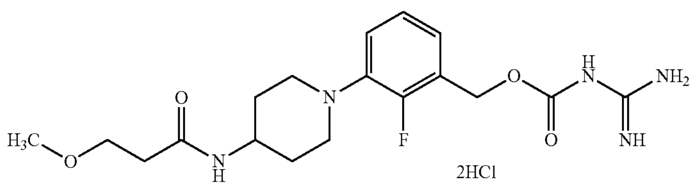 [SMILES: COCCC(=O)NC1CCN(c2cccc(COC(=O)NC(=N)N)c2F)CC1] |
| 95 | 23 | 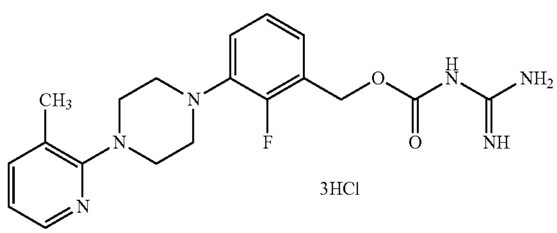 [SMILES: Cc1cccnc1N1CCN(c2cccc(COC(=O)NC(=N)N)c2F)CC1] |
| 96 | 23 | 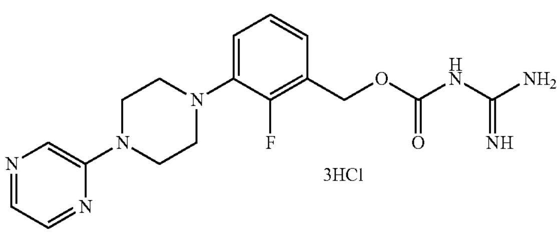 [SMILES: N=C(N)NC(=O)OCc1cccc(N2CCN(c3cnccn3)CC2)c1F] |
| 97 | 23 | 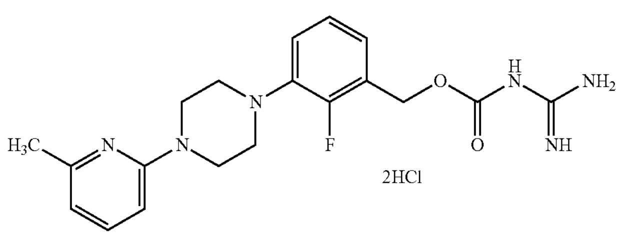 [SMILES: Cc1cccc(N2CCN(c3cccc(COC(=O)NC(=N)N)c3F)CC2)n1] |

TABLE 88-continued

| Ex | Syn | Structure |
|---|---|---|
| 98 | 23 | 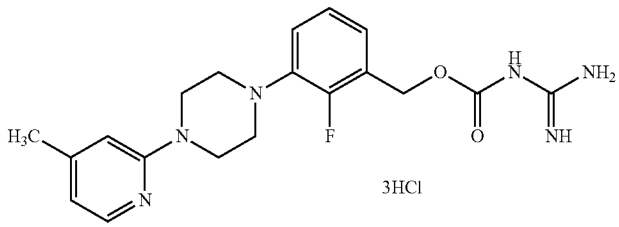 [SMILES: Cc1ccnc(N2CCN(c3cccc(COC(=O)NC(=N)N)c3F)CC2)c1] |
| 99 | 112 | 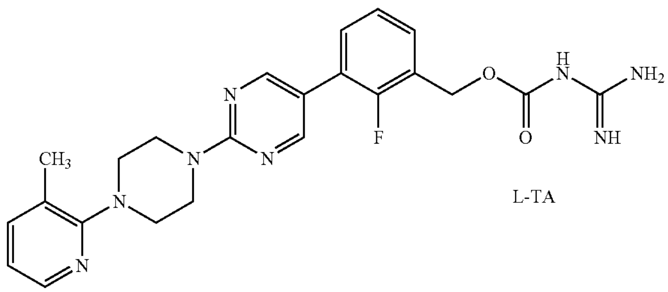 [SMILES: Cc1cccnc1N1CCN(c2ncc(-c3cccc(COC(=O)NC(=N)N)c3F)cn2)CC1] |
| 100 | 112 | 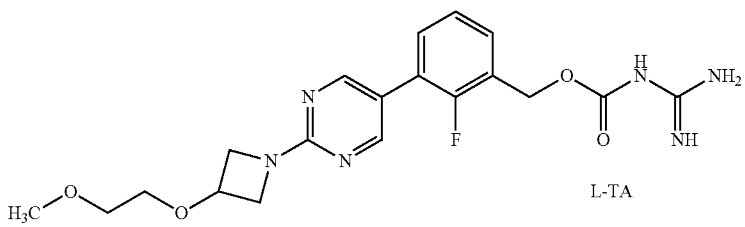 [SMILES: COCCOC1CN(c2ncc(-c3cccc(COC(=O)NC(=N)N)c3F)cn2)C1] |
| 101 | 112 | 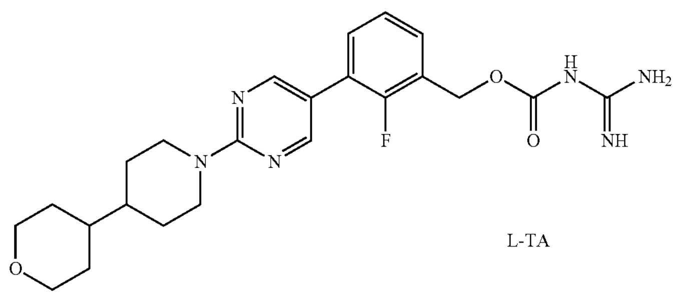 [SMILES: N=C(N)NC(=O)OCc1cccc(-c2cnc(N3CCC(C4CCOCC4)CC3)nc2)c1F] |
| 102 | 112 | 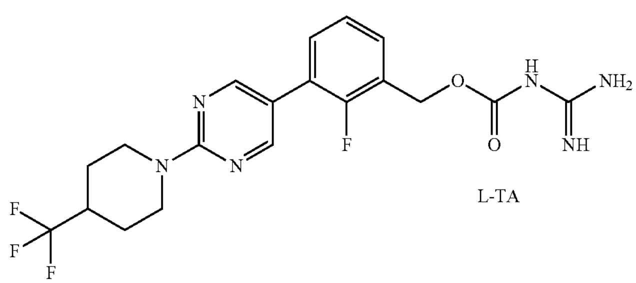 [SMILES: N=C(N)NC(=O)OCc1cccc(-c2cnc(N3CCC(C(F)(F)F)CC3)nc2)c1F] |
| 103 | 23 | 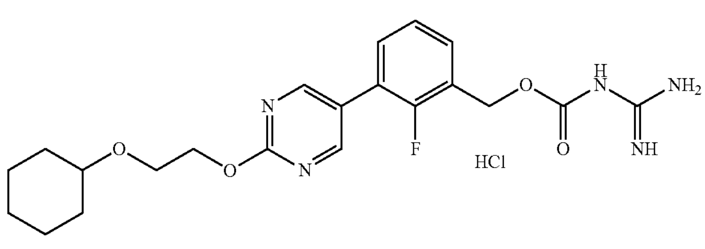 [SMILES: N=C(N)NC(=O)OCc1cccc(-c2cnc(OCCOC3CCCCC3)nc2)c1F ; Cl] |

TABLE 88-continued

| Ex | Syn | Structure |
|---|---|---|
| 104 | 112 | 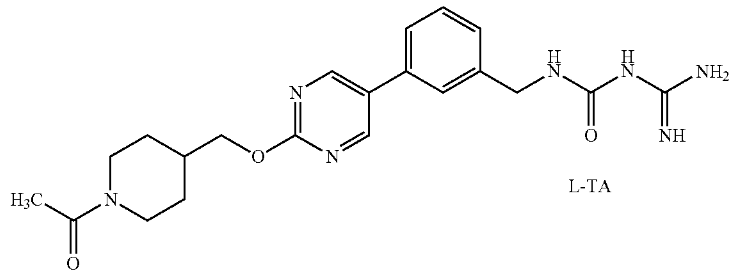 [SMILES: CC(=O)N1CCC(COc2ncc(-c3cccc(CNC(=O)NC(=N)N)c3)cn2)CC1] |
| 105 | 112 | 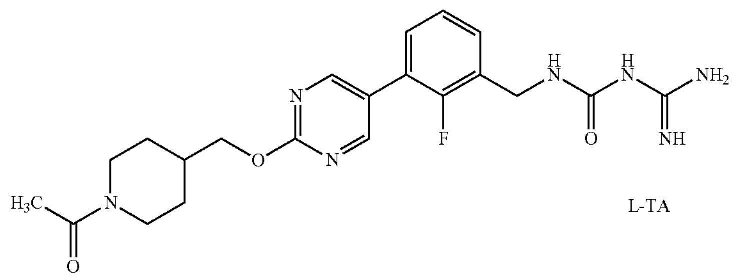 [SMILES: CC(=O)N1CCC(COc2ncc(-c3cccc(CNC(=O)NC(=N)N)c3F)cn2)CC1] |
| 106 | 112 | 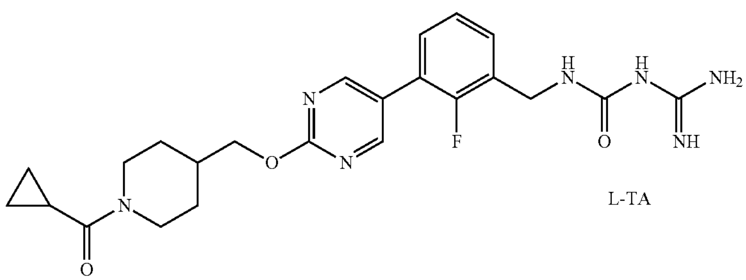 [SMILES: N=C(N)NC(=O)NCc1cccc(-c2cnc(OCC3CCN(C(=O)C4CC4)CC3)nc2)c1F] |
| 107 | 112 | 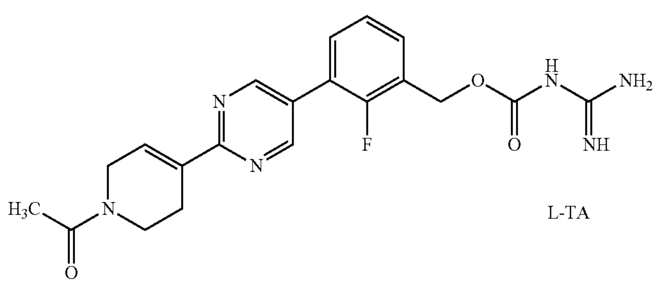 [SMILES: CC(=O)N1CC=C(c2ncc(-c3cccc(COC(=O)NC(=N)N)c3F)cn2)CC1] |
| 108 | 112 | 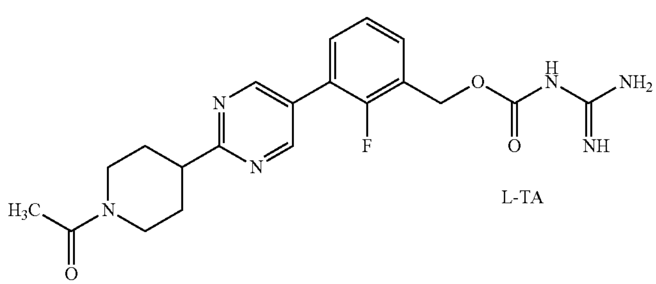 [SMILES: CC(=O)N1CCC(c2ncc(-c3cccc(COC(=O)NC(=N)N)c3F)cn2)CC1] |

TABLE 89
| Ex | Syn | Structure |
|---|---|---|
| 109 | 112 | 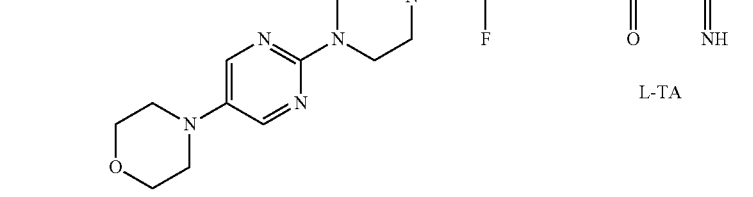 L-TA |
| 110 | 112 | 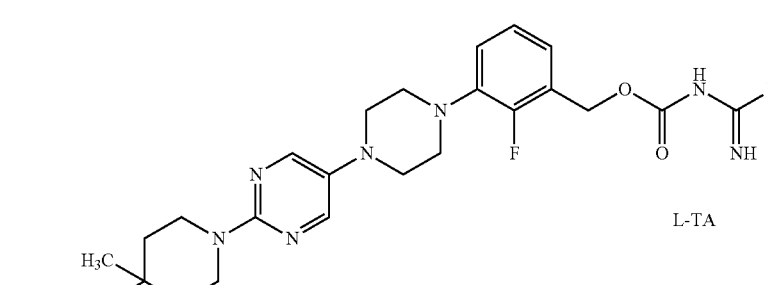 L-TA |
| 111 | 112 | 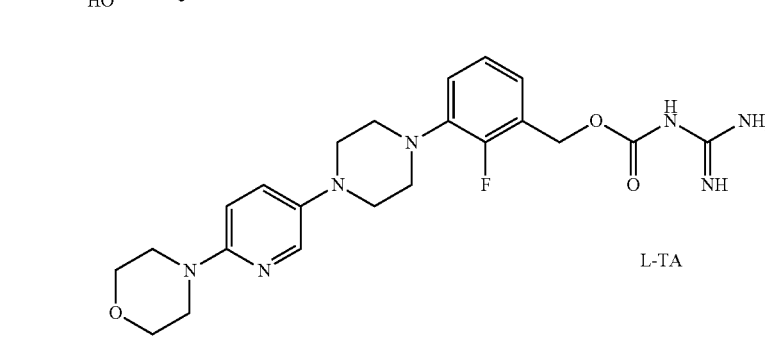 L-TA |
| 112 | 112 | 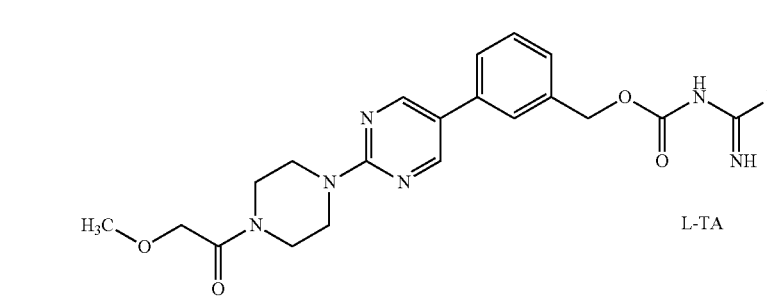 L-TA |
| 113 | 112 | 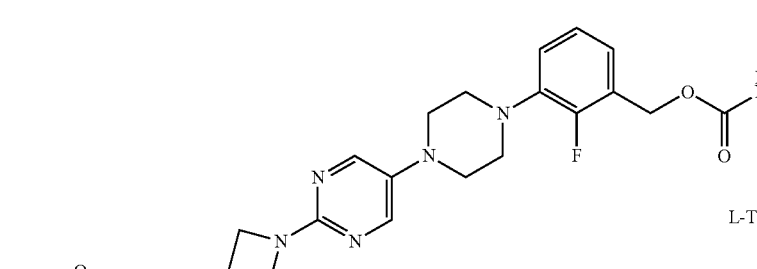 L-TA |

TABLE 89-continued
| Ex | Syn | Structure |
|----|-----|-----------|
| 114 | 112 | 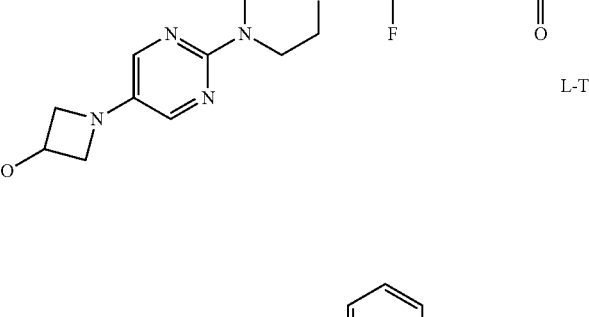 L-TA |
| 115 | 112 | 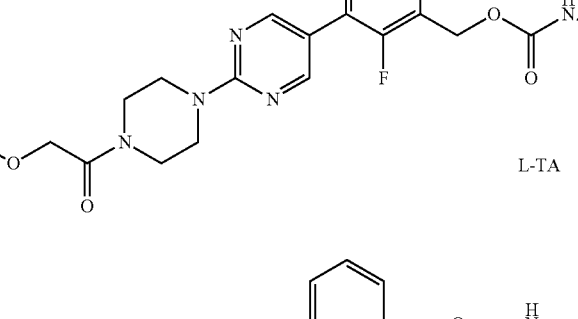 L-TA |
| 116 | 112 | 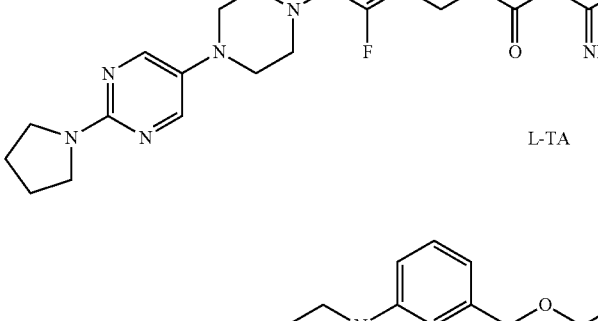 L-TA |
| 117 | 112 | 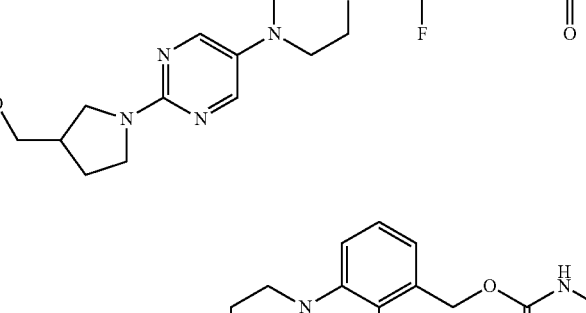 L-TA |
| 118 | 112 | 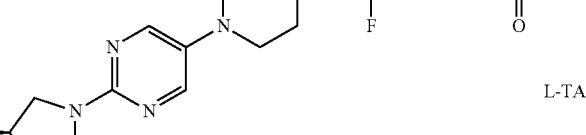 L-TA |

TABLE 89-continued

| Ex | Syn | Structure |
|---|---|---|
| 119 | 112 | (3-fluoropyrrolidin-1-yl)-pyrimidine-piperazine-fluorophenyl-methyl carbamate guanidine, L-TA |
| 120 | 112 | (3-methoxyazetidin-1-yl)-pyridine-piperazine-fluorophenyl-methyl carbamate guanidine, L-TA |
| 121 | 112 | (3,3-difluoropyrrolidin-1-yl)-pyrimidine-piperazine-fluorophenyl-methyl carbamate guanidine, L-TA |
| 122 | 112 | (1,4-oxazepan-4-yl)-pyrimidine-piperazine-fluorophenyl-methyl carbamate guanidine, L-TA |
| 123 | 112 | (4-acetylpiperazin-1-yl)-pyrimidine-piperazine-fluorophenyl-methyl carbamate guanidine, L-TA |

TABLE 89-continued
| Ex | Syn | Structure |
|---|---|---|
| 124 | 112 | 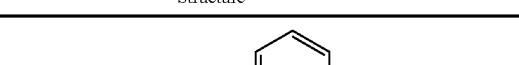 L-TA |
TABLE 90
| Ex | Syn | Structure |
|---|---|---|
| 125 | 112 | 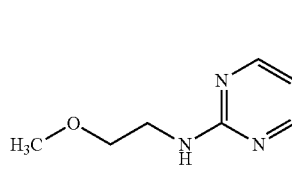 L-TA |
| 126 | 112 | 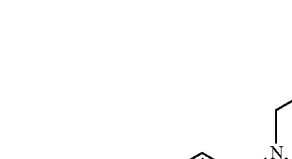 L-TA |
| 127 | 112 | 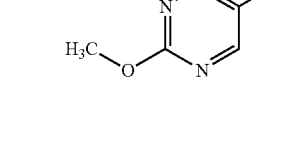 L-TA |
| 128 | 112 | 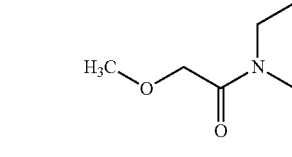 L-TA |
| 129 | 112 | 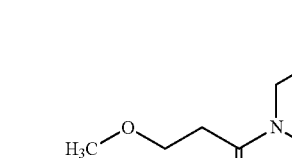 L-TA |

TABLE 90-continued
| Ex | Syn | Structure |
|---|---|---|
| 130 | 112 | 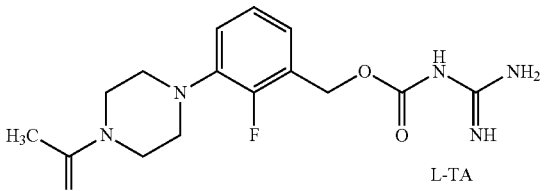 L-TA |
| 131 | 112 | 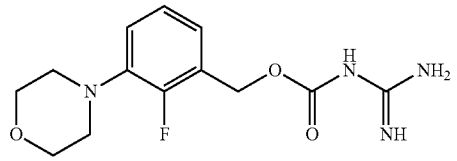 L-TA |
| 132 | 112 | 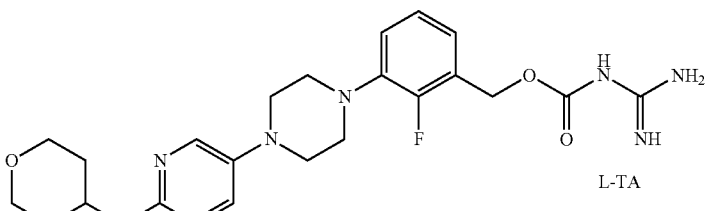 L-TA |
| 133 | 112 | 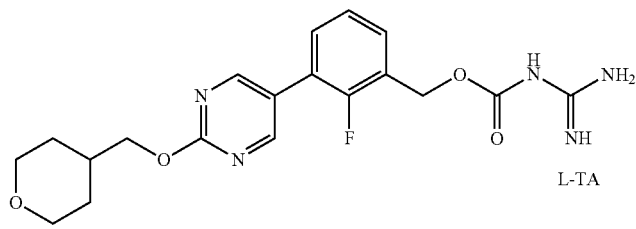 L-TA |
| 134 | 112 | 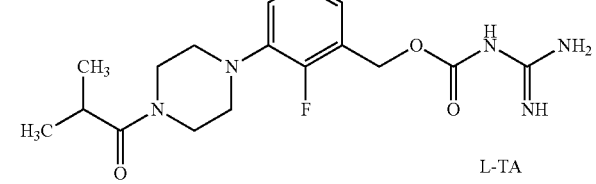 L-TA |
| 135 | 112 | 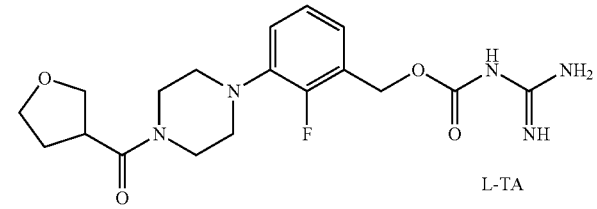 L-TA |
| 136 | 112 |  L-TA |

TABLE 90-continued
| Ex | Syn | Structure |
|---|---|---|
| 137 | 112 | 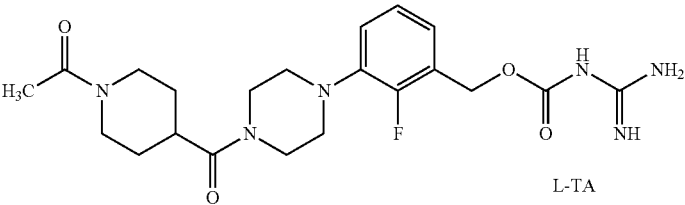 L-TA |
| 138 | 112 | 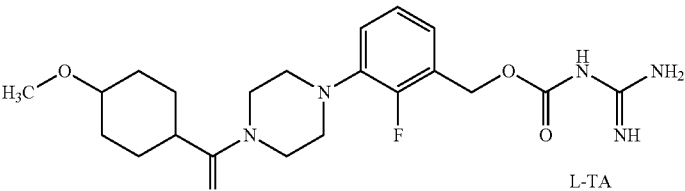 L-TA |
| 139 | 112 | 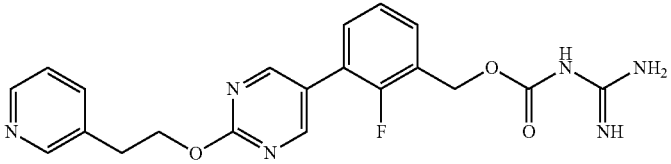 L-TA |
| 140 | 112 | 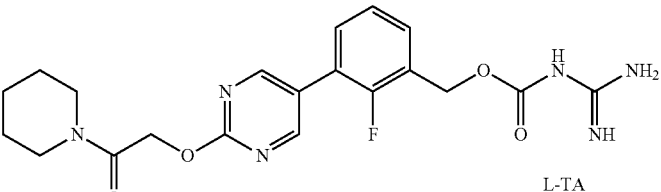 L-TA |
| 141 | 112 | 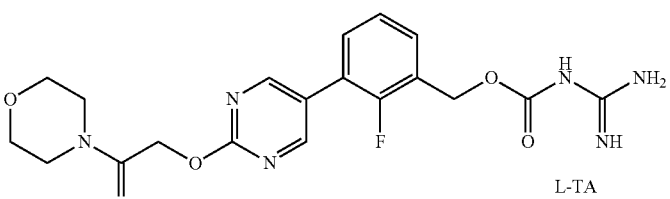 L-TA |
| 142 | 112 | trans- 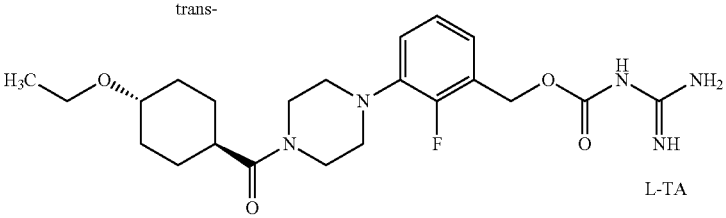 L-TA |

TABLE 91
| Ex | Syn | Structure |
|---|---|---|
| 143 | 112 | 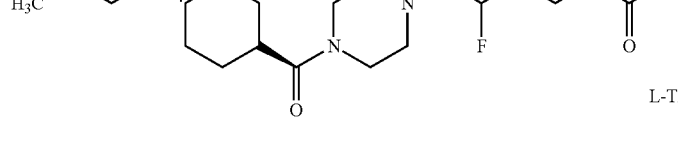 trans- L-TA |
| 144 | 112 | 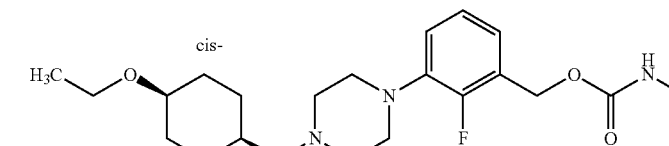 cis- L-TA |
| 145 | 112 | 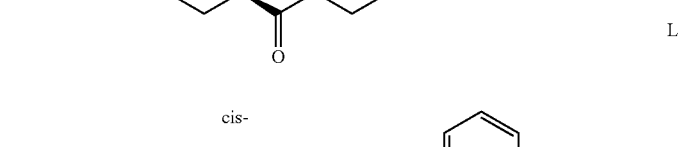 cis- L-TA |
| 146 | 112 |  L-TA |
| 147 | 112 |  L-TA |
| 148 | 112 | 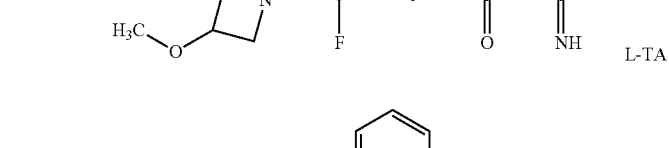 L-TA |
| 149 | 112 | 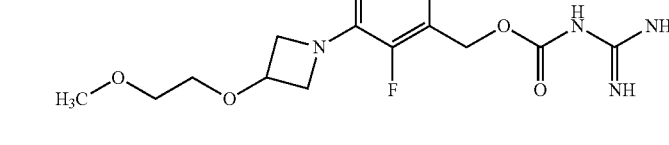 L-TA |

TABLE 91-continued
| Ex | Syn | Structure |
|---|---|---|
| 150 | 112 | 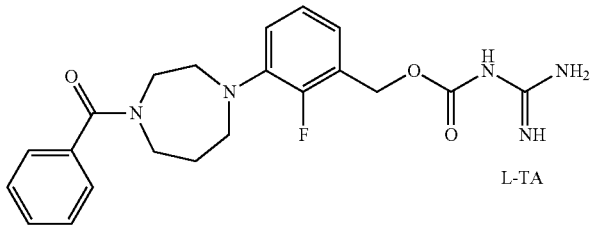 L-TA |
| 151 | 112 | 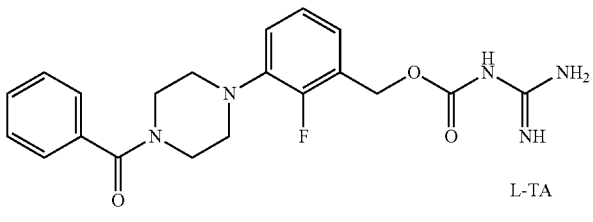 L-TA |
| 152 | 112 | 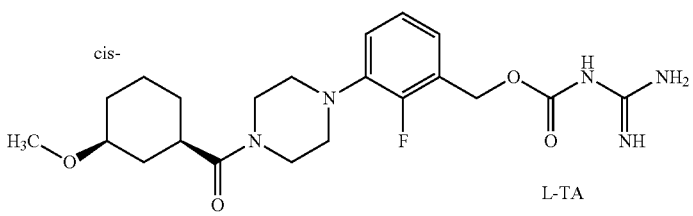 L-TA |
| 153 | 112 | 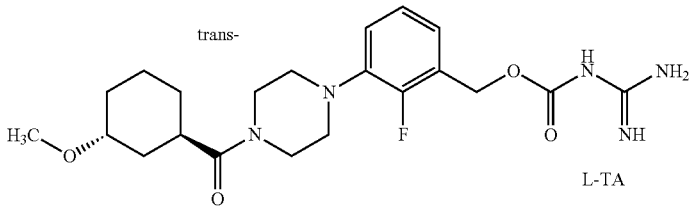 L-TA |
| 154 | 112 | 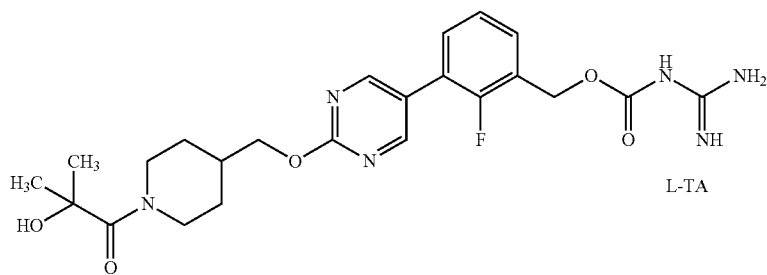 L-TA |
| 155 | 112 | 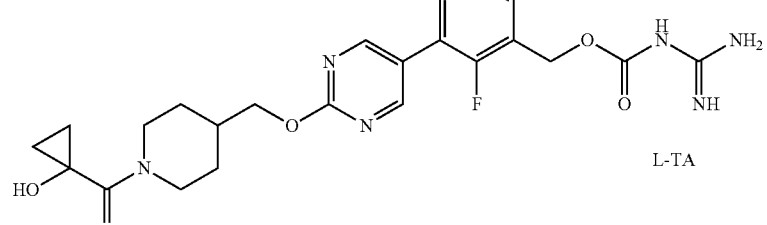 L-TA |

TABLE 91-continued

| Ex | Syn | Structure |
|---|---|---|
| 156 | 112 | [Structure: 4-(methylsulfonyl)piperazinyl-fluorobenzyl carbamimidoyl carbamate, L-TA] |
| 157 | 112 | [Structure: 4-(ethylsulfonyl)piperazinyl-fluorobenzyl carbamimidoyl carbamate, L-TA] |
| 158 | 112 | [Structure: 4-(cyclopropylsulfonyl)piperazinyl-fluorobenzyl carbamimidoyl carbamate, L-TA] |
| 159 | 112 | [Structure: 4-(propylsulfonyl)piperazinyl-fluorobenzyl carbamimidoyl carbamate, L-TA] |
| 160 | 112 | [Structure: 4-(isopropylsulfonyl)piperazinyl-fluorobenzyl carbamimidoyl carbamate, L-TA] |

TABLE 92

| Ex | Syn | Structure |
|---|---|---|
| 161 | 112 | [Structure: 4-(cyclohexylsulfonyl)piperazinyl-fluorobenzyl carbamimidoyl carbamate, L-TA] |

TABLE 92-continued
| Ex | Syn | Structure |
|---|---|---|
| 162 | 112 | 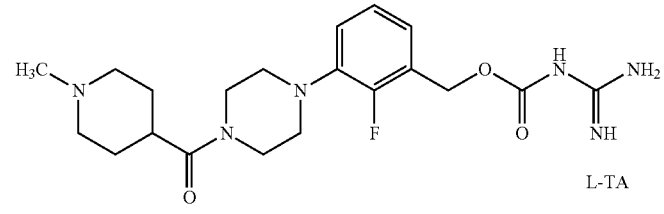 L-TA |
| 163 | 112 | 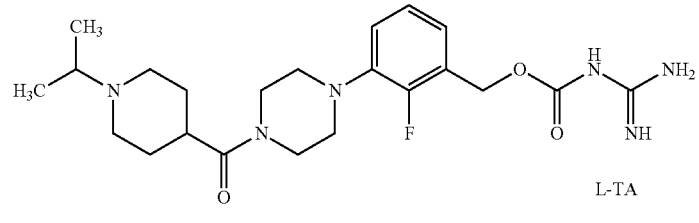 L-TA |
| 164 | 112 | 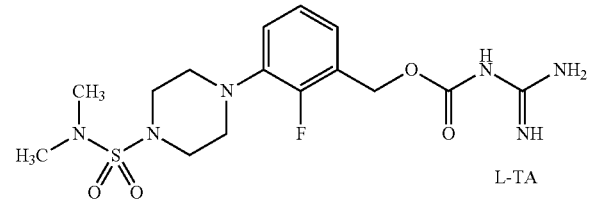 L-TA |
| 165 | 112 | 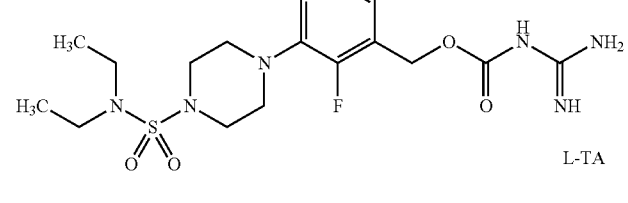 L-TA |
| 166 | 112 | 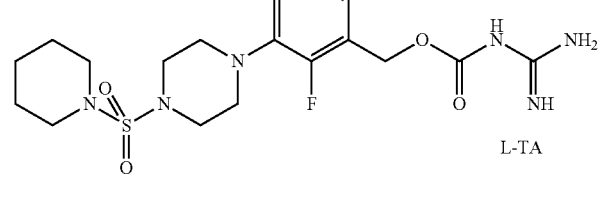 L-TA |
| 167 | 112 | 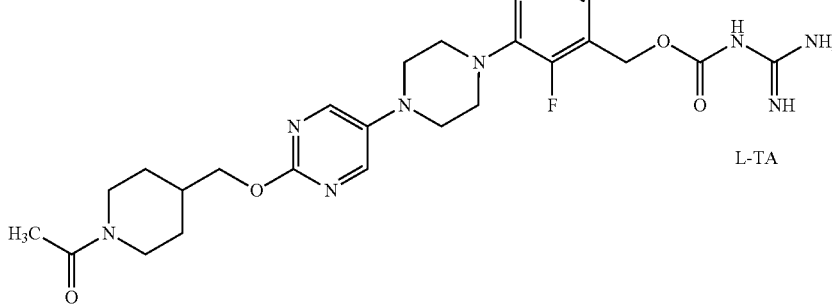 L-TA |

TABLE 92-continued

| Ex | Syn | Structure |
|---|---|---|
| 168 | 112 | 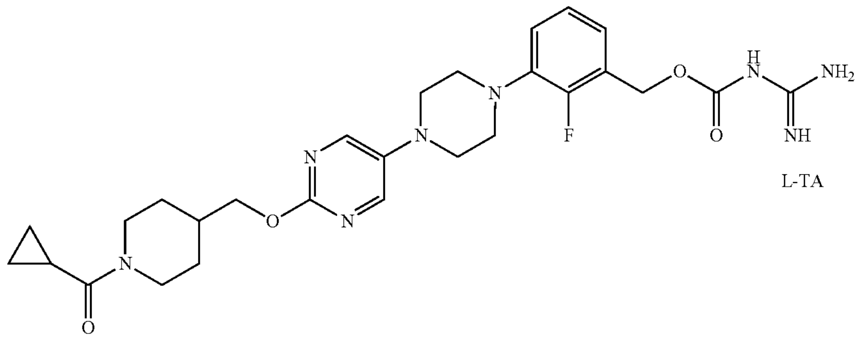 [SMILES: N=C(N)NC(=O)OCc1cccc(N2CCN(c3cnc(OCC4CCN(C(=O)C5CC5)CC4)nc3)CC2)c1F] |
| 169 | 112 | 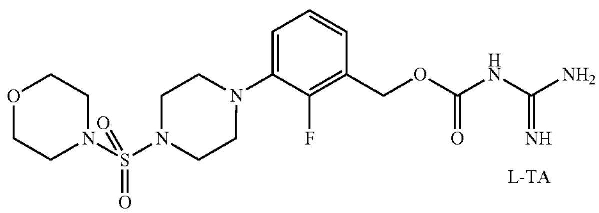 [SMILES: N=C(N)NC(=O)OCc1cccc(N2CCN(S(=O)(=O)N3CCOCC3)CC2)c1F] |
| 170 | 112 | 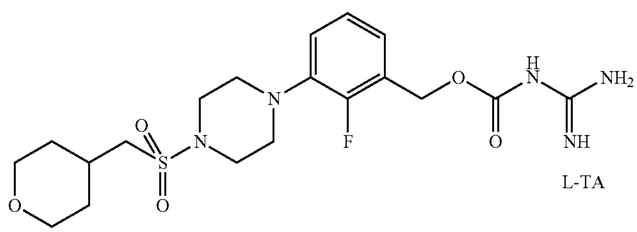 [SMILES: N=C(N)NC(=O)OCc1cccc(N2CCN(S(=O)(=O)CC3CCOCC3)CC2)c1F] |
| 171 | 112 | 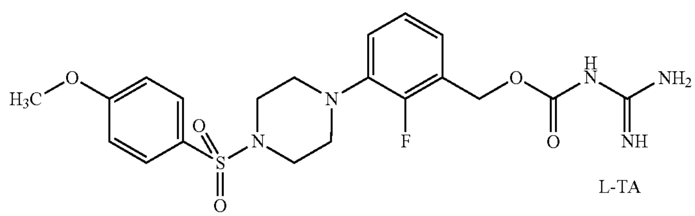 [SMILES: COc1ccc(S(=O)(=O)N2CCN(c3cccc(COC(=O)NC(=N)N)c3F)CC2)cc1] |
| 172 | 112 | 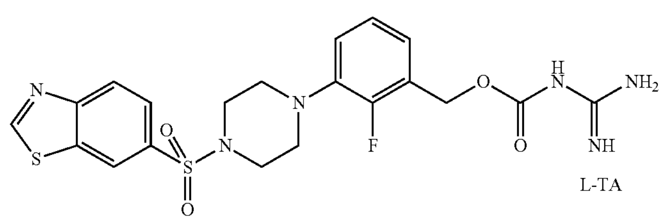 [SMILES: N=C(N)NC(=O)OCc1cccc(N2CCN(S(=O)(=O)c3ccc4ncsc4c3)CC2)c1F] |
| 173 | 112 | 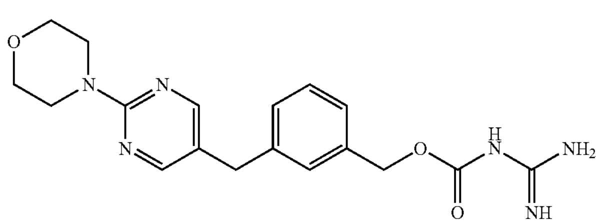 |

TABLE 92-continued

| Ex | Syn | Structure |
|---|---|---|
| 174 | 112 | 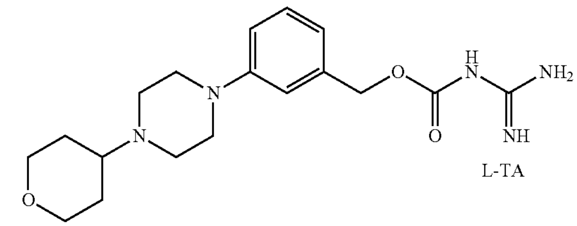 [SMILES: N=C(N)NC(=O)OCc1cccc(N2CCN(C3CCOCC3)CC2)c1] |
| 175 | 112 | 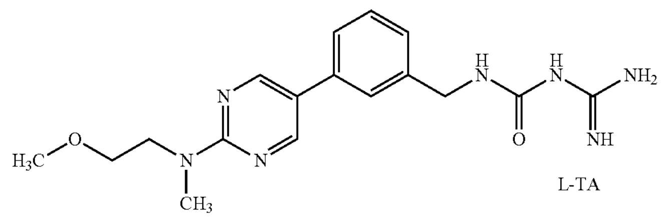 [SMILES: COCCN(C)c1ncc(-c2cccc(CNC(=O)NC(=N)N)c2)cn1] |
| 176 | 112 | 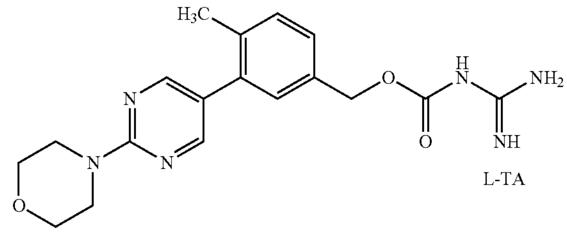 [SMILES: Cc1ccc(COC(=O)NC(=N)N)cc1-c1cnc(N2CCOCC2)nc1] |
| 177 | 112 | 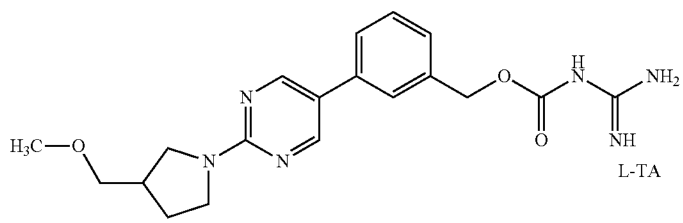 [SMILES: COCC1CCN(c2ncc(-c3cccc(COC(=O)NC(=N)N)c3)cn2)C1] |
| 178 | 112 | 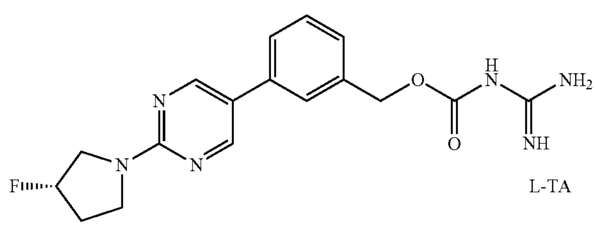 [SMILES: N=C(N)NC(=O)OCc1cccc(-c2cnc(N3CC[C@H](F)C3)nc2)c1] |

TABLE 93

| Ex | Syn | Structure |
|---|---|---|
| 179 | 112 | 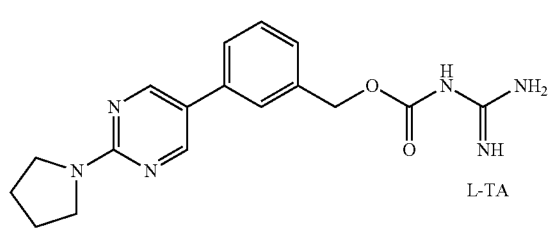 [SMILES: N=C(N)NC(=O)OCc1cccc(-c2cnc(N3CCCC3)nc2)c1] |

TABLE 93-continued

| Ex | Syn | Structure |
|---|---|---|
| 180 | 112 | (structure) L-TA |
| 181 | 112 | (structure) L-TA |
| 182 | 112 | (structure) L-TA |
| 183 | 112 | (structure) L-TA |
| 184 | 112 | (structure) L-TA |

TABLE 93-continued
| Ex | Syn | Structure |
|---|---|---|
| 185 | 112 | 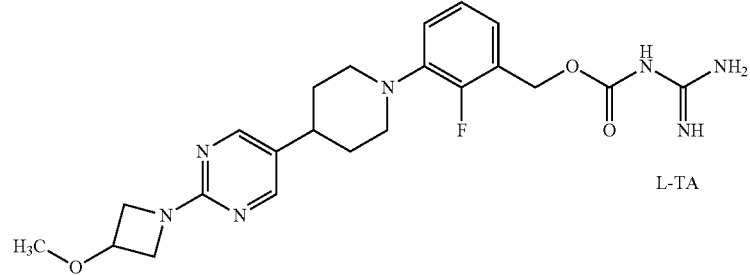 L-TA |
| 186 | 112 | 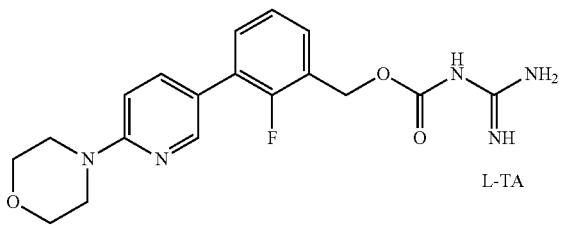 L-TA |
| 187 | 112 | 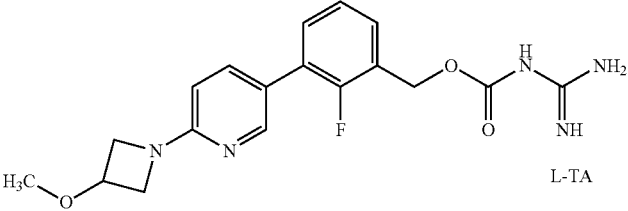 L-TA |
| 188 | 112 | 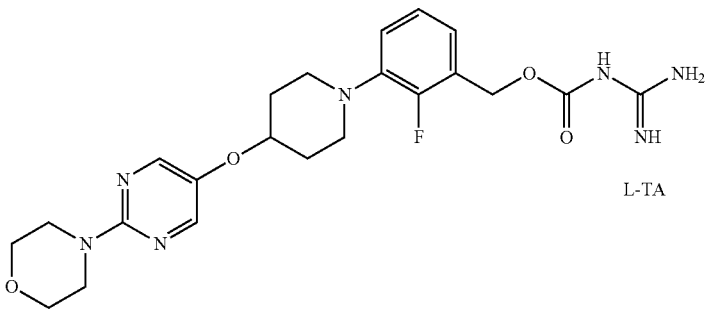 L-TA |
| 189 | 112 | 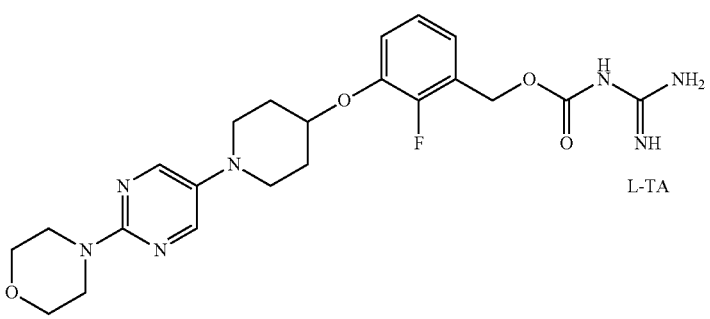 L-TA |

TABLE 93-continued
| Ex | Syn | Structure |
|---|---|---|
| 190 | 112 | 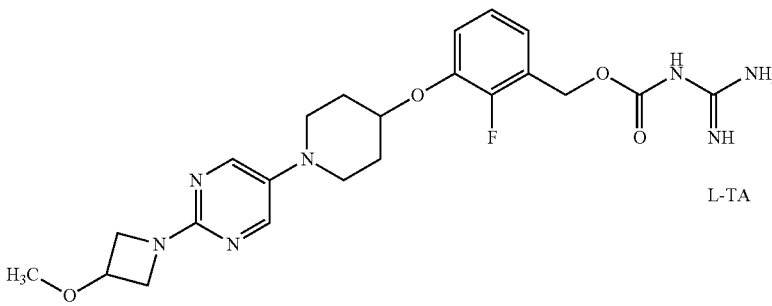 L-TA |
| 191 | 112 | 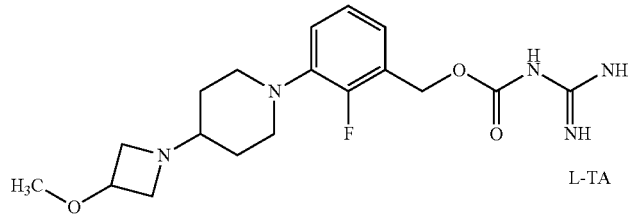 L-TA |
| 192 | 112 | 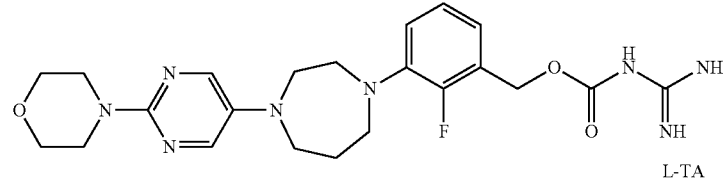 L-TA |
| 193 | 112 | 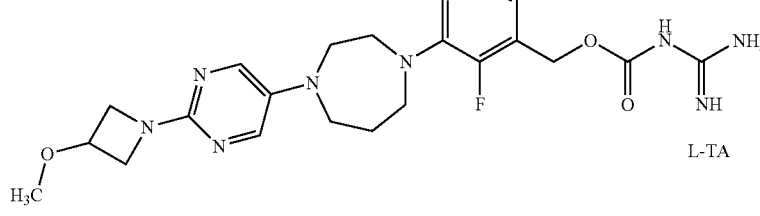 L-TA |
| 194 | 112 | 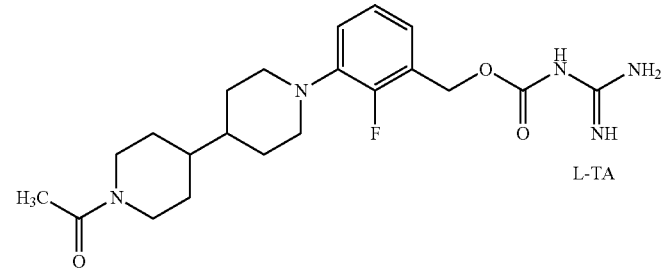 L-TA |

TABLE 94
| Ex | Syn | Structure |
|---|---|---|
| 195 | 112 | 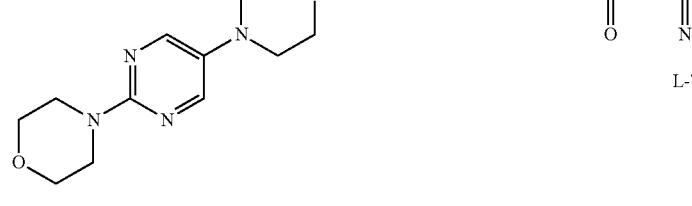 L-TA |
| 196 | 112 |  L-TA |
| 197 | 112 |  L-TA |
| 198 | 112 |  L-TA |
| 199 | 112 |  L-TA |
| 200 | 112 | 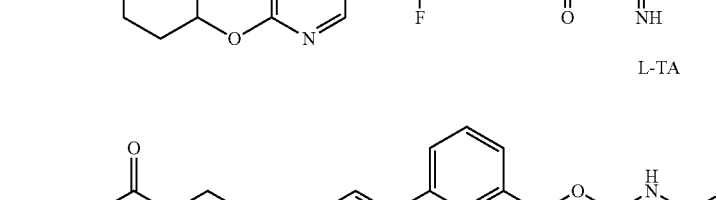 L-TA |

TABLE 94-continued

| Ex | Syn | Structure |
|---|---|---|
| 201 | 112 | (structure) L-TA |
| 202 | 112 | (structure) L-TA |
| 203 | 112 | (structure) L-TA |
| 204 | 112 | (structure) L-TA |
| 205 | 112 | (structure) L-TA |
| 206 | 112 | (structure) L-TA |
| 207 | 112 | (structure) L-TA |

TABLE 94-continued

| Ex | Syn | Structure |
|---|---|---|
| 208 | 112 | (structure) L-TA |
| 209 | 112 | (structure) L-TA |
| 210 | 112 | (structure) L-TA |
| 211 | 112 | (structure) L-TA |
| 212 | 112 | (structure) L-TA |

TABLE 95

| Ex | Syn | Structure |
|---|---|---|
| 213 | 112 | 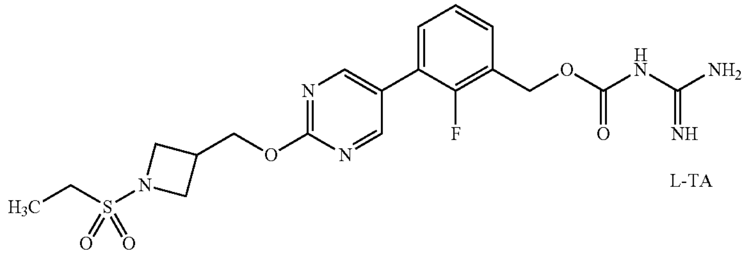 [SMILES: CCS(=O)(=O)N1CC(COc2ncc(-c3cccc(COC(=O)NC(=N)N)c3F)cn2)C1] |
| 214 | 112 | 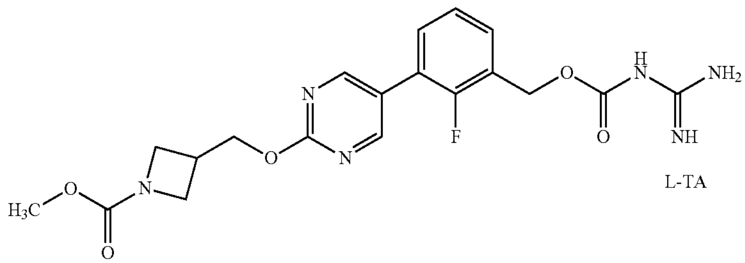 [SMILES: COC(=O)N1CC(COc2ncc(-c3cccc(COC(=O)NC(=N)N)c3F)cn2)C1] |
| 215 | 112 | 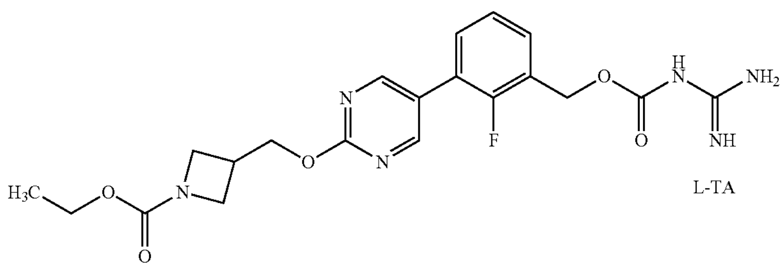 [SMILES: CCOC(=O)N1CC(COc2ncc(-c3cccc(COC(=O)NC(=N)N)c3F)cn2)C1] |
| 216 | 112 | 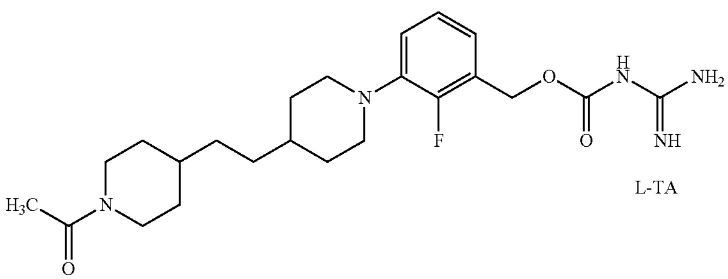 [SMILES: CC(=O)N1CCC(CCC2CCN(c3cccc(COC(=O)NC(=N)N)c3F)CC2)CC1] |
| 217 | 112 | 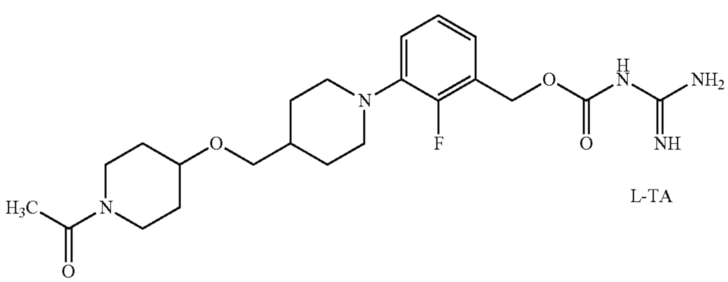 [SMILES: CC(=O)N1CCC(OCC2CCN(c3cccc(COC(=O)NC(=N)N)c3F)CC2)CC1] |

TABLE 95-continued

| Ex | Syn | Structure |
|---|---|---|
| 218 | 112 | 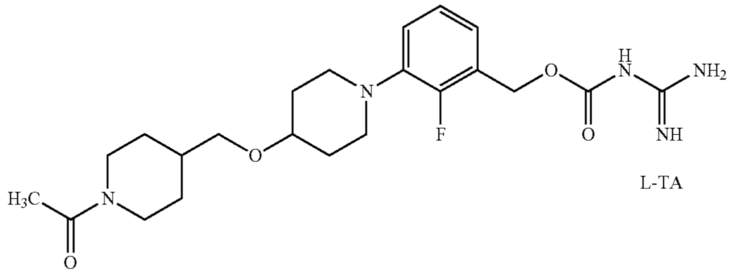 [SMILES: CC(=O)N1CCC(COC2CCN(c3cccc(COC(=O)NC(=N)N)c3F)CC2)CC1] |
| 219 | 112 | 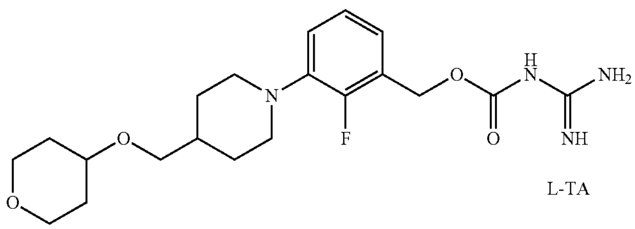 [SMILES: N=C(N)NC(=O)OCc1cccc(N2CCC(COC3CCOCC3)CC2)c1F] |
| 220 | 112 | 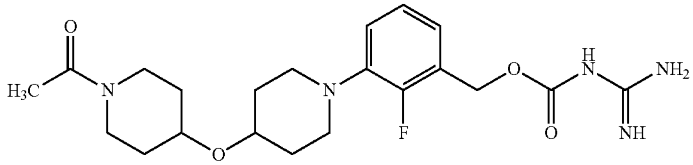 |
| 221 | 112 | 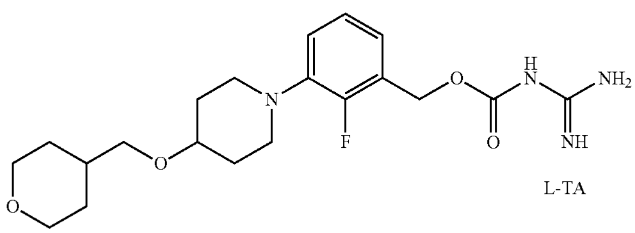 [SMILES: N=C(N)NC(=O)OCc1cccc(N2CCC(OCC3CCOCC3)CC2)c1F] |
| 222 | 112 | 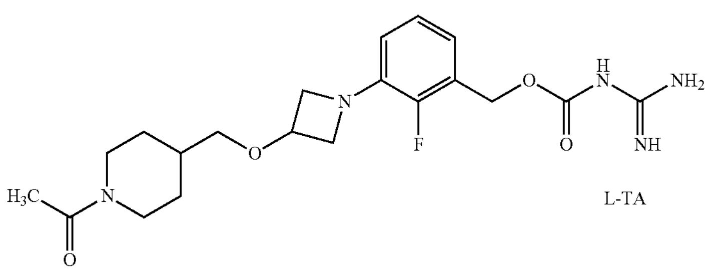 [SMILES: CC(=O)N1CCC(COC2CN(c3cccc(COC(=O)NC(=N)N)c3F)C2)CC1] |
| 223 | 112 | 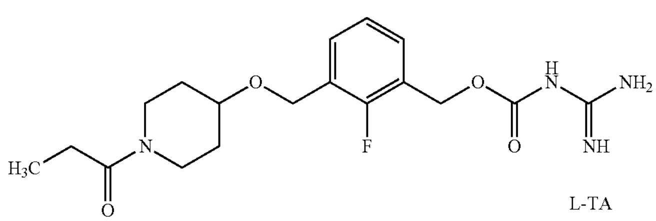 [SMILES: CCC(=O)N1CCC(OCc2cccc(COC(=O)NC(=N)N)c2F)CC1] |

455 456
TABLE 95-continued
| Ex | Syn | Structure |
|---|---|---|
| 224 | 112 | 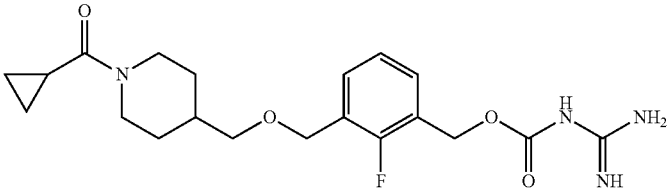 L-TA |
| 225 | 112 | 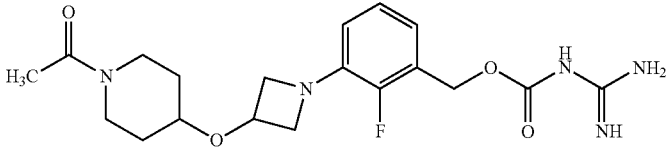 L-TA |
| 226 | 112 | 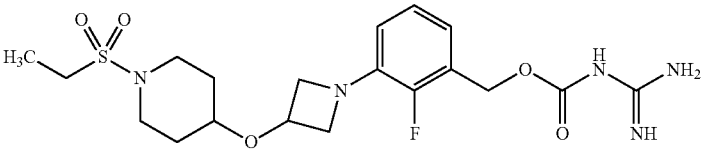 L-TA |
| 227 | 112 | 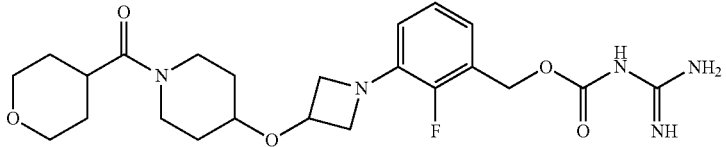 L-TA |
| 228 | 112 | 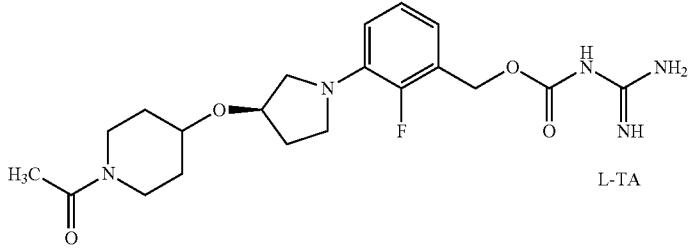 L-TA |

TABLE 95-continued
| Ex | Syn | Structure |
|---|---|---|
| 229 | 112 | 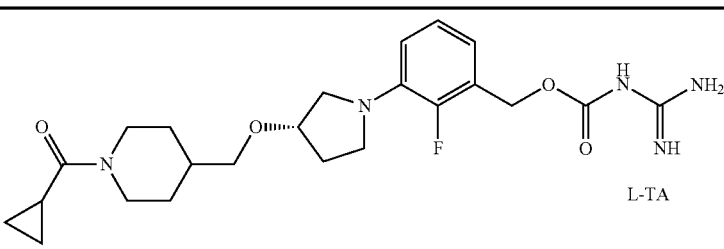<br>L-TA |
| 230 | 112 | 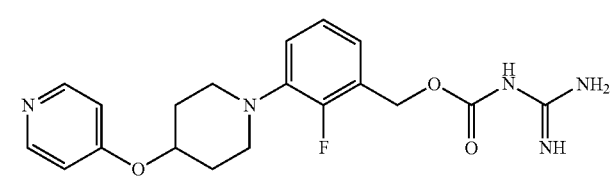<br>L-TA |
TABLE 96
| Ex | Syn | Structure |
|---|---|---|
| 231 | 112 | 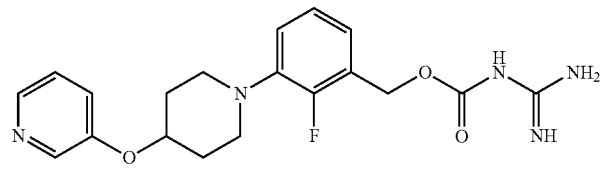<br>L-TA |
| 232 | 112 | 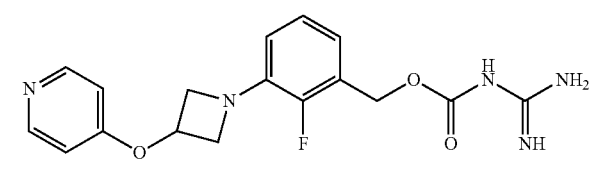<br>L-TA |
| 233 | 112 | 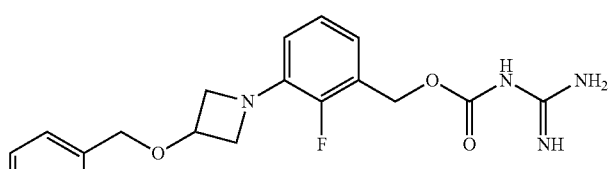<br>L-TA |
| 234 | 112 | 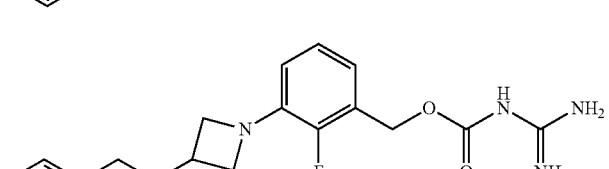<br>L-TA |

TABLE 96-continued

| Ex | Syn | Structure |
|---|---|---|
| 235 | 112 | L-TA |
| 236 | 112 | L-TA |
| 237 | 112 | L-TA |
| 238 | 112 | L-TA |
| 239 | 112 | L-TA |
| 240 | 112 | L-TA |

TABLE 96-continued

| Ex | Syn | Structure |
|----|-----|-----------|
| 241 | 112 | L-TA |
| 242 | 112 | L-TA |
| 243 | 112 | L-TA |
| 244 | 112 | L-TA |
| 245 | 112 | L-TA |

TABLE 96-continued

| Ex | Syn | Structure |
|---|---|---|
| 246 | 112 | (structure) L-TA |
| 247 | 112 | (structure) L-TA |
| 248 | 112 | (structure) L-TA |

TABLE 97

| Ex | Syn | Structure |
|---|---|---|
| 249 | 112 | (structure) L-TA |
| 250 | 112 | (structure) L-TA |

TABLE 97-continued

| Ex | Syn | Structure |
|---|---|---|
| 251 | 112 | (structure) L-TA |
| 252 | 112 | (structure) L-TA |
| 253 | 112 | (structure) L-TA |
| 254 | 112 | (structure) L-TA |
| 255 | 112 | (structure) L-TA |

TABLE 97-continued
| Ex | Syn | Structure |
|----|-----|-----------|
| 256 | 112 | 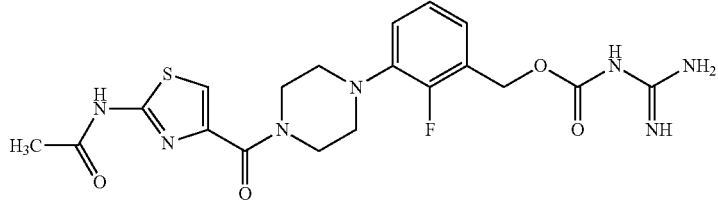<br>L-TA |
| 257 | 112 | 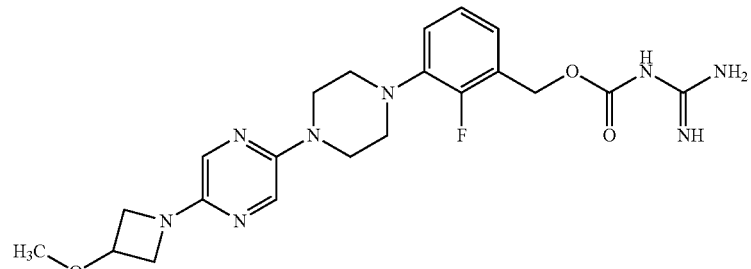<br>L-TA |
| 258 | 112 | 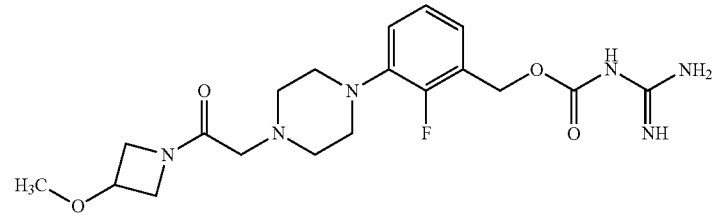<br>L-TA |
| 259 | 112 | 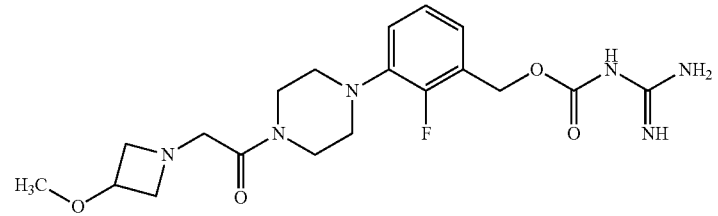<br>L-TA |
| 260 | 112 | 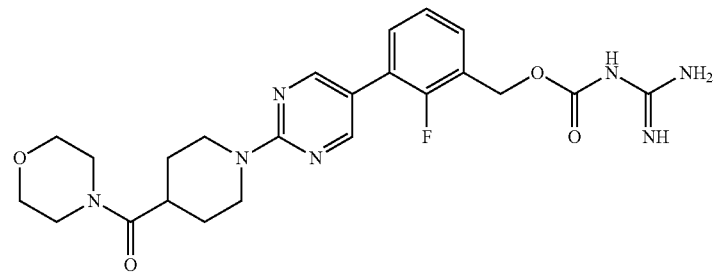<br>L-TA |

TABLE 97-continued
| Ex | Syn | Structure |
|---|---|---|
| 261 | 112 | 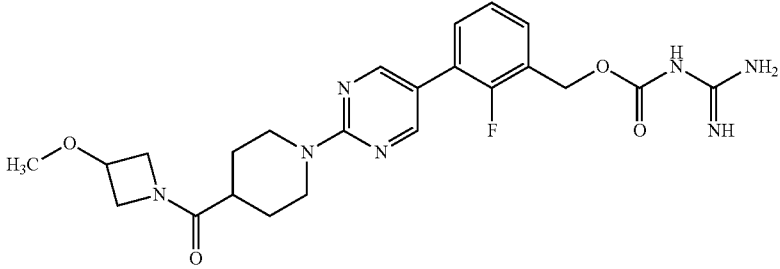<br>L-TA |
| 262 | 112 | 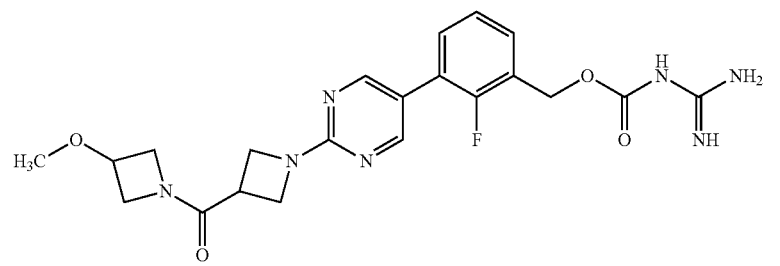<br>L-TA |
| 263 | 112 | 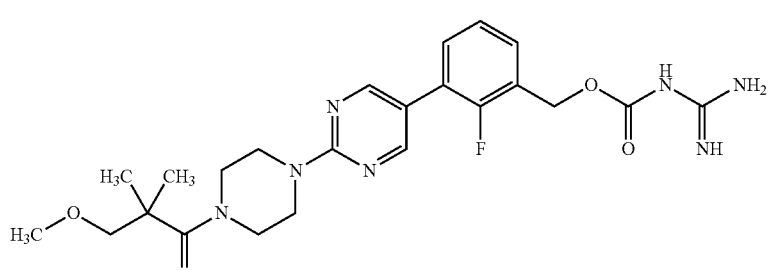<br>L-TA |
| 264 | 112 | 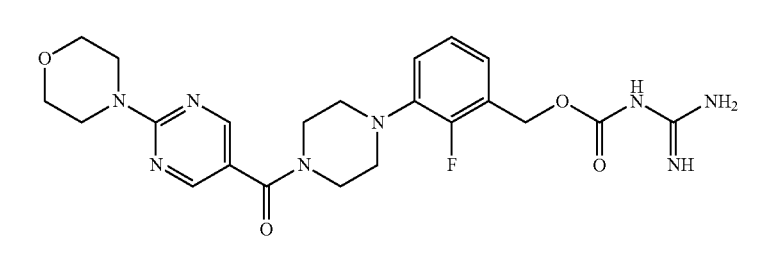<br>L-TA |
| 265 | 112 | 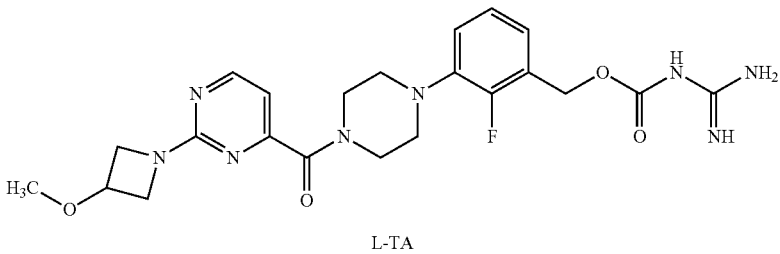 [SMILES: COC1CN(c2nccc(C(=O)N3CCN(c4cccc(COC(=O)NC(=N)N)c4F)CC3)n2)C1]<br>L-TA |

TABLE 97-continued
| Ex | Syn | Structure |
|---|---|---|
| 266 | 112 | 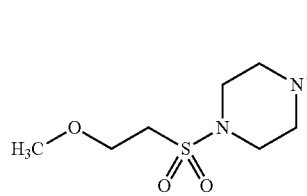 L-TA |
TABLE 98
| Ex | Syn | Structure |
|---|---|---|
| 267 | 112 | 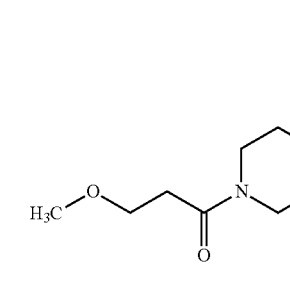 L-TA |
| 268 | 112 | 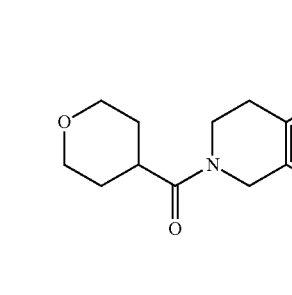 L-TA |
| 269 | 112 | 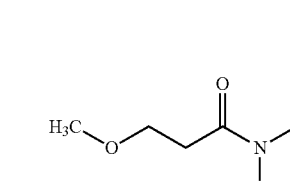 L-TA |
| 270 | 112 |  L-TA |

TABLE 98-continued
| Ex | Syn | Structure |
|---|---|---|
| 271 | 112 | 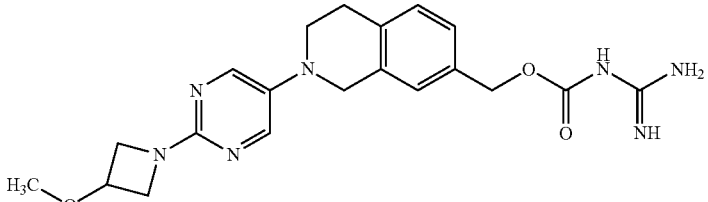<br>L-TA |
| 272 | 112 | 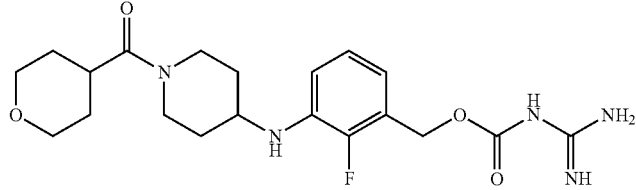<br>L-TA |
| 273 | 112 | 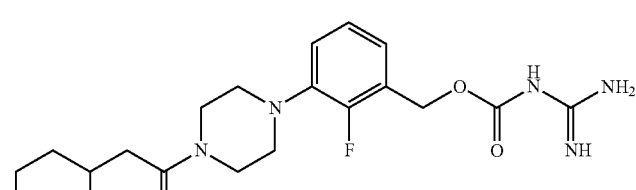<br>L-TA |
| 274 | 112 | 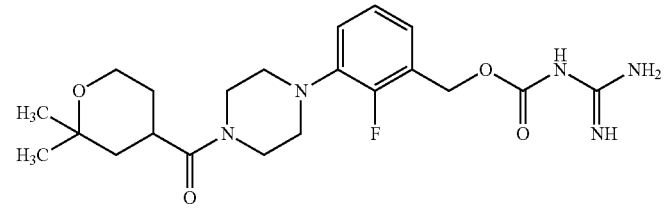<br>L-TA |
| 275 | 112 | 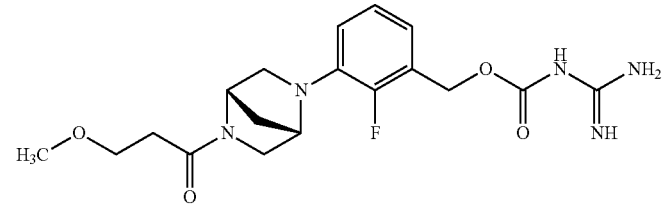<br>L-TA |
| 276 | 112 | 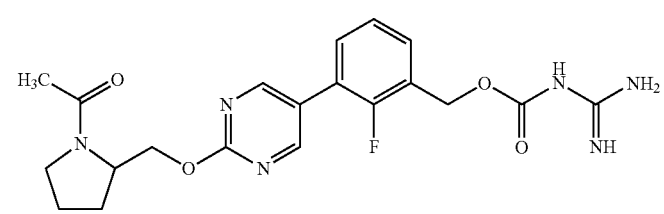<br>L-TA |

TABLE 98-continued
| Ex | Syn | Structure |
|---|---|---|
| 277 | 112 | 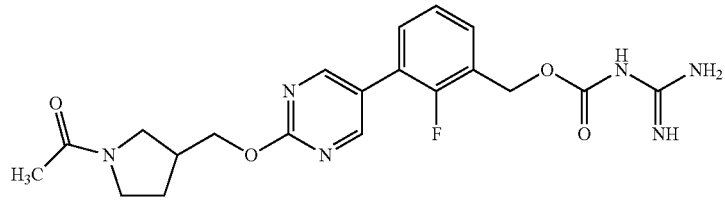<br>L-TA |
| 278 | 112 | 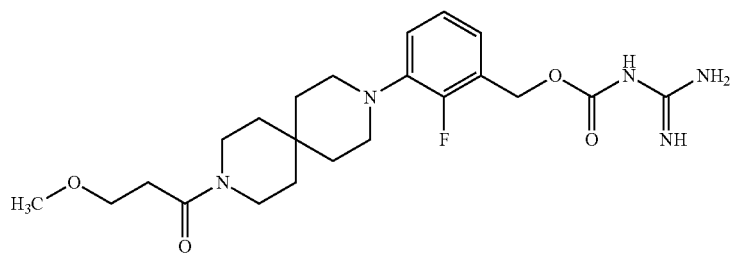<br>L-TA |
| 279 | 112 | 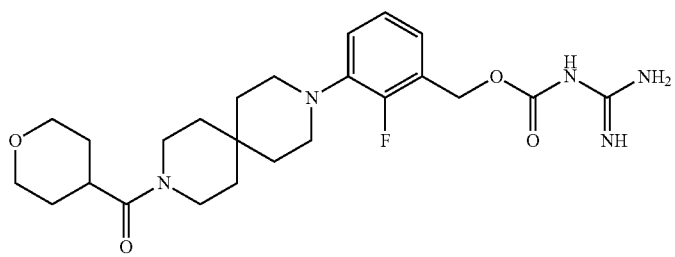<br>L-TA |
| 280 | 112 | 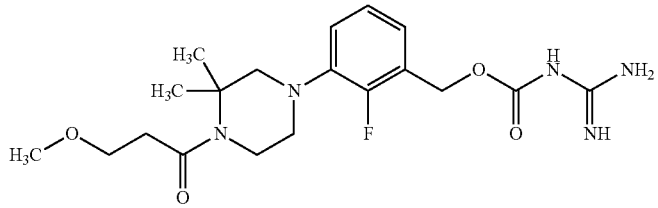<br>L-TA |
| 281 | 112 | 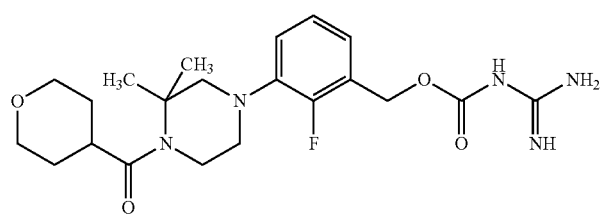<br>L-TA |

TABLE 98-continued
| Ex | Syn | Structure |
|---|---|---|
| 282 | 112 | 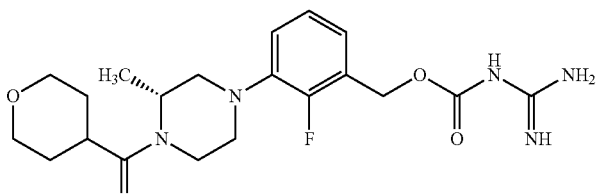 L-TA |
| 283 | 112 | L-TA |
| 284 | 112 | L-TA |
TABLE 99
| Ex | Syn | Structure |
|---|---|---|
| 285 | 112 | 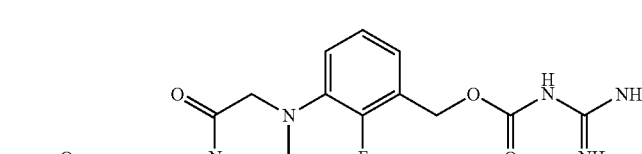 L-TA |
| 286 | 112 | L-TA |

TABLE 99-continued

| Ex | Syn | Structure |
|---|---|---|
| 287 | 112 | (structure) L-TA |
| 288 | 112 | (structure) L-TA |
| 289 | 112 | (structure) L-TA |
| 290 | 112 | (structure) L-TA |
| 291 | 112 | (structure) L-TA |
| 292 | 112 | (structure) L-TA |

TABLE 99-continued

| Ex | Syn | Structure |
|---|---|---|
| 293 | 112 | L-TA |
| 294 | 112 | L-TA |
| 295 | 112 | L-TA |
| 296 | 112 | L-TA |
| 297 | 112 | L-TA |

TABLE 99-continued
| Ex | Syn | Structure |
|---|---|---|
| 298 | 112 | 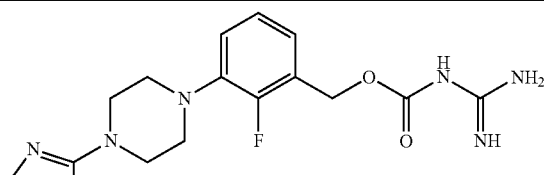 L-TA |
| 299 | 112 | L-TA |
| 300 | 112 | L-TA |
TABLE 100
| Ex | Syn | Structure |
|---|---|---|
| 301 | 112 | 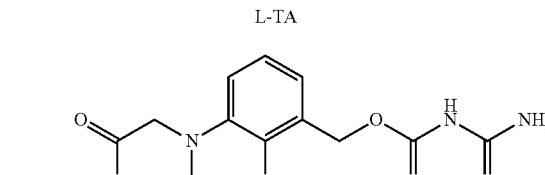 L-TA |
| 302 | 112 | L-TA |

TABLE 100-continued
| Ex | Syn | Structure |
|---|---|---|
| 303 | 112 | 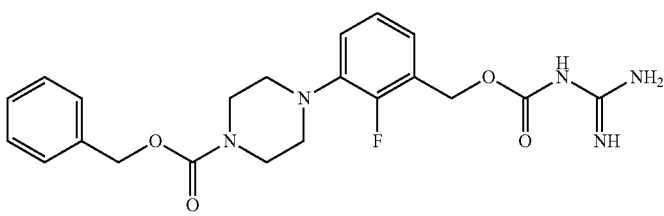<br>L-TA |
| 304 | 112 | 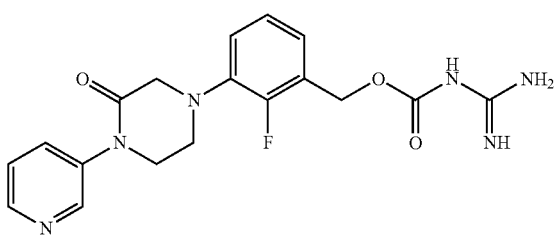<br>L-TA |
| 305 | 112 | 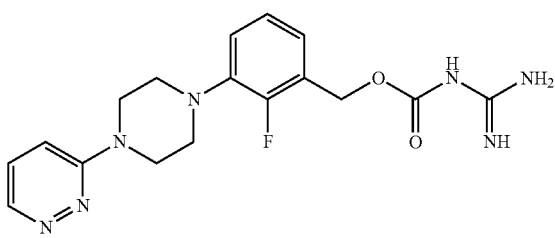<br>L-TA |
| 306 | 112 | 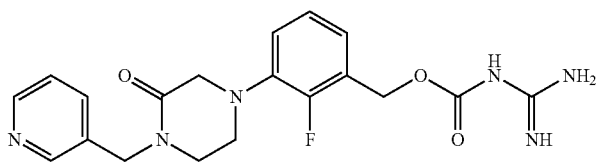<br>L-TA |
| 307 | 112 | 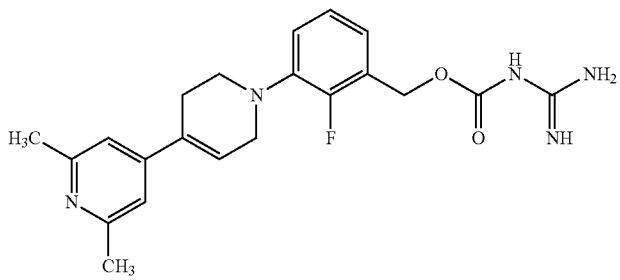<br>L-TA |

TABLE 100-continued

| Ex | Syn | Structure |
|---|---|---|
| 308 | 112 | (2,6-dimethylpyridin-4-yl-piperidinyl structure) L-TA |
| 309 | 112 | (pyridin-3-yl-tetrahydropyridinyl structure) L-TA |
| 310 | 112 | (2-methylpyridin-4-yl-tetrahydropyridinyl structure) L-TA |
| 311 | 112 | (pyridin-3-yl-piperidinyl structure) L-TA |
| 312 | 112 | (2-methylpyridin-4-yl-piperidinyl structure) L-TA |

TABLE 100-continued
| Ex | Syn | Structure |
|---|---|---|
| 313 | 112 | 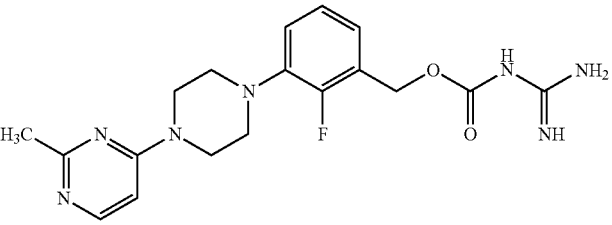<br>L-TA |
| 314 | 112 | 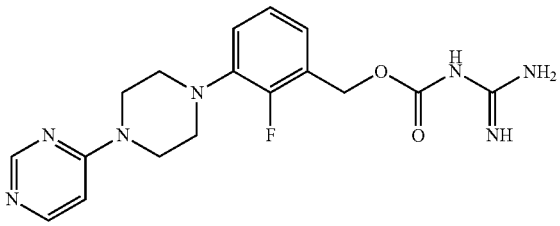<br>L-TA |
| 315 | 112 | 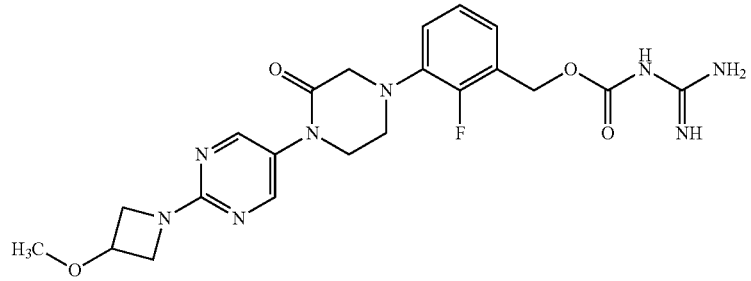<br>L-TA |
| 316 | 316 | 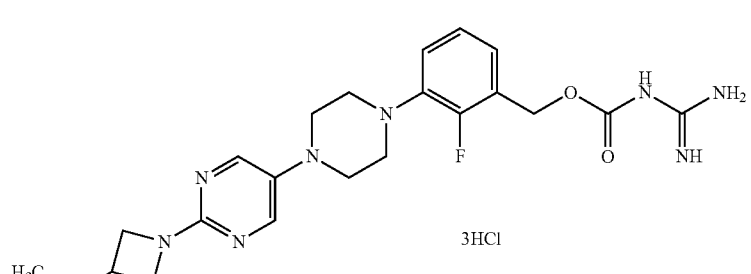<br>3HCl |

TABLE 101

| Ex | Syn | Structure |
|---|---|---|
| 317 | 317 | (structure) L-TA |
| 318 | 318 | (structure) 2HCl |
| 319 | 319 | (structure) L-TA |
| 320 | 319 | (structure) L-TA |
| 321 | 319 | (structure) L-TA |

TABLE 101-continued
| Ex | Syn | Structure |
|---|---|---|
| 322 | 319 | 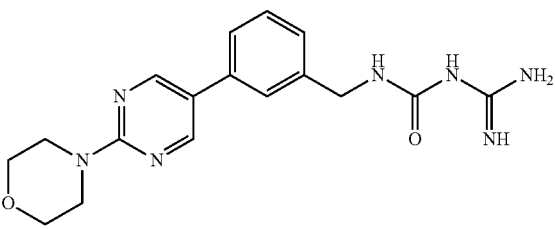 L-TA |
| 323 | 319 | 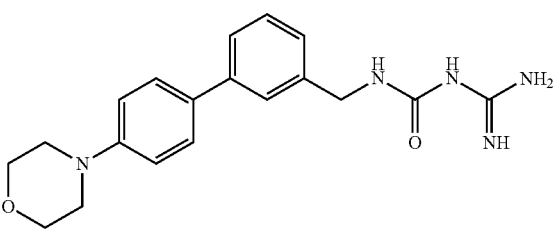 L-TA |
| 324 | 319 | 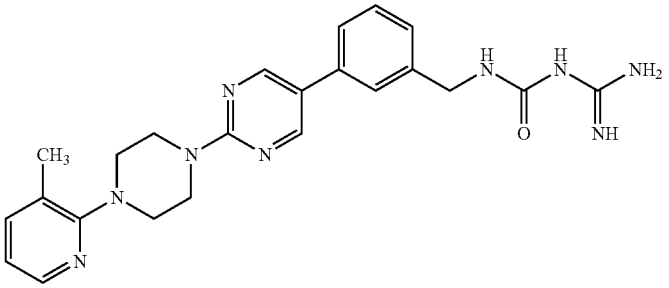 L-TA |
| 325 | 328 | 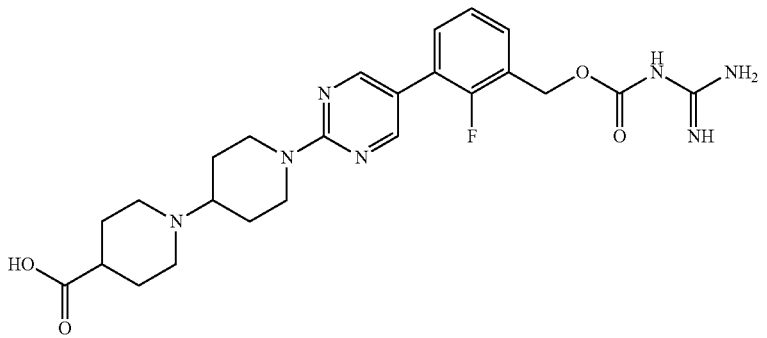 |
| 326 | 328 | 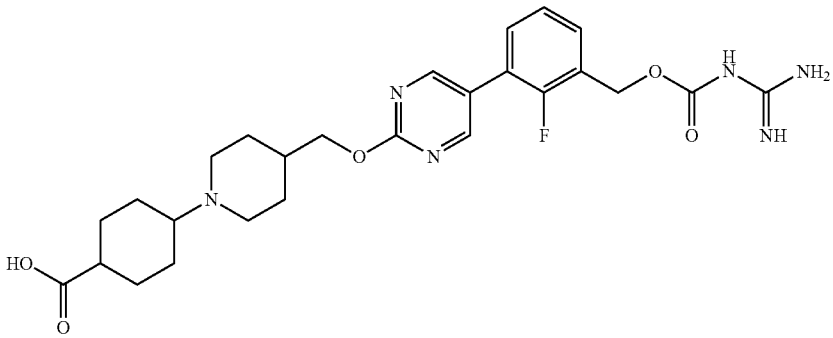 |

TABLE 101-continued

| Ex | Syn | Structure |
|---|---|---|
| 327 | 328 | 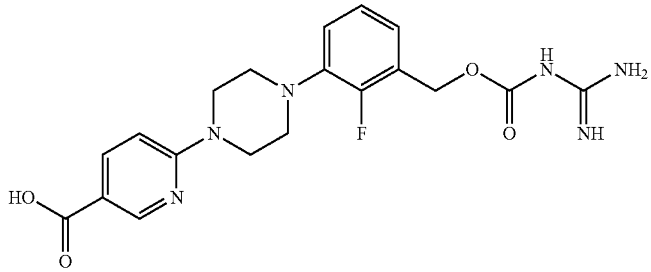 |
| 328 | 328 | 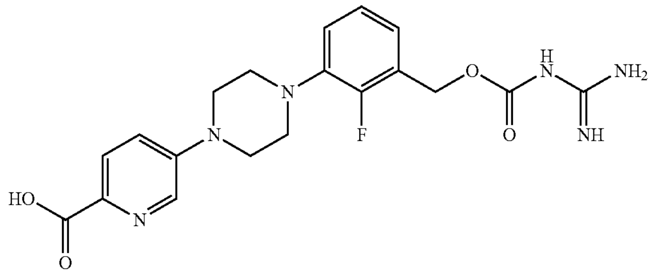 [SMILES: N=C(N)NC(=O)OCc1cccc(N2CCN(c3ccc(C(=O)O)nc3)CC2)c1F] |
| 329 | 318 | 2HCl |
| 330 | 318 | 3HCl |
| 331 | 318 | 2HCl |
| 332 | 318 | HCl |

TABLE 102
| Ex | Syn | Structure |
|---|---|---|
| 333 | 318 | 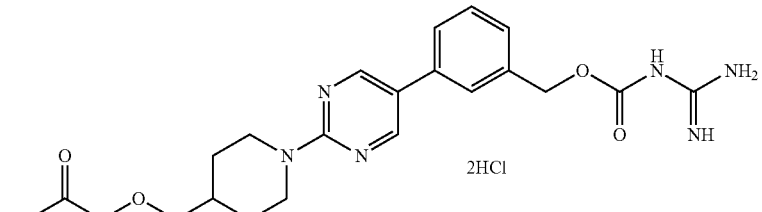 |
| 334 | 318 | 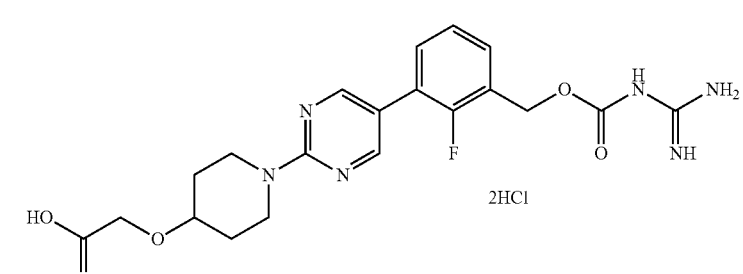 |
| 335 | 318 | 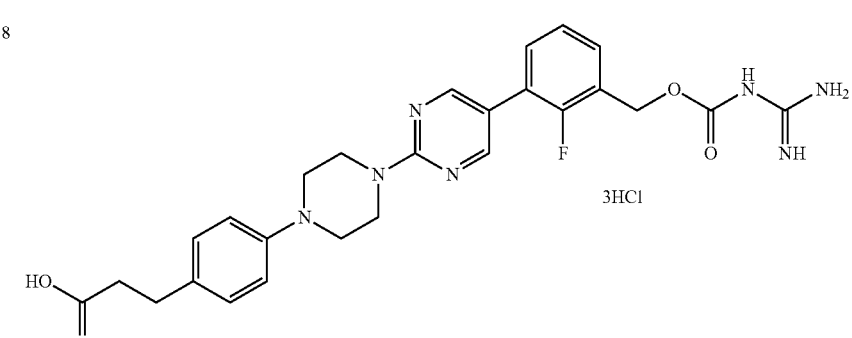 |
| 336 | 318 | 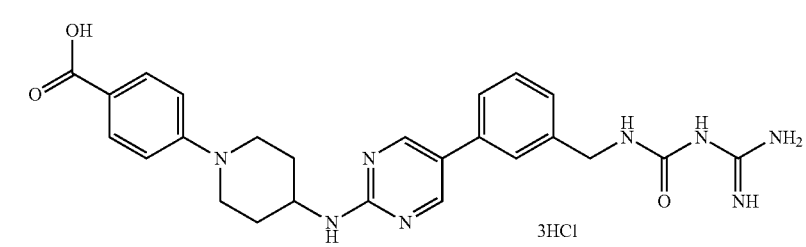 [SMILES: N=C(N)NC(=O)NCc1cccc(-c2cnc(NC3CCN(c4ccc(C(=O)O)cc4)CC3)nc2)c1] |
| 337 | 318 | 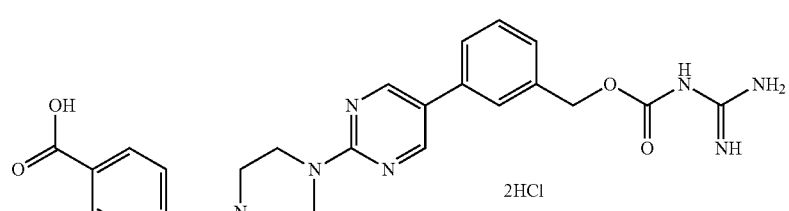 |
| 338 | 318 | 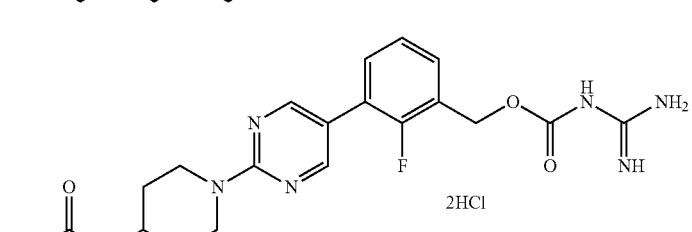 |

TABLE 102-continued

| Ex | Syn | Structure |
|---|---|---|
| 339 | 318 | 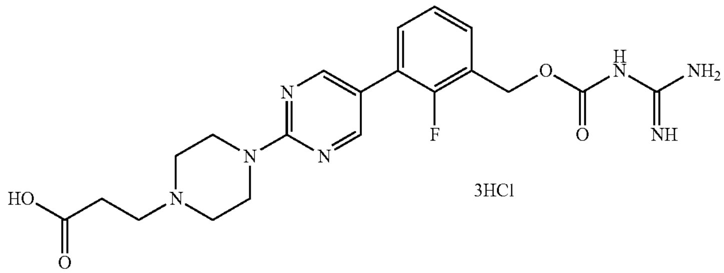 [SMILES: N=C(N)NC(=O)OCc1cccc(-c2cnc(N3CCN(CCC(=O)O)CC3)nc2)c1F] |
| 340 | 344 | 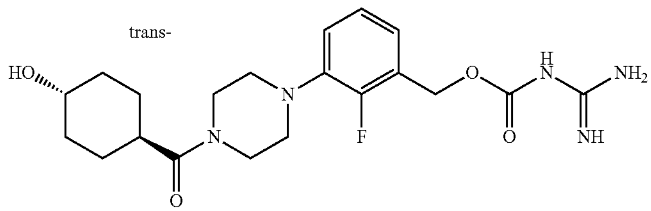 |
| 341 | 344 | 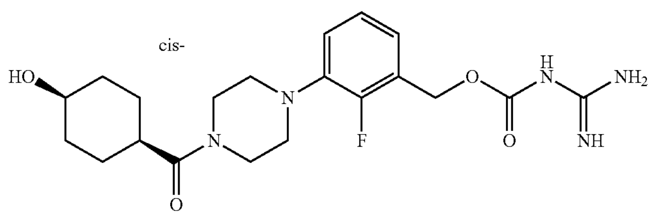 |
| 342 | 318 | 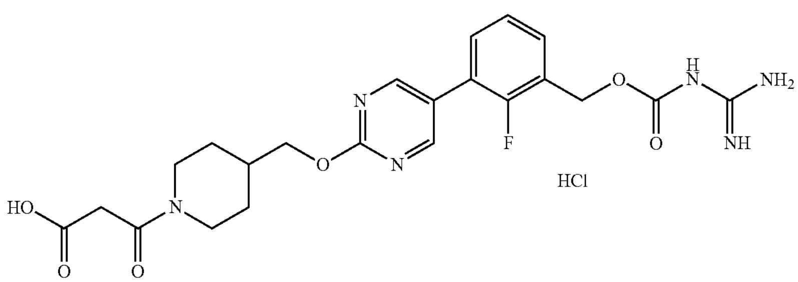 [SMILES: N=C(N)NC(=O)OCc1cccc(-c2cnc(OCC3CCN(C(=O)CC(=O)O)CC3)nc2)c1F ; Cl] |
| 343 | 344 | 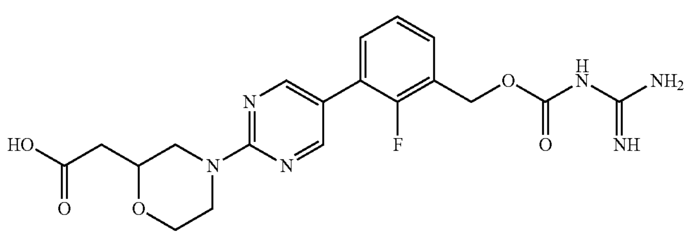 [SMILES: N=C(N)NC(=O)OCc1cccc(-c2cnc(N3CCOC(CC(=O)O)C3)nc2)c1F] |

TABLE 102-continued
| Ex | Syn | Structure |
|---|---|---|
| 344 | 344 | 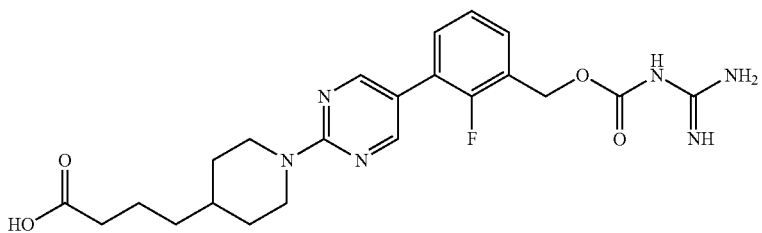<br>L-TA |
| 345 | 345 | 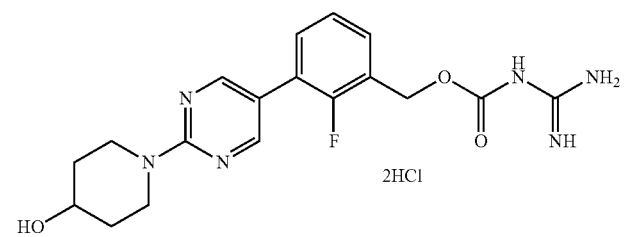 [SMILES: N=C(N)NC(=O)OCc1cccc(-c2cnc(N3CCC(O)CC3)nc2)c1F]<br>2HCl |
| 346 | 347 | 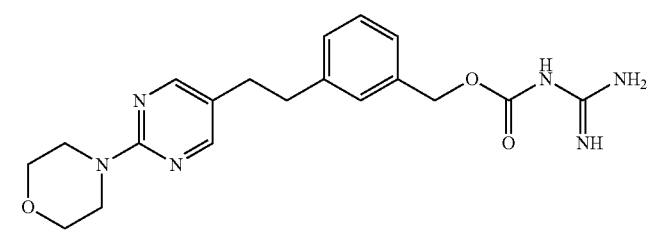<br>L-TA |
| 347 | 347 | 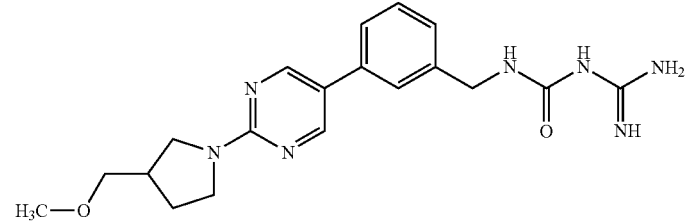<br>L-TA |
| 348 | 347 | 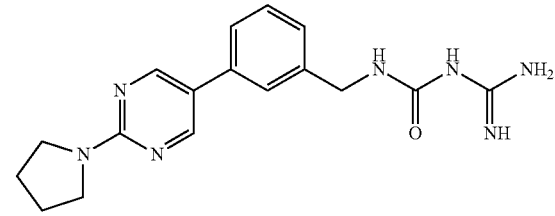<br>L-TA |

TABLE 102-continued

| Ex | Syn | Structure |
|---|---|---|
| 349 | 347 | (structure) L-TA |
| 350 | 347 | (structure) L-TA |

TABLE 103

| Ex | Syn | Structure |
|---|---|---|
| 351 | 347 | (structure) L-TA |
| 352 | 347 | (structure) L-TA |

TABLE 103-continued
| Ex | Syn | Structure |
|---|---|---|
| 353 | 347 | 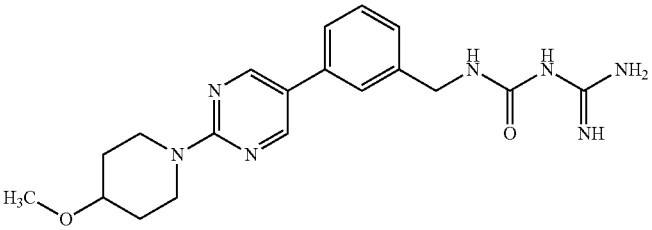<br>L-TA |
| 354 | 347 | 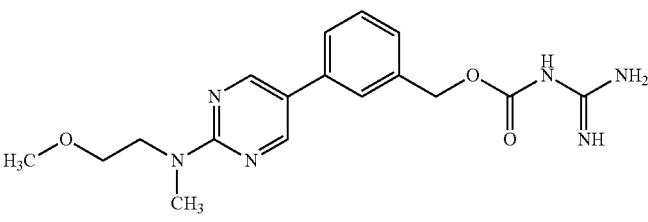<br>L-TA |
| 355 | 347 | 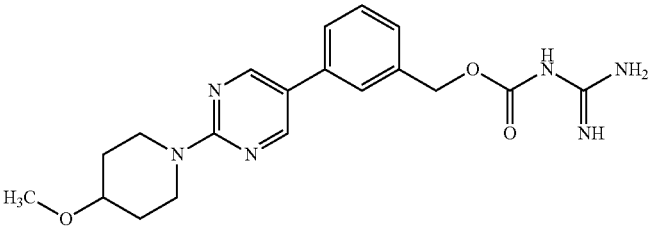<br>L-TA |
| 356 | 347 | 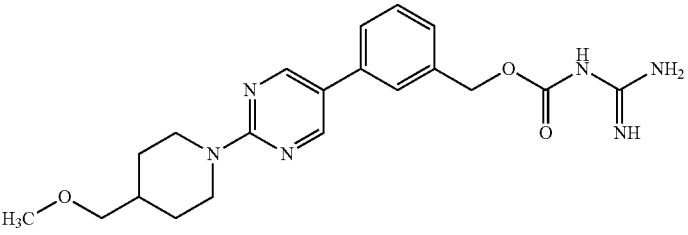<br>L-TA |
| 357 | 347 | 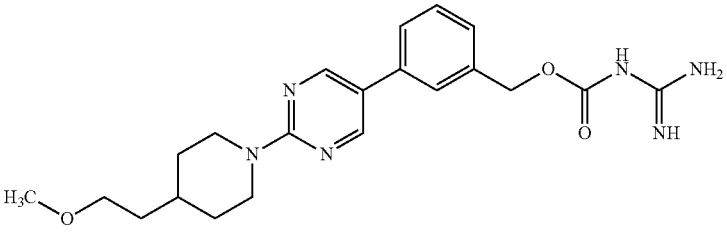<br>L-TA |

TABLE 103-continued

| Ex | Syn | Structure |
|---|---|---|
| 358 | 347 | (structure) L-TA |
| 359 | 347 | (structure) L-TA |
| 360 | 347 | (structure) L-TA |
| 361 | 347 | (structure) L-TA |
| 362 | 347 | (structure) L-TA |

TABLE 103-continued
| Ex | Syn | Structure |
|---|---|---|
| 363 | 347 | 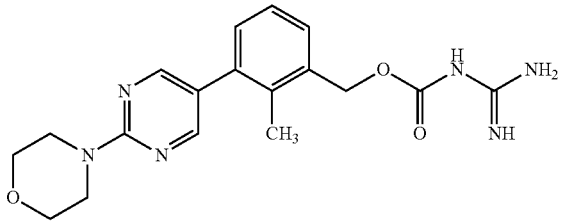 L-TA |
| 364 | 347 | 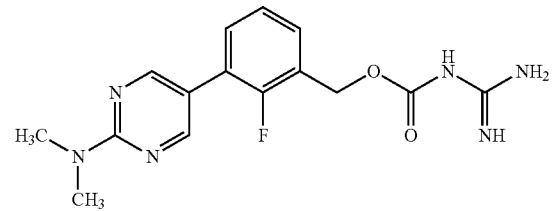 L-TA |
| 365 | 347 | 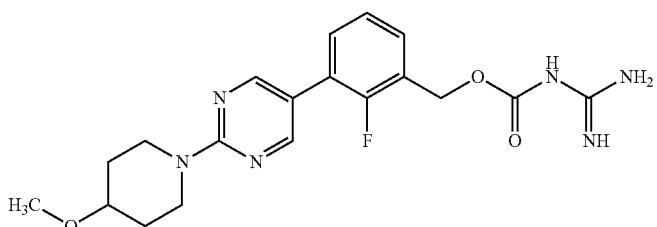 L-TA |
| 366 | 347 | 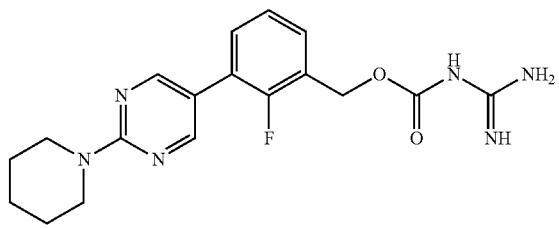 L-TA |
TABLE 104
| Ex | Syn | Structure |
|---|---|---|
| 367 | 347 | 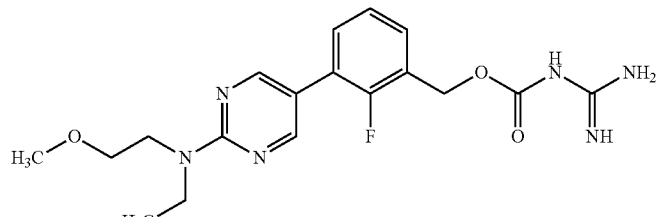 L-TA |

TABLE 104-continued
| Ex | Syn | Structure |
|---|---|---|
| 368 | 347 | 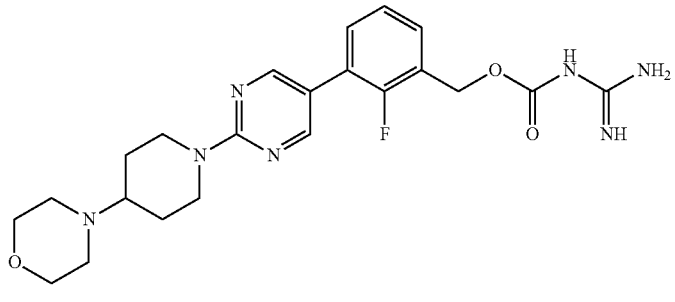<br>L-TA |
| 369 | 347 | 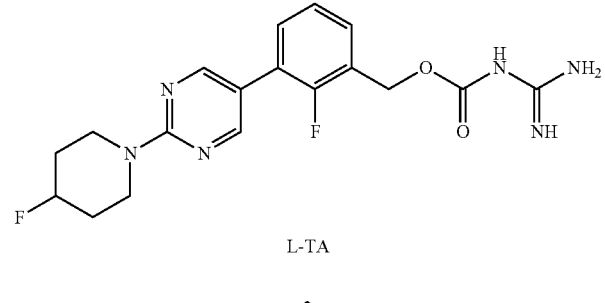<br>L-TA |
| 370 | 347 | 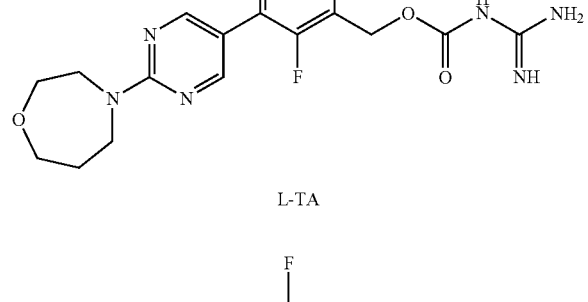<br>L-TA |
| 371 | 347 | 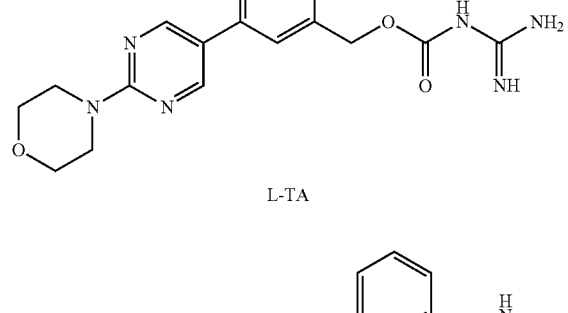<br>L-TA |
| 372 | 318 | 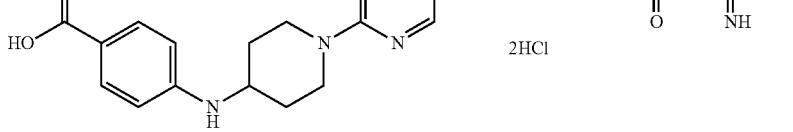 |

TABLE 104-continued

| Ex | Syn | Structure |
|---|---|---|
| 373 | 23 | 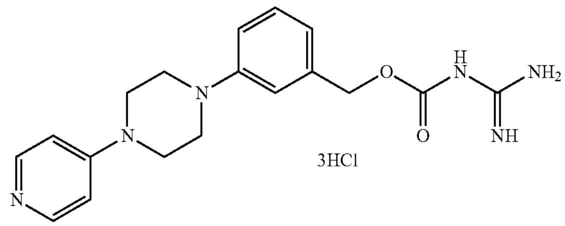 [SMILES: N=C(N)NC(=O)OCc1cccc(N2CCN(c3ccncc3)CC2)c1] |
| 374 | 112 | 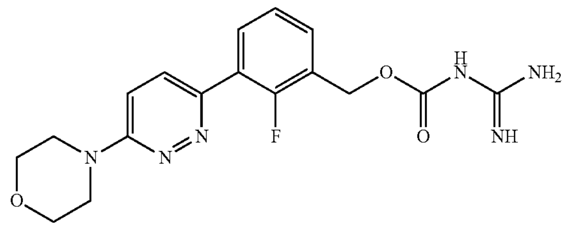 |
| 375 | 3 | 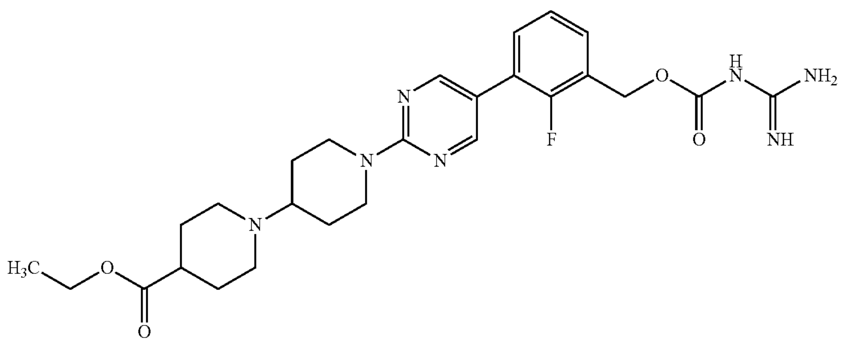 [SMILES: CCOC(=O)C1CCN(C2CCN(c3ncc(-c4cccc(COC(=O)NC(=N)N)c4F)cn3)CC2)CC1] |
| 376 | 3 | 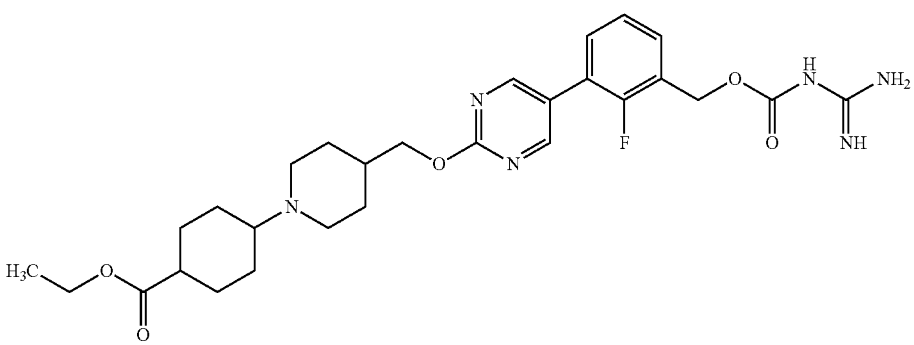 [SMILES: CCOC(=O)C1CCC(N2CCC(COc3ncc(-c4cccc(COC(=O)NC(=N)N)c4F)cn3)CC2)CC1] |
| 377 | 3 | 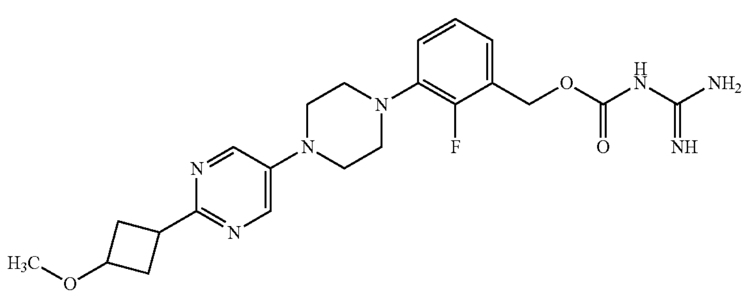 [SMILES: COC1CC(c2ncc(N3CCN(c4cccc(COC(=O)NC(=N)N)c4F)CC3)cn2)C1] |

TABLE 104-continued

| Ex | Syn | Structure |
|----|-----|-----------|
| 378 | 3 | trans- |
| 379 | 3 | cis- |
| 380 | 3 | 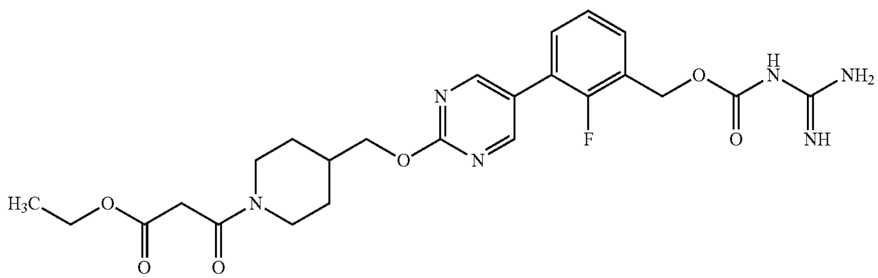 [SMILES: CCOC(=O)CC(=O)N1CCC(COc2ncc(-c3cccc(COC(=O)NC(=N)N)c3F)cn2)CC1] |
| 381 | 3 | 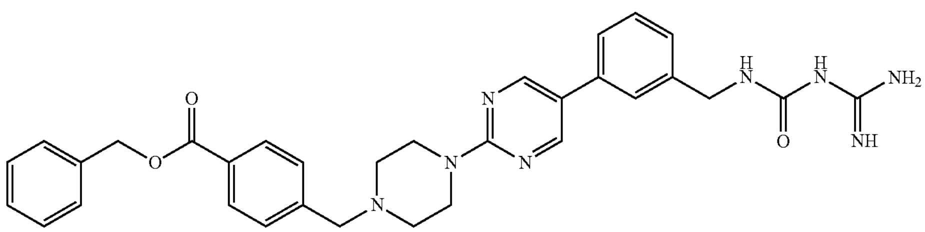 [SMILES: N=C(N)NC(=O)NCc1cccc(-c2cnc(N3CCN(Cc4ccc(C(=O)OCc5ccccc5)cc4)CC3)nc2)c1] |
| 382 | 3 | 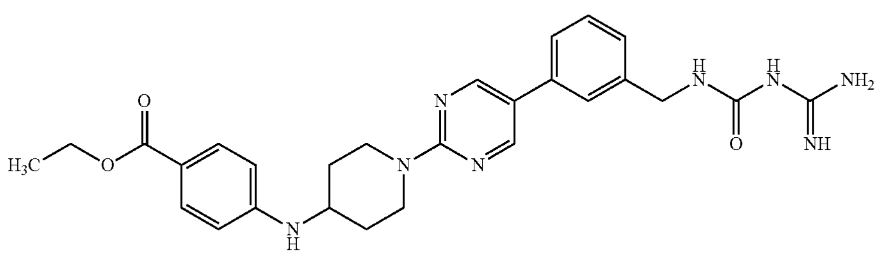 [SMILES: CCOC(=O)c1ccc(NC2CCN(c3ncc(-c4cccc(CNC(=O)NC(=N)N)c4)cn3)CC2)cc1] |
| 383 | 3 | 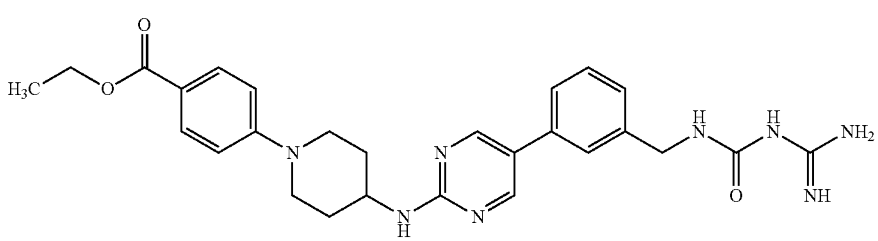 [SMILES: CCOC(=O)c1ccc(N2CCC(Nc3ncc(-c4cccc(CNC(=O)NC(=N)N)c4)cn3)CC2)cc1] |

TABLE 104-continued
| Ex | Syn | Structure |
|---|---|---|
| 384 | 3 | 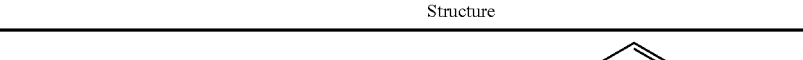 |
TABLE 105
| Ex | Syn | Structure |
|---|---|---|
| 385 | 3 | 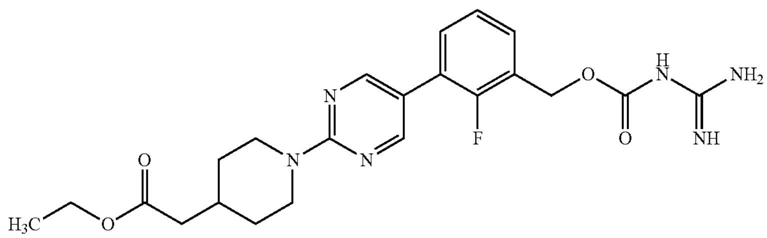 [SMILES: CCOC(=O)CC1CCN(c2ncc(-c3cccc(COC(=O)NC(=N)N)c3F)cn2)CC1] |
| 386 | 3 | 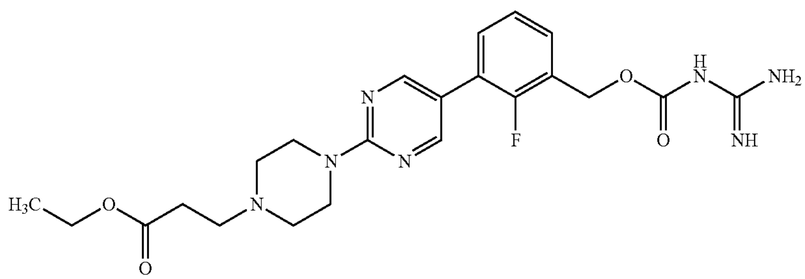 [SMILES: CCOC(=O)CCN1CCN(c2ncc(-c3cccc(COC(=O)NC(=N)N)c3F)cn2)CC1] |
| 387 | 3 | 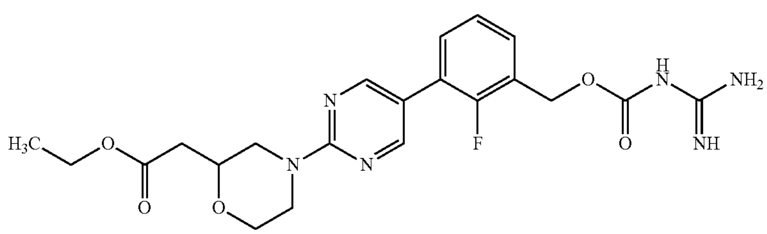 [SMILES: CCOC(=O)CC1CN(c2ncc(-c3cccc(COC(=O)NC(=N)N)c3F)cn2)CCO1] |
| 388 | 3 | 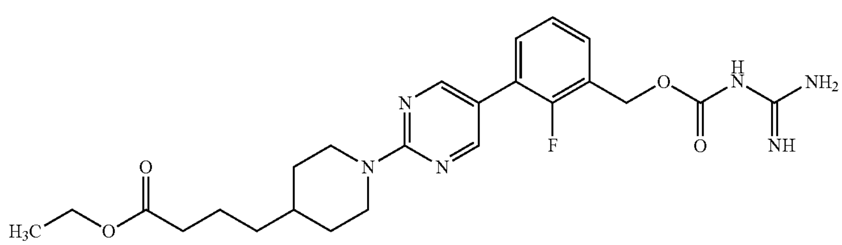 [SMILES: CCOC(=O)CCCC1CCN(c2ncc(-c3cccc(COC(=O)NC(=N)N)c3F)cn2)CC1] |

TABLE 105-continued
| Ex | Syn | Structure |
|---|---|---|
| 389 | 3 | 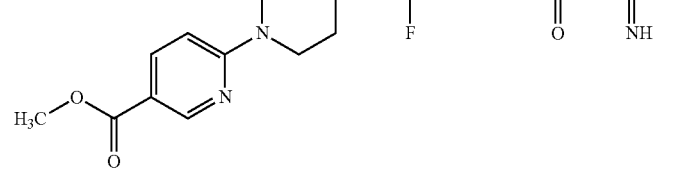 |
| 390 | 3 | 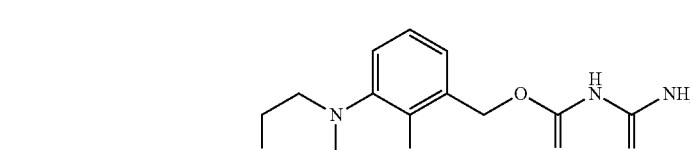 |
| 391 | 3 | 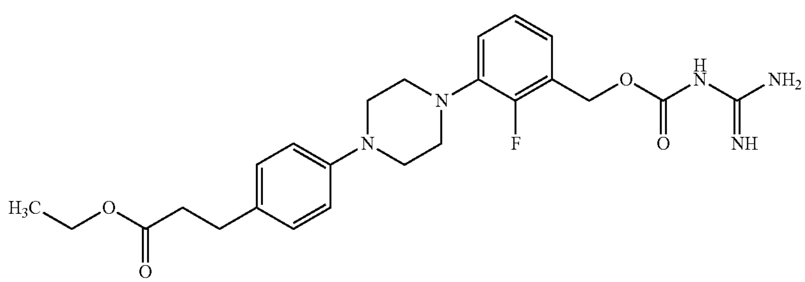 [SMILES: CCOC(=O)CCc1ccc(N2CCN(c3cccc(COC(=O)NC(=N)N)c3F)CC2)cc1] |
| 392 | 3 | 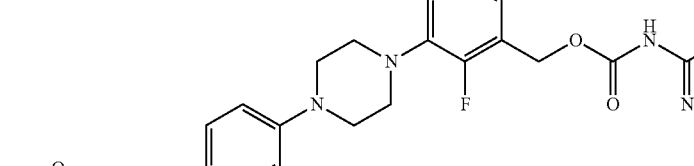 |
| 393 | 3 | 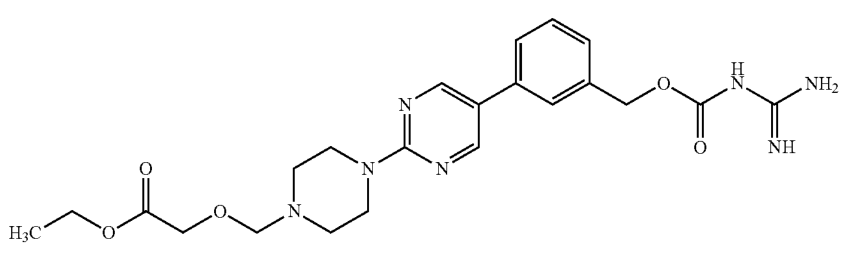 [SMILES: CCOC(=O)COCN1CCN(c2ncc(-c3cccc(COC(=O)NC(=N)N)c3)cn2)CC1] |

TABLE 105-continued

| Ex | Syn | Structure |
|---|---|---|
| 394 | 3 | 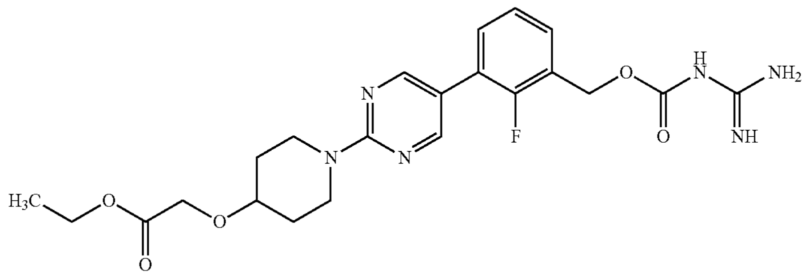 [SMILES: CCOC(=O)COC1CCN(c2ncc(-c3cccc(COC(=O)NC(=N)N)c3F)cn2)CC1] |
| 395 | 3 | 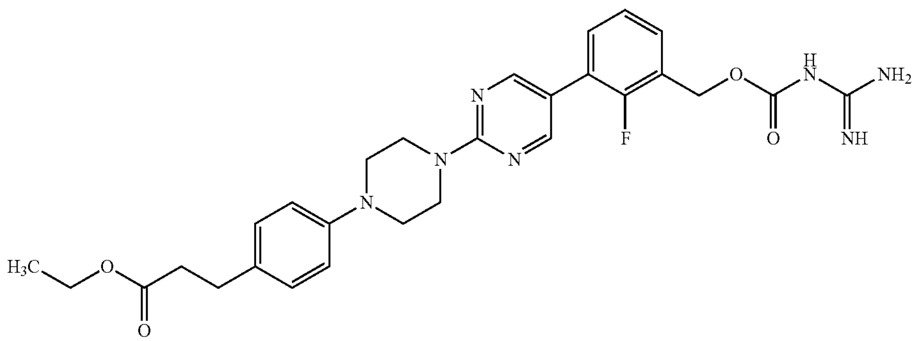 [SMILES: CCOC(=O)CCc1ccc(N2CCN(c3ncc(-c4cccc(COC(=O)NC(=N)N)c4F)cn3)CC2)cc1] |
| 396 | 3 | 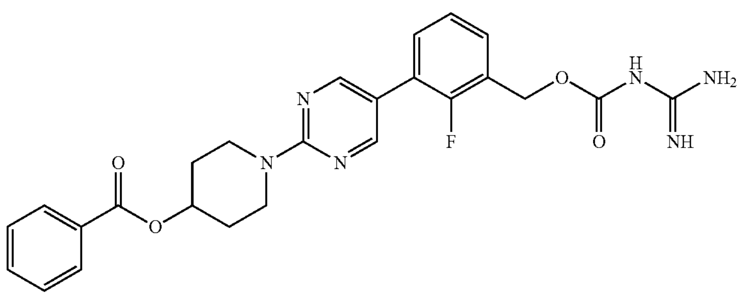 [SMILES: N=C(N)NC(=O)OCc1cccc(-c2cnc(N3CCC(OC(=O)c4ccccc4)CC3)nc2)c1F] |
| 397 | 397 | 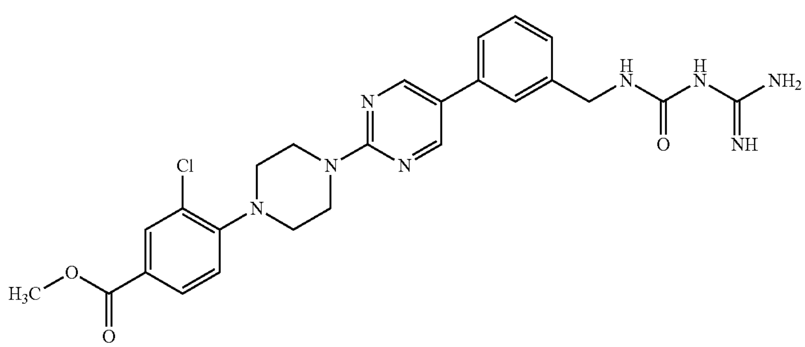 [SMILES: COC(=O)c1ccc(N2CCN(c3ncc(-c4cccc(CNC(=O)NC(=N)N)c4)cn3)CC2)c(Cl)c1] |
| 398 | 398 | 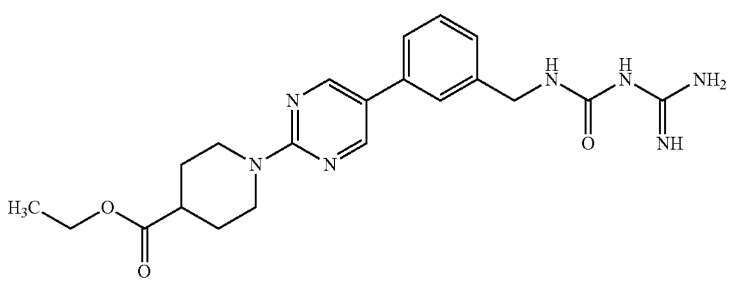 [SMILES: CCOC(=O)C1CCN(c2ncc(-c3cccc(CNC(=O)NC(=N)N)c3)cn2)CC1] |

TABLE 105-continued
| Ex | Syn | Structure |
|---|---|---|
| 399 | 546 | 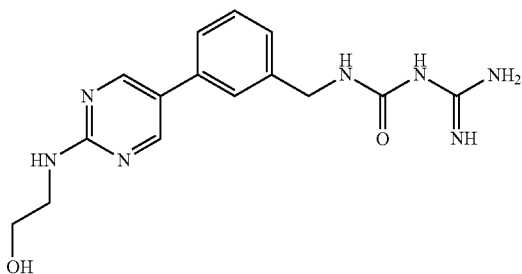 [SMILES: N=C(N)NC(=O)NCc1cccc(-c2cnc(NCCO)nc2)c1] |
| 400 | 546 | 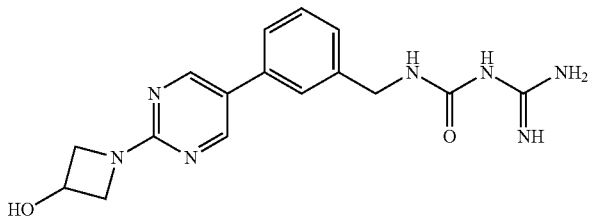 [SMILES: N=C(N)NC(=O)NCc1cccc(-c2cnc(N3CC(O)C3)nc2)c1] |
TABLE 106
| Ex | Syn | Structure |
|---|---|---|
| 401 | 546 | 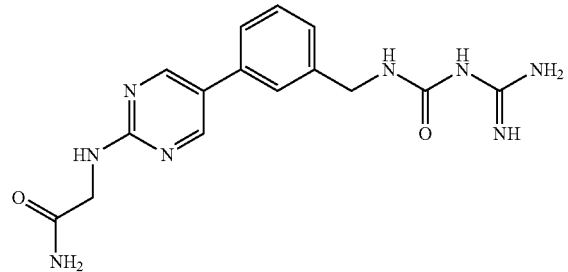 [SMILES: N=C(N)NC(=O)NCc1cccc(-c2cnc(NCC(N)=O)nc2)c1] |
| 402 | 546 | 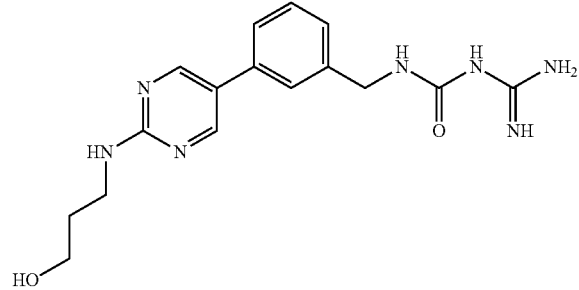 [SMILES: N=C(N)NC(=O)NCc1cccc(-c2cnc(NCCCO)nc2)c1] |
| 403 | 546 | 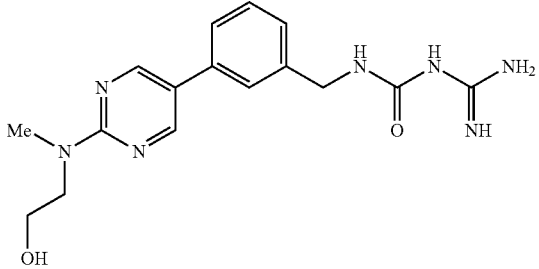 [SMILES: CN(CCO)c1ncc(-c2cccc(CNC(=O)NC(=N)N)c2)cn1] |

TABLE 106-continued

| Ex | Syn | Structure |
|---|---|---|
| 404 | 546 | 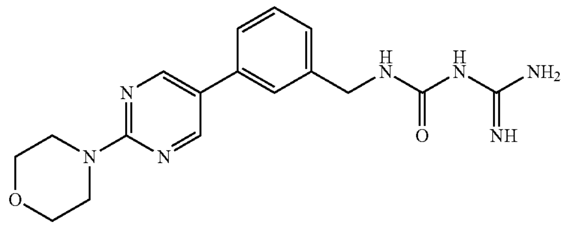 [SMILES: N=C(N)NC(=O)NCc1cccc(-c2cnc(N3CCOCC3)nc2)c1] |
| 405 | 546 | 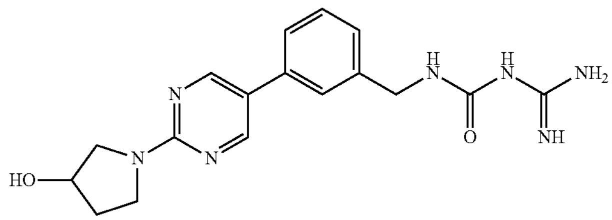 [SMILES: N=C(N)NC(=O)NCc1cccc(-c2cnc(N3CCC(O)C3)nc2)c1] |
| 406 | 546 | 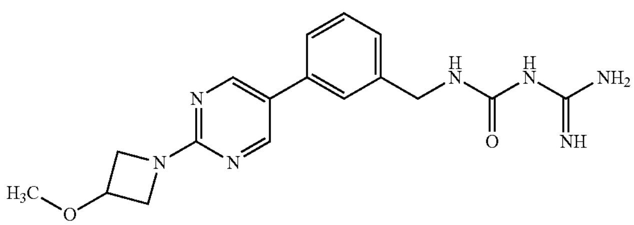 [SMILES: COC1CN(c2ncc(-c3cccc(CNC(=O)NC(=N)N)c3)cn2)C1] |
| 407 | 546 | 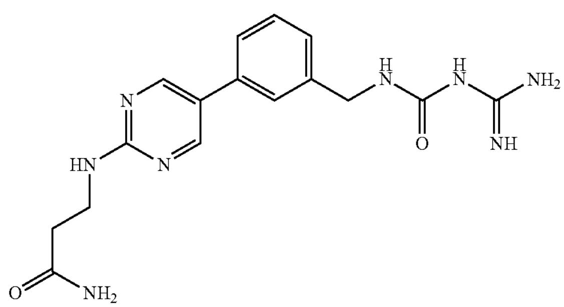 [SMILES: N=C(N)NC(=O)NCc1cccc(-c2cnc(NCCC(N)=O)nc2)c1] |
| 408 | 546 | 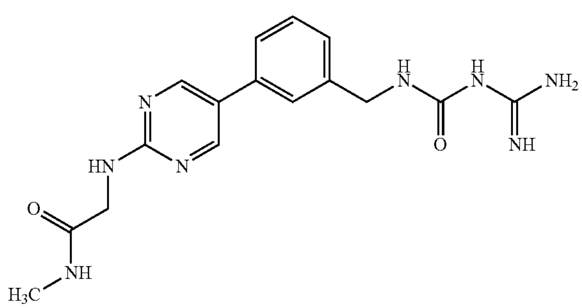 [SMILES: CNC(=O)CNc1ncc(-c2cccc(CNC(=O)NC(=N)N)c2)cn1] |

TABLE 106-continued
| Ex | Syn | Structure |
|---|---|---|
| 409 | 546 | 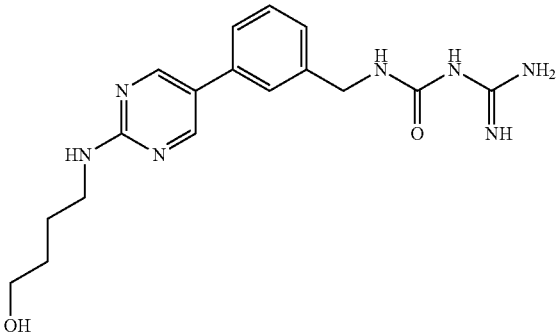 [SMILES: N=C(N)NC(=O)NCc1cccc(-c2cnc(NCCCCO)nc2)c1] |
| 410 | 546 | 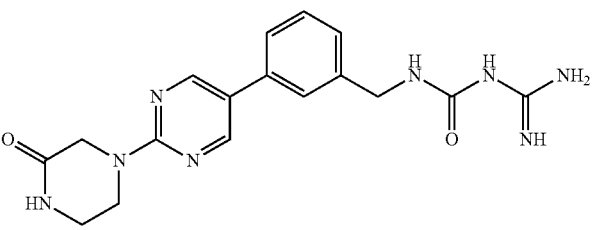 [SMILES: N=C(N)NC(=O)NCc1cccc(-c2cnc(N3CCNC(=O)C3)nc2)c1] |
| 411 | 546 | 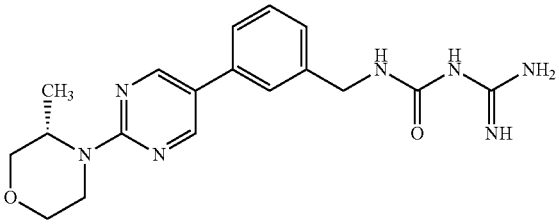 [SMILES: C[C@H]1COCCN1c1ncc(-c2cccc(CNC(=O)NC(=N)N)c2)cn1] |
| 412 | 546 | 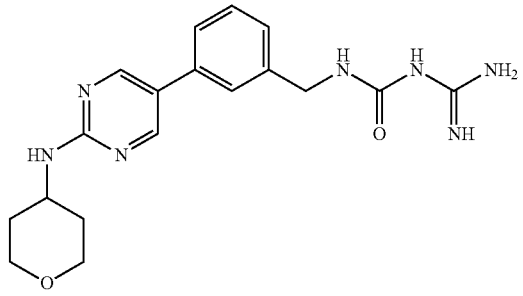 |
| 413 | 546 | 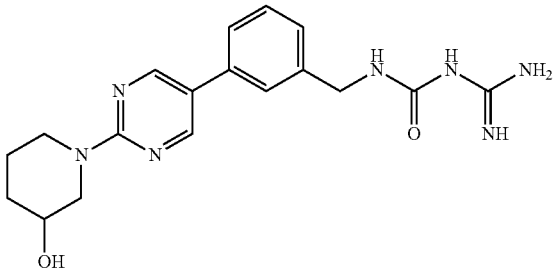 [SMILES: N=C(N)NC(=O)NCc1cccc(-c2cnc(N3CCCC(O)C3)nc2)c1] |

TABLE 106-continued

| Ex | Syn | Structure |
|---|---|---|
| 414 | 546 | 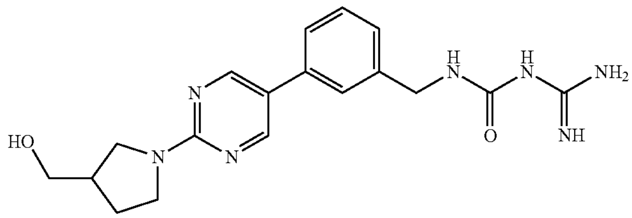 [SMILES: N=C(N)NC(=O)NCc1cccc(-c2cnc(N3CCC(CO)C3)nc2)c1] |

TABLE 107

| Ex | Syn | Structure |
|---|---|---|
| 415 | 546 | 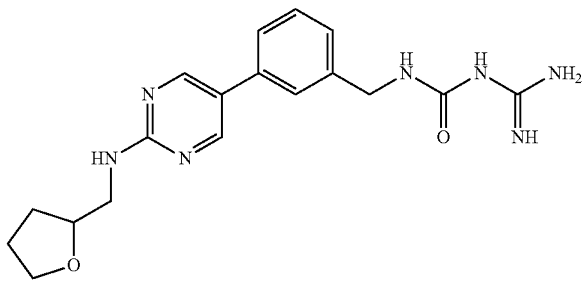 [SMILES: N=C(N)NC(=O)NCc1cccc(-c2cnc(NCC3CCCO3)nc2)c1] |
| 416 | 546 | 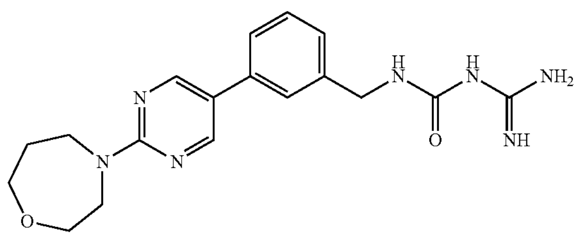 [SMILES: N=C(N)NC(=O)NCc1cccc(-c2cnc(N3CCCOCC3)nc2)c1] |
| 417 | 546 | 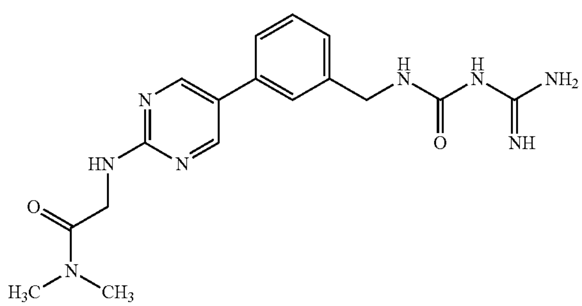 [SMILES: CN(C)C(=O)CNc1ncc(-c2cccc(CNC(=O)NC(=N)N)c2)cn1] |
| 418 | 546 | 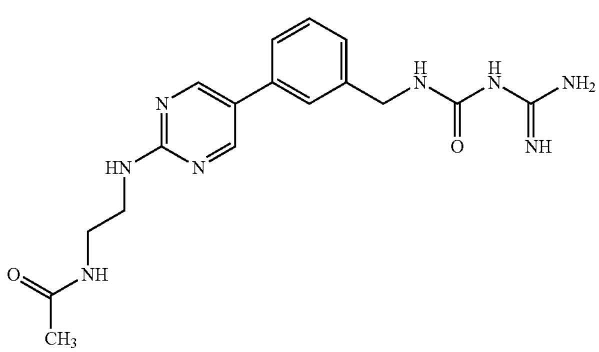 [SMILES: CC(=O)NCCNc1ncc(-c2cccc(CNC(=O)NC(=N)N)c2)cn1] |

TABLE 107-continued

| Ex | Syn | Structure |
|---|---|---|
| 419 | 546 | 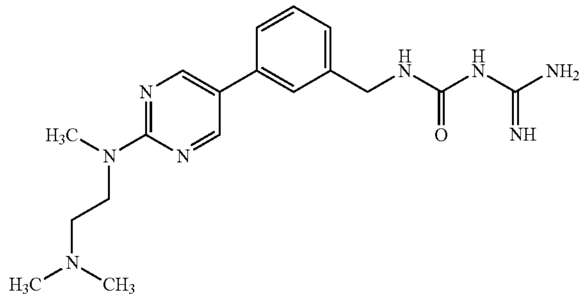 [SMILES: CN(C)CCN(C)c1ncc(-c2cccc(CNC(=O)NC(=N)N)c2)cn1] |
| 420 | 546 | 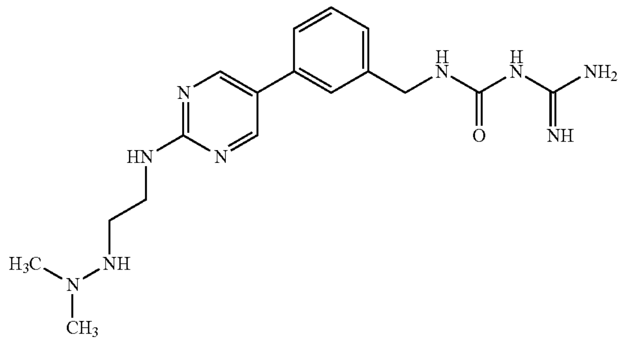 [SMILES: CN(C)NCCNc1ncc(-c2cccc(CNC(=O)NC(=N)N)c2)cn1] |
| 421 | 546 | 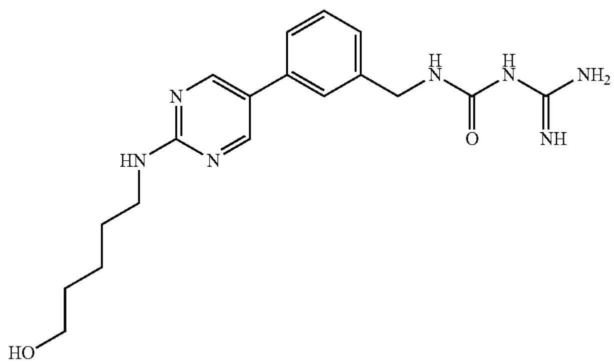 |
| 422 | 546 | 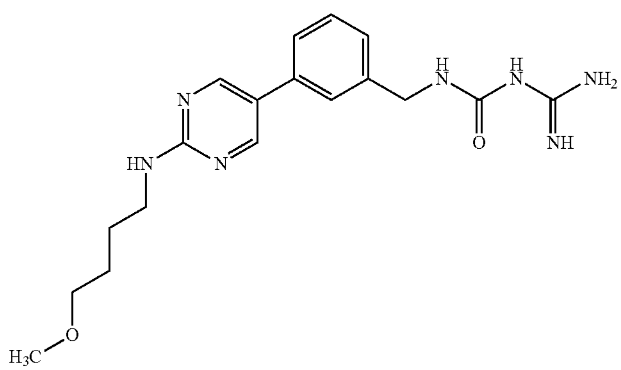 [SMILES: COCCCCNc1ncc(-c2cccc(CNC(=O)NC(=N)N)c2)cn1] |
| 423 | 546 | 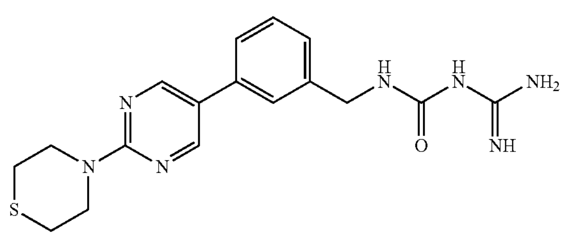 [SMILES: N=C(N)NC(=O)NCc1cccc(-c2cnc(N3CCSCC3)nc2)c1] |

TABLE 107-continued
| Ex | Syn | Structure |
|---|---|---|
| 424 | 546 | 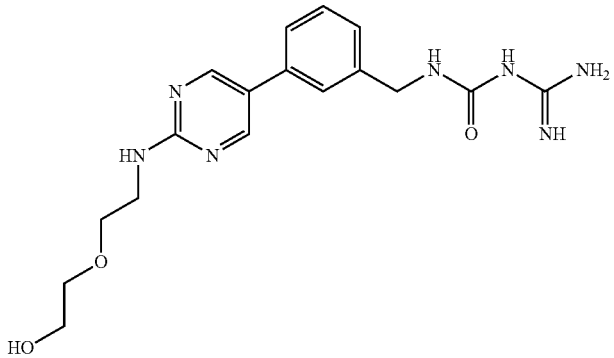 |
| 425 | 546 | 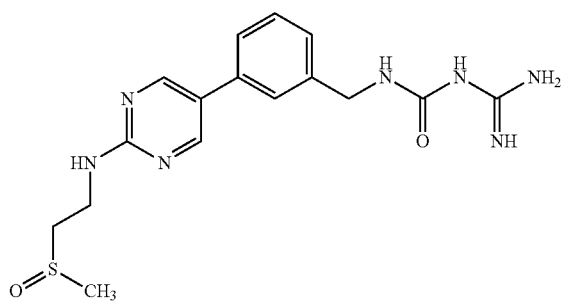 [SMILES: CS(=O)CCNc1ncc(-c2cccc(CNC(=O)NC(=N)N)c2)cn1] |
| 426 | 546 | 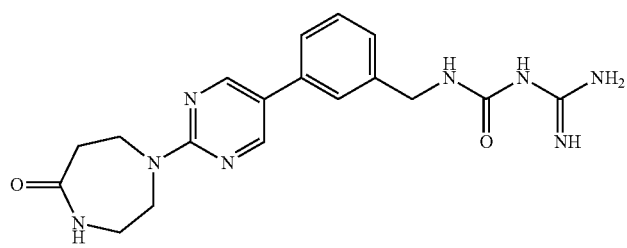 [SMILES: N=C(N)NC(=O)NCc1cccc(-c2cnc(N3CCNC(=O)CC3)nc2)c1] |
TABLE 108
| Ex | Syn | Structure |
|---|---|---|
| 427 | 546 | 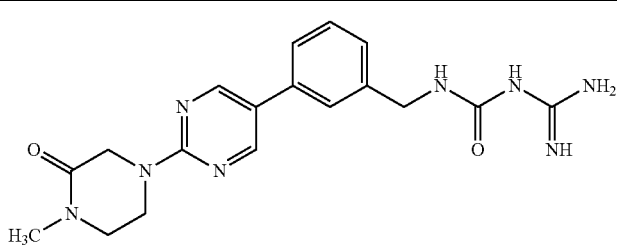 |

TABLE 108-continued

| Ex | Syn | Structure |
|---|---|---|
| 428 | 546 | 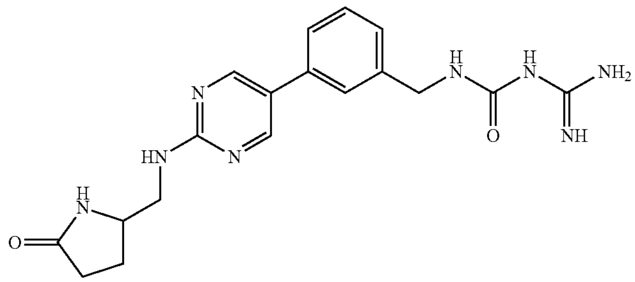 [SMILES: N=C(N)NC(=O)NCc1cccc(-c2cnc(NCC3CCC(=O)N3)nc2)c1] |
| 429 | 546 | 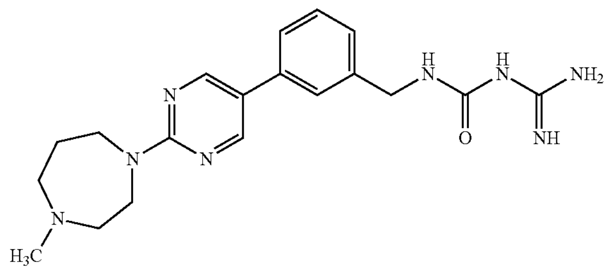 [SMILES: CN1CCCN(c2ncc(-c3cccc(CNC(=O)NC(=N)N)c3)cn2)CC1] |
| 430 | 546 | 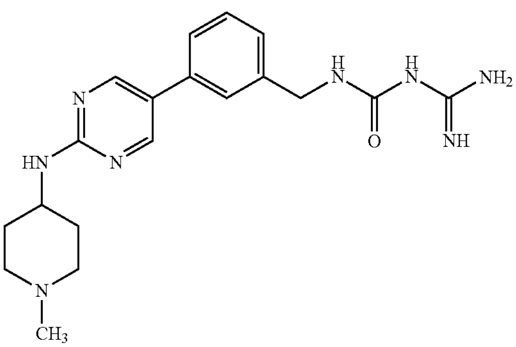 [SMILES: CN1CCC(Nc2ncc(-c3cccc(CNC(=O)NC(=N)N)c3)cn2)CC1] |
| 431 | 546 | 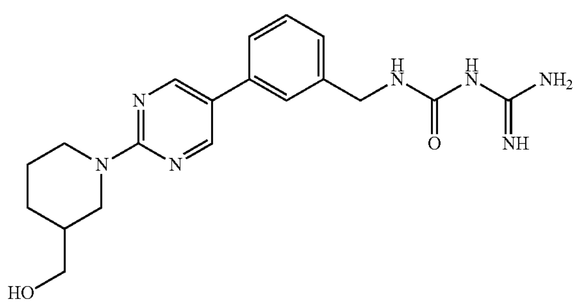 [SMILES: N=C(N)NC(=O)NCc1cccc(-c2cnc(N3CCCC(CO)C3)nc2)c1] |
| 432 | 546 | 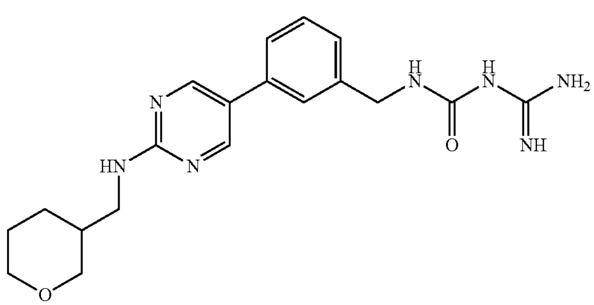 [SMILES: N=C(N)NC(=O)NCc1cccc(-c2cnc(NCC3CCCOC3)nc2)c1] |

TABLE 108-continued
| Ex | Syn | Structure |
|---|---|---|
| 433 | 546 | 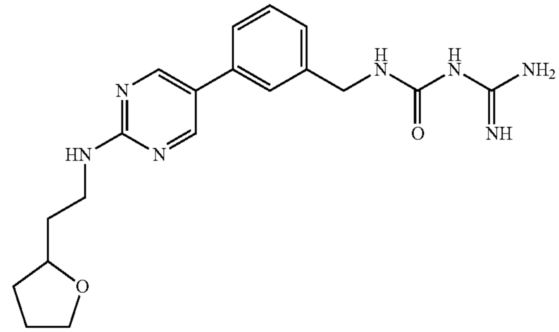 [SMILES: N=C(N)NC(=O)NCc1cccc(-c2cnc(NCCC3CCCO3)nc2)c1] |
| 434 | 546 | 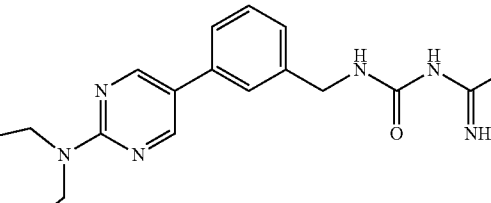 |
| 435 | 546 | 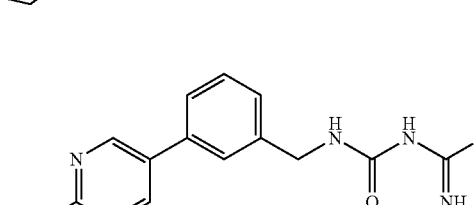 |
| 436 | 546 | 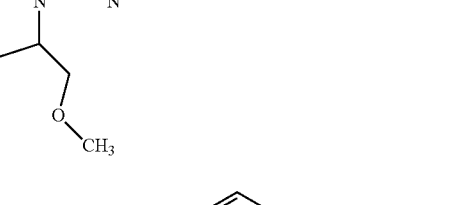 |
| 437 | 546 | trans- 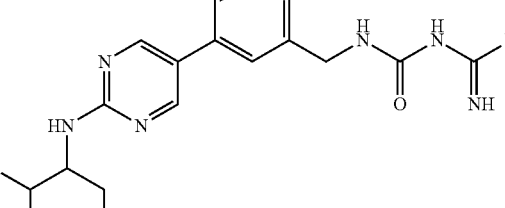 |

TABLE 108-continued
| Ex | Syn | Structure |
|---|---|---|
| 438 | 546 | 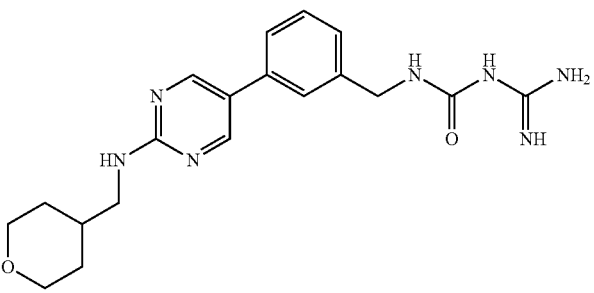 |
TABLE 109
| Ex | Syn | Structure |
|---|---|---|
| 439 | 546 | 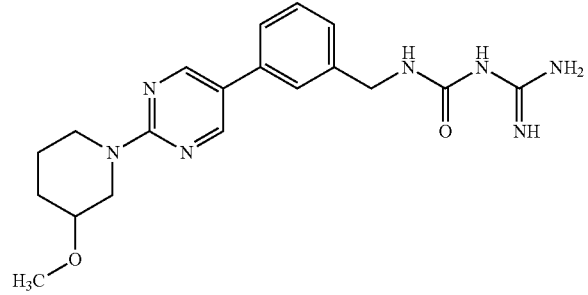 [SMILES: COC1CCCN(c2ncc(-c3cccc(CNC(=O)NC(=N)N)c3)cn2)C1] |
| 440 | 546 | 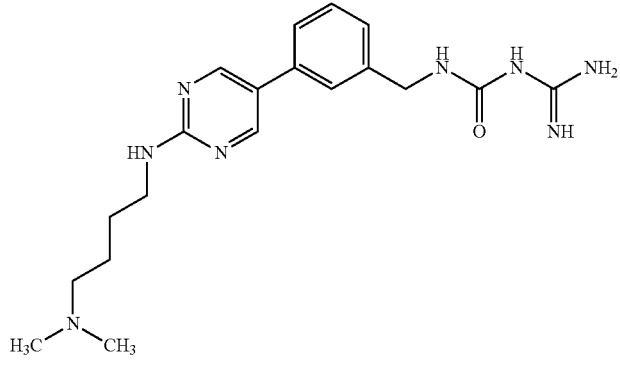 [SMILES: CN(C)CCCCNc1ncc(-c2cccc(CNC(=O)NC(=N)N)c2)cn1] |
| 441 | 546 | 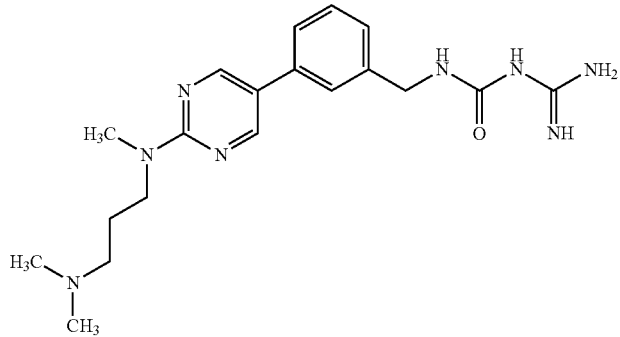 [SMILES: CN(C)CCCN(C)c1ncc(-c2cccc(CNC(=O)NC(=N)N)c2)cn1] |

TABLE 109-continued
| Ex | Syn | Structure |
|---|---|---|
| 442 | 546 | 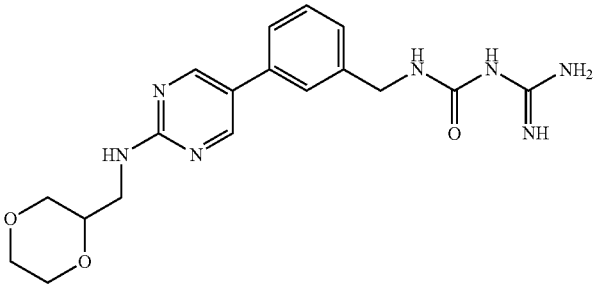 [SMILES: N=C(N)NC(=O)NCc1cccc(-c2cnc(NCC3COCCO3)nc2)c1] |
| 443 | 546 | 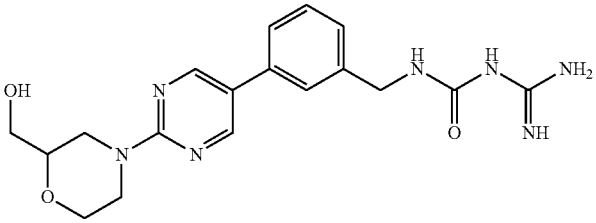 [SMILES: N=C(N)NC(=O)NCc1cccc(-c2cnc(N3CCOC(CO)C3)nc2)c1] |
| 444 | 546 | 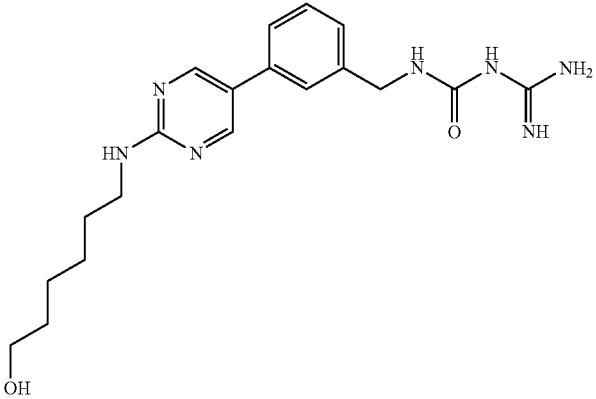 [SMILES: N=C(N)NC(=O)NCc1cccc(-c2cnc(NCCCCCCO)nc2)c1] |
| 445 | 546 | 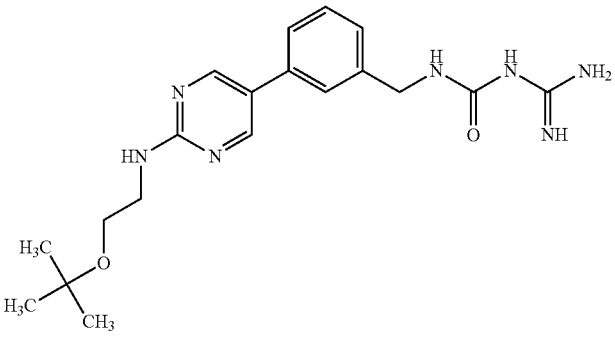 [SMILES: CC(C)(C)OCCNc1ncc(-c2cccc(CNC(=O)NC(=N)N)c2)cn1] |
| 446 | 546 | 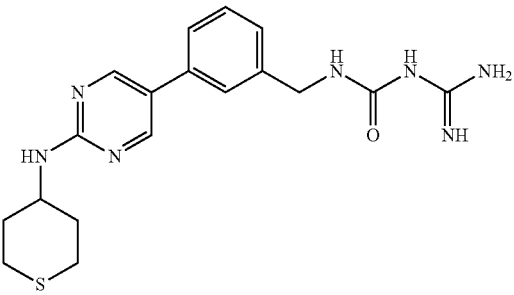 [SMILES: N=C(N)NC(=O)NCc1cccc(-c2cnc(NC3CCSCC3)nc2)c1] |

TABLE 109-continued

| Ex | Syn | Structure |
|---|---|---|
| 447 | 546 | 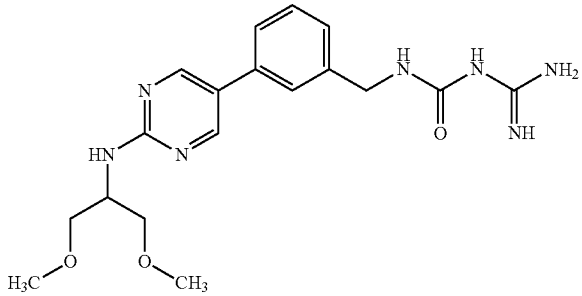 [SMILES: COCC(COC)Nc1ncc(-c2cccc(CNC(=O)NC(=N)N)c2)cn1] |
| 448 | 546 | 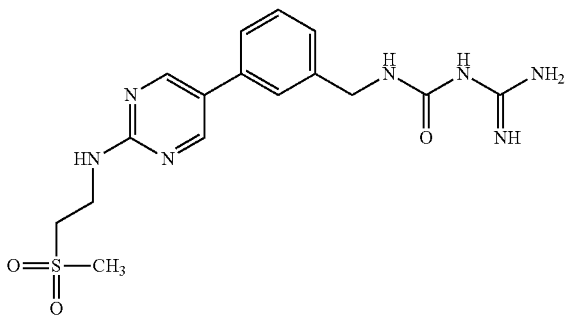 |
| 449 | 546 | 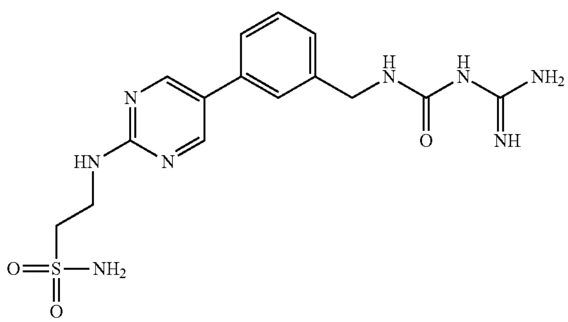 [SMILES: N=C(N)NC(=O)NCc1cccc(-c2cnc(NCCS(N)(=O)=O)nc2)c1] |
| 450 | 546 | 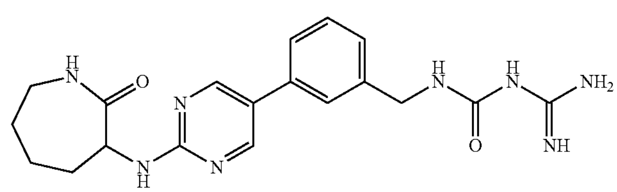 [SMILES: N=C(N)NC(=O)NCc1cccc(-c2cnc(NC3CCCCNC3=O)nc2)c1] |

TABLE 110

| Ex | Syn | Structure |
|---|---|---|
| 451 | 546 | 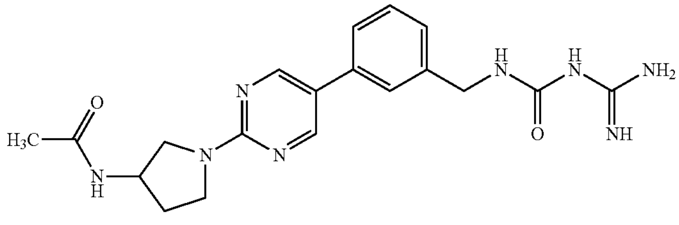 [SMILES: CC(=O)NC1CCN(c2ncc(-c3cccc(CNC(=O)NC(=N)N)c3)cn2)C1] |

TABLE 110-continued

| Ex | Syn | Structure |
|---|---|---|
| 452 | 546 | 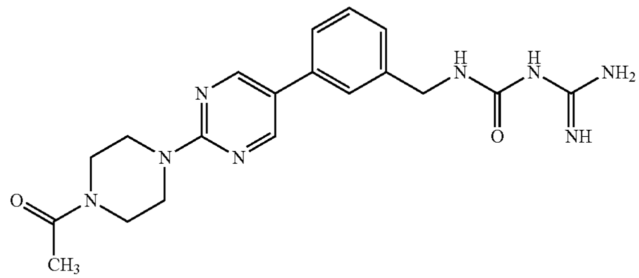 |
| 453 | 546 | 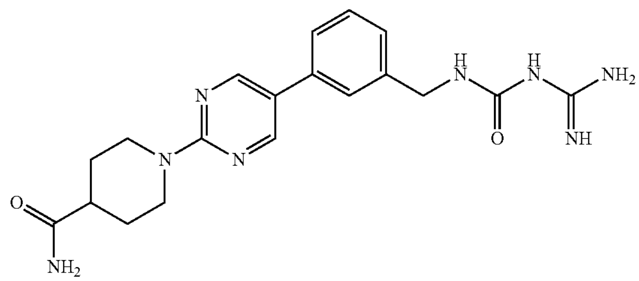 [SMILES: N=C(N)NC(=O)NCc1cccc(-c2cnc(N3CCC(C(N)=O)CC3)nc2)c1] |
| 454 | 546 | 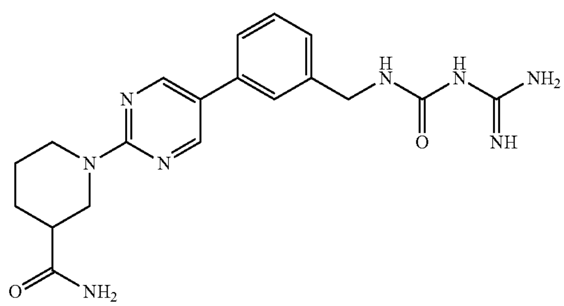 [SMILES: N=C(N)NC(=O)NCc1cccc(-c2cnc(N3CCCC(C(N)=O)C3)nc2)c1] |
| 455 | 546 | 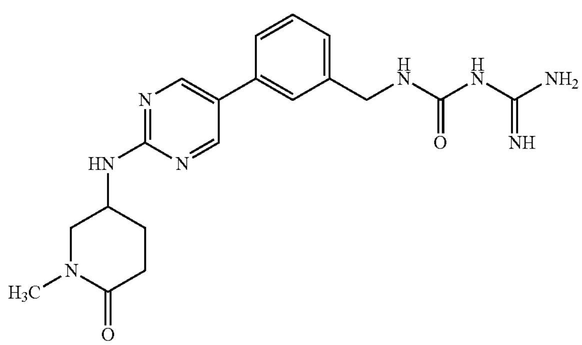 [SMILES: CN1CC(Nc2ncc(-c3cccc(CNC(=O)NC(=N)N)c3)cn2)CCC1=O] |
| 456 | 546 | 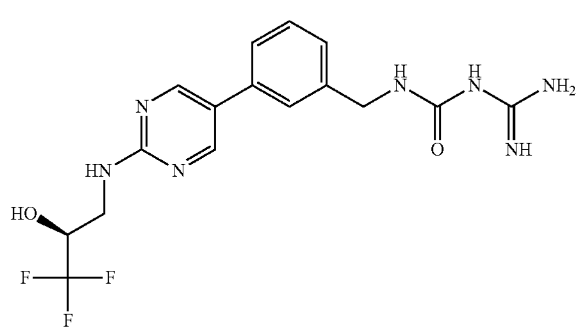 [SMILES: N=C(N)NC(=O)NCc1cccc(-c2cnc(NC[C@H](O)C(F)(F)F)nc2)c1] |

TABLE 110-continued

| Ex | Syn | Structure |
|---|---|---|
| 457 | 546 | 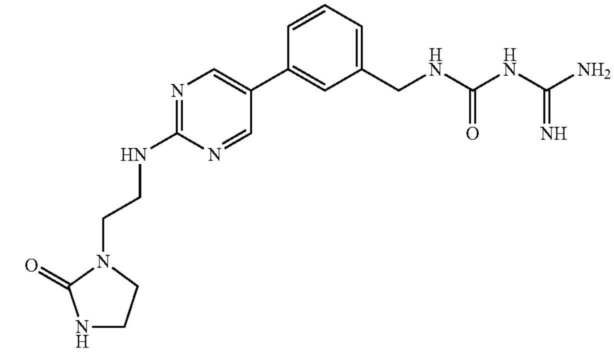 [SMILES: N=C(N)NC(=O)NCc1cccc(-c2cnc(NCCN3CCNC3=O)nc2)c1] |
| 458 | 546 | 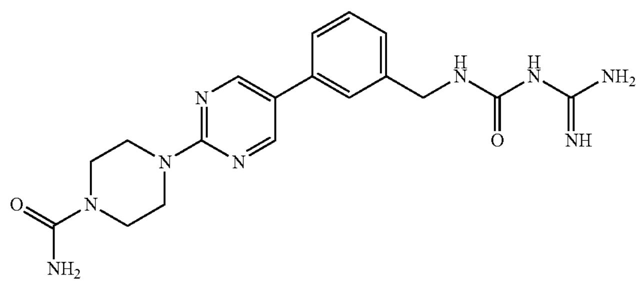 [SMILES: N=C(N)NC(=O)NCc1cccc(-c2cnc(N3CCN(C(N)=O)CC3)nc2)c1] |
| 459 | 546 | 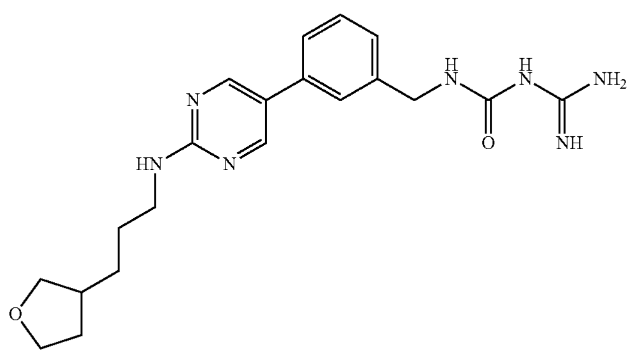 [SMILES: N=C(N)NC(=O)NCc1cccc(-c2cnc(NCCCC3CCOC3)nc2)c1] |
| 460 | 546 | 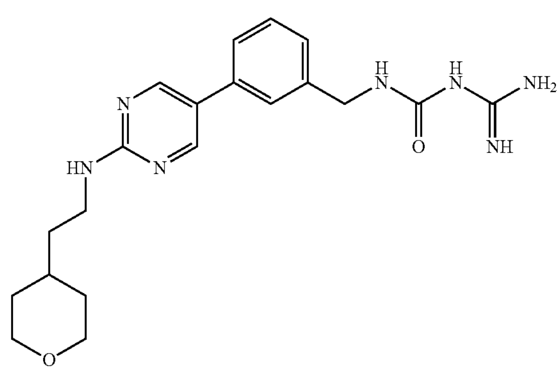 |

TABLE 110-continued

| Ex | Syn | Structure |
|---|---|---|
| 461 | 546 | (structure) |
| 462 | 546 | (structure) |

TABLE 111

| Ex | Syn | Structure |
|---|---|---|
| 463 | 546 | (structure) |
| 464 | 546 | (structure) |
| 465 | 546 | (structure) |

TABLE 111-continued

| Ex | Syn | Structure |
|---|---|---|
| 466 | 546 | 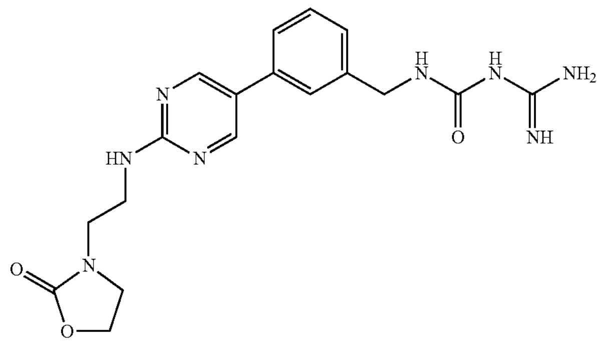 [SMILES: N=C(N)NC(=O)NCc1cccc(-c2cnc(NCCN3CCOC3=O)nc2)c1] |
| 467 | 546 | 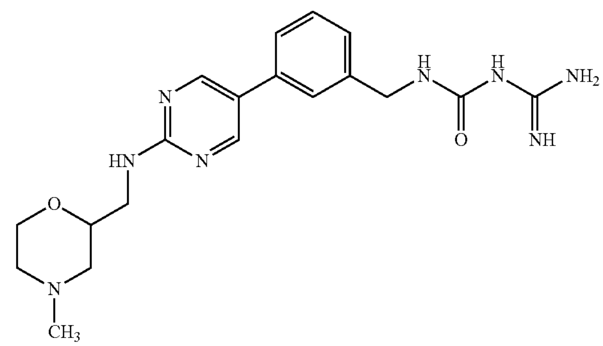 [SMILES: CN1CCOC(CNc2ncc(-c3cccc(CNC(=O)NC(=N)N)c3)cn2)C1] |
| 468 | 546 | 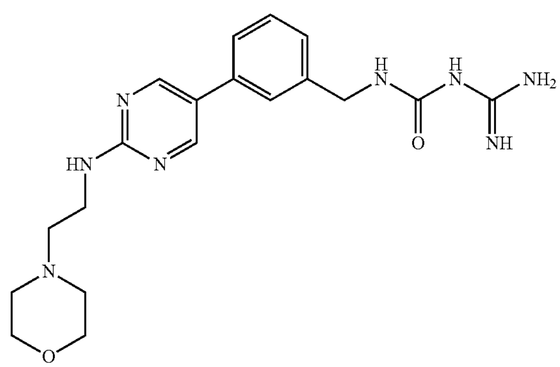 [SMILES: N=C(N)NC(=O)NCc1cccc(-c2cnc(NCCN3CCOCC3)nc2)c1] |
| 469 | 546 | 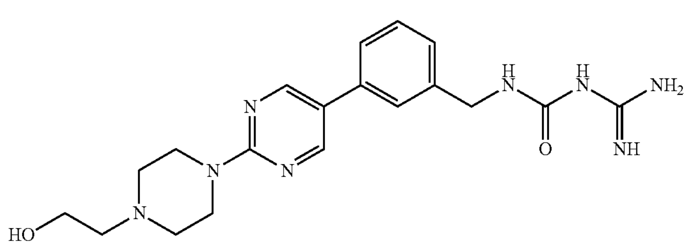 [SMILES: N=C(N)NC(=O)NCc1cccc(-c2cnc(N3CCN(CCO)CC3)nc2)c1] |

TABLE 111-continued

| Ex | Syn | Structure |
|---|---|---|
| 470 | 546 | 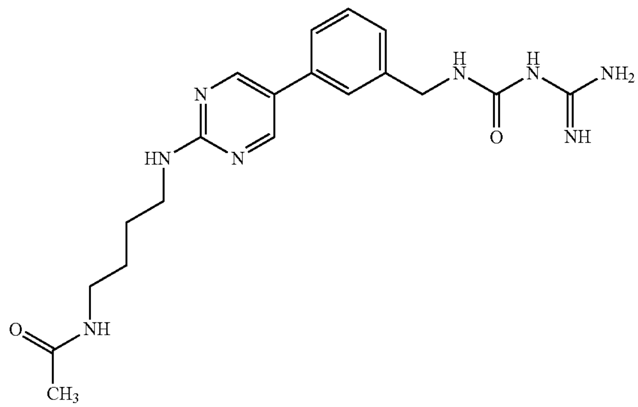 [SMILES: CC(=O)NCCCCNc1ncc(-c2cccc(CNC(=O)NC(=N)N)c2)cn1] |
| 471 | 546 | 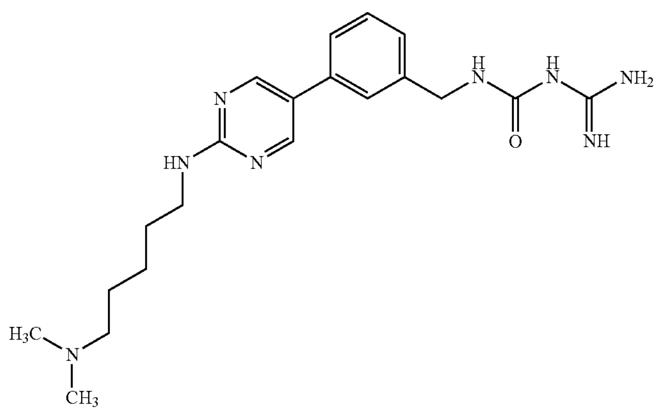 [SMILES: CN(C)CCCCCNc1ncc(-c2cccc(CNC(=O)NC(=N)N)c2)cn1] |
| 472 | 546 | 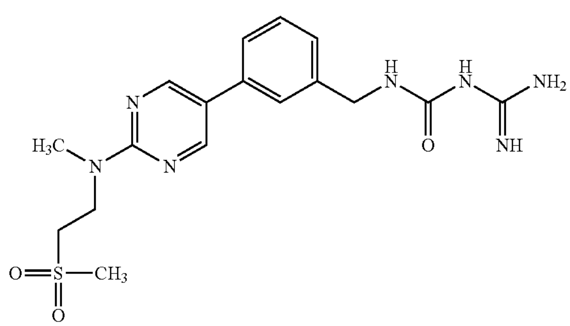 [SMILES: CN(CCS(C)(=O)=O)c1ncc(-c2cccc(CNC(=O)NC(=N)N)c2)cn1] |
| 473 | 546 | 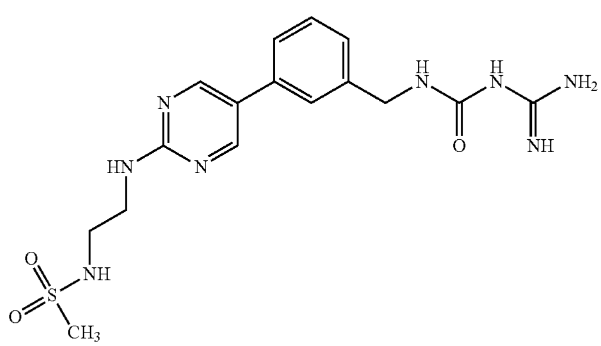 [SMILES: CS(=O)(=O)NCCNc1ncc(-c2cccc(CNC(=O)NC(=N)N)c2)cn1] |

TABLE 111-continued
| Ex | Syn | Structure |
|---|---|---|
| 474 | 546 | 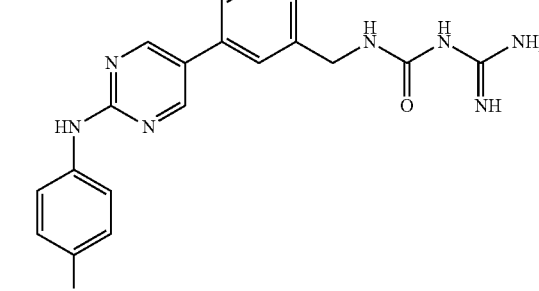 |
TABLE 112
| Ex | Syn | Structure |
|---|---|---|
| 475 | 546 | 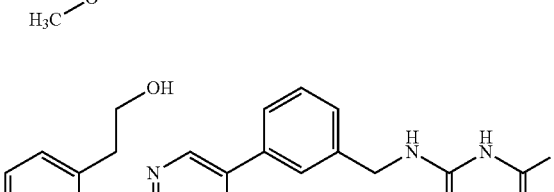 |
| 476 | 546 | 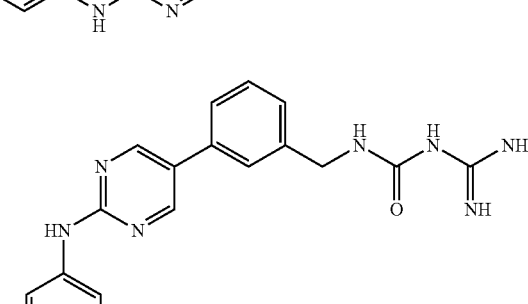 |
| 477 | 546 | 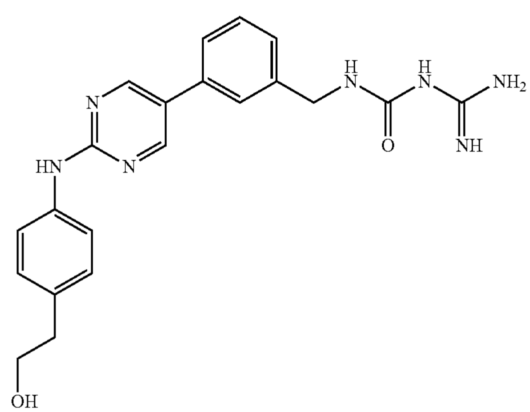 [SMILES: N=C(N)NC(=O)NCc1cccc(-c2cnc(Nc3ccc(CCO)cc3)nc2)c1] |

TABLE 112-continued

| Ex | Syn | Structure |
|---|---|---|
| 478 | 546 | 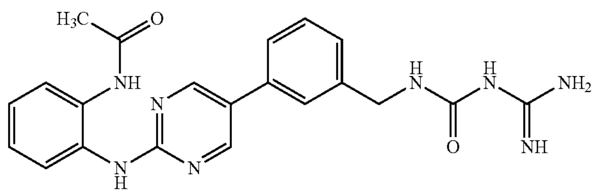 [SMILES: CC(=O)Nc1ccccc1Nc1ncc(-c2cccc(CNC(=O)NC(=N)N)c2)cn1] |
| 479 | 546 | 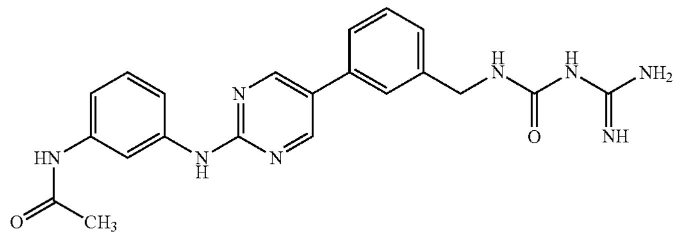 [SMILES: CC(=O)Nc1cccc(Nc2ncc(-c3cccc(CNC(=O)NC(=N)N)c3)cn2)c1] |
| 480 | 546 | 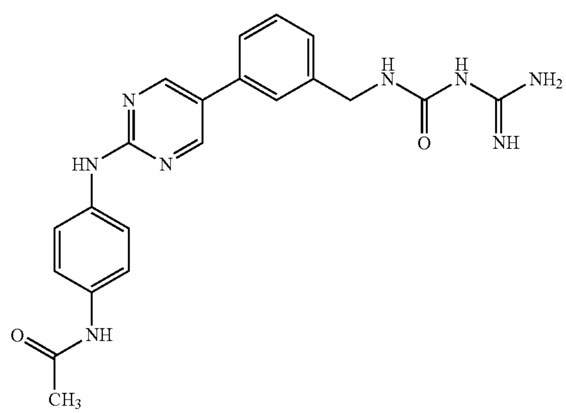 [SMILES: CC(=O)Nc1ccc(Nc2ncc(-c3cccc(CNC(=O)NC(=N)N)c3)cn2)cc1] |
| 481 | 546 | 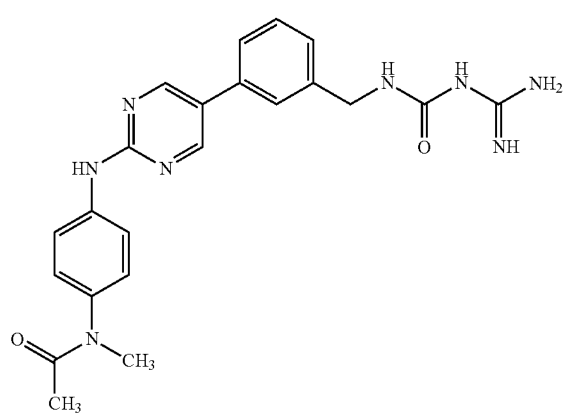 [SMILES: CC(=O)N(C)c1ccc(Nc2ncc(-c3cccc(CNC(=O)NC(=N)N)c3)cn2)cc1] |

TABLE 112-continued
| Ex | Syn | Structure |
|---|---|---|
| 482 | 546 | 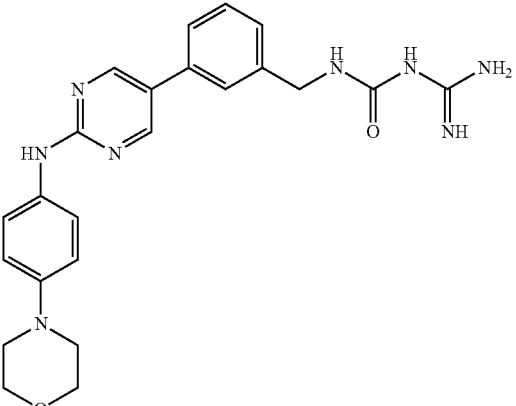 |
| 483 | 546 | 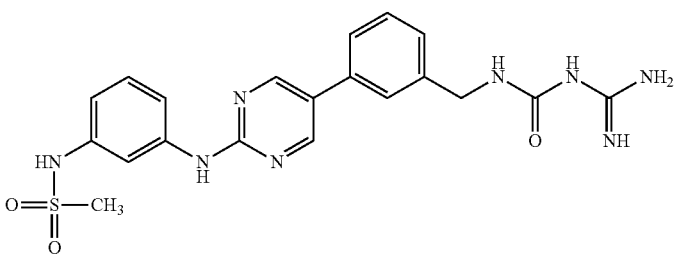 [SMILES: CS(=O)(=O)Nc1cccc(Nc2ncc(-c3cccc(CNC(=O)NC(=N)N)c3)cn2)c1] |
| 484 | 546 | 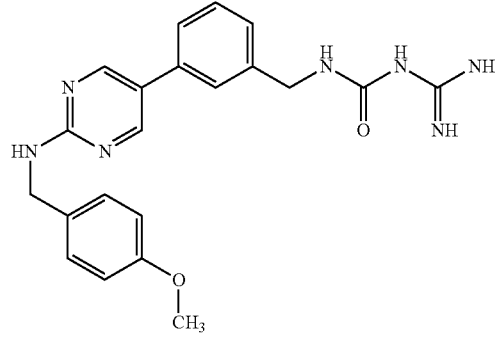 [SMILES: COc1ccc(CNc2ncc(-c3cccc(CNC(=O)NC(=N)N)c3)cn2)cc1] |
TABLE 113
| Ex | Syn | Structure |
|---|---|---|
| 485 | 546 | 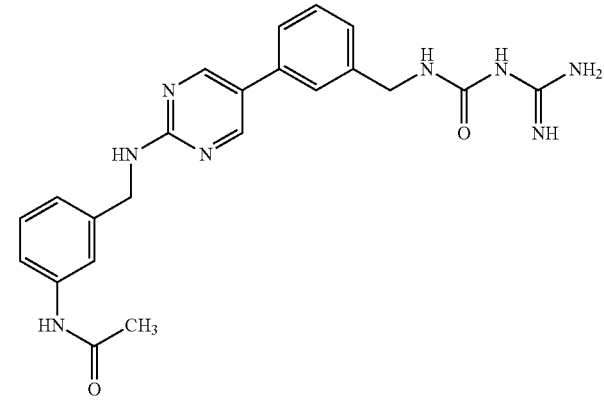 [SMILES: CC(=O)Nc1cccc(CNc2ncc(-c3cccc(CNC(=O)NC(=N)N)c3)cn2)c1] |

TABLE 113-continued

| Ex | Syn | Structure |
|---|---|---|
| 486 | 546 | 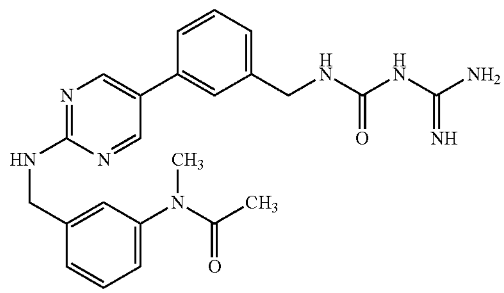 [SMILES: CC(=O)N(C)c1cccc(CNc2ncc(-c3cccc(CNC(=O)NC(=N)N)c3)cn2)c1] |
| 487 | 546 | 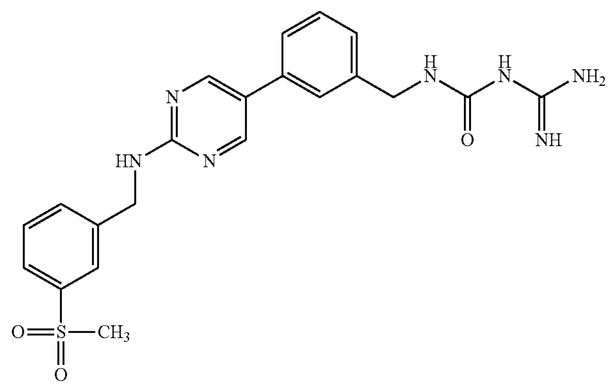 [SMILES: CS(=O)(=O)c1cccc(CNc2ncc(-c3cccc(CNC(=O)NC(=N)N)c3)cn2)c1] |
| 488 | 546 | 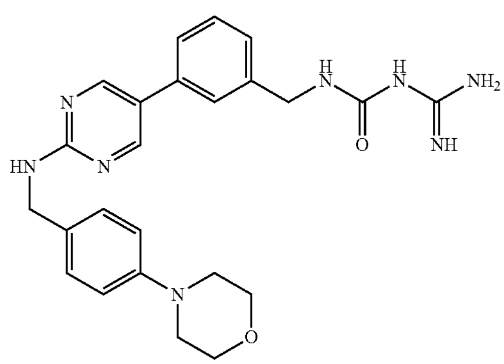 [SMILES: N=C(N)NC(=O)NCc1cccc(-c2cnc(NCc3ccc(N4CCOCC4)cc3)nc2)c1] |
| 489 | 546 | 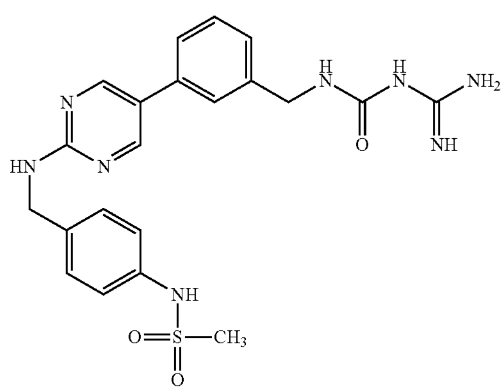 [SMILES: CS(=O)(=O)Nc1ccc(CNc2ncc(-c3cccc(CNC(=O)NC(=N)N)c3)cn2)cc1] |

TABLE 113-continued
| Ex | Syn | Structure |
|---|---|---|
| 490 | 546 | 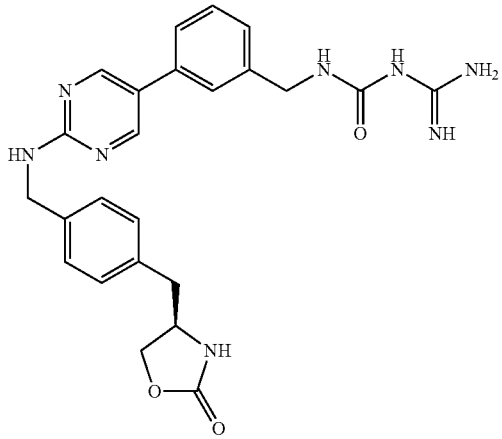 [SMILES: N=C(N)NC(=O)NCc1cccc(-c2cnc(NCc3ccc(C[C@@H]4COC(=O)N4)cc3)nc2)c1] |
| 491 | 546 | 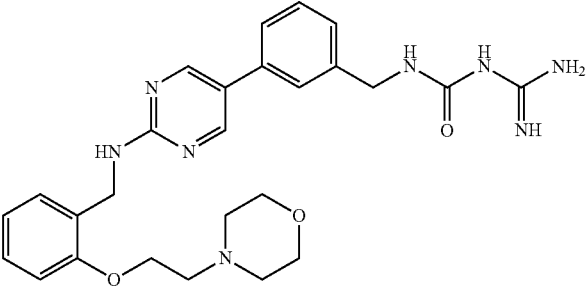 [SMILES: N=C(N)NC(=O)NCc1cccc(-c2cnc(NCc3ccccc3OCCN3CCOCC3)nc2)c1] |
| 492 | 546 | 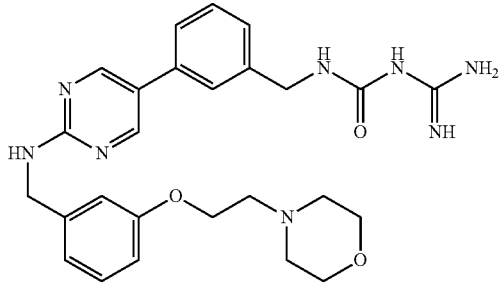 [SMILES: N=C(N)NC(=O)NCc1cccc(-c2cnc(NCc3cccc(OCCN4CCOCC4)c3)nc2)c1] |
| 493 | 546 | 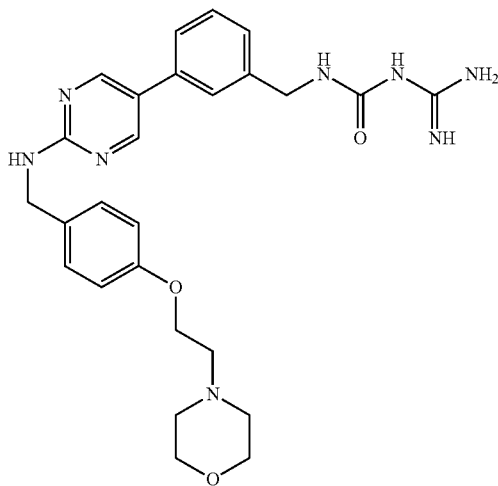 [SMILES: N=C(N)NC(=O)NCc1cccc(-c2cnc(NCc3ccc(OCCN4CCOCC4)cc3)nc2)c1] |

TABLE 113-continued
| Ex | Syn | Structure |
|---|---|---|
| 494 | 546 | 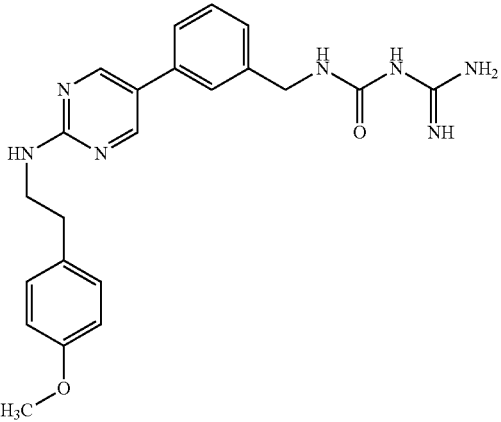 [SMILES: COc1ccc(CCNc2ncc(-c3cccc(CNC(=O)NC(=N)N)c3)cn2)cc1] |
TABLE 114
| Ex | Syn | Structure |
|---|---|---|
| 495 | 546 | 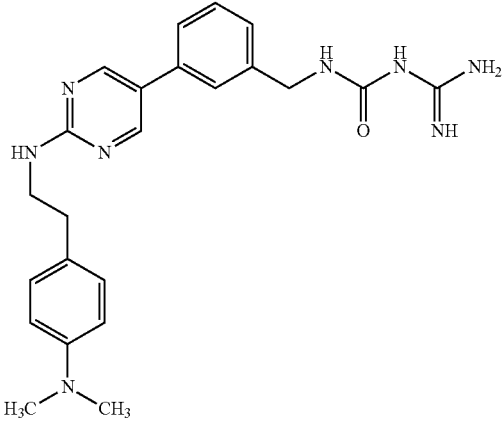 [SMILES: CN(C)c1ccc(CCNc2ncc(-c3cccc(CNC(=O)NC(=N)N)c3)cn2)cc1] |
| 496 | 546 | 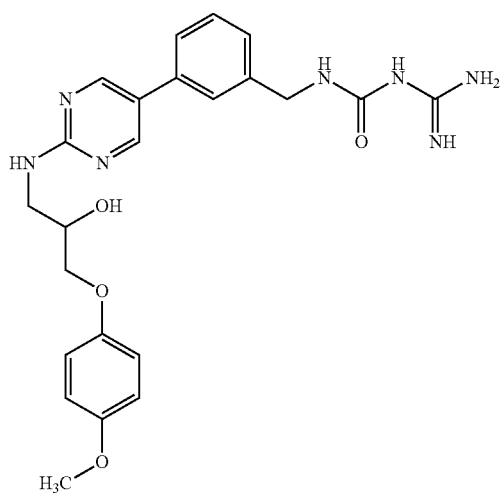 [SMILES: COc1ccc(OCC(O)CNc2ncc(-c3cccc(CNC(=O)NC(=N)N)c3)cn2)cc1] |

TABLE 114-continued

| Ex | Syn | Structure |
|---|---|---|
| 497 | 546 | 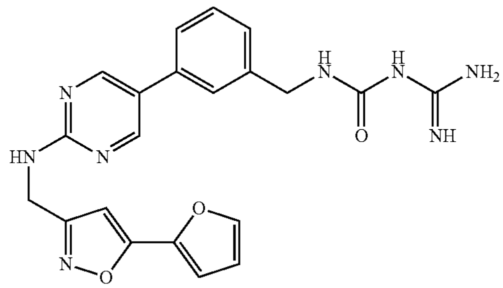 [SMILES: N=C(N)NC(=O)NCc1cccc(-c2cnc(NCc3cc(-c4ccco4)on3)nc2)c1] |
| 498 | 546 | 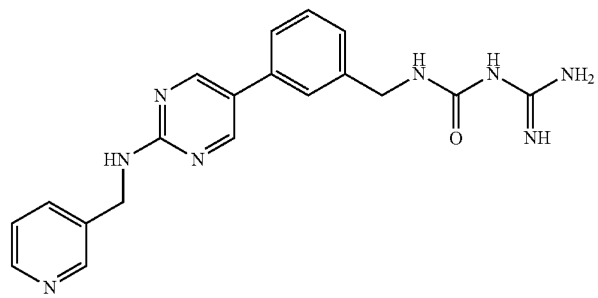 [SMILES: N=C(N)NC(=O)NCc1cccc(-c2cnc(NCc3cccnc3)nc2)c1] |
| 499 | 546 | 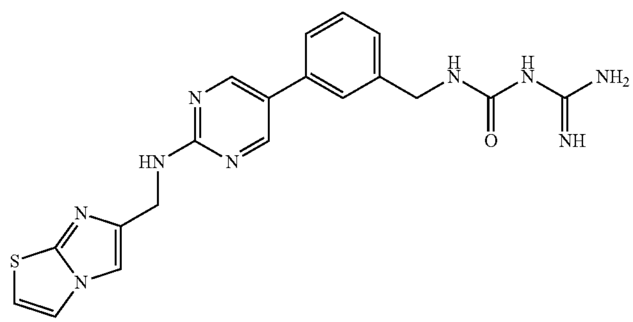 [SMILES: N=C(N)NC(=O)NCc1cccc(-c2cnc(NCc3cn4ccsc4n3)nc2)c1] |
| 500 | 546 | 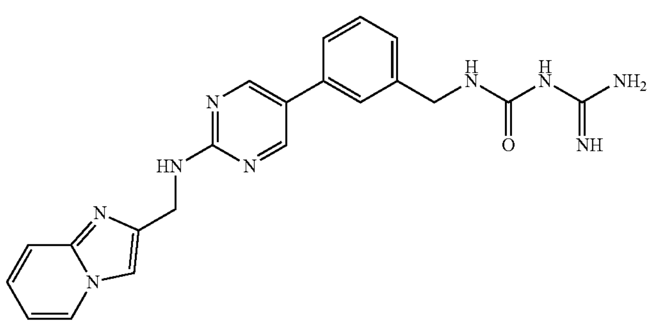 [SMILES: N=C(N)NC(=O)NCc1cccc(-c2cnc(NCc3cn4ccccc4n3)nc2)c1] |
| 501 | 546 | 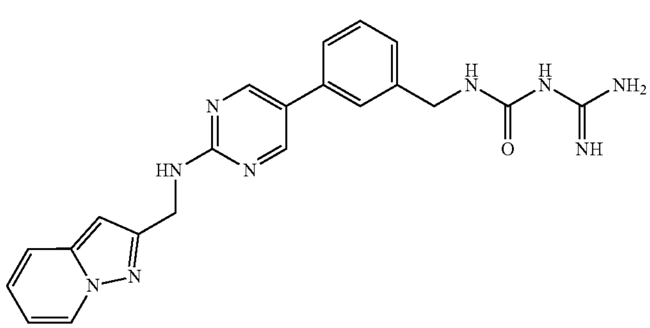 |

TABLE 114-continued
| Ex | Syn | Structure |
|----|-----|-----------|
| 502 | 546 | 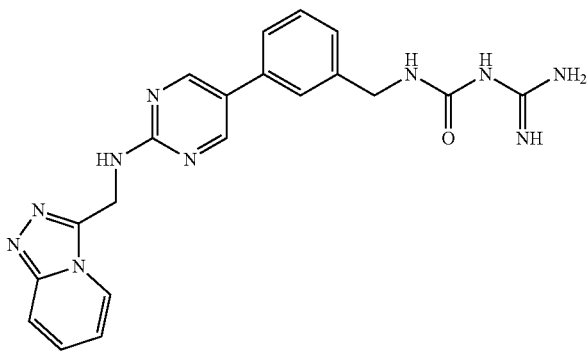 [SMILES: N=C(N)NC(=O)NCc1cccc(-c2cnc(NCc3nnc4ccccn34)nc2)c1] |
| 503 | 546 | 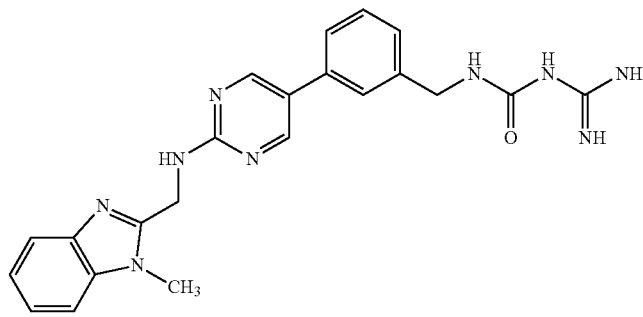 |
| 504 | 546 | 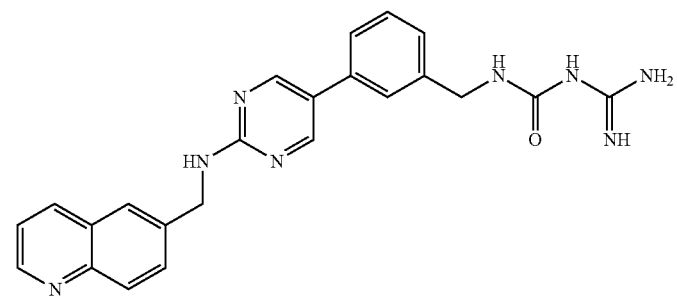 [SMILES: N=C(N)NC(=O)NCc1cccc(-c2cnc(NCc3ccc4ncccc4c3)nc2)c1] |
| 505 | 546 | 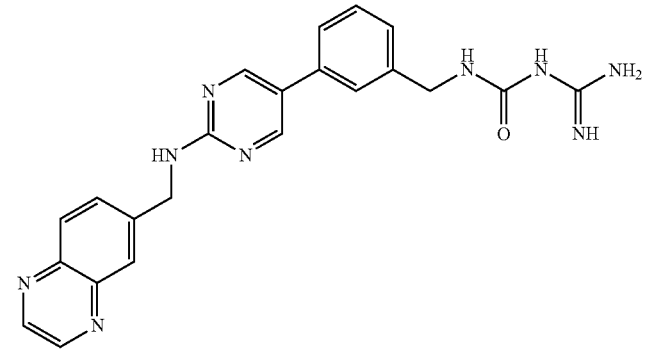 [SMILES: N=C(N)NC(=O)NCc1cccc(-c2cnc(NCc3ccc4nccnc4c3)nc2)c1] |

TABLE 114-continued
| Ex | Syn | Structure |
|---|---|---|
| 506 | 546 | 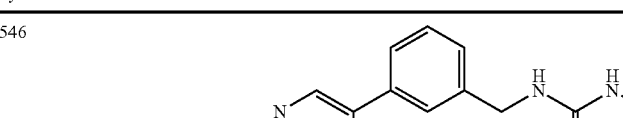 |
TABLE 115
| Ex | Syn | Structure |
|---|---|---|
| 507 | 546 | 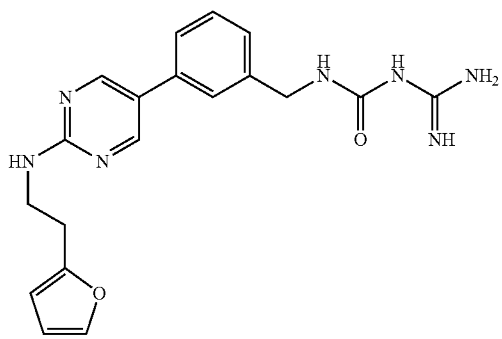 |
| 508 | 546 | 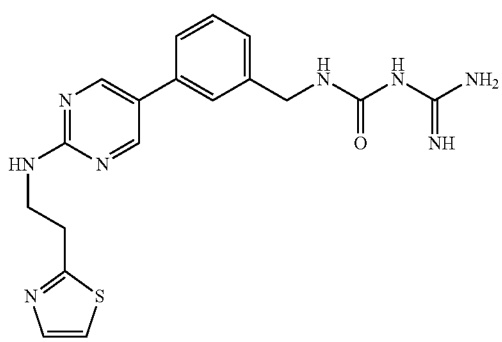 [SMILES: N=C(N)NC(=O)NCc1cccc(-c2cnc(NCCc3nccs3)nc2)c1] |
| 509 | 546 | 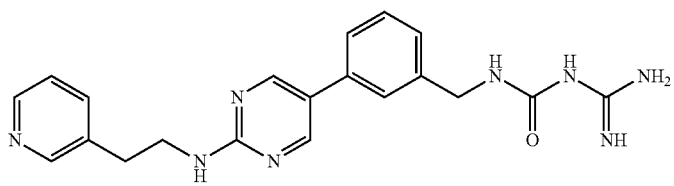 [SMILES: N=C(N)NC(=O)NCc1cccc(-c2cnc(NCCc3cccnc3)nc2)c1] |

TABLE 115-continued

| Ex | Syn | Structure |
|----|-----|-----------|
| 510 | 546 | 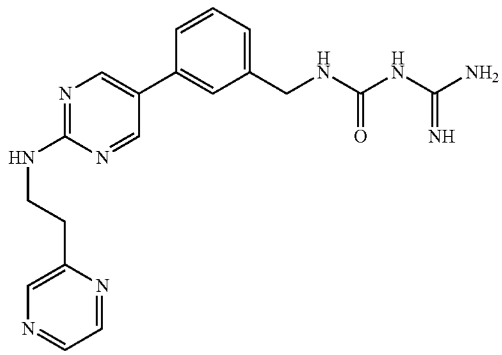 [SMILES: N=C(N)NC(=O)NCc1cccc(-c2cnc(NCCc3cnccn3)nc2)c1] |
| 511 | 546 | 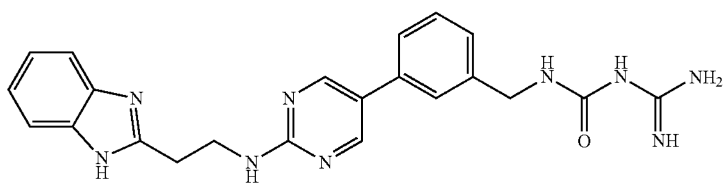 [SMILES: N=C(N)NC(=O)NCc1cccc(-c2cnc(NCCc3nc4ccccc4[nH]3)nc2)c1] |
| 512 | 546 | 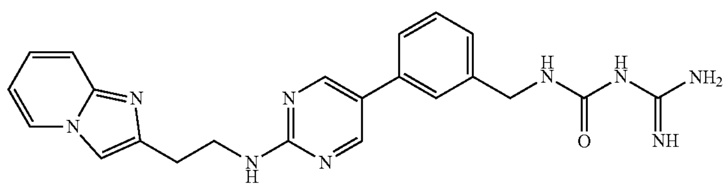 [SMILES: N=C(N)NC(=O)NCc1cccc(-c2cnc(NCCc3cn4ccccc4n3)nc2)c1] |
| 513 | 546 | 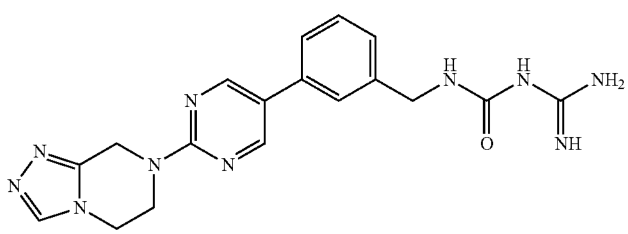 [SMILES: N=C(N)NC(=O)NCc1cccc(-c2cnc(N3CCn4cnnc4C3)nc2)c1] |
| 514 | 546 | 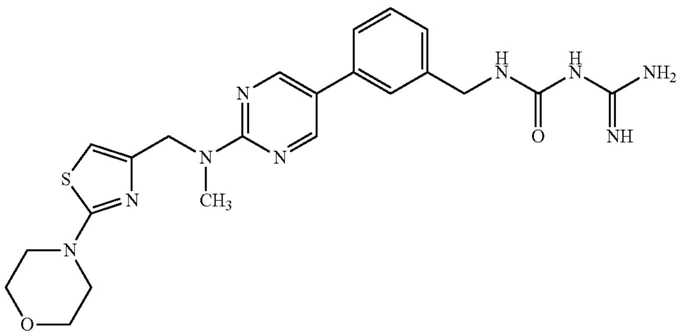 [SMILES: CN(Cc1csc(N2CCOCC2)n1)c1ncc(-c2cccc(CNC(=O)NC(=N)N)c2)cn1] |

TABLE 115-continued
| Ex | Syn | Structure |
|---|---|---|
| 515 | 546 | 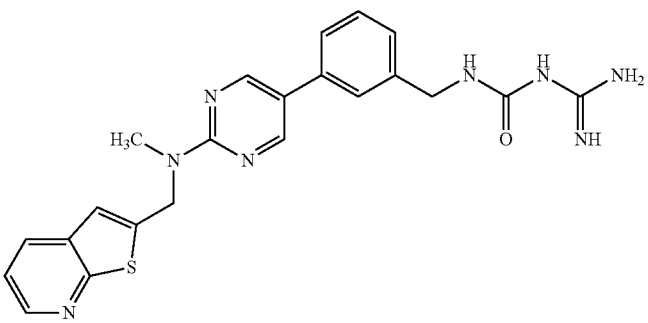 [SMILES: CN(Cc1cc2cccnc2s1)c1ncc(-c2cccc(CNC(=O)NC(=N)N)c2)cn1] |
| 516 | 546 | 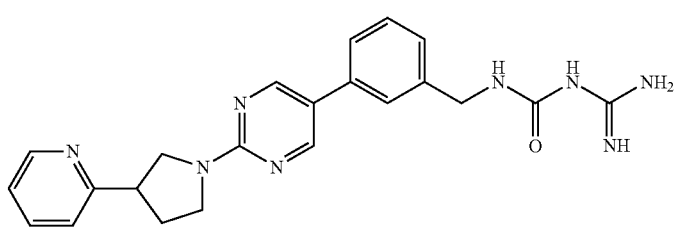 [SMILES: N=C(N)NC(=O)NCc1cccc(-c2cnc(N3CCC(c4ccccn4)C3)nc2)c1] |
| 517 | 546 | 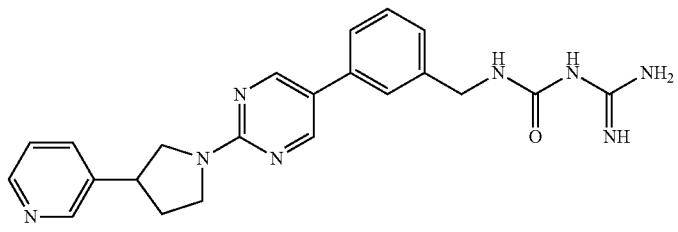 [SMILES: N=C(N)NC(=O)NCc1cccc(-c2cnc(N3CCC(c4cccnc4)C3)nc2)c1] |
| 518 | 546 | 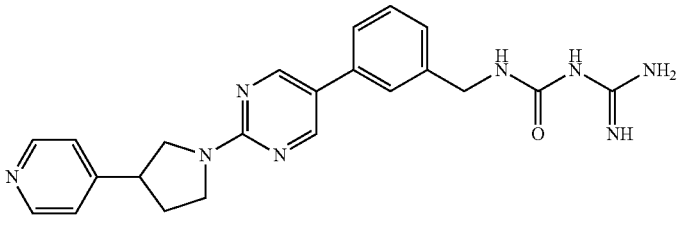 [SMILES: N=C(N)NC(=O)NCc1cccc(-c2cnc(N3CCC(c4ccncc4)C3)nc2)c1] |
| 519 | 546 | 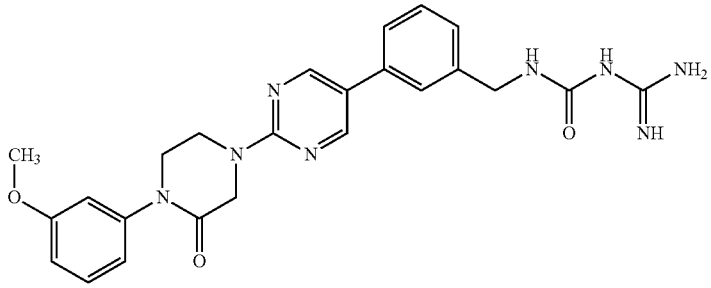 [SMILES: COc1cccc(N2CCN(c3ncc(-c4cccc(CNC(=O)NC(=N)N)c4)cn3)CC2=O)c1] |
| 520 | 546 | 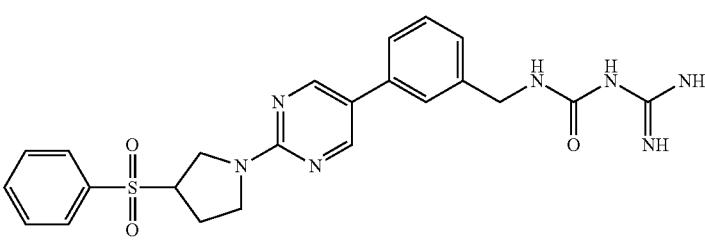 |

TABLE 116

| Ex | Syn | Structure |
|---|---|---|
| 521 | 546 | 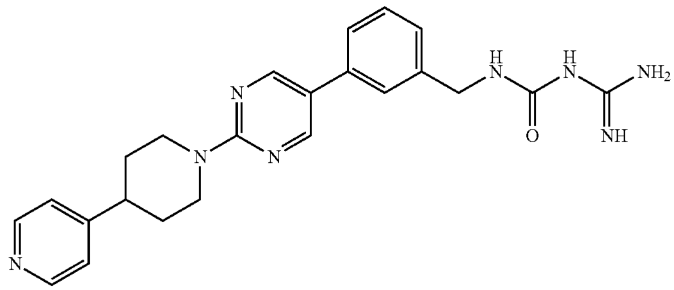 [SMILES: N=C(N)NC(=O)NCc1cccc(-c2cnc(N3CCC(c4ccncc4)CC3)nc2)c1] |
| 522 | 546 | 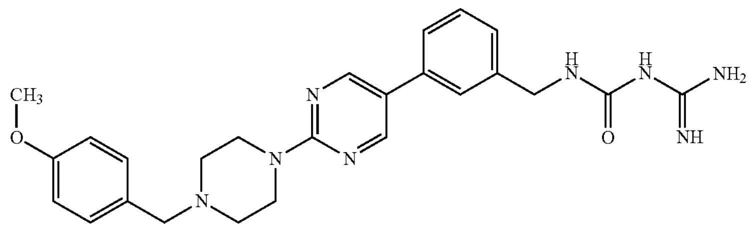 [SMILES: COc1ccc(CN2CCN(c3ncc(-c4cccc(CNC(=O)NC(=N)N)c4)cn3)CC2)cc1] |
| 523 | 546 | 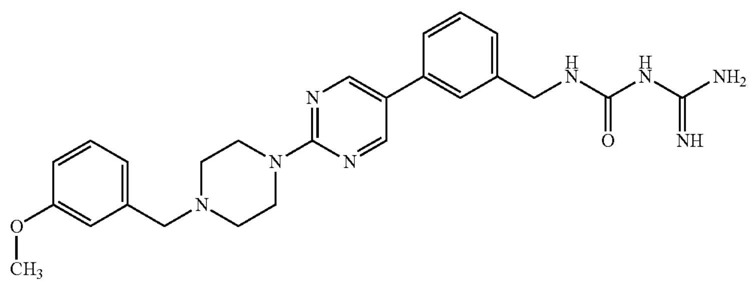 [SMILES: COc1cccc(CN2CCN(c3ncc(-c4cccc(CNC(=O)NC(=N)N)c4)cn3)CC2)c1] |
| 524 | 546 | 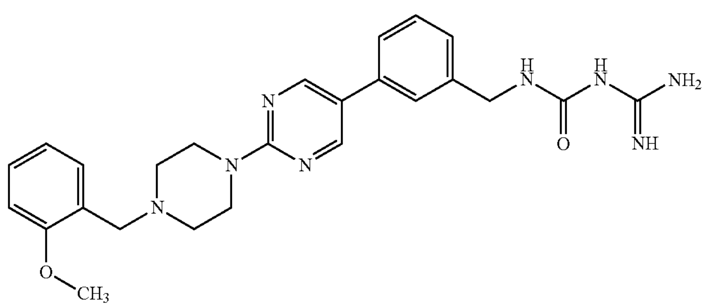 [SMILES: COc1ccccc1CN1CCN(c2ncc(-c3cccc(CNC(=O)NC(=N)N)c3)cn2)CC1] |
| 525 | 546 | 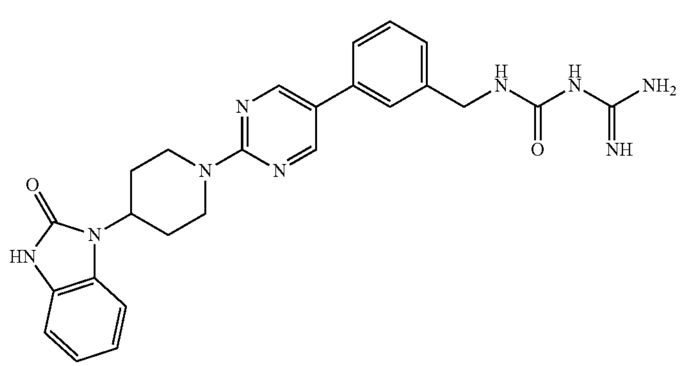 [SMILES: N=C(N)NC(=O)NCc1cccc(-c2cnc(N3CCC(n4c(=O)[nH]c5ccccc54)CC3)nc2)c1] |

TABLE 116-continued

| Ex | Syn | Structure |
|---|---|---|
| 526 | 546 | 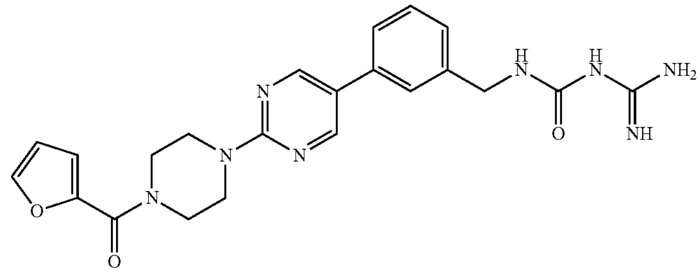 [SMILES: N=C(N)NC(=O)NCc1cccc(-c2cnc(N3CCN(C(=O)c4ccco4)CC3)nc2)c1] |
| 527 | 546 | 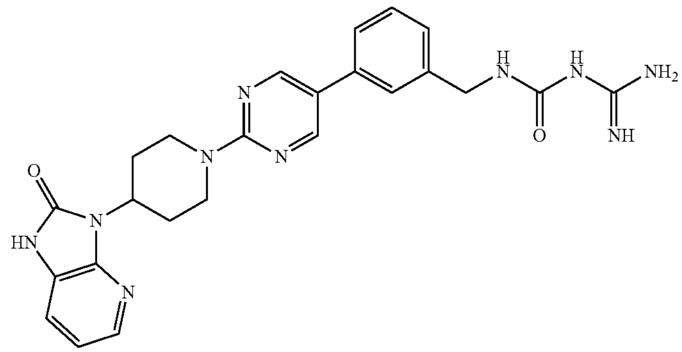 [SMILES: N=C(N)NC(=O)NCc1cccc(-c2cnc(N3CCC(n4c(=O)[nH]c5cccnc54)CC3)nc2)c1] |
| 528 | 546 | 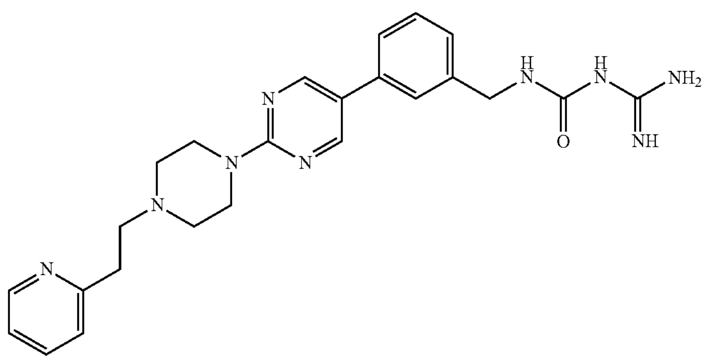 [SMILES: N=C(N)NC(=O)NCc1cccc(-c2cnc(N3CCN(CCc4ccccn4)CC3)nc2)c1] |
| 529 | 546 | 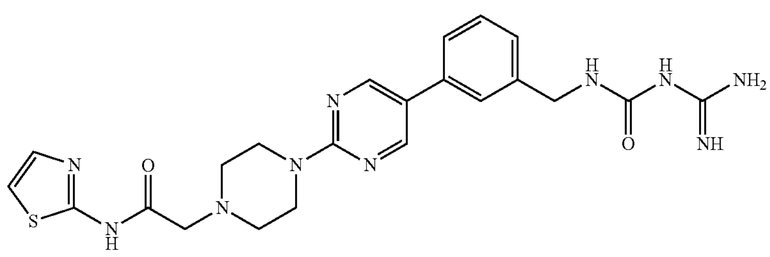 [SMILES: N=C(N)NC(=O)NCc1cccc(-c2cnc(N3CCN(CC(=O)Nc4nccs4)CC3)nc2)c1] |
| 530 | 546 | 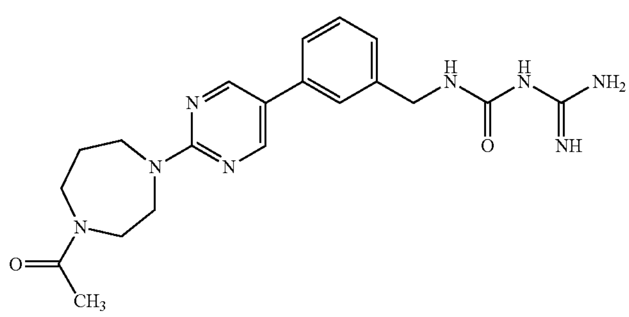 [SMILES: CC(=O)N1CCCN(c2ncc(-c3cccc(CNC(=O)NC(=N)N)c3)cn2)CC1] |

TABLE 116-continued
| Ex | Syn | Structure |
|---|---|---|
| 531 | 546 | 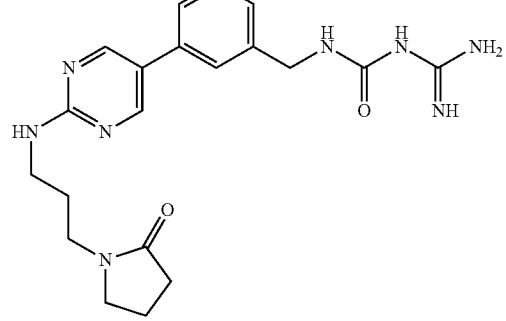 |
| 532 | 546 | 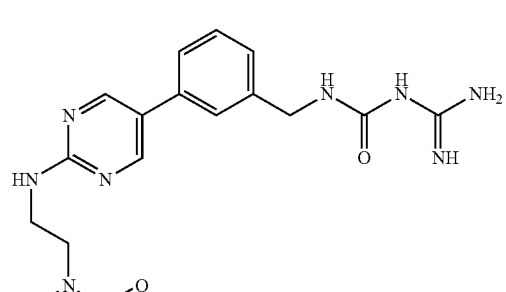 |
TABLE 117
| Ex | Syn | Structure |
|---|---|---|
| 533 | 546 | 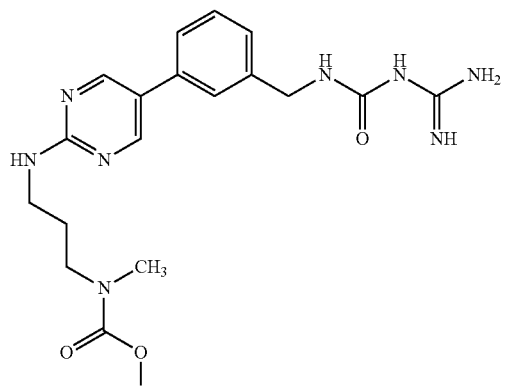 |
| 534 | 546 | 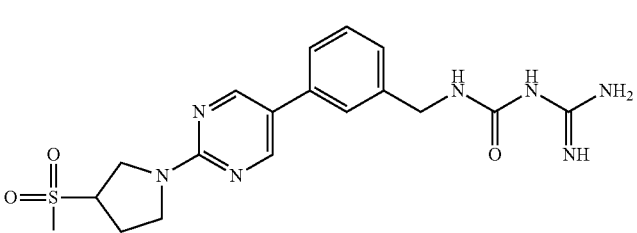 |

TABLE 117-continued

| Ex | Syn | Structure |
|---|---|---|
| 535 | 546 | 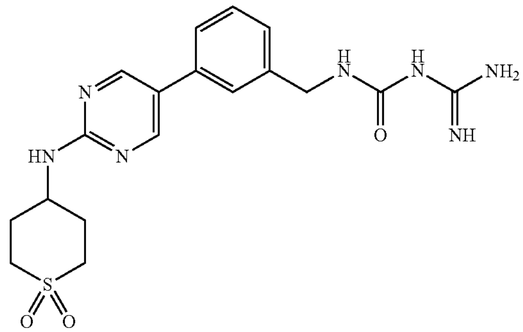 [SMILES: N=C(N)NC(=O)NCc1cccc(-c2cnc(NC3CCS(=O)(=O)CC3)nc2)c1] |
| 536 | 546 | 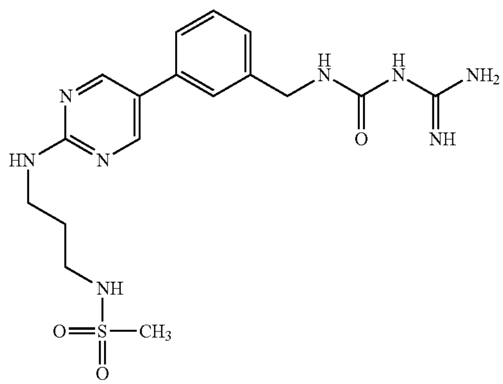 [SMILES: CS(=O)(=O)NCCCNc1ncc(-c2cccc(CNC(=O)NC(=N)N)c2)cn1] |
| 537 | 546 | 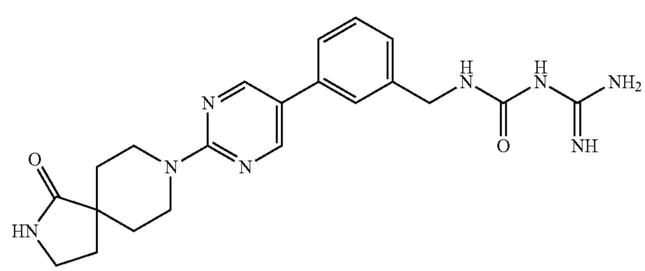 [SMILES: N=C(N)NC(=O)NCc1cccc(-c2cnc(N3CCC4(CCNC4=O)CC3)nc2)c1] |
| 538 | 546 | 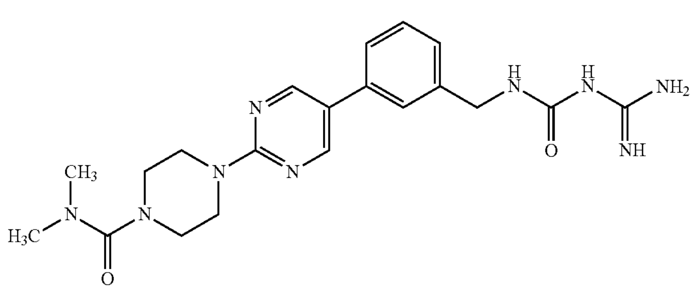 [SMILES: CN(C)C(=O)N1CCN(c2ncc(-c3cccc(CNC(=O)NC(=N)N)c3)cn2)CC1] |

TABLE 117-continued

| Ex | Syn | Structure |
|---|---|---|
| 539 | 546 | 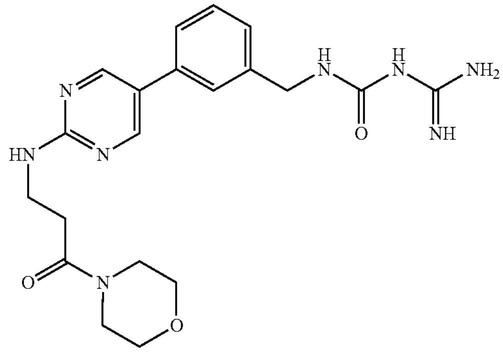 [SMILES: N=C(N)NC(=O)NCc1cccc(-c2cnc(NCCC(=O)N3CCOCC3)nc2)c1] |
| 540 | 546 | 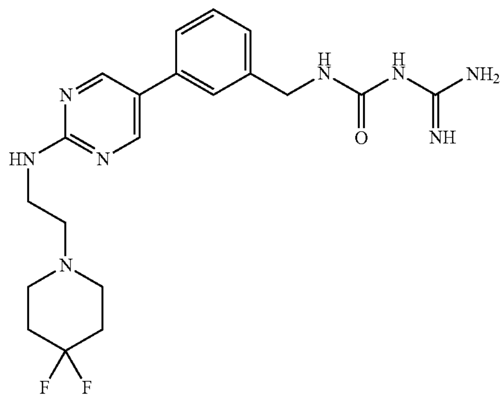 [SMILES: N=C(N)NC(=O)NCc1cccc(-c2cnc(NCCN3CCC(F)(F)CC3)nc2)c1] |
| 541 | 546 | 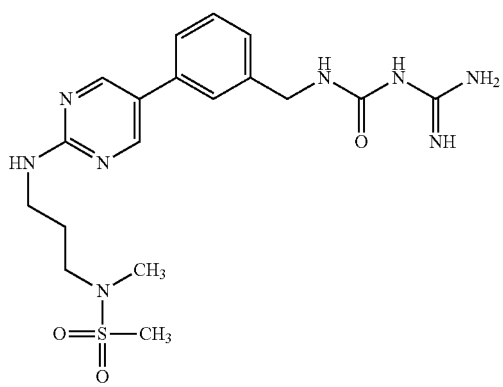 [SMILES: CN(CCCNc1ncc(-c2cccc(CNC(=O)NC(=N)N)c2)cn1)S(C)(=O)=O] |
| 542 | 546 | 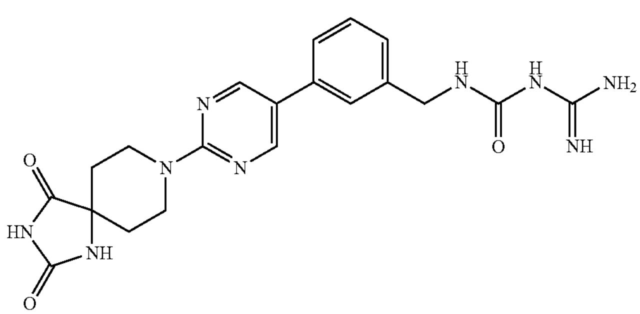 [SMILES: N=C(N)NC(=O)NCc1cccc(-c2cnc(N3CCC4(CC3)NC(=O)NC4=O)nc2)c1] |

TABLE 118

| Ex | Syn | Structure |
|---|---|---|
| 543 | 546 | 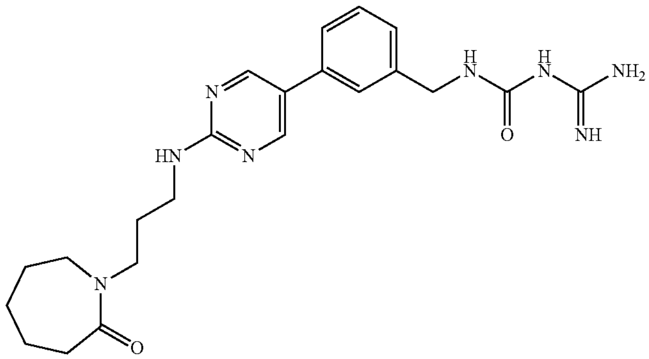 [SMILES: N=C(N)NC(=O)NCc1cccc(-c2cnc(NCCCN3CCCCCC3=O)nc2)c1] |
| 544 | 546 | 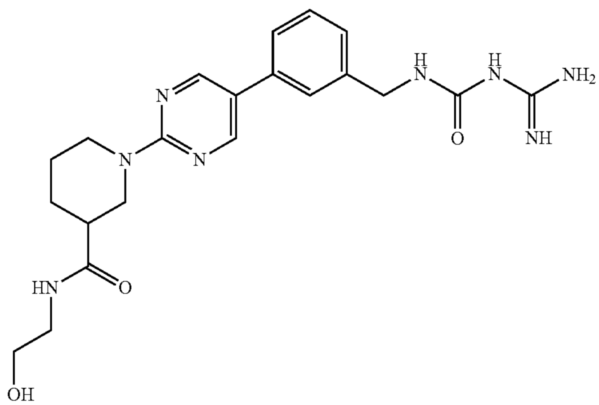 [SMILES: N=C(N)NC(=O)NCc1cccc(-c2cnc(N3CCCC(C(=O)NCCO)C3)nc2)c1] |
| 545 | 546 | 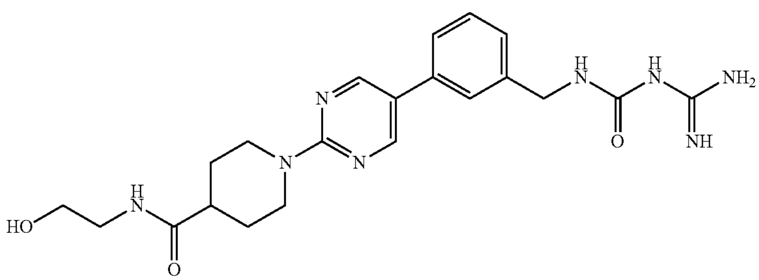 [SMILES: N=C(N)NC(=O)NCc1cccc(-c2cnc(N3CCC(C(=O)NCCO)CC3)nc2)c1] |
| 546 | 546 | 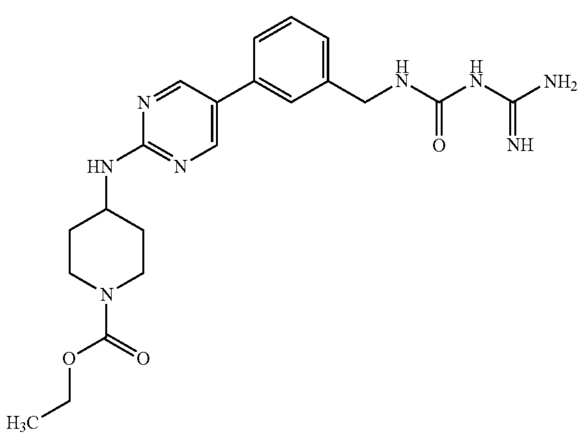 [SMILES: CCOC(=O)N1CCC(Nc2ncc(-c3cccc(CNC(=O)NC(=N)N)c3)cn2)CC1] |

TABLE 118-continued
| Ex | Syn | Structure |
|----|-----|-----------|
| 547 | 546 | 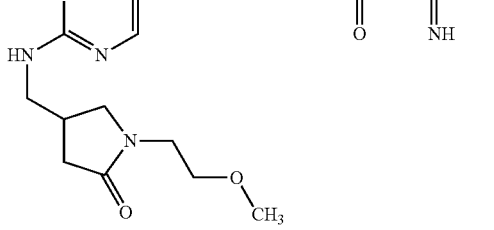 |
| 548 | 546 | 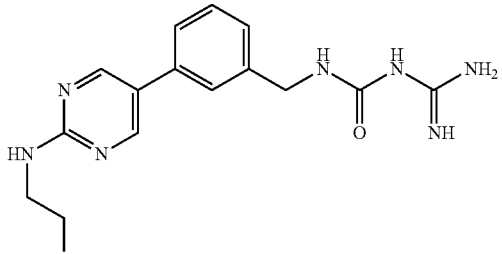 |
| 549 | 546 | 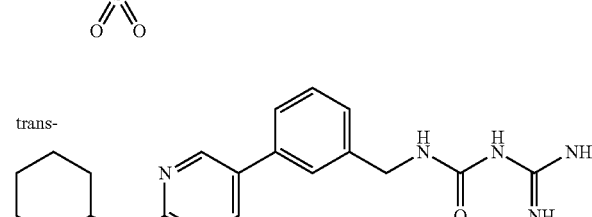 |
| 550 | 546 | 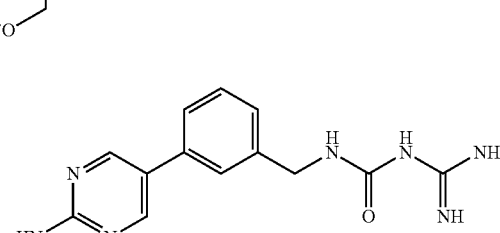 |

TABLE 118-continued

| Ex | Syn | Structure |
|---|---|---|
| 551 | 112 | (methyl 4-((1-(2-fluoro-3-(((guanidinocarbonyl)oxy)methyl)phenyl)azetidin-3-yl)oxy)piperidine-1-carboxylate) L-TA |
| 552 | 112 | (5-((1-(2-fluoro-3-(((guanidinocarbonyl)oxy)methyl)phenyl)azetidin-3-yl)oxy)-2-methylpyridine) L-TA |

TABLE 119

| Ex | Syn | Structure |
|---|---|---|
| 553 | 112 | (5-((1-(2-fluoro-3-(((guanidinocarbonyl)oxy)methyl)phenyl)azetidin-3-yl)oxy)-2-(methoxymethyl)pyridine) L-TA |
| 554 | 112 | (4-(6-(methoxymethyl)pyridin-3-yl)piperazine derivative) L-TA |
| 555 | 112 | (2,6-dimethylpyridin-4-yl methyl ether azetidine derivative) L-TA |

TABLE 119-continued
| Ex | Syn | Structure |
|---|---|---|
| 556 | 112 | 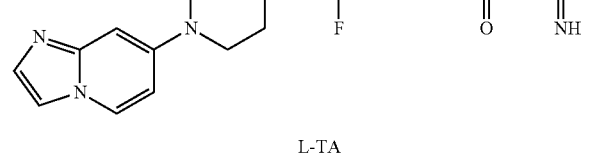<br>L-TA |
| 557 | 112 | 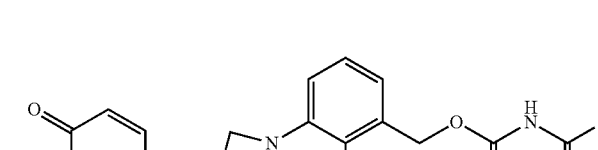<br>L-TA |
| 558 | 112 | 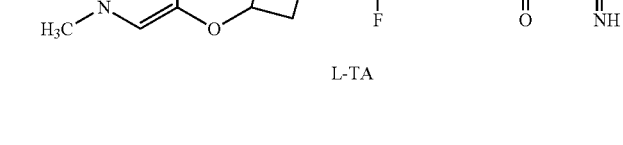<br>L-TA |
| 559 | 567 | 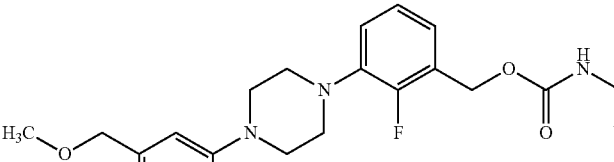<br>L-TA |
| 560 | 112 | <br>L-TA |

TABLE 119-continued

| Ex | Syn | Structure |
|---|---|---|
| 561 | 112 | (structure) L-TA |
| 562 | 112 | (structure) L-TA |
| 563 | 112 | (structure) L-TA |
| 564 | 112 | (structure) L-TA |
| 565 | 112 | (structure) L-TA |

TABLE 119-continued

| Ex | Syn | Structure |
|---|---|---|
| 566 | 112 | 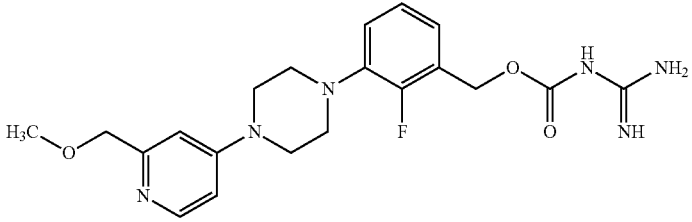<br>L-TA |
| 567 | 567 | 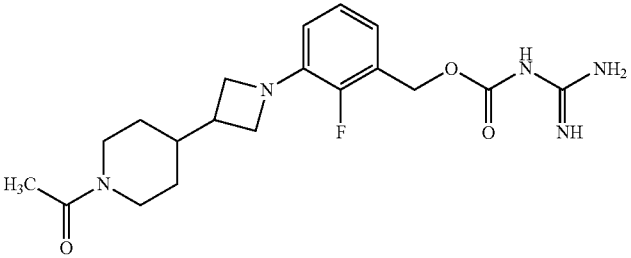<br>L-TA |

TABLE 120

| Ex | Data |
|---|---|
| 1 | ESI+: 384 |
| 2 | ESI+: 401 |
| 3 | ESI+: 388 |
| 4 | ESI+: 417 |
| 5 | ESI+: 418 |
| 6 | ESI+: 426 |
| 7 | ESI+: 430 |
| 8 | ESI+: 443 |
| 9 | ESI+: 431 |
| 10 | ESI+: 487<br>NMR-DMSO-$d_6$: 1.37-1.50 (2H, m), 1.83-1.94 (2H, m), 3.21-3.50 (14H, m), 4.06-4.18 (2H, m), 5.29 (2H, s), 7.08-7.22 (3H, m), 8.49 (2H, s) |
| 11 | ESI+: 445<br>NMR-DMSO-$d_6$: 1.06-1.34 (2H, m), 1.71-1.85 (2H, m), 2.00 (3H, s), 2.01-2.14 (1H, m), 2.50-2.60 (1H, m), 3.00-3.11 (1H, m), 3.80-3.90 (1H, m), 4.25 (2H, d, J = 6.4 Hz), 4.36-4.46 (1H, m), 5.37 (2H, s), 7.39 (1H, t, J = 7.6 Hz), 7.55-7.63 (1H, m), 7.64-7.72 (1H, m), 8.78-8.83 (2H, m) |
| 12 | ESI+: 475 |
| 13 | ESI+: 390 |
| 14 | ESI+: 390 |
| 15 | ESI+: 440 |
| 16 | ESI+: 430 |
| 17 | ESI+: 430 |
| 18 | ESI+: 430 |
| 19 | ESI+: 401 |
| 20 | ESI+: 401 |
| 21 | ESI+: 401 |
| 22 | ESI+: 507 |
| 23 | ESI+: 459<br>NMR-DMSO-$d_6$: 0.99 (3H, t, J = 7.4 Hz), 1.03-1.32 (2H, m), 1.71-1.87 (2H, m), 2.00-2.13 (1H, m), 2.32 (2H, q, J = 7.4 Hz), 2.50-2.62 (1H, m), 2.96-3.08 (1H, m), 3.84-3.95 (1H, m), 4.24 (2H, d, J = 6.25 Hz), 4.38-4.48 (1H, m), 5.37 (2H, s), 7.39 (1H, t, J = 7.7 Hz), 7.55-7.62 (1H, m), 7.64-7.71 (1H, m), 8.77-8.83 (2H, m) |
| 24 | ESI+: 473 |

TABLE 121

| Ex | Data |
|---|---|
| 25 | ESI+: 503 |
| 26 | ESI+: 489 |
| 27 | ESI+: 489 |
| 28 | ESI+: 508 |
| 29 | ESI+: 508 |
| 30 | ESI+: 508 |
| 31 | ESI+: 474 |
| 32 | ESI+: 461 |
| 33 | ESI+: 507 |
| 34 | ESI+: 481 |
| 35 | ESI+: 495 |
| 36 | ESI+: 474 |
| 37 | ESI+: 502 |
| 38 | ESI+: 486 |
| 39 | ESI+: 488 |
| 40 | ESI+: 488 |
| 41 | ESI+: 362 |
| 42 | ESI+: 362 |
| 43 | ESI+: 354 |
| 44 | ESI+: 441 |
| 45 | ESI+: 369 |
| 46 | ESI+: 416<br>NMR-DMSO-$d_6$: 2.06 (3H, s), 3.54-3.56 (4H, m), 3.77-3.86 (4H, m), 5.35 (2H, s), 7.33-7.37 (1H, m), 7.49-7.54 (1H, m), 7.60-7.64 (1H, m), 8.61 (2H, s) |
| 47 | ESI+: 404 |
| 48 | ESI+: 416 |
| 49 | ESI+: 412 |
| 50 | ESI+: 355 |
| 51 | ESI+: 355<br>NMR-DMSO-$d_6$: 3.36-3.38 (4H, m), 3.59-3.62 (4H, m), 5.20 (2H, s), 6.91 (1H, d, J = 7.6 Hz), 7.06-7.08 (1H, m), 7.13 (1H, s), 7.28-7.32 (1H, m), 7.87 (1H, dd, J = 9.0, 5.4 Hz), 8.15-8.18 (1H, m), 8.22 (1H, d, J = 5.3 Hz), 8.53 (1H, d, J = 2.7 Hz) |

TABLE 122

| Ex | Data |
|---|---|
| 52 | ESI+: 372<br>NMR-DMSO-$d_6$: 1.88-2.01 (4H, m), 2.83-2.89 (2H, m), 3.04-3.12 (1H, m), 3.49-3.52 (2H, m), 5.28 (2H, s), 7.08-7.12 (1H, m), 7.16-7.18 (2H, m), 8.08-8.09 (2H, m), 8.87-8.88 (2H, m) |
| 53 | ESI+: 373<br>NMR-DMSO-$d_6$: 3.17-3.19 (4H, m), 3.85-3.88 (4H, m), 5.29 (2H, s), 7.11-7.20 (3H, m), 7.27-7.28 (2H, m), 8.27-8.30 (2H, m) |
| 54 | ESI+: 459 |
| 55 | ESI+: 416 |
| 56 | ESI+: 430 |
| 57 | ESI+: 402 |
| 58 | ESI+: 372 |
| 59 | ESI+: 449 |
| 60 | ESI+: 391, 393 |
| 61 | ESI+: 397 |
| 62 | ESI+: 421 |
| 63 | ESI+: 375<br>NMR-DMSO-$d_6$: 3.27 (3H, s), 3.89-3.95 (2H, m), 4.27-4.39 (3H, m), 5.35 (2H, s), 7.31-7.38 (1H, m), 7.48-7.55 (1H, m), 7.57-7.64 (1H, m), 8.53-8.58 (2H, m) |
| 64 | ESI+: 403<br>NMR-DMSO-$d_6$: 1.17 (3H, s), 1.41-1.60 (4H, m), 3.41-3.54 (2H, m), 4.20-4.29 (2H, m), 5.35 (2H, s), 7.31-7.37 (1H, m), 7.46-7.54 (1H, m), 7.57-7.64 (1H, m), 8.53-8.58 (2H, m) |
| 65 | ESI+: 389 |
| 66 | ESI+: 403 |
| 67 | ESI+: 403 |
| 68 | ESI+: 445 |
| 69 | ESI+: 493 |
| 70 | ESI+: 494 |
| 71 | ESI+: 473 |
| 72 | ESI+: 499 |
| 73 | ESI+: 487 |

TABLE 123

| Ex | Data |
|---|---|
| 74 | ESI+: 471<br>NMR-DMSO-$d_6$: 0.61-0.78 (4H, m), 1.00-1.35 (2H, m), 1.66-1.91 (2H, m), 1.92-2.02 (1H, m), 2.02-2.17 (1H, m), 2.53-2.69 (1H, m), 3.00-3.21 (1H, m), 4.15-4.48 (4H, m), 5.37 (2H, s), 7.33-7.43 (1H, m), 7.52-7.63 (1H, m), 7.63-7.72 (1H, m), 8.74-8.84 (2H, m) |
| 75 | ESI+: 483 |
| 76 | ESI+: 490 |
| 77 | ESI+: 464 |
| 78 | ESI+: 478 |
| 79 | ESI+: 417 |
| 80 | ESI+: 427 |
| 81 | ESI+: 375<br>NMR-DMSO-$d_6$: 3.67-3.71 (4H, m), 3.74-3.78 (4H, m), 5.35 (2H, s), 7.34 (1H, dd, J = 7.7, 7.7 Hz), 7.49-7.53 (1H, m), 7.59-7.63 (1H, m), 8.59-8.60 (2H, m) |
| 82 | ESI+: 375 |
| 83 | ESI+: 361 |
| 84 | ESI+: 509 |
| 85 | ESI+: 510 |
| 86 | ESI+: 362 |
| 87 | ESI+: 402 |
| 88 | ESI+: 403 |
| 89 | ESI+: 419 |
| 90 | ESI+: 402 |
| 91 | ESI+: 473 |
| 92 | ESI+: 428 |
| 93 | ESI+: 458 |
| 94 | ESI+: 396 |
| 95 | ESI+: 387 |
| 96 | ESI+: 374 |
| 97 | ESI+: 387 |
| 98 | ESI+: 387 |

TABLE 123-continued

| Ex | Data |
|---|---|
| 99 | ESI+: 465 |
| 100 | ESI+: 419 |
| 101 | ESI+: 457 |

TABLE 124

| Ex | Data |
|---|---|
| 102 | ESI+: 441 |
| 103 | ESI+: 432 |
| 104 | ESI+: 426 |
| 105 | ESI+: 444<br>NMR-DMSO-$d_6$: 1.09-1.18 (1H, m), 1.22-1.32 (1H, m), 1.78 (2H, t, J = 16 Hz), 2.00 (3H, s), 2.01-2.11 (1H, m), 2.52-2.59 (1H, m), 3.00-3.09 (1H, m), 3.85 (1H, d, J = 14 Hz), 4.09 (2H, s), 4.24 (2H, d, J = 6 Hz), 4.40-4.42 (3H, m), 7.31 (1H, t, J = 7 Hz), 7.41 (1H, t, J = 7 Hz), 7.52 (1H, t, J = 7 Hz), 8.78-8.79 (2H, m) |
| 106 | ESI+: 470<br>NMR-DMSO-$d_6$: 0.62-0.75 (4H, m), 1.08-1.34 (2H, m), 1.72-1.89 (2H, m), 1.93-2.01 (1H, m), 2.05-2.15 (1H, m), 2.55-2.66 (1H, m), 3.05-3.17 (1H, m), 4.09 (2H, s), 4.20-4.45 (6H, m), 7.31 (1H, t, J = 7 Hz), 7.41 (1H, t, J = 7 Hz), 7.52 (1H, t, J = 7 Hz), 8.78-8.79 (2H, m) |
| 107 | ESI+: 413 |
| 108 | ESI+: 415 |
| 109 | ESI+: 459 |
| 110 | ESI+: 487 |
| 111 | ESI+: 458 |
| 112 | FAB+: 428 |
| 113 | ESI+: 503<br>NMR-DMSO-$d_6$: 3.10-3.19 (8H, m), 3.25 (3H, s), 3.42-3.55 (4H, m), 3.73-3.80 (2H, m), 4.12-4.21 (3H, m), 4.35-4.43 (1H, m), 5.04 (2H, s), 6.98-7.15 (3H, m), 8.25 (2H, s) |
| 114 | ESI+: 459 |
| 115 | ESI+: 446 |
| 116 | ESI+: 443 |
| 117 | ESI+: 487 |
| 118 | ESI+: 461 |
| 119 | ESI+: 461 |
| 120 | ESI+: 458 |
| 121 | ESI+: 479 |
| 122 | ESI+: 473 |
| 123 | ESI+: 500 |
| 124 | ESI+: 441 |

TABLE 125

| Ex | Data |
|---|---|
| 125 | ESI+: 447 |
| 126 | ESI+: 404 |
| 127 | ESI+: 368 |
| 128 | ESI+: 382 |
| 129 | ESI+: 408 |
| 130 | ESI+: 338 |
| 131 | ESI+: 297 |
| 132 | ESI+: 474 |
| 133 | ESI+: 404 |
| 134 | ESI+: 366 |
| 135 | ESI+: 394 |
| 136 | ESI+: 334 |
| 137 | ESI+: 449 |
| 138 | ESI+: 436 |
| 139 | ESI+: 411 |
| 140 | ESI+: 431 |
| 141 | ESI+: 433 |
| 142 | ESI+: 450 |
| 143 | ESI+: 464 |
| 144 | ESI+: 450<br>NMR-DMSO-$d_6$: 1.11 (3H, t, J = 7 Hz), 1.31-1.51 (4H, m), 1.59-1.73 (2H, m), 1.77-1.88 (2H, m), 2.59-2.70 (1H, m), 2.88-3.04 (4H, m), 3.39 (2H, q, J = 7 Hz), 3.47-3.53 |

TABLE 125-continued

| Ex | Data |
|---|---|
|  | (1H, m), 3.55-3.70 (4H, m), 4.21 (2H, s), 5.05 (2H, s), 6.97-7.05 (2H, m), 7.05-7.13 (1H, m) |
| 145 | ESI+: 464 |
| 146 | ESI+: 297 |
| 147 | ESI+: 341 |
| 148 | ESI+: 422 |
| 149 | ESI+: 352 |
| 150 | ESI+: 414 |
| 151 | ESI+: 400 |
| 152 | ESI+: 436 |
| 153 | ESI+: 436 |
| 154 | ESI+: 489 |

TABLE 126

| Ex | Data |
|---|---|
| 155 | ESI+: 487 |
| 156 | ESI+: 374 |
| 157 | ESI+: 388 |
| 158 | ESI+: 400 |
| 159 | ESI+: 402 |
| 160 | ESI+: 402 |
| 161 | ESI+: 442 |
| 162 | ESI+: 421 |
| 163 | ESI+: 449 |
| 164 | ESI+: 403 |
| 165 | ESI+: 431 |
| 166 | ESI+: 443 |
| 167 | ESI+: 529 |
| 168 | ESI+: 555 |
| 169 | ESI+: 445 |
| 170 | ESI+: 458 |
| 171 | ESI+: 466 |
| 172 | ESI+: 493 |
| 173 | ESI+: 371 |
| 174 | ESI+: 362 |
| 175 | ESI+: 358 |
| 176 | ESI+: 371 |
| 177 | ESI+: 385 |
| 178 | ESI+: 359 |
| 179 | ESI+: 341 |
| 180 | ESI+: 431 |
| 181 | ESI+: 405 |
| 182 | ESI+: 458 |
| 183 | ESI+: 458<br>NMR-DMSO-$d_6$: 1.76-1.92 (4H, m), 2.66-2.78 (2H, m), 2.87-2.98 (1H, m), 3.24 (3H, s), 3.50-3.60 (2H, m), 3.72-3.80 (2H, m), 4.10-4.18 (2H, m), 4.24 (1H, s), 4.25-4.31(1H, m), 5.10 (2H, s), 7.13-7.21 (1H, m), 7.25-7.32 (1H, m), 7.32-7.40 (1H, m), 8.22 (2H, s) |
| 184 | ESI+: 458 |

TABLE 127

| Ex | Data |
|---|---|
| 185 | ESI+: 458 |
| 186 | ESI+: 374 |
| 187 | ESI+: 374 |
| 188 | ESI+: 474 |
| 189 | ESI+: 474 |
| 190 | ESI+: 474 |
| 191 | ESI+: 380 |
| 192 | ESI+: 473 |
| 193 | ESI+: 473 |
| 194 | ESI+: 420 |
| 195 | ESI+: 483 |
| 196 | ESI+: 483 |
| 197 | ESI+: 364 |
| 198 | ESI+: 320 |
| 199 | ESI+: 390 |
| 200 | ESI+: 431 |

TABLE 127-continued

| Ex | Data |
|---|---|
| 201 | ESI+: 363 |
| 202 | ESI+: 461 |
| 203 | ESI+: 460 |
| 204 | ESI+: 325 |
| 205 | ESI+: 408 |
| 206 | ESI+: 406 |
| 207 | ESI+: 490 |
| 208 | ESI+: 422 |
| 209 | ESI+: 420 |
| 210 | ESI+: 383 |
| 211 | ESI+: 403 |
| 212 | ESI+: 453 |
| 213 | ESI+: 467 |
| 214 | ESI+: 433 |
| 215 | ESI+: 447 |
| 216 | ESI+: 448 |
| 217 | ESI+: 450 |

TABLE 128

| Ex | Data |
|---|---|
| 218 | ESI+: 450 |
| 219 | ESI+: 409 |
| 220 | ESI+: 436 |
| 221 | ESI+: 409 |
| 222 | ESI+: 422 |
| 223 | ESI+: 381 |
| 224 | ESI+: 407 |
| 225 | ESI+: 408 |
| 226 | ESI+: 458 |
| 227 | ESI+: 478 |
| 228 | ESI+: 422 |
| 229 | ESI+: 462 |
| 230 | ESI+: 388 |
| 231 | ESI+: 388 |
| 232 | ESI+: 360 |
| 233 | ESI+: 374 |
| 234 | ESI+: 374 |
| 235 | ESI+: 402 |
| 236 | ESI+: 416 |
| 237 | ESI+: 374<br>NMR-DMSO-$d_6$: 2.39 (3H, s), 3.84-3.92 (2H, m), 4.21 (1H, s), 4.40-4.48 (2H, m), 5.03 (2H, s), 5.12-5.21 (1H, m), 6.56-6.64 (1H, m), 6.75-6.82 (1H, m), 6.98-7.04 (1H, m), 7.13-7.22 (2H, m), 8.02-8.08 (1H, m) |
| 238 | ESI+: 388 |
| 239 | ESI+: 445 |
| 240 | ESI+: 514 |
| 241 | ESI+: 460<br>NMR-DMSO-$d_6$: 2.63 (2H, t, J = 6.7 Hz), 3.24 (3H, s), 3.57-3.60 (6H, m), 3.76-3.85 (4H, m), 5.14 (2H, s), 7.29 (1H, t, J = 7.6 Hz), 7.41-7.45 (1H, m), 7.50-7.55 (1H, m), 8.59-8.60 (2H, m) |
| 242 | ESI+: 460 |
| 243 | ESI+: 390 |

TABLE 129

| Ex | Data |
|---|---|
| 244 | ESI+: 374<br>NMR-DMSO-$d_6$: 3.67-3.70 (4H, m), 3.74-3.78 (4H, m), 4.40 (2H, d, J = 5.7 Hz), 7.26 (1H, t, J = 7.6 Hz), 7.31-7.35 (1H, m), 7.44-7.48 (1H, m), 7.58-7.59 (2H, m) |
| 245 | ESI+: 382 |
| 246 | ESI+: 362 |
| 247 | ESI+: 375 |
| 248 | ESI+: 402 |
| 249 | ESI+: 393 |
| 250 | ESI+: 458 |
| 251 | ESI+: 389 |
| 252 | ESI+: 405 |

TABLE 129-continued

| Ex | Data |
| --- | --- |
| 253 | ESI+: 418 |
| 254 | ESI+: 492 |
| 255 | ESI+: 459 |
| 256 | ESI+: 464 |
| 257 | ESI+: 459 |
| 258 | ESI+: 423 |
| 259 | ESI+: 423 |
| 260 | ESI+: 486 |
| 261 | ESI+: 486 |
| 262 | ESI+: 458 |
| 263 | ESI+: 488 |
| 264 | ESI+: 487 |
| 265 | ESI+: 487 |
| 266 | ESI+: 474 |
| 267 | ESI+: 496 |
| 268 | ESI+: 429 |
| 269 | ESI+: 455 |
| 270 | ESI+: 410 |
| 271 | ESI+: 412 |
| 272 | ESI+: 422 |
| 273 | ESI+: 422 |
| 274 | ESI+: 436 |
| 275 | ESI+: 394 |

TABLE 130

| Ex | Data |
| --- | --- |
| 276 | ESI+: 431 |
| 277 | ESI+: 431 |
| 278 | ESI+: 450 |
| 279 | ESI+: 476 |
| 280 | ESI+: 410 |
| 281 | ESI+: 436 |
| 282 | ESI+: 461 |
| 283 | ESI+: 422 |
| 284 | ESI+: 396 |
| 285 | ESI+: 422 |
| 286 | ESI+: 382 |
| 287 | ESI+: 473 |
| 288 | ESI+: 381 |
| 289 | ESI+: 408 |
| 290 | ESI+: 428 |
| 291 | ESI+: 394 |
| 292 | ESI+: 408 |
| 293 | ESI+: 373<br>NMR-DMSO-$d_6$: 3.15-3.17 (4H, m), 3.35-3.37 (4H, m), 5.07 (2H, s), 7.01-7.14 (3H, m), 7.24 (1H, dd, J = 4.6, 8.4 Hz), 7.37-7.40 (1H, m), 8.03 (1H, dd, J = 1.3, 4.6 Hz), 8.36 (1H, d, J = 2.8 Hz) |
| 294 | ESI+: 373 |
| 295 | ESI+: 387<br>NMR-DMSO-$d_6$: 2.38 (3H, s), 3.09-3.14 (4H, m), 3.52-3.57 (4H, m), 5.01 (2H, s), 6.80-6.85 (1H, m), 6.86-6.88 (1H, m), 7.00-7.05 (2H, m), 7.08-7.13 (1H, m), 8.10 (1H, d, J = 6.1 Hz) |
| 296 | ESI+: 387 |
| 297 | ESI+: 527 |
| 298 | ESI+: 435 |
| 299 | ESI+: 387 |
| 300 | ESI+: 387<br>NMR-DMSO-$d_6$: 2.37 (3H, s), 3.14-3.17 (4H, m), 3.28-3.30 (4H, m), 5.06 (2H, s), 7.01-7.14 (4H, m), 7.31 (1H, dd, J = 3.0, 8.5 Hz), 8.21 (1H, d, J = 2.9 Hz) |
| 301 | ESI+: 379 |
| 302 | ESI+: 387 |

TABLE 131

| Ex | Data |
| --- | --- |
| 303 | ESI+: 430 |
| 304 | ESI+: 387 |

TABLE 131-continued

| Ex | Data |
| --- | --- |
| 305 | ESI+: 374 |
| 306 | ESI+: 401 |
| 307 | ESI+: 398 |
| 308 | ESI+: 400 |
| 309 | ESI+: 370 |
| 310 | ESI+: 384 |
| 311 | ESI+: 372 |
| 312 | ESI+: 386 |
| 313 | ESI+: 388 |
| 314 | ESI+: 374 |
| 315 | ESI+: 473 |
| 316 | ESI+: 459<br>NMR-DMSO-$d_6$: 3.20-3.29 (8H, m), 3.30-3.39 (3H, m), 3.88-3.98 (2H, m), 4.28-4.37 (3H, m), 5.29 (2H, s), 7.09-7.22 (3H, m), 8.48 (2H, s) |
| 317 | ESI+: 457 |
| 318 | ESI+: 509 |
| 319 | ESI+: 357<br>NMR-DMSO-$d_6$: 3.67-3.70 (4H, m), 3.74-3.77 (4H, m), 5.09 (2H, s), 7.33 (1H, d, J = 7.6 Hz), 7.44 (1H, dd, J = 7.6, 7.6 Hz), 7.58 (1H, d, J = 7.6 Hz), 7.62 (1H, s), 8.71 (2H, s) |
| 320 | ESI+: 355 |
| 321 | ESI+: 370 |
| 322 | ESI+: 356<br>NMR-DMSO-$d_6$: 3.64-3.71 (4H, m), 3.72-3.78 (4H, m), 4.02 (1H, s), 4.27-4.38 (2H, m), 7.21-7.29 (1H, m), 7.35-7.43 (1H, m), 7.46-7.57 (2H, m), 8.70 (2H, s) |
| 323 | ESI+: 354 |
| 324 | FAB+: 446 |
| 325 | ESI+: 500 |
| 326 | FAB+: 529 |
| 327 | ESI+: 417 |
| 328 | ESI+: 417 |
| 329 | ESI+: 489 |

TABLE 132

| Ex | Data |
| --- | --- |
| 330 | ESI+: 412 |
| 331 | ESI+: 444 |
| 332 | ESI+: 398 |
| 333 | ESI+: 443 |
| 334 | ESI+: 447 |
| 335 | ESI+: 522<br>NMR-DMSO-$d_6$: 2.51-2.59 (2H, m), 2.77-2.86 (2H, m), 3.42-3.60 (8H, m), 7.30-7.40 (3H, m), 7.50-7.60 (3H, m), 7.61-7.68 (1H, m), 8.65-8.70 (2H, m) |
| 336 | ESI+: 489 |
| 337 | ESI+: 490 |
| 338 | ESI+: 431<br>NMR-DMSO-$d_6$: 1.09-1.20 (2H, m), 1.75-1.78 (2H, m), 1.93-2.04 (1H, m), 2.20 (2H, d, J = 6.9 Hz), 2.92-2.99 (2H, m), 4.67-4.72 (2H, m), 4.84 and 5.35 (2H, s and s), 7.28-7.35 (1H, m), 7.48-7.62 (2H, m), 8.55-8.56 (2H, m) |
| 339 | ESI+: 446 |
| 340 | ESI+: 422 |
| 341 | ESI+: 422 |
| 342 | ESI+: 489 |
| 343 | ESI+: 433 |
| 344 | ESI+: 459<br>NMR-DMSO-$d_6$: 1.00-1.11 (2H, m), 1.21-1.26 (2H, m), 1.51-1.59 (3H, m), 1.72-1.76 (2H, m), 2.21 (2H, t, J = 7.3 Hz), 2.87-2.94 (2H, m), 4.68-4.73 (2H, m), 5.11 (2H, s), 7.27 (1H, dd, J = 7.6, 7.6 Hz), 7.38-7.42 (1H, m), 7.48-7.52 (1H, m), 8.53-8.54 (2H, m) |
| 345 | ESI+: 389 |
| 346 | ESI+: 385 |
| 347 | ESI+: 384 |
| 348 | ESI+: 340 |
| 349 | ESI+: 439 |
| 350 | ESI+: 389 |
| 351 | ESI+: 432 |
| 352 | FAB+: 439 |
| 353 | ESI+: 384 |

TABLE 133

| Ex | Data |
|---|---|
| 354 | ESI+: 359 |
| 355 | ESI+: 385 |
| 356 | ESI+: 399 |
| 357 | ESI+: 413 |
| 358 | ESI+: 433 |
| 359 | ESI+: 377 |
| 360 | ESI+: 377 |
| 361 | ESI+: 359 |
| 362 | ESI+: 373 |
| 363 | ESI+: 371 |
| 364 | ESI+: 333 |
| 365 | ESI+: 403 |
| | NMR-DMSO-$d_6$: 1.37-1.52 (2H, m), 1.85-1.97 (2H, m), 3.29 (3H, s), 3.40-3.52 (3H, m), 4.16-4.27 (3H, m), 5.11 (2H, s), 7.23-7.32 (1H, m), 7.36-7.43 (1H, m), 7.46-7.54 (1H, m), 8.52-8.57 (2H, m) |
| 366 | ESI+: 373 |
| 367 | ESI+: 391 |
| 368 | ESI+: 458 |
| 369 | ESI+: 391 |
| 370 | ESI+: 389 |
| 371 | ESI+: 375 |
| 372 | ESI+: 489 |
| 373 | ESI+: 355 |
| 374 | ESI+: 375 |
| 375 | ESI+: 528 |
| 376 | ESI+: 557 |
| 377 | APCI/ESI+: 459 |
| 378 | APCI/ESI+: 526 |
| 379 | APCI/ESI+: 526 |
| 380 | APCI/ESI+: 517 |
| 381 | ESI+: 579 |
| 382 | ESI+: 517 |
| 383 | ESI+: 517 |
| 384 | ESI+: 580 |

TABLE 134

| Ex | Data |
|---|---|
| 385 | ESI+: 459 |
| 386 | ESI+: 474 |
| 387 | ESI+: 461 |
| 388 | ESI+: 487 |
| 389 | ESI+: 431 |
| 390 | ESI+: 431 |
| 391 | ESI+: 472 |
| 392 | APCI/ESI+: 457 |
| 393 | APCI/ESI+: 471 |
| 394 | APCI/ESI+: 475 |
| 395 | APCI/ESI+: 550 |
| 396 | ESI+: 493 |
| 397 | ESI+: 523, 525 |
| 398 | ESI+: 426 |
| 399 | ESI+: 330 |
| 400 | ESI+: 342 |
| 401 | ESI+: 343 |
| 402 | ESI+: 344 |
| 403 | ESI+: 344 |
| 404 | ESI+: 356 |
| 405 | ESI+: 356 |
| 406 | ESI+: 356 |
| 407 | ESI+: 357 |
| 408 | ESI+: 357 |
| 409 | ESI+: 358 |
| 410 | ESI+: 369 |
| 411 | ESI+: 370 |
| 412 | ESI+: 370 |
| 413 | ESI+: 370 |
| 414 | ESI+: 370 |
| 415 | ESI+: 370 |
| 416 | ESI+: 370 |
| 417 | ESI+: 371 |

TABLE 135

| Ex | Data |
|---|---|
| 418 | ESI+: 371 |
| 419 | ESI+: 371 |
| 420 | ESI+: 371 |
| 421 | ESI+: 372 |
| 422 | ESI+: 372 |
| 423 | ESI+: 372 |
| 424 | ESI+: 374 |
| 425 | ESI+: 376 |
| 426 | ESI+: 383 |
| 427 | ESI+: 383 |
| 428 | ESI+: 383 |
| 429 | ESI+: 383 |
| 430 | ESI+: 383 |
| 431 | ESI+: 384 |
| 432 | ESI+: 384 |
| 433 | ESI+: 384 |
| 434 | ESI+: 384 |
| 435 | ESI+: 384 |
| 436 | ESI+: 384 |
| 437 | ESI+: 384 |
| 438 | ESI+: 384 |
| 439 | ESI+: 384 |
| 440 | ESI+: 385 |
| 441 | ESI+: 385 |
| 442 | ESI+: 386 |
| 443 | ESI+: 386 |
| 444 | ESI+: 386 |
| 445 | ESI+: 386 |
| 446 | ESI+: 386 |
| 447 | ESI+: 388 |
| 448 | ESI+: 392 |
| 449 | ESI+: 393 |
| 450 | ESI+: 397 |

TABLE 136

| Ex | Data |
|---|---|
| 451 | ESI+: 397 |
| 452 | ESI+: 397 |
| 453 | ESI+: 397 |
| 454 | ESI+: 397 |
| 455 | ESI+: 397 |
| 456 | ESI+: 398 |
| 457 | ESI+: 398 |
| 458 | ESI+: 398 |
| 459 | ESI+: 398 |
| 460 | ESI+: 398 |
| 461 | ESI+: 398 |
| 462 | ESI+: 398 |
| 463 | ESI+: 398 |
| 464 | ESI+: 398 |
| 465 | ESI+: 398 |
| 466 | ESI+: 399 |
| 467 | ESI+: 399 |
| 468 | ESI+: 399 |
| 469 | ESI+: 399 |
| 470 | ESI+: 399 |
| 471 | ESI+: 399 |
| 472 | ESI+: 406 |
| 473 | ESI+: 407 |
| 474 | ESI+: 411 |
| 475 | ESI+: 392 |
| 476 | ESI+: 406 |
| 477 | ESI+: 406 |
| 478 | ESI+: 419 |
| 479 | ESI+: 419 |
| 480 | ESI+: 419 |
| 481 | ESI+: 433 |
| 482 | ESI+: 447 |
| 483 | ESI+: 455 |

TABLE 137

| Ex | Data |
|---|---|
| 484 | ESI+: 406 |
| 485 | ESI+: 433 |
| 486 | ESI+: 447 |
| 487 | ESI+: 454 |
| 488 | ESI+: 461 |
| 489 | ESI+: 469 |
| 490 | ESI+: 475 |
| 491 | ESI+: 505 |
| 492 | ESI+: 505 |
| 493 | ESI+: 505 |
| 494 | ESI+: 420 |
| 495 | ESI+: 433 |
| 496 | ESI+: 466 |
| 497 | ESI+: 433 |
| 498 | ESI+: 377 |
| 499 | ESI+: 422 |
| 500 | ESI+: 416 |
| 501 | ESI+: 416 |
| 502 | ESI+: 417 |
| 503 | ESI+: 430 |
| 504 | ESI+: 427 |
| 505 | ESI+: 428 |
| 506 | ESI+: 444 |
| 507 | ESI+: 380 |
| 508 | ESI+: 397 |
| 509 | ESI+: 391 |
| 510 | ESI+: 392 |
| 511 | ESI+: 430 |
| 512 | ESI+: 430 |
| 513 | ESI+: 393 |
| 514 | ESI+: 482 |
| 515 | ESI+: 447 |
| 516 | ESI+: 417 |

TABLE 138

| Ex | Data |
|---|---|
| 517 | ESI+: 417 |
| 518 | ESI+: 417 |
| 519 | ESI+: 475 |
| 520 | ESI+: 480 |
| 521 | ESI+: 431 |
| 522 | ESI+: 475 |
| 523 | ESI+: 475 |
| 524 | ESI+: 475 |
| 525 | ESI+: 486 |
| 526 | ESI+: 449 |
| 527 | ESI+: 487 |
| 528 | ESI+: 460 |
| 529 | ESI+: 495 |
| 530 | ESI+: 411 |
| 531 | ESI+: 411 |
| 532 | ESI+: 413 |
| 533 | ESI+: 415 |
| 534 | ESI+: 418 |
| 535 | ESI+: 418 |
| 536 | ESI+: 421 |
| 537 | ESI+: 423 |
| 538 | ESI+: 426 |
| 539 | ESI+: 427 |
| 540 | ESI+: 433 |
| 541 | ESI+: 435 |
| 542 | ESI+: 438 |
| 543 | ESI+: 439 |
| 544 | ESI+: 441 |
| 545 | ESI+: 441 |
| 546 | ESI+: 441 |
| 547 | ESI+: 441 |
| 548 | ESI+: 447 |
| 549 | ESI+: 453 |
| 550 | ESI+: 461 |

TABLE 139

| Ex | Data |
|---|---|
| 551 | ESI+: 422<br>NMR-DMSO-$d_6$: 1.02 (3H, t, J = 7.4 Hz), 1.27-1.50 (2H, m), 1.77-1.93 (2H, m), 2.35 (2H, q, J = 7.4 Hz), 3.03 (1H, t, J = 9.9 Hz), 3.19 (1H, t, J = 9.9 Hz), 3.57-3.80 (4H, m), 3.91-4.04 (1H, m), 4.19-4.27 (3H, m), 4.54-4.63 (1H, m), 5.05 (2H, s), 6.57 (1H, t, J = 8.0 Hz), 6.79 (1H, t, J = 6.4 Hz), 7.03 (1H, t, J = 7.8 Hz). |
| 552 | ESI+: 374<br>NMR-DMSO-$d_6$: 2.40 (3H, s), 3.82-3.89 (2H, m), 4.21 (2H, s), 4.37-4.44 (2H, m), 5.03 (2H, s), 5.13-5.20 (1H, m), 6.55-6.61 (1H, m), 6.74-6.81 (1H, m), 7.01 (1H, t, J = 7.8 Hz), 7.17-7.27 (2H, m), 8.12 (1H, d, J = 2.7 Hz). |
| 553 | ESI+: 404<br>NMR-DMSO-$d_6$: 3.28 (3H, s), 3.84-3.91 (2H, m), 4.21 (2H, s), 4.38-4.45 (4H, m), 5.02 (2H, s), 5.18-5.24 (1H, m), 6.55-6.62 (1H, m), 6.75-6.80 (1H, m), 7.01 (1H, t, J = 7.8 Hz), 7.34-7.37 (2H, m), 8.19-8.22 (1H, m). |
| 554 | ESI+: 417<br>NMR-DMSO-$d_6$: 3.13-3.20 (4H, m), 3.31 (3H, s), 3.32-3.39 (4H, m), 4.21 (2H, s), 4.39 (2H, s), 5.07 (2H, s), 7.00-7.15 (3H, m), 7.26 (1H, d, J = 7.6 Hz), 7.37-7.42 (1H, m), 8.29 (1H, d, J = 2.8 Hz). |
| 555 | ESI+: 402<br>NMR-DMSO-$d_6$: 2.41 (6H, s), 3.72-3.78 (2H, m), 4.12-4.19 (2H, m), 4.20 (2H, s), 4.45 (2H, s), 4.46-4.51 (1H, m), 5.01 (2H, s), 6.50-6.56 (1H, m), 6.71-6.77 (1H, m), 6.95-7.02 (3H, m). |
| 556 | ESI+: 412<br>NMR-DMSO-$d_6$: 3.12-3.20 (4H, m), 3.37-3.45 (4H, m), 4.06 (1H, s), 5.03 (2H, s), 6.77 (1H, d, J = 2.2 Hz), 6.94-7.14 (4H, m), 7.42 (1H, d, J = 1.4 Hz), 7.69 (1H, d, J = 0.8 Hz), 8.37 (1H, d, J = 7.6 Hz). |
| 557 | ESI+: 390<br>NMR-DMSO-$d_6$: 3.39 (3H, s), 3.79-3.86 (2H, m), 4.20 (2H, s), 4.29-4.37 (2H, m), 4.87-4.94 (1H, m), 5.02 (2H, s), 6.35-6.40 (1H, m), 6.57 (1H, t, J = 8.0 Hz), 6.77 (1H, t, J = 6.4 Hz), 7.01 (1H, t, J = 7.8 Hz), 7.29-7.35 (2H, m). |
| 558 | ESI+: 417<br>NMR-DMSO-$d_6$: 3.13-3.19 (4H, m), 3.30 (3H, s), 3.33-3.40 (4H, m), 4.21 (2H, s), 4.41 (2H, s), 5.08 (2H, s), 7.01-7.15 (3H, m), 7.31 (1H, s), 7.99 (1H, d, J = 1.4 Hz), 8.29 (1H, d, J = 2.7 Hz). |

TABLE 140

| Ex | Data |
|---|---|
| 559 | ESI+: 392<br>NMR-DMSO-$d_6$: 0.81-1.09 (2H, m), 1.59-1.75 (3H, m), 1.98 (3H, s), 2.39-2.52 (2H, m), 2.93-3.03 (1H, m), 3.58-3.65 (2H, m), 3.77-3.85 (1H, m), 3.93-4.01 (2H, m), 4.21 (2H, s), 4.34-4.42 (1H, m), 5.01 (2H, s), 6.46-6.52 (1H, m), 6.69-6.74 (1H, m), 6.97 (1H, t, J = 7.8 Hz). |
| 560 | ESI+: 406<br>NMR-DMSO-$d_6$: 0.82-1.04 (5H, m), 1.59-1.78 (3H, m), 2.29 (2H, q, J = 7.4 Hz), 2.37-2.49 (2H, m), 2.89-2.99 (1H, m), 3.57-3.65 (2H, m), 3.79-3.89 (1H, m), 3.93-4.00 (2H, m), 4.18 (1H, s), 4.34-4.43 (1H, m), 4.98 (2H, s), 6.44-6.52 (1H, m), 6.67-6.74 (1H, m), 6.97 (1H, t, J = 7.8 Hz). |
| 561 | ESI: 418<br>NMR-DMSO-$d_6$: 0.63-0.75 (4H, m), 0.83-1.07 (2H, m), 1.56-1.80 (3H, m), 1.89-2.00 (1H, m), 2.38-2.59 (2H, m), 2.99-3.11 (1H, m), 3.57-3.65 (2H, m), 3.92-4.01 (2H, m), 4.18 (1H, s), 4.19-4.22 (2H, m), 4.98 (2H, s), 6.44-6.52 (1H, m), 6.67-6.73 (1H, m), 6.97 (1H, t, J = 7.7 Hz). |
| 562 | ESI+: 422<br>NMR-DMSO-$d_6$: 0.85-1.09 (2H, m), 1.62-1.76 (3H, m), 2.38-2.59 (2H, m), 2.87-2.97 (1H, m), 3.27 (3H, s), 3.58-3.65 (2H, m), 3.72-3.80 (1H, m), 3.93-4.11 (4H, m), 4.20 (2H, s), 4.30-4.38 (1H, m), 5.00 (2H, s), 6.45-6.52 (1H, m), 6.68-6.74 (1H, m), 6.97 (1H, t, J = 7.7 Hz). |
| 563 | ESI+: 436<br>NMR-DMSO-$d_6$: 0.83-1.05 (2H, m), 1.60-1.75 (3H, m), 2.37-2.58 (4H, m), 2.90-3.00 (1H, m), 3.22 (3H, s), 3.53 (2H, t, J =6.4 Hz), 3.58-3.65 (2H, m), 3.85-3.92 (1H, m), 3.93-4.01 (2H, m), 4.18 (1H, s), 4.34-4.42 (1H, m), 4.98 (2H, s), 6.45-6.50 (1H, m), 6.67-6.73 (1H, m), 6.97 (1H, t, J = 7.8 Hz). |

TABLE 140-continued

| Ex | Data |
|---|---|
| 564 | ESI+: 428<br>NMR-DMSO-$d_6$: 1.08-1.19 (2H, m), 1.53-1.64 (1H, m), 1.70-1.80 (2H, m), 2.41-2.51 (2H, m), 2.62-2.72 (2H, m), 2.84 (3H, s), 3.53-3.65 (4H, m), 3.94-4.01 (2H, m), 4.18 (1H, s), 4.98 (1H, s), 6.44-6.52 (1H, m), 6.67-6.73 (1H, m), 6.97 (1H, t, J = 7.8 Hz). |
| 565 | ESI+: 447<br>NMR-DMSO-$d_6$: 3.05-3.12 (4H, m), 3.28 (3H, s), 3.41-3.47 (4H, m), 3.59-3.63 (2H, m), 4.18 (1H, s), 4.28-4.33 (2H, m), 5.04 (2H, s), 6.19 (1H, d, J = 2.2 Hz), 6.59-6.63 (1H, m), 6.98-713 (3H, m), 7.81 (1H, d, J = 6.1 Hz). |

TABLE 141

| Ex | Data |
|---|---|
| 566 | ESI+: 417<br>NMR-DMSO-$d_6$: 3.10-3.15 (4H, m), 3.36 (3H, s), 3.49-3.55 (4H, m), 4.15 (2H, s), 4.39 (2H, s), 5.04 (2H, s), 6.82-6.86 (1H, m), 6.91 (1H, d, J = 2.4 Hz), 7.00-7.14 (3H, m), 8.15 (1H, d, J = 6.1 Hz). |
| 567 | ESI+: 392<br>NMR-DMSO-$d_6$: 0.81-1.09 (2H, m), 1.59-1.75 (3H, m), 1.98 (3H, s), 2.39-2.52 (2H, m), 2.93-3.03 (1H, m), 3.58-3.65 (2H, m), 3.77-3.85 (1H, m), 3.93-4.01 (2H, m), 4.21 (2H, s), 4.34-4.42 (1H, m), 5.01 (2H, s), 6.46-6.52 (1H, m), 6.69-6.74 (1H, m), 6.97 (1H, t, J = 7.8 Hz). |

The compounds of Preparation Examples shown in the tables below were prepared using the respective corresponding starting materials in the same manner as the methods of Preparation Examples above. The structures, the preparation methods, and the physicochemical data for the compounds of Preparation Examples are shown in the tables below.

TABLE 142

| Rf | Syn | Structure |
|---|---|---|
| 843 | R12 | 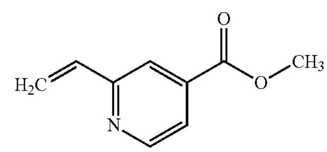 |
| 844 | R845 | 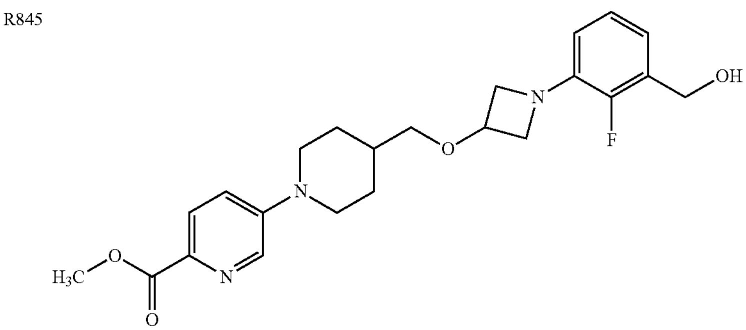 |
| 845 | R845 | 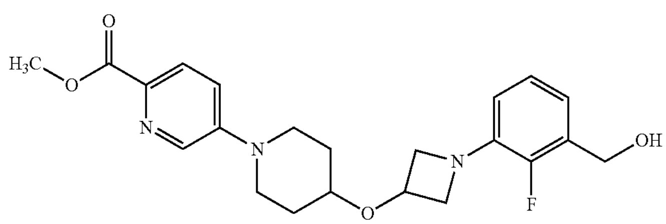 [SMILES: COC(=O)c1ccc(N2CCC(OC3CN(c4cccc(CO)c4F)C3)CC2)cn1] |
| 846 | R70 | 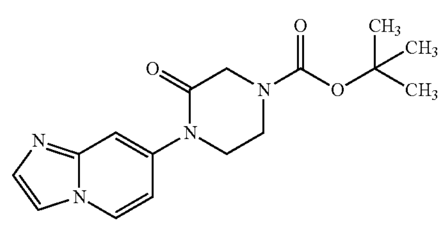 [SMILES: CC(C)(C)OC(=O)N1CCN(c2ccn3ccnc3c2)C(=O)C1] |

TABLE 142-continued

| Rf | Syn | Structure |
|---|---|---|
| 847 | R847 | 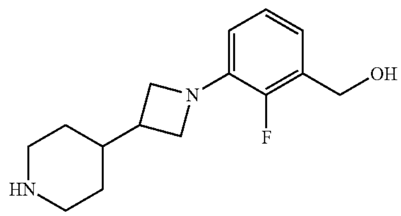 [SMILES: OCc1cccc(N2CC(C3CCNCC3)C2)c1F] |
| 848 | R806 | 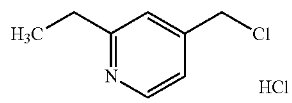 |
| 849 | R806 | 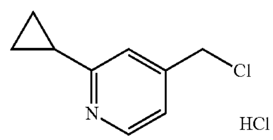 [SMILES: ClCc1ccnc(C2CC2)c1 ; Cl] |
| 850 | R806 | 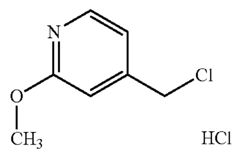 |
| 851 | R807 | 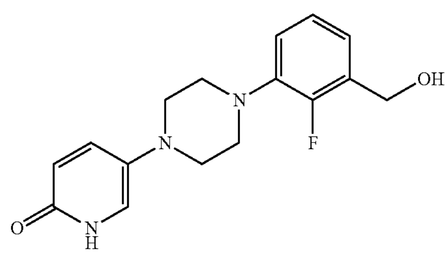 [SMILES: O=c1ccc(N2CCN(c3cccc(CO)c3F)CC2)c[nH]1] |
| 852 | R809 | 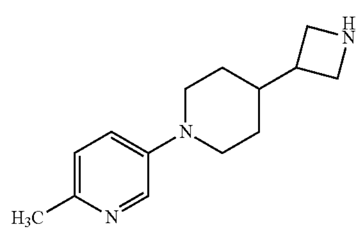 [SMILES: Cc1ccc(N2CCC(C3CNC3)CC2)cn1] |
| 853 | R853 | 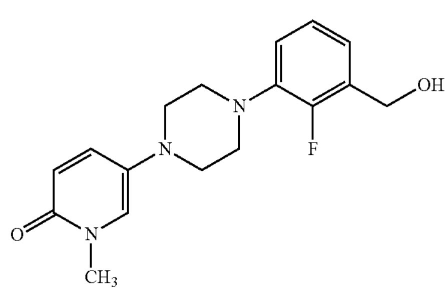 [SMILES: Cn1cc(N2CCN(c3cccc(CO)c3F)CC2)ccc1=O] |

TABLE 142-continued
| Rf | Syn | Structure |
|---|---|---|
| 854 | R853 | 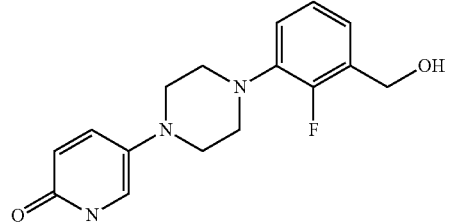 |
| 855 | R855 | 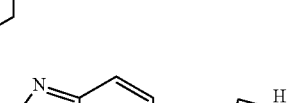 |
| 856 | R855 | 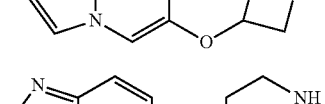 |
TABLE 143
| Rf | Syn | Structure |
|---|---|---|
| 857 | R857 | 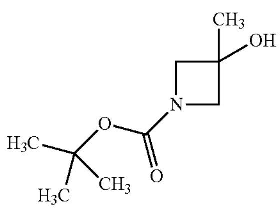 |
| 858 | R859 | 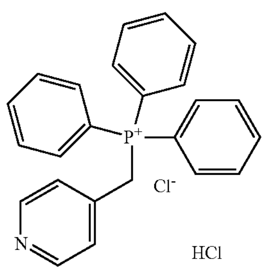 [SMILES: c1ccc([P+](Cc2ccncc2)(c2ccccc2)c2ccccc2)cc1 ; [Cl-] ; Cl] |
| 859 | R859 | 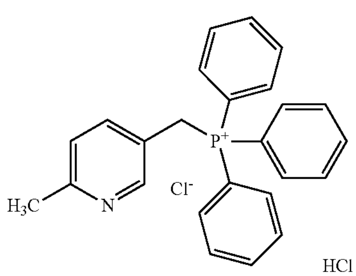 [SMILES: Cc1ccc(C[P+](c2ccccc2)(c2ccccc2)c2ccccc2)cn1 ; [Cl-] ; Cl] |
| 860 | R860 | 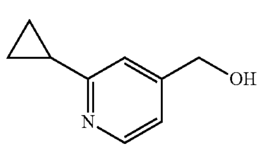 [SMILES: OCc1ccnc(C2CC2)c1] |

TABLE 143-continued
| Rf | Syn | Structure |
|---|---|---|
| 861 | R228 | 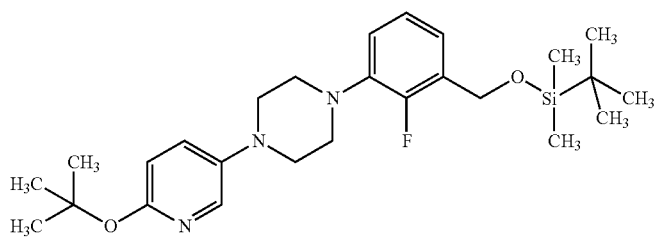 [SMILES: CC(C)(C)Oc1ccc(N2CCN(c3cccc(CO[Si](C)(C)C(C)(C)C)c3F)CC2)cn1] |
| 862 | R228 | 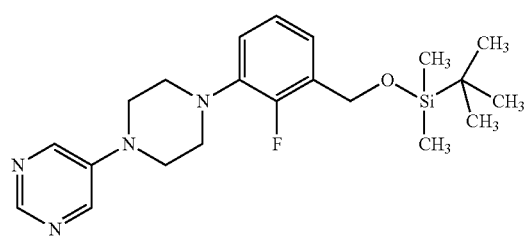 [SMILES: CC(C)(C)[Si](C)(C)OCc1cccc(N2CCN(c3cncnc3)CC2)c1F] |
| 863 | R228 | 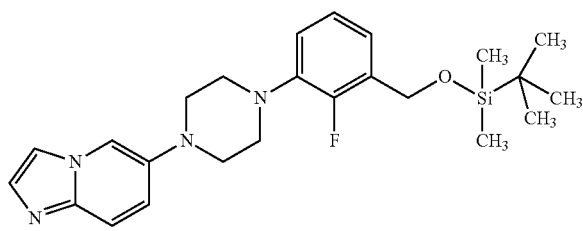 [SMILES: CC(C)(C)[Si](C)(C)OCc1cccc(N2CCN(c3ccc4nccn4c3)CC2)c1F] |
| 864 | R228 | 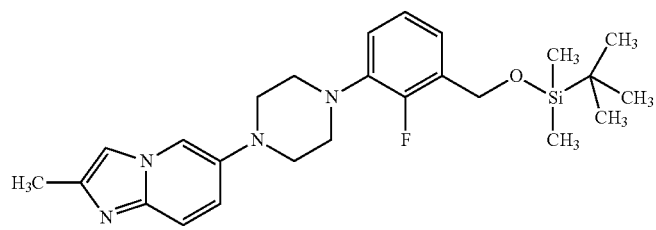 [SMILES: Cc1cn2cc(N3CCN(c4cccc(CO[Si](C)(C)C(C)(C)C)c4F)CC3)ccc2n1] |
| 865 | R228 | 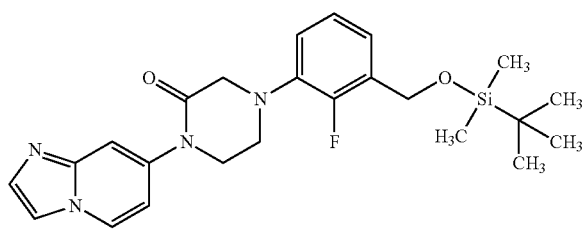 [SMILES: CC(C)(C)[Si](C)(C)OCc1cccc(N2CCN(c3ccn4ccnc4c3)C(=O)C2)c1F] |
| 866 | R228 | 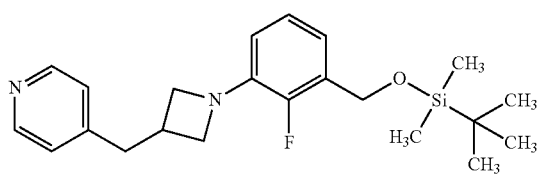 [SMILES: CC(C)(C)[Si](C)(C)OCc1cccc(N2CC(Cc3ccncc3)C2)c1F] |

TABLE 143-continued
| Rf | Syn | Structure |
|---|---|---|
| 867 | R228 | 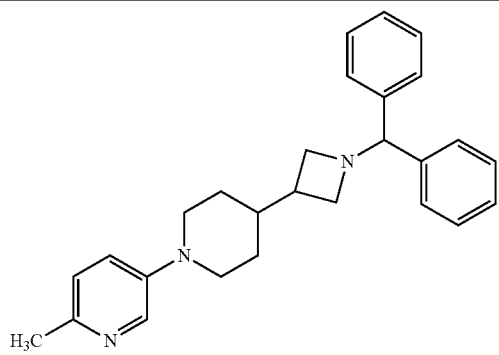 |
| 868 | R228 | 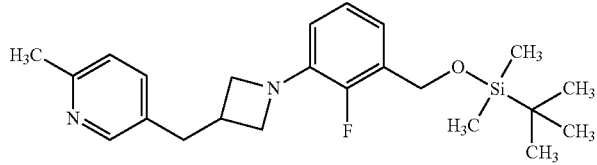 [SMILES: Cc1ccc(CC2CN(c3cccc(CO[Si](C)(C)C(C)(C)C)c3F)C2)cn1] |
TABLE 144
| Rf | Syn | Structure |
|---|---|---|
| 869 | R285 | 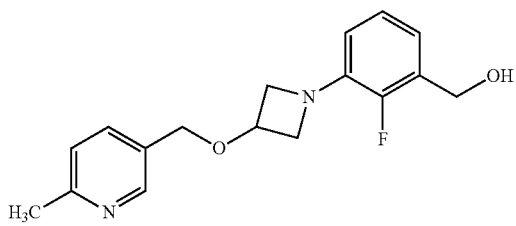 [SMILES: Cc1ccc(COC2CN(c3cccc(CO)c3F)C2)cn1] |
| 870 | R285 | 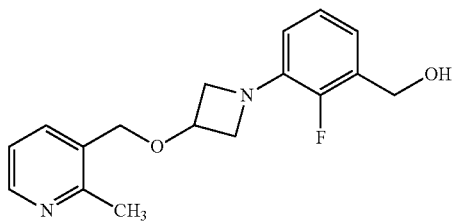 [SMILES: Cc1ncccc1COC1CN(c2cccc(CO)c2F)C1] |
| 871 | R285 | 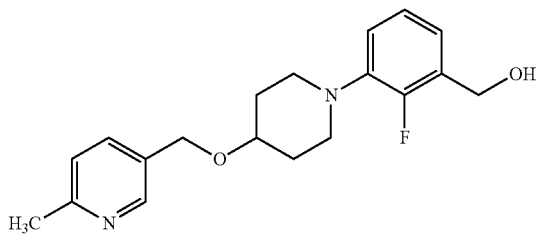 [SMILES: Cc1ccc(COC2CCN(c3cccc(CO)c3F)CC2)cn1] |

TABLE 144-continued

| Rf | Syn | Structure |
|---|---|---|
| 872 | R285 | 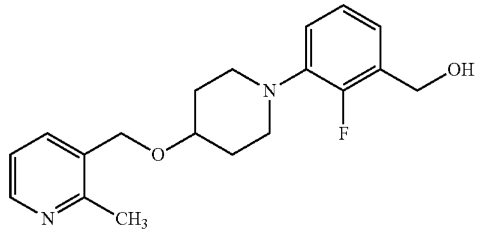 [SMILES: Cc1ncccc1COC1CCN(c2cccc(CO)c2F)CC1] |
| 873 | R285 | 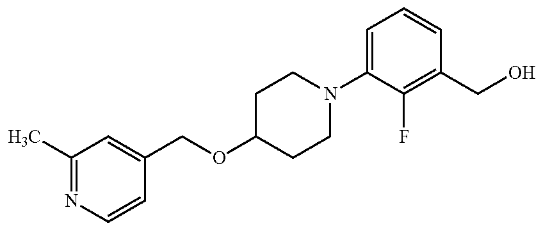 [SMILES: Cc1cc(COC2CCN(c3cccc(CO)c3F)CC2)ccn1] |
| 874 | R285 | 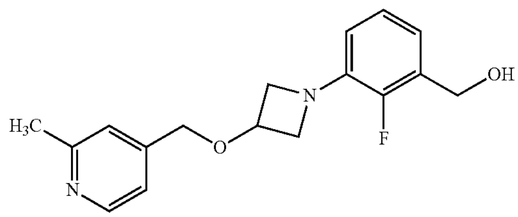 [SMILES: Cc1cc(COC2CN(c3cccc(CO)c3F)C2)ccn1] |
| 875 | R285 | 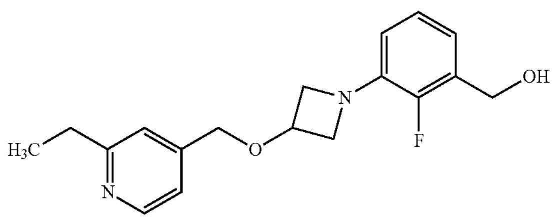 [SMILES: CCc1cc(COC2CN(c3cccc(CO)c3F)C2)ccn1] |
| 876 | R285 | 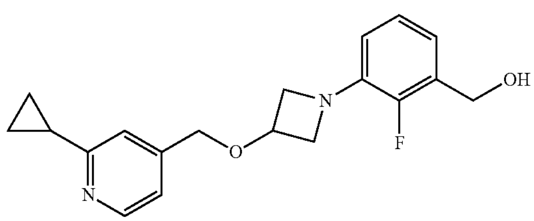 [SMILES: OCc1cccc(N2CC(OCc3ccnc(C4CC4)c3)C2)c1F] |
| 877 | R285 | 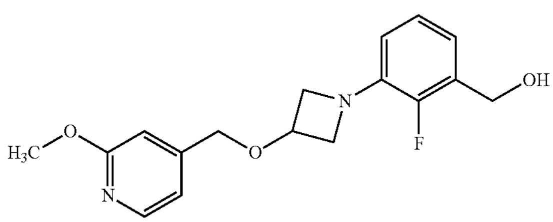 [SMILES: COc1cc(COC2CN(c3cccc(CO)c3F)C2)ccn1] |
| 878 | R285 | 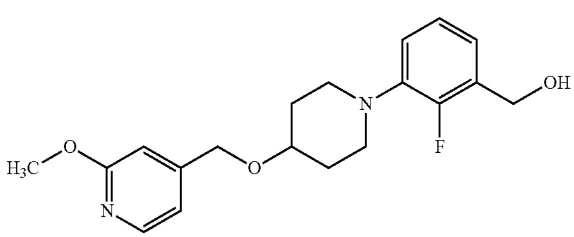 [SMILES: COc1cc(COC2CCN(c3cccc(CO)c3F)CC2)ccn1] |

TABLE 144-continued
| Rf | Syn | Structure |
|---|---|---|
| 879 | R285 | 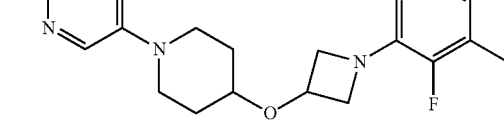 |
| 880 | R285 | 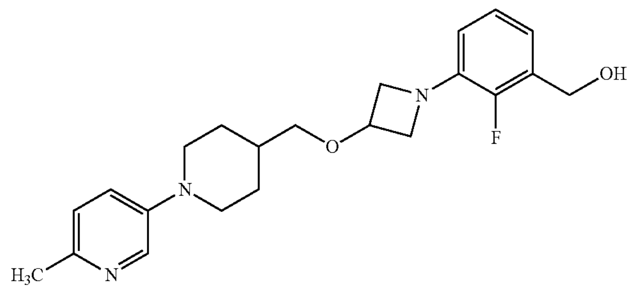 [SMILES: Cc1ccc(N2CCC(COC3CN(c4cccc(CO)c4F)C3)CC2)cn1] |
| 881 | R285 | 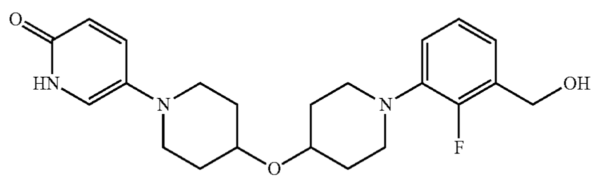 [SMILES: O=c1ccc(N2CCC(OC3CCN(c4cccc(CO)c4F)CC3)CC2)c[nH]1] |
| 882 | R285 | 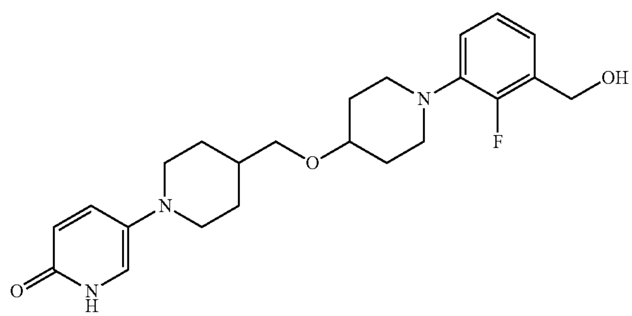 [SMILES: O=c1ccc(N2CCC(COC3CCN(c4cccc(CO)c4F)CC3)CC2)c[nH]1] |
TABLE 145
| Rf | Syn | Structure |
|---|---|---|
| 883 | R285 | 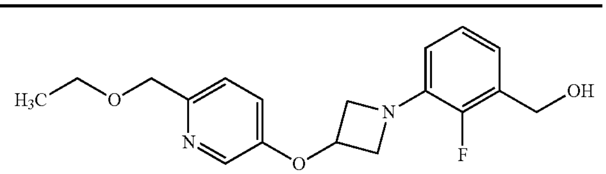 |
| 884 | R285 | 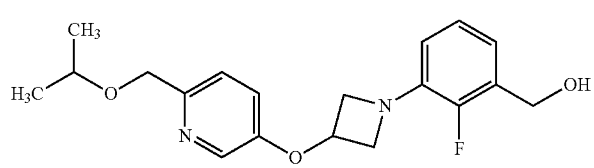 [SMILES: CC(C)OCc1ccc(OC2CN(c3cccc(CO)c3F)C2)cn1] |

TABLE 145-continued
| Rf | Syn | Structure |
|---|---|---|
| 885 | R285 | 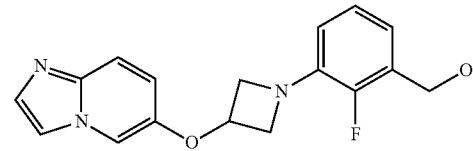 |
| 886 | R285 | 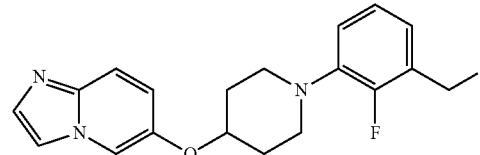 |
| 887 | R285 | 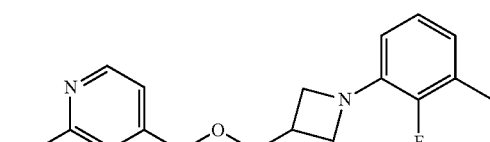 |
| 888 | R285 | 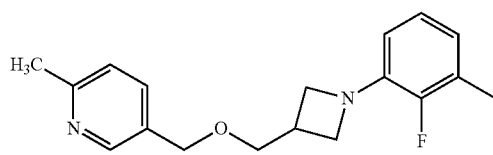 |
| 889 | R285 | 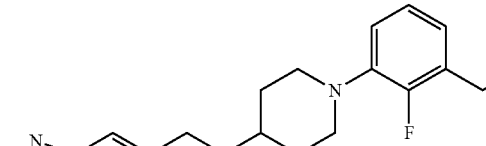 |
| 890 | R285 | 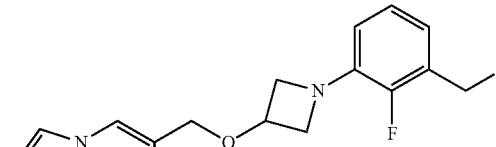 |
| 891 | R285 | 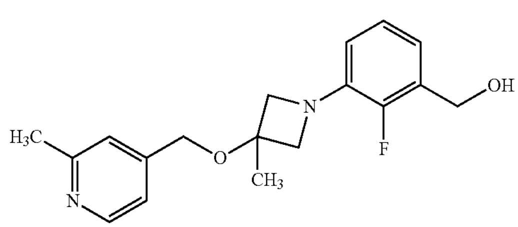 [SMILES: Cc1cc(COC2(C)CN(c3cccc(CO)c3F)C2)ccn1] |

TABLE 145-continued
| Rf | Syn | Structure |
|---|---|---|
| 892 | R285 | 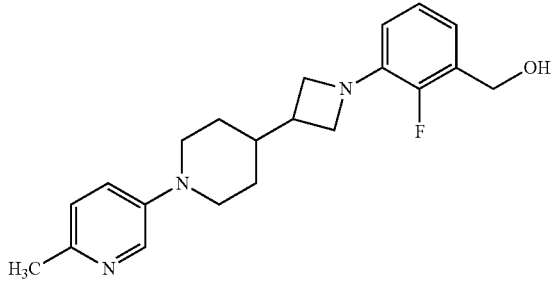 [SMILES: Cc1ccc(N2CCC(C3CN(c4cccc(CO)c4F)C3)CC2)cn1] |
| 893 | R893 | 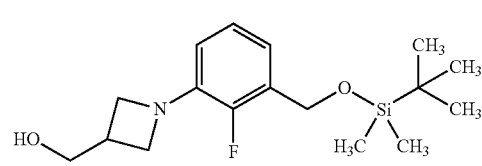 [SMILES: CC(C)(C)[Si](C)(C)OCc1cccc(N2CC(CO)C2)c1F] |
| 894 | R894 | 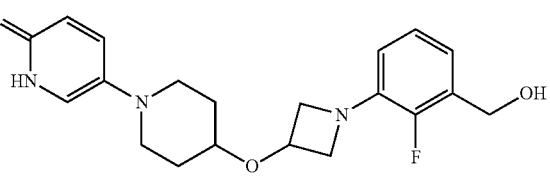 |
| 895 | R894 | 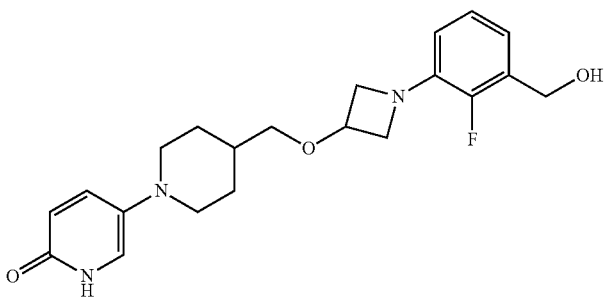 [SMILES: O=c1ccc(N2CCC(COC3CN(c4cccc(CO)c4F)C3)CC2)c[nH]1] |
| 896 | R821 | 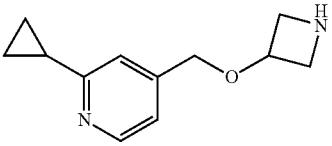 [SMILES: c1cc(COC2CNC2)cc(C2CC2)n1] |
| 897 | R821 | 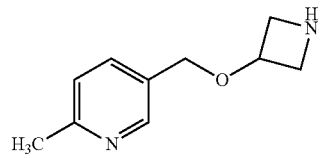 |
| 898 | R821 | 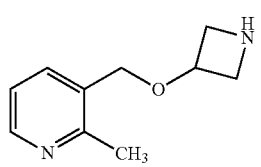 |

TABLE 146
| Rf | Syn | Structure |
|---|---|---|
| 899 | R821 | 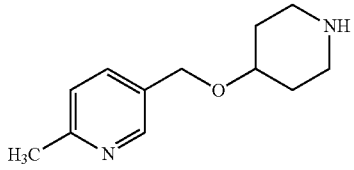 |
| 900 | R821 | 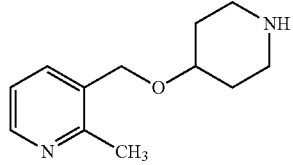 |
| 901 | R821 | 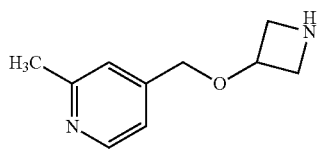 |
| 902 | R821 | 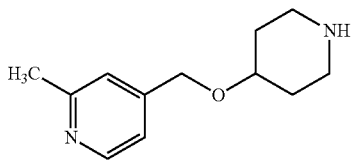 |
| 903 | R821 | 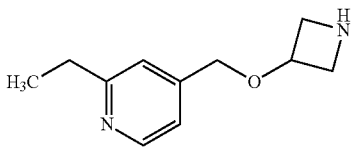 |
| 904 | R821 | 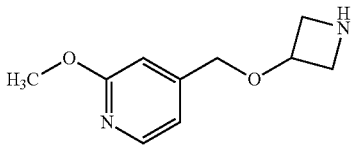 |
| 905 | R821 | 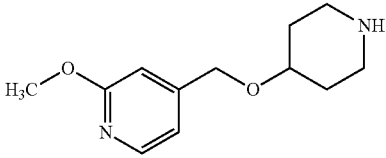 [SMILES: COc1cc(COC2CCNCC2)ccn1] |
| 906 | R821 | 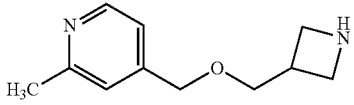 |
| 907 | R821 | 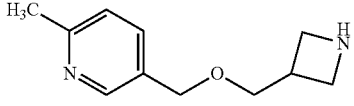 |
| 908 | R821 | 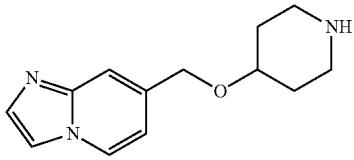 [SMILES: c1cn2ccc(COC3CCNCC3)cc2n1] |

TABLE 146-continued

| Rf | Syn | Structure |
|---|---|---|
| 909 | R821 | 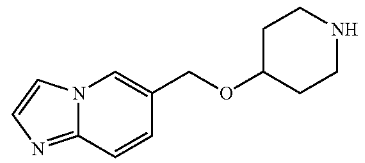 [SMILES: c1cn2cc(COC3CCNCC3)ccc2n1] |
| 910 | R821 | 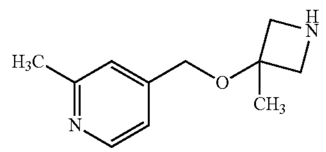 |
| 911 | R343 | 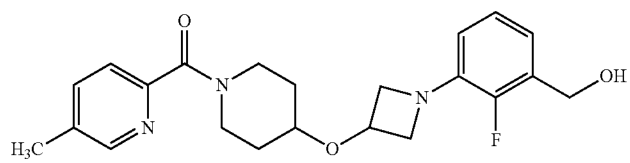 [SMILES: Cc1ccc(C(=O)N2CCC(OC3CN(c4cccc(CO)c4F)C3)CC2)nc1] |
| 912 | R343 | 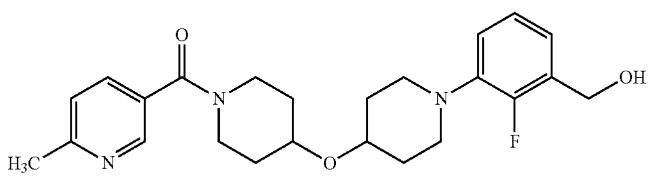 [SMILES: Cc1ccc(C(=O)N2CCC(OC3CCN(c4cccc(CO)c4F)CC3)CC2)cn1] |
| 913 | R376 | 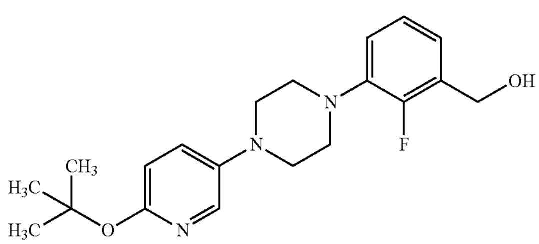 [SMILES: CC(C)(C)Oc1ccc(N2CCN(c3cccc(CO)c3F)CC2)cn1] |
| 914 | R376 | 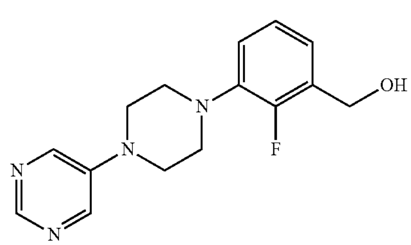 [SMILES: OCc1cccc(N2CCN(c3cncnc3)CC2)c1F] |

TABLE 147

| Rf | Syn | Structure |
|---|---|---|
| 915 | R376 | (structure) |
| 916 | R376 | (structure) |
| 917 | R376 | (structure) |
| 918 | R376 | (structure) |
| 919 | R478 | (structure) |
| 920 | R518 | (structure) |
| 921 | R574 | (structure) |

TABLE 147-continued

| Rf | Syn | Structure |
|---|---|---|
| 922 | R922 | (structure) |
| 923 | R922 | (structure) |
| 924 | R581 | (structure) |
| 925 | R581 | (structure) |
| 926 | R926 | (structure) |
| 927 | R926 | (structure) |
| 928 | R584 | (structure) |
| 929 | R584 | (structure) |
| 930 | R603 | (structure) |

TABLE 148

| Rf | Syn | Structure |
|---|---|---|
| 931 | R603 | (structure) |

TABLE 148-continued

| Rf | Syn | Structure |
|---|---|---|
| 932 | R663 | 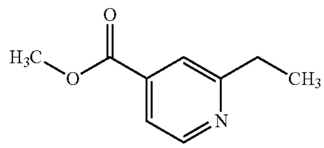 |
| 933 | R677 | 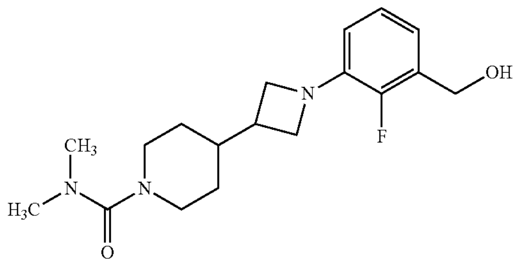 [SMILES: CN(C)C(=O)N1CCC(C2CN(c3cccc(CO)c3F)C2)CC1] |
| 934 | R680 | 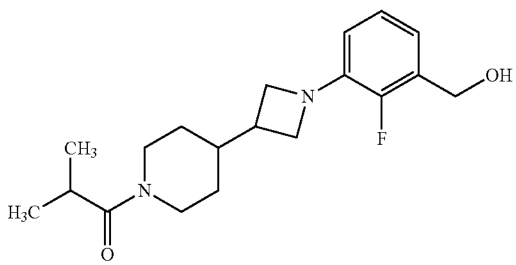 [SMILES: CC(C)C(=O)N1CCC(C2CN(c3cccc(CO)c3F)C2)CC1] |
| 935 | R686 | 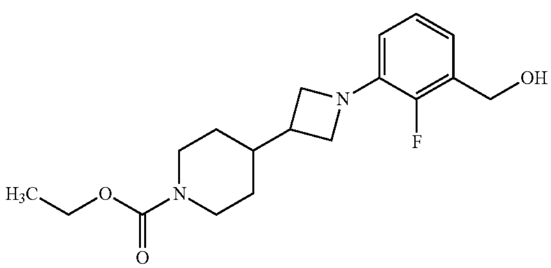 [SMILES: CCOC(=O)N1CCC(C2CN(c3cccc(CO)c3F)C2)CC1] |
| 936 | R712 | 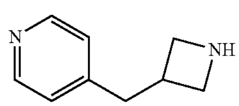 [SMILES: c1cc(CC2CNC2)ccn1] |
| 937 | R712 | 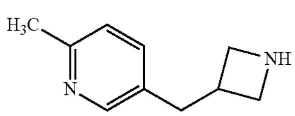 |
| 938 | R938 | 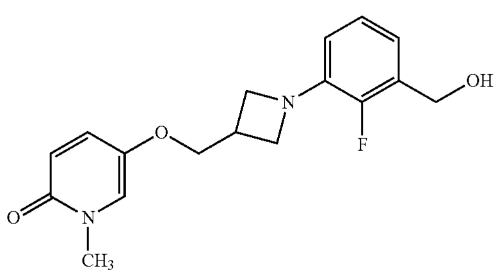 [SMILES: Cn1cc(OCC2CN(c3cccc(CO)c3F)C2)ccc1=O] |

TABLE 148-continued

| Rf | Syn | Structure |
|---|---|---|
| 939 | R758 | 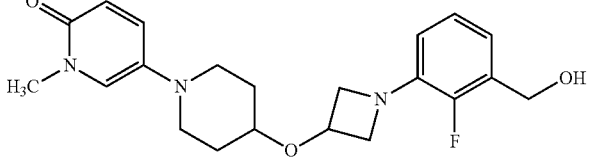 |
| 940 | R758 | 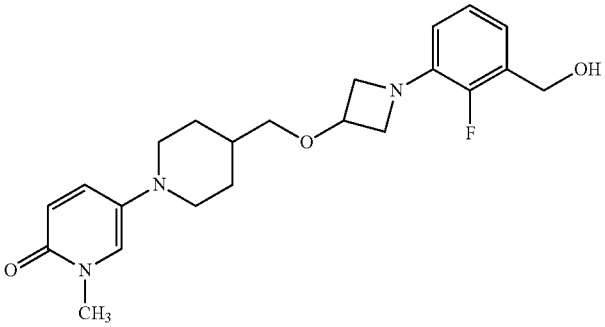 [SMILES: Cn1cc(N2CCC(COC3CN(c4cccc(CO)c4F)C3)CC2)ccc1=O] |
| 941 | R772 | 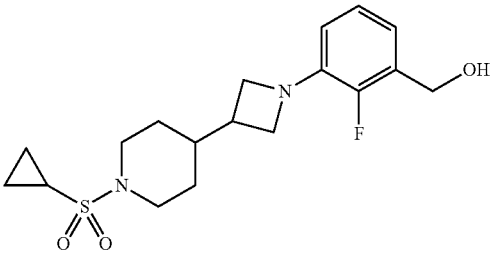 [SMILES: O=S(=O)(C1CC1)N1CCC(C2CN(c3cccc(CO)c3F)C2)CC1] |

TABLE 149

| Rf | Data |
|---|---|
| 843 | ESI+: 164 |
| 844 | ESI+: 430 |
| 845 | ESI+: 416 |
| 846 | APCI/ESI+: 317 |
| 847 | ESI+: 265 |
| 848 | ESI+: 156, 158 |
| 849 | ESI+: 168, 170 |
| 850 | ESI+: 158, 160 |
| 851 | ESI+: 304 |
| 852 | ESI+: 232 |
| 853 | ESI+: 318 |
| 854 | ESI+: 332 |
| 855 | ESI+: 190 |
| 856 | ESI+: 218 |
| 857 | NMR-CDCl$_3$: 1.44 (9H, s), 1.51 (3H, s), 3.81-3.87 (4H, m) |
| 858 | APCI/ESI+: 354 |
| 859 | APCI/ESI+: 368 |
| 860 | ESI+: 150 |
| 861 | ESI+: 474 |
| 862 | ESI+: 403 |
| 863 | ESI+: 441 |
| 864 | ESI+: 455 |
| 865 | APCI/ESI+: 455 |
| 866 | APCI/ESI+: 387 |
| 867 | ESI+: 398 |
| 868 | APCI/ESI+: 401 |
| 869 | ESI+: 303 |
| 870 | ESI+: 303 |
| 871 | ESI+: 331 |
| 872 | ESI+: 331 |
| 873 | ESI+: 331 |
| 874 | ESI+: 303 |
| 875 | ESI+: 317 |

TABLE 150

| Rf | Data |
|---|---|
| 876 | ESI+: 329 |
| 877 | ESI+: 319 |
| 878 | ESI+: 347 |
| 879 | ESI+: 372 |
| 880 | ESI+: 386 |
| 881 | ESI+: 402 |
| 882 | ESI+: 416 |
| 883 | ESI+: 333 |
| 884 | ESI+: 347 |
| 885 | ESI+: 314 |
| 886 | ESI+: 342 |
| 887 | ESI+: 317 |
| 888 | ESI+: 317 |
| 889 | ESI+: 356 |
| 890 | ESI+: 356 |
| 891 | ESI+: 317 |
| 892 | ESI+: 356 |
| 893 | ESI+: 326 |
| 894 | ESI+: 374 |
| 895 | ESI+: 388 |
| 896 | ESI+: 205 |
| 897 | ESI+: 179 |
| 898 | ESI+: 179 |
| 899 | ESI+: 207 |

TABLE 150-continued

| Rf | Data |
|---|---|
| 900 | ESI+: 207 |
| 901 | ESI+: 179 |
| 902 | ESI+: 207 |
| 903 | ESI+: 193 |
| 904 | ESI+: 195 |
| 905 | ESI+: 223 |
| 906 | ESI+: 193 |
| 907 | ESI+: 193 |
| 908 | ESI+: 232 |
| 909 | ESI+: 232 |

TABLE 151

| Rf | Data |
|---|---|
| 910 | ESI+: 193 |
| 911 | ESI+: 400 |
| 912 | ESI+: 428 |
| 913 | ESI+: 360 |
| 914 | ESI+: 289 |
| 915 | ESI+: 327 |
| 916 | ESI+: 341 |
| 917 | APCI/ESI+: 273 |
| 918 | APCI/ESI+: 287 |
| 919 | NMR-CDCl$_3$: 1.80 (1H, br), 3.26 (2H, t, J = 5 Hz), 3.73 (2H, s), 3.77 (2H, t, J = 5 |
| 920 | APCI/ESI+: 341 |

TABLE 151-continued

| Rf | Data |
|---|---|
| 921 | ESI+: 404 |
| 922 | ESI+: 209 |
| 923 | ESI+: 223 |
| 924 | APCI/ESI+: 247 |
| 925 | APCI/ESI+: 261 |
| 926 | ESI+: 303 |
| 927 | ESI+: 361 |
| 928 | ESI+: 140 |
| 929 | ESI+: 138 |
| 930 | APCI/ESI+: 249 |
| 931 | APCI/ESI+: 263 |
| 932 | ESI+: 166 |
| 933 | ESI+: 336 |
| 934 | ESI+: 335 |
| 935 | ESI+: 337 |
| 936 | APCI/ESI+: 149 |
| 937 | APCI/ESI+: 163 |
| 938 | ESI+: 319 |
| 939 | ESI+: 388 |
| 940 | ESI+: 402 |
| 941 | ESI+: 369 |

The compounds of Examples shown in the tables below were prepared using the respective corresponding starting materials in the same manner as the methods of Examples above. The structures, the preparation methods, and the physicochemical data for the compounds of Examples are shown in the tables below.

TABLE 152

| Ex | Syn | Structure |
|---|---|---|
| 568 | 568 | L-TA |
| 569 | 3 | 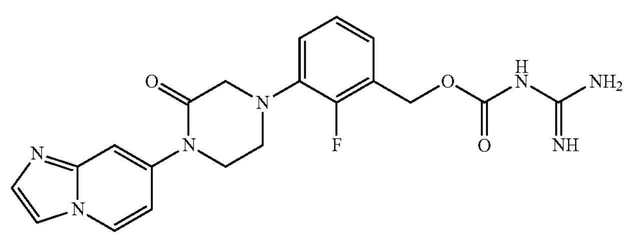 |
| 570 | 112 | L-TA |
| 571 | 112 | L-TA |

TABLE 152-continued
| Ex | Syn | Structure |
|---|---|---|
| 572 | 112 | 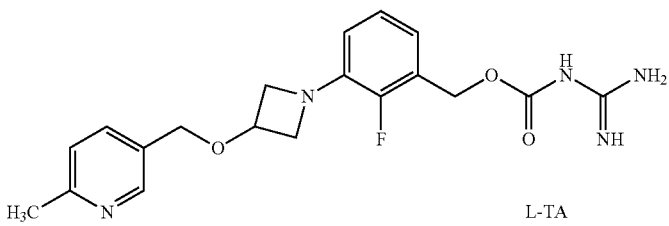 L-TA |
| 573 | 112 | 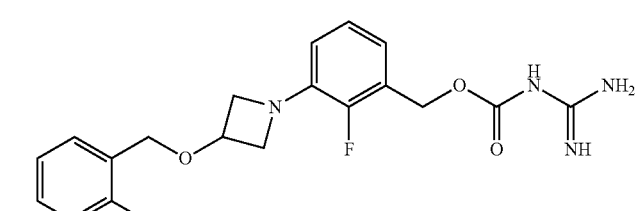 L-TA |
| 574 | 112 | 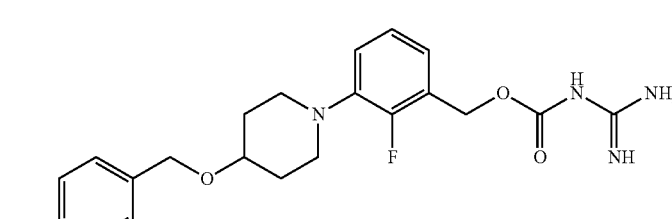 L-TA |
| 575 | 112 | 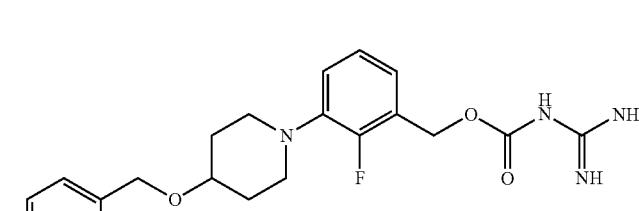 L-TA |
| 576 | 112 | 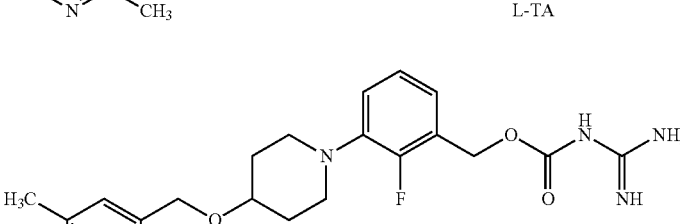 L-TA |
| 577 | 112 | 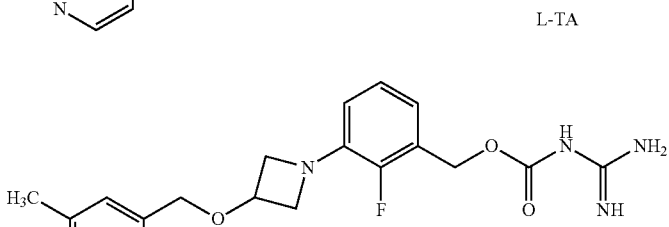 L-TA |

TABLE 152-continued

| Ex | Syn | Structure |
|---|---|---|
| 578 | 112 | (1-methyl-6-oxo-1,6-dihydropyridin-3-yl)piperazinyl-fluorobenzyl carbamimidoyl carbamate, L-TA |
| 579 | 112 | (pyrimidin-5-yl)piperazinyl-fluoropyridinyl carbamimidoyl carbamate, L-TA |
| 580 | 112 | (2-ethylpyridin-4-yl)methoxyazetidinyl-fluorobenzyl carbamimidoyl carbamate, L-TA |
| 581 | 112 | (2-cyclopropylpyridin-4-yl)methoxyazetidinyl-fluorobenzyl carbamimidoyl carbamate, L-TA |
| 582 | 112 | (2-methoxypyridin-4-yl)methoxyazetidinyl-fluorobenzyl carbamimidoyl carbamate, L-TA |
| 583 | 112 | (2-methoxypyridin-4-yl)methoxypiperidinyl-fluorobenzyl carbamimidoyl carbamate, L-TA |

TABLE 153

| Ex | Syn | Structure |
|---|---|---|
| 584 | 112 | (structure) L-TA |
| 585 | 112 | (structure) L-TA |
| 586 | 112 | (structure) L-TA |
| 587 | 588 | (structure) |
| 588 | 588 | (structure) |
| 589 | 112 | (structure) L-TA |

TABLE 153-continued
| Ex | Syn | Structure |
|---|---|---|
| 590 | 112 | 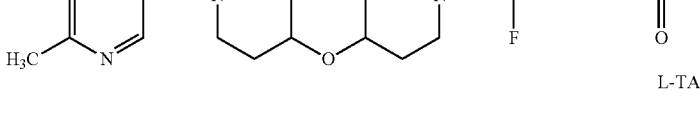 L-TA |
| 591 | 112 |  L-TA |
| 592 | 112 | 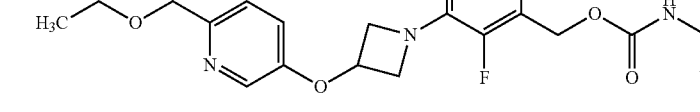 L-TA |
| 593 | 112 |  L-TA |
| 594 | 112 |  L-TA |
| 595 | 112 | 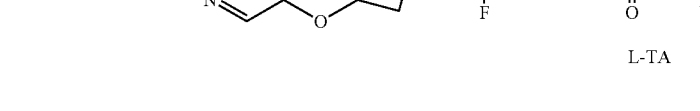 L-TA |

TABLE 153-continued
| Ex | Syn | Structure |
|---|---|---|
| 596 | 112 | (structure) L-TA |
| 597 | 112 | (structure) L-TA |
| 598 | 112 | (structure) L-TA |
| 599 | 112 | (structure) L-TA |
TABLE 154
| Ex | Syn | Structure |
|---|---|---|
| 600 | 112 | 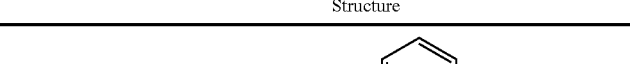 L-TA |

TABLE 154-continued

| Ex | Syn | Structure |
|---|---|---|
| 601 | 112 | (structure) L-TA |
| 602 | 112 | (structure) L-TA |
| 603 | 112 | (structure) L-TA |
| 604 | 112 | (structure) L-TA |
| 605 | 112 | (structure) L-TA |
| 606 | 112 | (structure) L-TA |

TABLE 154-continued

| Ex | Syn | Structure |
|---|---|---|
| 607 | 112 | 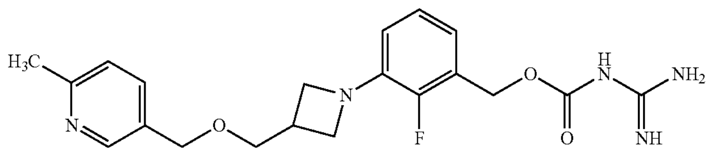 |
| 608 | 112 | 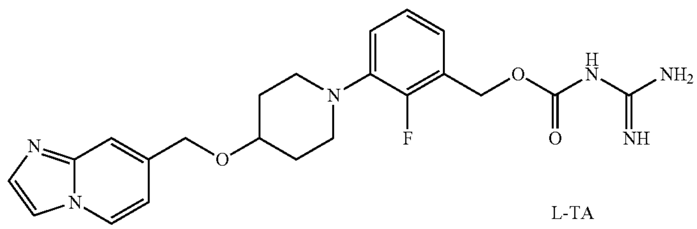 [SMILES: N=C(N)NC(=O)OCc1cccc(N2CCC(OCc3ccn4ccnc4c3)CC2)c1F] |
| 609 | 112 | 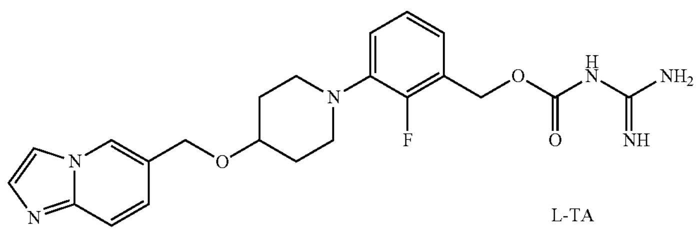 [SMILES: N=C(N)NC(=O)OCc1cccc(N2CCC(OCc3ccc4nccn4c3)CC2)c1F] |
| 610 | 112 | 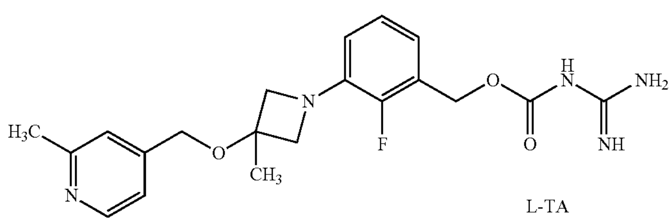 [SMILES: Cc1cc(COC2(C)CN(c3cccc(COC(=O)NC(=N)N)c3F)C2)ccn1] |
| 611 | 112 | 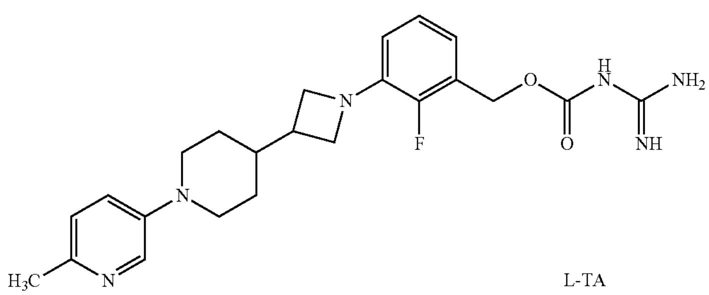 [SMILES: Cc1ccc(N2CCC(C3CN(c4cccc(COC(=O)NC(=N)N)c4F)C3)CC2)cn1] |
| 612 | 112 | 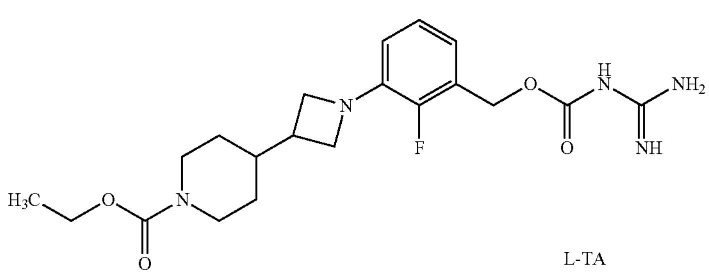 [SMILES: CCOC(=O)N1CCC(C2CN(c3cccc(COC(=O)NC(=N)N)c3F)C2)CC1] |

TABLE 154-continued
| Ex | Syn | Structure |
|---|---|---|
| 613 | 112 |  L-TA |
TABLE 155
| Ex | Syn | Structure |
|---|---|---|
| 614 | 112 | 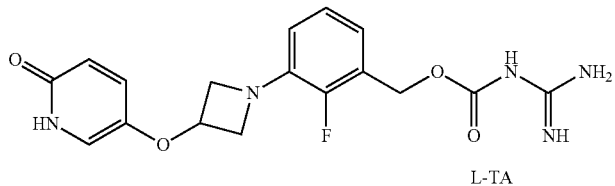 L-TA |
| 615 | 615 | 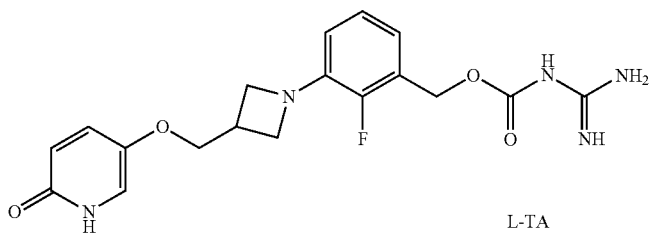 L-TA |
| 616 | 615 | 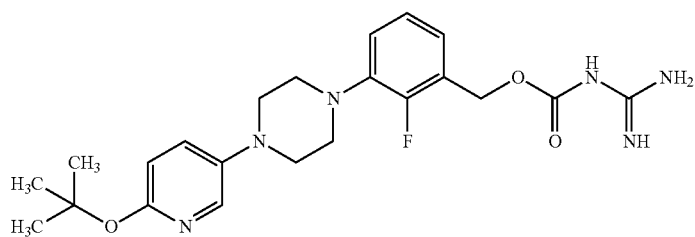 L-TA |
| 617 | 3 | 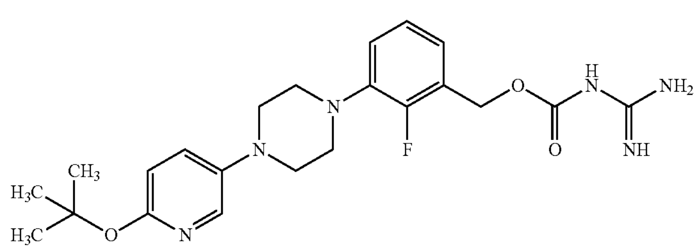 |

TABLE 155-continued
| Ex | Syn | Structure |
|---|---|---|
| 618 | 112 | 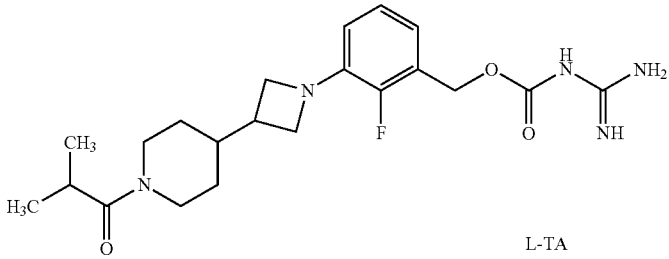 L-TA |
| 619 | 619 | 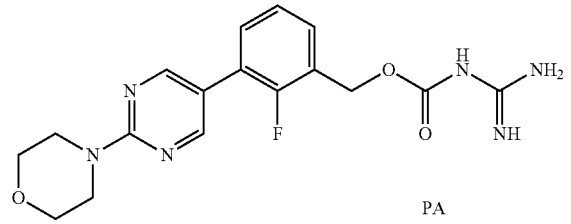 PA |
| 620 | 619 | 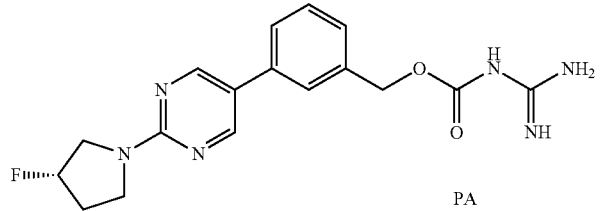 PA |
| 621 | 619 | 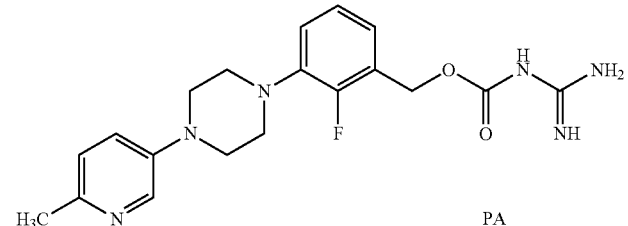 PA |
| 622 | 619 | 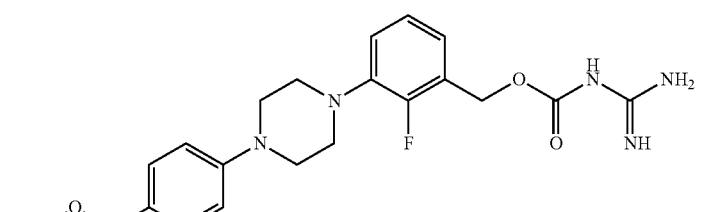 PA |
| 623 | 619 | 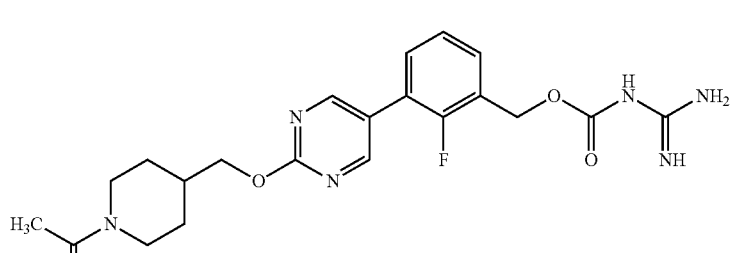 PA |

TABLE 156

| Ex | Data |
|---|---|
| 568 | ESI+: 389 |
| 569 | APCI/ESI+: 426 |
| 570 | APCI/ESI+: 358 |
| 571 | APCI/ESI+: 372 |
| 572 | ESI+: 388 |
| 573 | ESI+: 388 |
| 574 | ESI+: 416 |
| 575 | ESI+: 416 |
| 576 | ESI+: 416 |
| 577 | ESI+: 388 |
| 578 | ESI+: 403 |
| 579 | ESI+: 374 |
| 580 | ESI+: 402 |
| 581 | ESI+: 414 |
| 582 | ESI+: 404 |
| 583 | ESI+: 432 |
| 584 | ESI+: 412 |
| 585 | ESI+: 457 |
| 586 | ESI+: 471 |
| 587 | ESI+: 487 |
| 588 | ESI+: 501 |
| 589 | ESI+: 485 |
| 590 | ESI+: 513 |
| 591 | ESI+: 418 |
| 592 | ESI+: 432 |
| 593 | ESI+: 459 |
| 594 | ESI+: 473 |
| 595 | ESI+: 487 |
| 596 | ESI+: 501 |
| 597 | ESI+: 473 |
| 598 | ESI+: 487 |
| 599 | ESI+: 390 |
| 600 | ESI+: 426 |

TABLE 157

| Ex | Data |
|---|---|
| 601 | ESI+: 417 |
| 602 | ESI+: 388 |
| 603 | ESI+: 404 |
| 604 | ESI+: 399 |
| 605 | ESI+: 427 |
| 606 | ESI+: 402 |
| 607 | ESI+: 402 |
| 608 | ESI+: 441 |
| 609 | ESI+: 441 |
| 610 | ESI+: 402 |
| 611 | ESI+: 441 |
| 612 | ESI+: 422 |
| 613 | ESI+: 454 |
| 614 | ESI+: 421 |
| 615 | ESI+: 376 |
| 616 | ESI+: 390 |
| 617 | ESI+: 445 |
| 618 | ESI+: 420 |
| 619 | ESI+: 375 DSC endothermic onset temperature: 197.4° C. |
| 620 | ESI+: 359 DSC endothermic onset temperature: 184.7° C. |
| 621 | ESI+: 387 DSC endothermic onset temperature: 173.0° C. |
| 622 | ESI+: 417 DSC endothermic onset temperature: 207.8° C. |
| 623 | ESI+: 445 DSC endothermic onset temperature: 204.0° C. |

INDUSTRIAL APPLICABILITY

The compound of the formula (I) or a salt thereof has a VAP-1 inhibitory action, and can be used as an agent for preventing and/or treating VAP-1-related diseases.

The invention claimed is:

1. A compound, which is selected from the group consisting of
2-fluoro-3-[2-(morpholin-4-yl)pyrimidin-5-yl]benzyl carbamimidoylcarbamate,
2-fluoro-3-[2-(3-methoxyazetidin-1-yl)pyrimidin-5-yl]benzyl carbamimidoylcarbamate,
3-(4-{4-[5-(3-{[(carbamimidoylcarbamoyl)oxy]methyl}-2-fluorophenyl) pyrimidin-2-yl]piperazin-1-yl}phenyl) propanoic acid,
3-{2-[(1-acetylpiperidin-4-yl)methoxy]pyrimidin-5-yl}-2-fluorobenzyl carbamimidoylcarbamate, and
3-(2-{[1-(cyclopropylcarbonyl)piperidin-4-yl]methoxy}pyrimidin-5-yl)-2-fluorobenzyl carbamimidoylcarbamate;
or a salt of said compound.

2. The compound or a salt of said compound according to claim 1, which is 2-fluoro-3-[2-(morpholin-4-yl)pyrimidin-5-yl]benzyl carbamimidoylcarbamate or a salt of said compound.

3. The compound or a salt of said compound according to claim 1, which is 2-fluoro-3-[2-(3-methoxyazetidin-1-yl)pyrimidin-5-yl]benzyl carbamimidoylcarbamate or a salt of said compound.

4. The compound or a salt of said compound according to claim 1, which is 3-(4-{4-[5-(3-{[(carbamimidoylcarbamoyl)oxy]methyl}-2-fluorophenyl)pyrimidin-2-yl]piperazin-1-yl}phenyl)propanoic acid or a salt of said compound.

5. The compound or a salt of said compound according to claim 1, which is 3-{2-[(1-acetylpiperidin-4-yl)methoxy]pyrimidin-5-yl}-2-fluorobenzyl carbamimidoylcarbamate or a salt of said compound.

6. The compound or a salt of said compound according to claim 1, which is 3-(2-{[1-(cyclopropylcarbonyl)piperidin-4-yl]methoxy}pyrimidin-5-yl)-2-fluorobenzyl carbamimidoylcarbamate or a salt of said compound.

7. A pharmaceutical composition comprising the compound according to claim 1 or a salt of said compound and a pharmaceutically acceptable carrier or excipient.

8. A method for treating diabetic nephropathy or diabetic macular edema in a patient in need thereof, comprising administering to said patient an effective amount of the compound according to claim 1 or a salt of said compound.

9. A method for treating diabetic nephropathy in a patient in need thereof, comprising administering to said patient an effective amount of the compound according to claim 1 or a salt of said compound.

10. A method for treating diabetic macular edema in a patient in need thereof, comprising administering to said patient an effective amount of the compound according to claim 1 or a salt of said compound.

* * * * *